(12) United States Patent
Nishimae et al.

(10) Patent No.: US 11,691,983 B2
(45) Date of Patent: Jul. 4, 2023

(54) SPECIFICALLY SUBSTITUTED BENZOFURO- AND BENZOTHIENOQUINOLINES FOR ORGANIC LIGHT EMITTING DIODES

(71) Applicant: IDEMITSU KOSAN CO., LTD., Chiyoda-ku (JP)

(72) Inventors: Yuichi Nishimae, Basel (CH); Michelle Groarke, Binningen (CH); Heinz Wolleb, Fehren (CH); Annemarie Wolleb, Fehren (CH); Yuki Nakano, Kisarazu (JP); Hideaki Nagashima, Ichihara (JP); Tasuku Haketa, Chiba (JP); Masahiro Kawamura, Basel (CH); Takushi Shiomi, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 479 days.

(21) Appl. No.: 16/312,378

(22) PCT Filed: Jun. 13, 2017

(86) PCT No.: PCT/JP2017/022938
§ 371 (c)(1),
(2) Date: Dec. 21, 2018

(87) PCT Pub. No.: WO2017/221999
PCT Pub. Date: Dec. 28, 2017

(65) Prior Publication Data
US 2019/0161497 A1  May 30, 2019

(30) Foreign Application Priority Data
Jun. 22, 2016 (EP) .................... 16175773

(51) Int. Cl.
*H01L 51/00* (2006.01)
*C07D 495/04* (2006.01)
(Continued)

(52) U.S. Cl.
CPC ....... *C07D 495/04* (2013.01); *C07D 491/048* (2013.01); *C07D 519/00* (2013.01);
(Continued)

(58) Field of Classification Search
None
See application file for complete search history.

(56) References Cited

U.S. PATENT DOCUMENTS

2007/0141387 A1   6/2007   Nakano et al.
2007/0232640 A1  10/2007   Ablordeppey
(Continued)

FOREIGN PATENT DOCUMENTS

CN       1546473 A    11/2004
CN     102448945 A     5/2012
(Continued)

OTHER PUBLICATIONS

Jewell D.M. et al. "Identification of Nitrogen Bases in Heavy Gas Oil; Chromatographic Methods of Separation" Journal of Chemical and Engineering Data 1964, 9(2), 297-304. (Year: 1964).*
(Continued)

*Primary Examiner* — Robert S Loewe
(74) *Attorney, Agent, or Firm* — Oblon, McClelland, Maier & Neustadt, L.L.P.

(57) ABSTRACT

Specifically substituted benzofuro- and benzothienoquinolines and their use in electronic devices, especially electroluminescent devices. When used as charge transport material, charge blocker material and/or host material in electroluminescent devices, the specifically substituted benzofuro- and benzothienoquinolines may provide improved efficiency, stability, manufacturability, or spectral characteristics of electroluminescent devices and reduced driving voltage of electroluminescent devices.

29 Claims, 1 Drawing Sheet

(51) Int. Cl.
    *C07D 491/048* (2006.01)
    *C07D 519/00* (2006.01)
    *H01L 51/50* (2006.01)

(52) U.S. Cl.
    CPC ...... *H01L 51/0052* (2013.01); *H01L 51/0054* (2013.01); *H01L 51/0067* (2013.01); *H01L 51/0071* (2013.01); *H01L 51/0072* (2013.01); *H01L 51/5096* (2013.01); *H01L 51/0059* (2013.01); *H01L 51/0073* (2013.01); *H01L 51/0085* (2013.01); *H01L 51/5012* (2013.01); *H01L 51/5016* (2013.01); *H01L 51/5072* (2013.01); *Y02E 10/549* (2013.01)

(56) References Cited

U.S. PATENT DOCUMENTS

| | | |
|---|---|---|
| 2009/0309488 A1 | 12/2009 | Kato et al. |
| 2010/0084971 A1 | 4/2010 | Nakano et al. |
| 2011/0266526 A1 | 11/2011 | Ma et al. |
| 2012/0126208 A1 | 5/2012 | Kawamura et al. |
| 2012/1262051 | 5/2012 | Kawamura et al. |
| 2012/0138914 A1 | 6/2012 | Kawamura et al. |
| 2012/0157493 A1 | 6/2012 | Ablordeppey |
| 2013/0254560 A1 | 10/2013 | Dobbs et al. |
| 2013/0264561 A1 | 10/2013 | Dobbs et al. |
| 2014/0001456 A1 | 1/2014 | Mizutani et al. |
| 2014/0034915 A1 | 2/2014 | Lee et al. |
| 2014/0034931 A1 | 2/2014 | Inoue et al. |
| 2014/0110686 A1* | 4/2014 | Fujita ................ H05B 33/14 257/40 |
| 2014/0117331 A1 | 5/2014 | Kim et al. |
| 2014/0159005 A1* | 6/2014 | Kawamura ........ C07D 333/50 257/40 |
| 2014/0231769 A1 | 8/2014 | Nishimura et al. |
| 2014/0312338 A1 | 10/2014 | Mizutani et al. |
| 2014/0361252 A1* | 12/2014 | Dyatkin ............... C07F 5/069 257/40 |
| 2015/0005512 A1 | 1/2015 | Kawamura et al. |
| 2015/0034914 A1* | 2/2015 | Lee ................. H01L 51/0067 257/40 |
| 2015/0053936 A1* | 2/2015 | Takaku ............. C07D 403/04 257/40 |
| 2015/0076483 A1 | 3/2015 | Tsurutani et al. |
| 2015/0207082 A1* | 7/2015 | Dyatki .............. C07D 491/147 257/40 |
| 2015/0236276 A1* | 8/2015 | Boudreault ........ H01L 51/0085 257/40 |
| 2015/0243907 A1* | 8/2015 | Wolleb .............. C07D 405/14 252/500 |
| 2015/0249223 A1* | 9/2015 | Szigethy ........... H01L 51/0058 257/40 |
| 2015/0325800 A1* | 11/2015 | Ito .................... C07D 307/77 257/40 |
| 2015/0333271 A1* | 11/2015 | Chung .............. C07F 7/0896 257/40 |
| 2015/0349268 A1* | 12/2015 | Zeng ................ C07D 409/10 257/40 |
| 2015/0372237 A1 | 12/2015 | Kawamura et al. |
| 2016/0028025 A1 | 1/2016 | Ogiwara et al. |
| 2016/0079546 A1* | 3/2016 | Park ................... C07F 9/65586 257/40 |
| 2016/0093808 A1 | 3/2016 | Adamovich et al. |
| 2016/0118594 A1* | 4/2016 | Itoi ................... H01L 51/0071 257/40 |
| 2016/0141515 A1 | 5/2016 | Hayama et al. |
| 2016/0141522 A1* | 5/2016 | Ma ..................... C09K 11/025 257/40 |
| 2016/0163997 A1* | 6/2016 | Noh .................. C09K 11/06 257/40 |
| 2016/0190477 A1 | 6/2016 | Kawakami et al. |
| 2016/0225992 A1 | 8/2016 | Ito et al. |
| 2016/0254459 A1 | 9/2016 | Kawamura et al. |
| 2016/0329503 A1* | 11/2016 | Yeager ............. C07D 517/04 |
| 2016/0351817 A1* | 12/2016 | Kim ................... H01L 51/006 |
| 2017/0012211 A1 | 1/2017 | Cho et al. |
| 2017/0033295 A1* | 2/2017 | Xia .................... H01L 51/0072 |
| 2017/0104163 A1 | 4/2017 | Lee et al. |
| 2017/0104167 A1 | 4/2017 | Sim et al. |
| 2017/0155049 A1 | 6/2017 | Kim et al. |
| 2017/0186964 A1 | 6/2017 | Cho et al. |
| 2017/0186975 A1 | 6/2017 | Kim et al. |
| 2017/0222160 A1 | 8/2017 | Lee et al. |
| 2017/0294613 A1 | 10/2017 | Cho et al. |
| 2017/0317291 A1 | 11/2017 | Hayashi et al. |
| 2017/0317293 A1 | 11/2017 | Kim et al. |
| 2017/0338432 A1 | 11/2017 | Adamovich et al. |
| 2017/0373259 A1* | 12/2017 | Su ..................... H01L 51/0058 |
| 2018/0083197 A1* | 3/2018 | Park ................... H01L 51/50 |
| 2018/0233669 A1 | 8/2018 | Lee et al. |
| 2018/0269402 A1 | 9/2018 | Huh et al. |
| 2018/0315930 A1 | 11/2018 | Han et al. |
| 2019/0106391 A1 | 4/2019 | Wucherer-Plietker et al. |
| 2019/0214577 A1 | 7/2019 | Pan et al. |

FOREIGN PATENT DOCUMENTS

| | | |
|---|---|---|
| CN | 102516355 | 6/2012 |
| CN | 103666452 | 3/2014 |
| CN | 105153193 | 12/2015 |
| CN | 105283977 A | 1/2016 |
| CN | 105810837 A | 7/2016 |
| CN | 106565689 A | 4/2017 |
| EP | 1 962 354 A1 | 8/2008 |
| EP | 2 436 679 A1 | 4/2012 |
| EP | 3 010 055 A1 | 4/2016 |
| JP | 2-256667 | 10/1990 |
| JP | 2015-205235 A | 11/2015 |
| KR | 10-2011-0002156 A | 1/2011 |
| KR | 10-2011-0083442 | 7/2011 |
| KR | 10-2011-0083442 A | 7/2011 |
| KR | 10-2012-0013279 A | 2/2012 |
| KR | 10-2012-0104064 | 9/2012 |
| KR | 10-2012-0104067 A | 9/2012 |
| KR | 10-2013-0122602 A | 11/2013 |
| KR | 10-2014-0103007 | 8/2014 |
| KR | 10-2014-0145965 A | 12/2014 |
| KR | 10-2015-0002072 A | 1/2015 |
| KR | 10-2016-0018458 A | 2/2016 |
| KR | 10-2017-0058619 A | 5/2017 |
| KR | 10-2017-0058625 A | 5/2017 |
| KR | 10-2017-0086211 A | 7/2017 |
| KR | 10-2017-0086243 A | 7/2017 |
| KR | 10-2017-0086277 A | 7/2017 |
| KR | 10-2017-0086329 A | 7/2017 |
| KR | 10-2017-0111387 A | 10/2017 |
| SU | 1051092 A | 10/1983 |
| WO | WO 92/21661 A1 | 12/1992 |
| WO | WO 98/45272 A1 | 10/1998 |
| WO | WO 2007069569 A | 6/2007 |
| WO | WO 2011/034518 A1 | 3/2011 |
| WO | WO 2014/024750 A1 | 2/2014 |
| WO | WO 2014/199637 A1 | 12/2014 |
| WO | WO 2014/208755 A1 | 12/2014 |
| WO | WO 2015/199489 A2 | 12/2015 |
| WO | WO 2016/013732 A1 | 1/2016 |
| WO | WO 2016/076384 A1 | 5/2016 |
| WO | WO 2016/080622 A | 5/2016 |
| WO | WO 2017/023021 A1 | 2/2017 |
| WO | WO 2017/074052 A1 | 5/2017 |
| WO | WO 2017/032495 A1 | 6/2017 |

OTHER PUBLICATIONS

Benati et al. "Cascade Radical Reaction of 2-Alkynyl-Substituted Aryl Radicals with Aryl Isothiocyanates: A Noverl Entry to Benzothieno[2,3-b]quinolines through a-(Arylsulfanyl)imidoyl Radicals" J. Org. Chem. 2000, 65, 8669-8674. (Year: 2000).*

Combined Office Action and Search Report in Chinese Patent Application No. 201780038756.7, dated Jan. 6, 2021, citing documents AK,AL,AM,AN,AY therein, 12 pages.

(56) References Cited

OTHER PUBLICATIONS

Office Action in Japanese Patent Application No. 2018-566613, dated Feb. 2, 2021, citing documents AA,AO,AP,AQ,AR,AS,AT,AU,AV therein, 7 pages.

K. Goerlitzer et al., "Tetracyclic derivatives of diltiazem from Aurones and Thioaurones", Pharmazie. (CPCH1862805P) vol. 58, No. 3, pp. 177-180, 2003, 4 pages (177-180).

International Search Report dated Sep. 4, 2017 in PCT/JP2017/022938 filed on Jun. 13, 2017.

Elslager, E.F. et al. "Inhibitors of Platelet Aggregation. 3. {[(Dialkylamino)alkyl]thiof heterocyclic Compounds", Journal of Medicinal Chemistry, Jan. 1, 1972, vol. 15, No. 1, pp. 61-65, XP055292550.

Zhu, X.Y. et al. "Synthesis and evaluation of isosteres of N-methyl indolo[3,2-b]-quinoline (cryptolepine) as new antiinfective agents", Bioorganic & Medicinal Chemistry, vol. 15, No. 2, Dec. 12, 2006, pp. 686-695, XP005882789.

Boateng, C.A. et al. "Benzothieno[3,2-b]quinolinium and 3-(phenylthio)quinolinium compounds: Synthesis and evaluation against opportunistic fungal pathogens" Bioorganic & Medicinal Chemistry, vol. 19, No. 1, Jan. 1, 2011, pp. 458-470, XP027577781.

Yamaguchi, S. et al. "The Synthesis of Benzofuroquinolines. V. Some Benzofuro[3,2-b]quinolone Derivatives", Journal of Heterocyclic Chemistry, Mar. 1, 1989, pp. 285-287, XP055292564.

Yang, C L. et al. "Identification of benzofuro[2,3-b]quinoline derivatives as a new class of antituberculosis agents", European Journal of Medicinal Chemistry, vol. 45, No. 2, Feb. 1, 2010, pp. 602-607, XP026835685.

Raj T. T. et al: "Synthesis of 4-aminopyrimido[4'5':4,5]thieno[2,3-b]quinolines", J. Chem. Eng. Data 1988, Oct. 1, 1988, pp. 530-531, XP055292571.

Benati, L. et al. "Cascade Radical Reaction of 2-Alkynyl-Substituted Aryl Radicals with Aryl Isothiocyanates: A Novel Entry to Benzothieno[2,3-b]quinolines through [alpha]-(Arylsulfanyl)imidoyl Radicals", The Journal of Organic Chemistry, vol. 65, No. 25, Dec. 1, 2000, pp. 8669-8674, XP055292576.

Stadlbauer, W. et al. "Synthese von Benzofuranen durch Cyclodehydrierung von Phenylmalonylheterocyclen", Monatshefte fuer Chemie, Jan. 1, 1980, pp. 1005-1013, XP055292697.

Office Action as received in CN patent application No. 201780038756.7 dated Jul. 12, 2021 w/English Translation, citing document AW, 13 pages.

Office Action as received in the corresponding KR patent application No. 10-2018-7037051, dated Nov. 30, 2021, citing document AW, 9 pages.

\* cited by examiner

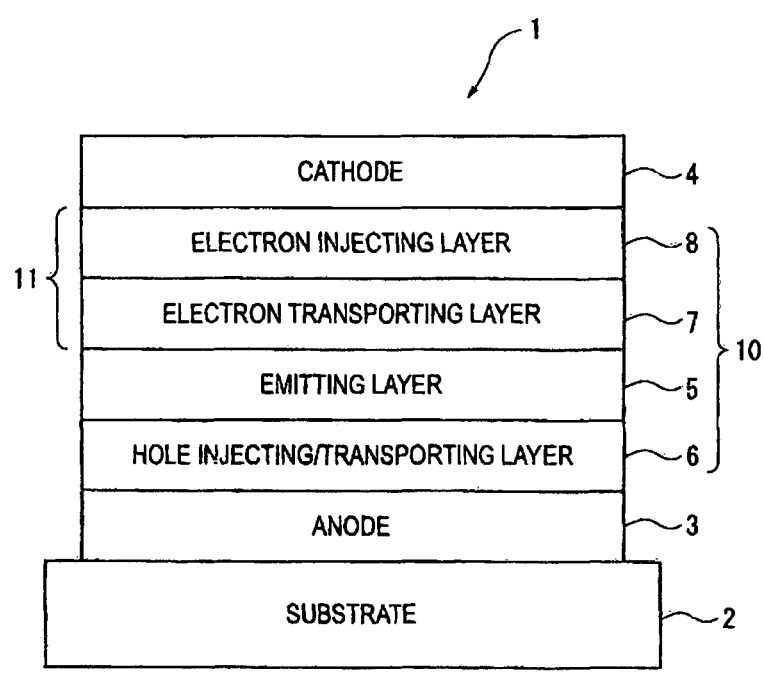

SPECIFICALLY SUBSTITUTED BENZOFURO- AND BENZOTHIENOQUINOLINES FOR ORGANIC LIGHT EMITTING DIODES

TECHNICAL FIELD

The present invention relates to specifically substituted benzofuro- and benzothienoquinolines and their use in electronic devices, especially electroluminescent devices. When used as charge transport material, charge blocker material and/or host material in electroluminescent devices, the specifically substituted benzofuro- and benzothienoquinolines may provide improved efficiency, stability, manufacturability, or spectral characteristics of electroluminescent devices and reduced driving voltage of electroluminescent devices.

BACKGROUND ART

KR 20110083442 concerns an organic optical device comprising an organic layer comprising an organic optical compound of formula A:

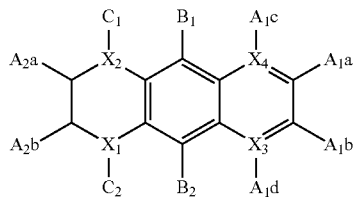

wherein $X_1$, $X_2$, $X_3$ and $X_4$ are each 0 (zero), Si, Se, O C or N, whereby if any one of $X_1$ and $X_2$ is 0, the other one is not 0 and if any one of $X_3$ and $X_4$ is 0, the other one is not 0. However, benzofuro- and benzothienoquinolines having a specific position of N are not disclosed.

US 20110266526 discloses compounds comprising a triphenylene moiety and a benzo- or dibenzo-moiety, wherein the benzo- or dibenzo-moiety has in particular a fused substituent. The compounds may be used in organic light emitting devices, particularly in combination with yellow, orange or red emitters. Under numerous examples, one compound of the following formula is mentioned:

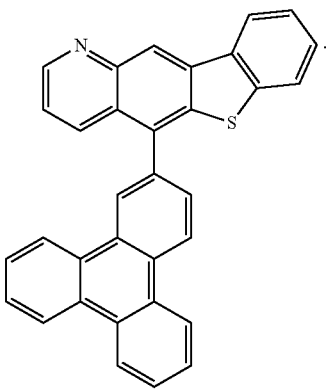 [SMILES: c1ccc2c(c1)sc1c(-c3ccc4c5ccccc5c5ccccc5c4c3)c3cccnc3cc12]

However, benzofuro- and benzothienoquinolines having a specific position of N are not disclosed.

KR 20120104064 concerns an organic optical device comprising an organic layer comprising an organic optical compound of formula F:

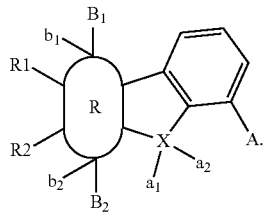

An example for the compounds explicitly mentioned is:

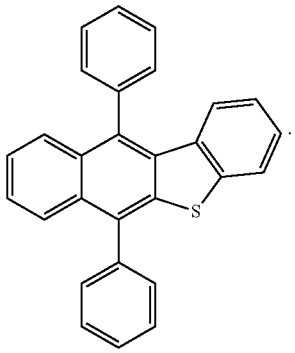 [SMILES: c1ccc(-c2c3ccccc3c(-c3ccccc3)c3c2sc2ccccc23)cc1]

However, benzofuro- and benzothienoquinolines having a specific position of N are not disclosed.

KR 20140103007 concerns organic optical compounds of the following formulae, especially thiophene derivatives, and an organic optical device comprising an organic layer comprising at least one of said compounds:

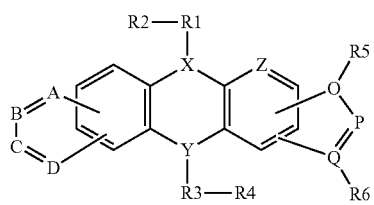

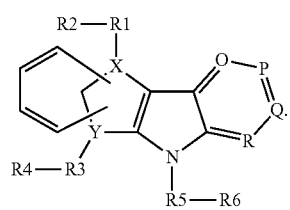

Under numerous compounds explicitly mentioned, the following compound is shown:

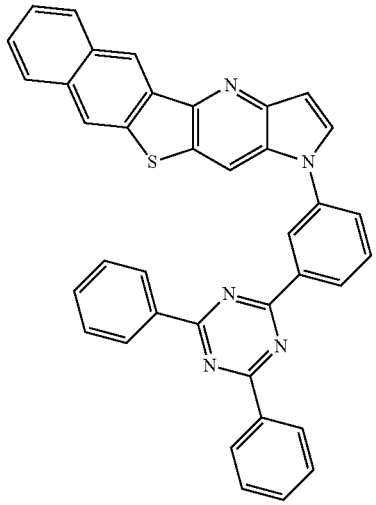 [SMILES: c1ccc(-c2nc(-c3ccccc3)nc(-c3cccc(-n4ccc5nc6c(cc54)sc4cc5ccccc5cc46)c3)n2)cc1]

However, benzofuro- and benzothienoquinolines having a specific position of N are not disclosed.

US 20140117331 concerns heterocyclic compounds of formula 1 and organic light emitting device including said compounds:

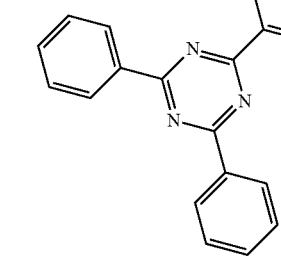

However, benzofuro- and benzothienoquinolines having a specific position of N are not disclosed.

US 20140034915 concerns a heterocyclic compound of formula (I) and an organic light emitting device comprising an organic layer comprising the compound of formula (I):

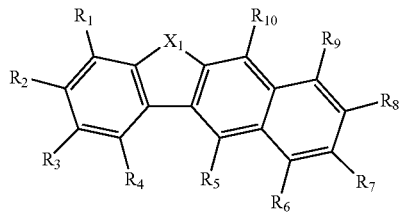

wherein $A_1$, $A_2$, $B_1$ and $B_2$ form optional rings. However, benzofuro- and benzothienoquinolines having a specific position of N are not disclosed.

WO 2014/024750 A1 concerns heterocyclic compounds of formula (1) and an organic light emitting device including said compounds:

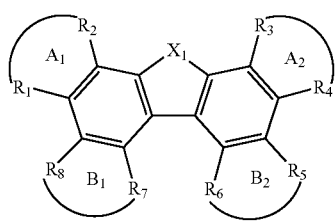

wherein $Ar^2$ may be under numerous substituents

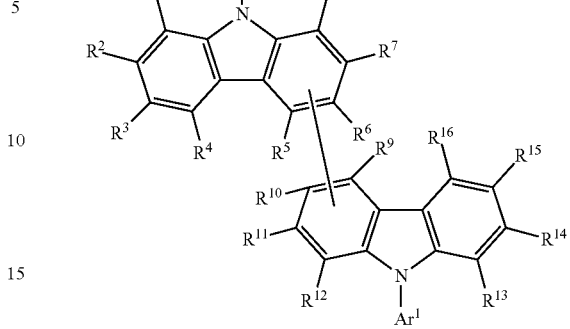

However, benzofuro- and benzothienoquinolines having a specific position of N are not disclosed.

WO 2014/199637 A1 concerns a material for organic electroluminescent elements having one of the following formulae (1), (2) or (3), organic electroluminescent elements using the same and an electronic device comprising said materials.

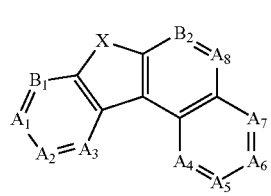

(1)

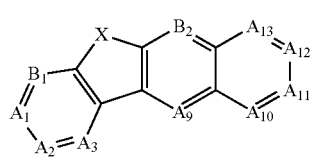

(2)

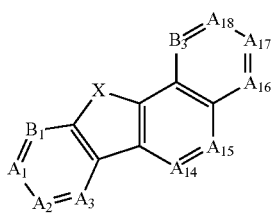

(3)

Wherein $A_1$-$A_{18}$ may be H, $CR_1$ or N; $B_1$-$B_3$ may be H, $CR_2$ or N; wherein
(1) At least one of $A_1$-$A_8$, $B_1$ or $B_2$ is in formula (1) N;
(2) At least one of $A_1$-$A_1$; $A_9$-$A_{13}$, $B_1$ or $B_2$ in formula (2) is N; and
(3) At least one of $A_1$-$A_3$, $A_{14}$ to $A_{18}$, $B_1$ or $B_3$ in formula (3) is N.

There are numerous compounds explicitly mentioned in WO 2014/199637 A1, wherein no particular preference for the position of N is given and in most cases, the compounds explicitly mentioned are substituted at the $A_2$ position. However, benzofuro- and benzothienoquinolines having a specific position of N and a specific substitution pattern are not explicitly disclosed.

WO2015/199489 A2 concerns benzofuro- and benzothienoisoquinolines of the following formula

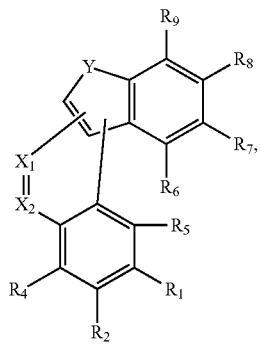

and an organic light emitting device including said compounds. However, benzofuro- and benzothienoquinolines having a specific position of N and a specific substitution pattern are not disclosed.

CITATION LIST

Patent Literature

KR 20110083442
US 20110266526
KR 20120104064
KR 20140103007
US 20140117331
US 20140034915
WO 2014/024750 A1
WO 2014/199637 A1
WO 2015/199489 A2

SUMMARY OF INVENTION

Technical Problem

Notwithstanding these developments, there remains a need for organic light emitting devices comprising new materials, especially host (=matrix) materials, charge transport materials, i.e. hole transport materials and electron transport materials, and/or charge/exciton blocker materials, i.e. electron/exciton blocker materials and hole/exciton blocker materials, to provide long lifetimes, improved efficiency, stability, manufacturability, driving voltage and/or spectral characteristics of electroluminescent devices.

Accordingly, it is an object of the present invention, with respect to the aforementioned related art, to provide further materials suitable for use in OLEDs and further applications in organic electronics. More particularly, it should be possible to provide charge transport materials, i.e. hole transport materials and electron transport materials, and/or charge/exciton blocker materials, i.e. electron/exciton blocker materials and hole/exciton blocker materials, and host (=matrix) materials for use in OLEDs. The materials should be suitable especially for OLEDs which comprise at least one emitter, which is a phosphorescence emitter and/or a fluorescent emitter, for example at least one blue, green, red or yellow emitter, especially at least one blue emitter (fluorescent system), at least one green emitter or at least one red emitter.

Furthermore, the materials should be suitable for providing OLEDs which ensure good efficiencies, good operative lifetimes and a high stability to thermal stress, and a low use and operating voltage of the OLEDs.

Solution to Problem

Said object is solved by a heterocyclic derivative of formulae (1);

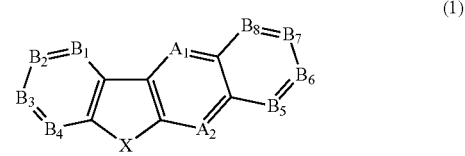

(1)

wherein
X is O or S;
$A_1$ is N or $CR^{41}$;
$A_2$ is N or $CR^{42}$;
wherein at least one of $A_1$ and $A_2$ is N; preferably, $A_1$ is N and $A_2$ is $CR^{42}$, or $A_1$ is $CR^{41}$ and $A_2$ is N,
$B_1$ is $CR^1$ or N;
$B_2$ is CH or N;
$B_3$ is $CR^3$ or N;
$B_4$ is $CR^4$ or N;
$B_5$ is $CR^5$ or N;
$B_6$ is $CR^6$ or N;
$B_7$ is $CR^7$ or N;
$B_8$ is $CR^8$ or N;
wherein $B_1$ and $B_2$ or $B_2$ and $B_3$ or $B_3$ and $B_4$ optionally form together a six membered ring system;
and/or $B_5$ and $B_6$ or $B_6$ and $B_7$ or $B_7$ and $B_8$ optionally form together a six membered ring system;
$R^{41}$, $R^{42}$, $R^1$, $R^3$, $R^4$, $R^5$, $R^6$, $R^7$, and $R^8$ are independently of each other H; E; a group of formula -$(A^1)_o$-$(A^2)_p$-$(A^3)_q$-$(A^4)_r$-$R^{20}$; or a $C_1$-$C_{25}$alkyl group, which is unsubstituted or substituted by at least one group E and/or interrupted by D,
wherein at least one of $R^{41}$, $R^{42}$, $R^1$, $R^3$, $R^4$, $R^5$, $R^6$, $R^7$, and $R^8$ is a group of formula -$(A^1)_o$-$(A^2)_p$-$(A^3)_q$-$(A^4)_r$-$R^{20}$;
o is 0 or 1, p is 0 or 1, q is 0 or 1, r is 0 or 1, preferably o is 0 or 1, p is 0 or 1, q is 0 and r is 0;
$A^1$, $A^2$, $A^3$, and $A^4$ are independently of each other a $C_6$-$C_{24}$ arylene group which is unsubstituted or substituted by G or a $C_1$-$C_{24}$ heteroarylene group which is unsubstituted or substituted by G;
$R^{20}$ is H; E; a $C_6$-$C_{60}$ aryl group which is unsubstituted or substituted by G; a $C_1$-$C_{60}$ heteroaryl group which is unsubstituted or substituted by G; or a $C_1$-$C_{25}$alkyl group which is unsubstituted or substituted by at least one group G and/or interrupted by D;

D is —CO—, —COO—, —S—, —SO—, —SO$_2$—, —O—, —CR$^{63}$=CR$^{64}$—, —NR$^{65}$—, —SiR$^{70}$R$^{71}$—, —POR$^{73}$—, or —C≡C—, preferably —O—, —NR$^{65}$—, or —SiR$^{70}$R$^{71}$—;

E is —OR$^{69}$, —SR$^{69}$, —NR$^{65}$R$^{66}$, —COR$^{68}$, —COOR$^{67}$, —CONR$^{65}$R$^{66}$, —CN, —SiR$^{70}$R$^{71}$R$^{72}$, halogen or —POR$^{74}$R$^{75}$; preferably —NR$^{65}$R$^{66}$, —CN, —SiR$^{70}$R$^{71}$R$^{72}$ or —POR$^{74}$R$^{75}$;

G is E; a C$_1$-C$_{24}$alkyl group; a C$_1$-C$_{24}$alkyl group which is interrupted by O; a C$_6$-C$_{60}$aryl group; a C$_6$-C$_{60}$aryl group which is substituted by F, —CF$_3$, —CF$_2$CF$_3$, —CF$_2$CF$_2$CF$_3$, —CF(CF$_3$)$_2$, —(CF$_2$)$_3$CF$_3$, or —C(CF$_3$)$_3$, a C$_1$-C$_{24}$alkyl, or a C$_1$-C$_{24}$alkyl which is interrupted by O; a C$_2$-C$_{60}$heteroaryl group; or a C$_2$-C$_{60}$heteroaryl group which is substituted by F, —CF$_3$, —CF$_2$CF$_3$, —CF$_2$CF$_2$CF$_3$, —CF(CF$_3$)$_2$, —(CF$_2$)$_3$CF$_3$, —C(CF$_3$)$_3$, a C$_1$-C$_{24}$alkyl or a C$_1$-C$_{24}$alkyl which is interrupted by O;

R$^{63}$ and R$^{64}$ are independently of each other a C$_6$-C$_{18}$aryl; a C$_6$-C$_{18}$aryl which is substituted by a C$_1$-C$_{18}$alkyl or a C$_1$-C$_{18}$alkoxy; a C$_1$-C$_{18}$alkyl; a C$_1$-C$_{18}$alkyl which is interrupted by —O—; or H;

R$^{65}$ and R$^{66}$ are independently of each other a C$_6$-C$_{18}$aryl group; a C$_6$-C$_{18}$aryl which is substituted by a C$_1$-C$_{18}$alkyl or a C$_1$-C$_{18}$alkoxy; a C$_1$-C$_{18}$alkyl group; or a C$_1$-C$_{18}$alkyl group which is interrupted by —O—; or R$^{65}$ and R$^{66}$ together form a five or six membered ring which can be substituted or benzanullated (e.g. carbazole);

R$^{67}$ is a C$_6$-C$_{18}$aryl group; a C$_6$-C$_{18}$aryl group which is substituted by a C$_1$-C$_{18}$alkyl or a C$_1$-C$_{18}$alkoxy; a C$_1$-C$_{18}$alkyl group; or a C$_1$-C$_{18}$alkyl group which is interrupted by —O—;

R$^{68}$ is H; a C$_6$-C$_{18}$aryl group; a C$_6$-C$_{18}$aryl group which is substituted by a C$_1$-C$_{18}$alkyl or a C$_1$-C$_{18}$alkoxy; a C$_1$-C$_{18}$alkyl group; or a C$_1$-C$_{18}$alkyl group which is interrupted by —O—;

R$^{69}$ is a C$_6$-C$_{18}$aryl; a C$_6$-C$_{18}$aryl which is substituted by a C$_1$-C$_{18}$alkyl or a C$_1$-C$_{18}$alkoxy; a C$_1$-C$_{18}$alkyl group; or a C$_1$-C$_{18}$alkyl group which is interrupted by —O—;

R$^{70}$, R$^{71}$ and R$^{72}$ are independently of each other a C$_1$-C$_{18}$alkyl group, a C$_6$-C$_{18}$aryl group, or a C$_6$-C$_{18}$aryl group which is substituted by a C$_1$-C$_{18}$alkyl; and R$^{73}$, R$^{74}$, and R$^{75}$ are independently of each other a C$_1$-C$_{18}$alkyl group, a C$_6$-C$_{18}$aryl group, or a C$_6$-C$_{18}$aryl group which is substituted by a C$_1$-C$_{18}$alkyl;

wherein in the case that A$_1$ is CR$^{41}$ and A$_2$ is N, B$_3$ is CH or N and o, p, q and r in the definition of R$^6$ and R$^7$ are 0.

Advantageous Effects of Invention

The specific substitution of the benzofuro- and benzothienoquinolines according to formula (1) gives rise to materials, especially host, charge transport or charge blocking materials, that are highly suitable in devices that emit blue, green, red or yellow light, preferably blue, green or red light, more preferably blue and red light. Moreover, a balanced charge transport, i.e. hole transport or electron transport, and/or charge/exciton blocking, i.e. electron/exciton blocking or hole/exciton blocking, in devices is achieved resulting in low voltages and high external quantum efficiencies (EQE's) and/or long lifetimes.

Especially, the compounds of formula (1) according to the present invention can be synthesized in fewer steps than similar compounds known in the art.

BRIEF DESCRIPTION OF DRAWINGS

FIG. 1 shows a schematic configuration of one example of the organic EL device of the invention.

DESCRIPTION OF EMBODIMENTS

The specifically substituted compounds of formula (1) according to the present invention are characterized by a higher triplet energy than the compounds disclosed in the related art. Further, the glass transition temperature (TG) of the specifically substituted compounds of the present invention is high, which results in a high stability of a device comprising said compounds.

The compounds of the present invention may be used for electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and electroluminescent devices, such as, for example, organic light-emitting diodes (OLEDs).

Accordingly, a further subject of the present invention is directed to an electronic device, comprising a compound according to the present invention. The electronic device is preferably an electroluminescent device, such as an organic light-emitting diode (OLED).

The compounds of formula (1) can in principal be used in any layer of an EL device, but are preferably used as host, charge transport, i.e. hole transport or electron transport, and/or charge/exciton blocking, i.e. electron/exciton blocking or hole/exciton blocking, material. Particularly, the compounds of formula (1) are used as host material for green, red and yellow, preferably green, and red, more preferably red light emitting phosphorescent or fluorescent emitters, preferably phosphorescent emitters and/or as electron transport material, in combination with phosphorescent or fluorescent emitters, preferably fluorescent emitters.

Hence, a further subject of the present invention is directed to a charge transport, i.e. hole transport or electron transport, layer, preferably an electron transport layer, comprising a compound of formula (1) according to the present invention.

Hence, a further subject of the present invention is directed to a charge/exciton blocking, i.e. electron/exciton blocking or hole/exciton blocking, layer, preferably a hole/exciton blocking layer, comprising a compound of formula (1) according to the present invention.

A further subject of the present invention is directed to an emitting layer, comprising a compound of formula (1) according to the present invention. In said embodiment a compound of formula (1) is preferably used as host material or as co-host material together with one or more, preferably one, further host materials. More preferably, a combination of a compound of formula (1) and a co-host material together with a phosphorescent emitter is used.

A further subject of the present invention is directed to a hole/exciton blocking layer, comprising a compound of formula (1) according to the present invention.

A further subject of the present invention is directed to an electron/exciton blocking layer, comprising a compound of formula (1) according to the present invention.

The terms halogen, alkyl, alkoxy, cycloalkyl, aryl, aryloxy, aralkyl, heteroaryl, arylene, heteroarylene are known in the art and generally have the following meaning, if said groups are not further specified in specific embodiments mentioned below:

Halogen is fluorine, chlorine, bromine and iodine, preferably fluorine.

$C_1$-$C_{25}$alkyl, preferably $C_1$-$C_{24}$alkyl and more preferably $C_1$-$C_{18}$alkyl are typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

The alkyl groups mentioned above can optionally be substituted by E and/or interrupted by D. Preferably, the alkyl groups mentioned above are unsubstituted or can optionally be substituted by E.

$C_1$-$C_{25}$alkoxy groups and preferably $C_1$-$C_{18}$alkoxy groups are straight-chain or branched alkoxy groups, e.g. methoxy, ethoxy, n-propoxy, isopropoxy, n-butoxy, sec.-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

The term "cycloalkyl group" is preferably $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted by G.

$C_6$-$C_{60}$aryl, preferably $C_6$-$C_{30}$aryl, more preferably $C_6$-$C_{24}$aryl and most preferably $C_6$-$C_{18}$aryl, which is unsubstituted or optionally can be substituted by G, is most preferably phenyl, 4-methylphenyl, 4-methoxyphenyl, naphthyl, especially 1-naphthyl, or 2-naphthyl, biphenylyl, triphenylenyl, fluoranthenyl, terphenylyl, pyrenyl, 2- or 9-fluorenyl, phenanthryl, or anthryl, which may be unsubstituted or substituted by G. Phenyl, 1-naphthyl and 2-naphthyl are examples of a $C_6$-$C_{10}$aryl group.

$C_1$-$C_{60}$heteroaryl, preferably $C_1$-$C_{30}$heteroaryl, more preferably $C_2$-$C_{13}$ heteroaryl represents a ring with five, six or seven ring atoms or a condensed ring system, wherein nitrogen, oxygen or sulfur are the possible heteroatoms, and is typically a heterocyclic group with five to 60 atoms, preferably with five to 30 atoms, more preferably with five to 13 atoms having at least six conjugated π-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, 4-imidazo[1,2-a]benzimidazolyl, 5-benzimidazo[1,2-a]benzimidazolyl, benzimidazolo[2,1-b][1,3]benzothiazolyl, carbazolyl, azatriphenylenyl, azadibenzofuryl, azadibenzothiophenyl, azacarbazolyl, quinolonyl, isoquinolinyl, quinoxalinyl, quinazolinyl, phenanthrolinyl, phenanthridinyl, benzo[h]quinolonyl, benz[h]isoquinolinyl, benzo[f]isoquinolinyl, benzo[f]quinolinyl, benzo[h]quinazolinyl, benzo[f]quinazolinyl, dibenzo[f,h]quinolonyl, dibenzo[f,h]isoquinolonyl, dibenzo[f,h]quinoxalinyl, dibenzo[f,h]quinazolinyl or phenoxazinyl, which can be unsubstituted or substituted by G. Benzimidazo[1,2-a]benzimidazo-5-yl, benzimidazo[1,2-a]benzimidazo-2-yl, carbazolyl and dibenzofuranyl are examples of a $C_2$-$C_{14}$heteroaryl group.

The group $C_1$-$C_{60}$heteroaryl, preferably $C_1$-$C_{30}$heteroaryl, more preferably $C_1$-$C_{24}$heteroaryl, most preferably $C_2$-$C_{13}$ heteroaryl, even more preferably $C_2$-$C_{60}$heteroaryl, $C_2$-$C_{30}$heteroaryl, $C_2$-$C_{24}$heteroaryl, $C_2$-$C_{13}$heteroaryl may be unsubstituted or substituted by G.

A $C_2$-$C_{13}$heteroaryl group is for example, benzimidazo[1,2-a]benzimidazo-5-yl

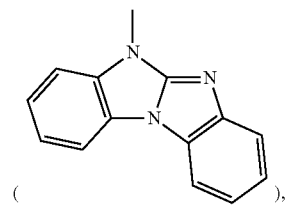

( ), benzimidazo[1,2-a]benzimidazo-2-yl

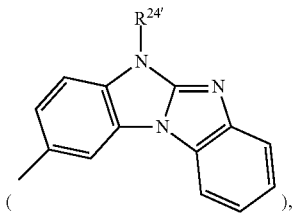

( ), benzimidazolo[2,1-b][1,3]benzothiazolyl, benzimidazolo[2,1-b][1,3]benzoxazole, carbazolyl, dibenzofuranyl, or dibenzotihophenyl, which can be unsubstituted or substituted by G, especially by $C_6$-$C_{10}$aryl, or $C_6$-$C_{10}$aryl, which is substituted by $C_1$-$C_4$alkyl; or $C_2$-$C_{13}$heteroaryl. $C_1$-$C_{60}$heteroaryl, preferably $C_1$-$C_3$heteroaryl, more preferably $C_1$-$C_{24}$heteroaryl, most preferably-$C_2$-$C_{13}$ heteroaryl, even more preferably $C_2$-$C_{60}$heteroaryl, $C_2$-$C_{30}$heteroaryl, $C_2$-$C_{24}$heteroaryl, $C_2$-$C_{13}$heteroaryl means that the heteroaryl residue comprises at least one, preferably at least 2 carbon atoms and at most 60 carbon atoms in the base skeleton (without substituents). The further atoms in the heteroaryl base skeleton are heteroatoms (N, O and/or S).

$R^{24'}$ is in each case independently $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, phenanthronyl, triphenylenyl, fluoranthenyl or biphenylyl.

$C_1$-$C_{24}$heterocyclic group, preferably $C_1$-$C_{13}$heterocyclic group, more preferably $C_2$-$C_{13}$ heterocyclic group represents a ring with five, six or seven ring atoms or a condensed ring system, wherein nitrogen, oxygen or sulfur are the possible heteroatoms, and is typically a heterocyclic group with five to 24 atoms, preferably with five to 13 atoms. The heterocyclic group may be a $C_1$-$C_{24}$heteroaryl group as defined above or a $C_1$-$C_{24}$heterocycloalkyl group which may be unsubstituted or substituted by G. Typical $C_1$-$C_{24}$heterocycloalkyl groups are oxetan, tetrahydrofuran, tetrahydropyran, oxepane, dioxane, azetidine, pyrrolidine, piperidine, hexahydroazepine, hexahydrodiazepin, tetrahydrothiophene, thietan, tetrahydrothiopyran, thiepan, morpholine as well as bridged heterocycloalkyl systems such as oxabicyclo[4.4.0]decane and azabicyclo[2,2,1]undecane.

$C_6$-$C_{24}$arylene groups, preferably $C_6$-$C_{10}$arylene groups, which optionally can be substituted by G, preferably $C_6$-$C_{10}$arylene groups, which optionally can be substituted by G, are more preferably phenylene, 4-methylphenylene, 4-methoxyphenylene, naphthylene, especially 1-naphthylene, or 2-naphthylene, biphenylylene, triphenylenylene, fluoranthenylene, terphenylylene, pyrenylene, 2- or 9-fluorenylene, phenanthrylene, or anthrylene, which may be unsubstituted or substituted by G. Preferred $C_6$-$C_{24}$arylene groups, preferably $C_6$-$C_{10}$arylene groups are 1,3-phenylene, 3,3'-biphenylylene, 3,3'-m-terphenylene, 2- or 9-fluorenylene, phenanthrylene, which may be unsubstituted or substituted by G.

$C_1$-$C_{30}$heteroarylene groups, preferably $C_2$-$C_{14}$heteroarylene groups, which are unsubstituted or optionally can be substituted by G, represent a ring with five to seven ring atoms or a condensed ring system, wherein nitrogen, oxygen or sulfur are the possible heteroatoms, and is typically a heterocyclic group with five to 30 atoms having at least six conjugated-electrons such as thienylene, benzothiophenylene, dibenzothiophenylene, thianthrenylene, furylene, furfurylene, 2H-pyranylene, benzofuranylene, isobenzofuranylene, dibenzofuranylene, phenoxythienylene, pyrrolylene, imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, quinolylene, isoquinolylene, phthalazinylene, naphthyridinylene, quinoxalinylene, quinazolinylene, cinnolinylene, pteridinylene, carbolinylene, benzotriazolylene, benzoxazolylene, phenanthridinylene, acridinylene, pyrimidinylene, phenanthrolinylene, phenazinylene, isothiazolylene, phenothiazinylene, isoxazolylene, furazanylene, carbazolylene, benzimidazo[1,2-a]benzimidazo-2,5-ylene, or phenoxazinylene, which can be unsubstituted or substituted by G. Preferred $C_2$-$C_{30}$heteroarylen groups are pyridylene, triazinylene, pyrimidinylene, carbazolylene, dibenzofuranylene, azatriphenylenylene, azadibenzofurylene, azadibenzothiophenylene, azacarbazolylene, quinolonylene, isoquinolinylene, quinoxalinylene, quinazolinylene, phenanthrolinylene, phenanthridinylene, benzo[h]quinolonylene, benz[h]isoquinolinylene, benzo[f]isoquinolinylene, benzo[f]quinolinylene, benzo[h]quinazolinylene, benzo[f]quinazolinylene, dibenzo[f,h]quinolonylene, dibenzo[f,h]isoquinolonylene, dibenzo[f,h]quinoxalinylene, dibenzo[f,h]quinazolinylene and benzimidazo[1,2-a]benzimidazo-2,5-ylene

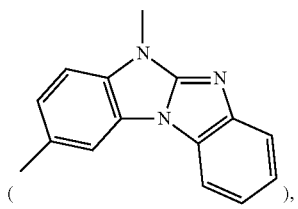 [SMILES: Cc1ccc2c(c1)n1c3ccccc3nc1n2C]

which can be unsubstituted or substituted by G, preferably substituted by $C_6$-$C_{10}$aryl, $C_6$-$C_{10}$aryl which is substituted by $C_1$-$C_4$alkyl; or $C_2$-$C_{13}$heteroaryl.

If a substituent occurs more than one time in a group, it can be different in each occurrence.

Halo-$C_1$-$C_8$alkyl is an alkyl group (as defined above) where at least one of the hydrogen atoms is replaced by a halogen atom. Examples are —$CF_3$, —$CF_2CF_3$, —$CF_2CF_2CF_3$, —$CF(CF_3)_2$, —$(CF_2)_3CF_3$, and —$C(CF_3)_3$.

The wording "substituted by G" means that one, or more, especially one, two or three substituents G might be present. Preferred substituents G are mentioned below.

The wording "substituted by E" means that one, or more, especially one, two or three substituents E might be present. Preferred substituents E are mentioned below.

As described above, the aforementioned alkyl groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$)$C_4H_9$), $CH_2$—CH(O$R^{3''}$)—$CH_2$—O—$R^{y}$, where $R^y$ is $C_1$-$C_{18}$alkyl, $C_5$-$C_{12}$cycloalkyl, phenyl, $C_7$-$C_{15}$phenylalkyl, and $R^{3''}$ embraces the same definitions as $R^y$ or is H.

An alkyl group substituted by E is, for example, an alkyl group where at least one of the hydrogen atoms is replaced by F. Examples are —$CF_3$, —$CF_2CF_3$, —$CF_2CF_2CF_3$, —CF$(CF_3)_2$, —$(CF_2)_3CF_3$, and —$C(CF_3)_3$.

D is —CO—, —COO—, —S—, —SO—, —$SO_2$—, —O—, —$NR^{65}$—, —$SiR^{70}R^{71}$—, —$POR^{72}$—, —$CR^{63}$═$CR^{64}$— or —C≡C—. Suitable residues $R^{63}$, $R^{64}$, $R^{65}$, $R^{70}$ $R^{71}$ and $R^{72}$ are mentioned above. D is preferably —CO—, —COO—, —S—, —SO—, —$SO_2$—, —O—, —$NR^{65}$—, wherein $R^{65}$ is preferably $C_1$-$C_{18}$alkyl, such as methyl, ethyl, n-propyl, iso-propyl, n-butyl, isobutyl, or sec-butyl, or $C_6$-$C_{14}$aryl, such as phenyl, tolyl, naphthyl, triphenylenyl or biphenylyl, or $C_2$-$C_{30}$heteroaryl, such as, for example, benzimidazo[1,2-a]benzimidazo-2-yl

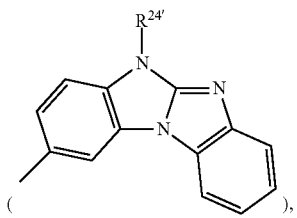

carbazolyl, dibenzofuranyl, which can be unsubstituted or substituted especially by $C_6$-$C_{10}$aryl, or $C_6$-$C_{10}$aryl, which is substituted by $C_1$-$C_4$alkyl; or $C_2$-$C_{13}$heteroaryl.

E is —$OR^{69}$, —$SR^{69}$, —$NR^{65}R^{66}$, —$COR^{68}$, —$COOR^{67}$, —$CONR^{65}R^{66}$, —CN, —$SiR^{70}R^{71}R^{72}$, halogen or —$POR^{74}R^{75}$; preferably —$NR^{65}R^{66}$, —CN, —$SiR^{70}R^{71}R^{72}$ or —$POR^{74}R^{75}$; wherein $R^{65}$, $R^{66}$, $R^{67}$, $R^{68}$, $R^{69}$, $R^{70}$, $R^{71}$, $R^{72}$, $R^{73}$, $R^{74}$ and $R^{75}$ are preferably independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, triphenylenyl or biphenylyl.

G is E, or a $C_1$-$C_{24}$alkyl group, a $C_6$-$C_{30}$aryl group, a $C_6$-$C_{30}$aryl group, which is substituted by F, $C_1$-$C_{24}$alkyl, or $C_1$-$C_{24}$alkyl which is interrupted by O; a $C_2$-$C_{60}$heteroaryl group, or a $C_2$-$C_{60}$heteroaryl group, which is substituted by F, $C_1$-$C_{18}$alkyl, or $C_1$-$C_{18}$alkyl which is interrupted by O. G is preferably —$OR^{69}$, —$SR^{69}$, —$NR^{65}R^{66}$; a $C_1$-$C_{18}$alkyl group, a $C_6$-$C_{18}$aryl group, a $C_6$-$C_{18}$aryl group, which is substituted by F, or $C_1$-$C_{18}$alkyl; a $C_2$-$C_{24}$heteroaryl group, or a $C_2$-$C_{24}$heteroaryl group, which is substituted by F, or $C_1$-$C_{18}$alkyl; wherein $R^{65}$, $R^{66}$ and $R^{69}$ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, or biphenylyl. More preferably, G is a $C_6$-$C_{18}$aryl group like phenyl, tolyl, triphenylenyl or biphenylyl, phenanthryl, anthranyl or a $C_6$-$C_{24}$heteroaryl group like dibenzothiophenylyl, dibenzofuranyl, pyridyl, triazinyl, pyrimidinyl, azatriphenylenyl, azadibenzofuryl, azadibenzothiophenyl, azacarbazolyl, quinolonyl, isoquinolinyl, quinoxalinyl, quinazolinyl, phenanthrolinyl, phenanthridinyl, benzo[h]quinolonyl, benz[h]isoquinolinyl, benzo[f]isoquinolinyl, benzo[f]quinolinyl, benzo[h]quinazolinyl, benzo[f]quinazolinyl, dibenzo[f,h]quinolonyl, dibenzo[f,h]isoquinolonyl, dibenzo[f,h]quinoxalinyl or dibenzo[f,h]quinazolinyl.

$A_1$, $A_2$

In the benzofuro- and benzothienoquinolines according to the present invention, at least one of $A_1$ and $A_2$ is N; preferably, $A_1$ is N and $A_2$ is $CR^{42}$, or $A_1$ is $CR^{41}$ and $A_2$ is N.

$B_1$, $B_2$, $B_3$, $B_4$, $B_5$, $B_6$, $B_7$, $B_8$

Further, in the benzofuro- and benzothienoquinolines according to formula (1) of the present invention, $B_1$ is $CR^1$ or N, preferably $CR^1$; $B_2$ is CH or N, preferably CH; $B_3$ is $CR^3$ or N, preferably $CR^3$; $B_4$ is $CR^4$ or N, preferably $CR^4$; $B_5$ is $CR^5$ or N, preferably $CR^5$; $B_6$ is $CR^6$ or N, preferably $CR^6$; $B_7$ is $CR^7$ or N, preferably $CR^7$; and $B_8$ is $CR^8$ or N, preferably $CR^8$;

wherein $B_1$ and $B_2$ or $B_2$ and $B_3$ or $B_3$ and $B_4$ optionally form together a six membered ring system;
and/or $B_5$ and $B_6$ or $B_6$ and $B_7$ or $B_7$ and $B_8$ optionally form together a six membered ring system;
the groups $B_1$, $B_2$, $B_3$, $B_4$, $B_5$, $B_6$, $B_7$, and $B_8$ which are directly connected to each other are usually not at the same time N.

The six membered ring system is preferably a ring structure of the following formula:

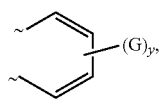

wherein G is defined above, and y is 0, 1, 2, 3 or 4, preferably 0, 1 or 2, more preferably 0 or 1, most preferably 0; and ~ are bonding sites to the atoms to which the two adjacent groups of the groups $R^1$ to $R^8$ are bonded. Preferably, the two adjacent groups of the groups $R^1$ to $R^8$ may form together with the atoms to which they are bonded an aromatic 6 membered ring structure, which can optionally be substituted by G.

Preferably, 0 or 1, more preferably 0, of the groups $B_1$ and $B_2$ or $B_2$ and $B_3$ or $B_3$ and $B_4$ or $B_5$ and $B_6$ or $B_6$ and $B_7$ or $B_7$ and $B_8$ optionally form together a six membered ring system, preferably a six membered ring system as defined above.

In a preferred embodiment of the present invention, 0, 1 or 2 of $B_1$ to $B_8$, preferably $B^1$ and/or $B^5$, more preferably 0 or 1 of $B_1$ to $B_8$, preferably $B^1$ or $B^5$, most preferably 0 of $B_1$ to $B_8$ are N.

Most preferably, $A_2$ is $CR^{42}$, $B_5$ is $CR^5$ or $B_6$ is $CR^6$ or $B_7$ is $CR^7$ or $B_8$ is $CR^8$, preferably $B_6$ is $CR^6$ or $B_7$ is $CR^7$ and the other of $B_1$, $B_2$, $B_3$, $B_4$, $B_5$, $B_6$, $B_7$, and $B_8$ are CH, and $A_1$ is N; or $A_2$ is N, $B_6$ is $CR^6$ or $B_7$ is $CR^7$ and the other of $B_1$, $B_2$, $B_3$, $B_4$, $B_5$, $B_6$, $B_7$, and $B_8$ are CH, and $A_1$ is $CR^{41}$. Especially most preferably, $A_2$ is $CR^{42}$ and $B_1$, $B_2$, $B_3$, $B_4$, $B_5$, $B_6$, $B_7$, and $B_8$ are CH, and $A_1$ is N; $A_2$ is N, $B_1$, $B_2$, $B_3$, $B_4$, $B_5$, $B_6$, $B_7$, and $B_8$ are CH, and $A_1$ is $CR^{41}$; or $A_2$ is CH, $B_5$ is $CR^5$ or $B_6$ is $CR^6$ or $B_7$ is $CR^7$ or $B_8$ is $CR^8$, preferably $B_6$ is $CR^6$ and the other of $B_1$, $B_2$, $B_3$, $B_4$, $B_5$, $B_6$, $B_7$, and $B_8$ are CH, and $A_1$ is N.

$R^{41}$, $R^{42}$, $R^1$, $R^3$, $R^4$, $R^5$, $R^6$, $R^7$, and $R^8$ are independently of each other H; E; a group of formula-$(A^1)_o$-$(A^2)_p$-$(A^3)_q$-$(A^4)_r$-$R^{20}$; or a $C_1$-$C_{25}$alkyl group which is unsubstituted or substituted by at least one group E and/or interrupted by D, wherein at least one of $R^{41}$, $R^{42}$, $R^1$, $R^3$, $R^4$, $R^5$, $R^6$, $R^7$, and $R^8$ is a group of formula -$(A^1)_o$-$(A^2)_p$-$(A^3)_q$-$(A^4)_r$-$R^{20}$.

The groups $A^1$, $A^2$, $A^3$, and $A^4$, the indices o, p, q and r and the residue $R^{20}$ are defined below.

Preferably, $R^{41}$, $R^{42}$, $R^1$, $R^3$, $R^4$, $R^5$, $R^6$, $R^7$, and $R^8$ are independently of each other H; —$NR^{65}R^{66}$; —CN; —$SiR^{70}R^{71}R^{72}$; —$POR^{74}R^{75}$; wherein $R^{65}$, $R^{66}$, $R^{70}$, $R^{71}$, $R^{72}$, $R^{74}$ and $R^{75}$ are preferably independently of each other a $C_1$-$C_{18}$alkyl, such as methyl, ethyl, n-propyl, iso-propyl, n-butyl, isobutyl, sec-butyl, hexyl, octyl, or 2-ethyl-hexyl, or a $C_6$-$C_{14}$aryl, such as phenyl, tolyl, naphthyl, triphenylenyl or biphenylyl; $C_1$-$C_4$alkyl, preferably methyl, ethyl, n-propyl, isopropyl, n-butyl, sec.-butyl, isobutyl, tert.-butyl; or a group of formula -$(A^1)_o$-$(A^2)_p$-$(A^3)_q$-$(A^4)_r$-$R^{20}$.

More preferably, $R^{41}$, $R^{42}$, $R^1$, $R^3$, $R^4$, $R^5$, $R^6$, $R^7$, and $R^8$ are independently of each other H, CN, methyl, tert-butyl or a group of formula -$(A^1)_o$-$(A^2)_p$-$(A^3)_q$-$(A^4)_r$-$R^{20}$.

Most preferably, $R^{41}$, $R^{42}$, $R^1$, $R^3$, $R^4$, $R^5$, $R^6$, $R^7$, and $R^8$ are independently of each other H or a group of formula -$(A^1)_o$-$(A^2)_p$-$(A^3)_q$-$(A^4)_r$-$R^{20}$.

Preferably, in the compounds of formula (1) according to the present invention, one, two, three or four, preferably one or two, more preferably one of $R^{41}$, $R^{42}$, $R^1$, $R^3$, $R^4$, $R^5$, $R^6$, $R^7$, and $R^8$ are independently of each other E; a group of formula -$(A^1)_o$-$(A^2)_p$-$(A^3)_q$-$(A^4)_r$-$R^{20}$; or a $C_1$-$C_{25}$alkyl group which is unsubstituted or substituted by at least one group E and/or interrupted by D; preferably a group of formula -$(A^1)_o$-$(A^2)_p$-$(A^3)_q$-$(A^4)_r$-$R^{20}$, and the other of $R^{41}$, $R^{42}$, $R^1$, $R^3$, $R^4$, $R^5$, $R^6$, $R^7$, and $R^8$ are H;

more preferably one, two, three or four, preferably one or two, more preferably one of $R^{41}$, $R^{42}$, $R^1$, $R^3$, $R^4$, $R^5$, $R^6$, $R^7$, and $R^8$ are independently of each other H; —$NR^{65}R^{66}$; —CN; —$SiR^{70}R^{71}R^{72}$; —$POR^{74}R^{75}$; wherein $R^{65}$, $R^{66}$, $R^{70}$, $R^{71}$, $R^{72}$, $R^{74}$ and $R^{75}$ are preferably independently of each other a $C_1$-$C_{18}$alkyl, such as methyl, ethyl, n-propyl, iso-propyl, n-butyl, isobutyl, sec-butyl, hexyl, octyl, or 2-ethyl-hexyl, or a $C_6$-$C_{14}$aryl, such as phenyl, tolyl, naphthyl, triphenylenyl or biphenylyl; a $C_1$-$C_4$alkyl, preferably methyl, ethyl, n-propyl, isopropyl, n-butyl, sec.-butyl, isobutyl, tert.-butyl; or a group of formula -$(A^1)_o$-$(A^2)_p$-$(A^3)_q$-$(A^4)_r$-$R^{20}$.

Most preferably, one of $R^{41}$, $R^{42}$, $R^1$, $R^3$, $R^4$, $R^5$, $R^6$, $R^7$, and $R^8$ is a group of formula -$(A^1)_o$-$(A^2)_p$-$(A^3)_q$-$(A^4)_r$-$R^{20}$ and the other of $R^{41}$, $R^{42}$, $R^1$, $R^3$, $R^4$, $R^5$, $R^6$, $R^7$, and $R^8$ are H, CN, methyl, tert-butyl.

Further most preferably, one of $R^{41}$, $R^{42}$, $R^1$, $R^3$, $R^4$, $R^5$, $R^6$, $R^7$, and $R^8$ is a group of formula -$(A^1)_o$-$(A^2)_p$-$(A^3)_q$-$(A^4)_r$-$R^{20}$ and the other of $R^{41}$, $R^{42}$, $R^1$, $R^3$, $R^4$, $R^5$, $R^6$, $R^7$, and $R^8$ are H.

Still further most preferably, one of $R^{41}$, $R^{42}$, $R^5$, $R^6$, $R^7$, and $R^8$ is a group of formula -$(A^1)_o$-$(A^2)_p$-$(A^3)_q$-$(A^4)_r$-$R^{20}$ and the other of $R^{41}$, $R^{42}$, $R^1$, $R^3$, $R^4$, $R^5$, $R^6$, $R^7$, and $R^8$ are H.

Even further most preferably, one of $R^{41}$, $R^{42}$, $R^6$ and $R^7$ is a group of formula -$(A^1)_o$-$(A^2)_p$-$(A^3)_q$-$(A^4)_r$-$R^{20}$ and the other of $R^{41}$, $R^{42}$, $R^1$, $R^3$, $R^4$, $R^5$, $R^6$, $R^7$, and $R^8$ are H.

Especially most preferably, one of $R^{41}$ and $R^{42}$ is a group of formula -$(A^1)_o$-$(A^2)_p$-$(A^3)_q$-$(A^4)_r$-$R^{20}$ and the other of $R^{41}$ and $R^{42}$, $R^1$, $R^3$, $R^4$, $R^5$, $R^6$, $R^7$, and $R^8$ are H.

$A^1$, $A^2$, $A^3$, $A^4$ $A^1$, $A^2$, $A^3$, $A^4$ are independently of each other a $C_6$-$C_{24}$ arylene group which is unsubstituted or substituted by G or a $C_1$-$C_{24}$ heteroarylene group which is unsubstituted or substituted by G.

$A^1$, $A^2$, $A^3$, $A^4$ are preferably independently of each other a $C_6$-$C_{24}$arylene groups, which optionally can be substituted by G, selected from the group consisting of phenylene, naphthylene, especially 1-naphthylene, or 2-naphthylene, biphenylene, triphenylene, terphenylene, pyrenylene, 2- or 9-fluorenylene, phenanthrylene, or anthrylene, which may be unsubstituted or substituted by G; or a $C_5$-$C_{24}$heteroarylene groups, which optionally can be substituted by G, characterized by a ring with five to seven ring atoms or a condensed ring system, wherein nitrogen, oxygen or sulfur are the possible heteroatoms, and having at least six conjugated-electrons, preferably selected from benzothiophenylene, thianthrenylene, furylene, furfurylene, 2H-pyranylene, benzofuranylene, isobenzofuranylene, dibenzofuranylene

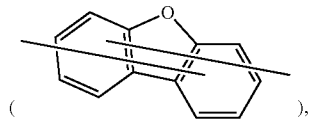

( ), dibenzothiophenylene

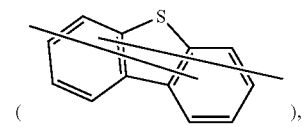

( ), carbazolylene

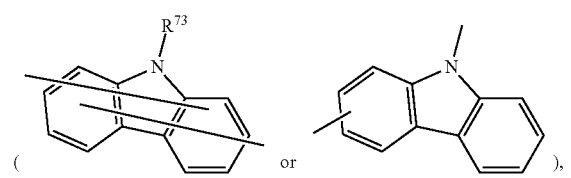

( or ), imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, quinolylene, isoquinolylene, phthalazinylene, naphthyridinylene, quinoxalinylene, quinazolinylene, cinnolinylene, pteridinylene, carbolinylene, benzotriazolylene, benzoxazolylene, phenanthridinylene, pyrimidinylene, benzimidazo[1,2-a]benzimidazo-2,5-ylene, which can be unsubstituted or substituted by G; $R^{73}$ is a $C_6$-$C_{24}$aryl group or a $C_2$-$C_{30}$heteroaryl group, which can optionally be substituted by G; wherein the lines are bonding sites.

More preferably, $A^1$, $A^2$, $A^3$, $A^4$ are independently of each other

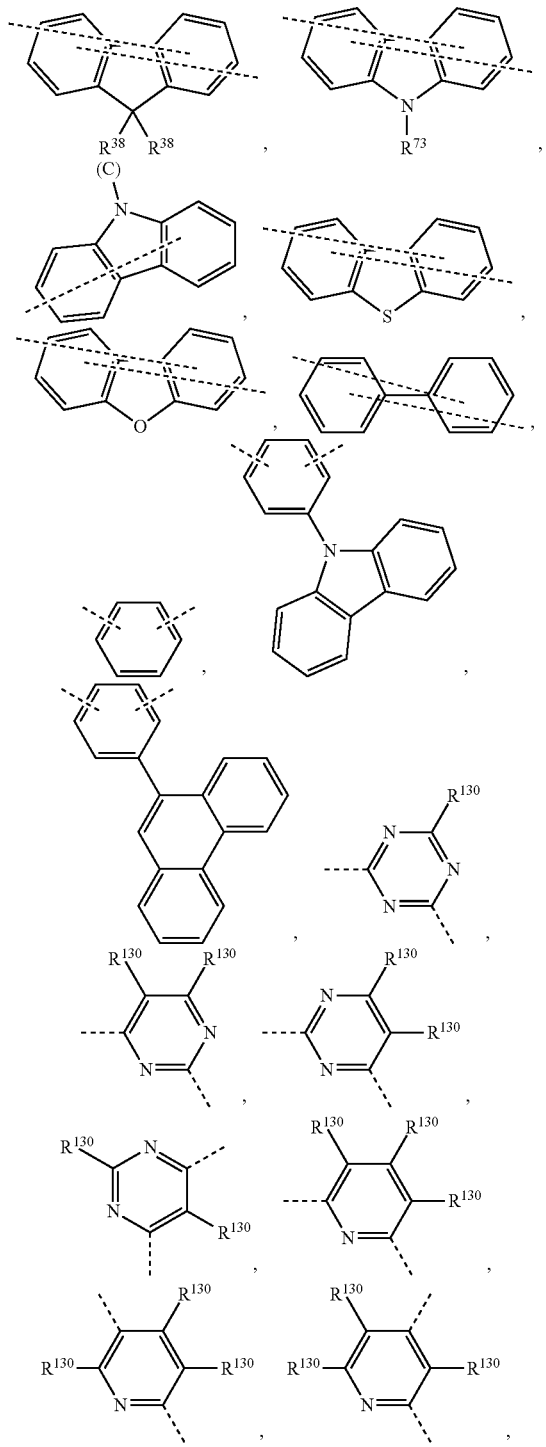

-continued

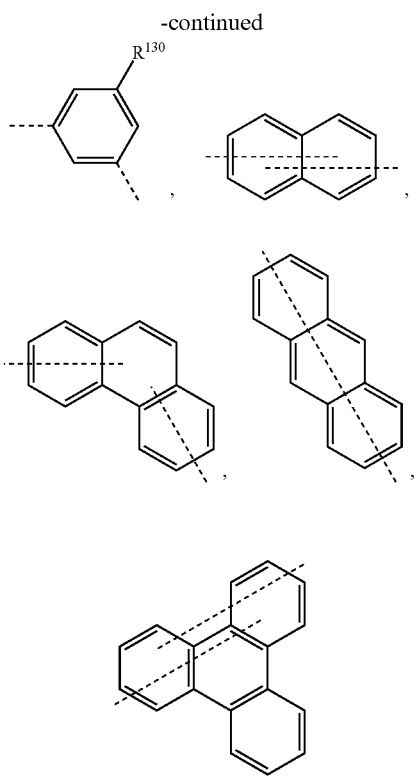

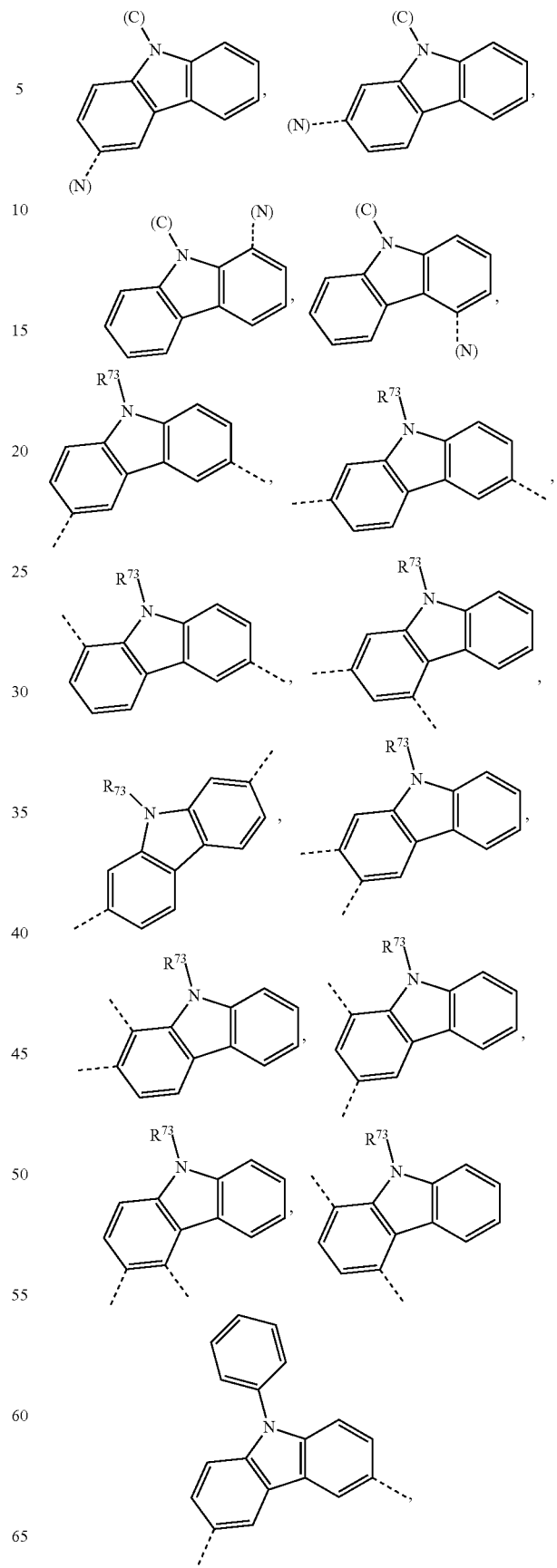

which can be unsubstituted or substituted by G, preferably unsubstituted or substituted by 1, 2, 3 or 4 groups G, more preferably unsubstituted or substituted by 1 or 2 groups G; whereby G is most preferably —NR$^{65}$R$^{66}$, —CN, —SiR$^{70}$R$^{71}$R$^{72}$, a $C_1$-$C_{24}$alkyl group, an unsubstituted $C_6$-$C_{30}$aryl group or a $C_2$-$C_{30}$heteroaryl group;

R$^{73}$ is a $C_6$-$C_{18}$aryl group; a $C_6$-$C_{18}$aryl which is substituted by a $C_1$-$C_{18}$alkyl or a $C_1$-$C_{18}$alkoxy; a $C_1$-$C_{18}$alkyl group; or a $C_1$-$C_{18}$alkyl group which is interrupted by —O—; preferably a $C_1$-$C_{18}$alkyl, such as methyl, ethyl, n-propyl, iso-propyl, n-butyl, isobutyl, sec-butyl, hexyl, octyl, or 2-ethylhexyl, or a $C_6$-$C_{14}$aryl, such as phenyl, tolyl, naphthyl, or biphenylyl;

R$^{38}$ is a $C_1$-$C_{25}$alkyl group which can optionally be substituted by E and or interrupted by D; a $C_6$-$C_{24}$aryl group which can optionally be substituted by G; or a $C_1$-$C_{24}$heteroaryl group which can optionally be substituted by G; and/or two adjacent groups of the groups may form together with the atom to which they are bonded a ring structure which can optionally be substituted by G;

R$^{130}$ is independently in each occurrence H, a $C_6$-$C_{24}$arylene group which can optionally be substituted by G, or a $C_1$-$C_{30}$heteroarylene group which can optionally be substituted by G; wherein G is as defined in above; wherein the dotted lines are bonding sites;

wherein (C)— has the meaning that the bonding site of the group A$^1$, A$^2$, A$^3$, A$^4$ is linked to a C-atom, and (N)— has the meaning that the bonding site of the group A$^3$, A$^4$, A$^5$ and A$^6$ is linked to a N-atom, and (C,N) has the meaning that the bonding site of the group A$^1$, A$^2$, A$^3$, A$^4$ is linked to a C or N-atom.

A$^1$, A$^2$, A$^3$, A$^4$ are more preferably in each occurrence independently of each other a group of the formula:

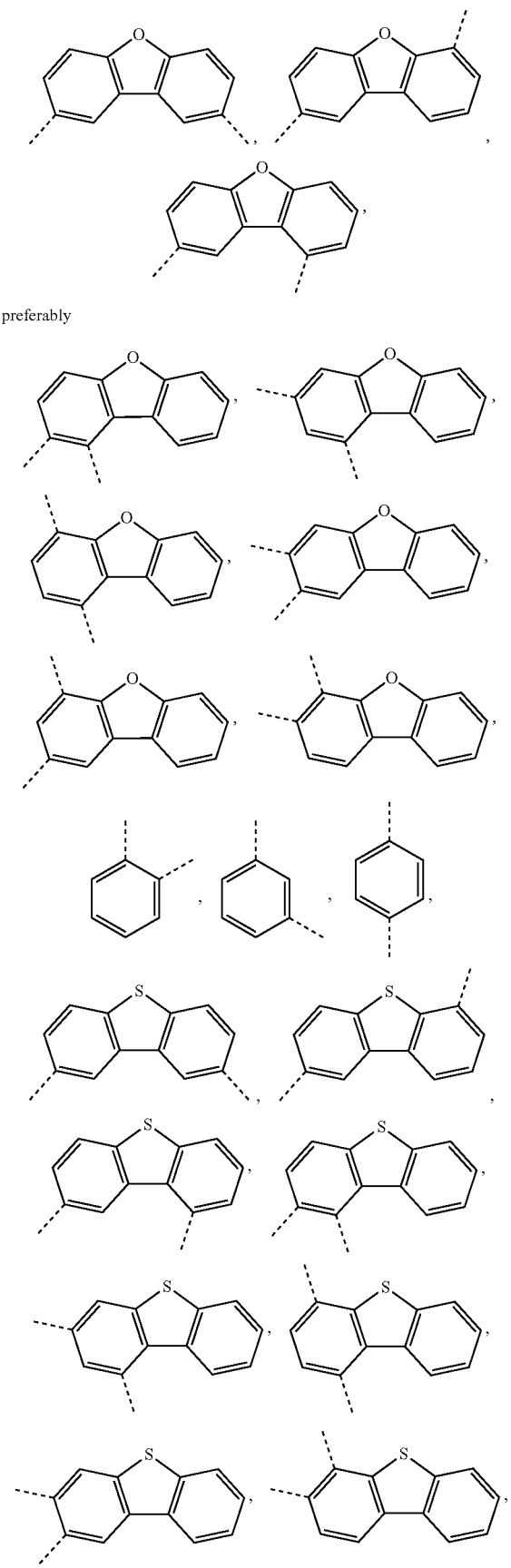
preferably
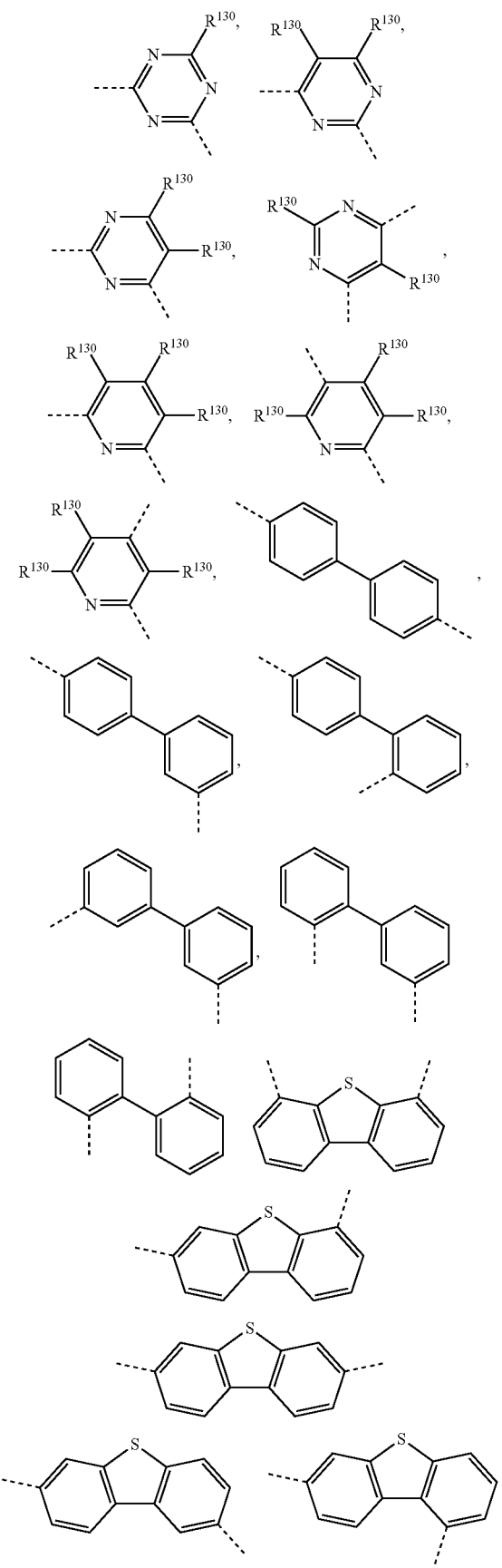

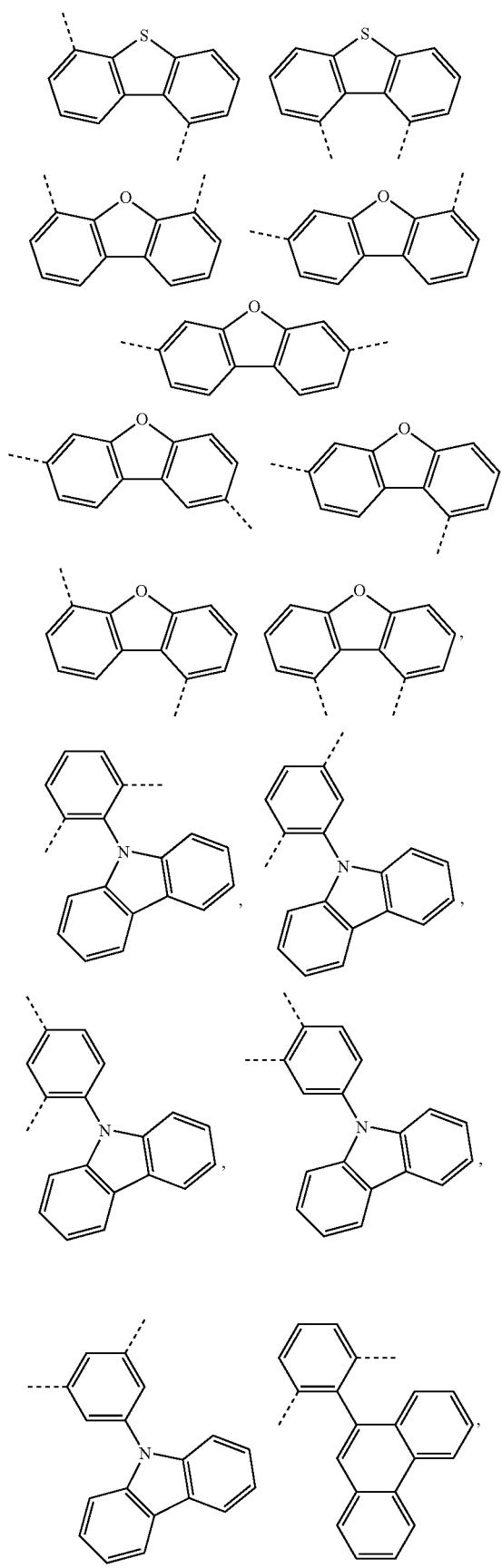

-continued

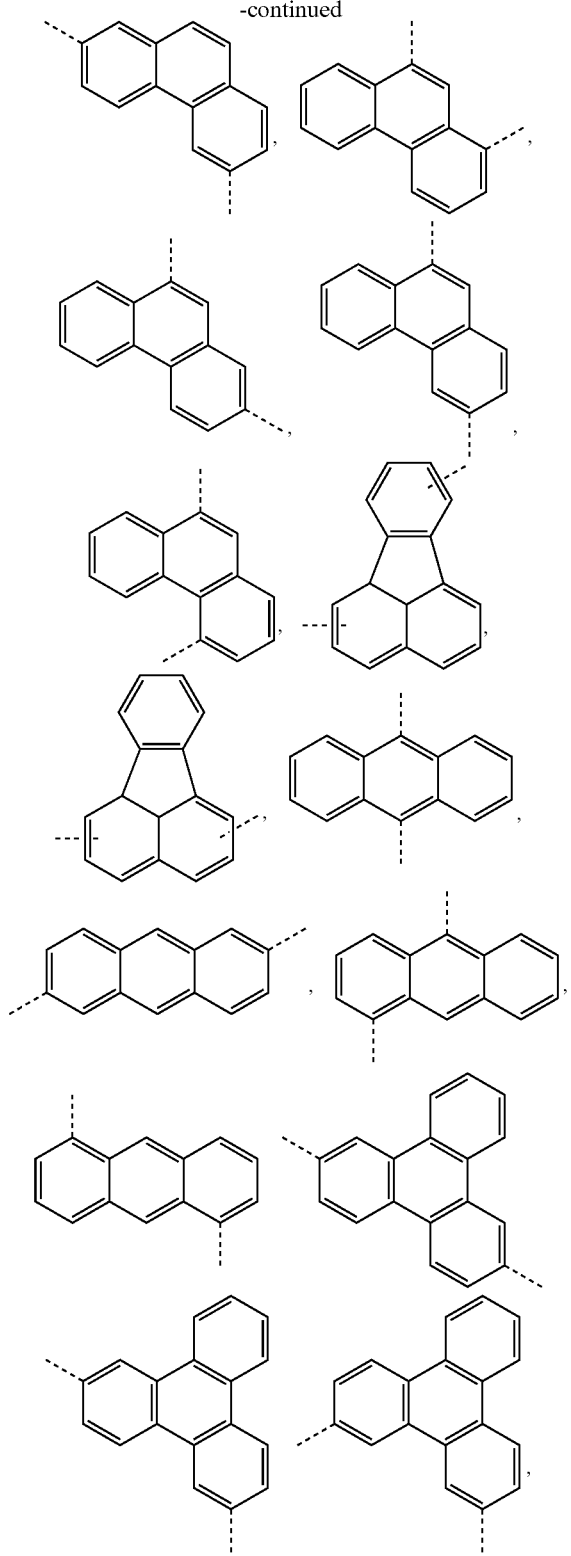

which can be unsubstituted or substituted by G, preferably unsubstituted or substituted by 1, 2, 3 or 4 groups G, more preferably unsubstituted or substituted by 1 or 2 groups G, most preferably unsubstituted; whereby G is defined above and is most preferably —$NR^{65}R^{66}$, —CN, —$Si(R^{70})_3$, a $C_1$-$C_{24}$alkyl group, an unsubstituted $C_6$-$C_{30}$aryl group or a $C_2$-$C_{30}$heteroaryl group; $R^{73}$ is a $C_6$-$C_{18}$aryl group; a $C_6$-$C_{18}$aryl which is substituted by a $C_1$-$C_{18}$alkyl or a $C_1$-$C_{18}$alkoxy; a $C_1$-$C_{18}$alkyl group; or a $C_1$-$C_{18}$alkyl group which is interrupted by —O—; preferably a $C_1$-$C_{18}$alkyl, such as methyl, ethyl, n-propyl, iso-propyl, n-butyl, isobutyl, sec-butyl, hexyl, octyl, or 2-ethyl-hexyl, or a $C_6$-$C_{14}$aryl, such as phenyl, tolyl, naphthyl, or biphenylyl; $R^{130}$ is independently in each occurrence H; a $C_6$-$C_{24}$arylene group which can optionally be substituted by G, or a $C_1$-$C_{30}$heteroarylene group which can optionally be substituted by G; wherein G is as defined in above;

wherein (C)— has the meaning that the bonding site of the group $A^1$, $A^2$, $A^3$, $A^4$ is linked to a C-atom, and (N)— has the meaning that the bonding site of the group $A^1$, $A^2$, $A^3$, $A^4$ is linked to a N-atom, and (C,N) has the meaning that the bonding site of the group $A^1$, $A^2$, $A^3$, $A^4$ is linked to a C or N-atom; and the dotted lines are bonding sites.

$A^1$, $A^2$, $A^3$, $A^4$ are most preferably in each occurrence independently of each other a group of the formula:

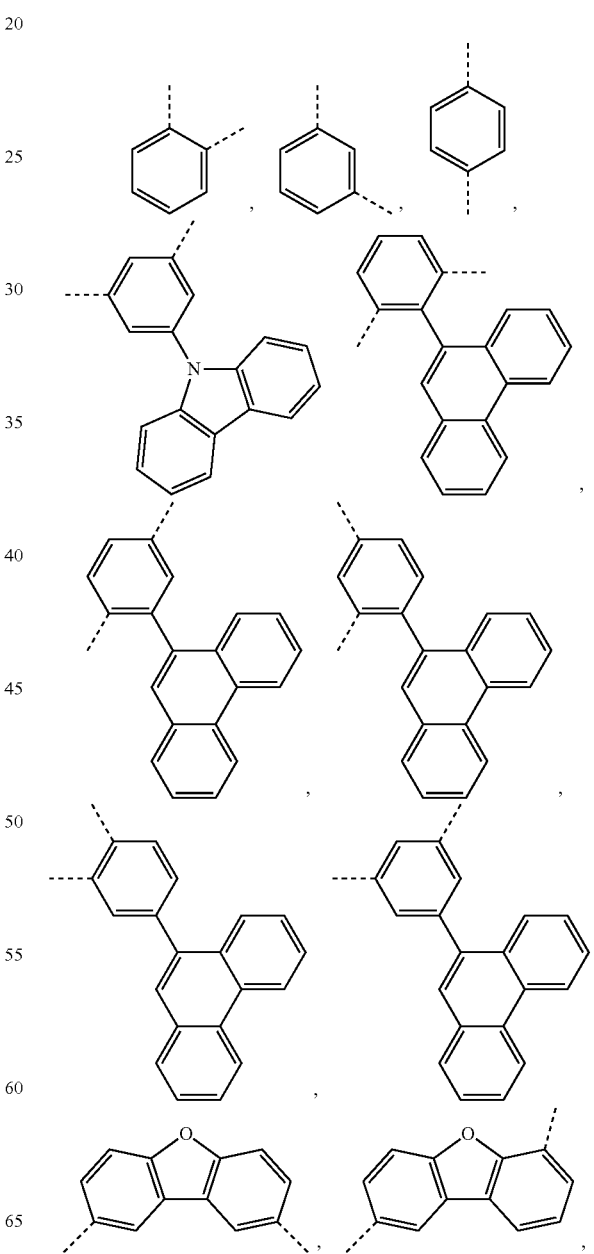

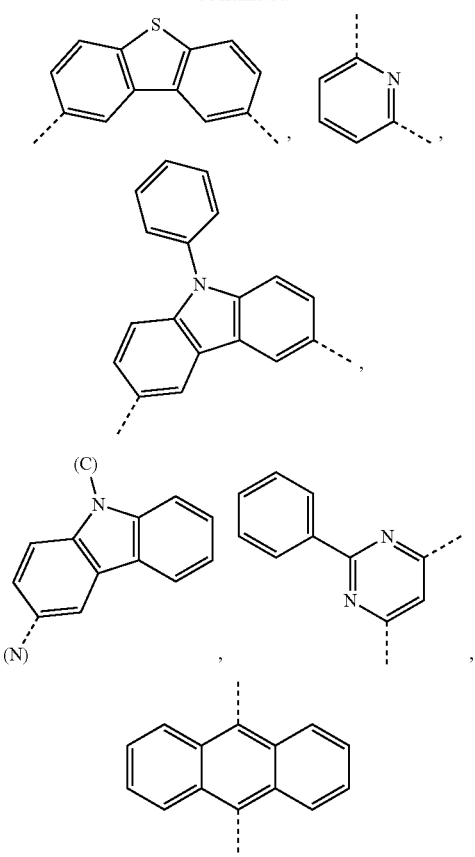

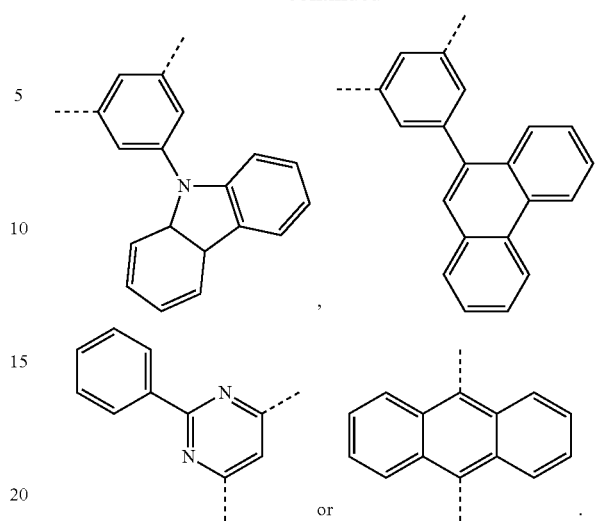

which can be unsubstituted or substituted by G, preferably unsubstituted or substituted by 1, 2, 3 or 4 groups G, more preferably unsubstituted or substituted by 1 or 2 groups G, most preferably unsubstituted; whereby G is defined above and is most preferably $NR^{65}R^{66}$, —CN, a $C_1$-$C_{24}$alkyl group, an unsubstituted $C_6$-$C_{30}$aryl group or a $C_2$-$C_{30}$heteroaryl group, wherein the dotted lines are bonding sites.

Further most preferably, $A^1$, $A^2$, $A^3$, $A^4$ are in each occurrence independently of each other 1,3-phenylene, 1,4-phenylene, $R^{20}$ is H; CN; E; a $C_6$-$C_{60}$ aryl group which is unsubstituted or substituted by G, a $C_1$-$C_{60}$ heteroaryl group which is unsubstituted or substituted by G, a $C_1$-$C_{25}$alkyl group which is unsubstituted or substituted by at least one group G and/or interrupted by D.

Suitable and preferred groups E, G and D are mentioned before.

Preferably, $R^{20}$ is H, —$OR^{69}$, —$SiR^{70}R^{71}R^{72}$, CN, or a group of the following formula

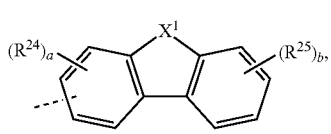

(4)

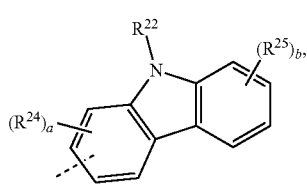

(5)

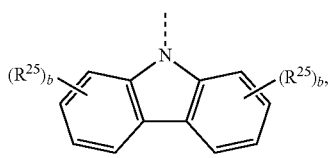

(6)

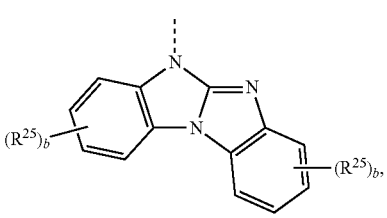

(7)

-continued (8)

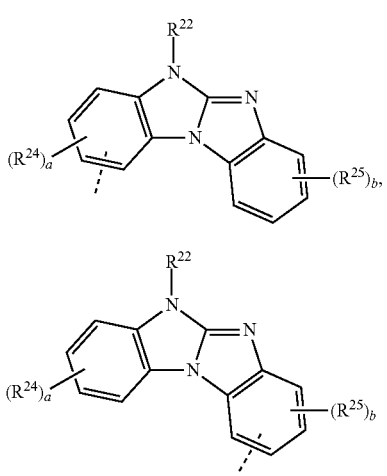

(8a)

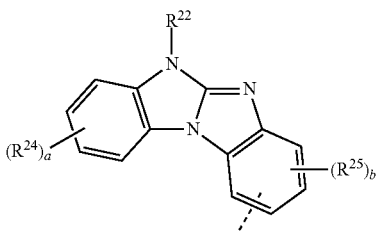

wherein $X^1$ is S, O, $C(R^{21})_2$, or $NR^{23}$;

$R^{21}$ is a $C_1$-$C_{25}$alkyl group which can optionally be substituted by E and or interrupted by D; a $C_6$-$C_{24}$aryl group which can optionally be substituted by G, or a $C_1$-$C_{24}$heteroaryl group which can optionally be substituted by G; and/or two adjacent groups of the groups may form together with the atom to which they are bonded a ring structure which can optionally be substituted by G;

$R^{22}$ is a $C_6$-$C_{18}$ aryl group which is unsubstituted or substituted by G or a $C_2$-$C_{18}$ heteroaryl group which is unsubstituted or substituted by G;

$R^{23}$ is H, a $C_6$-$C_{18}$ aryl group which is unsubstituted or substituted by G, or a $C_2$-$C_{18}$ heteroaryl group which is unsubstituted or substituted by G;

$R^{24}$ and $R^{25}$ are independently of each other H, a $C_6$-$C_{18}$ aryl group which is unsubstituted or substituted by G, a $C_2$-$C_{18}$ heteroaryl group which is unsubstituted or substituted by G, a $C_1$-$C_{25}$alkyl group which can optionally be substituted by E and or interrupted by D, or —CN;

a is 0, 1, 2 or 3, preferably 0, 1 or 2;

b is 0, 1, 2, 3 or 4, preferably 0, 1 or 2;

the dotted lines are bonding sites;

or (9)

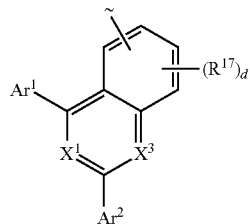

(10)

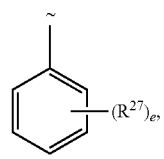

or (11)

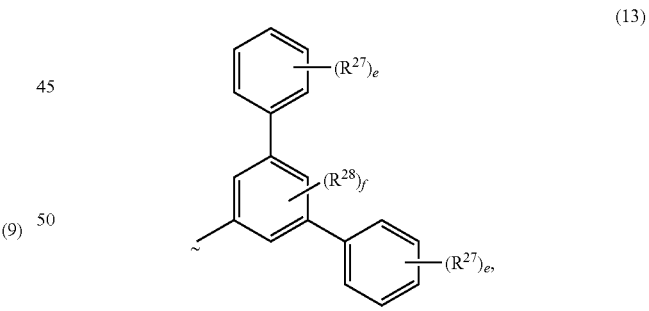

wherein $X^1$, $X^2$ and $X^3$ are independently of each other $CR^{19}$ or N, wherein in formula (9) at least one of $X^1$ to $X^3$ is N, and wherein in formulae (10) and (11) at least one of $X^1$ and $X^3$ is N;

$Ar^1$ and $Ar^2$ are independently of each other a $C_6$-$C_{24}$ aryl group which is optionally substituted by G, or a $C_1$-$C_{24}$ heteroaryl group which is optionally substituted by G;

$R^{17}$, $R^{18}$ and $R^{19}$ are independently of each other H, a $C_6$-$C_{24}$ aryl group which can be substituted by G, a $C_1$-$C_{24}$ heteroaryl group which can be substituted by G, or a $C_1$-$C_{25}$alkyl group which can optionally be substituted by E and/or interrupted by D; preferably, H;

c is 0, 1, 2, 3 or 4; preferably 0, 1 or 2; more preferably 0 or 1;

d is 0, 1, 2 or 3; preferably 0, 1 or 2; more preferably 0;

or (12)

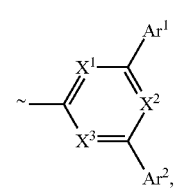

(13)

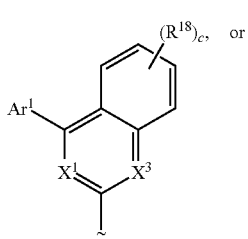

(14)

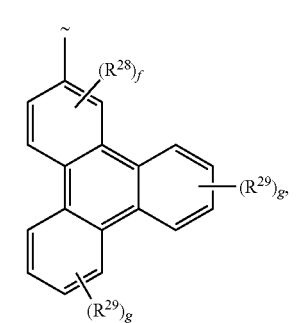

-continued
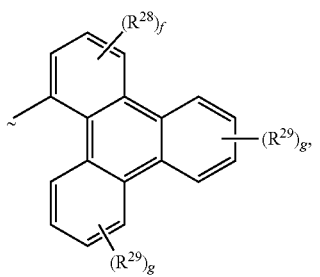 (15)
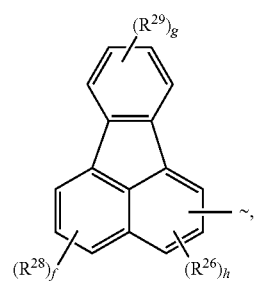 (16)
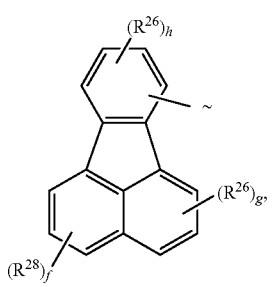 (17)
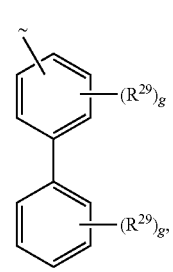 (18)
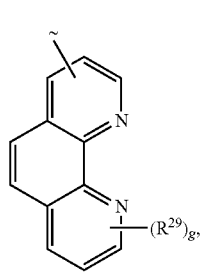 (19)
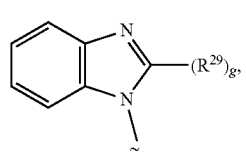 (20)
-continued
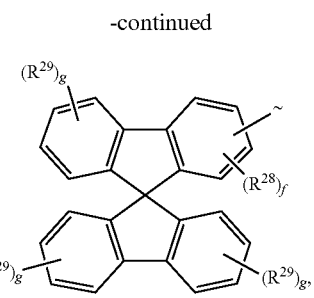 (21)
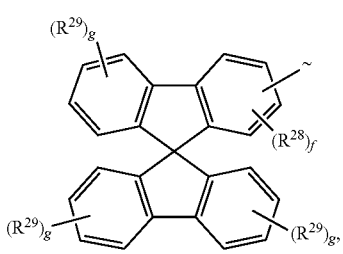 (22)
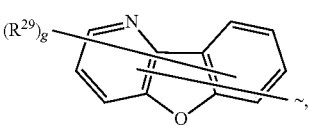 (23)
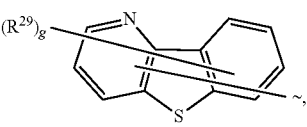 (24)
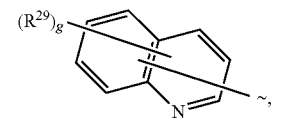 (25)
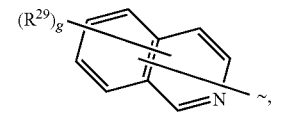 (26)
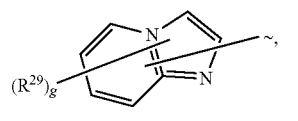 (27)
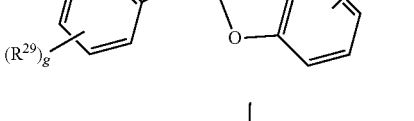 (28)
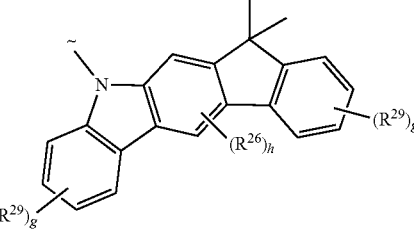 (29)

-continued

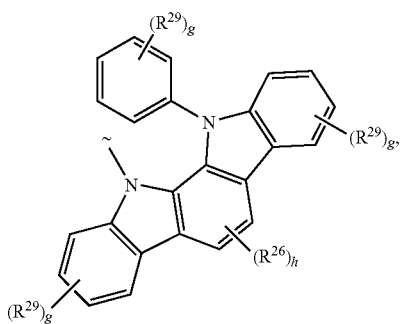
(30)

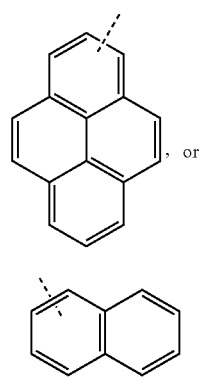
, or
(31)

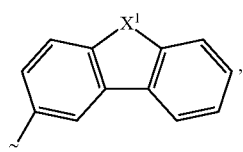
(32)

wherein
$R^{26}$, $R^{27}$, $R^{28}$ and $R^{29}$ are independently of each other H, a $C_6$-$C_{24}$ aryl group which can be substituted by G, a $C_1$-$C_{24}$ heteroaryl group which can be substituted by G, a $C_1$-$C_{25}$alkyl group which can optionally be substituted by E and/or interrupted by D, or a substituent E; preferably, H or CN, more preferably H;

e is 0, 1, 2, 3, 4 or 5; preferably 0, 1, 2 or 3; more preferably 0, 1 or 2;

f is 0, 1, 2 or 3; preferably 0, 1 or 2; more preferably 0;

g is 0, 1, 2, 3 or 4; preferably 0, 1 or 2; more preferably 0 or 1;

h is 0, 1 or 2, preferably 0 or 1; more preferably 0;

or two adjacent groups $R^{26}$, $R^{27}$, $R^{28}$ or $R^{29}$ may form together with the atoms to which they are bonded a ring structure which may be substituted by G, wherein ~ is a bonding site and the dotted lines are bonding sites.

Preferred groups (4), (5), (6), (7), (8) are:

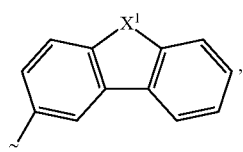
(4')

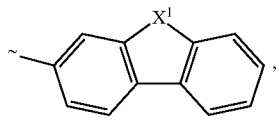
(4")

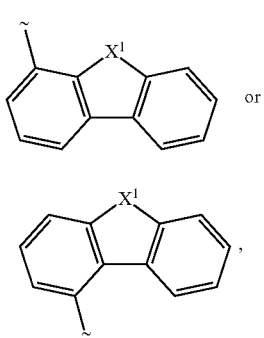
or
(4''')

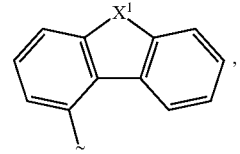
(4'''')

wherein $X^1$ is O or S;

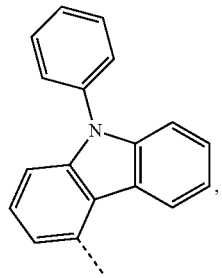
(5')

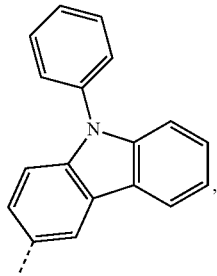
(5")

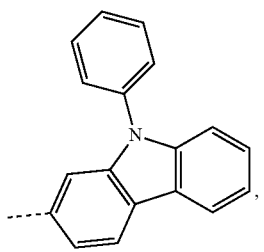
(5''')

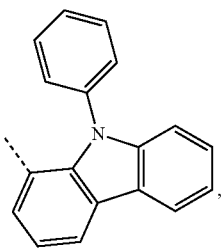
(5'''')

-continued
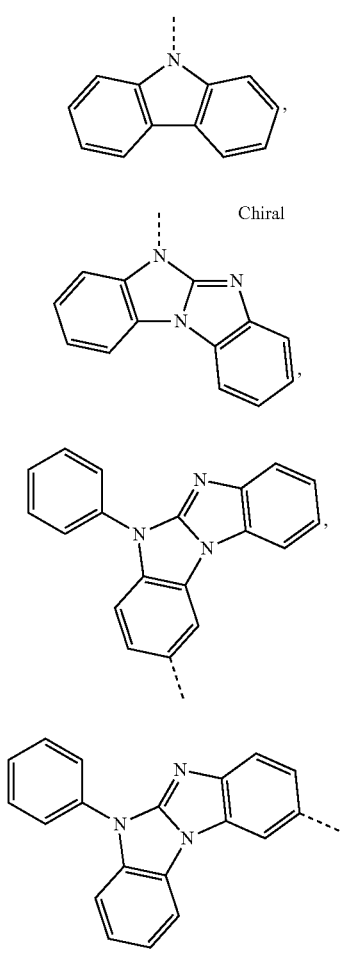
(6′)
(7′) Chiral
(8′)
(8a′)
wherein ~ is a bonding site and the dotted lines are bonding sites.
Most preferred groups (4), (5) and (6) are:
(4′a)
(4′b)
(4′′′a)
-continued
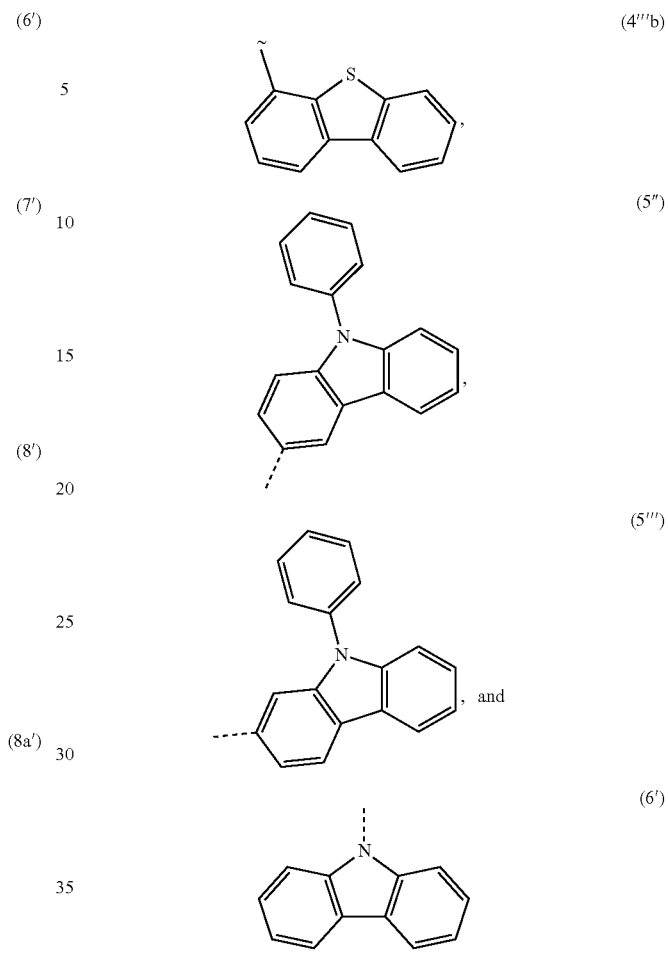
(4′′′b)
(5″)
(5′′′)
(6′)
wherein ~ is a bonding site.
Preferred groups (9), (10) and (11) are:

-continued
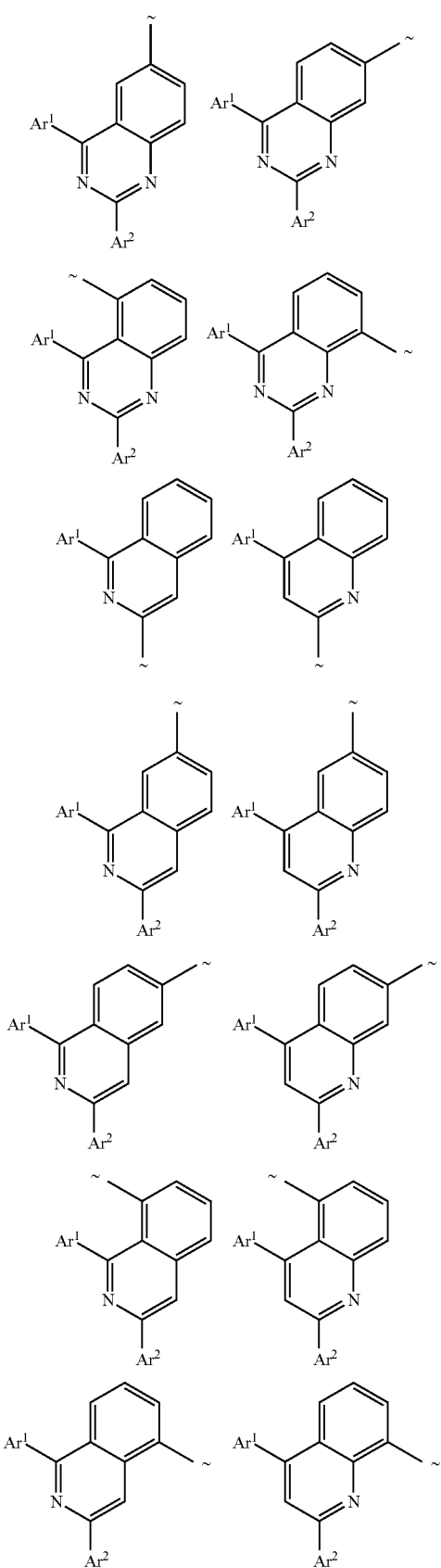
wherein
Ar$^1$ and Ar$^2$ are independently of each other a C$_6$-C$_{24}$ aryl group which is optionally substituted by G, or a C$_1$-C$_{24}$ heteroaryl group which is optionally substituted by G;
~ are bonding sites to the neighboring groups.
The group G is described above.
Preferably, Ar$^1$ and Ar$^2$ are unsubstituted phenyl or a group of the following formula
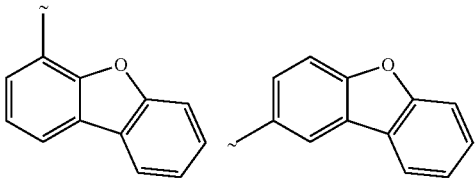
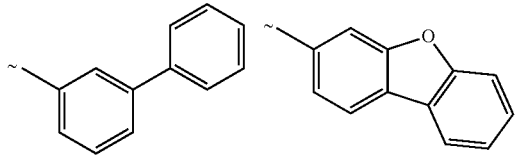
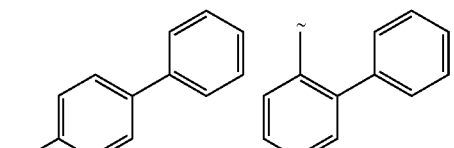
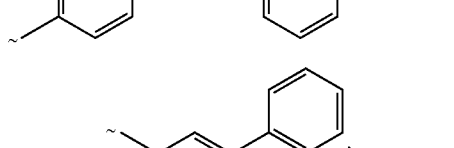
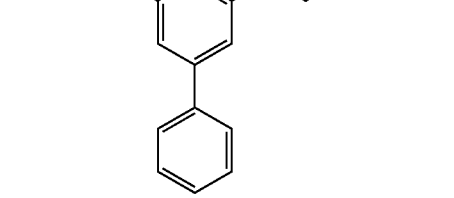
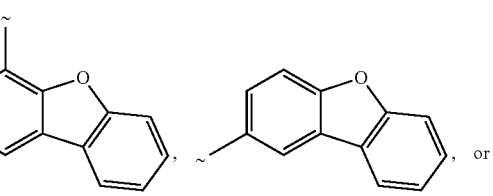, or
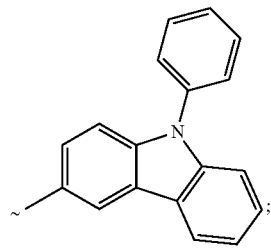;

wherein
~ are bonding sites to the neighboring groups.
Most preferably, Ar$^1$ and Ar$^2$ are unsubstituted phenyl.
Most preferably, the groups (9), (10) and (11) are
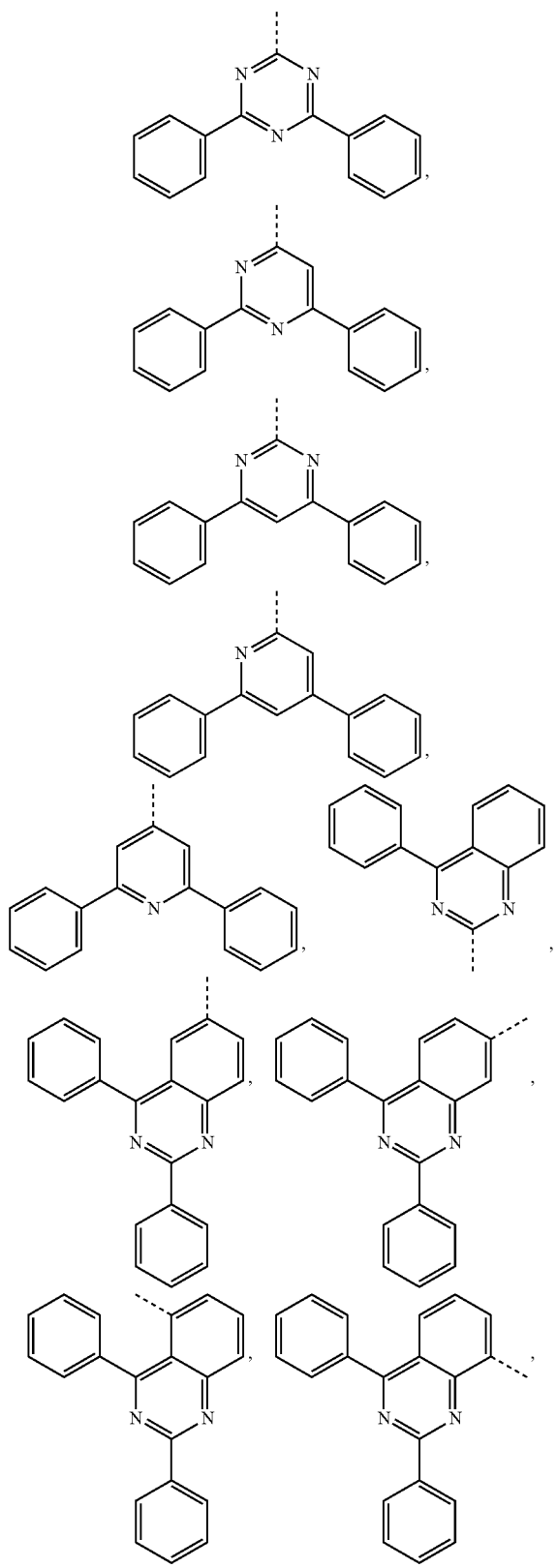
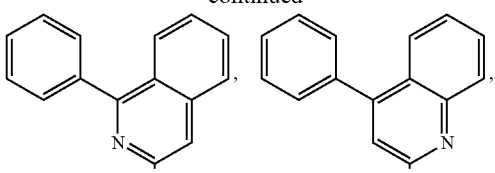
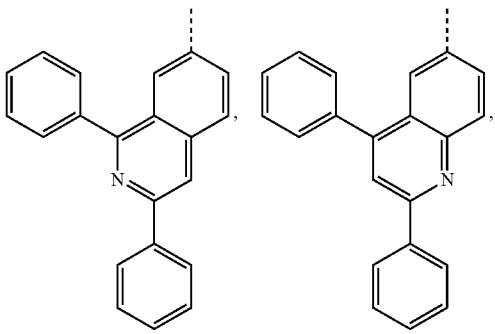
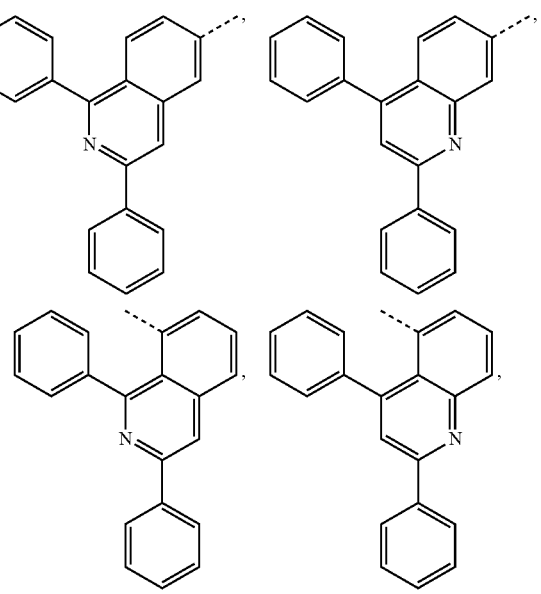
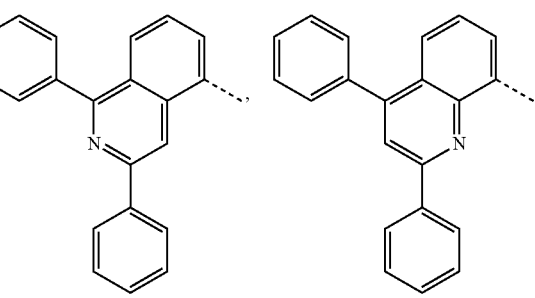
wherein
the dotted lines are bonding sites to the neighboring groups.
Preferred groups (12), (13), (14), (15), (16), (17), (18), (19), (20), (21), (22), (23), (24), (25), (26), (27), (28), (29), (30), (31), and (32) are

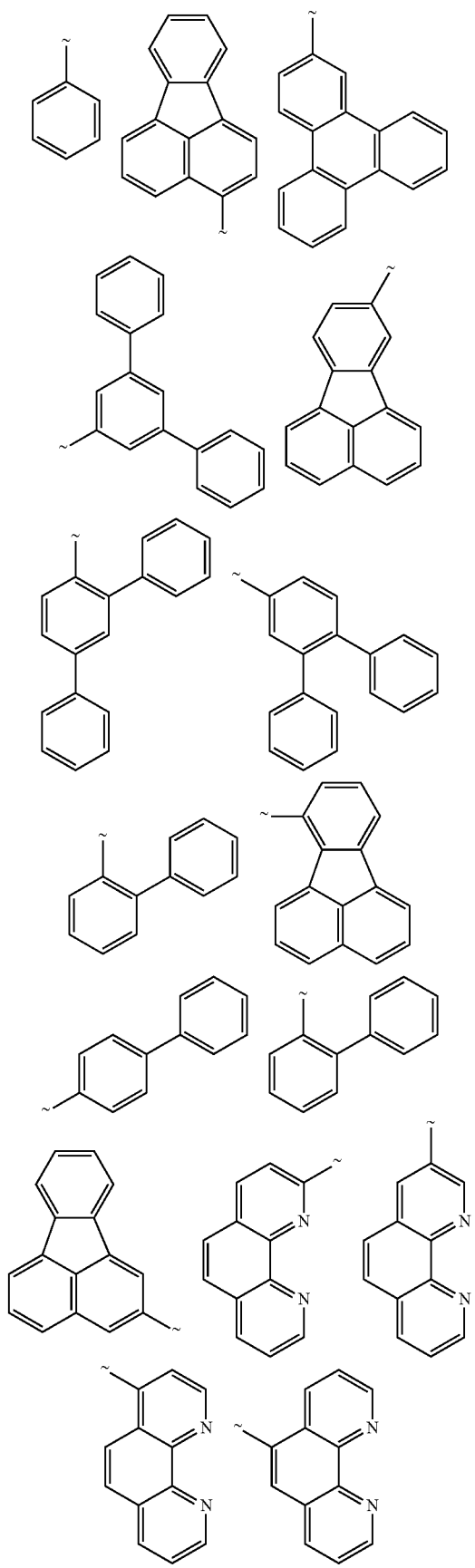
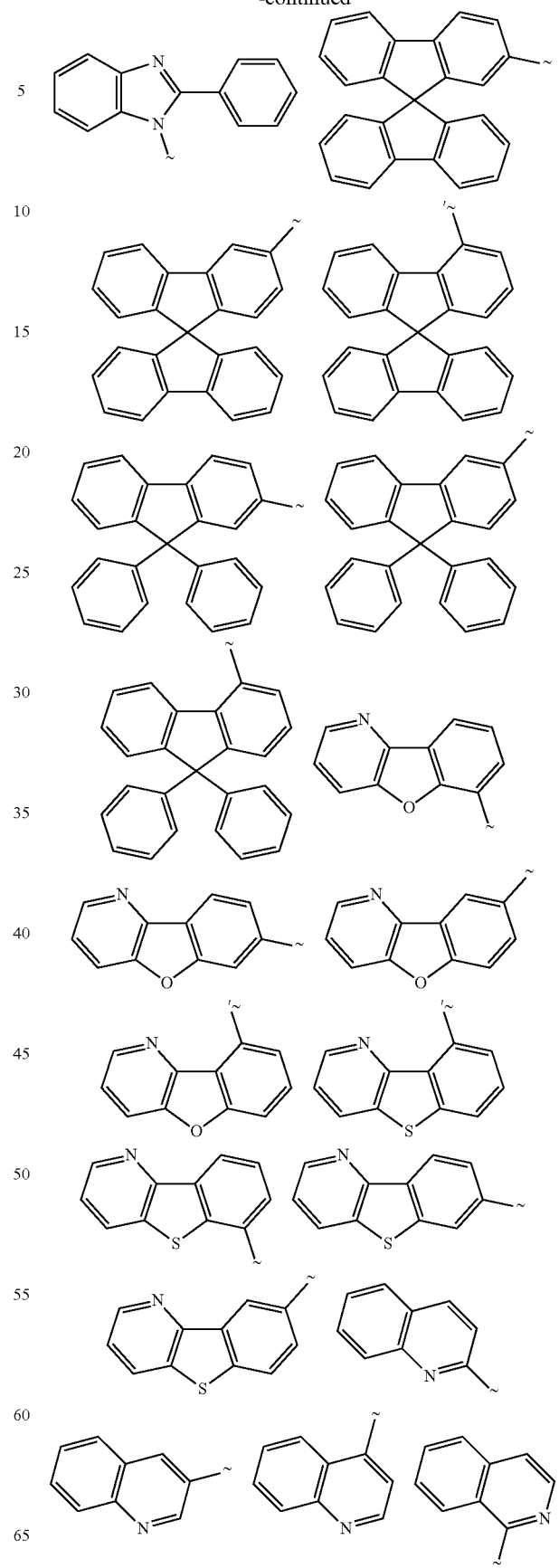

-continued
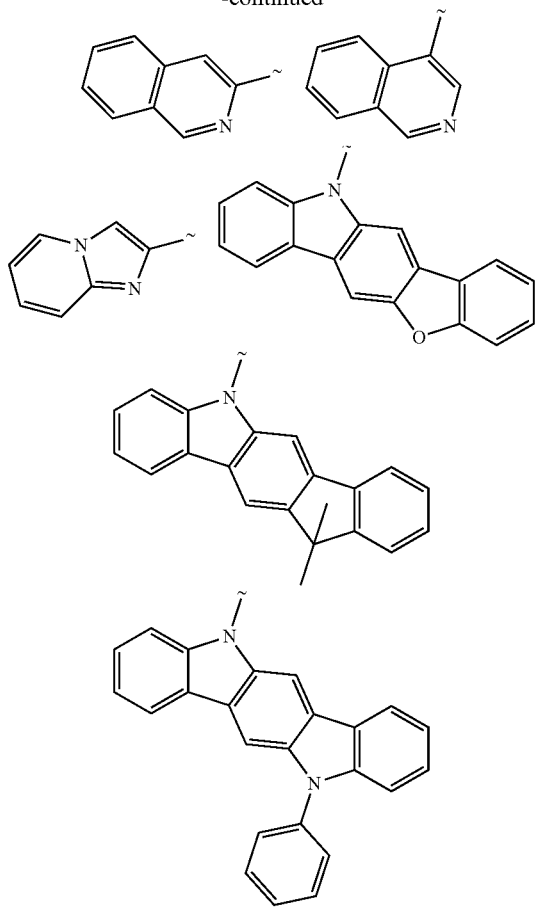
wherein
~ are bonding sites to the neighboring groups.
Most preferred groups (12), (13), (14), (15), (16), (17), (18), (19), (20), (21), (22), (23), (24), (25), (26), (27), (28), (29), (30), (31), and (32) are:
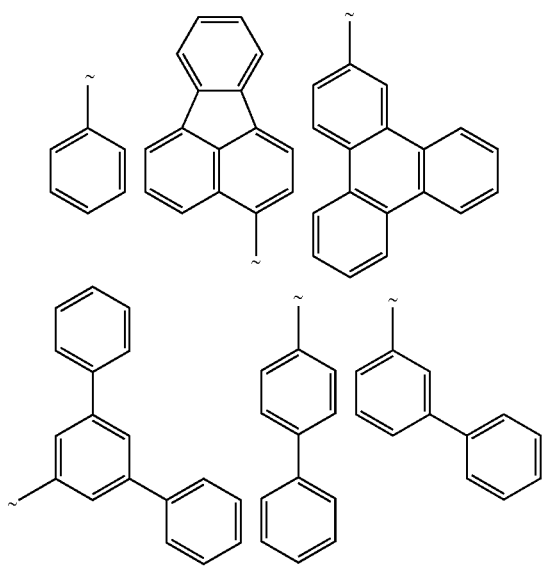
-continued
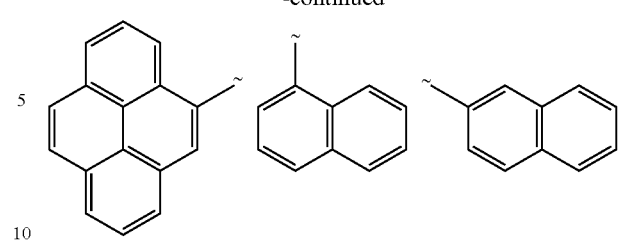
wherein
~ are bonding sites to the neighboring groups.
Most preferably, $R^{20}$ is H or has one of the definitions mentioned below:
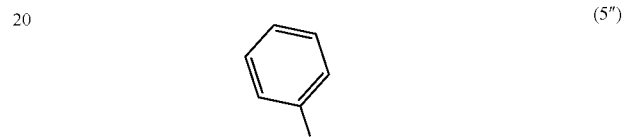
(5″)

(5‴)
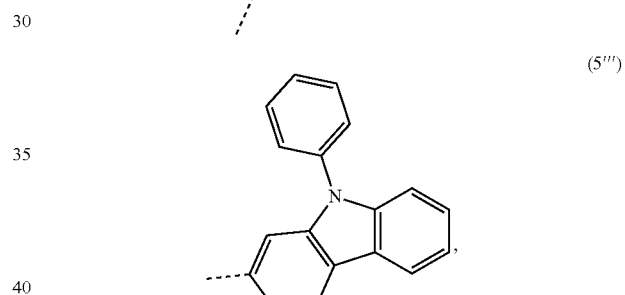
(6′)
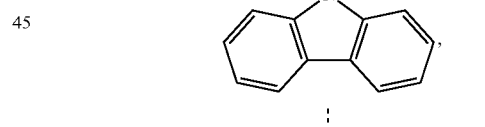
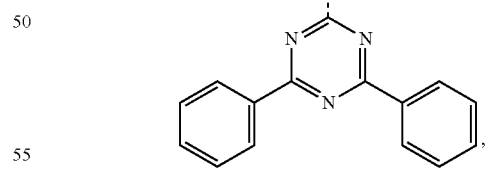
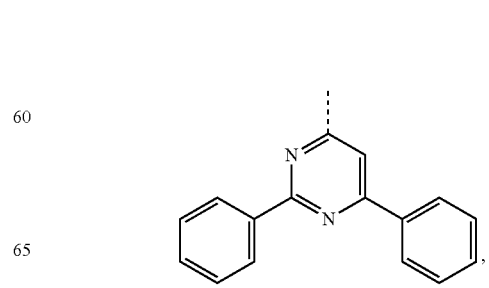

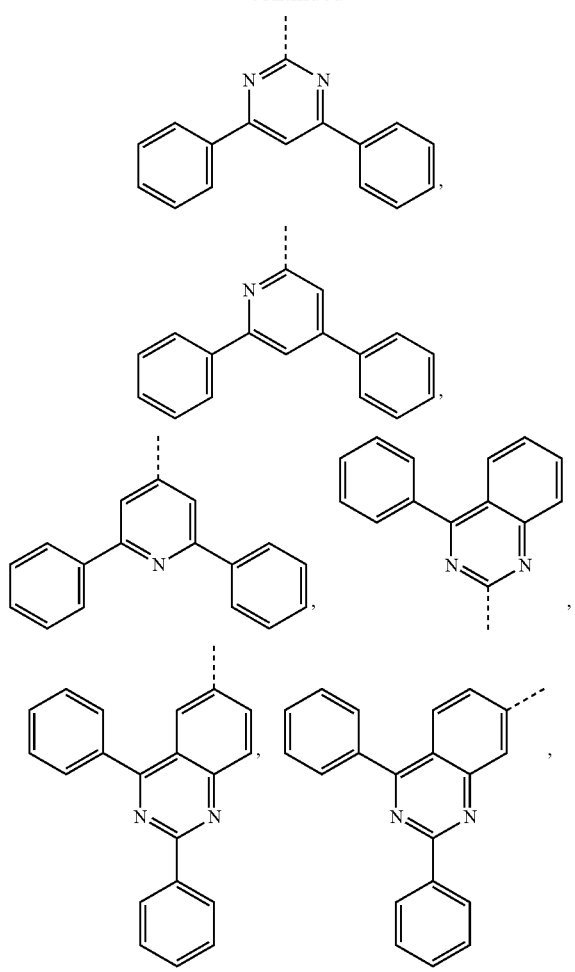
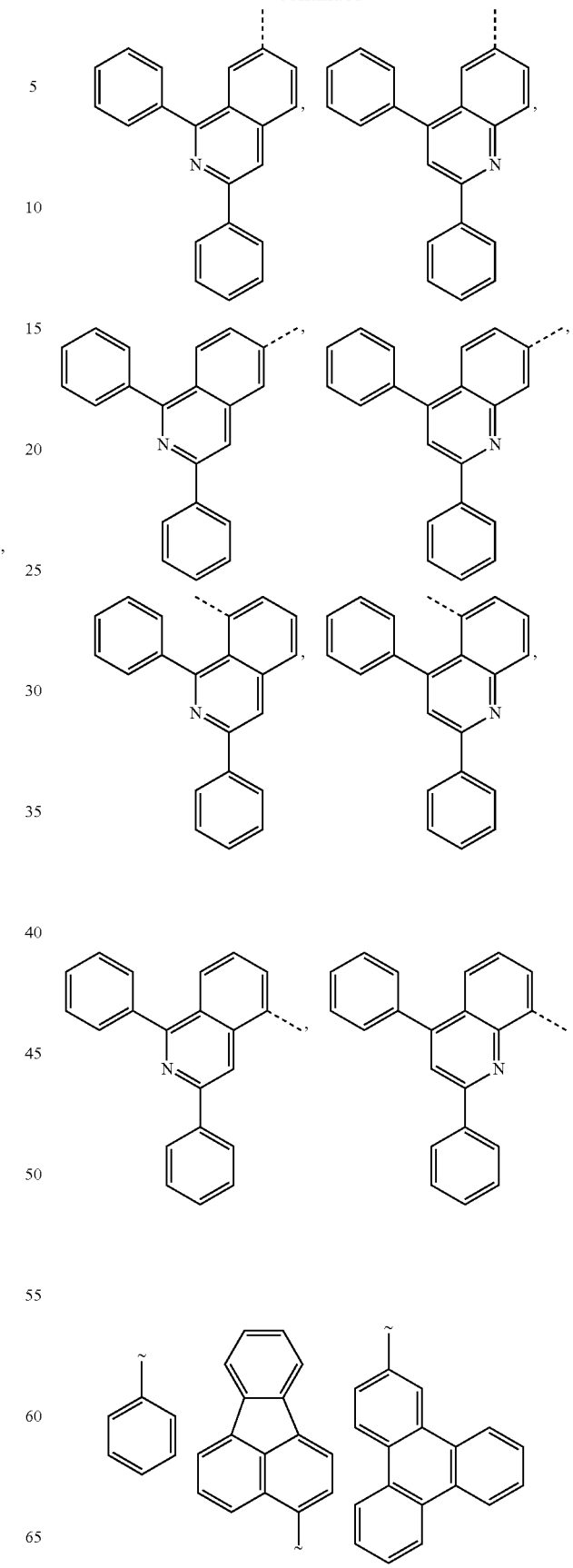

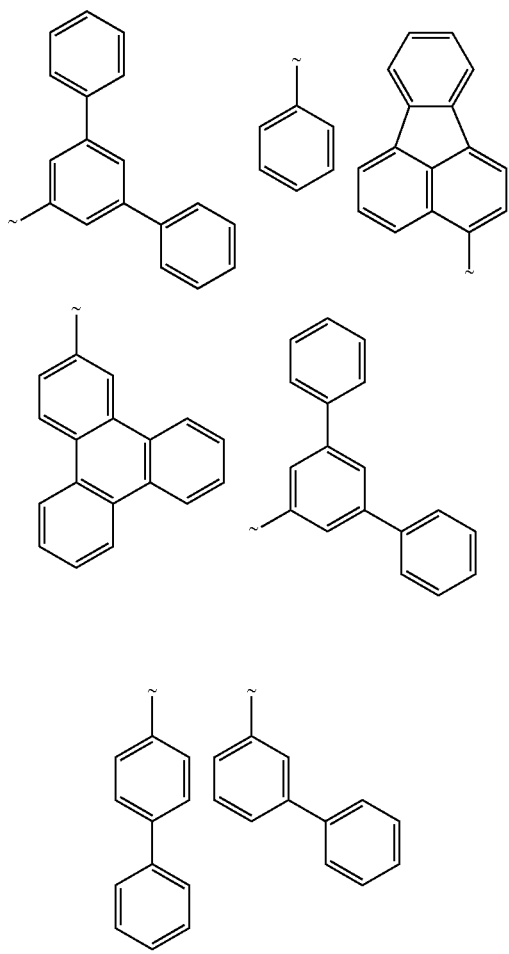
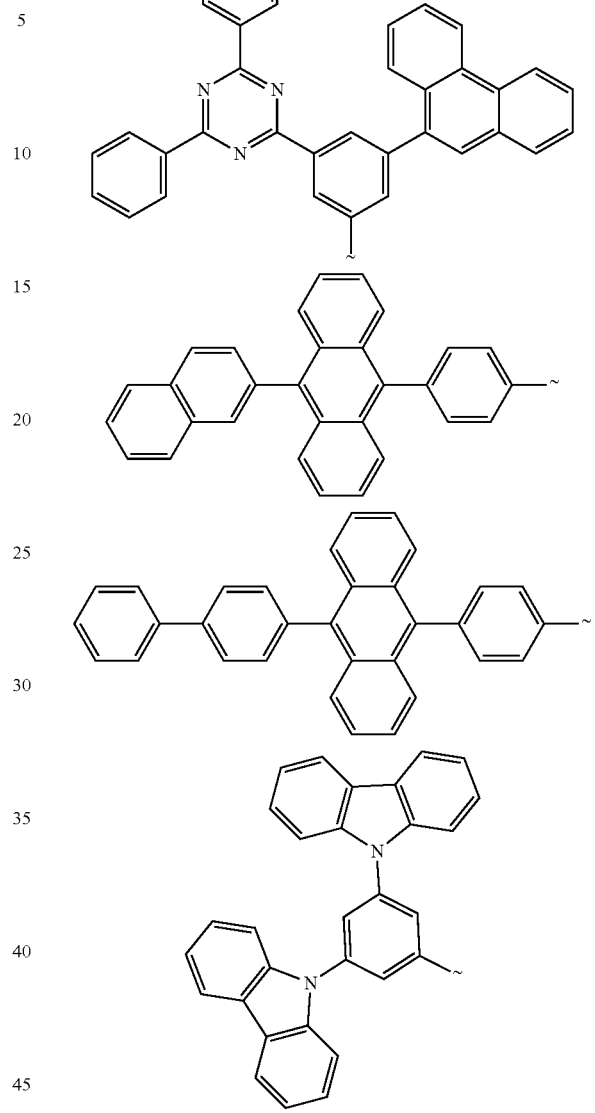
wherein
~ and the dotted lines are bonding sites to the neighboring groups.
The group $-(A^1)_o-(A^2)_p-(A^3)_q-(A^4)_r-R^{20}$
In the group $-(A^1)_o-(A^2)_p-(A^3)_q-(A^4)_r-R^{20}$ o is 0 or 1, p is 0 or 1, q is 0 or 1, r is 0 or 1, preferably o is 0 or 1, p is 0 or 1, q is 0 and r is 0.
Preferred groups, $A^1$, $A^2$, $A^3$, $A^4$, and $R^{20}$ are mentioned above.
Most preferred groups $-(A^1)_o-(A^2)_p-(A^3)_q-(A^4)_r-R^{20}$ are the following groups:
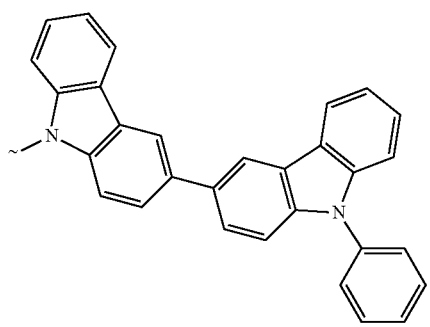
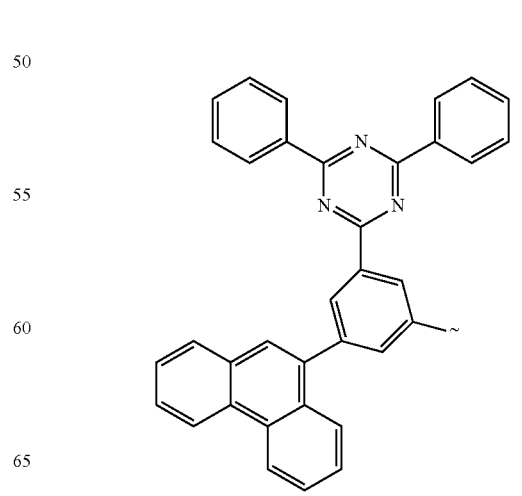

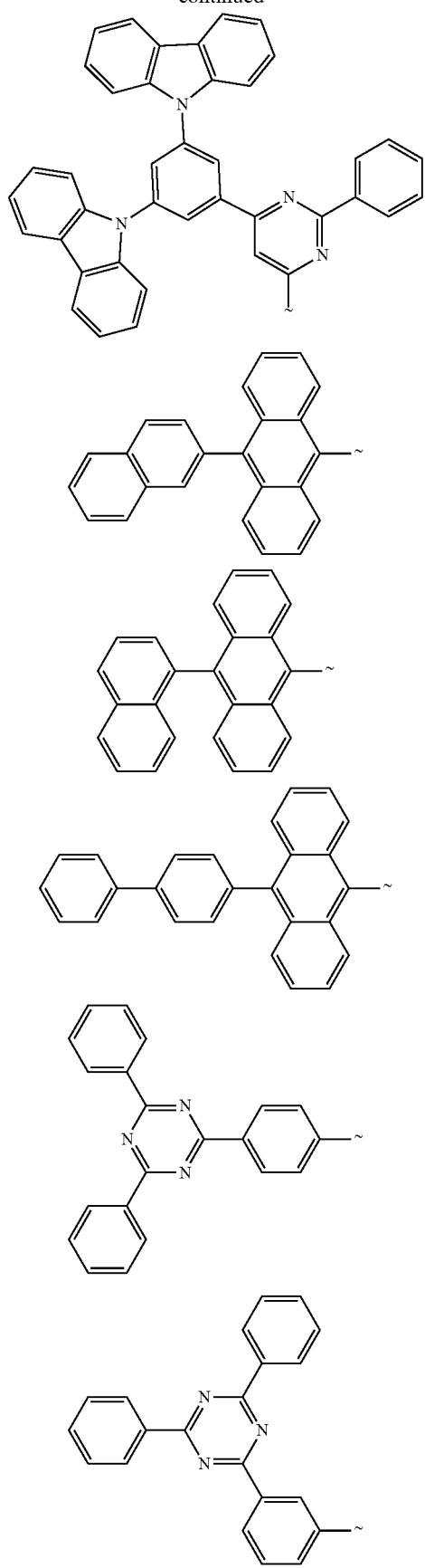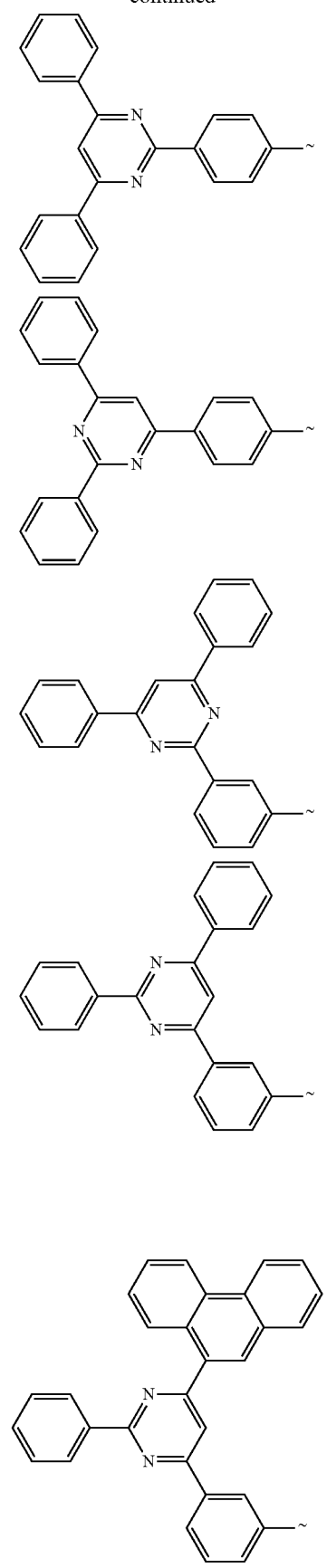

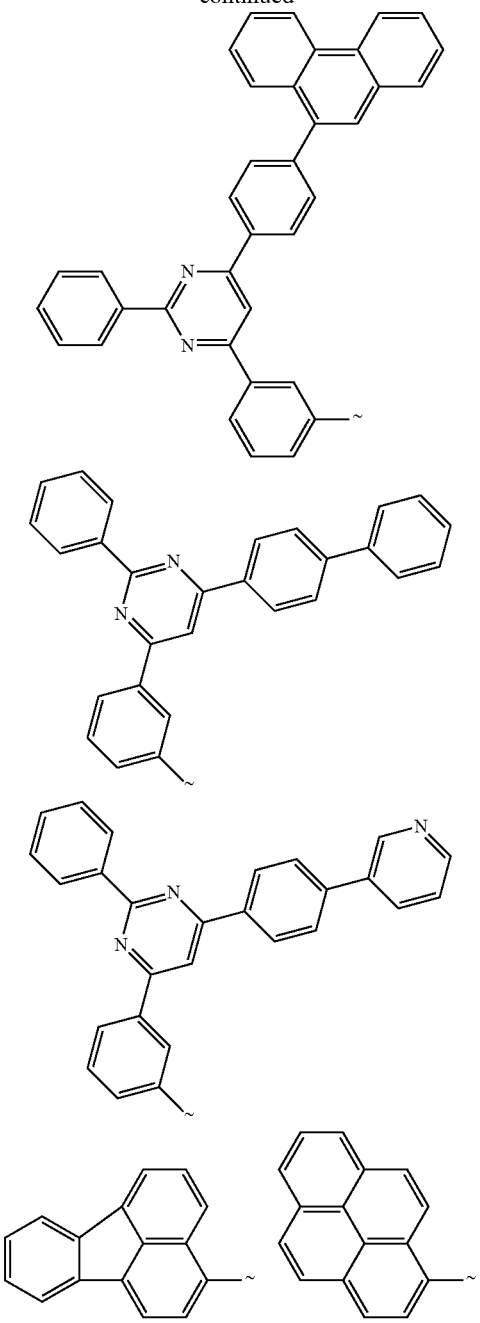
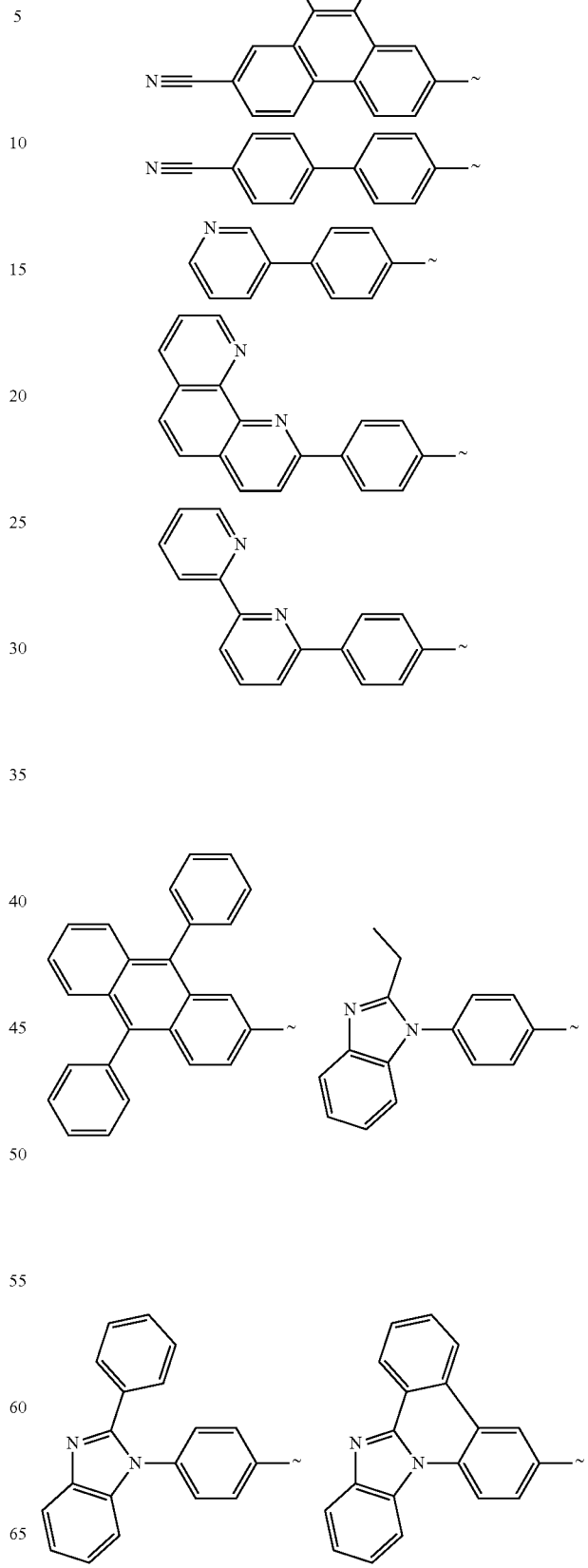

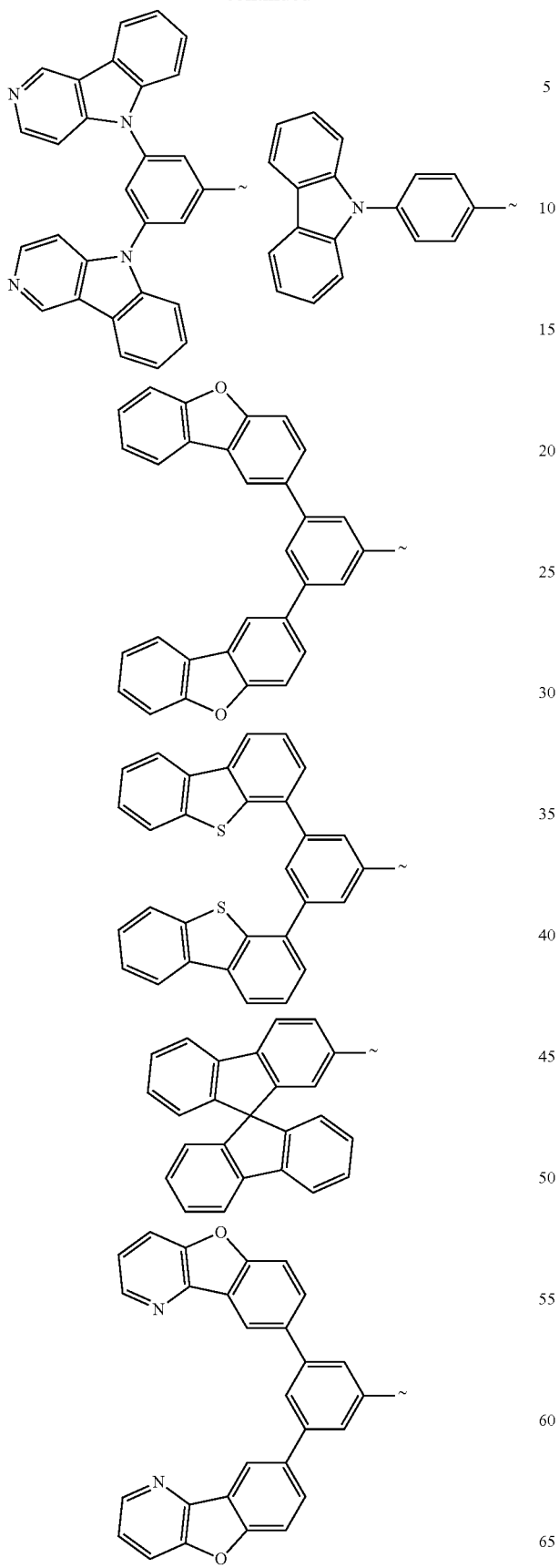
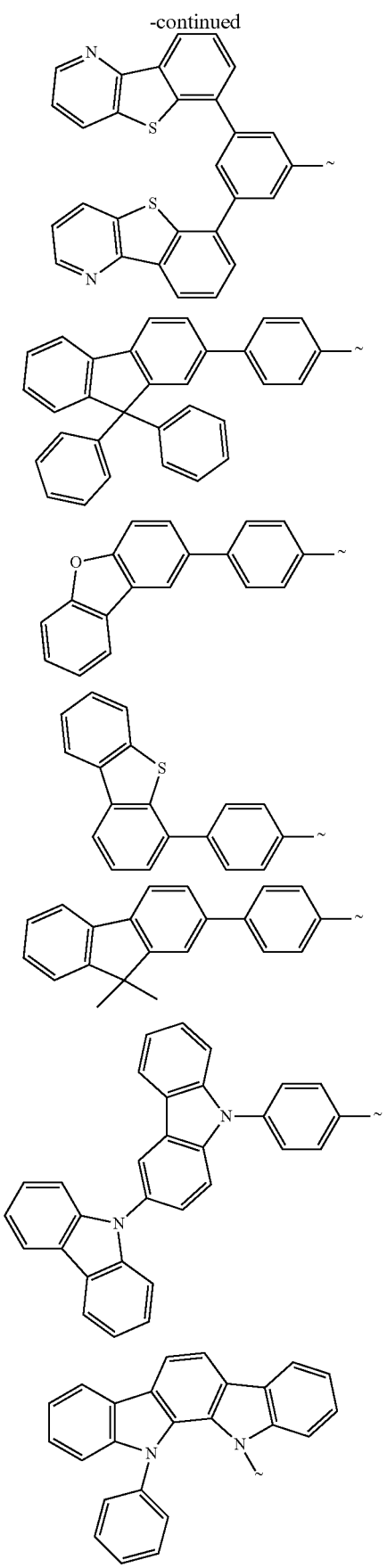

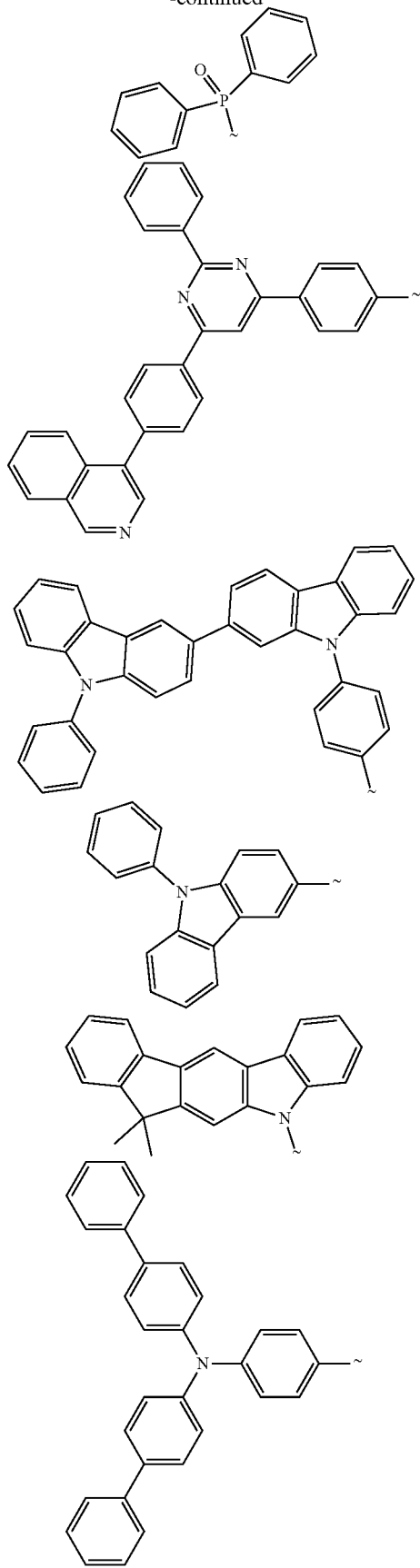
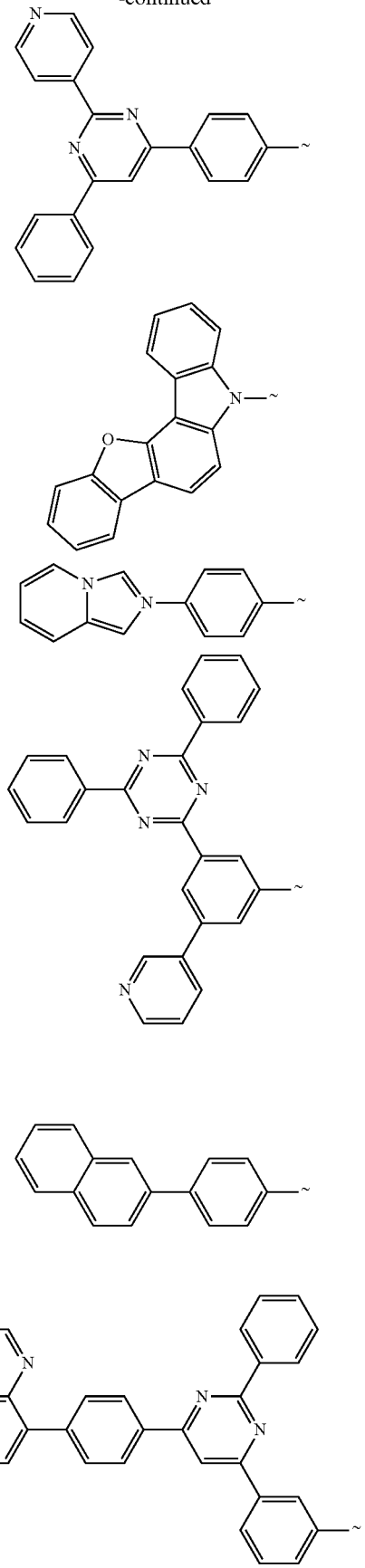

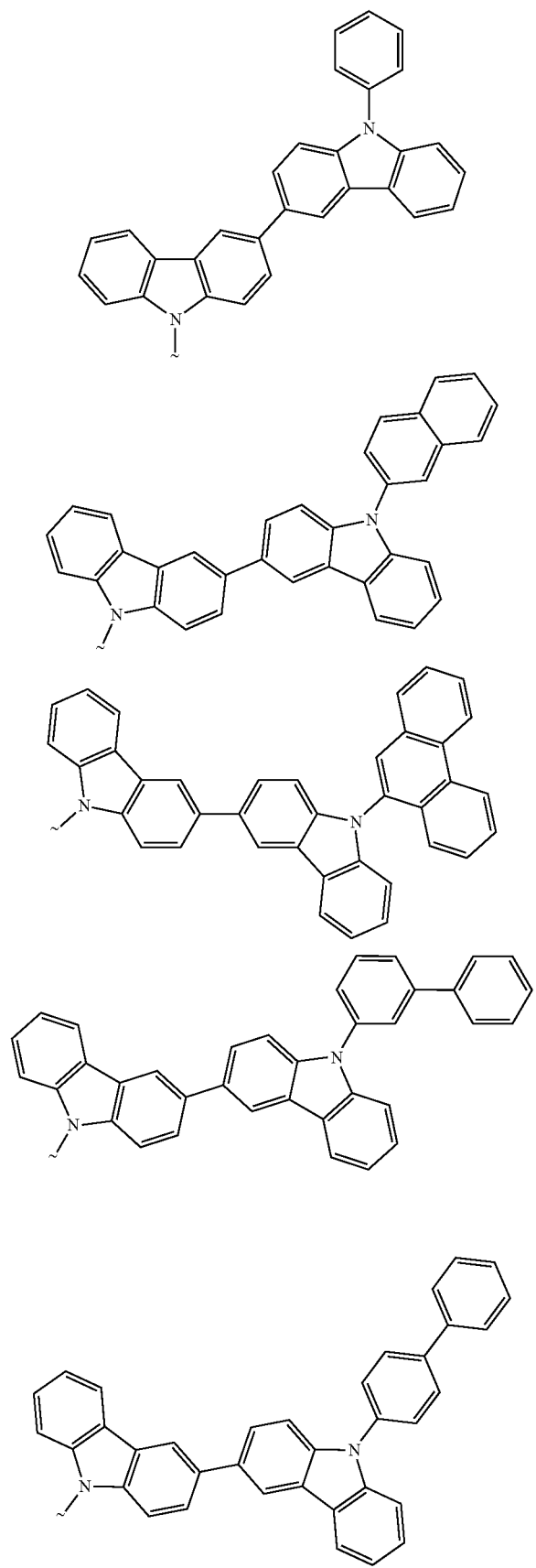
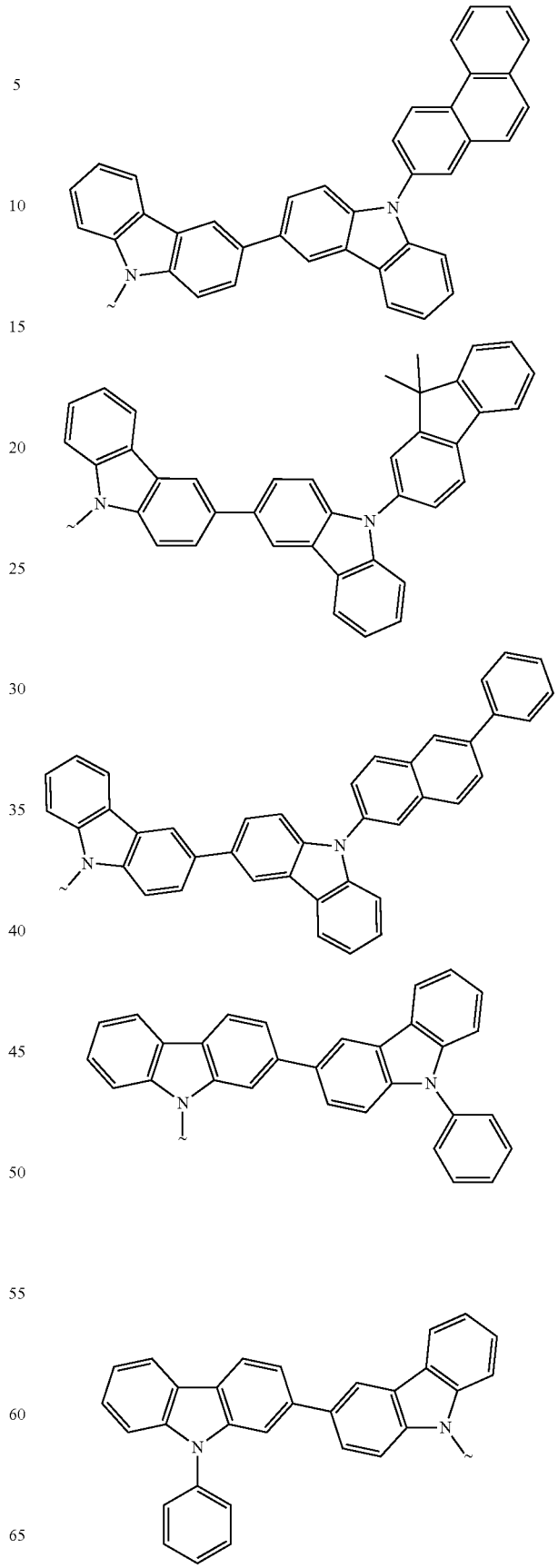

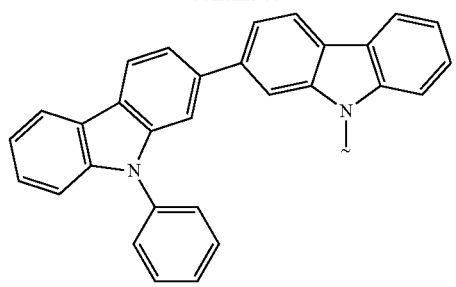
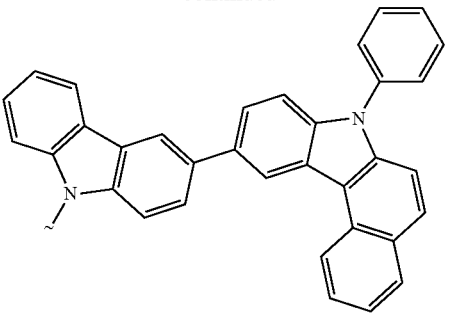
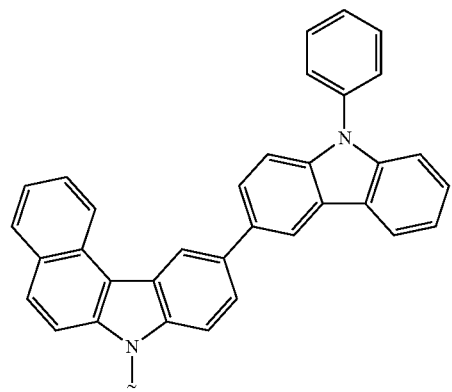
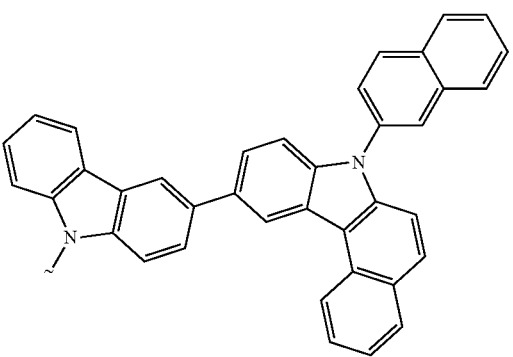
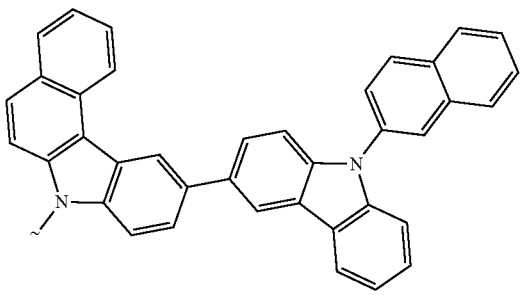
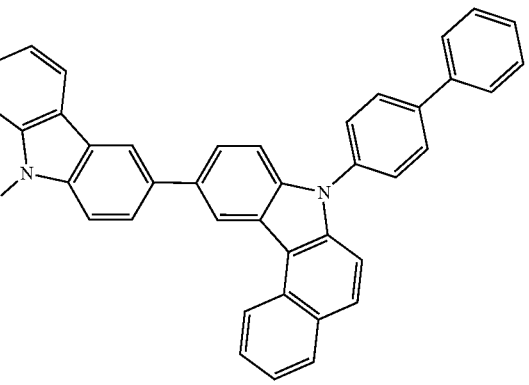
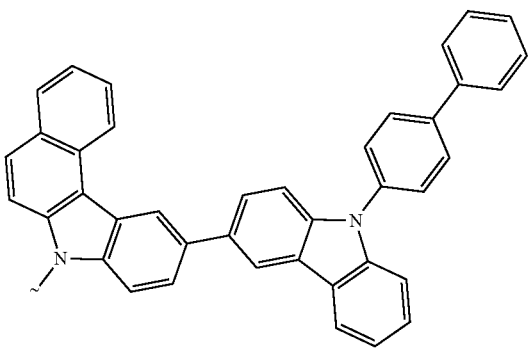
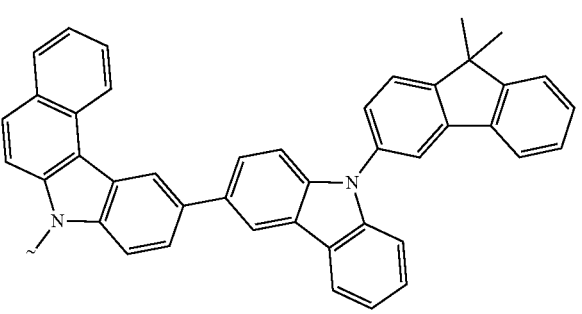
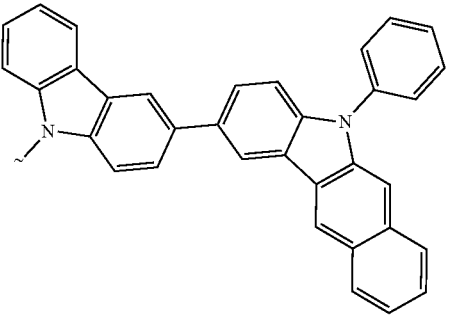

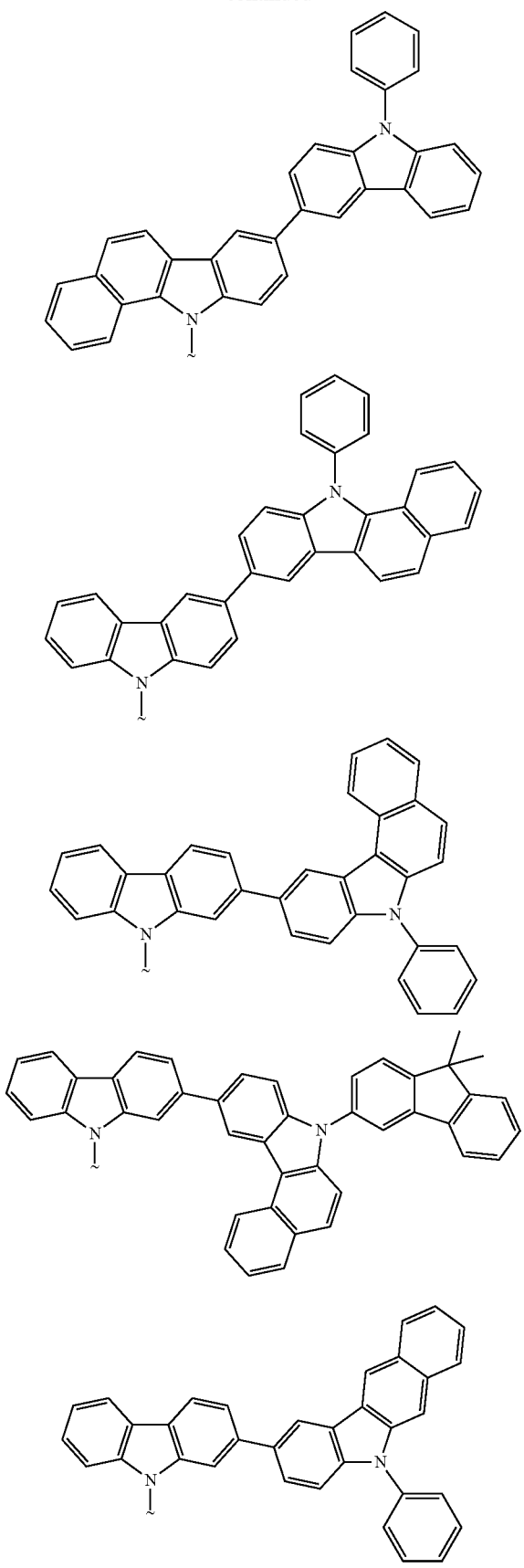
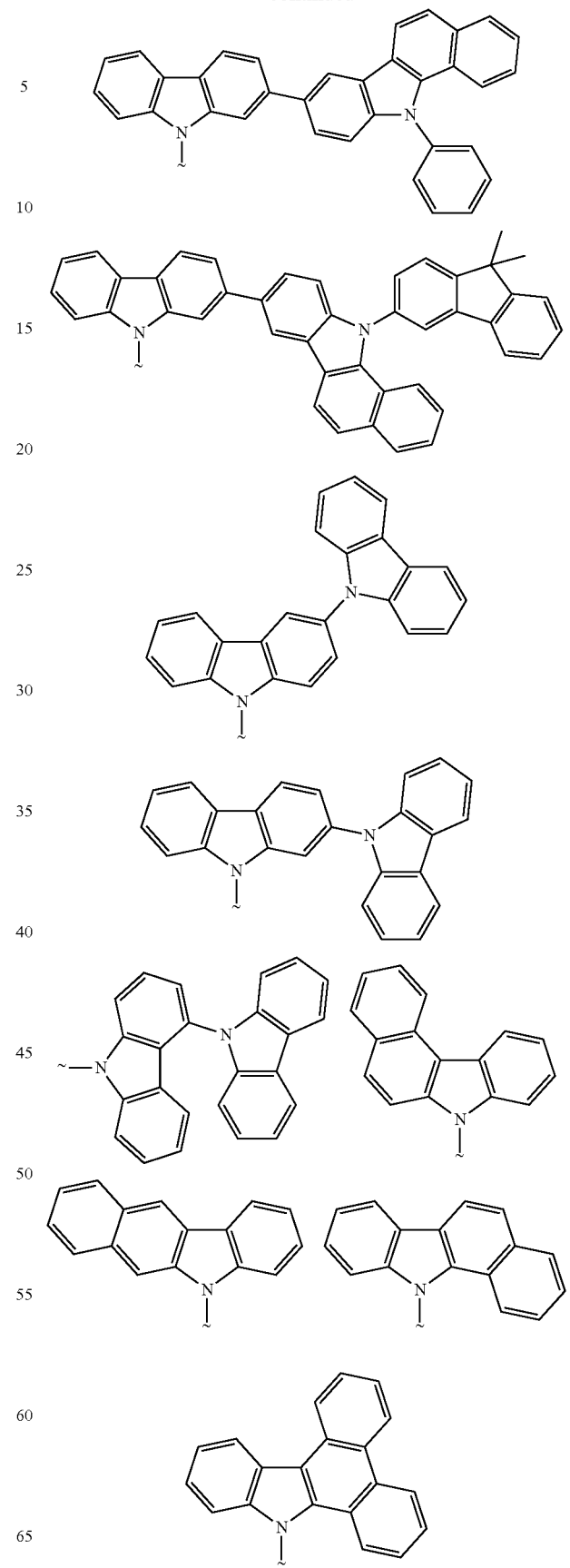

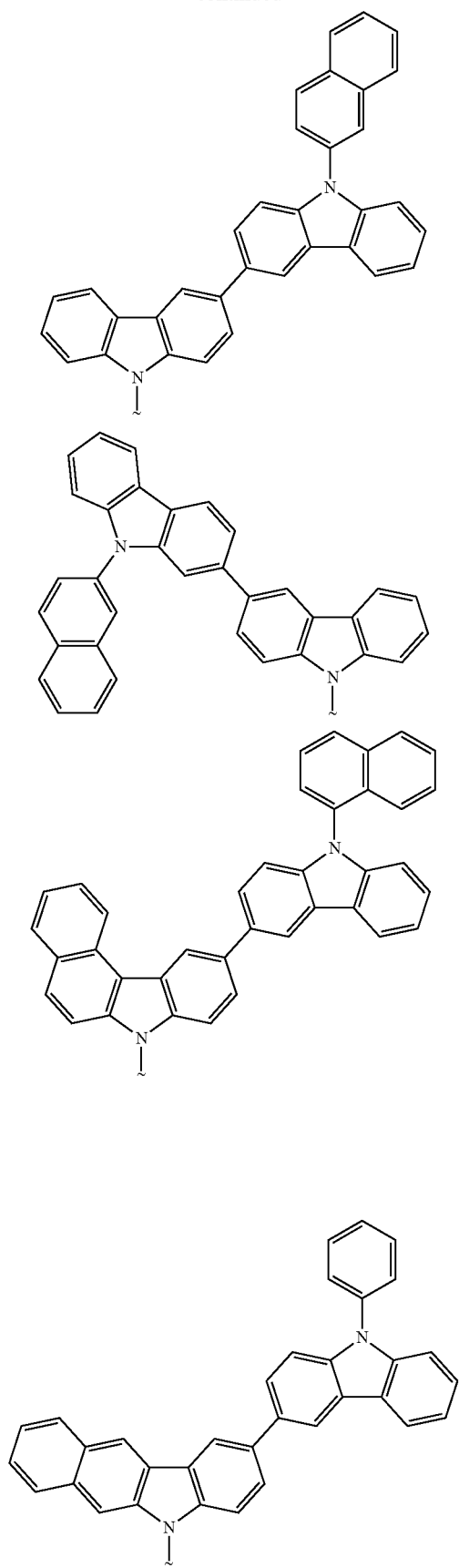
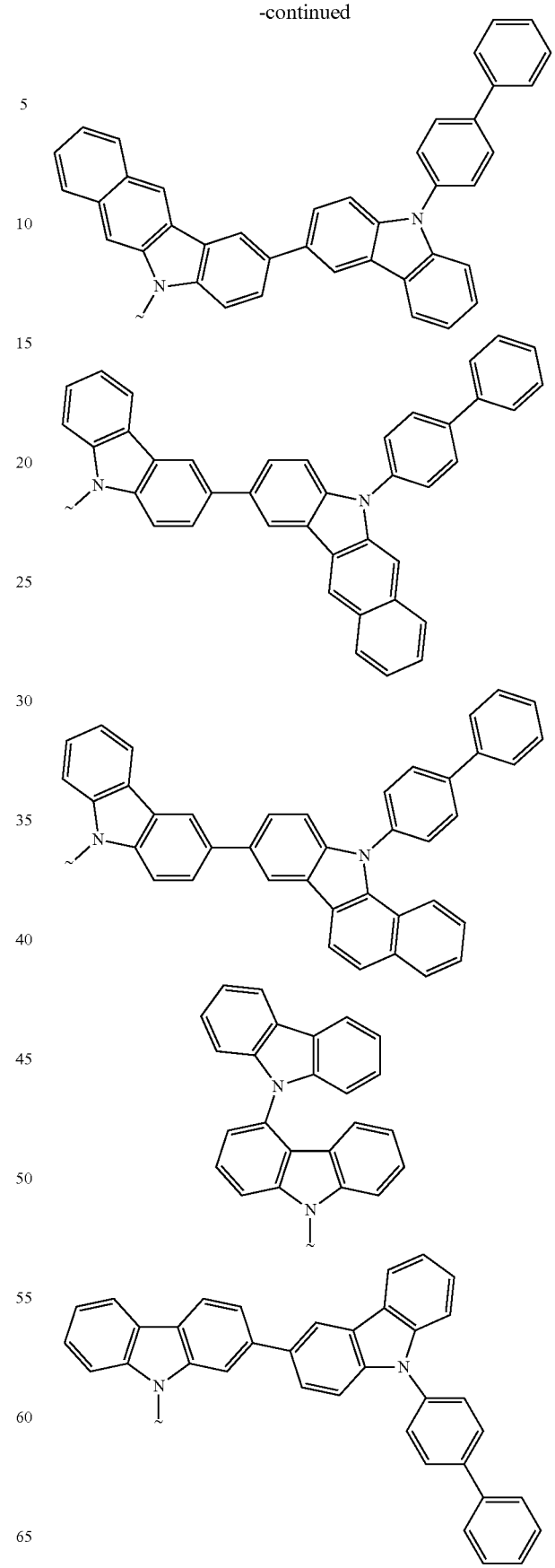

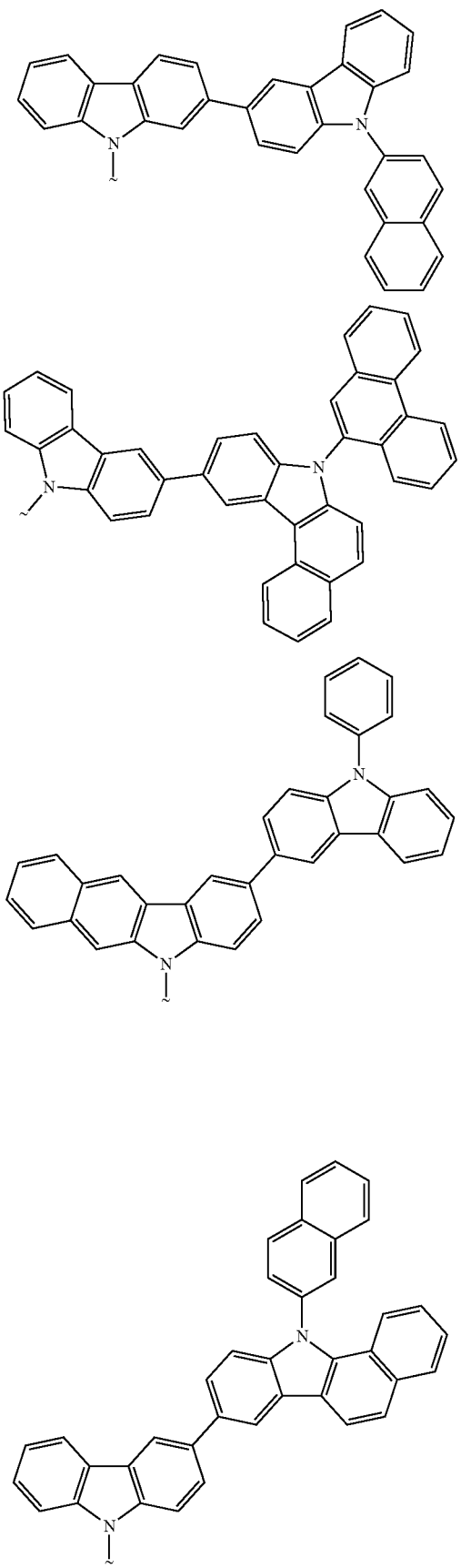

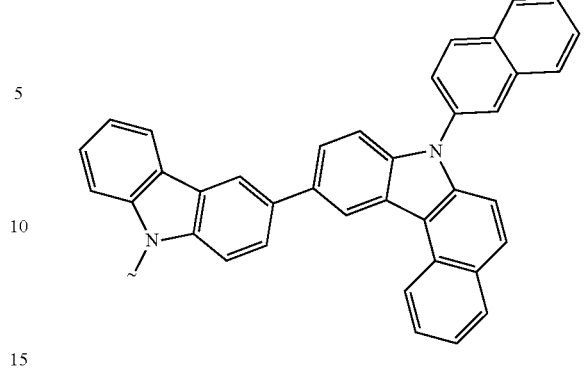

Compounds of Formula (1)

In a preferred embodiment, in the compounds (heterocyclic derivatives) of formula (1), $A_1$ is N and $A_2$ is $CR^{42}$. More preferably, in the compounds (heterocyclic derivatives) of formula (1), $R^{42}$ is E; a group of formula $-(A^1)_o-(A^2)_p-(A^3)_q-(A^4)_r-R^{20}$; or a $C_1$-$C_{25}$alkyl group which is unsubstituted or substituted by at least one group E and/or interrupted by D; preferably a group of formula $-(A^1)_o-(A^2)_p-(A^3)_q-(A^4)_r-R^{20}$, and the residues $R^1$, $R^3$, $R^4$, $R^5$, $R^6$, $R^7$, and $R^8$ are H. Most preferred are compounds (heterocyclic derivatives) of formula (1) having the formula (1a):

(1a)

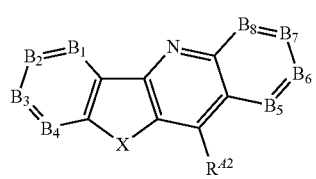

wherein the groups and residues X, $B_1$, $B_2$, $B_3$, $B_4$, $B_5$, $B_6$, $B_7$, $B_8$, and $R^{42}$ are defined above.

In another preferred embodiment, in the compounds (heterocyclic derivatives) of formula (1), $A_1$ is $CR^{41}$ and $A_2$ is N. More preferably, in the compounds (heterocyclic derivatives) of formula (1), $R^{41}$ is E; a group of formula $-(A^1)_o-(A^2)_p-(A^3)_q-(A^4)_r-R^{20}$; or a $C_1$-$C_{25}$alkyl group which is unsubstituted or substituted by at least one group E and/or interrupted by D; preferably a group of formula $-(A^1)_o-(A^2)_p-(A^3)_q-(A^4)_r-R^{20}$, and the residues $R^1$, $R^3$, $R^4$, $R^5$, $R^6$, $R^7$, and $R^8$ are H. Most preferred are compounds (heterocyclic derivatives) of formula (1) having the formula (1b):

(1b)

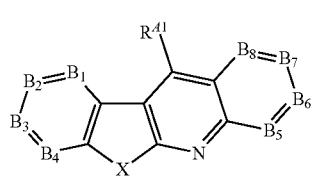

wherein the groups and residues X, $B_1$, $B_2$, $B_3$, $B_4$, $B_5$, $B_6$, $B_7$, BE, and $R^{41}$ are defined above.

In still another preferred embodiment, in the compounds (heterocyclic derivatives) of formula (1), $A_1$ is N and $A_2$ is $CR^{42}$. More preferably, in the compounds (heterocyclic derivatives) of formula (1), one of $R^5$, $R^6$, $R^7$, and $R^8$, preferably $R^6$, is E; a group of formula $-(A^1)_o\text{-}(A^2)_p\text{-}(A^3)_q\text{-}(A^4)_r\text{-}R^{20}$; or a $C_1\text{-}C_{25}$alkyl group which is unsubstituted or substituted by at least one group E and/or interrupted by D; preferably a group of formula $-(A^1)_o\text{-}(A^2)_p\text{-}(A^3)_q\text{-}(A^4)_r\text{-}R^{20}$, and the other of the residues $R^{42}$, $R^1$, $R^3$, $R^4$, $R^5$, $R^6$, $R^7$, and $R^8$ are H. Most preferred are compounds (heterocyclic derivatives) of formula (1) having the formula (1c):

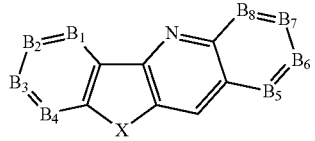
(1c)

wherein the groups and residues X, $B_1$, $B_2$, $B_3$, $B_4$, $B_5$, $B_6$, $B_7$, and $B_8$ are defined above.

Preferred compounds (heterocyclic derivatives) of formula (1) have the following structures:

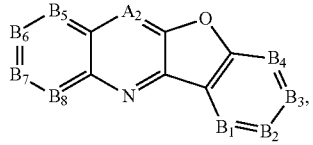
(1-1)

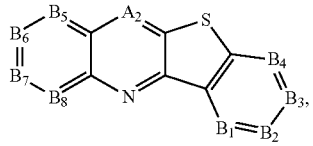
(1-2)

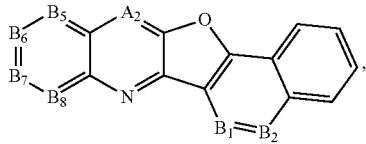
(1-3)

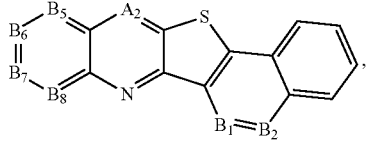
(1-4)

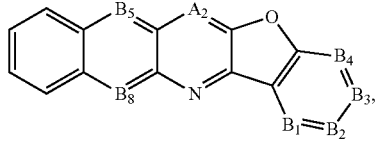
(1-5)

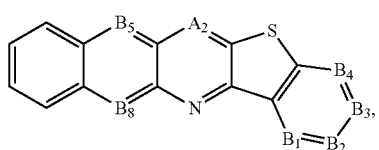
(1-6)

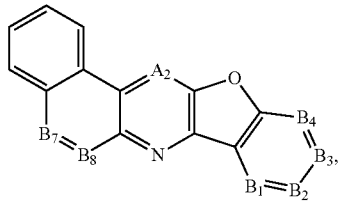
(1-7)

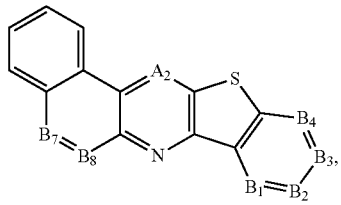
(1-8)

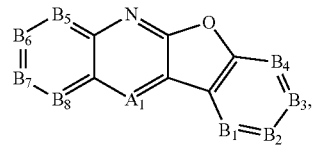
(1-9)

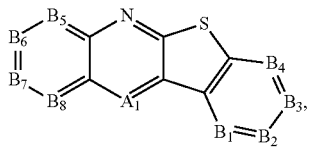
(1-10)

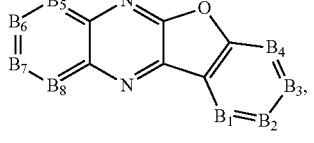
(1-11)

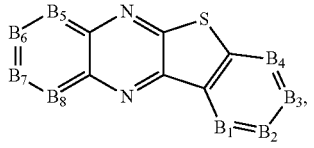
(1-12)

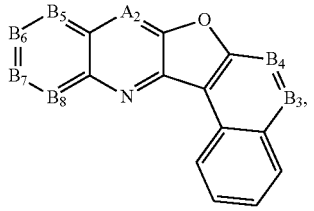
(1-13)

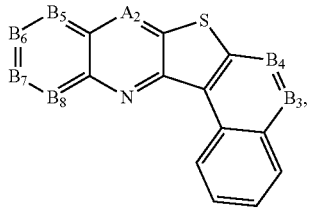
(1-14)

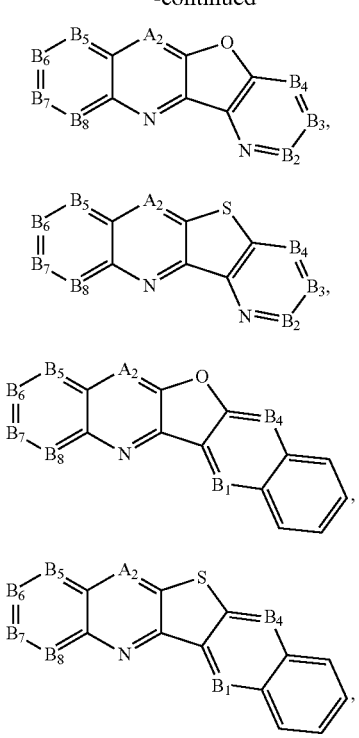

wherein
$B_1$ is $CR^1$ or N;
$B_2$ is CH or N;
$B_3$ is $CR^3$ or N;
$B_4$ is $CR^4$ or N;
$B_5$ is $CR^5$ or N;
$B_6$ is $CR^6$ or N;
$B_7$ is $CR^7$ or N;
$B_8$ is $CR^8$ or N;
preferably, the heterocyclic derivative has one of the formulae (1-1), (1-2), (1-3), (1-4), (1-5), 1-6), (1-7), (1-8), wherein preferably, $A_2$ is $CR^{42}$, $R^{42}$ is E; a group of formula -$(A^1)_o$-$(A^2)_p$-$(A^3)_q$-$(A^4)_r$-$R^{20}$; or a $C_1$-$C_{25}$alkyl group which is unsubstituted or substituted by at least one group E and/or interrupted by D; preferably a group of formula -$(A^1)_o$-$(A^2)_p$-$(A^3)_q$-$(A^4)_r$-$R^{20}$, and $R^1$, $R^3$, $R^4$, $R^5$, $R^6$, $R^7$, and $R^8$ are H.

More preferably,
the heterocyclic derivative has one of the formulae (1-1) and (1-2), wherein preferably, $A_2$ is $CR^{42}$, $R^{42}$ is E; a group of formula -$(A^1)_o$-$(A^2)_p$-$(A^3)_q$-$(A^4)_r$-$R^{20}$; or a $C_1$-$C_{25}$alkyl group which is unsubstituted or substituted by at least one group E and/or interrupted by D; preferably a group of formula -$(A^1)_o$-$(A^2)_p$-$(A^3)_q$-$(A^4)_r$-$R^{20}$, and $R^1$, $R^3$, $R^4$, $R^5$, $R^6$, $R^7$, and $R^8$ are H; or
the heterocyclic derivative has one of the formulae (1-9) and (1-10), wherein preferably, $A_1$ is $CR^{41}$, $R^{41}$ is E; a group of formula -$(A^1)_o$-$(A^2)_p$-$(A^3)_q$-$(A^4)_r$-$R^{20}$; or a $C_1$-$C_{25}$alkyl group which is unsubstituted or substituted by at least one group E and/or interrupted by D; preferably a group of formula -$(A^1)_o$-$(A^2)_p$-$(A^3)_q$-$(A^4)_r$-$R^{20}$, and $R^1$, $R^3$, $R^4$, $R^5$, $R^6$, $R^7$, and $R^8$ are H; or
the heterocyclic derivative has one of the formulae (1-1) and (1-2), wherein preferably, $A_2$ is $CR^{42}$, one of $R^5$, $R^6$, $R^7$, and $R^8$, preferably $R^6$, is E; a group of formula -$(A^1)_o$-$(A^2)_p$-$(A^3)_q$-$(A^4)_r$-$R^{20}$; or a $C_1$-$C_{25}$alkyl group which is unsubstituted or substituted by at least one group E and/or interrupted by D; preferably a group of formula -$(A^1)_o$-$(A^2)_p$-$(A^3)_q$-$(A^4)_r$-$R^{20}$, and $R^{42}$, $R^1$, $R^3$, $R^4$, and the other of $R^5$, $R^6$, $R^7$, and $R^8$ are H.

The groups and residues $A_1$, $A_2$, $R^1$, $R^3$, $R^4$, $R^5$, $R^6$, $R^7$, and $R^8$ have been described above.

Each of formulae (1a), (1-1) and (1-2) is preferably (1a')

wherein X, $B_1$, $B_2$, $B_3$, $B_4$, $B_5$, $B_6$, $B_7$, $B_8$, $A^1$, $A^2$, $A^3$, $A^4$, o, p, q, r, and $R^{20}$ are defined above with respect to formula (1).

Each of formulae (1b), (1-9) and (1-10) is preferably (1b')

wherein X, $B_1$, $B_2$, $B_3$, $B_4$, $B_5$, $B_6$, $B_7$, BE, $A^1$, $A^2$, $A^3$, $A^4$, O, p, q, r, and $R^{20}$ are defined above with respect to formula (1).

Each of formulae (1c), (1-1) and (1-2) is preferably (1c')

wherein X, $B_1$, $B_2$, $B_3$, $B_4$, $B_5$, $B_6$, $B_7$, $B_8$, $A^1$, $A^2$, $A^3$, $A^4$, O, p, q, r, and $R^{20}$ are defined above with respect to formula (1), provided that one of $B_5$, $B_6$, $B_7$, and $B_8$, preferably $B_6$, is a group of formula C-$(A^1)_o$-$(A^2)_p$-$(A^3)_q$-$(A^4)_r$-$R^{20}$.

In a preferred embodiment, in the compounds of formulae (1a'), (1b'), and (1c'), $B_1$, $B_2$, $B_3$, and $B_4$ are CH.

In a preferred embodiment, in the compounds of formulae (1a') and (1b'), $B_5$, $B_6$, $B_7$, and $B_8$ are CH.

In a preferred embodiment, in the compounds of formula (1c'), $B_5$, $B_6$, $B_7$, and $B_8$ not a group of formula C-$(A^1)_o$-$(A^2)_p$-$(A^3)_q$-$(A^4)_r$-$R^{20}$ are CH.

In the compounds of formulae (1a), (1b), (1c), (1a'), (1b'), and (1c'), $A^1$, $A^2$, $A^3$, and $A^4$ are preferably independently of each other a $C_6$-$C_{24}$ arylene group which is unsubstituted or substituted by G. $C_6$-$C_{24}$ arylene group and G have been described above with respect to formula (1).

$A^1$, $A^2$, $A^3$, $A^4$ are more preferably independently of each other phenylene, naphthylene, biphenylene, or terphenylene, which optionally can be substituted by G Still more preferably, $A^1, A^2, A^3, A^4$ are independently of each other

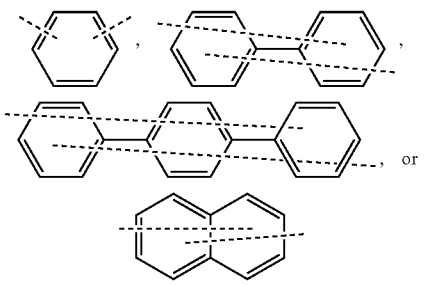, or wherein the dotted lines are bonding sites.

$A^1, A^2, A^3, A^4$ are even more preferably in each occurrence independently of each other a group of the formula:

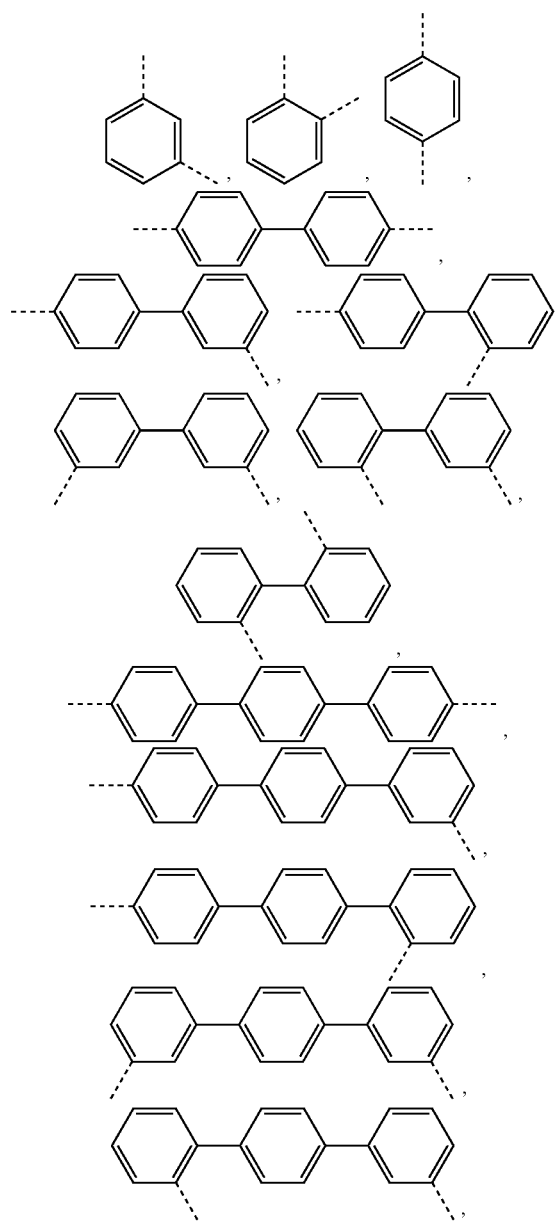

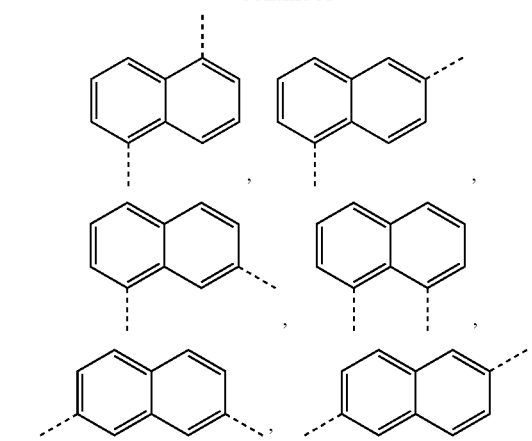

wherein the dotted lines are bonding sites.

In the compounds of formulae (1a), (1b), (1c), (1a'), (1b'), and (1c'), a group of formula $-(A^1)_o-(A^2)_p-(A^3)_q-(A^4)_r-$ is preferably a $C_6$-$C_{24}$ arylene group which is unsubstituted or substituted by G, more preferably phenylene, naphthylene, biphenylene, or terphenylene which is unsubstituted or substituted by G:

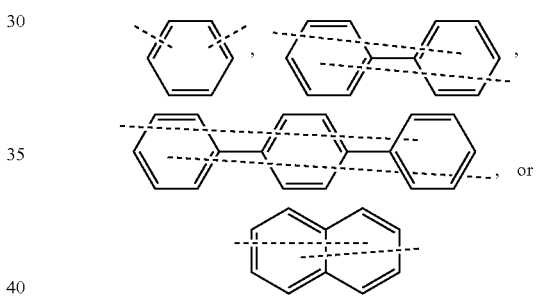

wherein the dotted lines are bonding sites.

Still more preferably, a group of formula $-(A^1)_o-(A^2)_p-(A^3)_q-(A^4)_r-$ is a group of the formula:

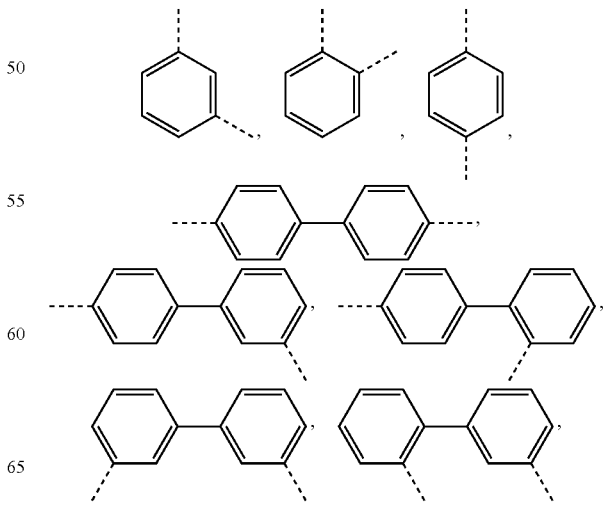

-continued

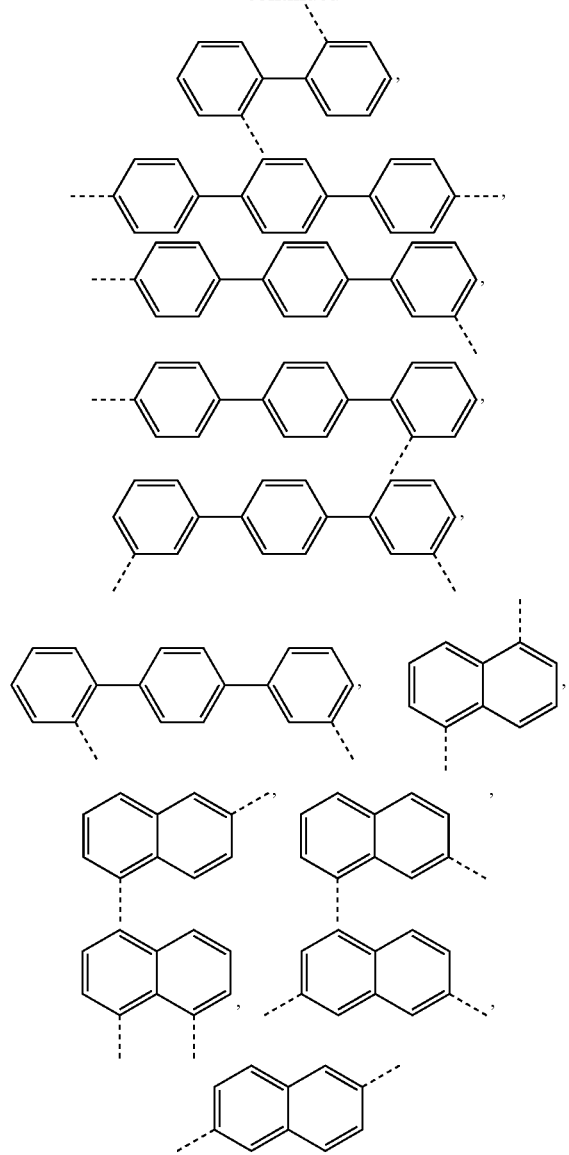

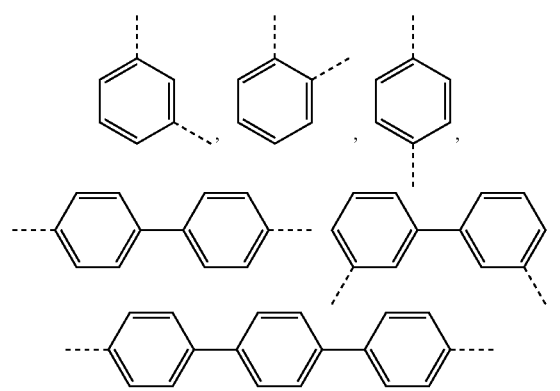

wherein the dotted lines are bonding sites.

Further more preferably, a group of formula $-(A^1)_o-(A^2)_p-(A^3)_q-(A^4)_r-$ is a group of the formula:

-continued

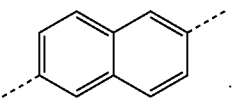

In the compounds of formulae (1a), (1b), (1c), (1a'), (1b'), and (1c'), o is 0 or 1, p is 0 or 1, q is 0 or 1, and r is 0 or 1, preferably o is 0 or 1, p is 0 or 1, q is 0, and r is 0, wherein $(A^1)_o$ is a direct bond when o is 0, $(A^2)_p$ is a direct bond when p is 0, $(A^3)_q$ is a direct bond when q is 0, and $(A^4)_r$ is a direct bond when r is 0.

$R^{20}$ in the compounds of formulae (1a), (1b), (1c), (1a'), (1b'), and (1c') has been described above with respect to formula (1), and preferably a $C_6$-$C_{60}$ aryl group which is unsubstituted or substituted by G or a $C_1$-$C_{60}$ heteroaryl group which is unsubstituted or substituted by G. $C_6$-$C_{60}$ aryl group, $C_1$-$C_{60}$ heteroaryl group, and G have been described above with respect to formula (1).

The $C_6$-$C_{60}$ aryl group is preferably a fused (condensed) $C_{10}$-$C_{60}$ aryl group, more preferably a fused $C_{10}$-$C_{30}$ aryl group, and still more preferably a fused $C_{14}$-$C_{25}$ aryl group, such as anthryl, fluoranthenyl, triphenylenyl, or fluorenyl, which may be unsubstituted or substituted by G.

Preferably, the fused $C_{10}$-$C_{60}$ aryl group is a group of the following formula which may be unsubstituted or substituted by G:

(4a)

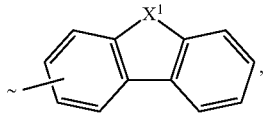

(14a)

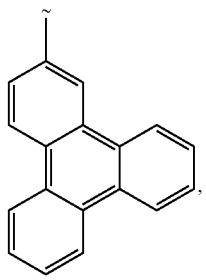

(15a)

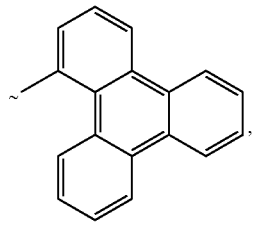

(16a)

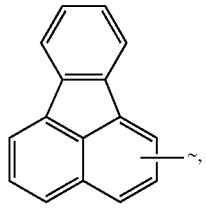

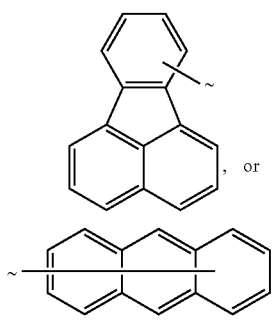

(17a)

wherein $X^1$ is $C(R^{21})_2$;

$R^{21}$ is a $C_1$-$C_{25}$alkyl group which can optionally be substituted by E and or interrupted by D, a $C_6$-$C_{24}$aryl group which can optionally be substituted by G, or a $C_1$-$C_{24}$heteroaryl group which can optionally be substituted by G; and/or two adjacent groups of the groups may form together with the atom to which they are bonded a ring structure which can optionally be substituted by G; and ~ are bonding sites.

More preferably, the fused $C_{10}$-$C_{60}$ aryl group is a group of the following formula which is unsubstituted or substituted by G:

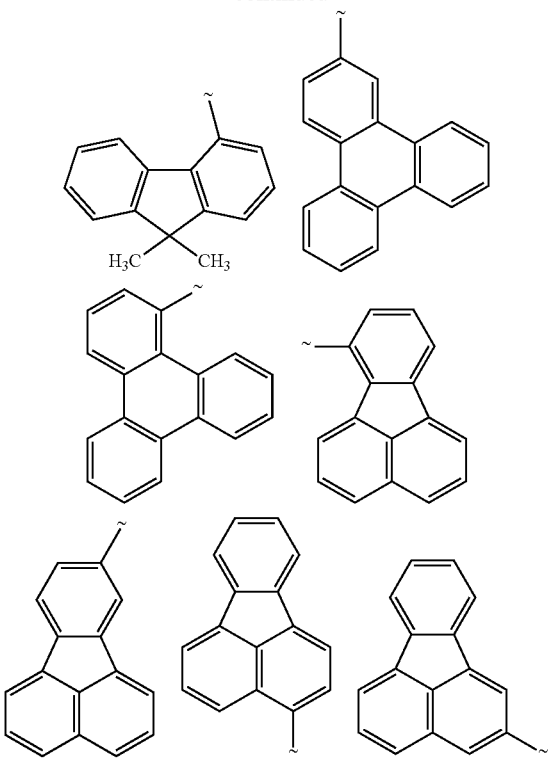

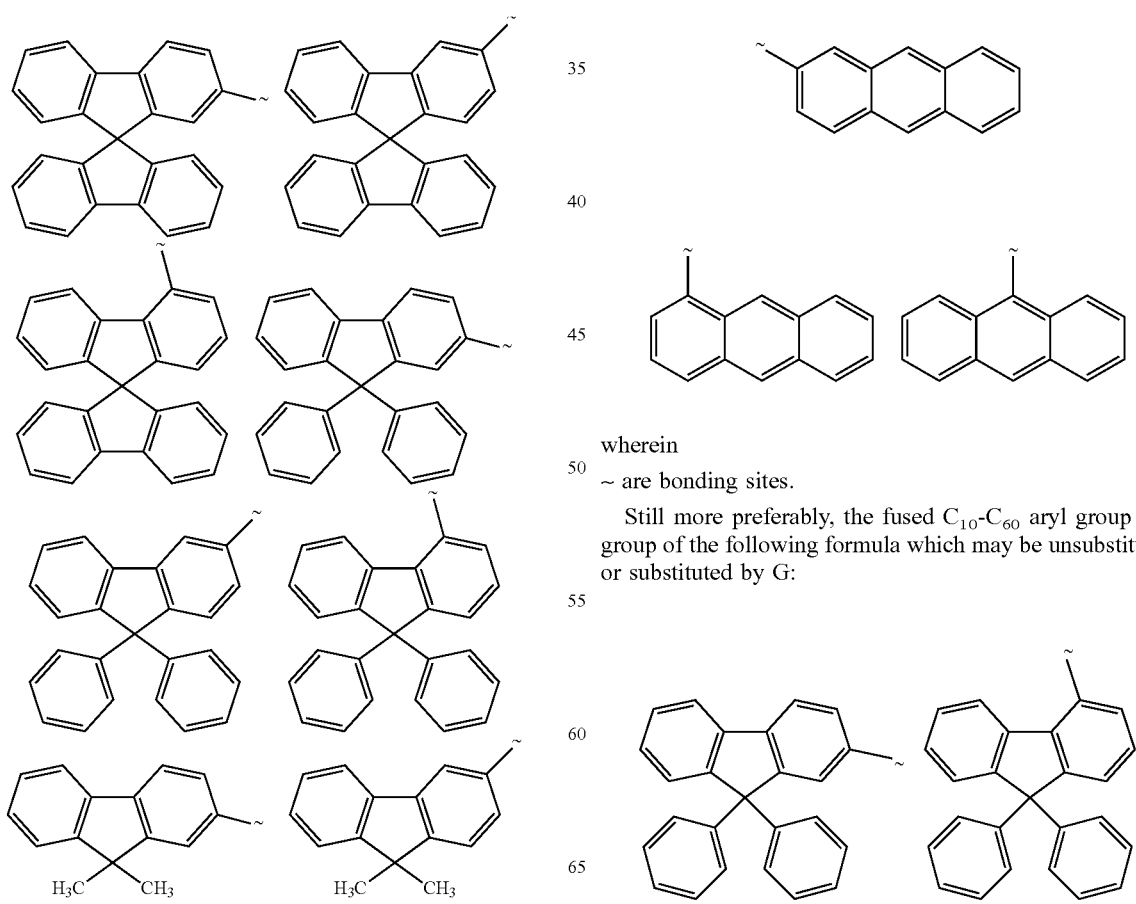

wherein

~ are bonding sites.

Still more preferably, the fused $C_{10}$-$C_{60}$ aryl group is a group of the following formula which may be unsubstituted or substituted by G:

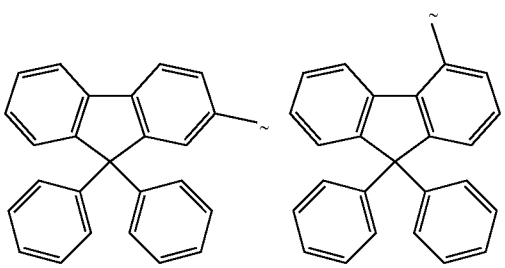

-continued

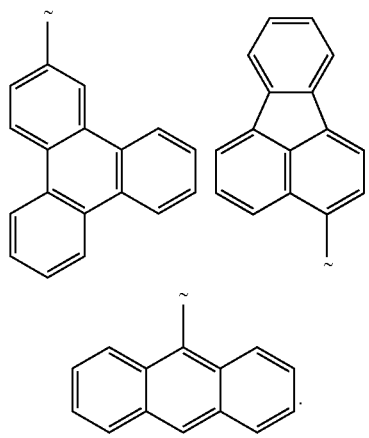

The $C_1$-$C_{60}$ heteroaryl group is preferably a $C_1$-$C_{30}$ heteroaryl group, more preferably a $C_1$-$C_{12}$ heteroaryl group, still more preferably an aromatic heterocyclic ring with six ring atoms, each of which may have a fused ring, wherein the hetero ring atom is N, and each of the heteroaryl group, the ring with six ring atoms and the fused ring is unsubstituted or substituted by G; further more preferably pyridyl which may have a fused ring, pyrimidyl which may have a fused ring, triazinyl, or phenanthrolinyl, which is unsubstituted or substituted by G; still further more preferably pyridyl, pyrimidyl, triazinyl, or phenanthrolinyl, which is unsubstituted or substituted by G; and even further more preferably pyrimidyl, triazinyl, or phenanthrolinyl, which is unsubstituted or substituted by G.

The $C_1$-$C_{60}$ heteroaryl group is preferably the group of formula (9), (10), or (19), more preferably the group of formula (9) or (19), which are described above with respect to $R^{20}$ of formula (1):

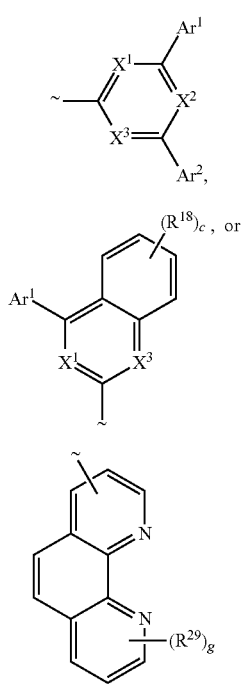

wherein
$X^1$, $X^2$ and $X^3$ are independently of each other $CR^{19}$ or N, wherein in formula (9) at least one of $X^1$ to $X^3$ is N, and wherein in formulae (10) and (19) at least one of $X^1$ and $X^3$ is N;
$Ar^1$ and $Ar^2$ are independently of each other a $C_6$-$C_{24}$ aryl group which is optionally substituted by G, or a $C_1$-$C_{24}$ heteroaryl group which is optionally substituted by G;
$R^{18}$, $R^{19}$, and $R^{29}$ are independently of each other H, a $C_6$-$C_{24}$ aryl group which can be substituted by G, a $C_1$-$C_{24}$ heteroaryl group which can be substituted by G, or a $C_1$-$C_{25}$alkyl group which can optionally be substituted by E and/or interrupted by D; preferably, H;
c is 0, 1, 2, 3 or 4; preferably 0, 1 or 2; more preferably 0 or 1; still more preferably 0;
g is 0, 1, 2 or 3; preferably 0, 1 or 2; more preferably 0; and
~ are bonding sites.
Preferred groups (9), (10), and (19) are:

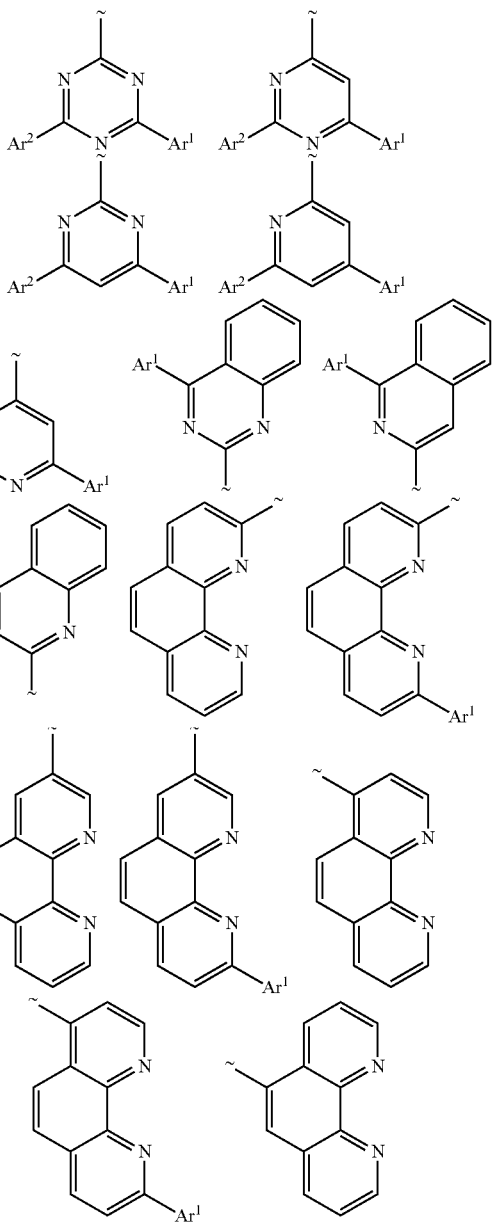

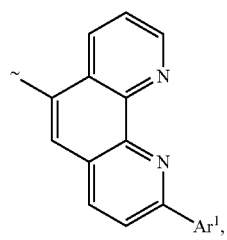
wherein
Ar[1] and Ar[2] are preferably independently of each other a $C_6$-$C_{24}$ aryl group which is optionally substituted by G, more preferably an unsubstituted $C_6$-$C_{24}$ aryl group, and still more preferably an unsubstituted phenyl or an unsubstituted biphenyl; and
~ are bonding sites.
The groups (9) are preferably:
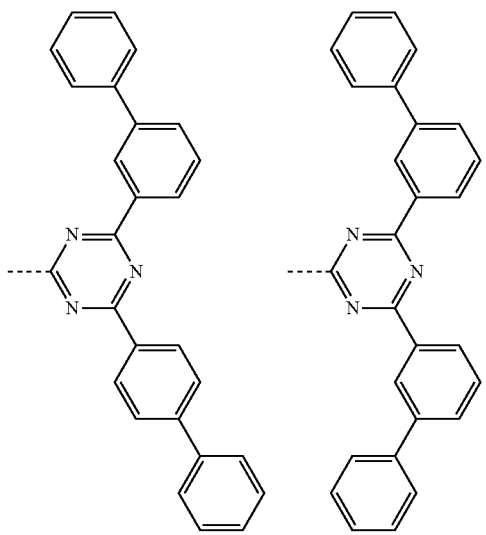
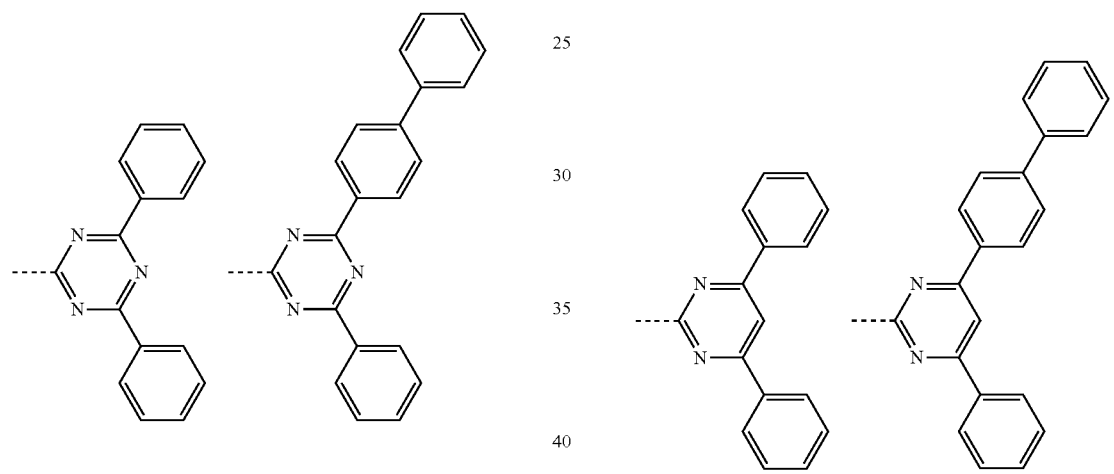
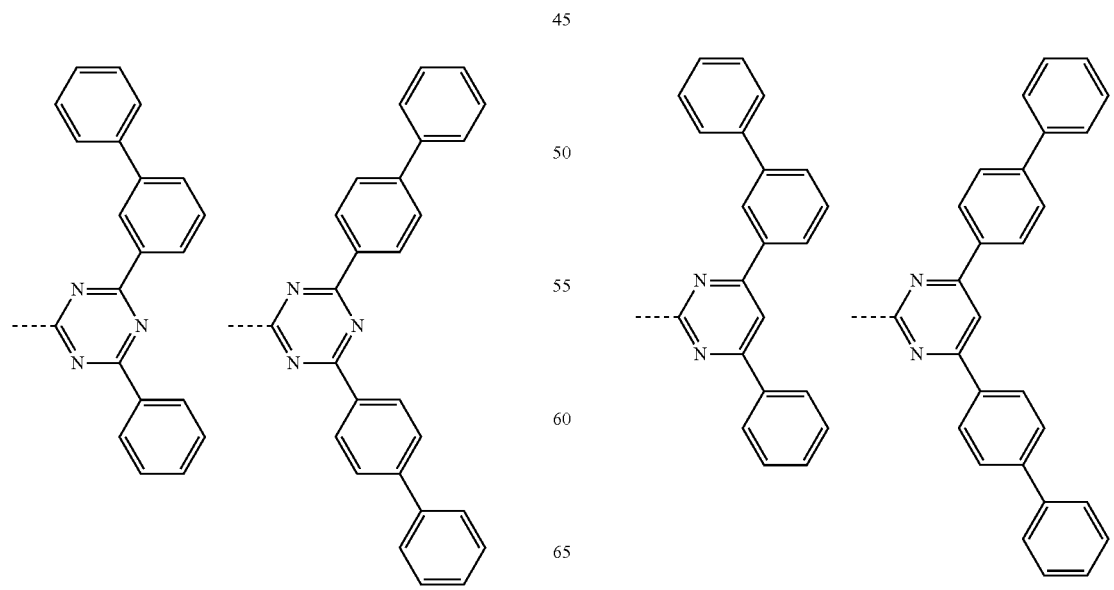

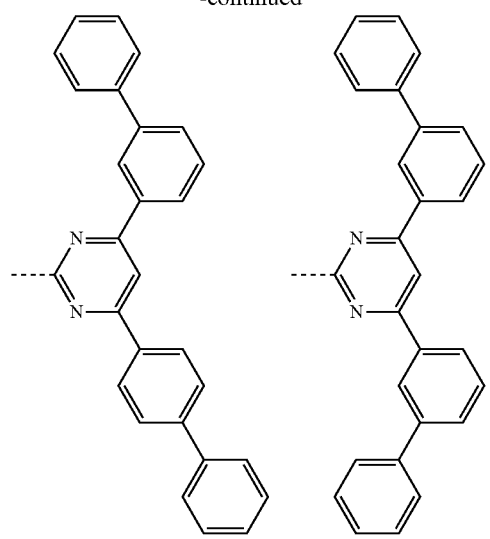
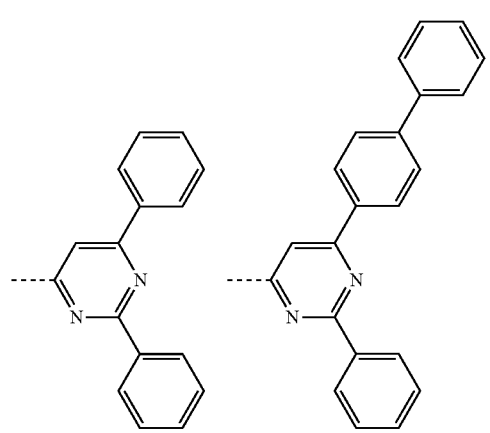
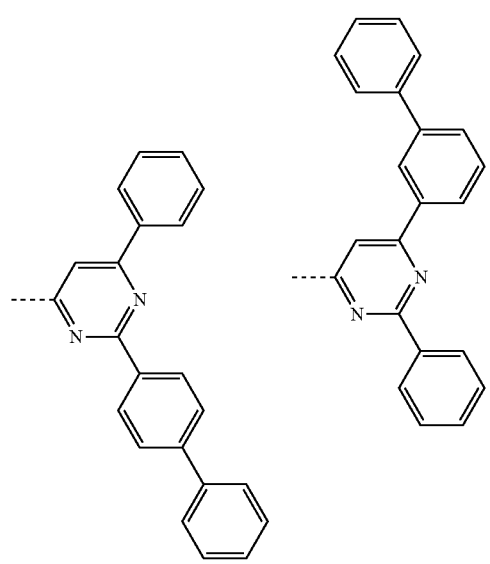
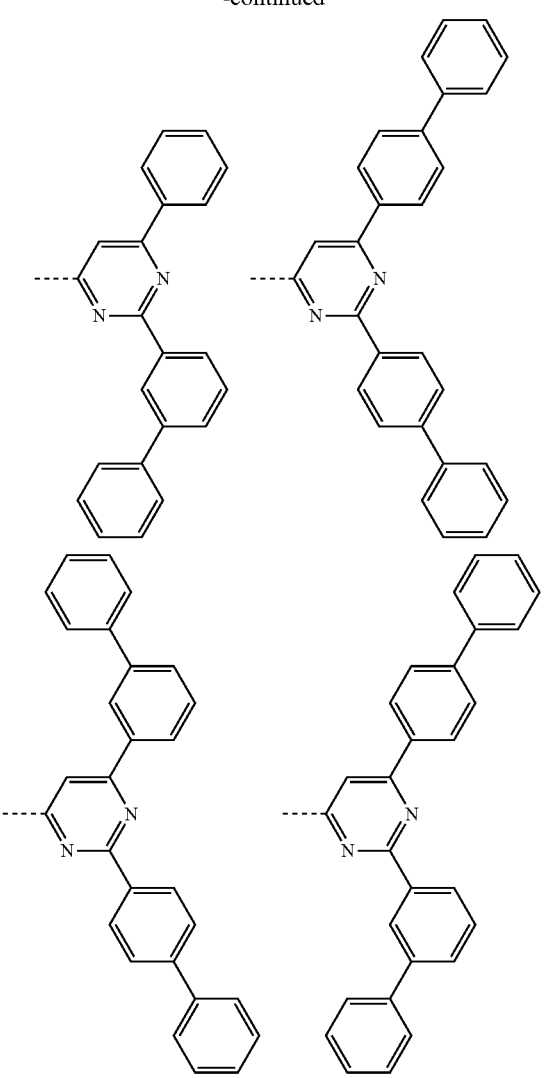
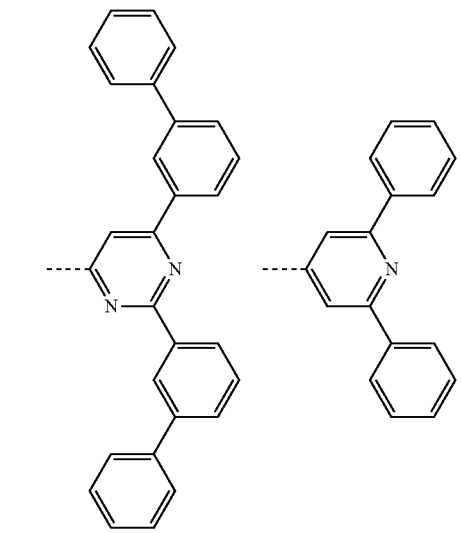

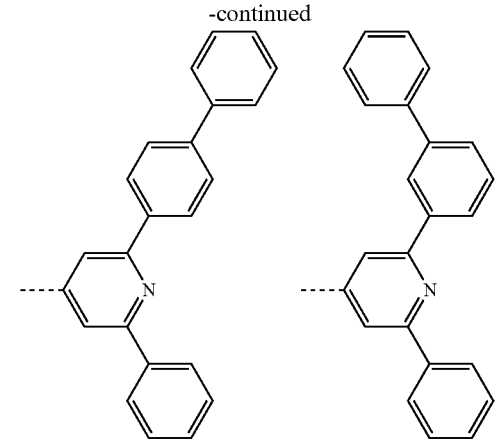
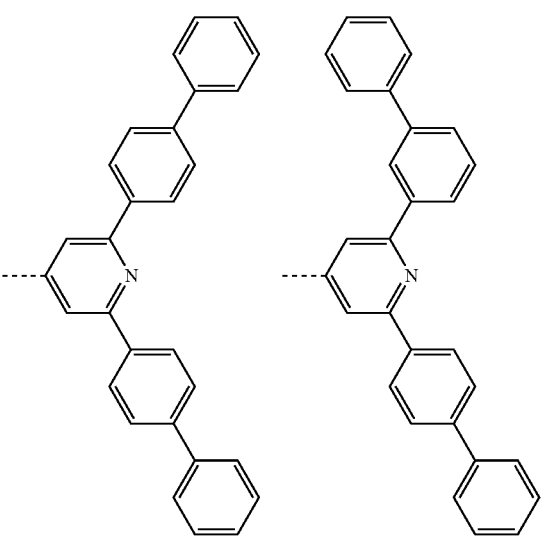
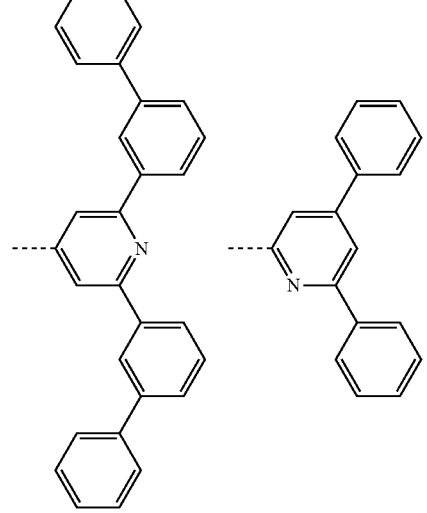
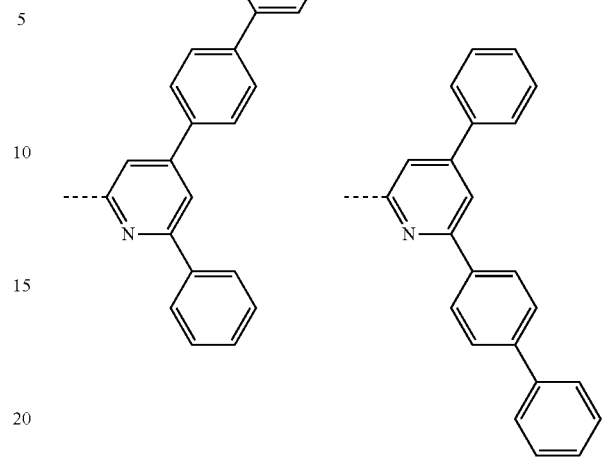
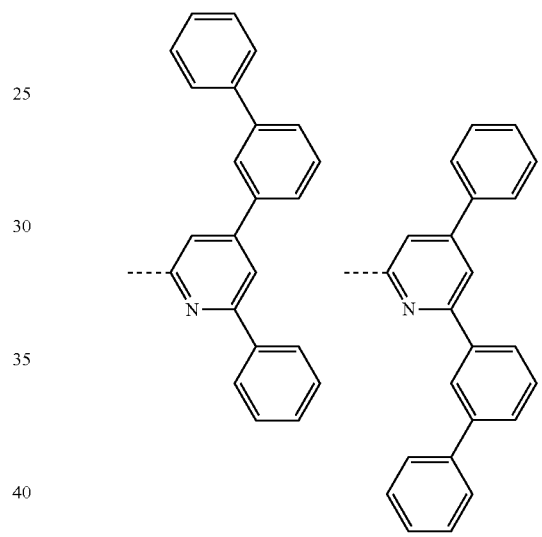
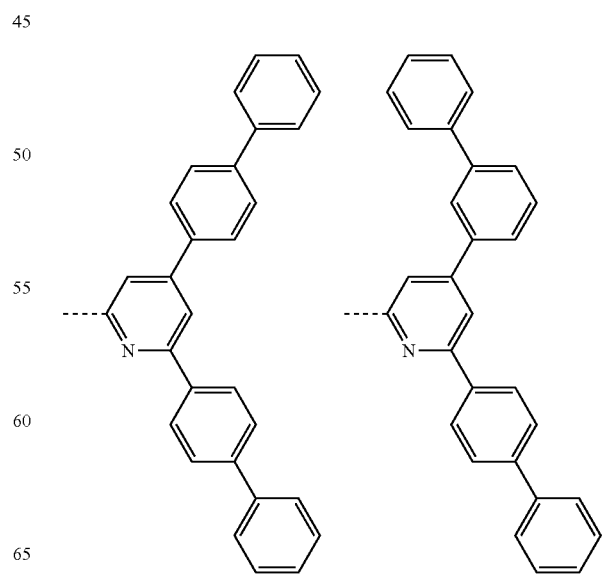

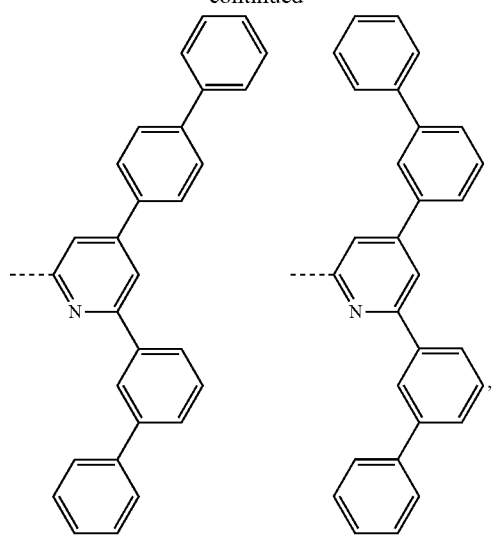
wherein the dotted lines are bonding sites; and more preferably:
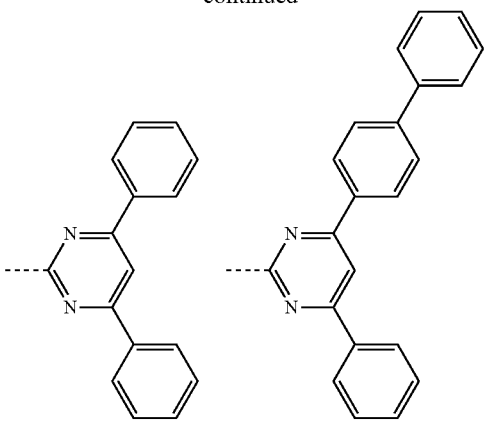
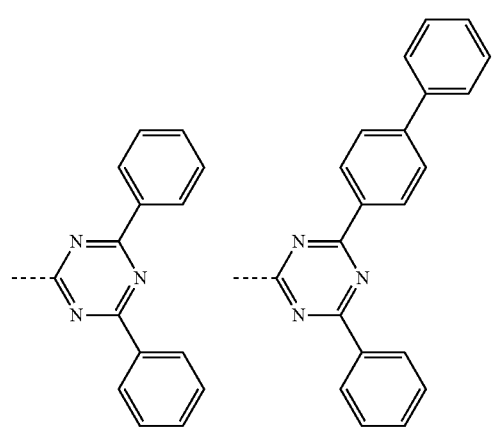
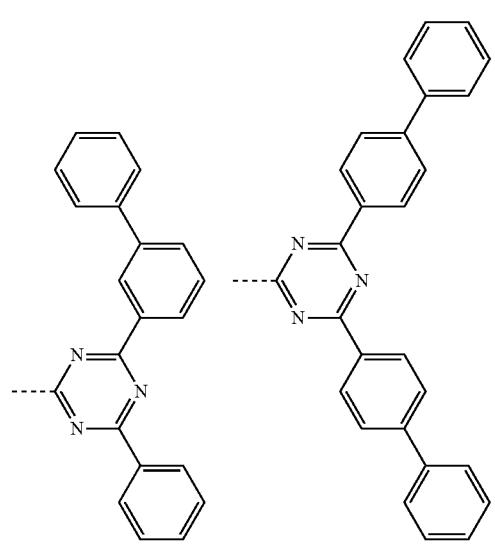
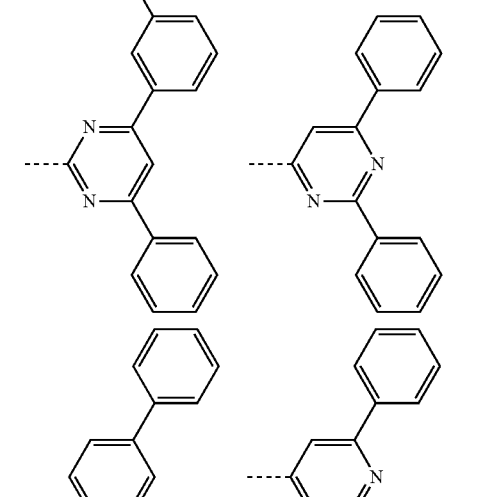
wherein the dotted lines are bonding sites.

The groups (10) are preferably:
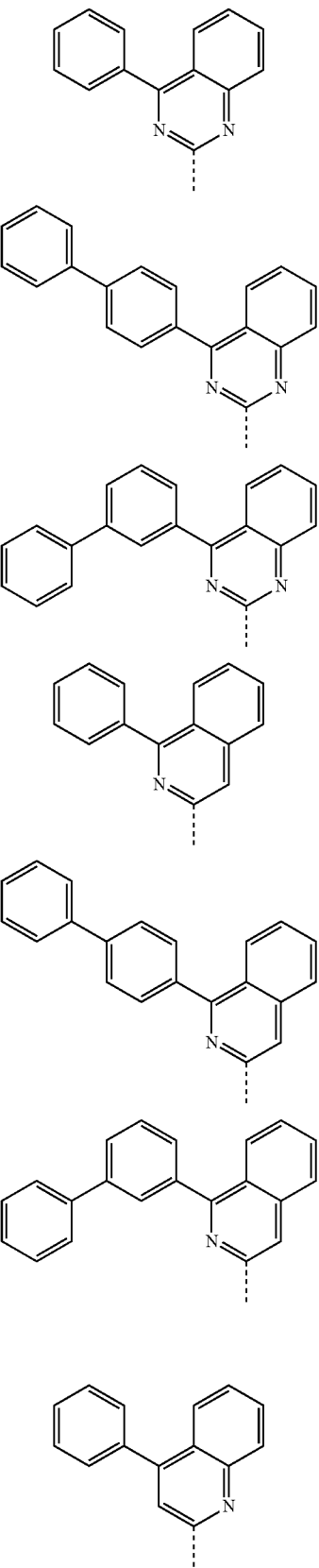
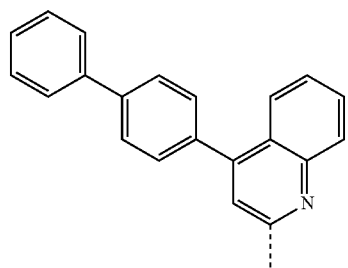
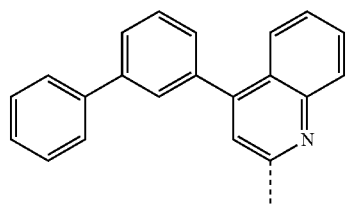
wherein the dotted lines are bonding sites.
The groups (19) are preferably:
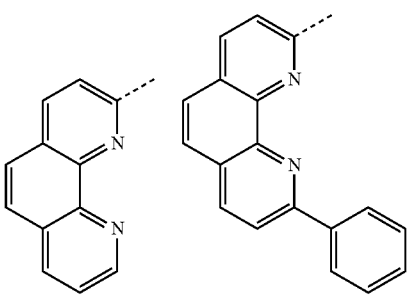
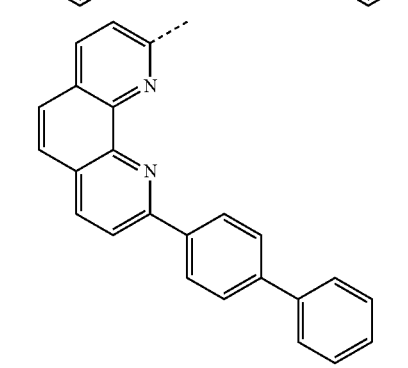
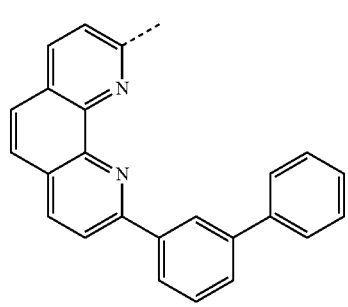

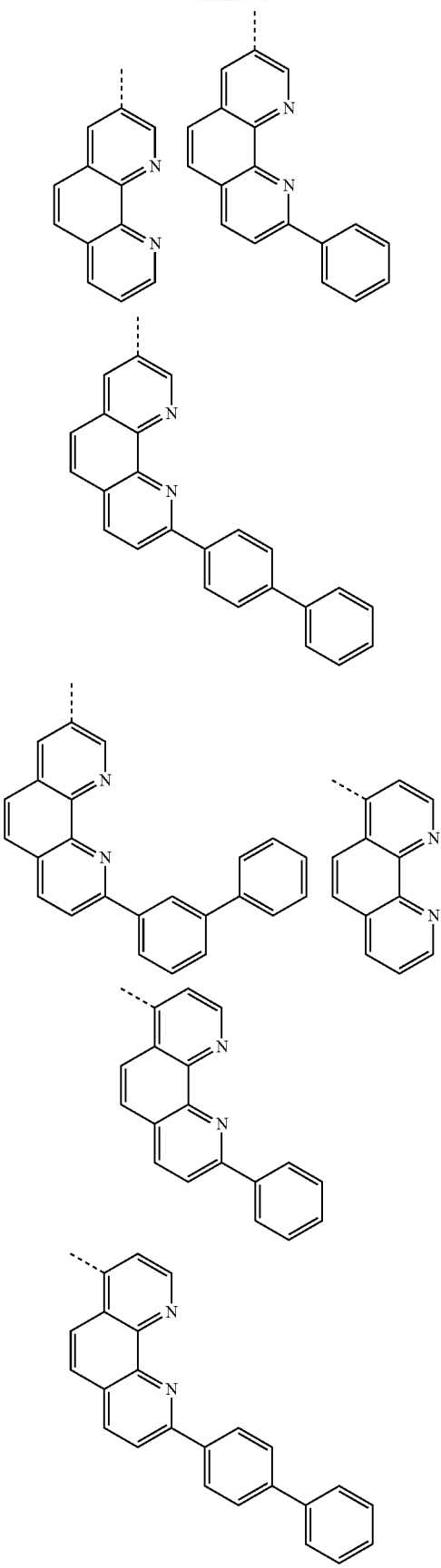
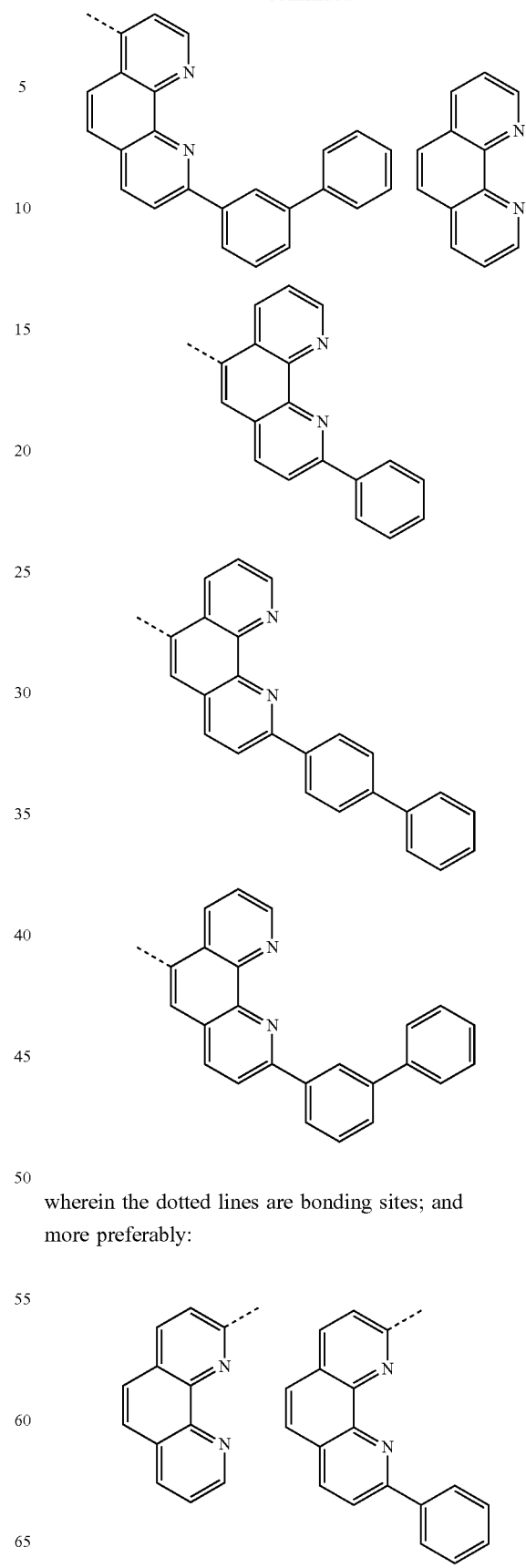
wherein the dotted lines are bonding sites; and more preferably:

-continued

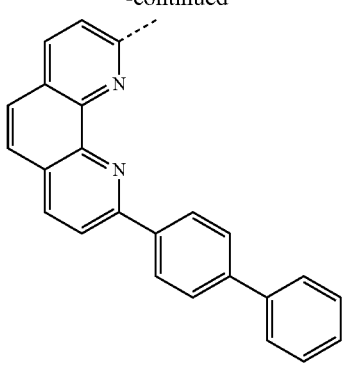

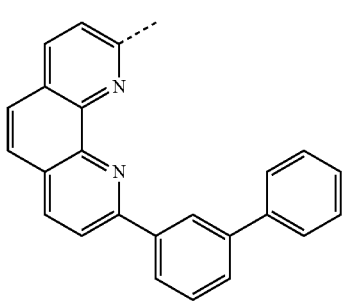

wherein the dotted lines are bonding sites.

In a preferred embodiment of the present invention, the group of formula $-(A^1)_o-(A^2)_p-(A^3)_q-(A^4)_r-R^{20}$ can be

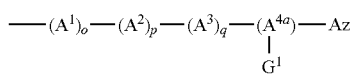

wherein
$A^1$, $A^2$, $A^3$, o, p, and q have been described above;
Az is a $C_1$-$C_{60}$ heteroaryl group, preferably a $C_1$-$C_{30}$ heteroaryl group, more preferably a $C_1$-$C_{12}$ heteroaryl group, and still more preferably an aromatic heterocyclic ring with six ring atoms, each of which may have a fused ring; and $A^{4a}$-$G^1$ corresponds to $A^4$ which is substituted by $G^1$, $G^1$ being the same as G in formula (1).

$A^{4a}$-$G^1$ is preferably a $C_6$-$C_{24}$arylene group substituted by $G^1$, wherein $G^1$ is preferably a $C_6$-$C_{60}$ aryl group, more preferably a fused $C_{10}$-$C_{30}$ aryl group, and still more preferably a fused $C_{14}$-$C_{25}$ aryl group, which are unsubstituted or substituted by G.

The aromatic heterocyclic ring with six ring atoms which may have a fused ring has been described above with respect to $R^{20}$ of formulae (1a), (1b), (1c), (1a'), (1b'), and (1c').

$A^4$ of the group $A^{4a}$-$G^1$ has been described above with respect to $A^1$, $A^2$, $A^3$, $A^4$ of formulae (1a), (1b), (1c), (1a'), (1b'), and (1c').

The $C_6$-$C_{24}$ arylene group for $G^1$ has described above with respect to $R^{20}$ of formulae (1a), (1b), (1c), (1a'), (1b'), and (1c').

Most preferred compounds of formula (1) are mentioned below:

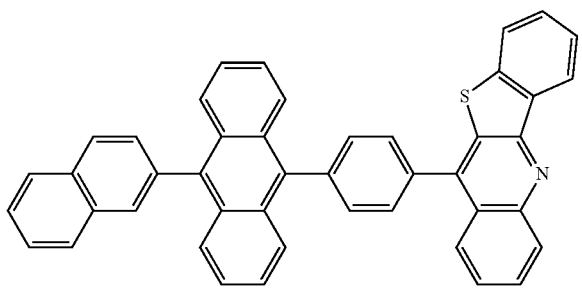

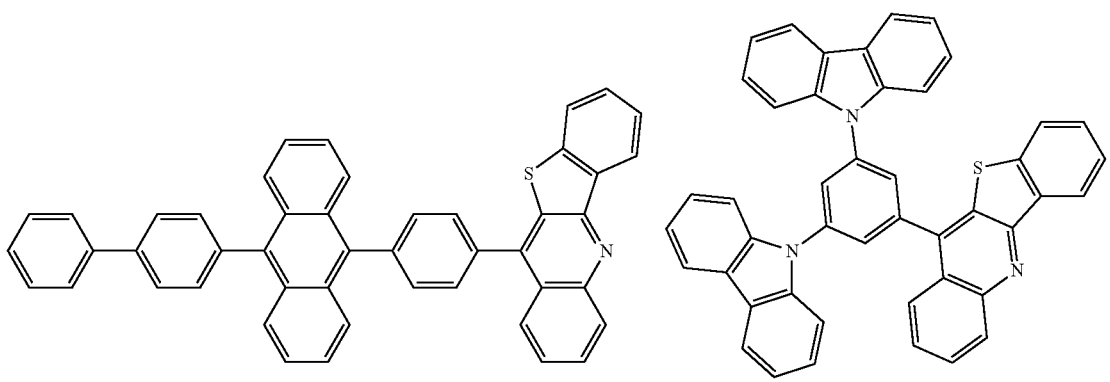

-continued
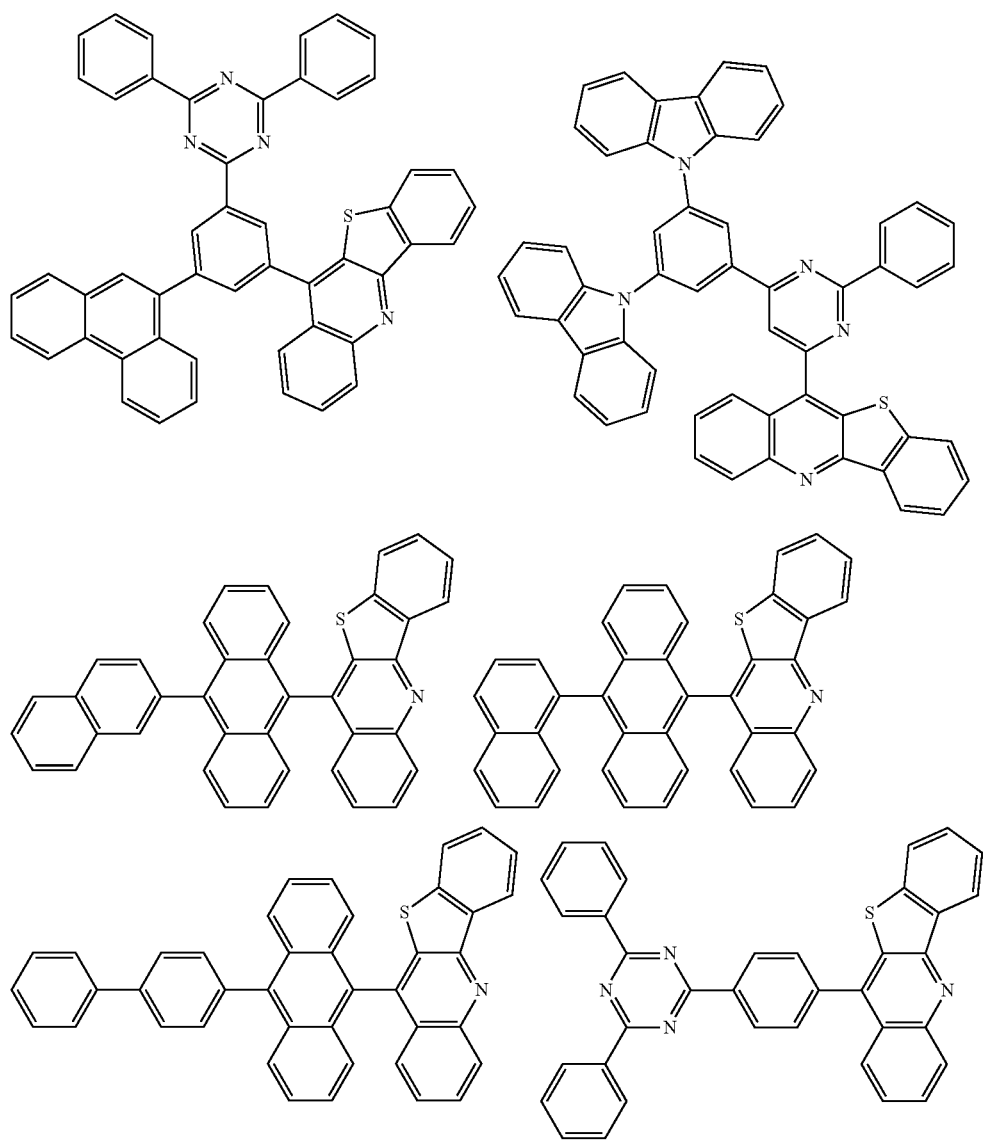
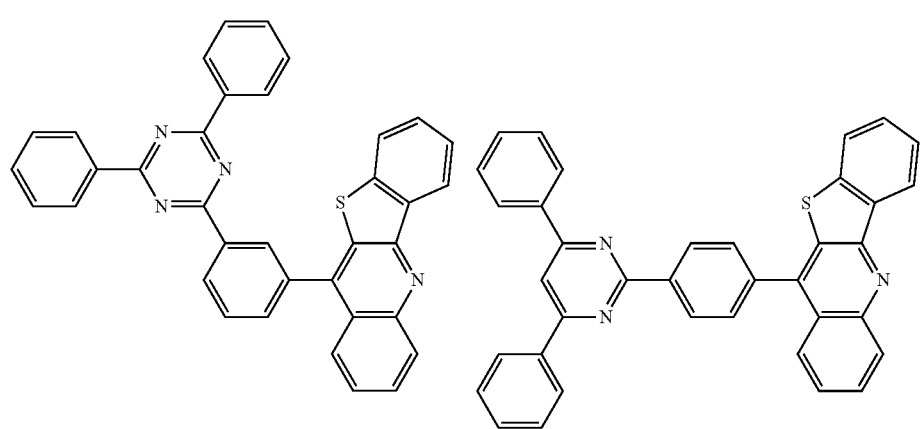

-continued
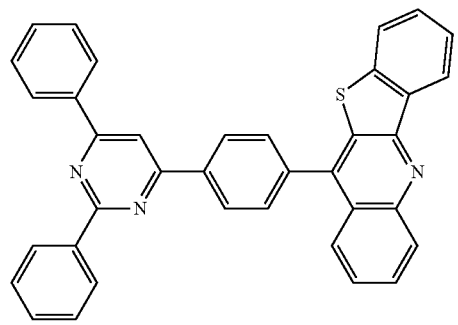
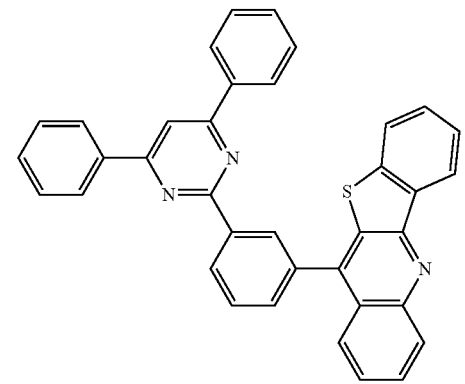
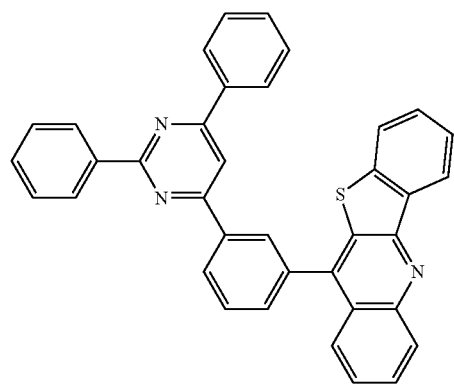
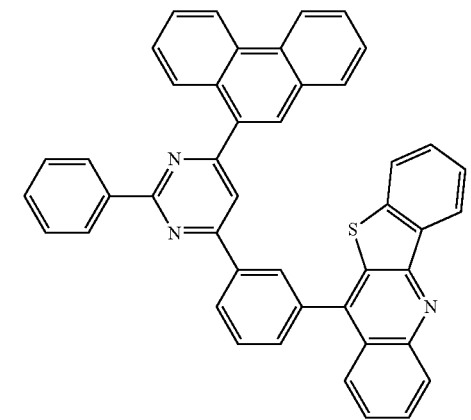
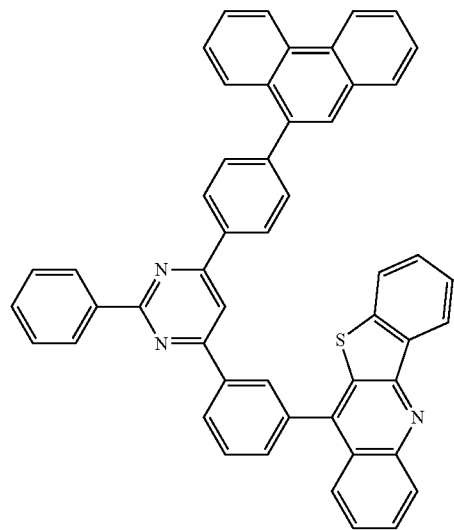
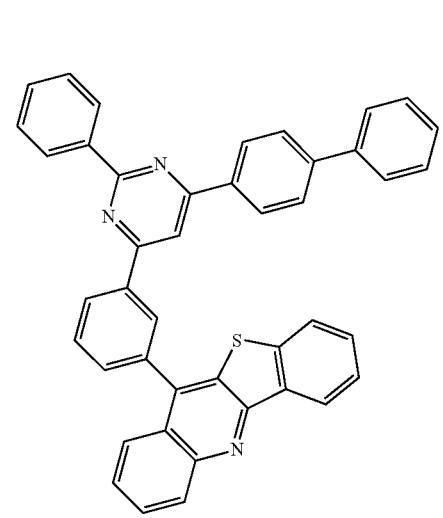

-continued
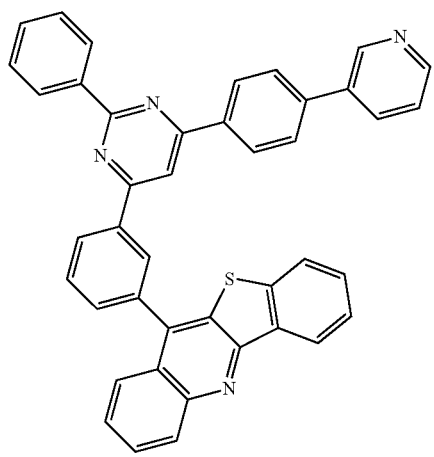
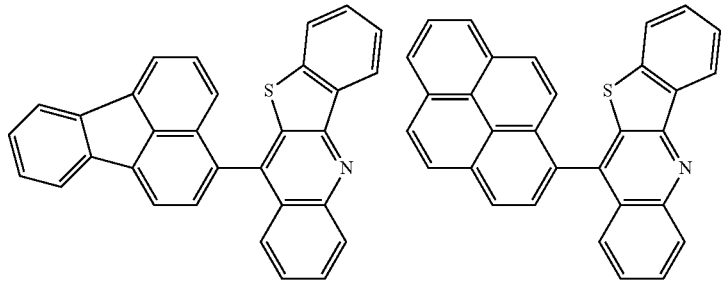
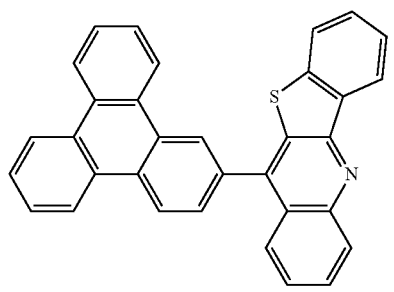
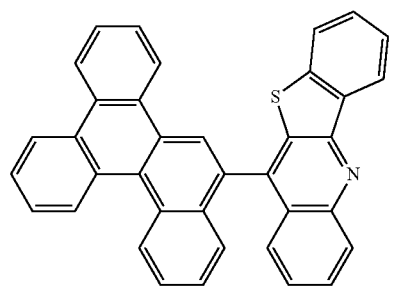
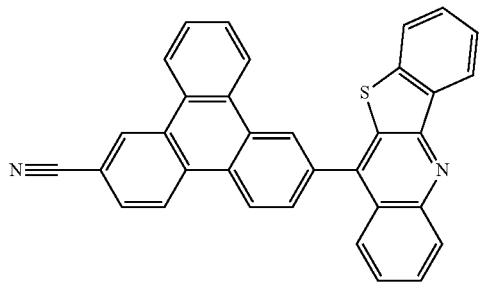
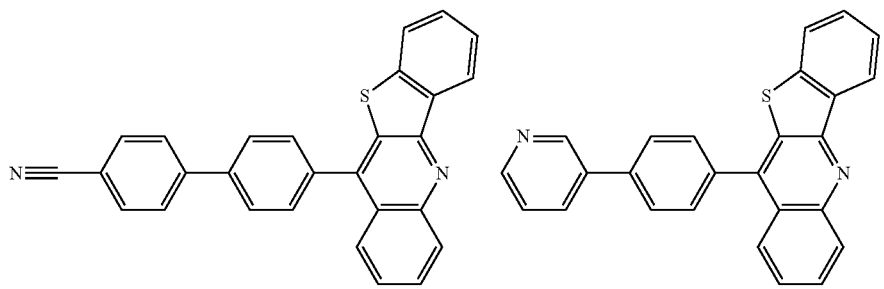
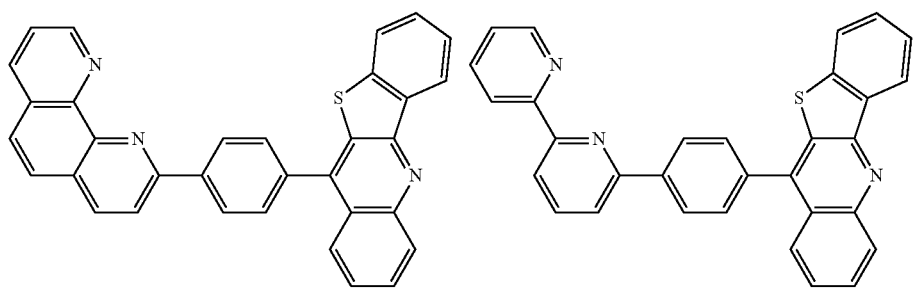

-continued
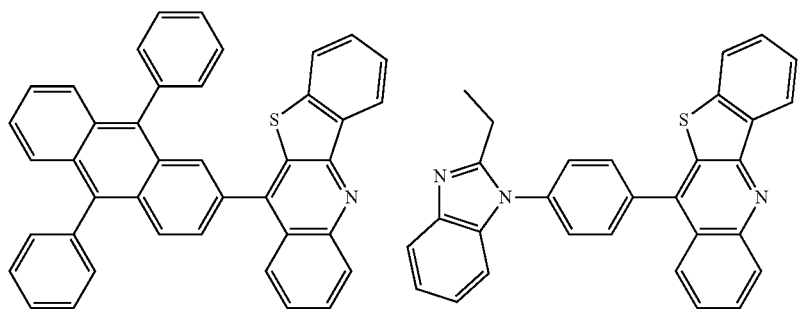
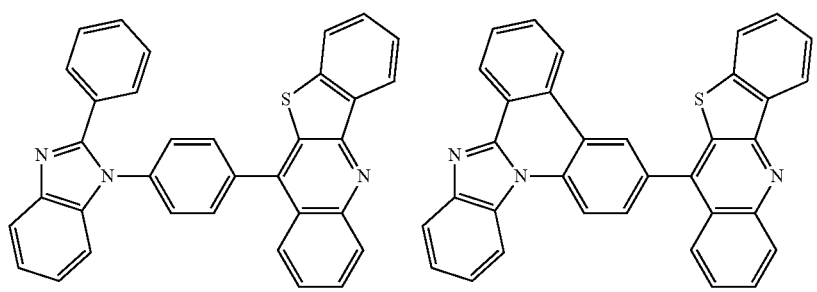
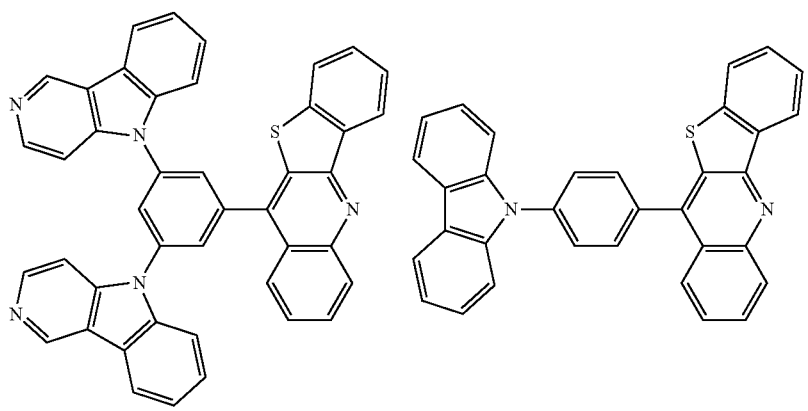
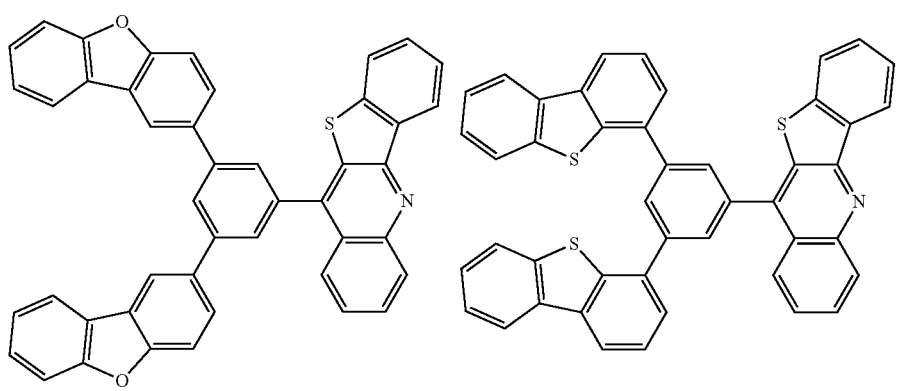

-continued
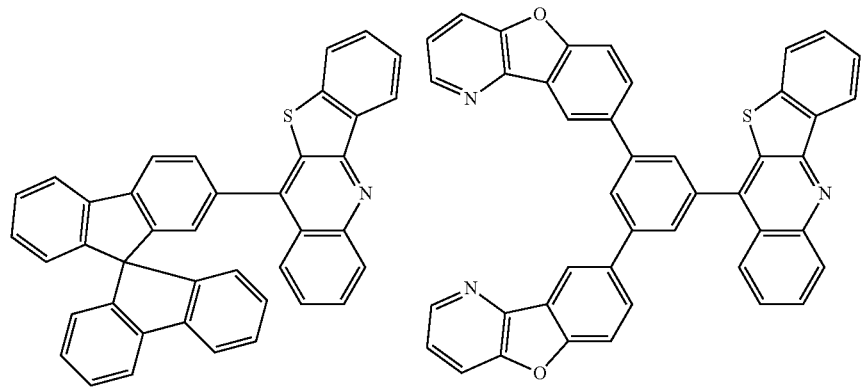
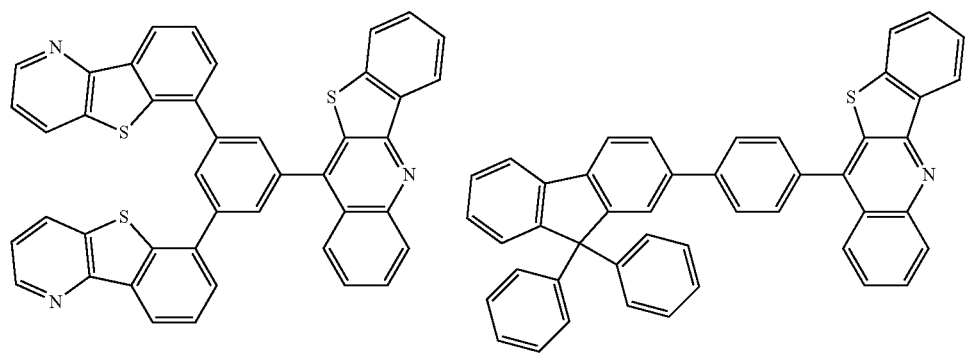
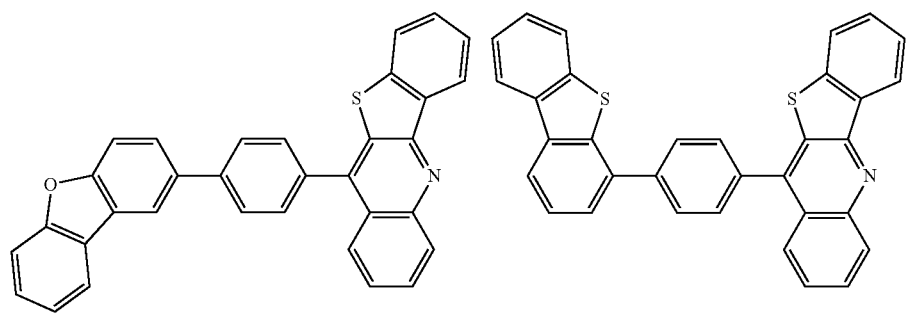
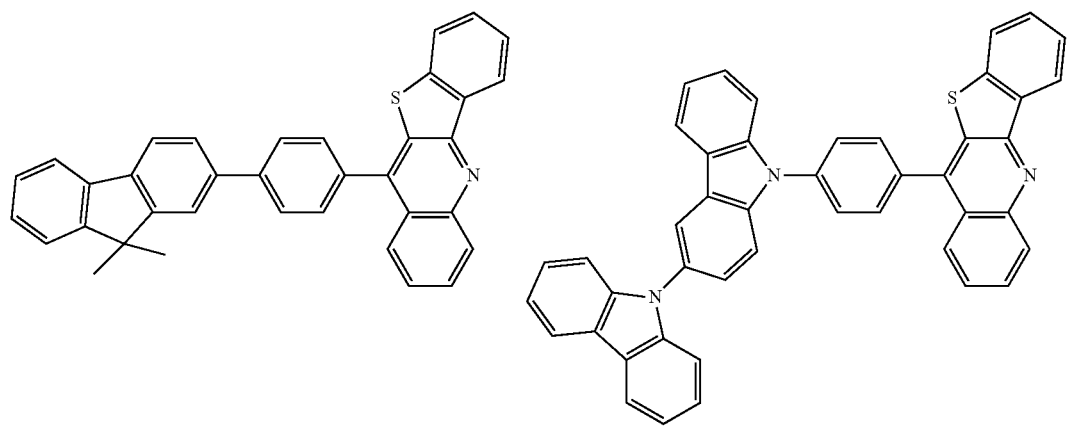

-continued
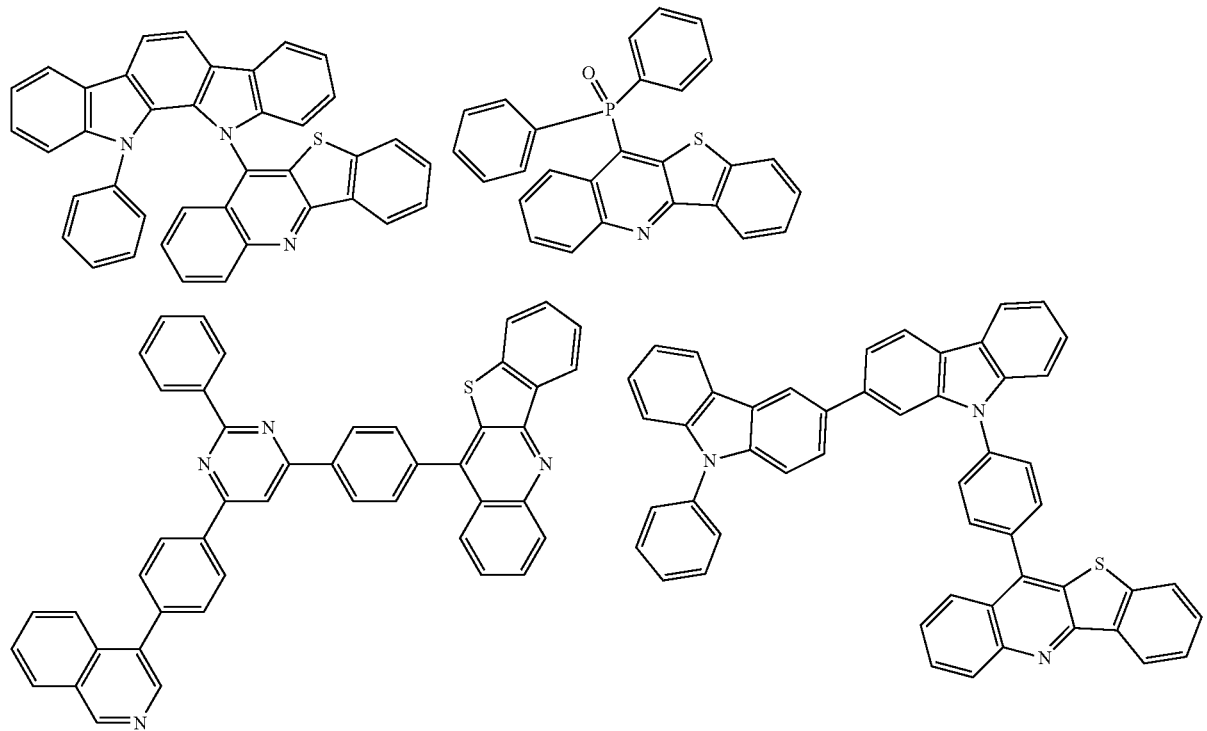
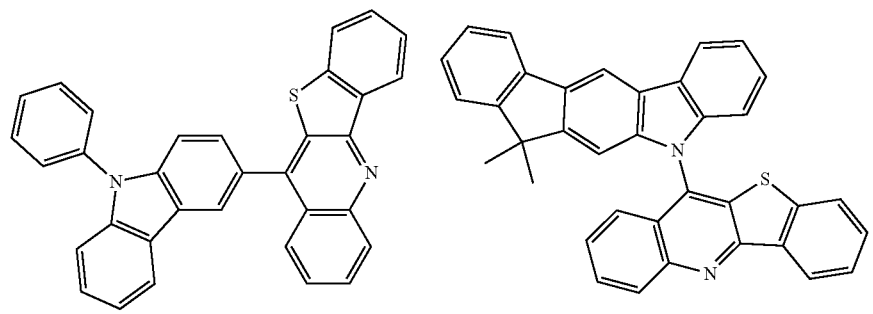
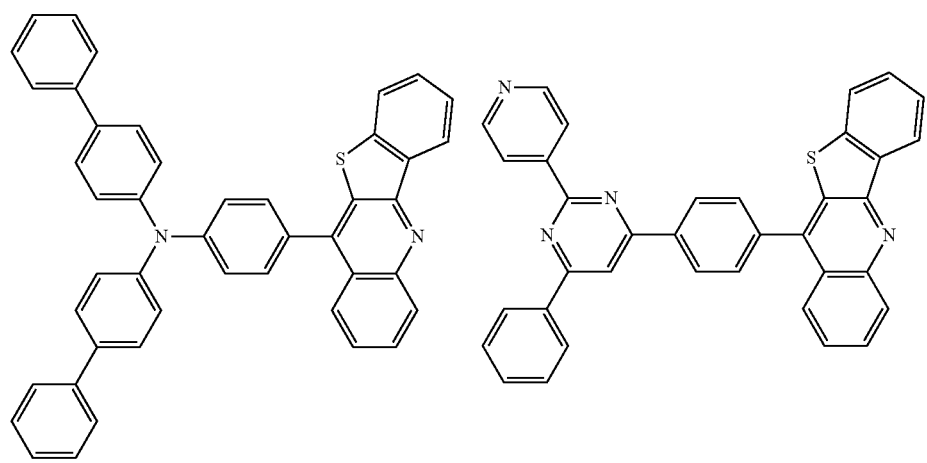

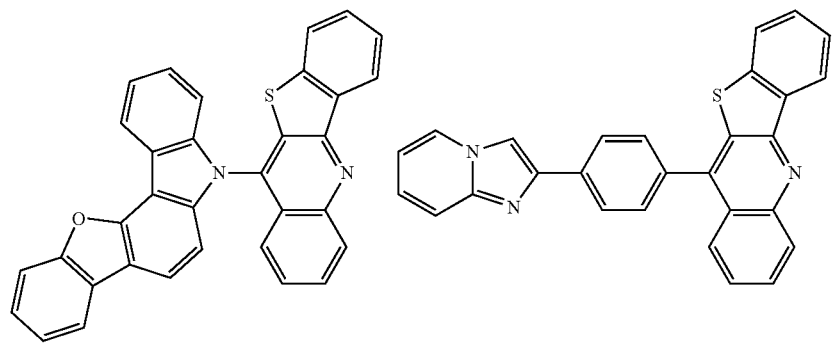
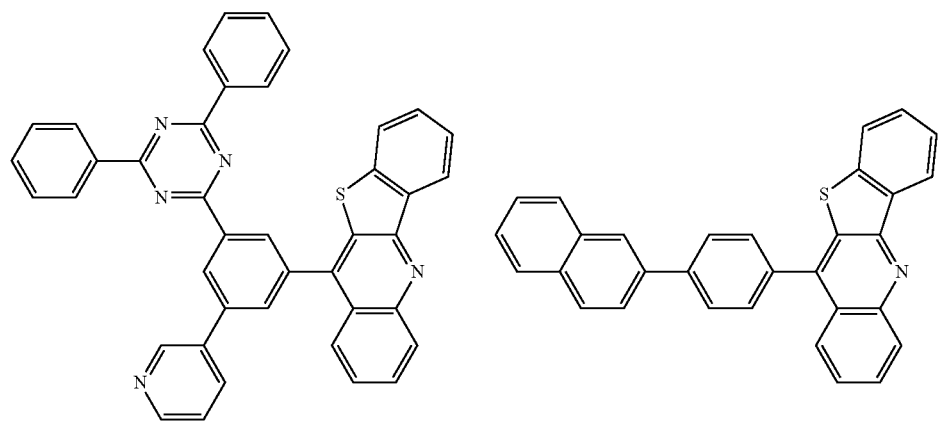
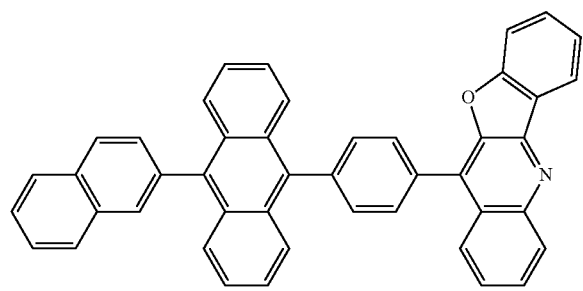

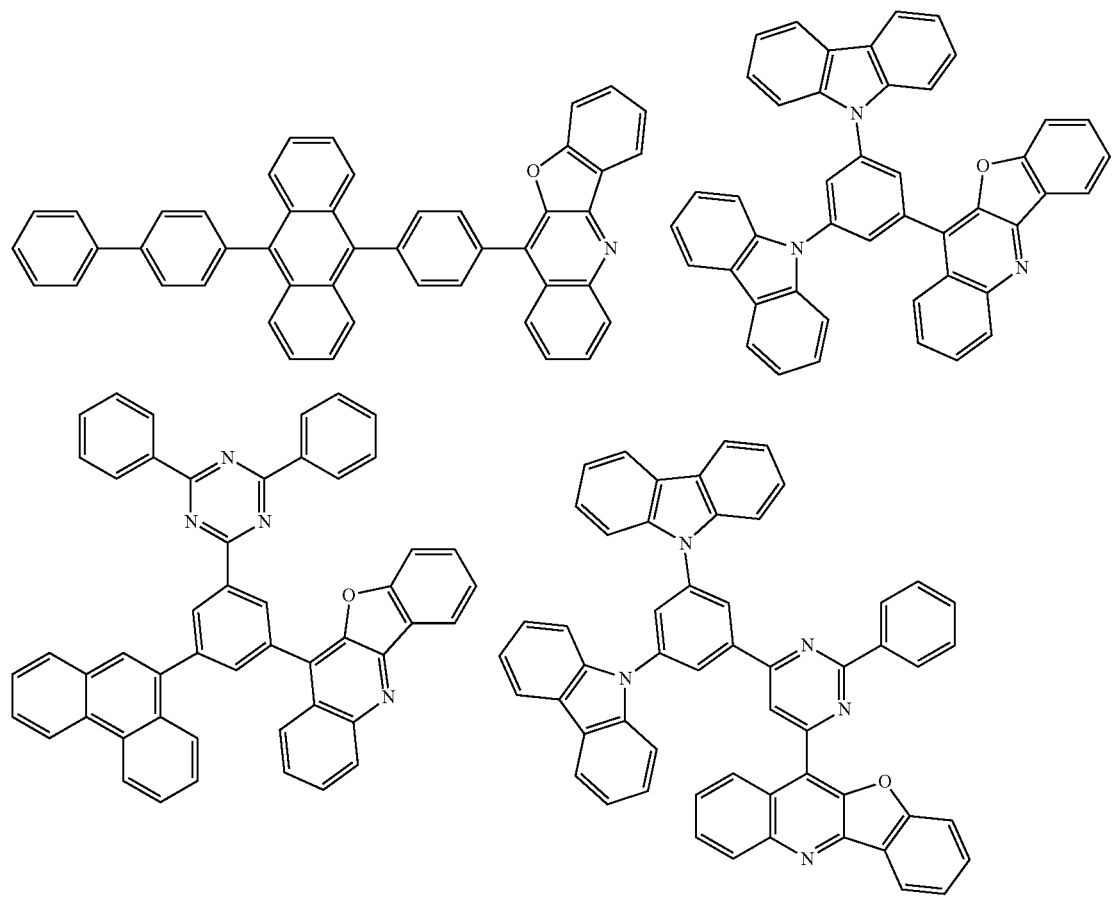
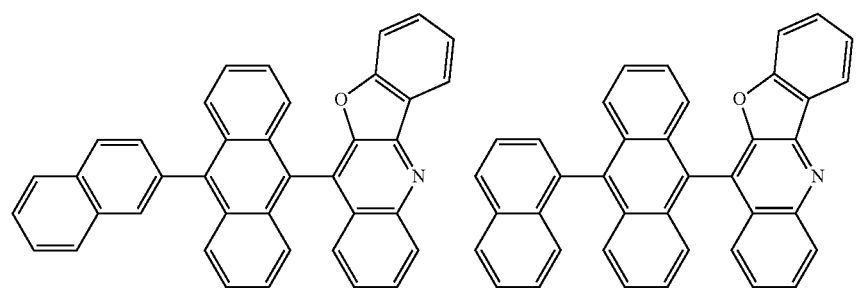
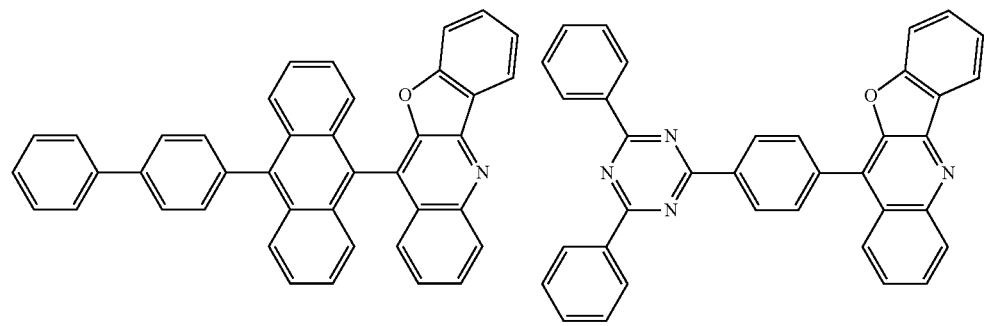

-continued
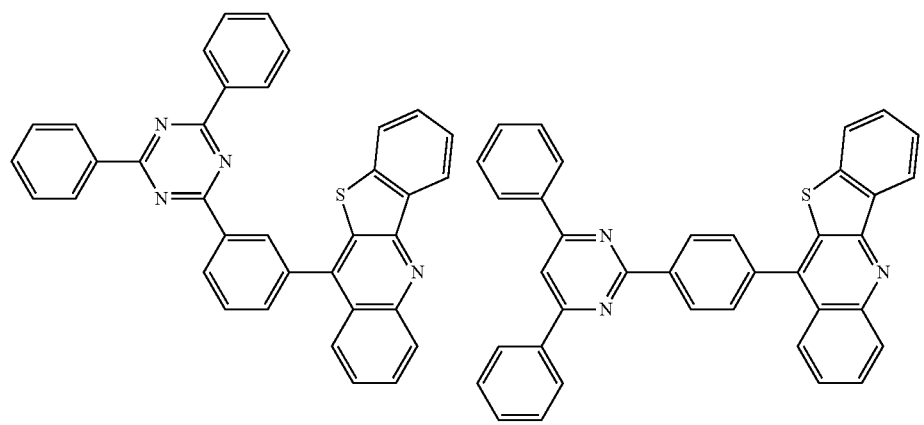
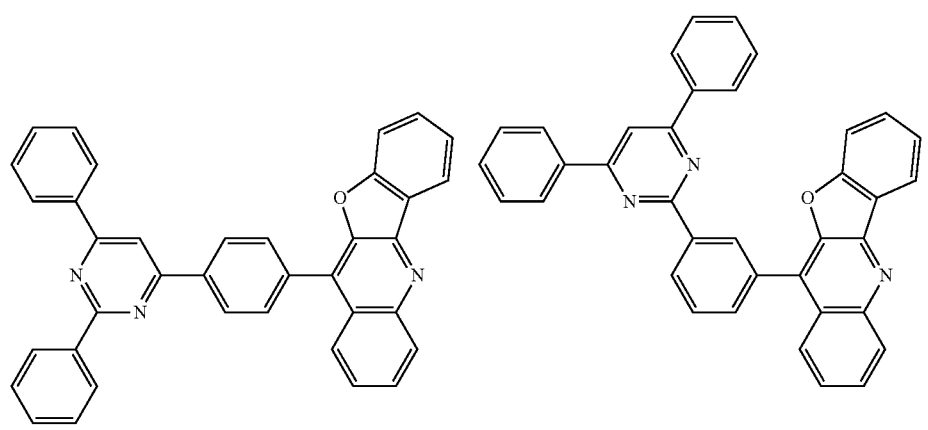
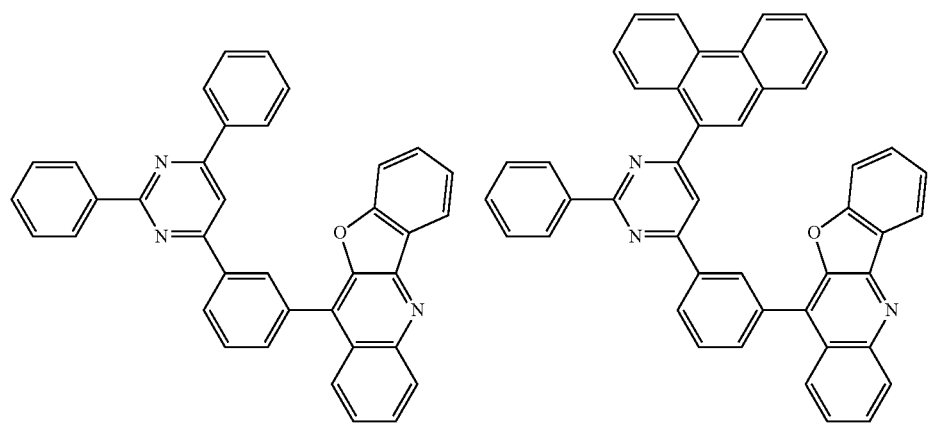

-continued
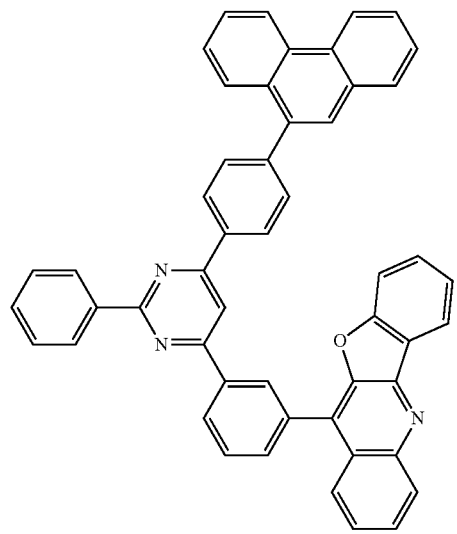
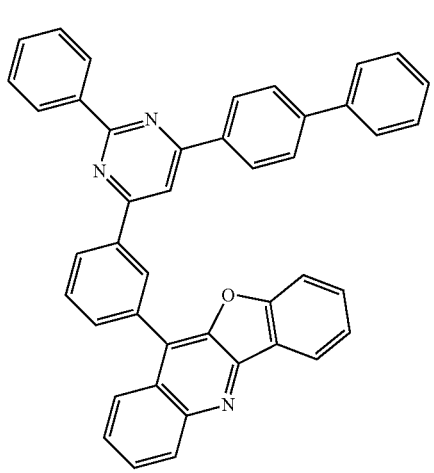
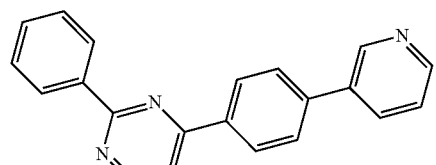
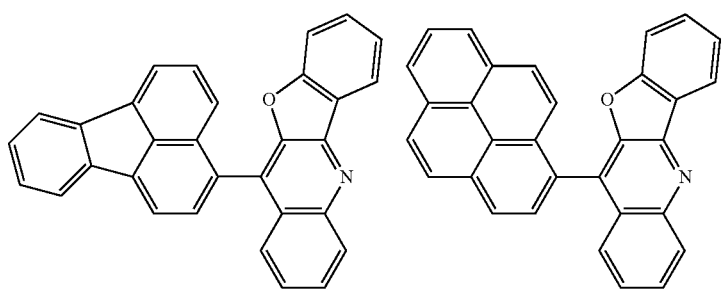
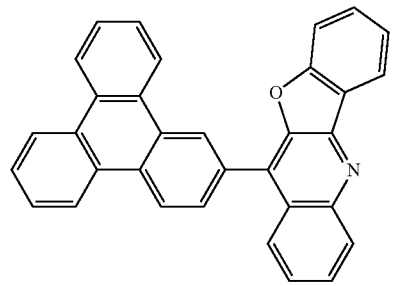
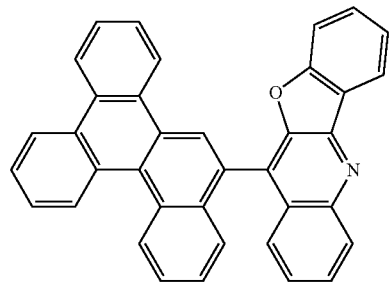
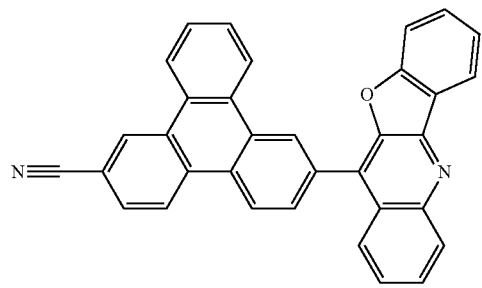

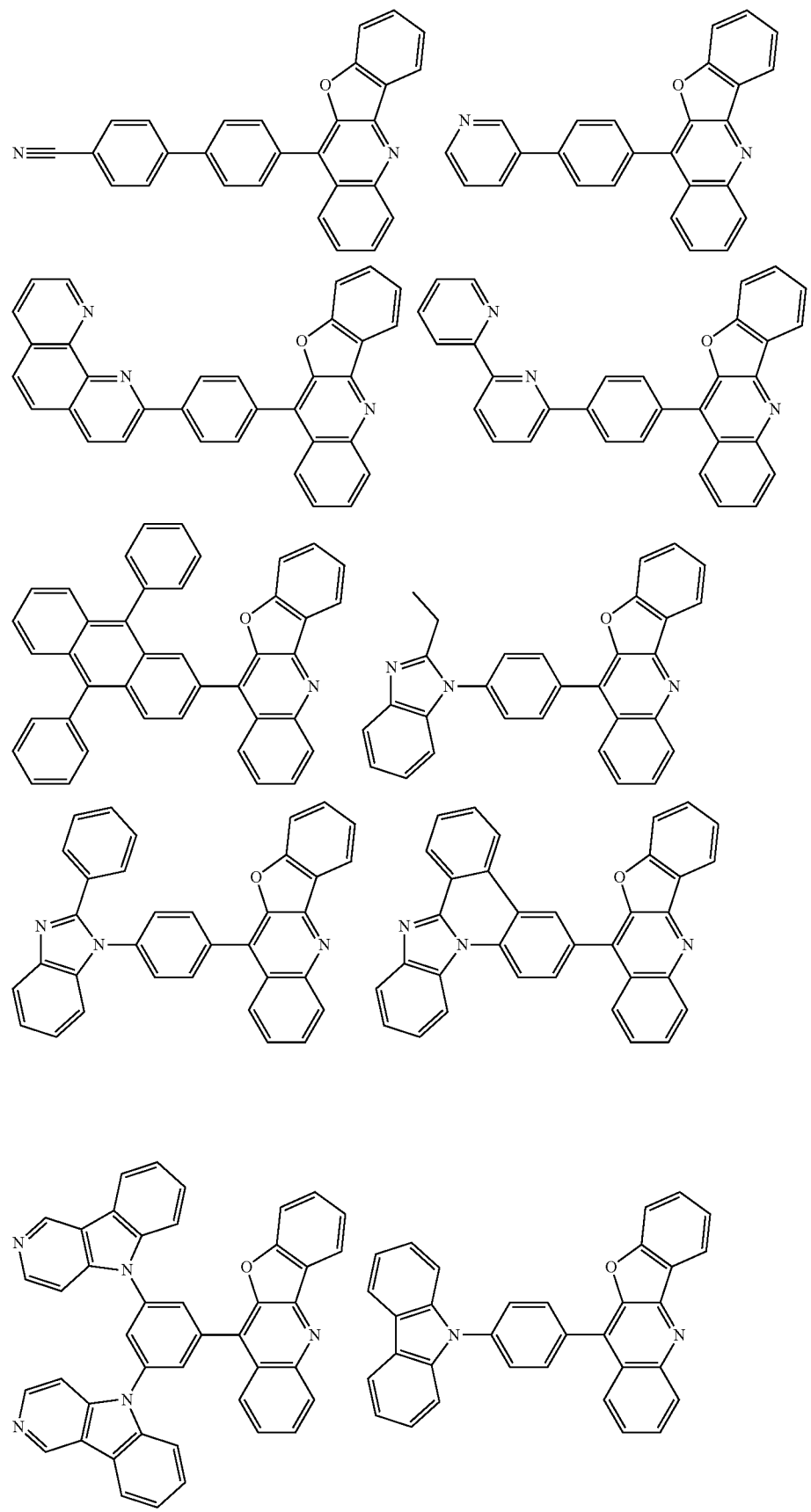

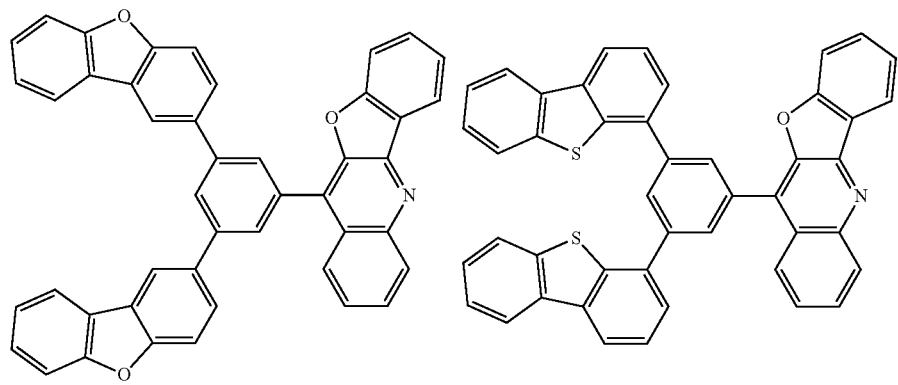
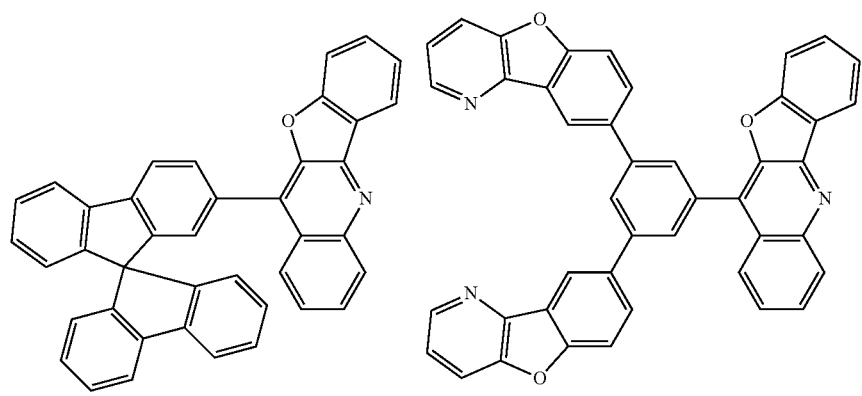
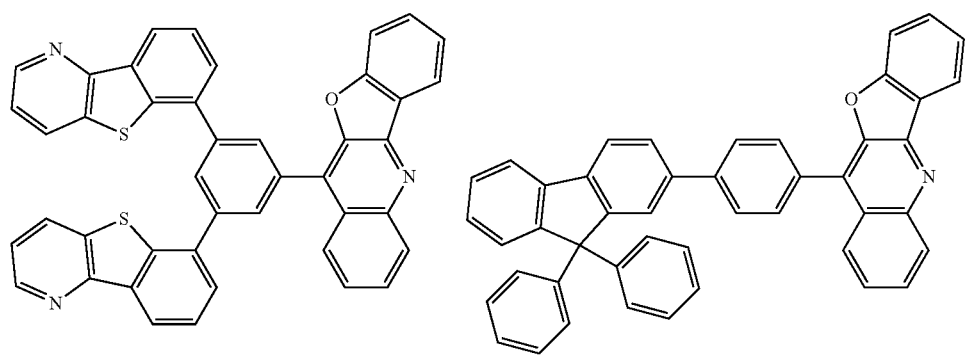
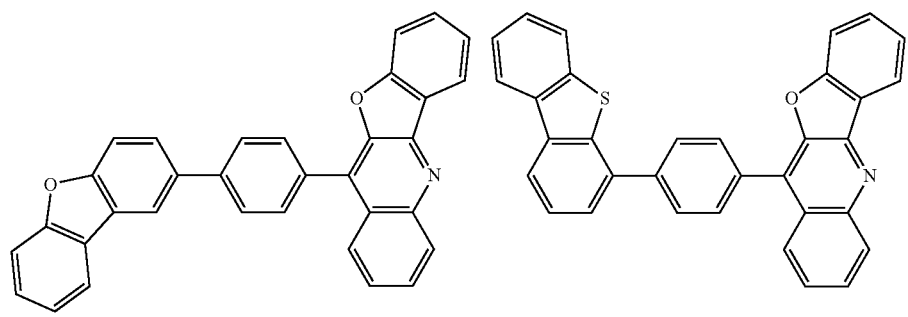

-continued
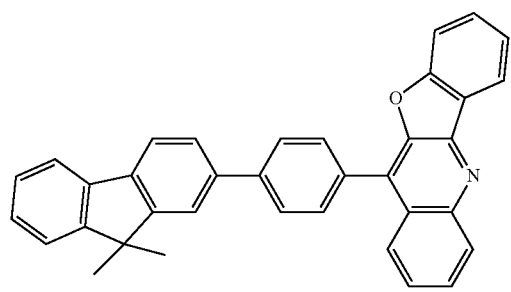
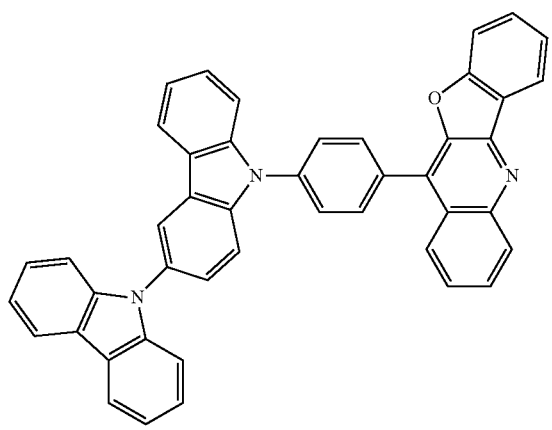
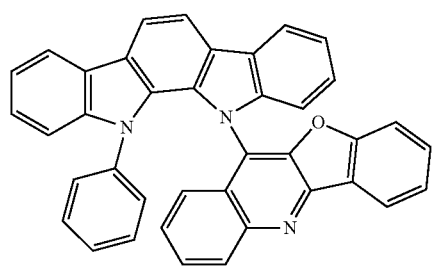
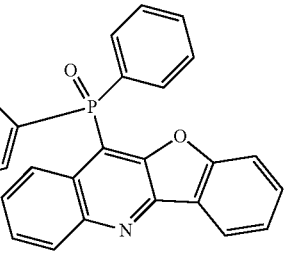
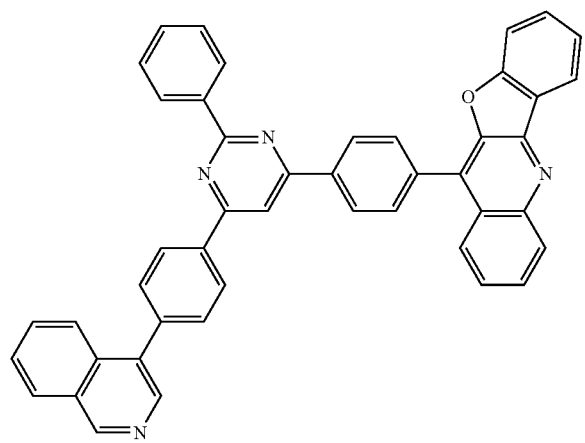
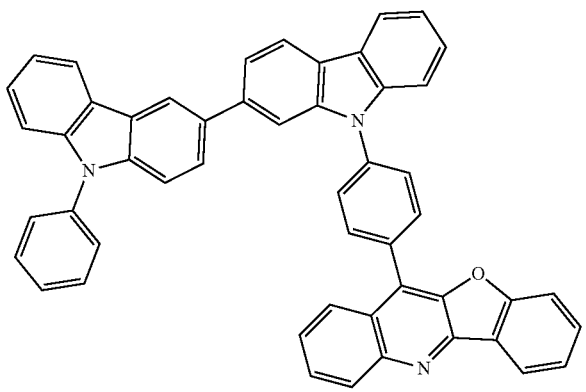
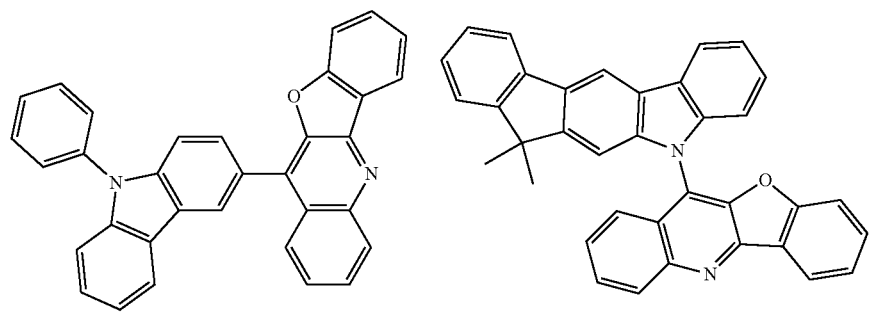

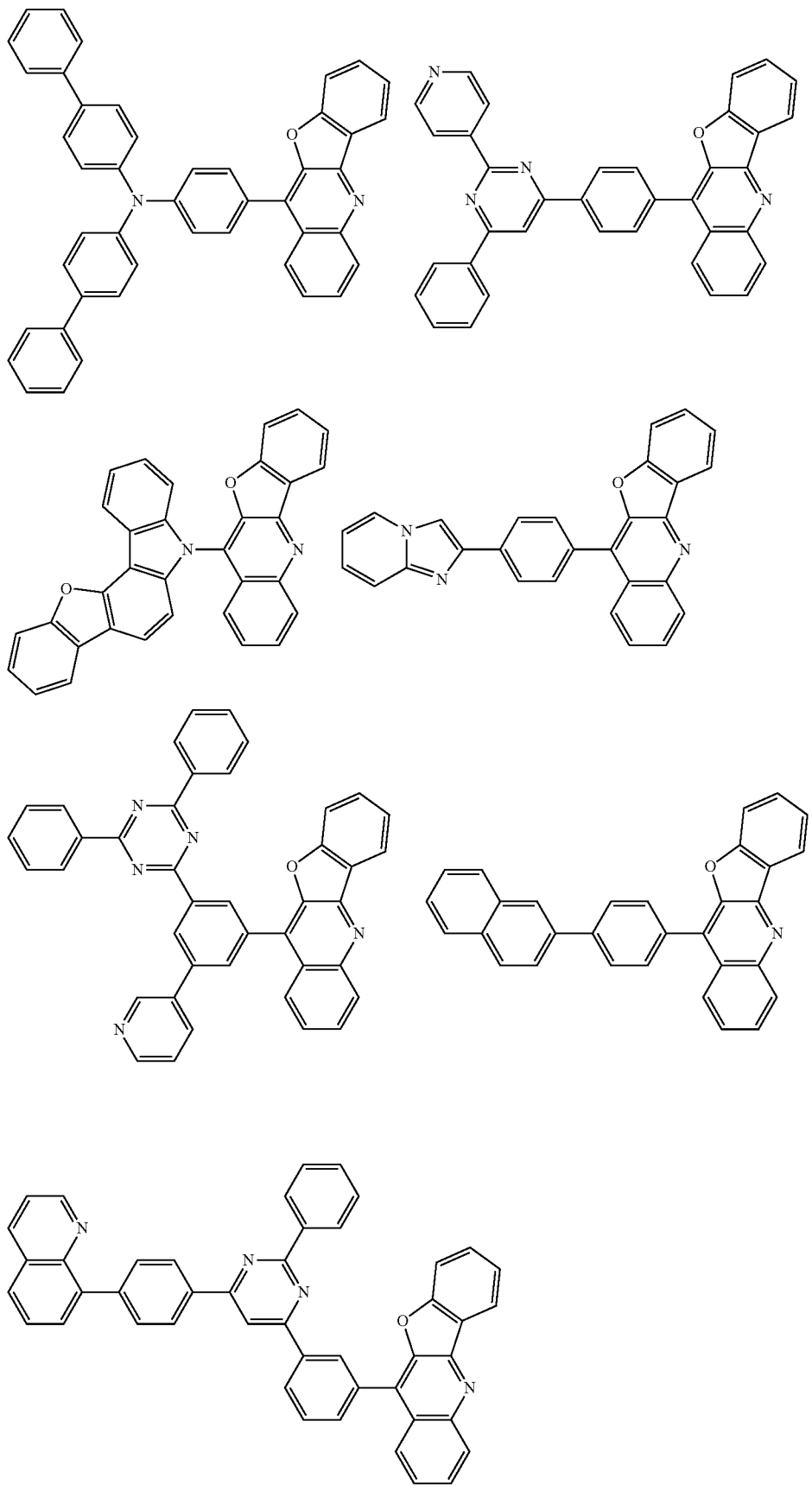

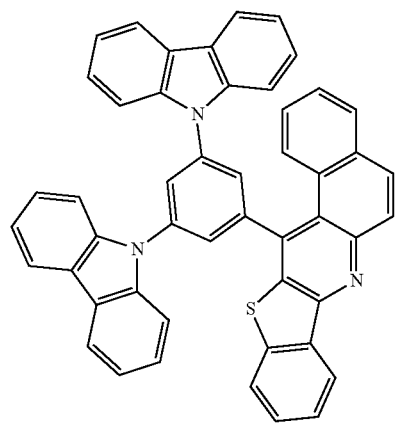
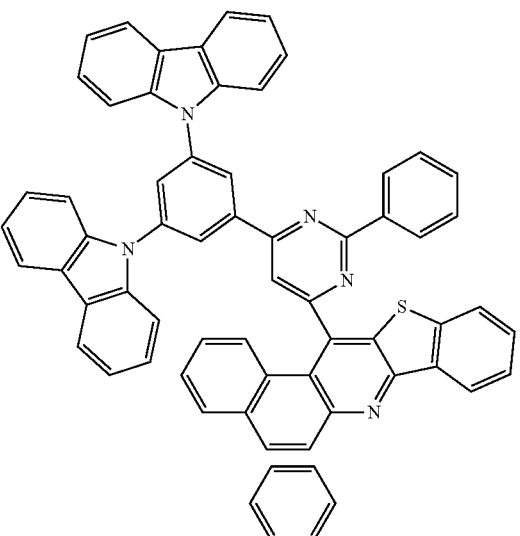
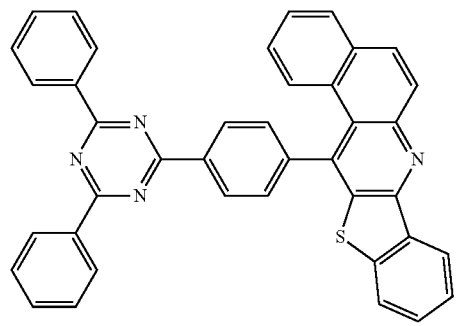
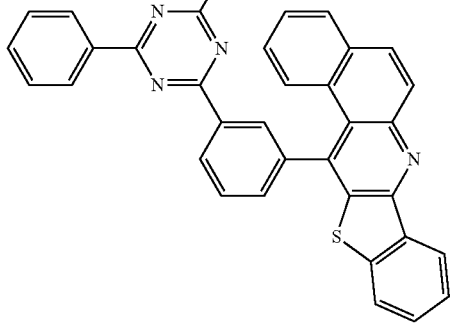
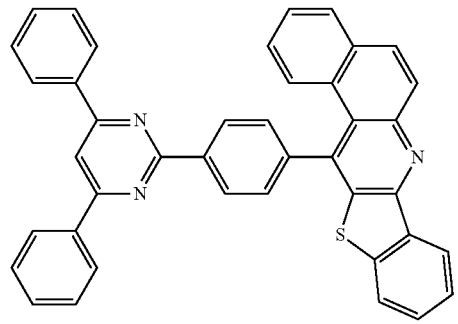
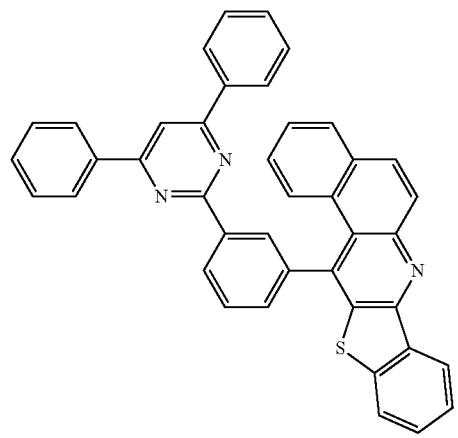
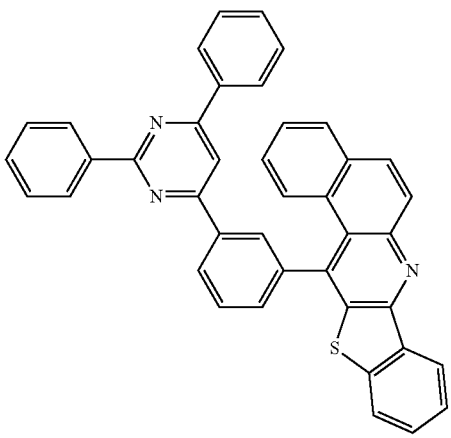

121
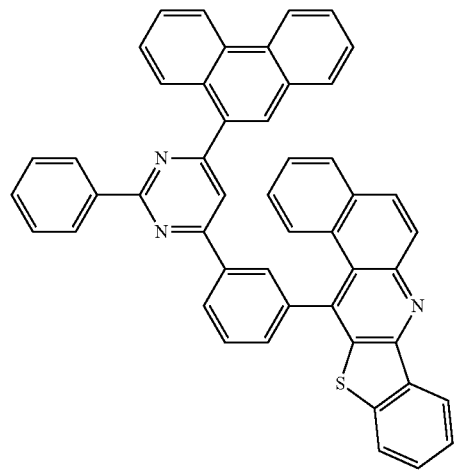
122
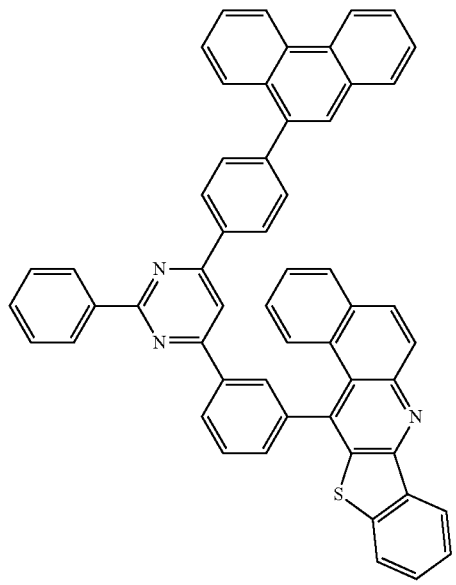
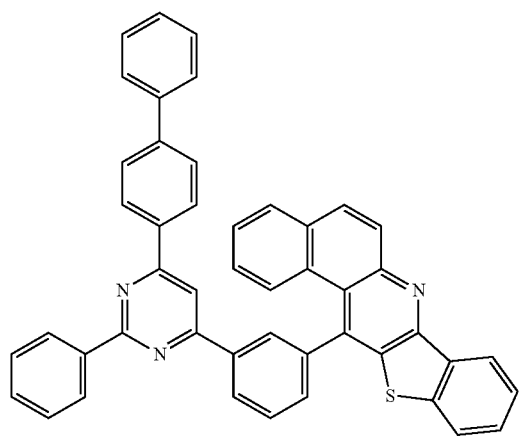
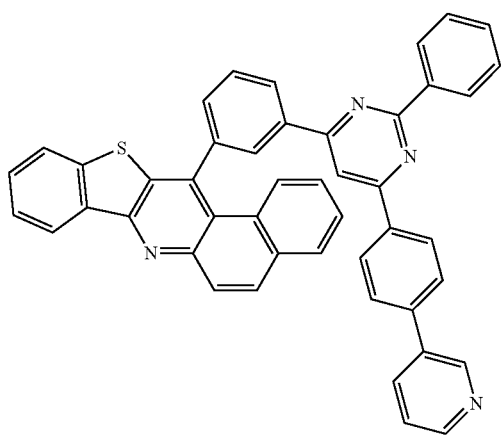
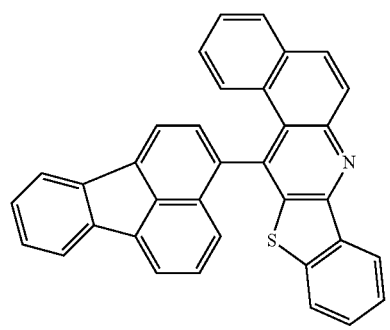
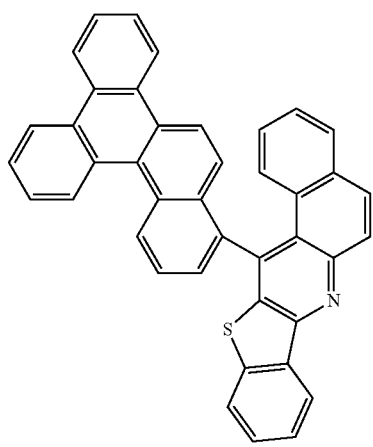

-continued
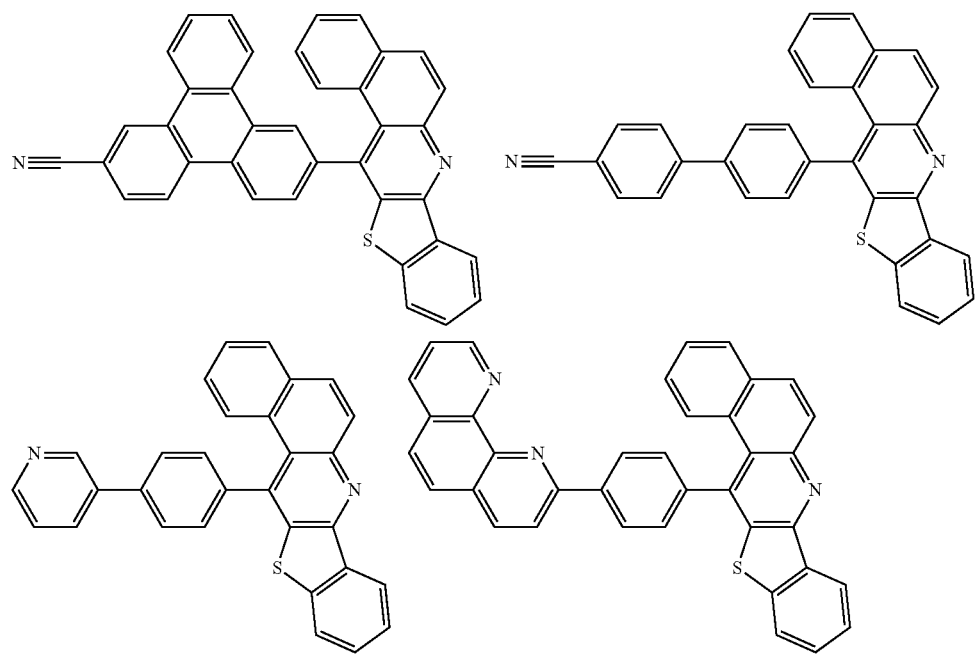
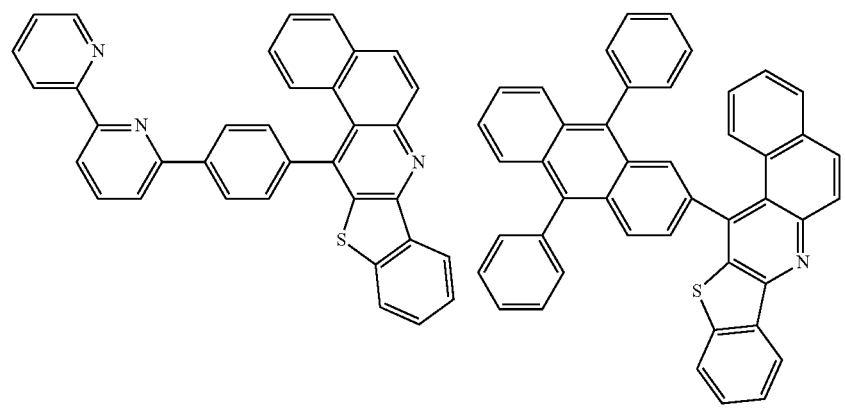
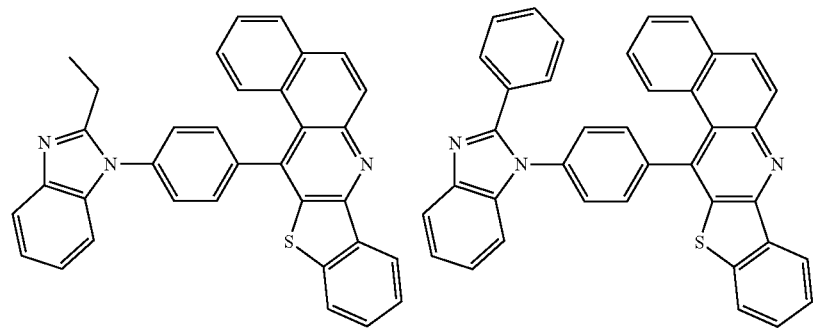

-continued
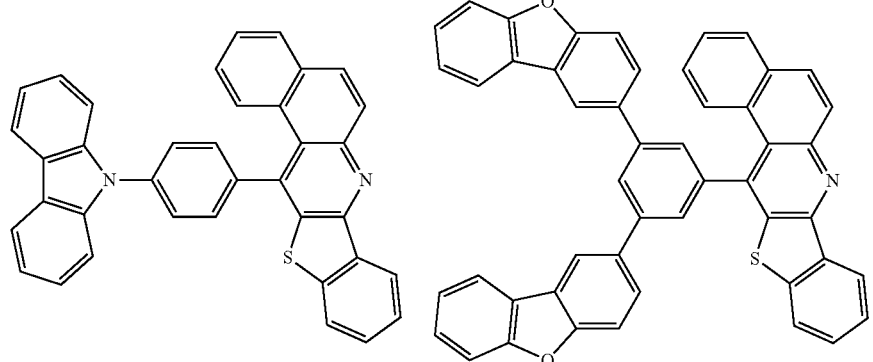
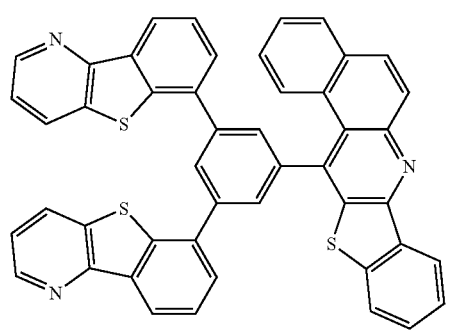
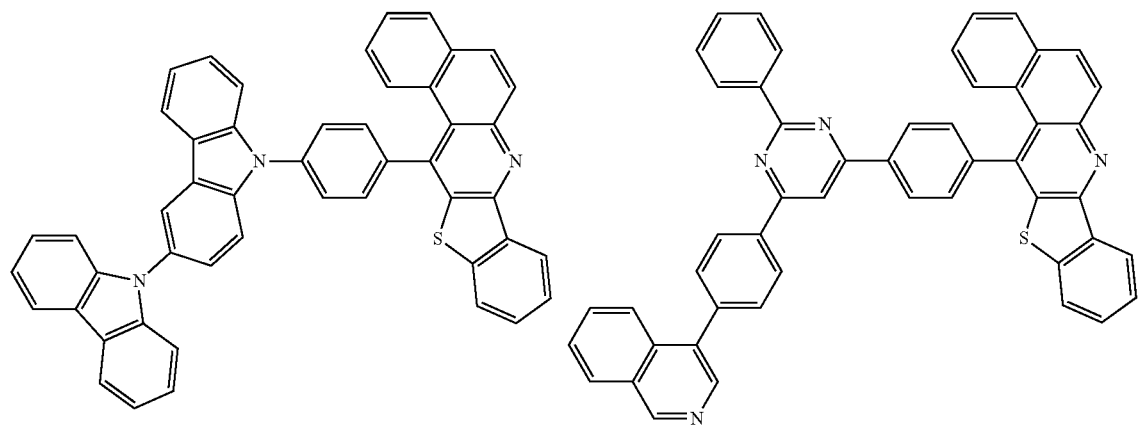
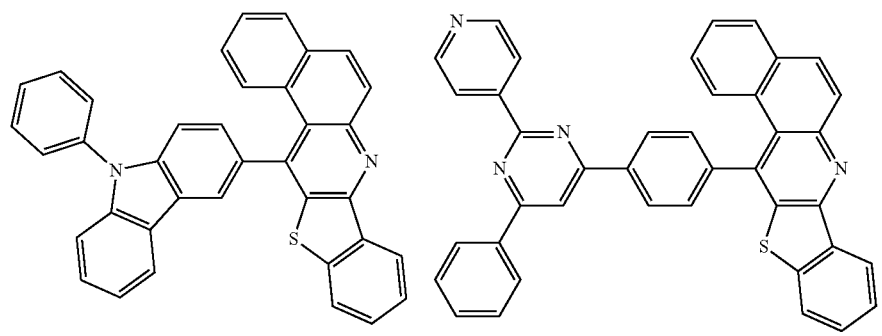

-continued
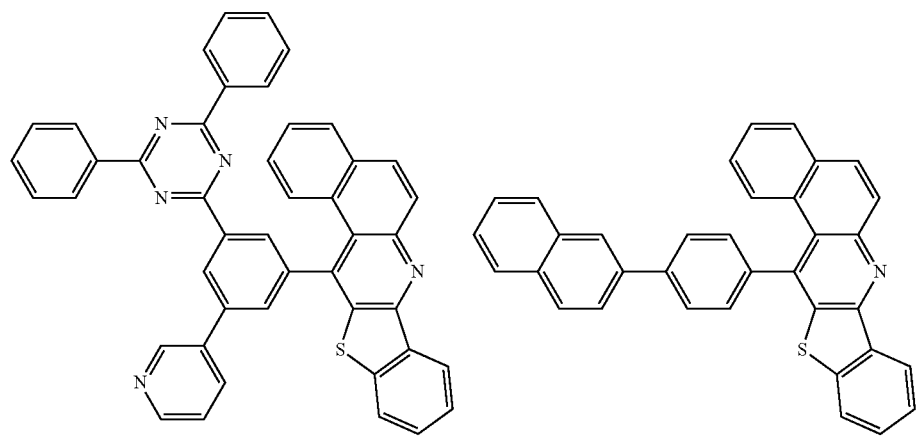
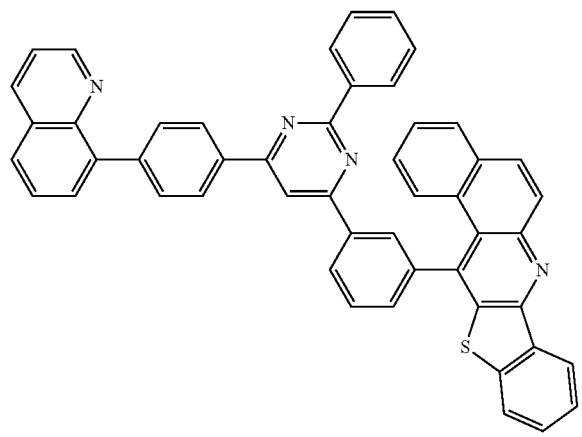
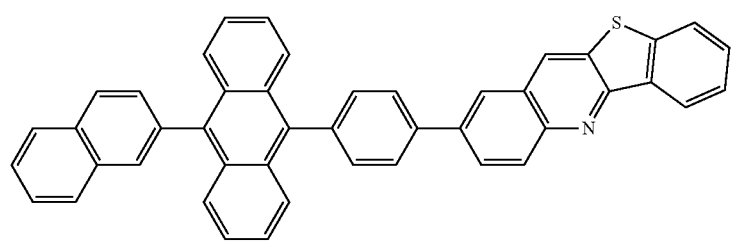
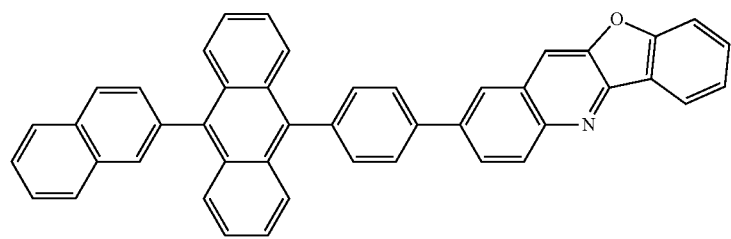
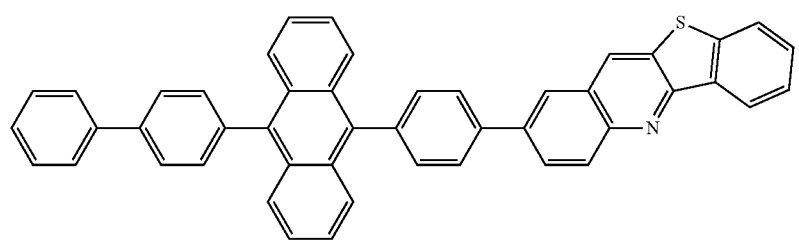

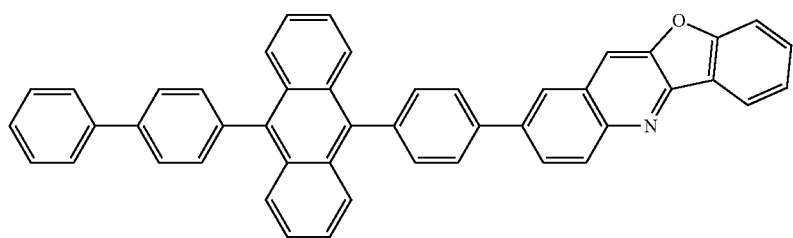
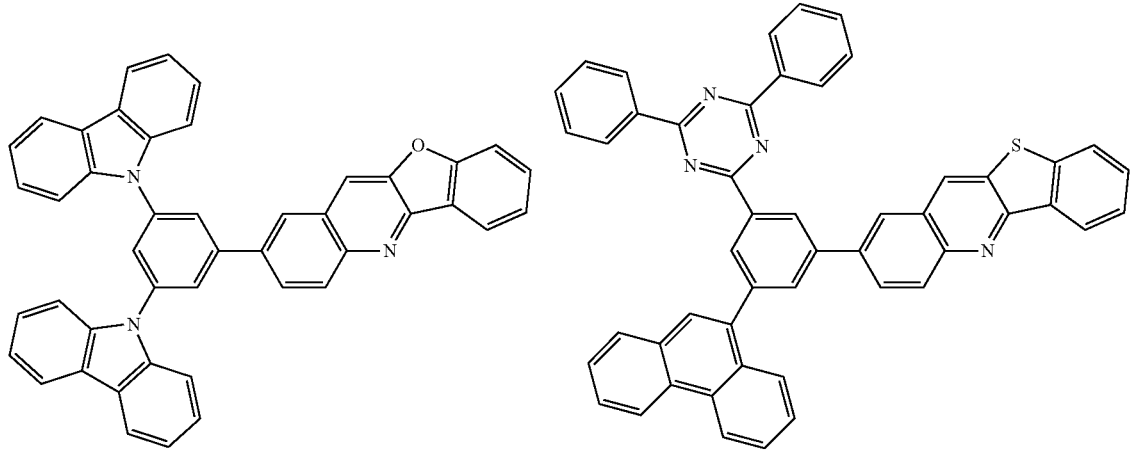
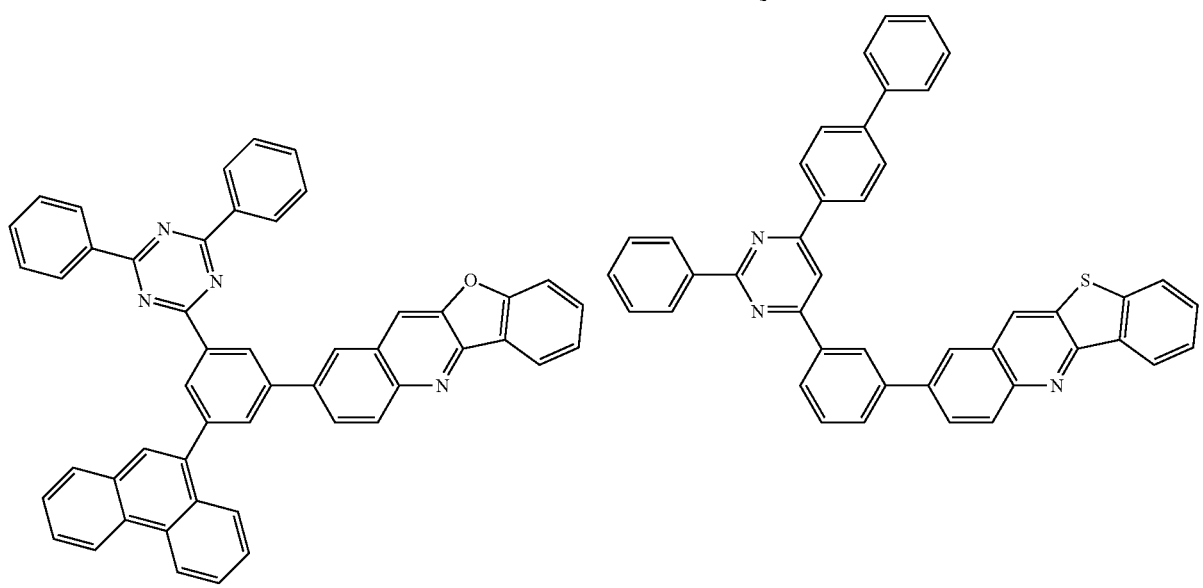
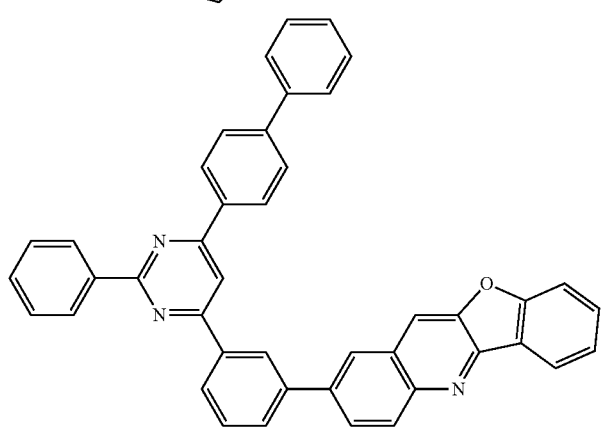

-continued
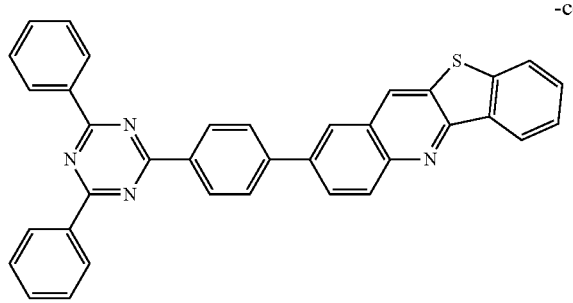
131
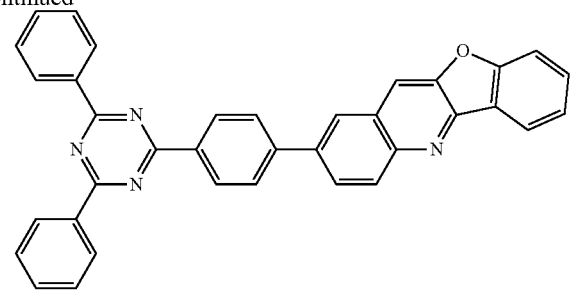
132
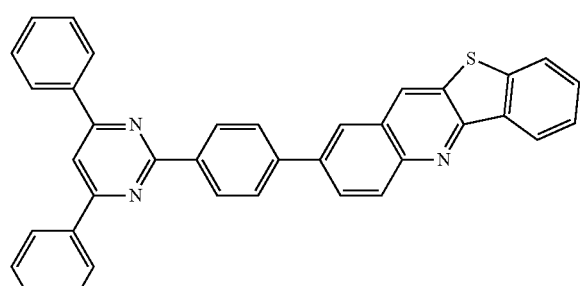
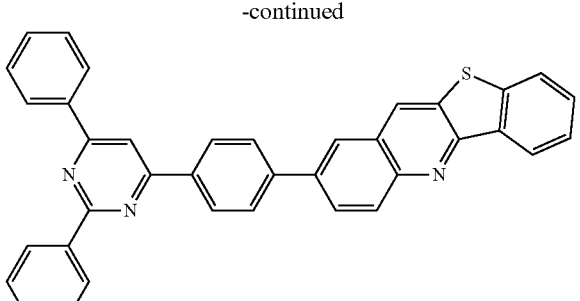
-continued
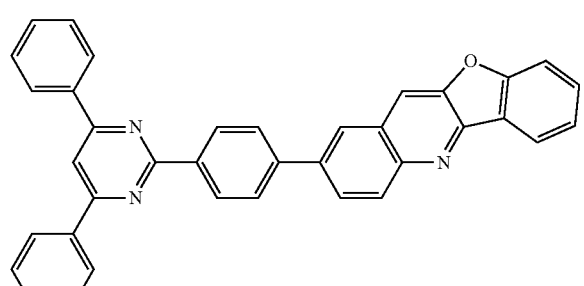
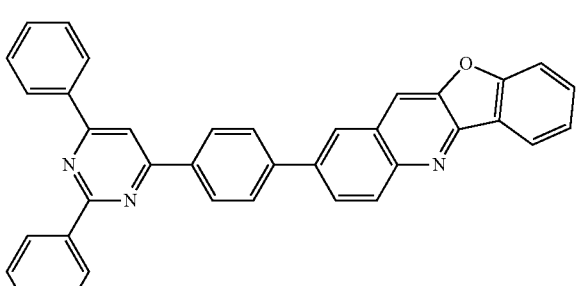
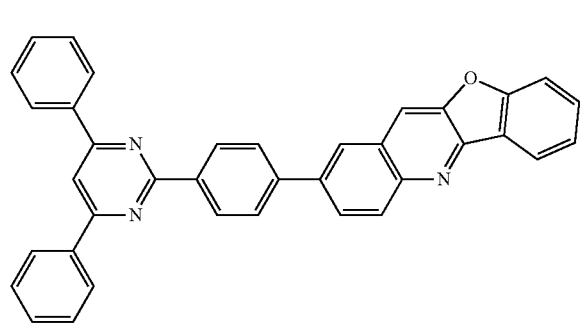
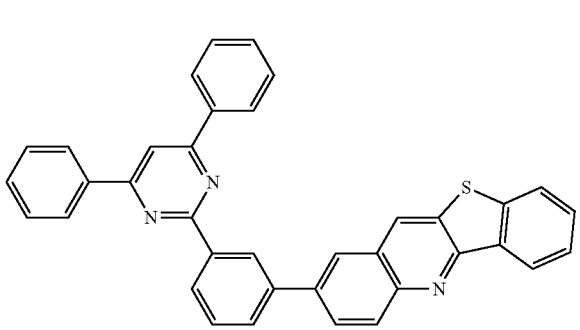

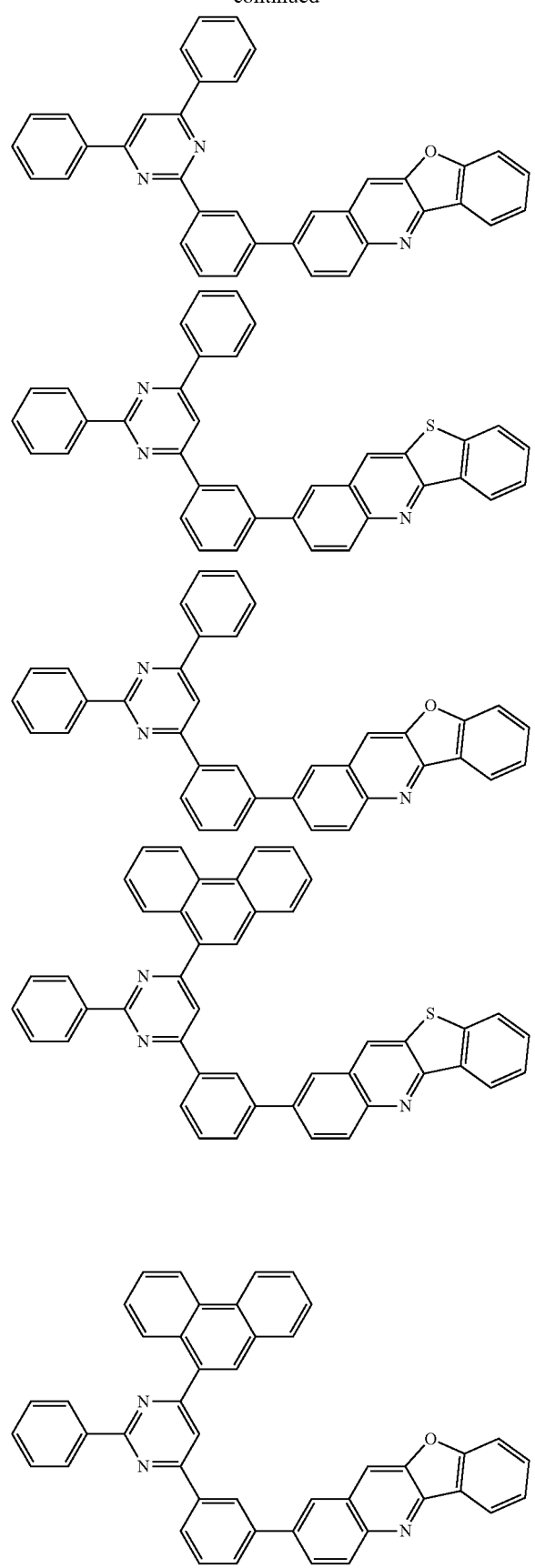
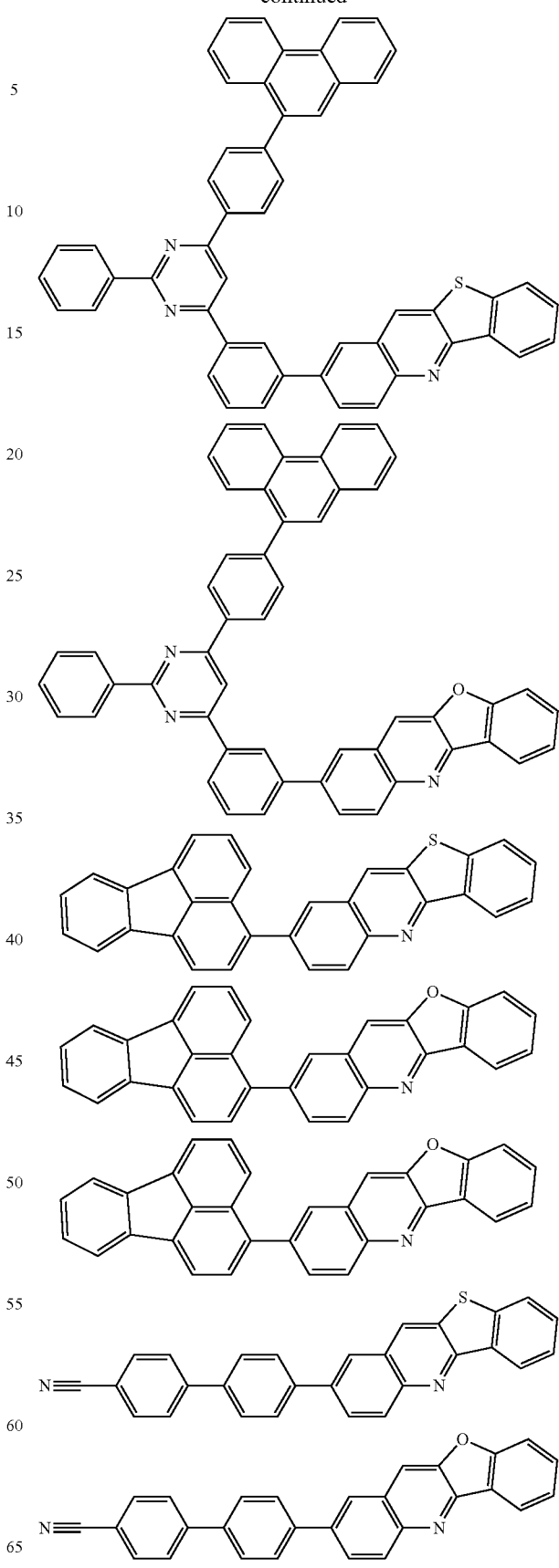

135
-continued
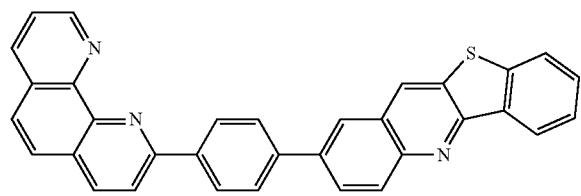
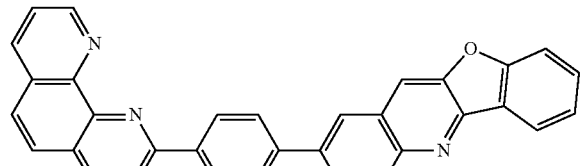
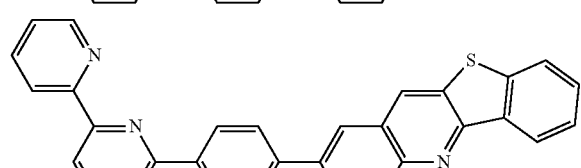
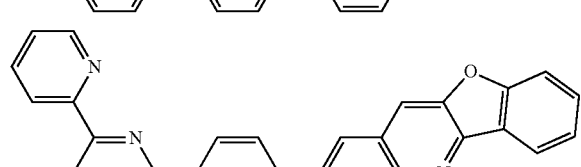
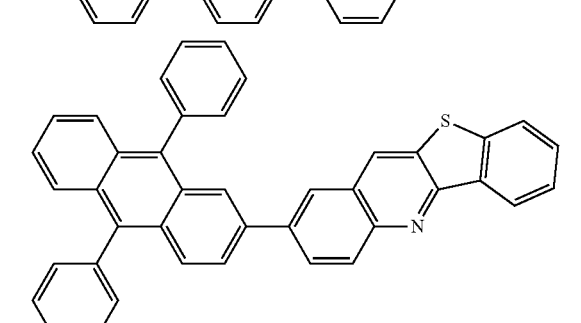
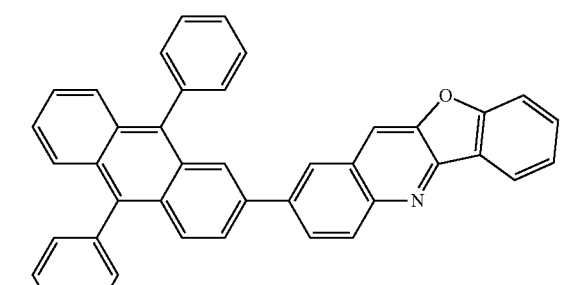
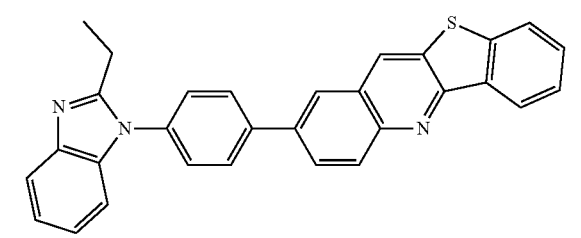
136
-continued
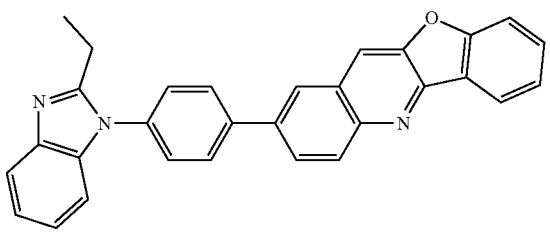
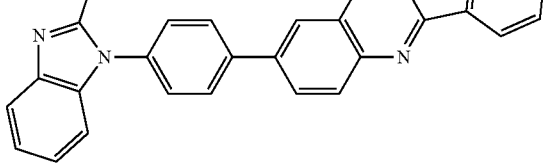
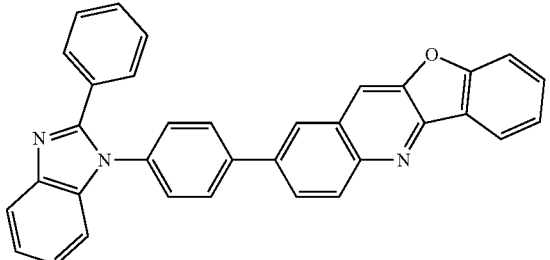
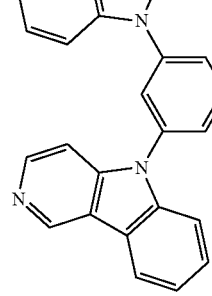
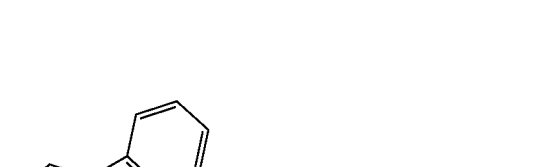
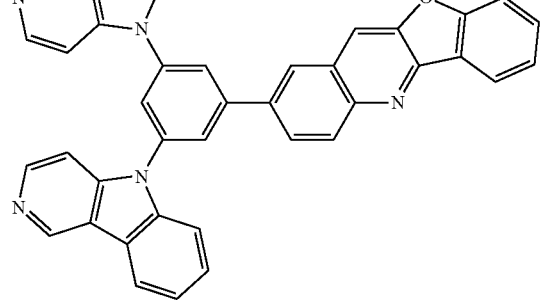

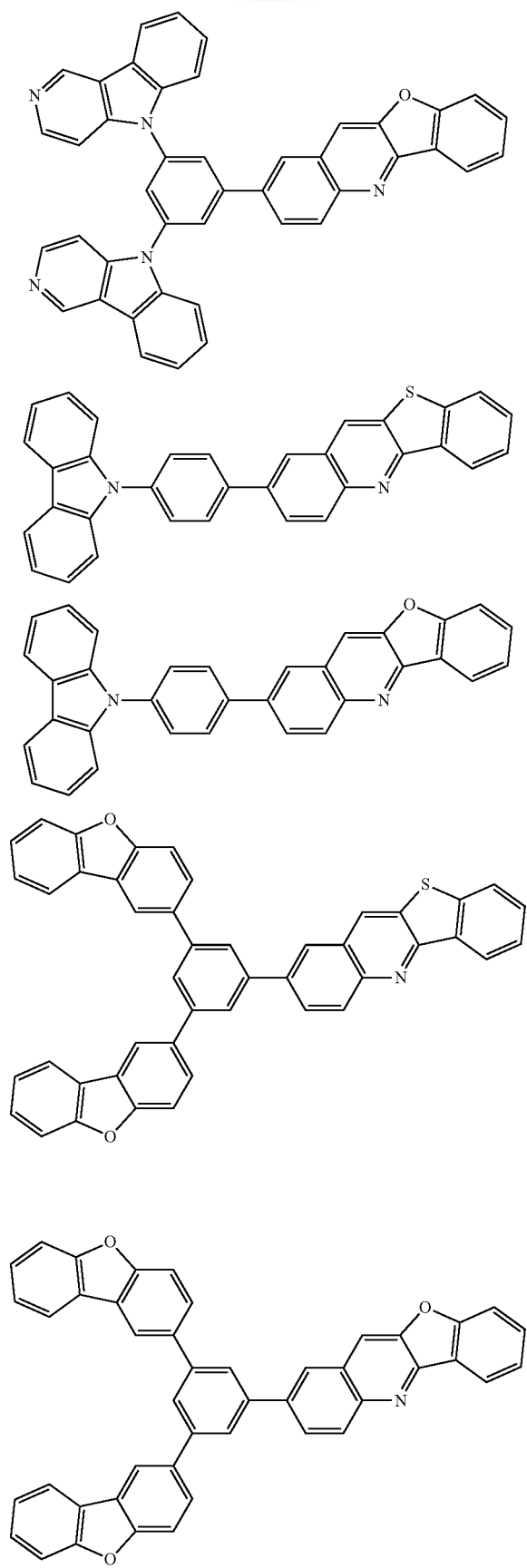
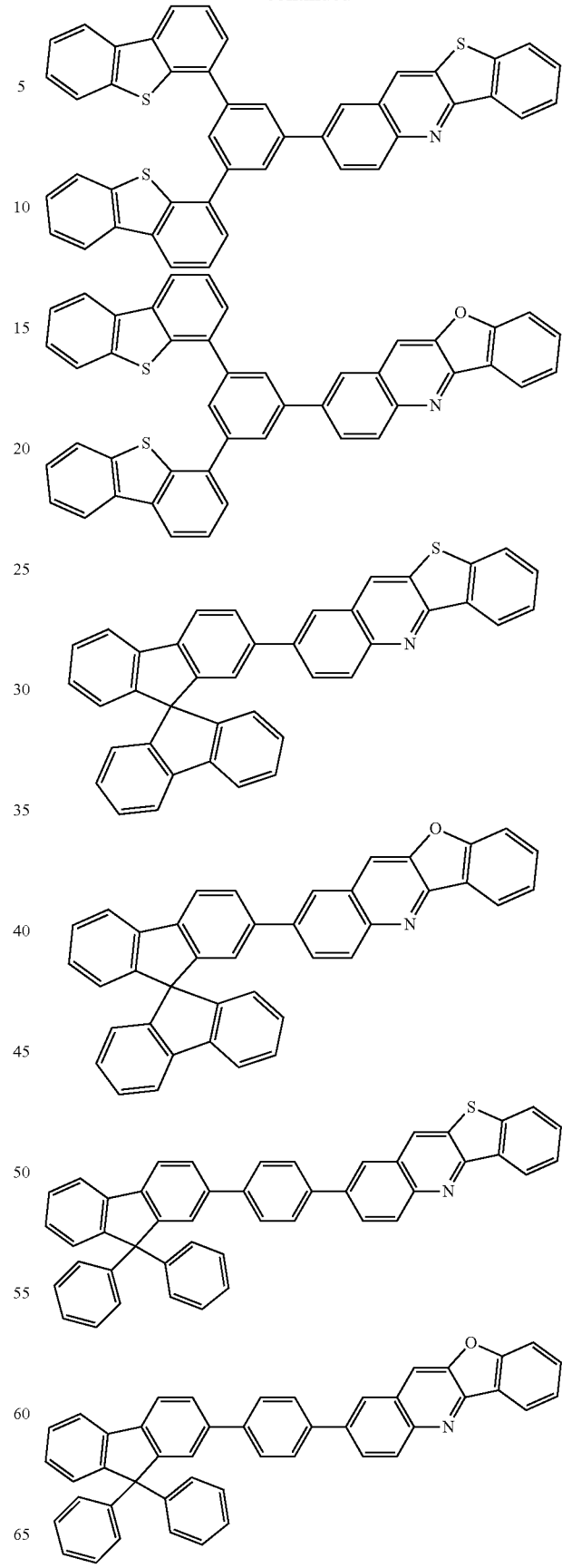

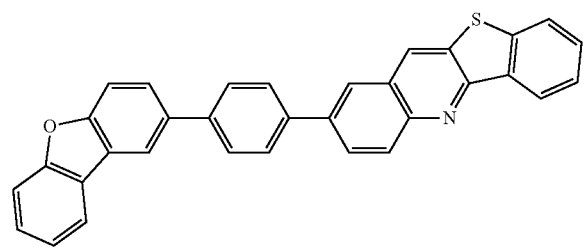
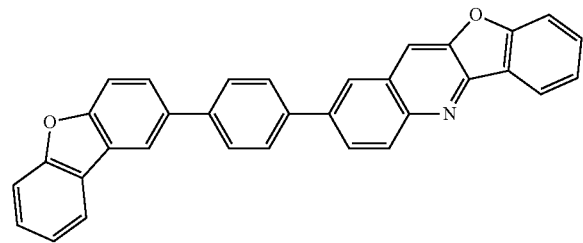
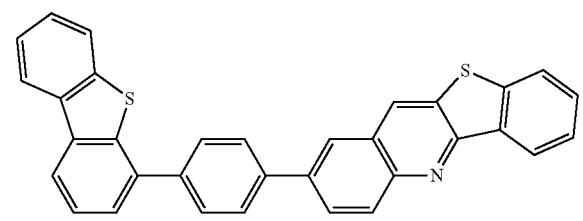
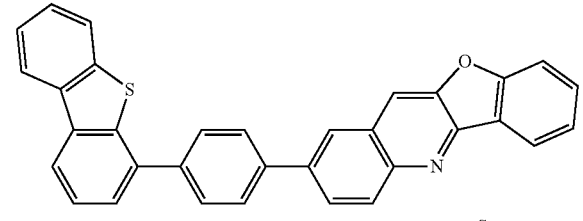
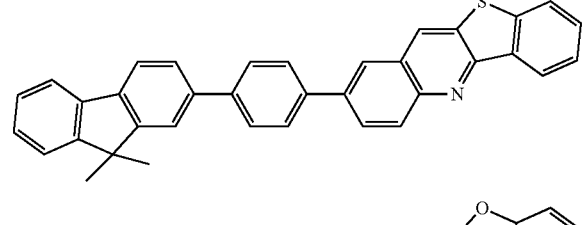
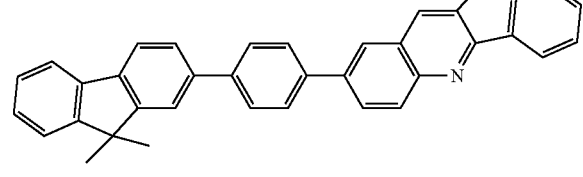
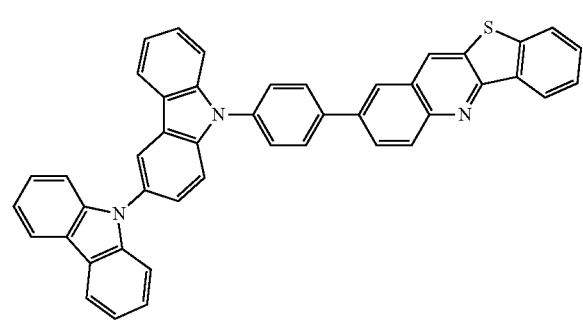
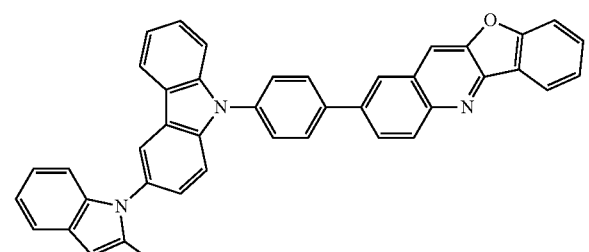
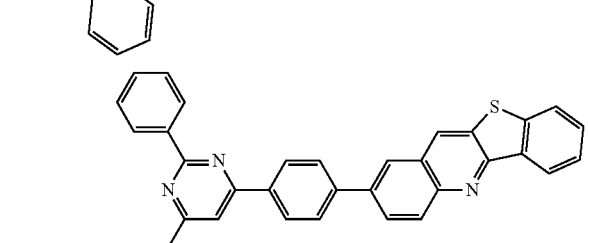
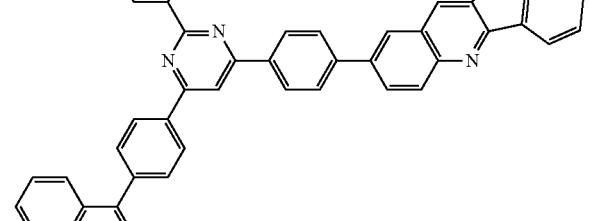
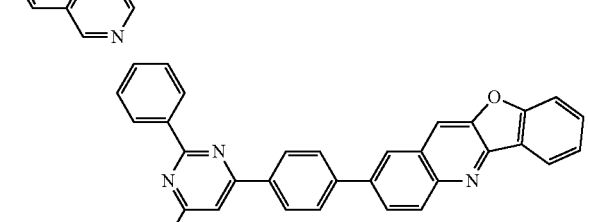
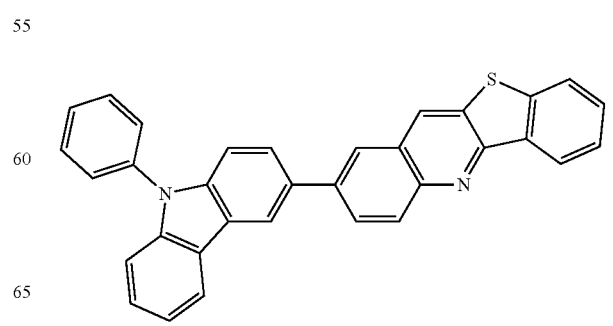

141
-continued
142
-continued
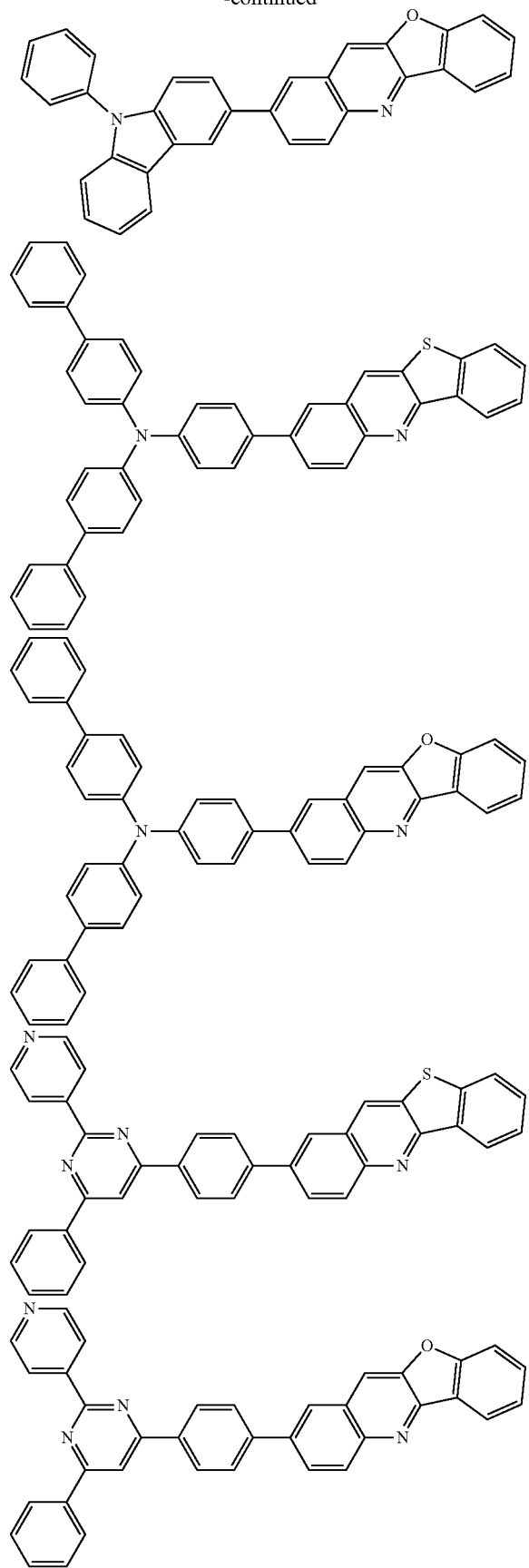
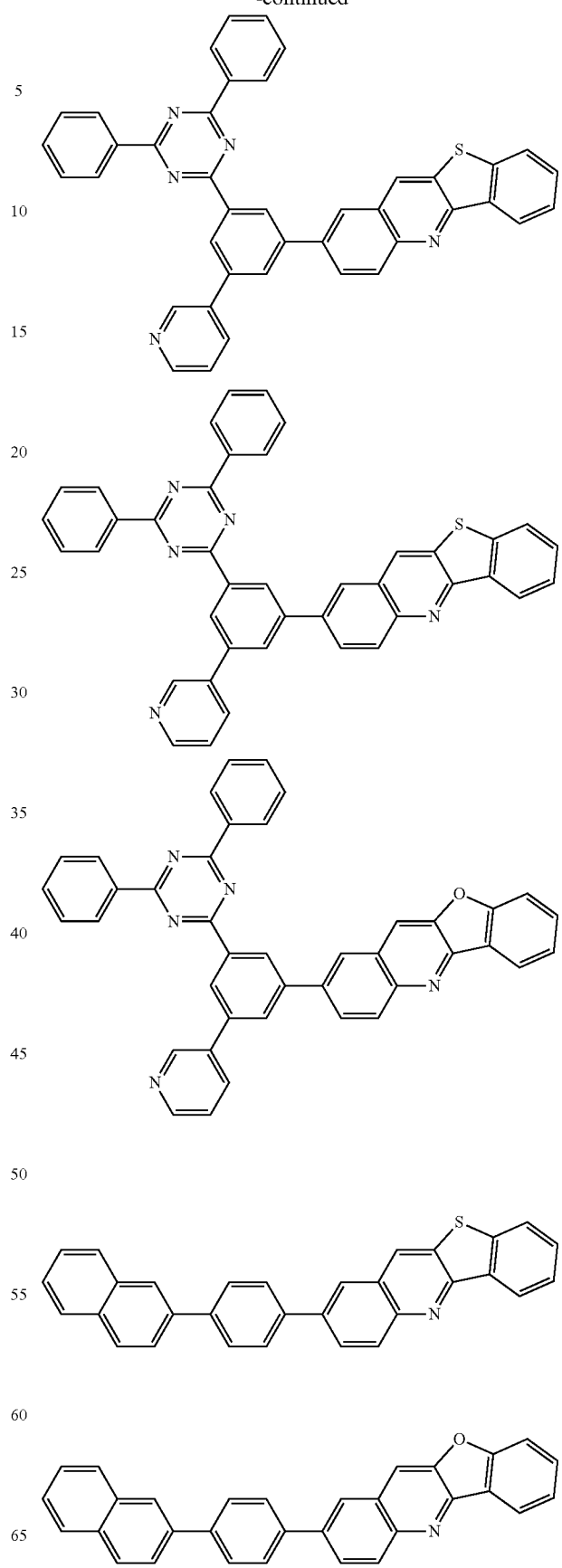

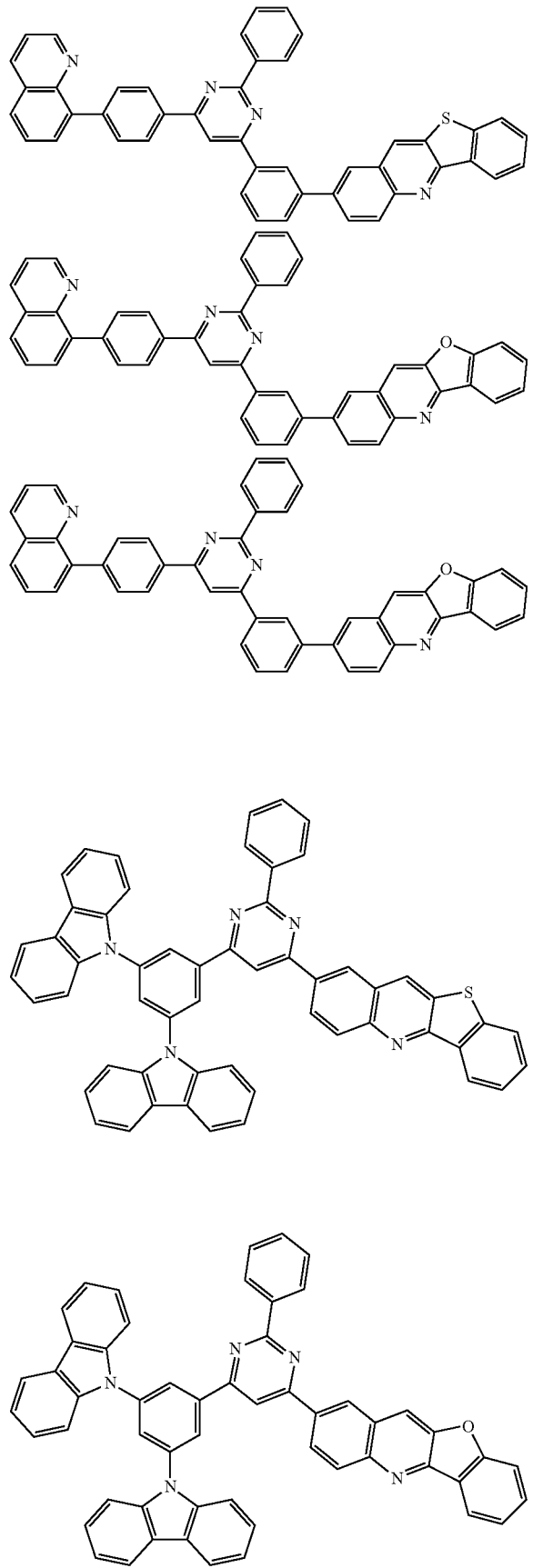
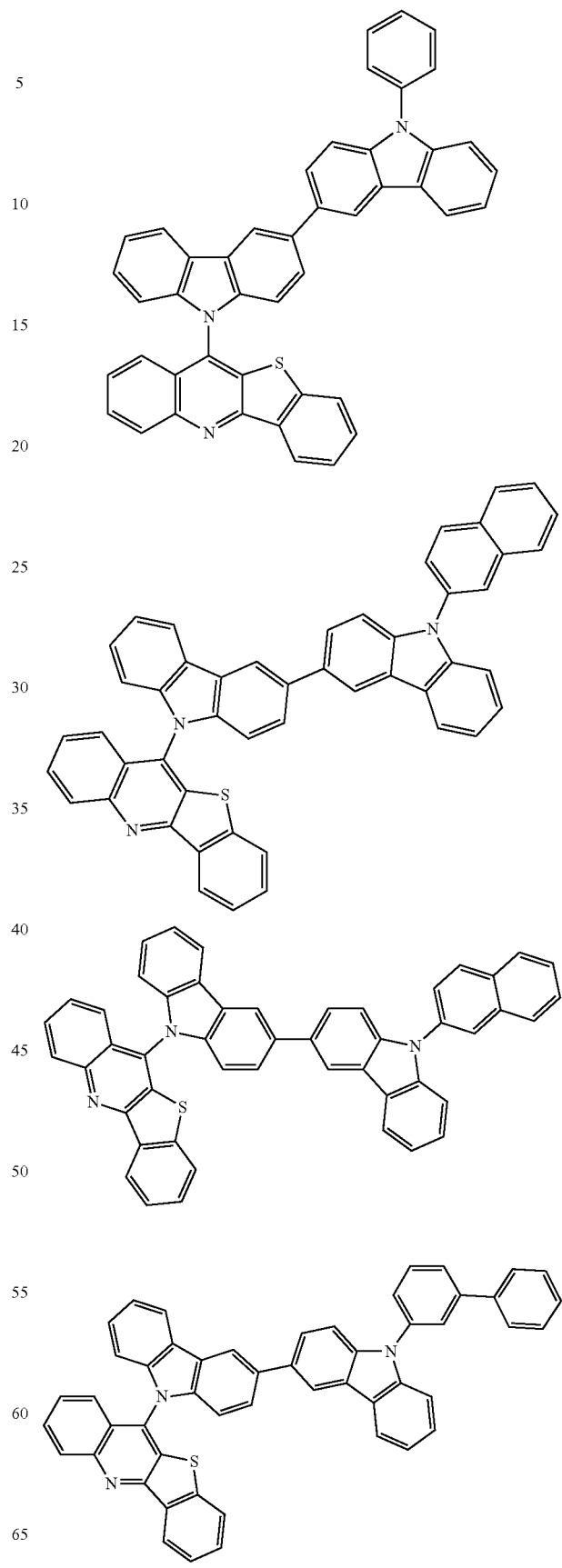

145
-continued
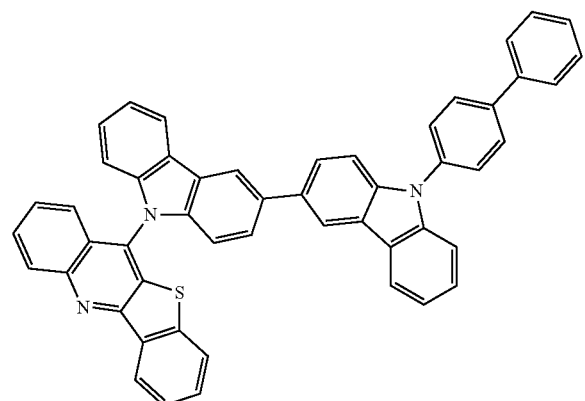
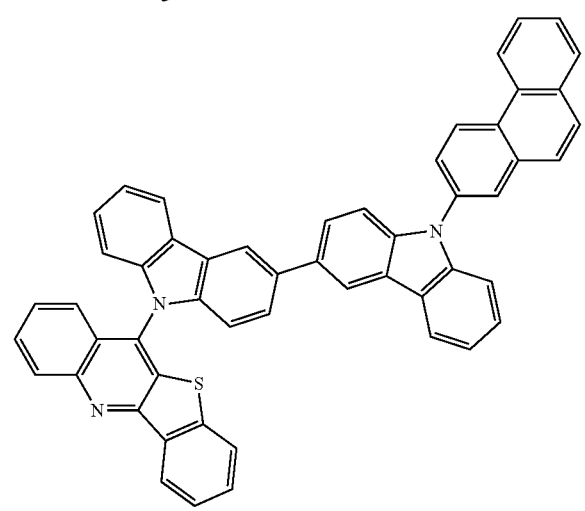
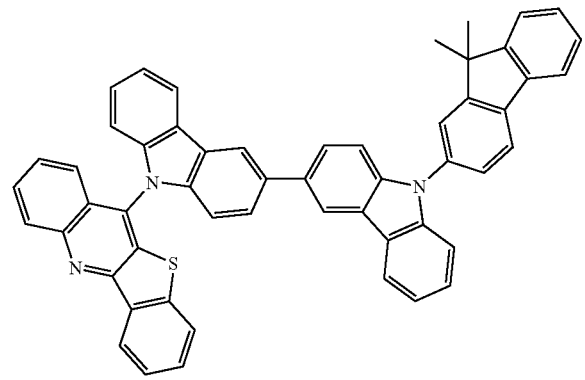
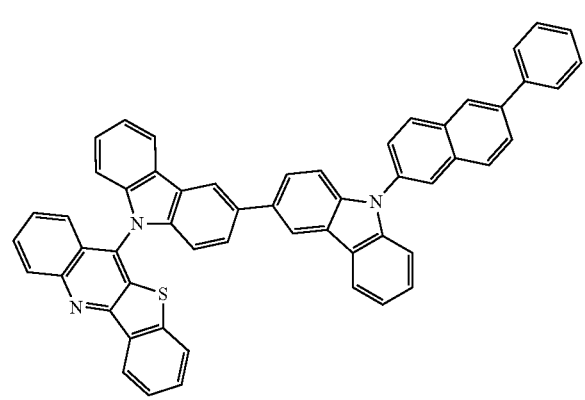
146
-continued
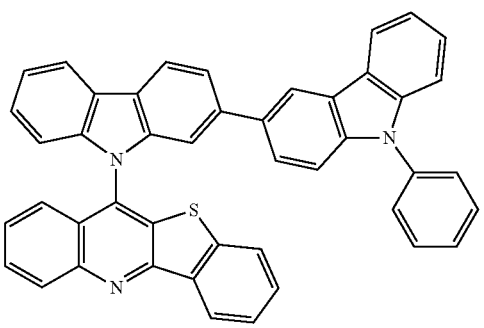
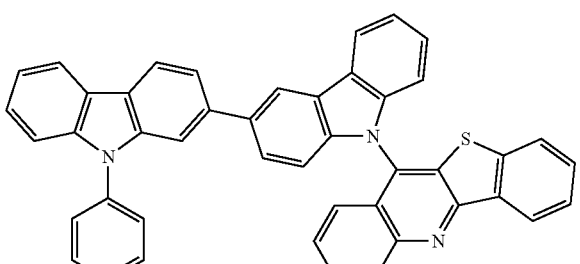
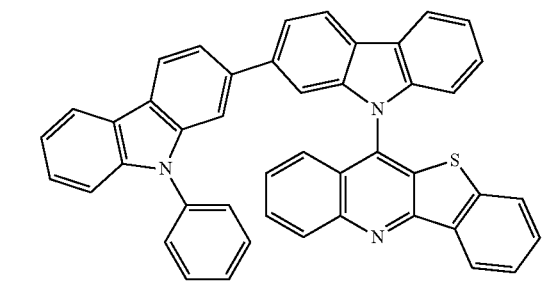
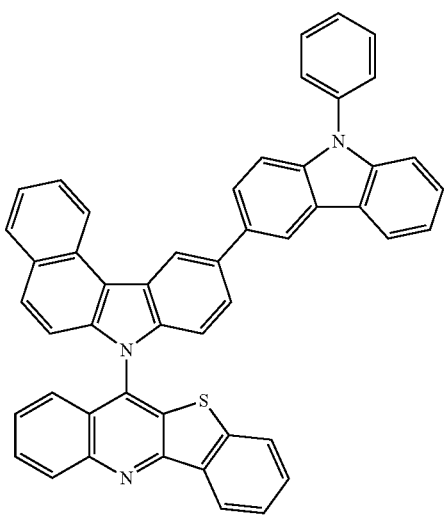

147
-continued
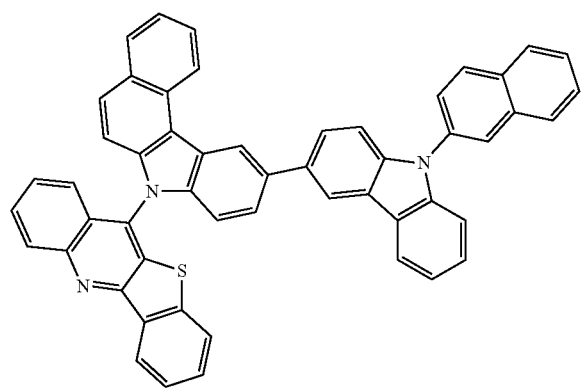
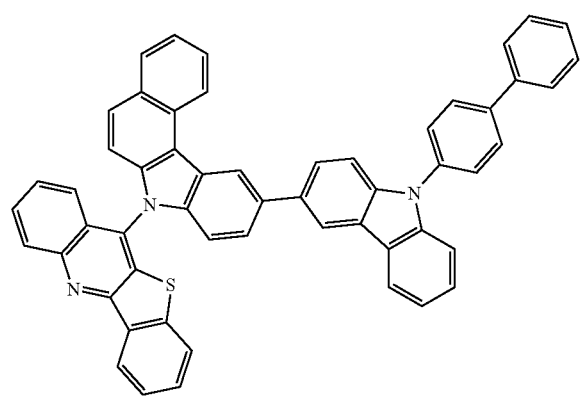
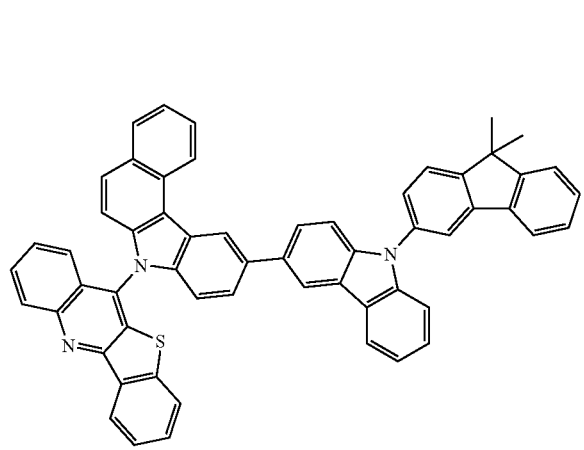
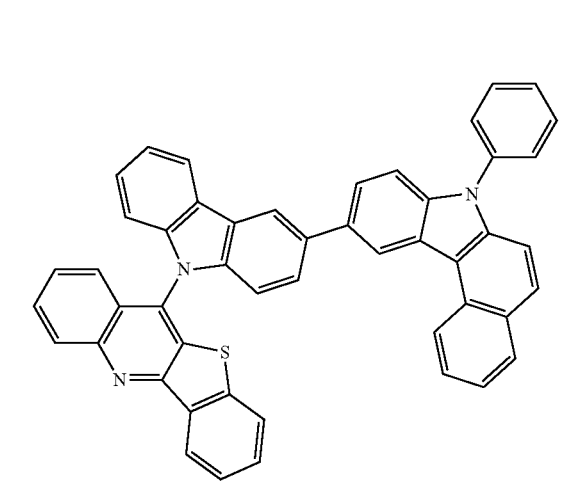
148
-continued
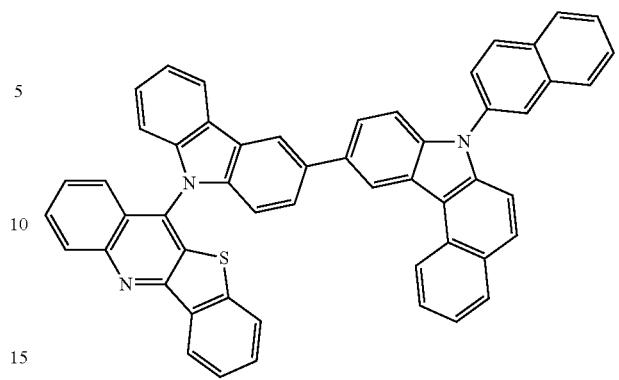
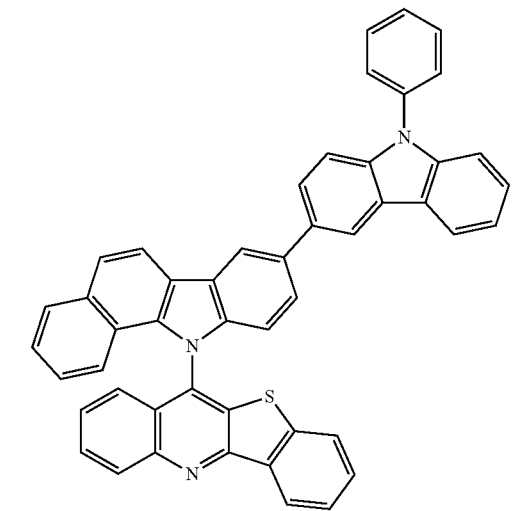

149
-continued
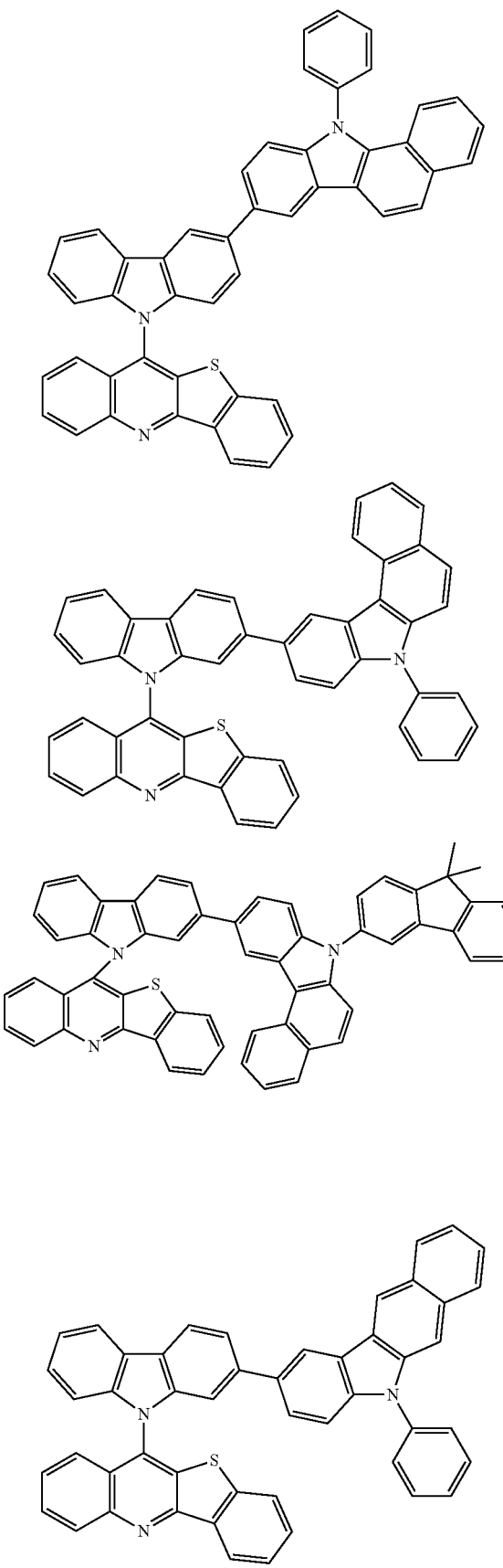
150
-continued
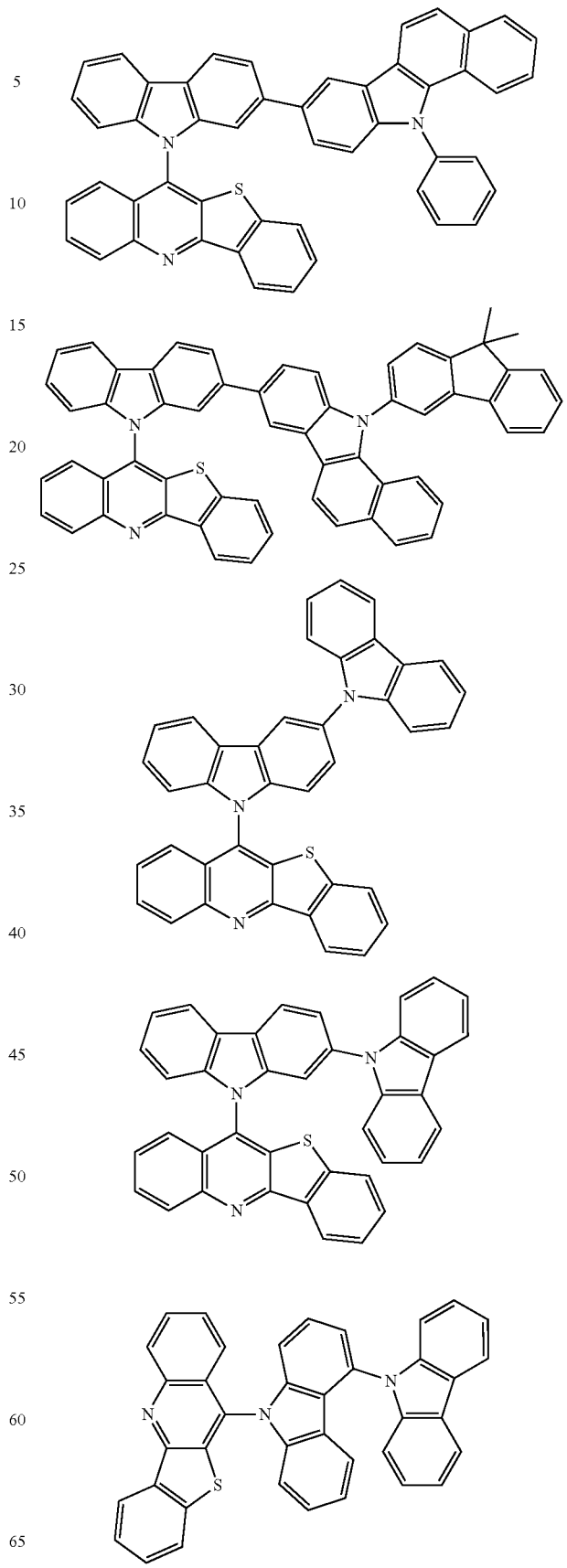

151
-continued
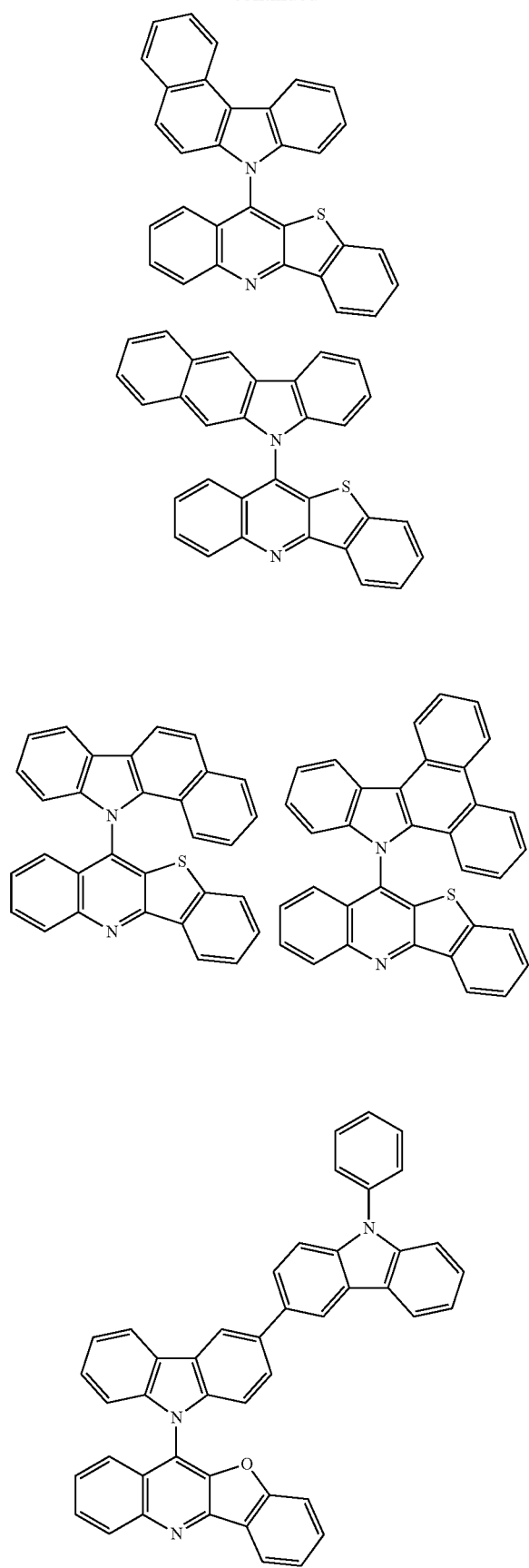
152
-continued
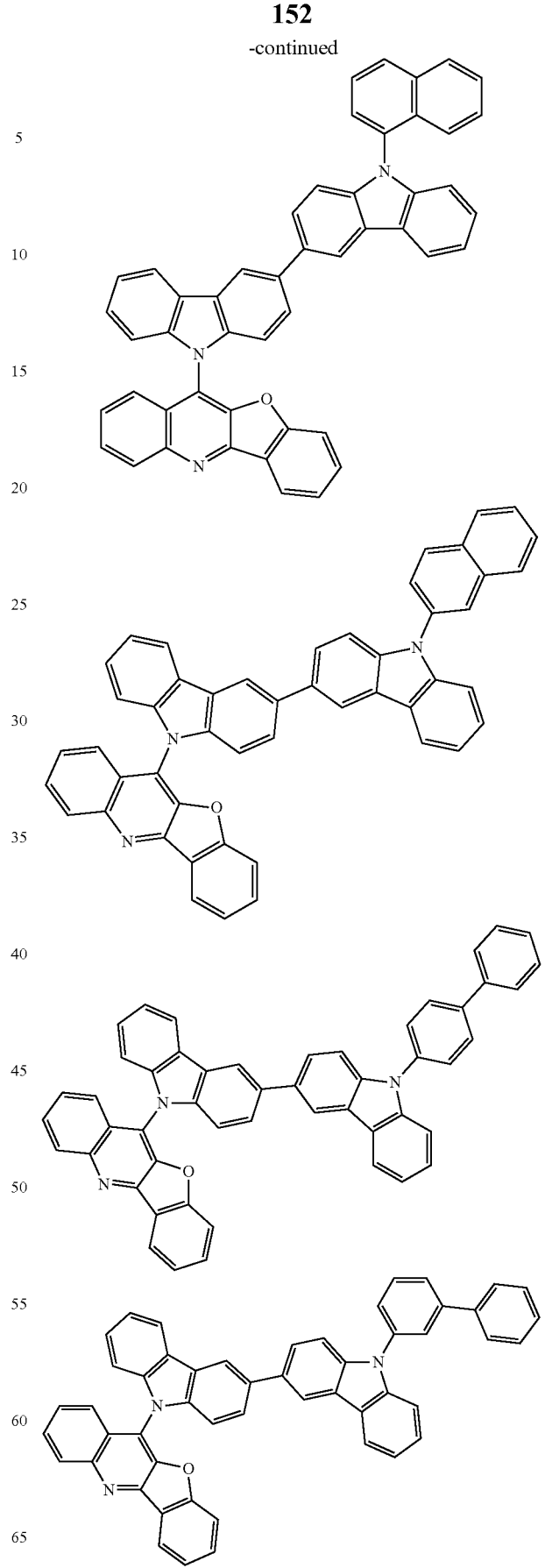

153
-continued
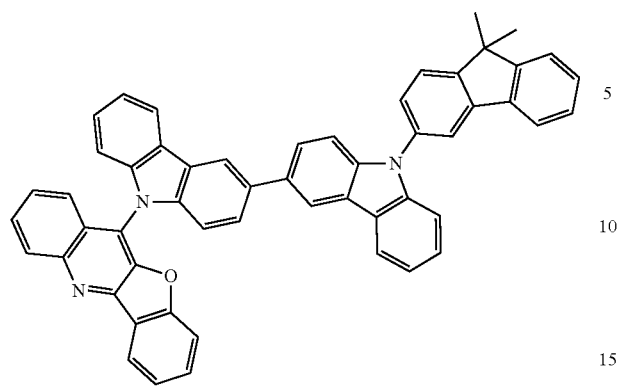
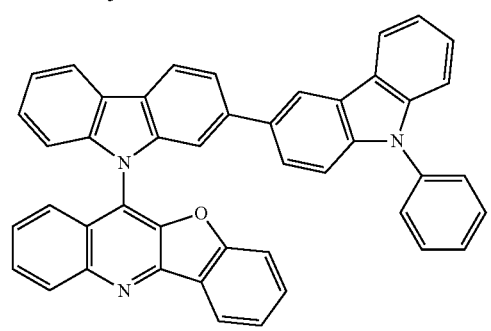
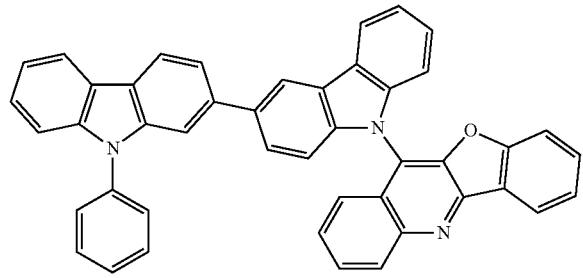
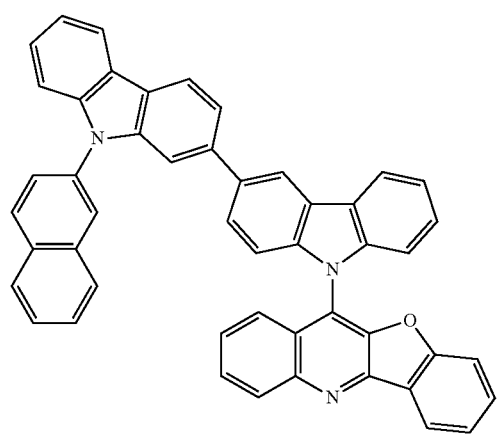
154
-continued
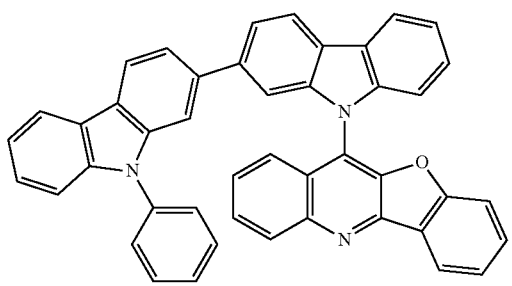
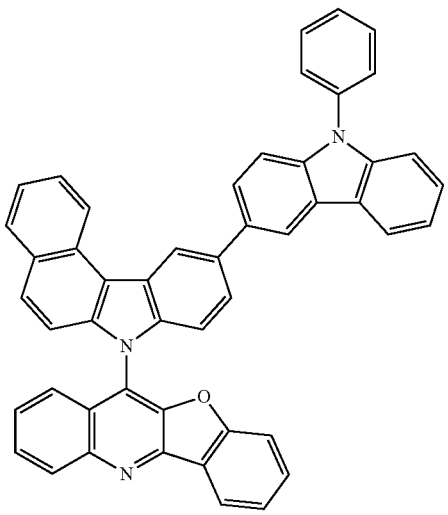
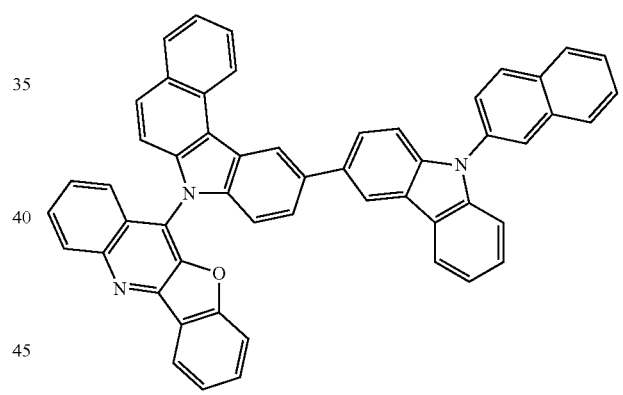
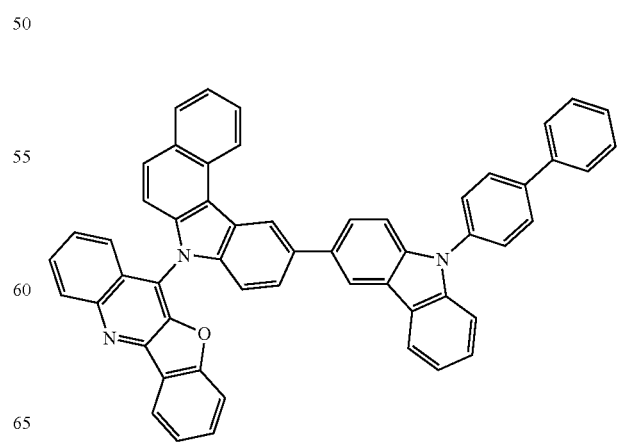

155
-continued
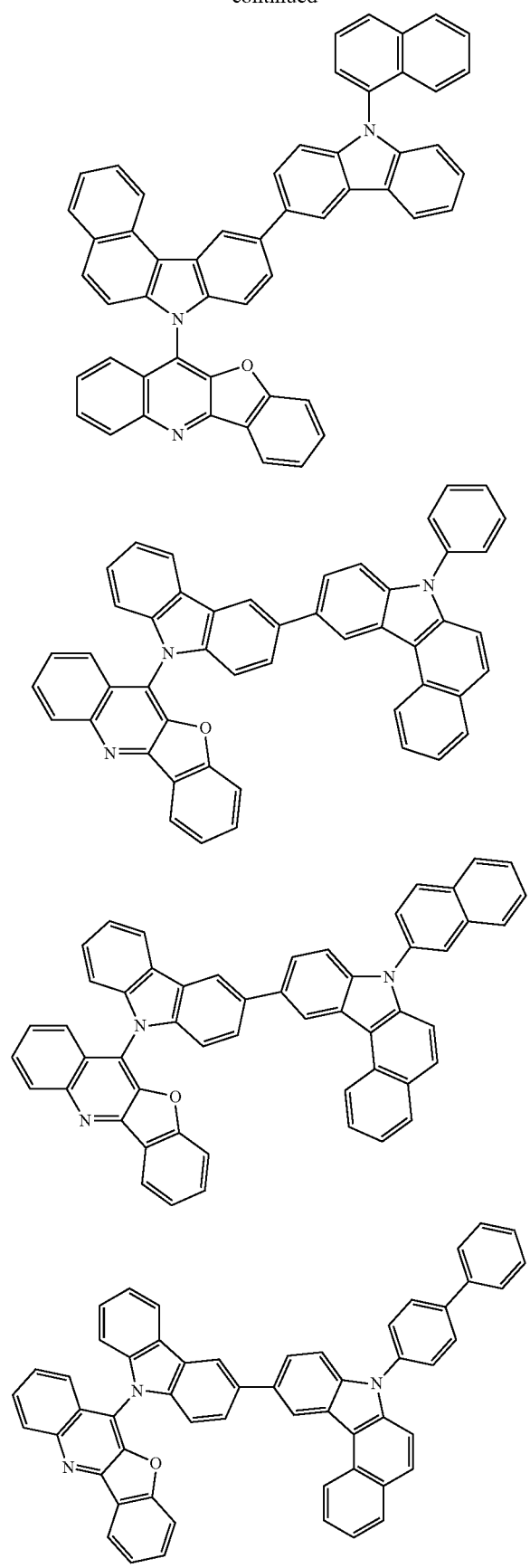
156
-continued
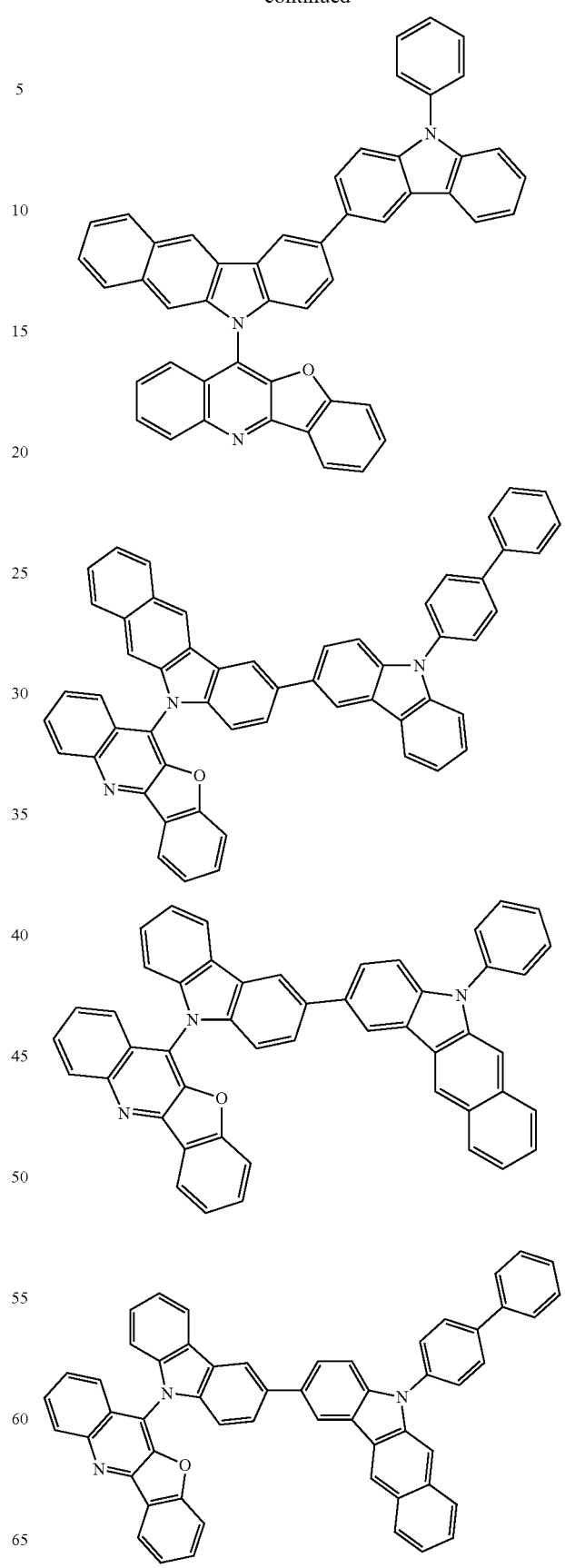

157
-continued

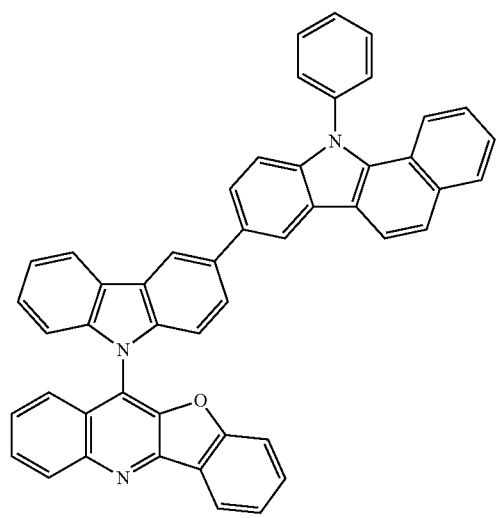
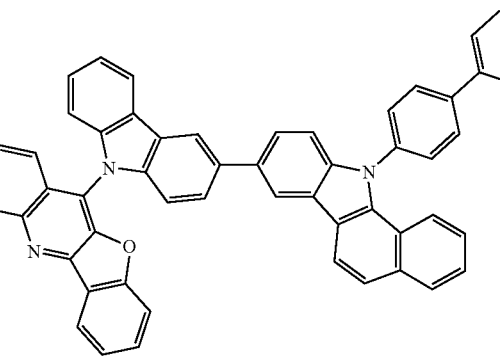
158
-continued
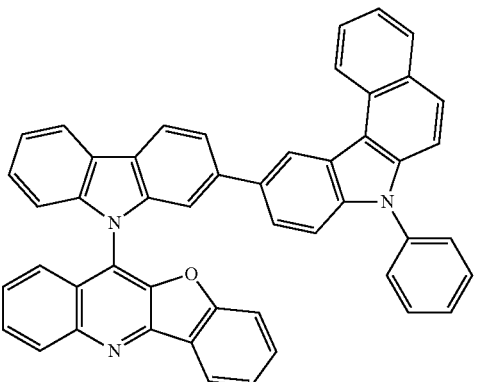
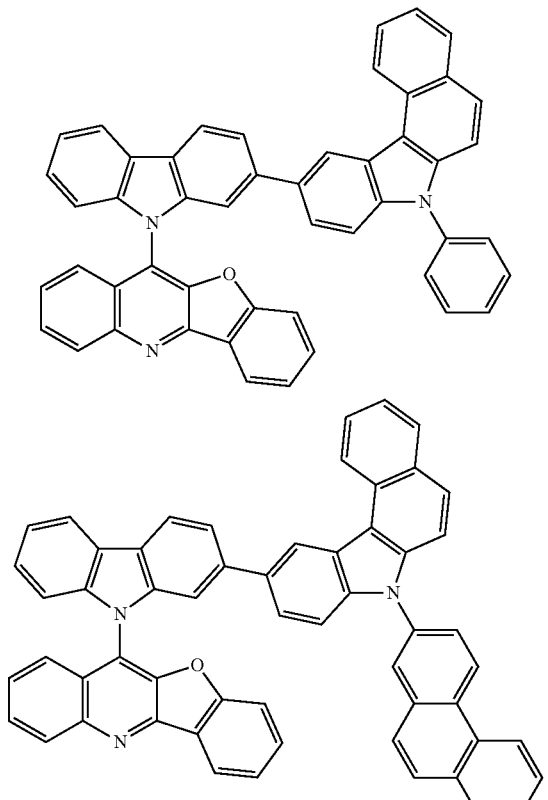
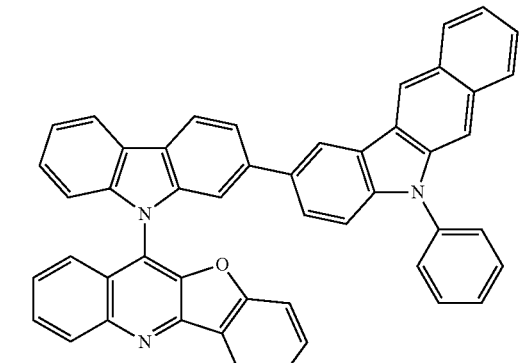
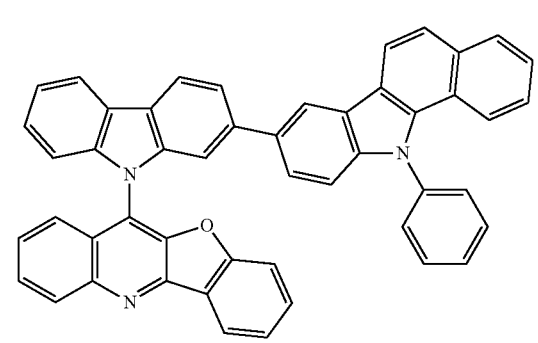

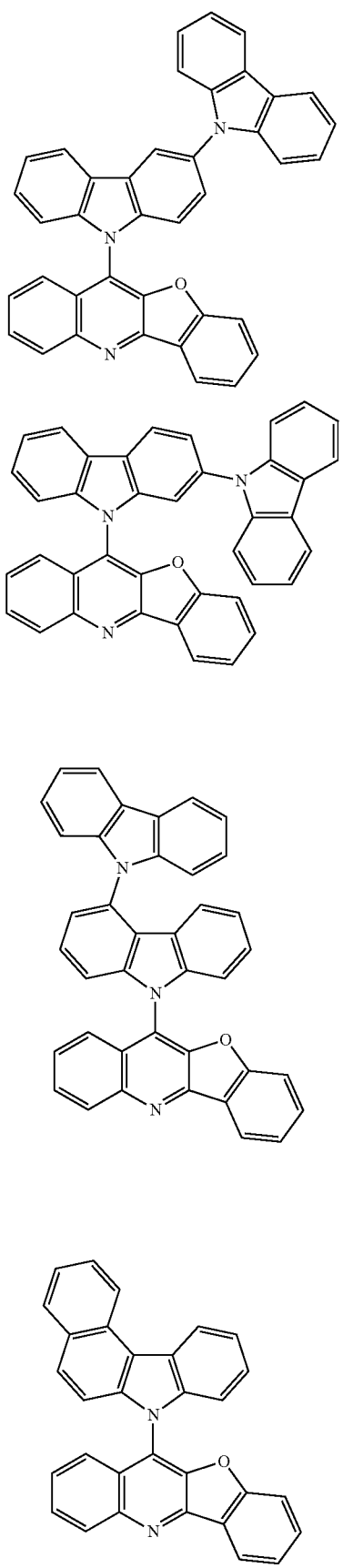
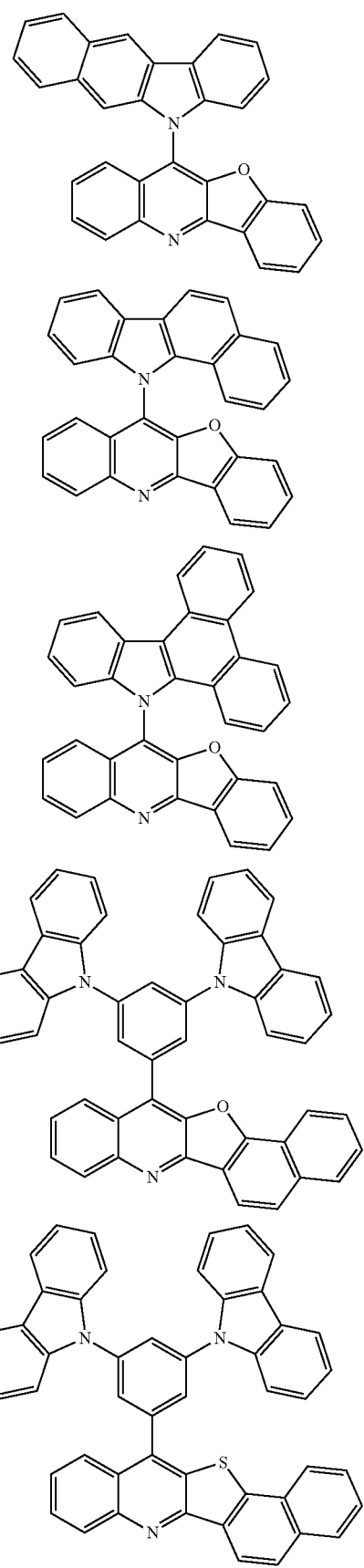

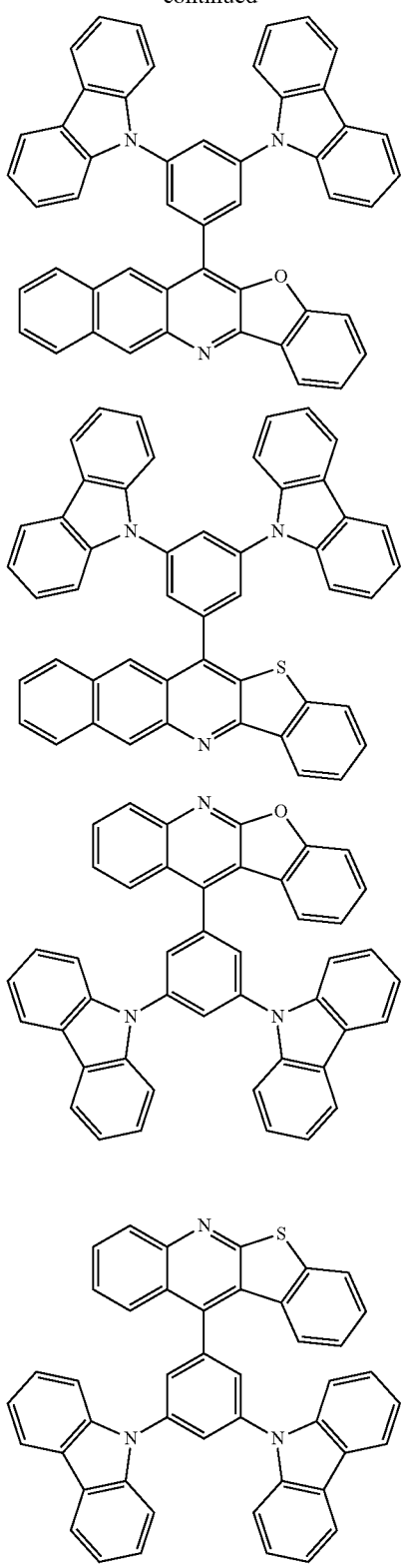
Most preferred compounds are the specific compounds mentioned above, wherein $A_2$ is $CR^{Ar2}$, wherein $R^{Ar2}$ is a substituent mentioned in the structures above and the other groups $B^1$ to $B^8$ are CH.
Further most preferred compounds are the following compounds:
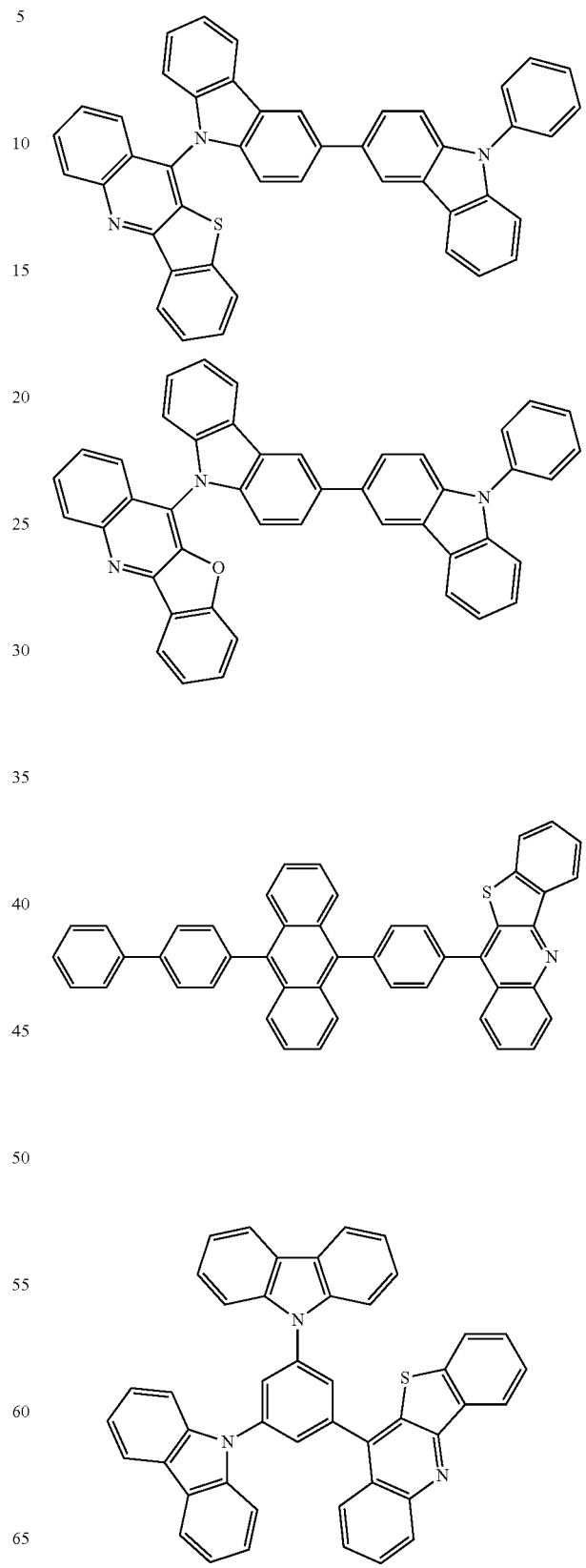

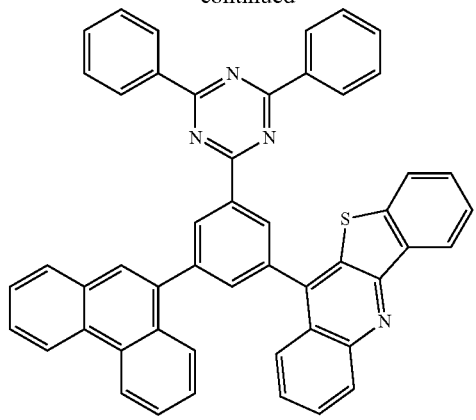
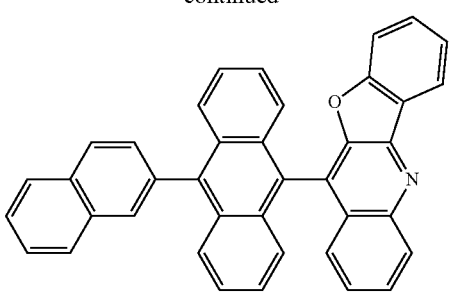
Other most preferred compounds of formula (1) are mentioned below.
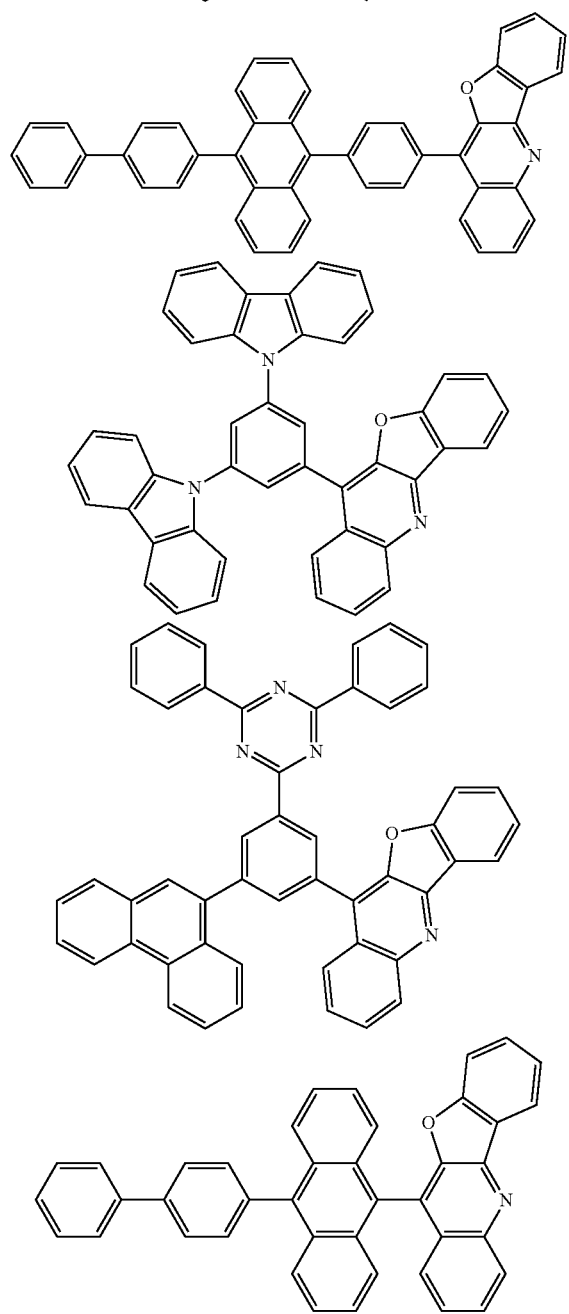
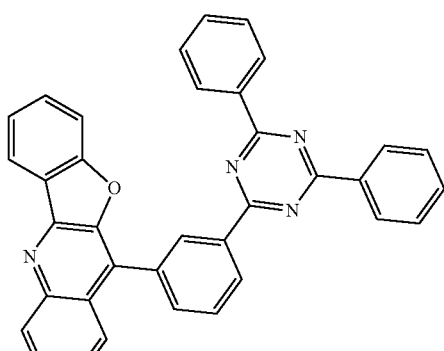
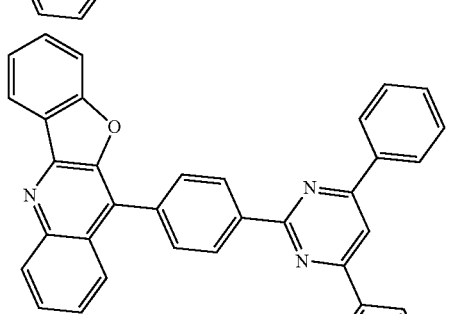
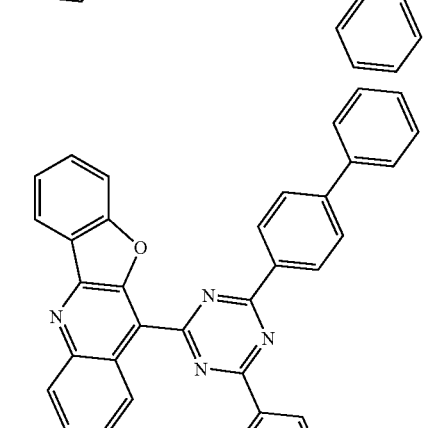
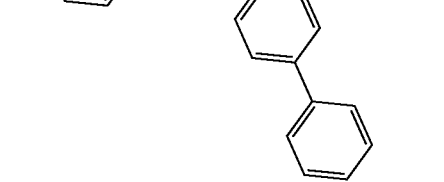

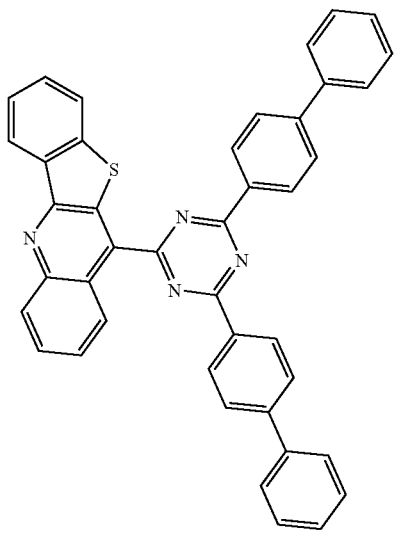
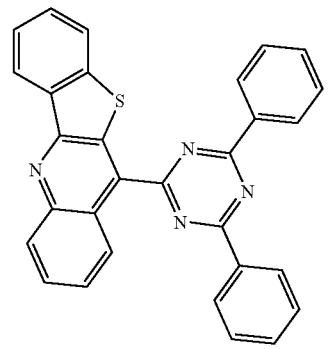
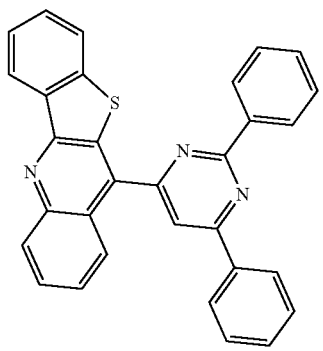
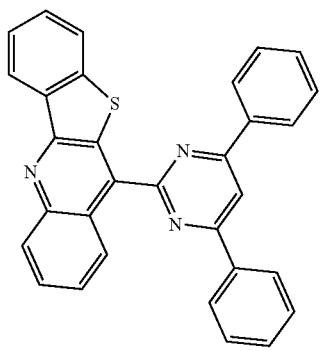
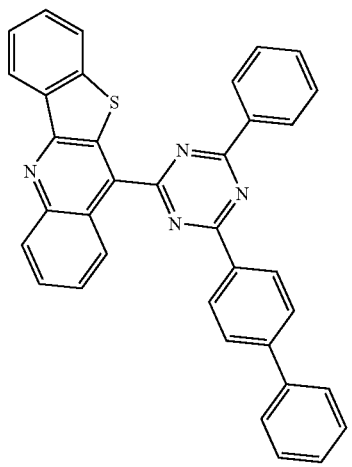
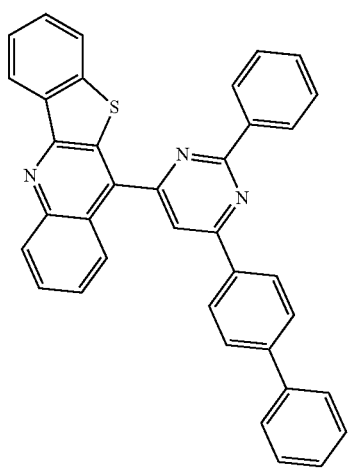
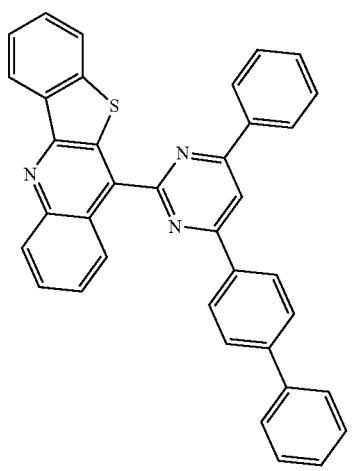

167
-continued
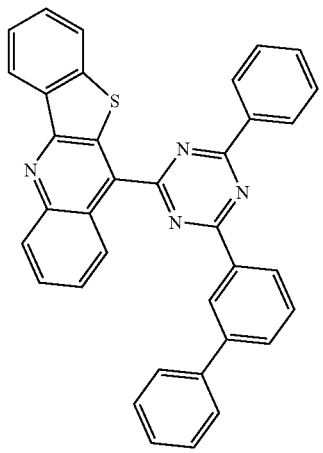
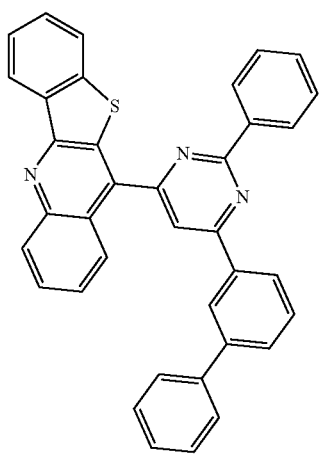
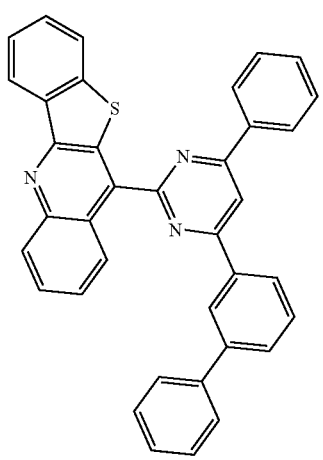
168
-continued
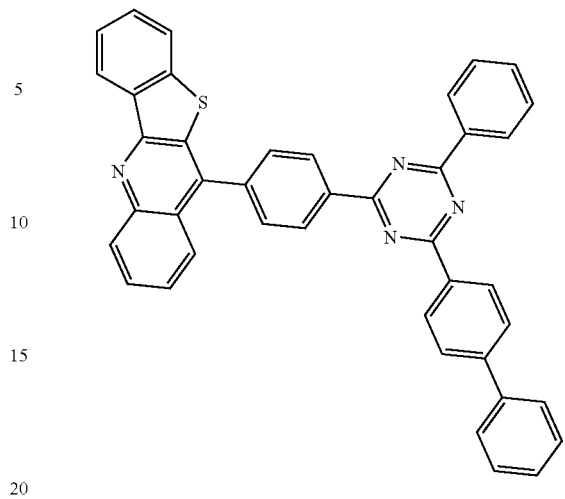
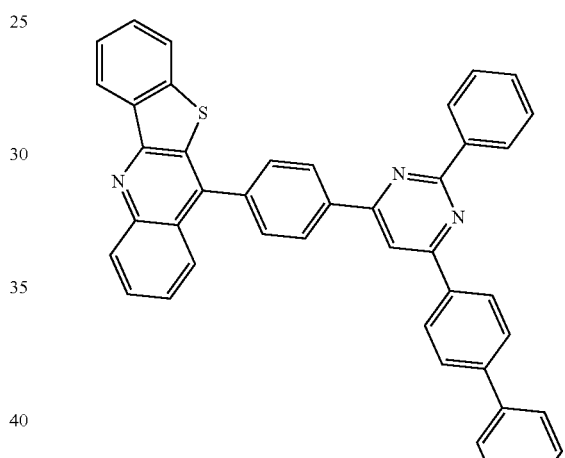
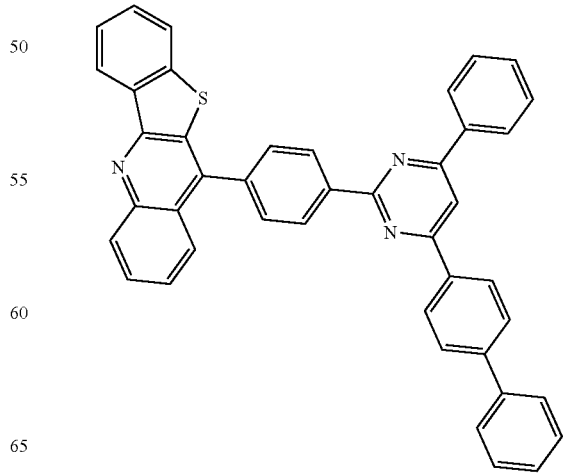

-continued
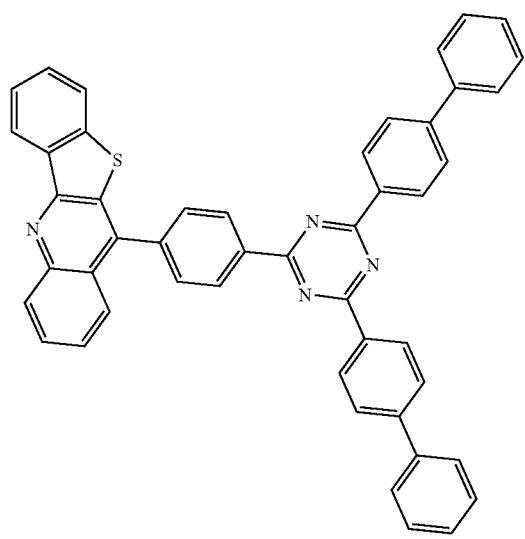
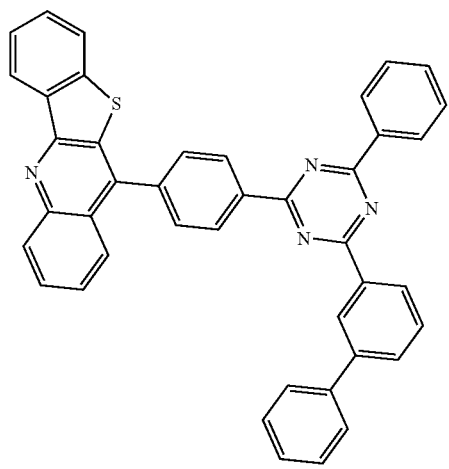
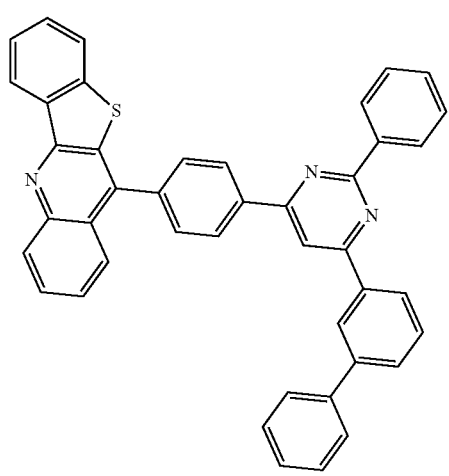
-continued
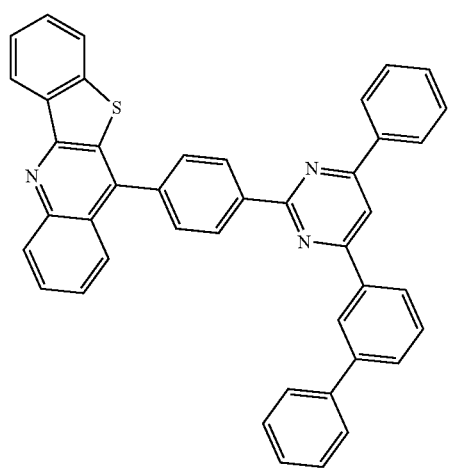
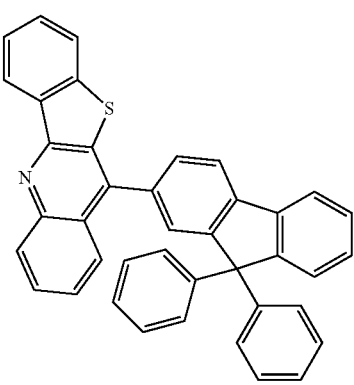
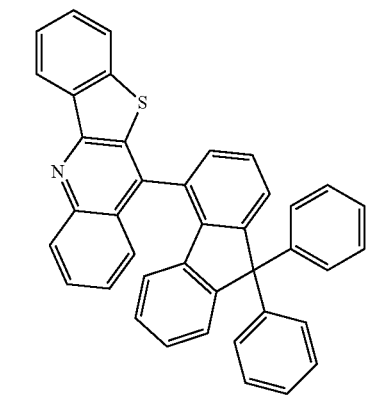
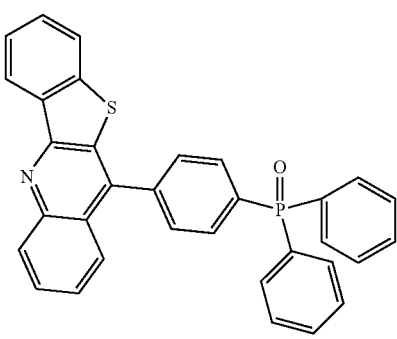

171
-continued
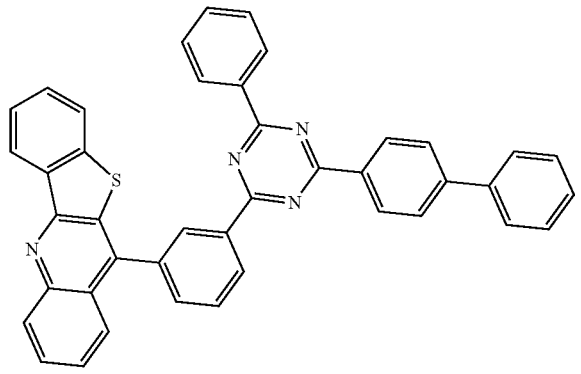
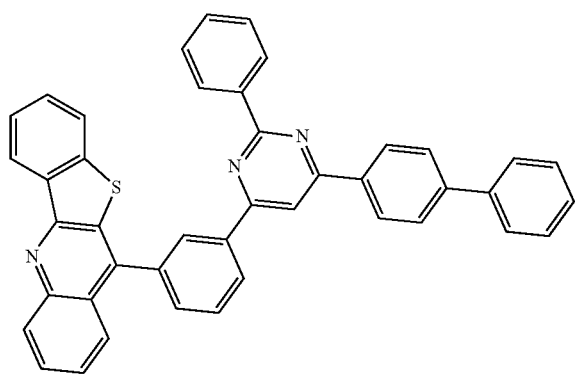
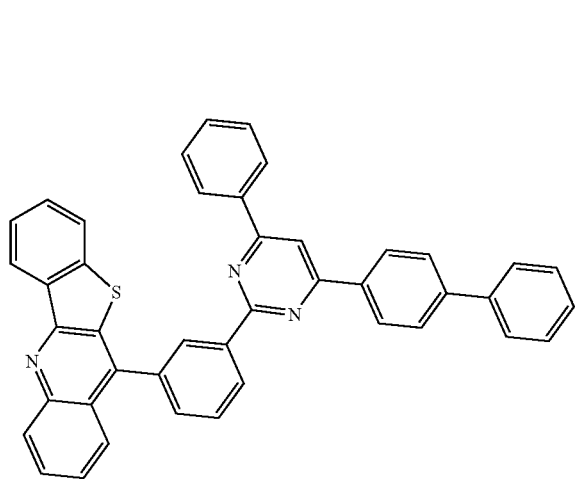
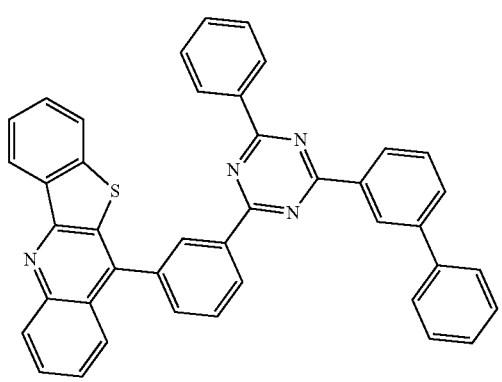
172
-continued
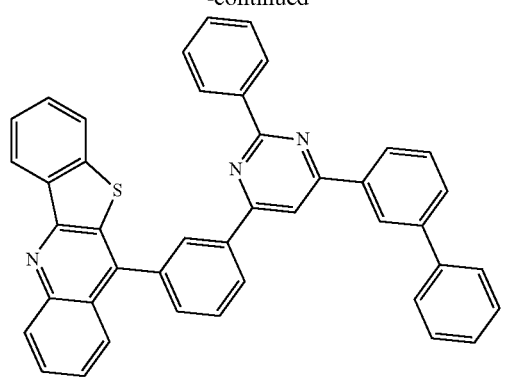
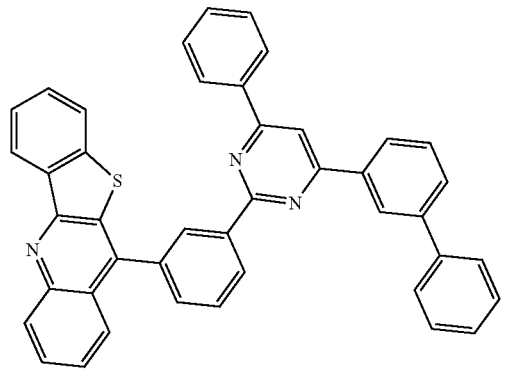
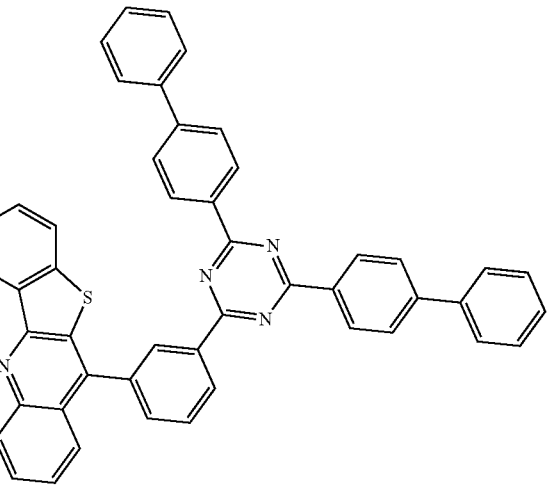
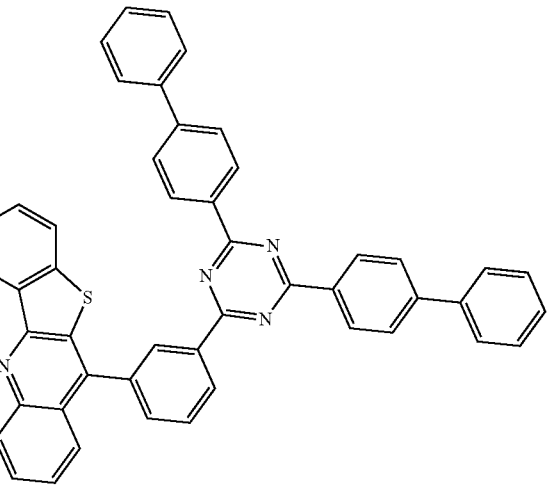

173
-continued
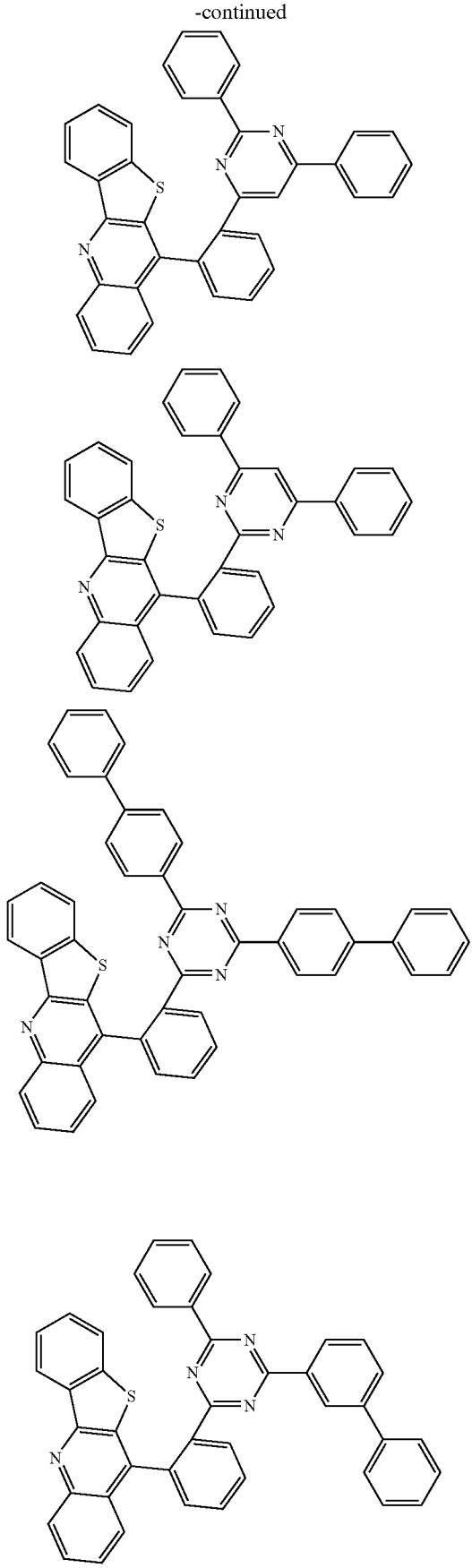
174
-continued
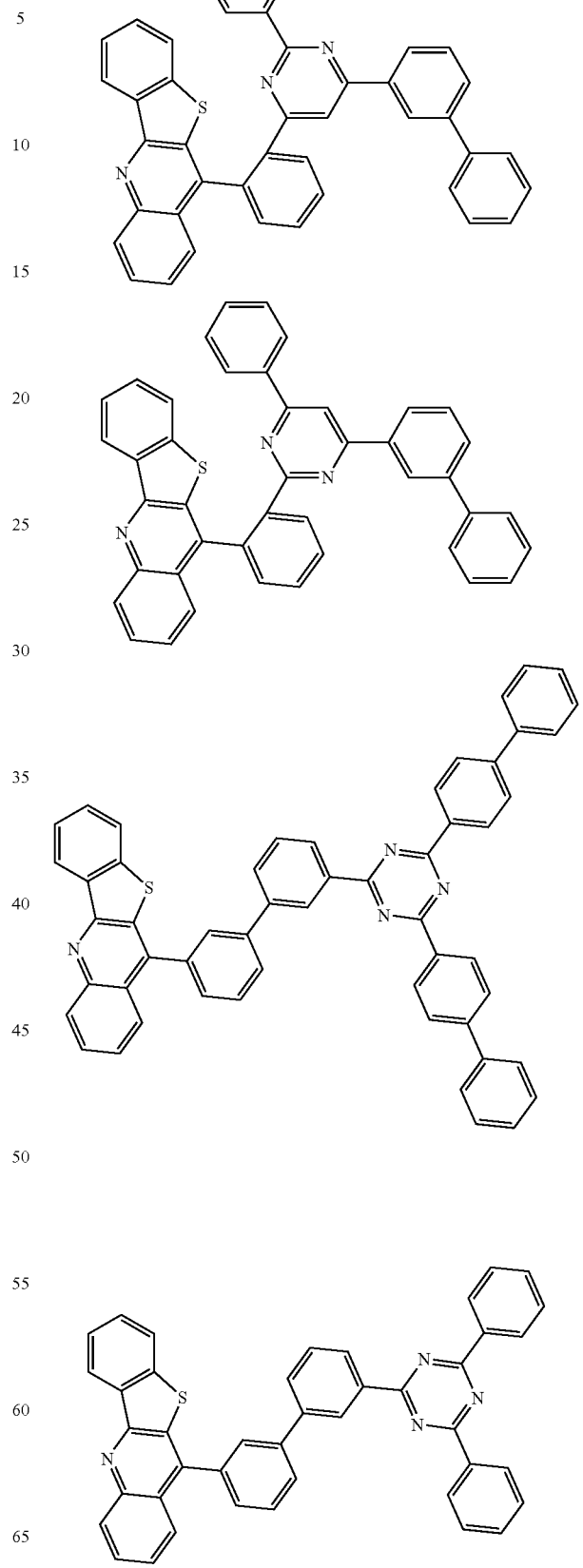

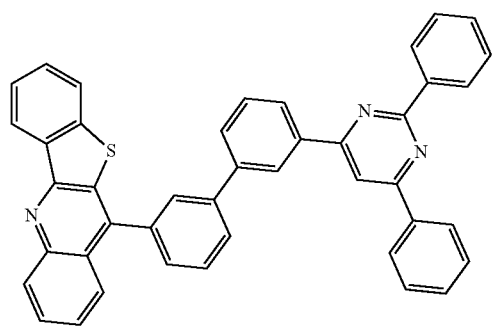
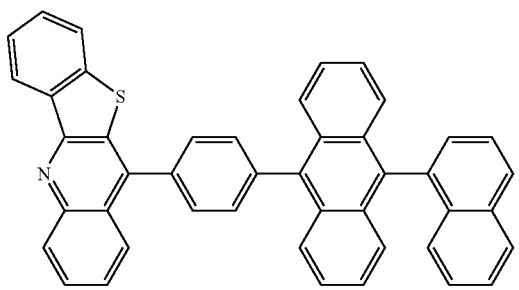
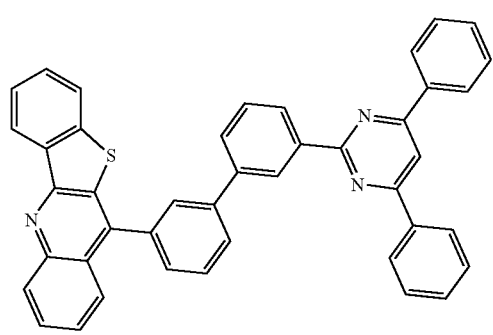
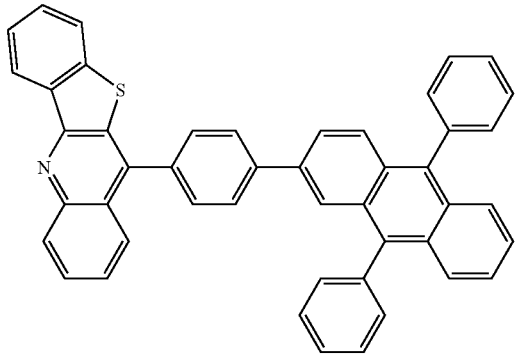
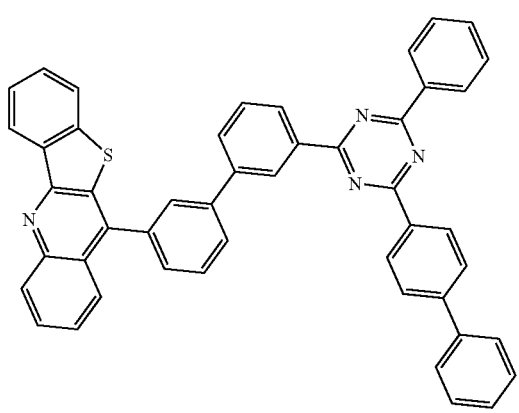
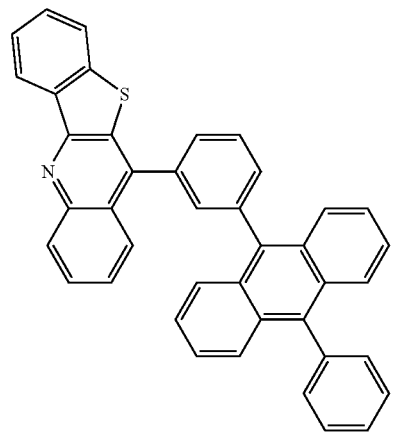
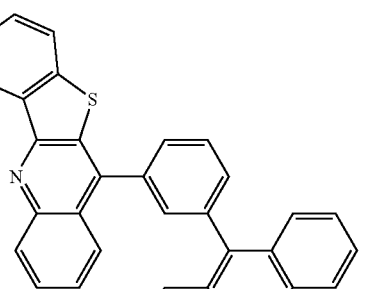
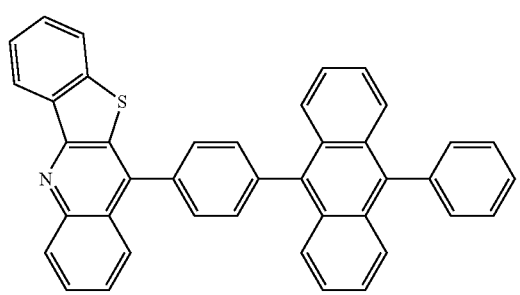
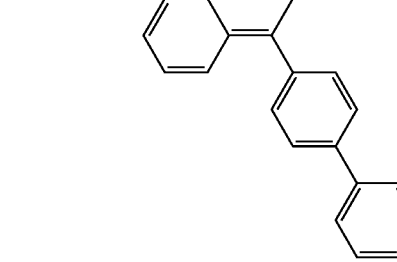

177
-continued
178
-continued
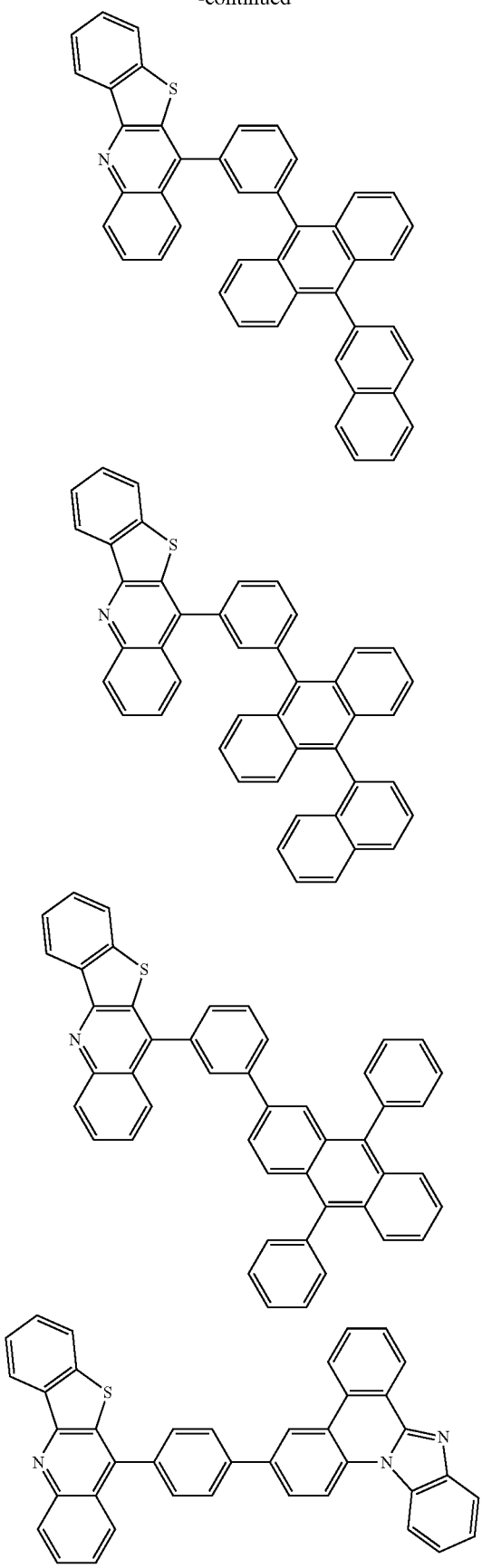
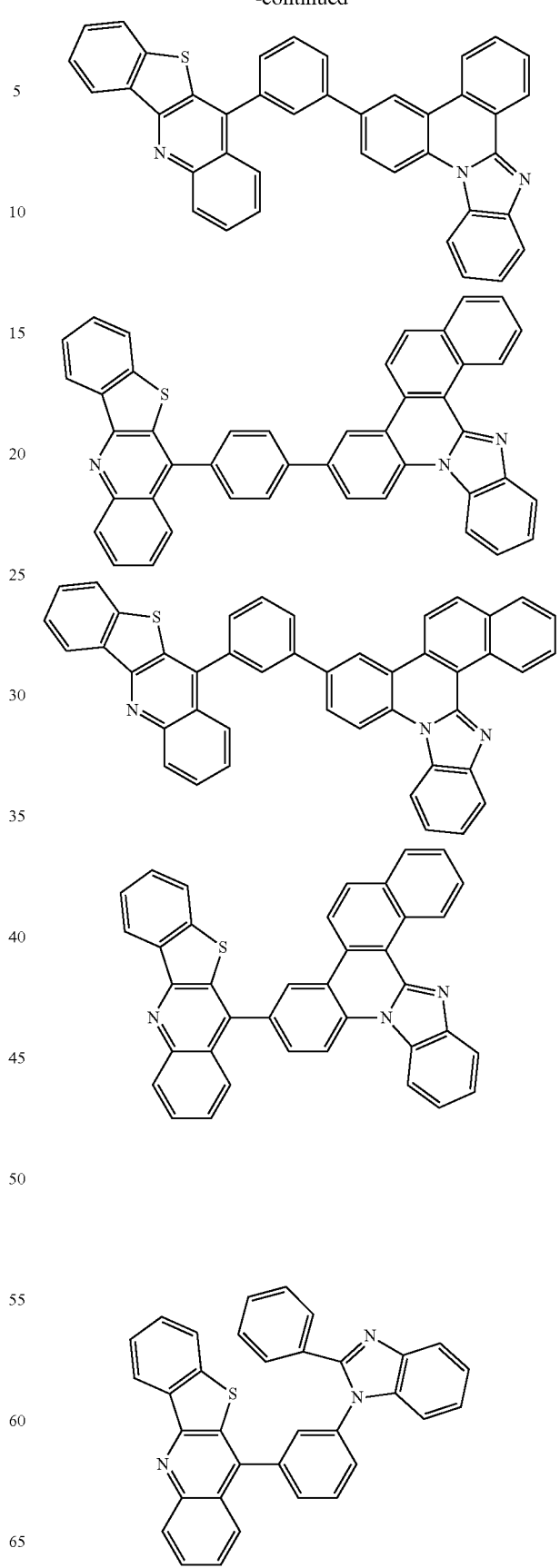

-continued
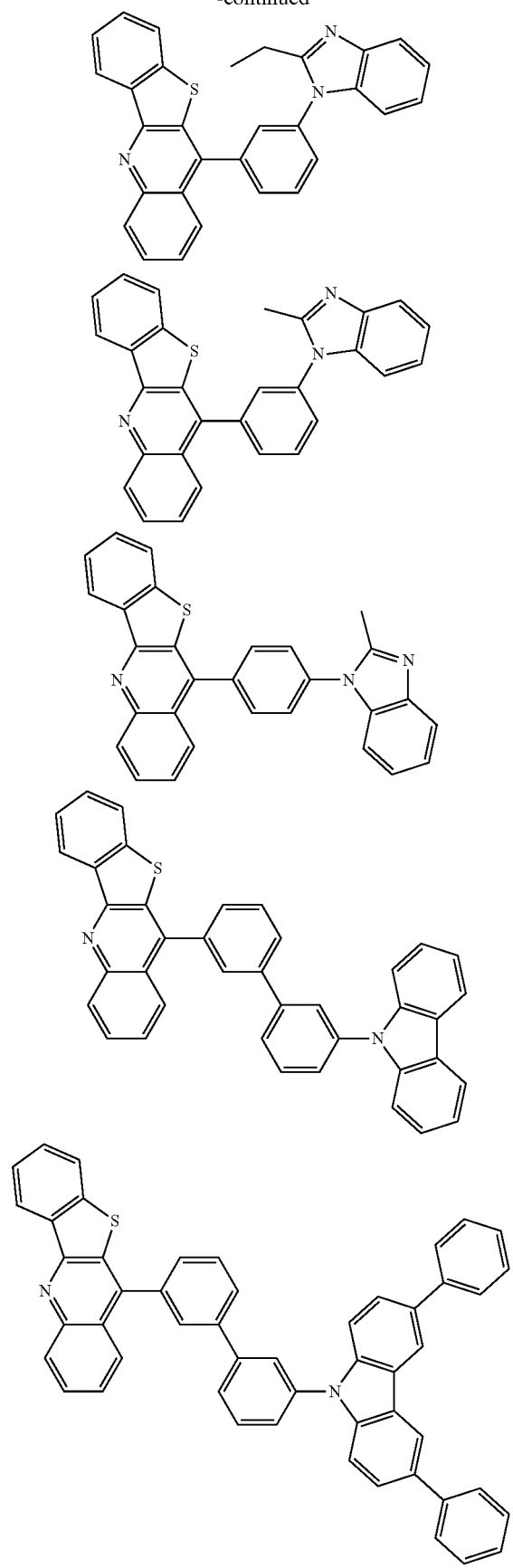
-continued
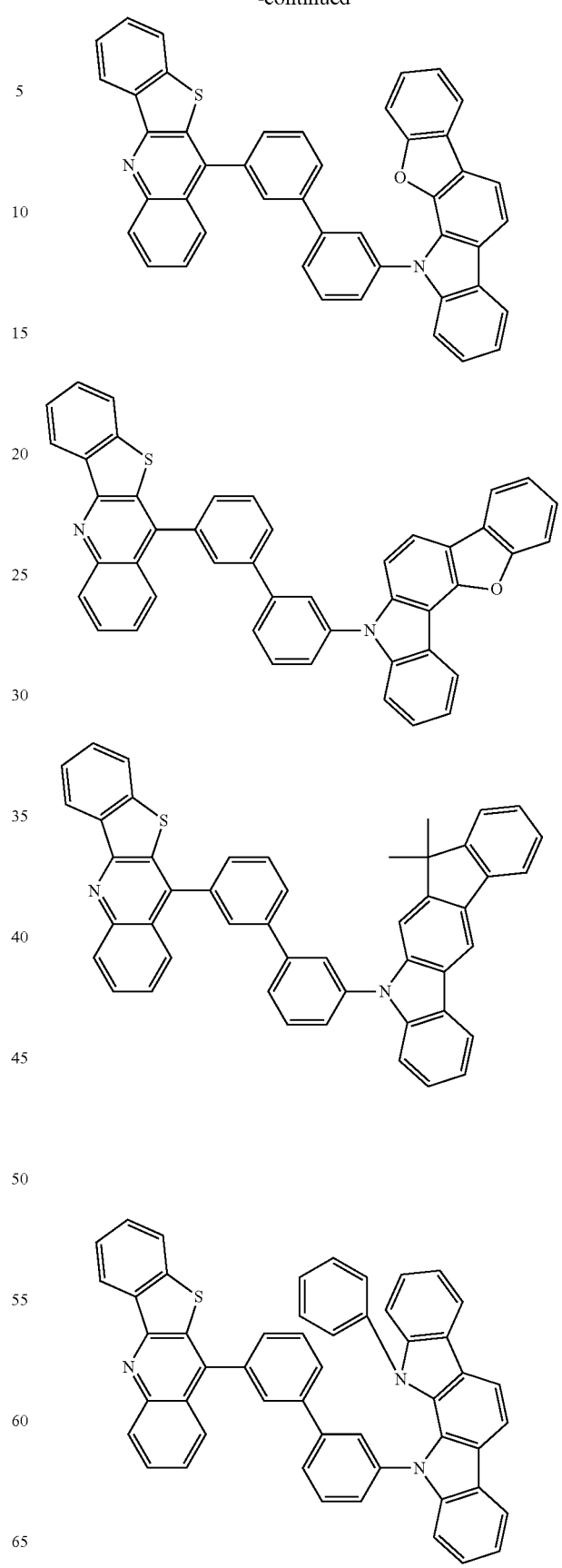

181
-continued
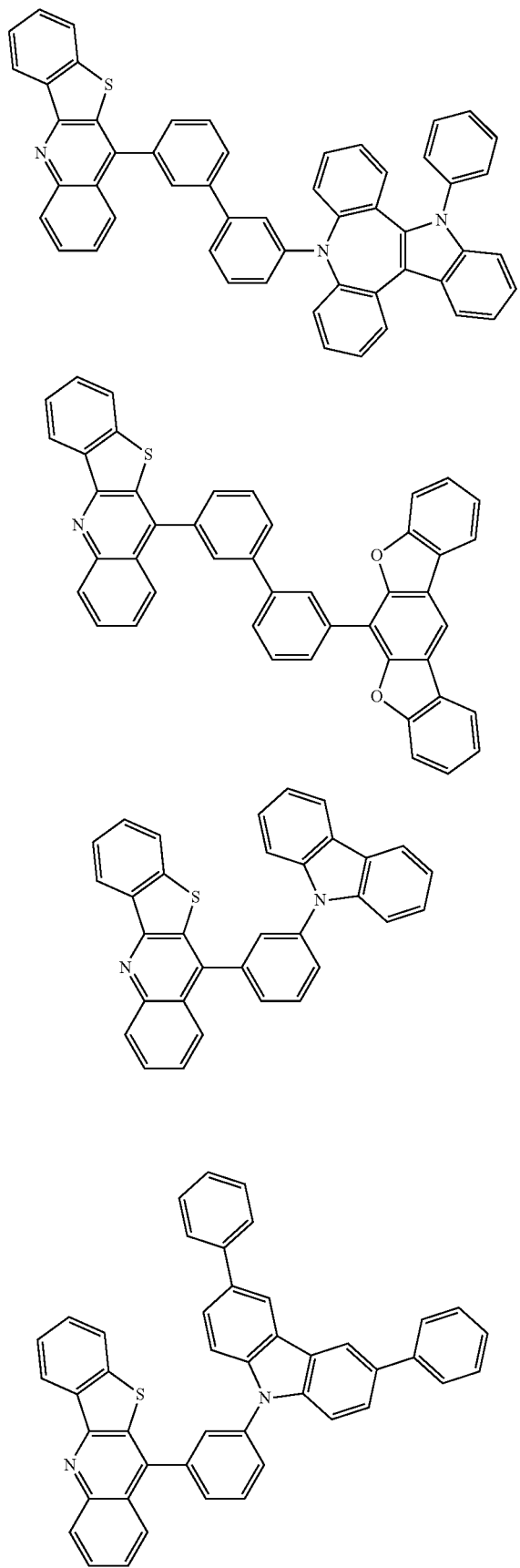
182
-continued
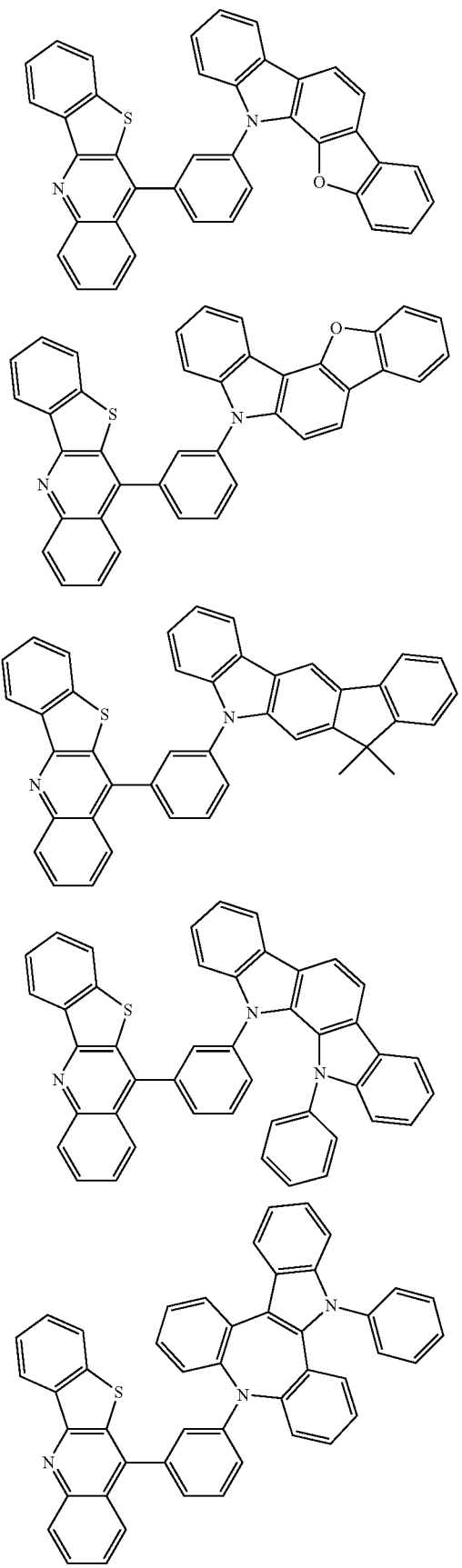

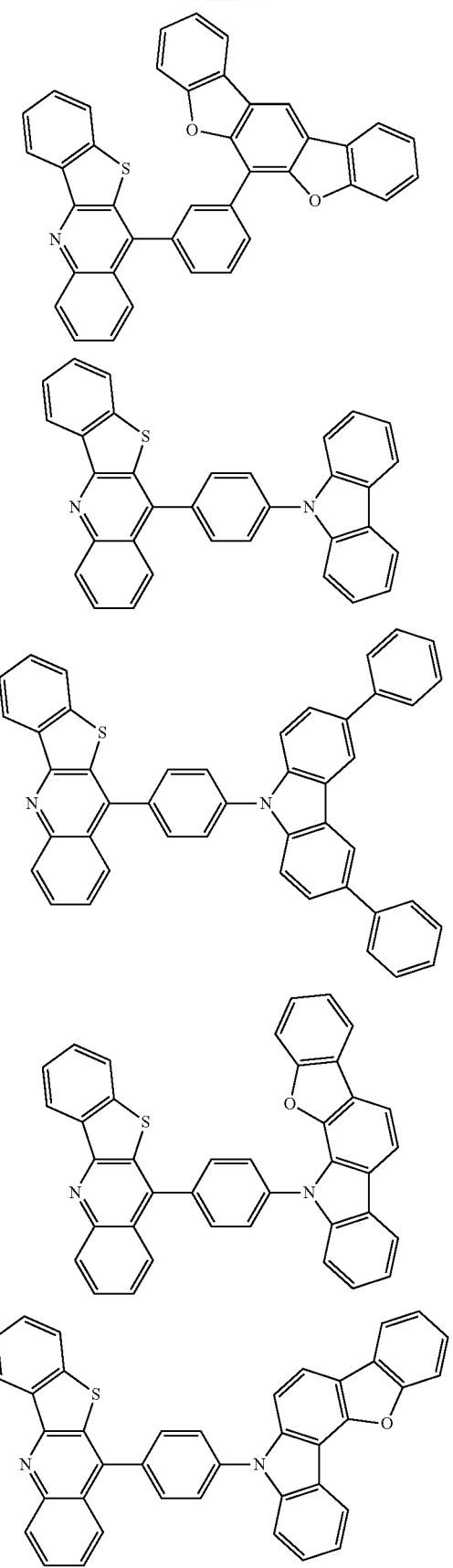
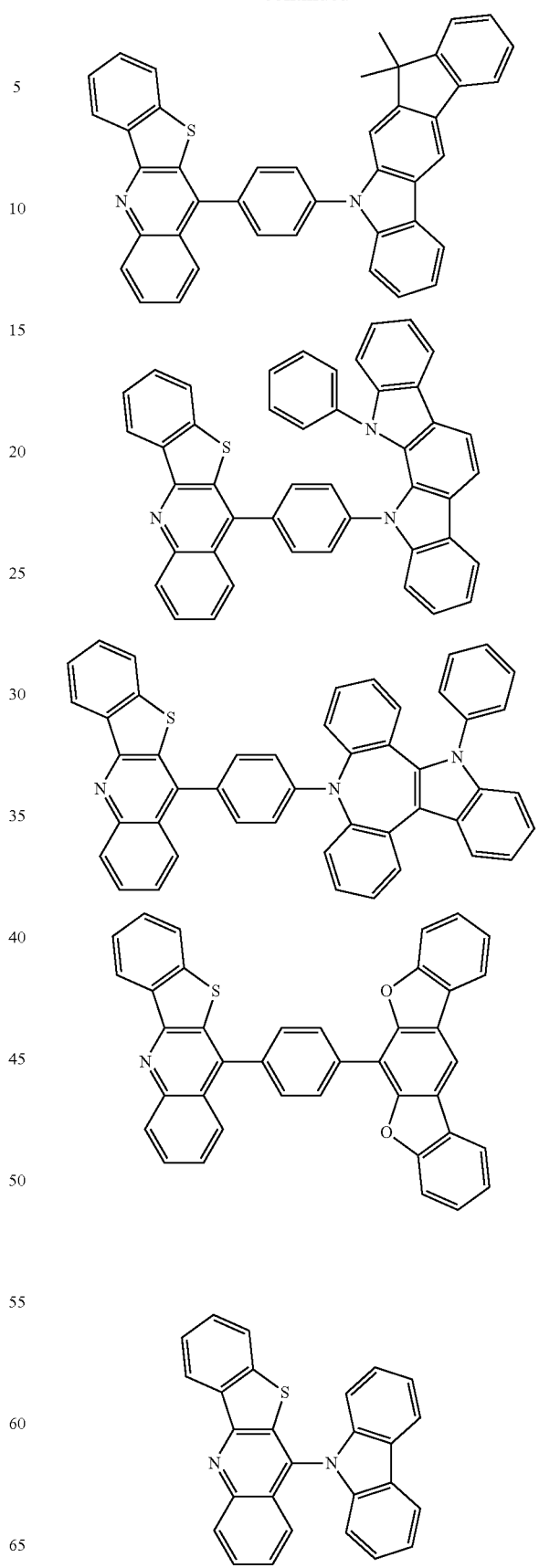

185
-continued
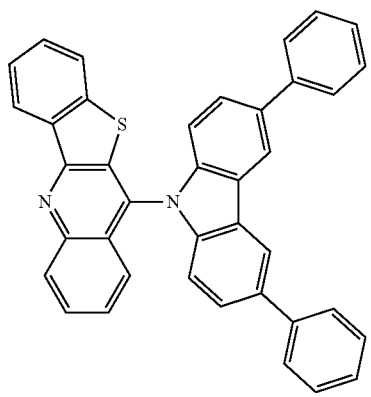
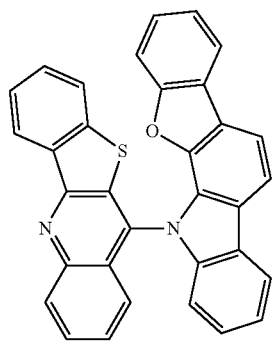
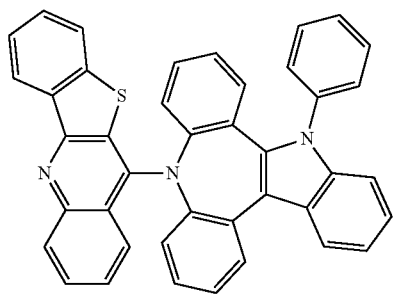
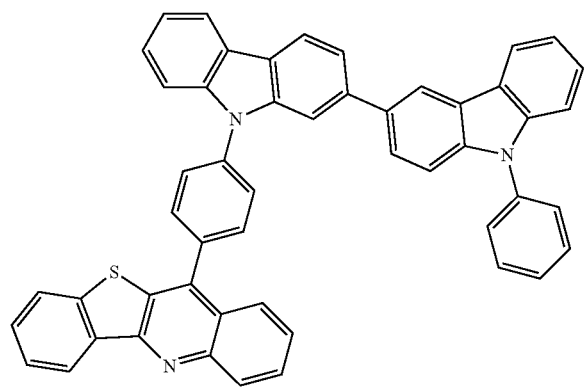
186
-continued
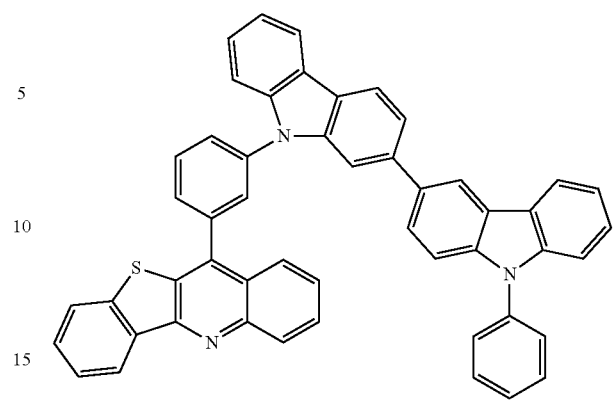
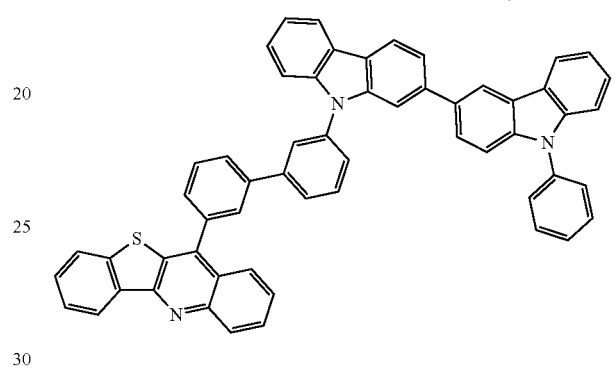
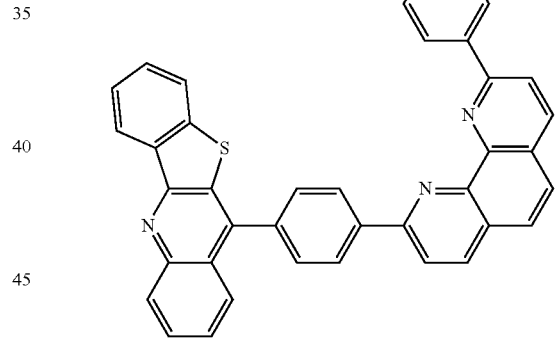
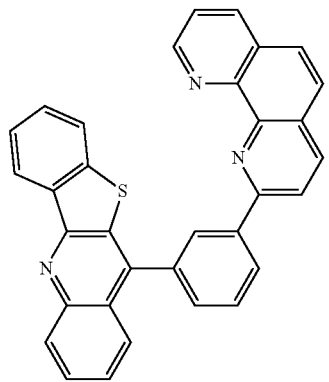

187
-continued
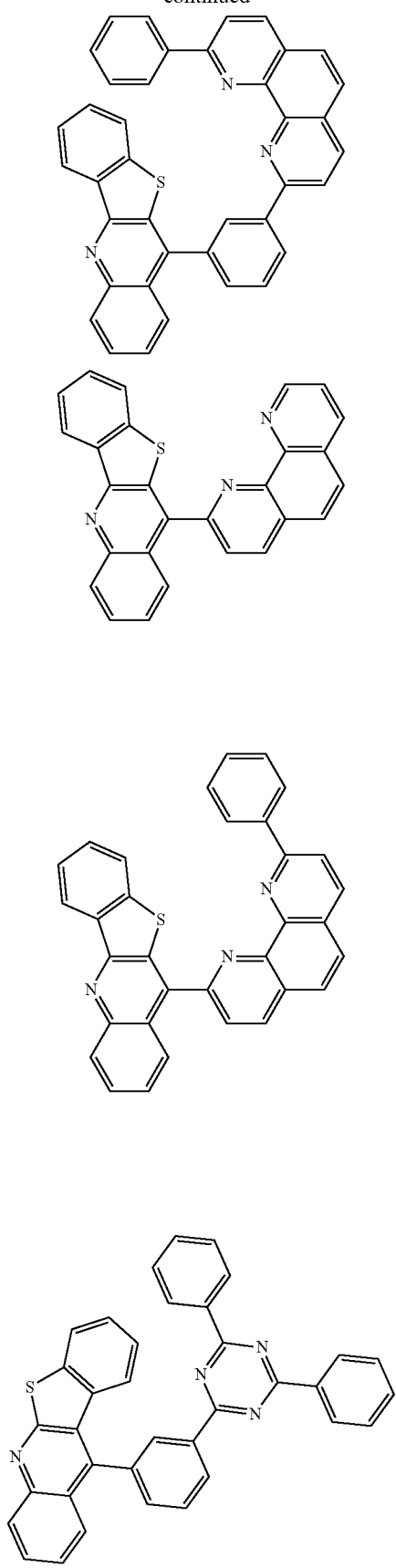
188
-continued
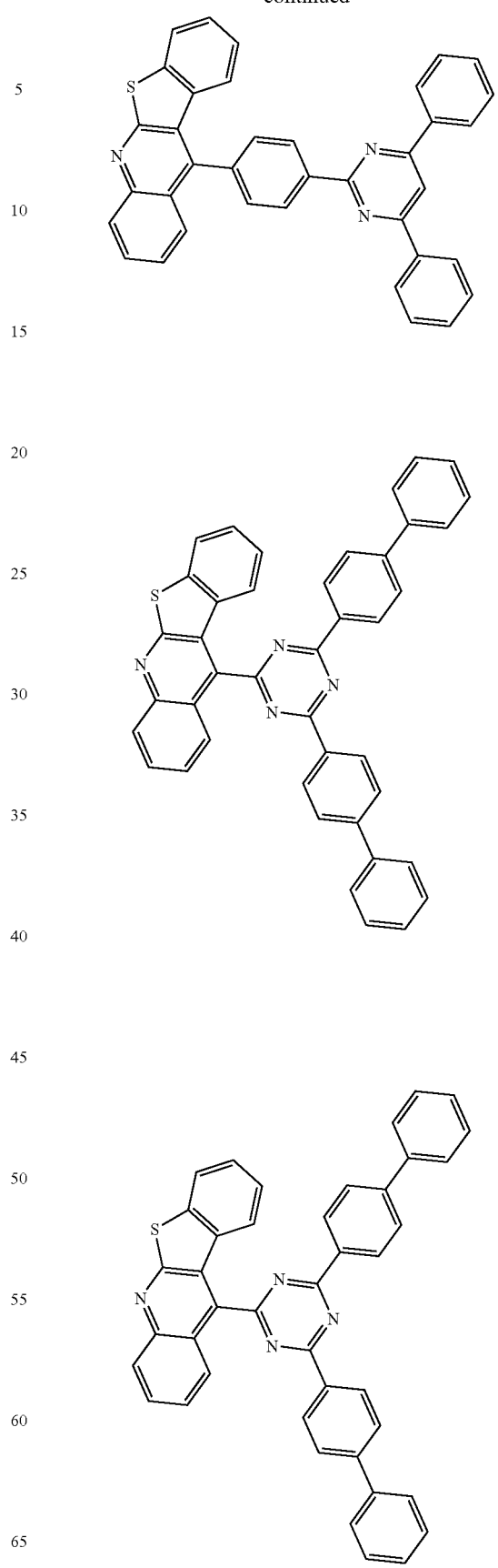

189
-continued
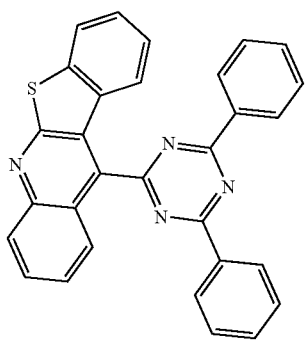
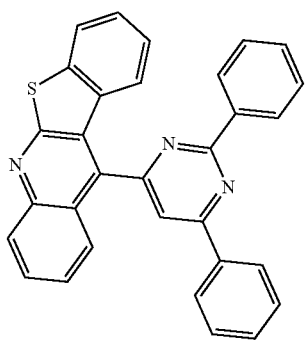
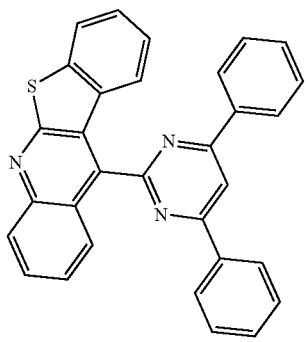
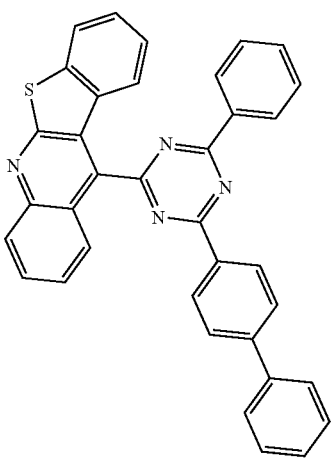
190
-continued
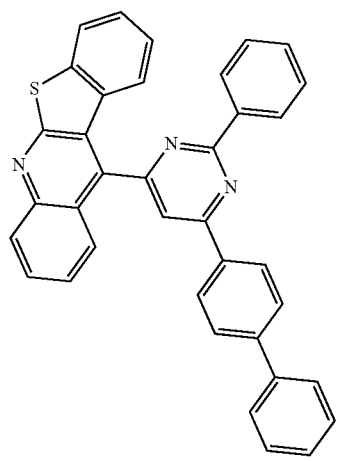
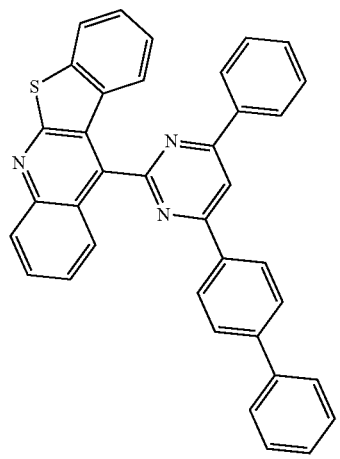
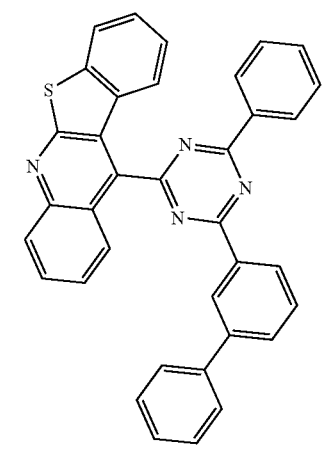

191
-continued
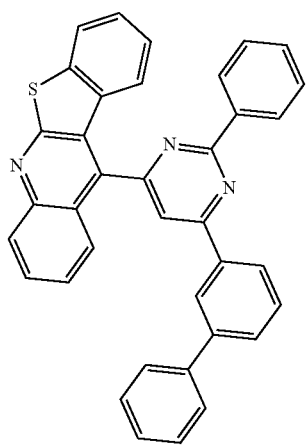
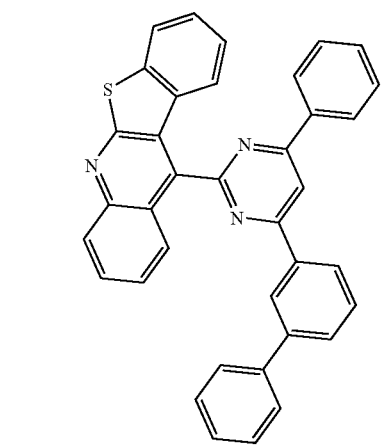
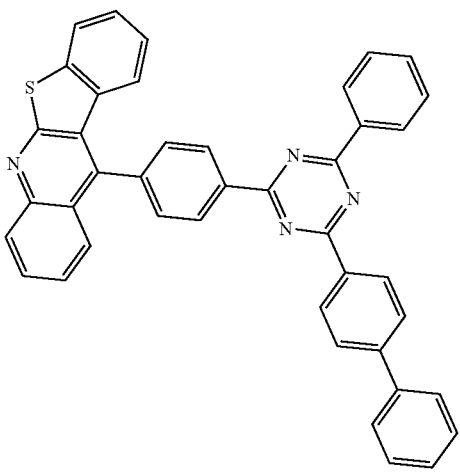
192
-continued
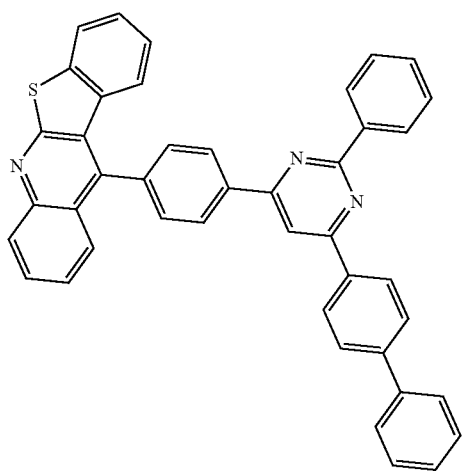
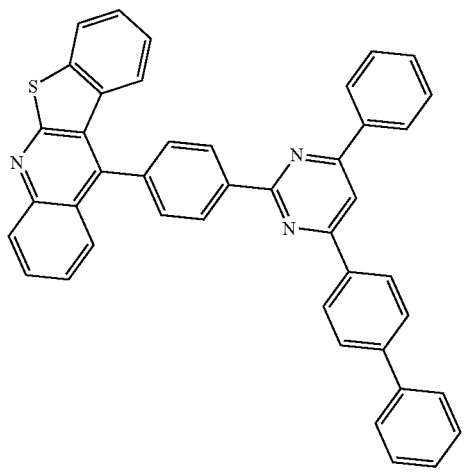
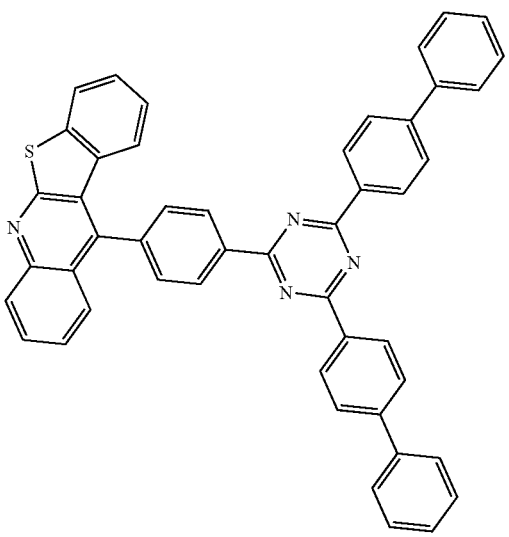

193
-continued
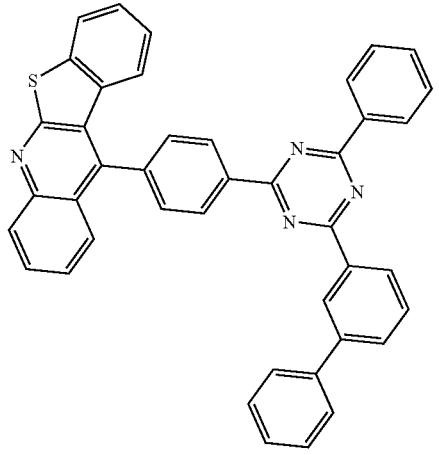
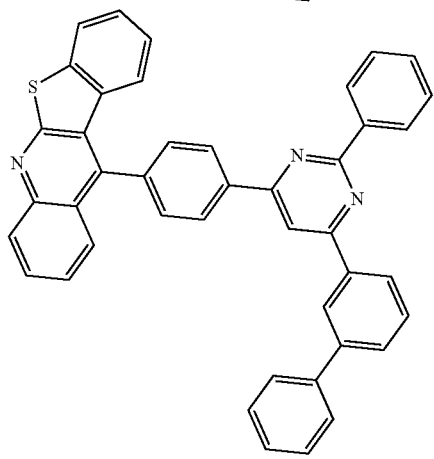
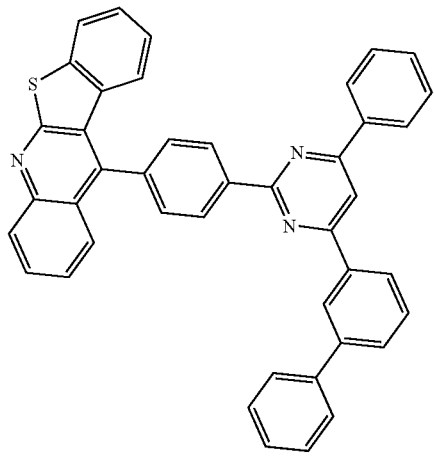
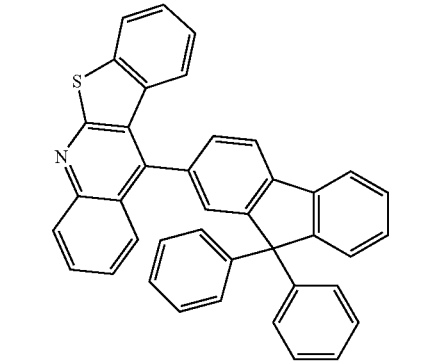
194
-continued
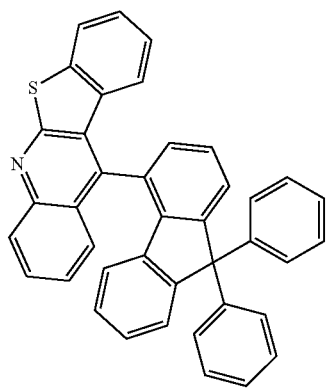
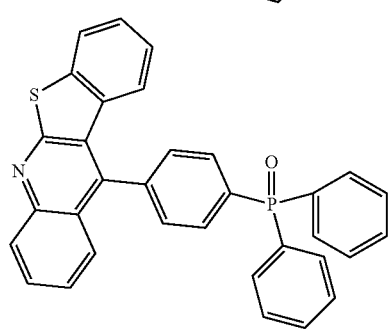
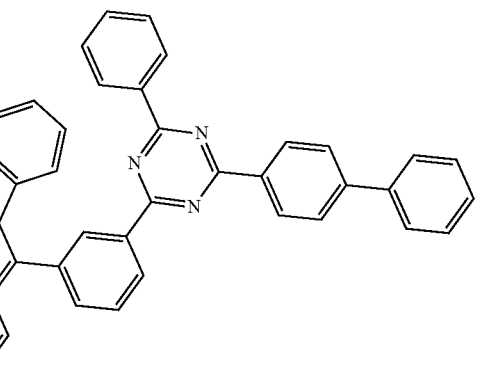
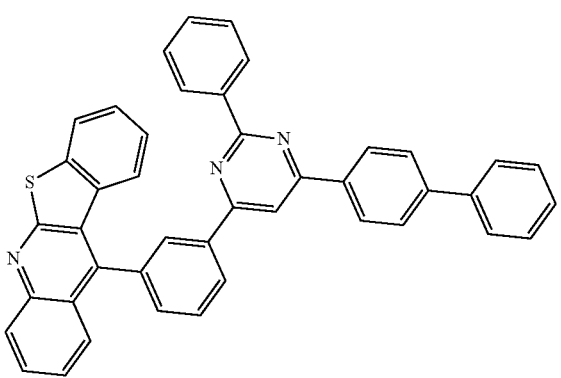

-continued
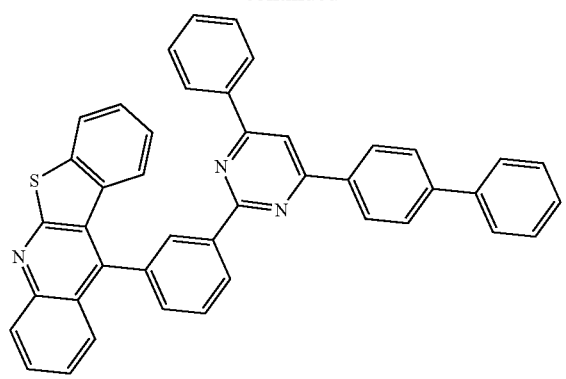
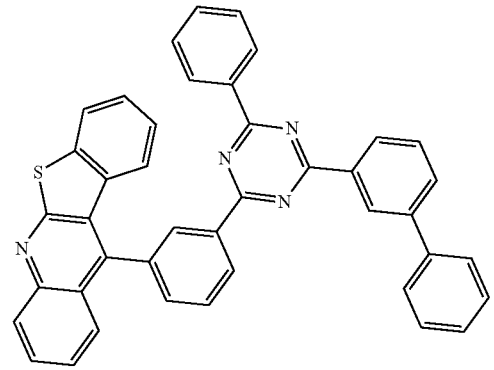
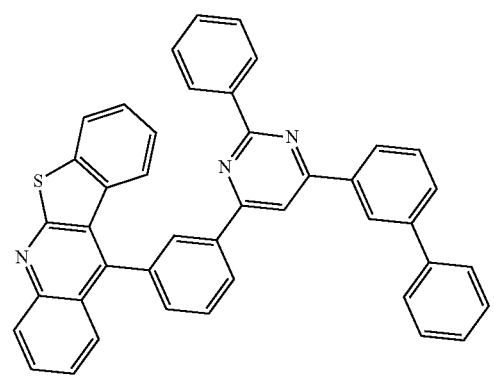
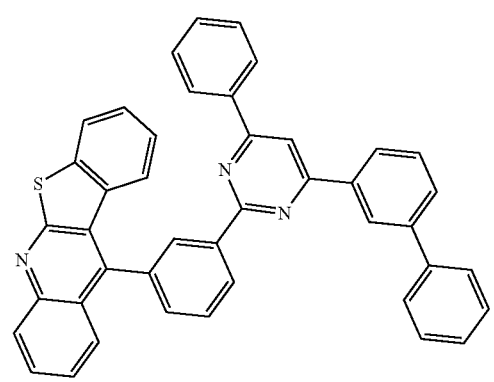
-continued
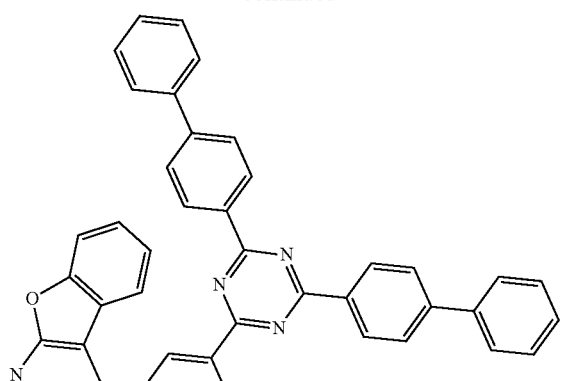
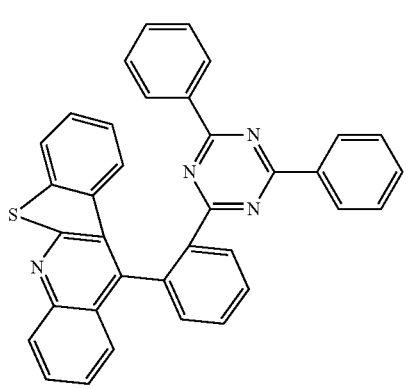
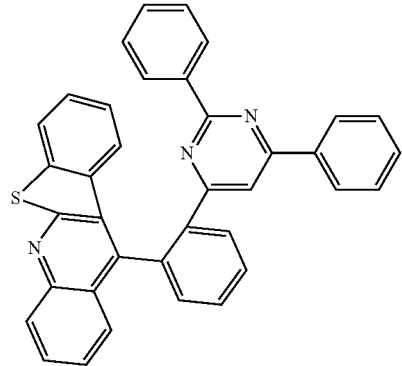
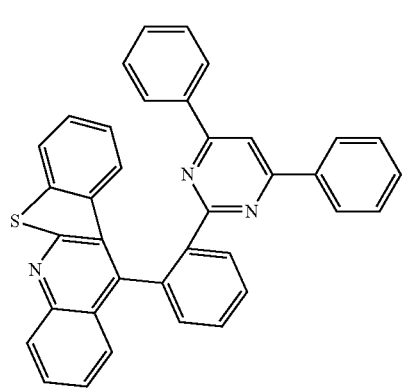

197
-continued
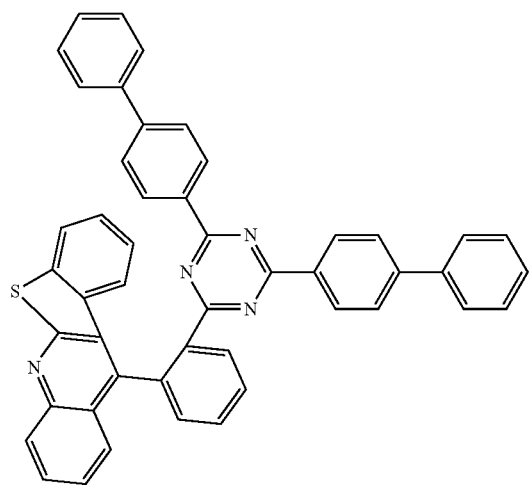
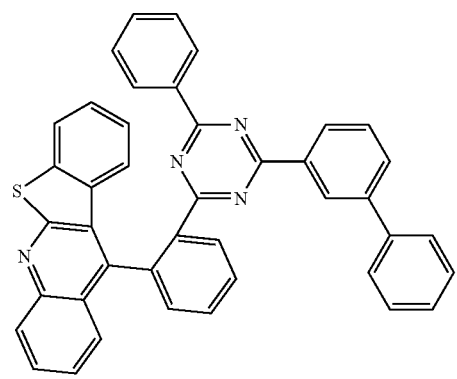
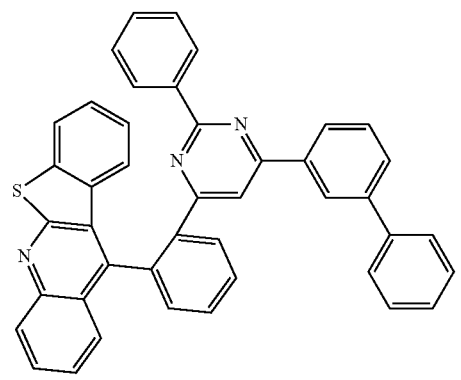
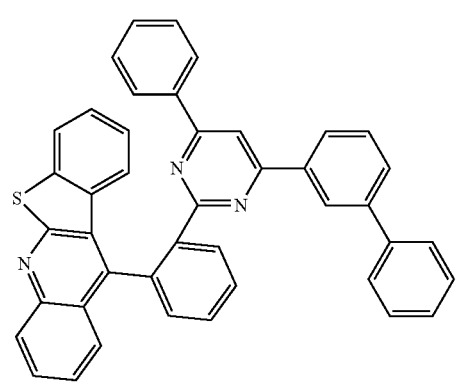
198
-continued
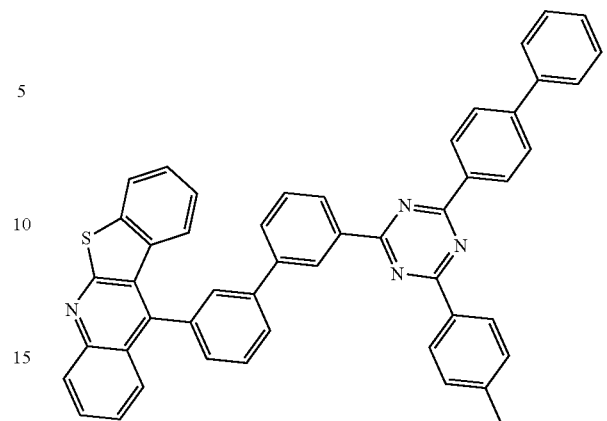
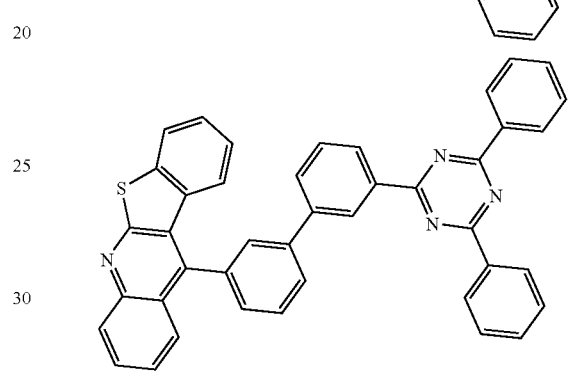
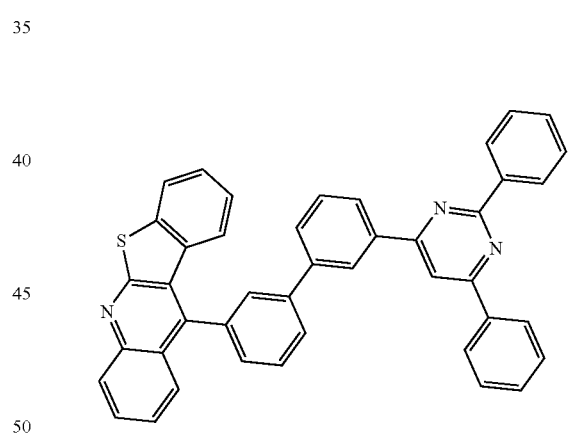

199
-continued
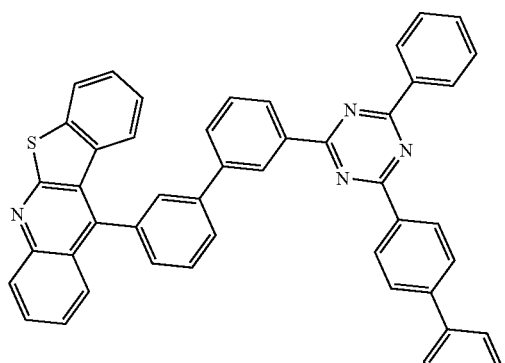
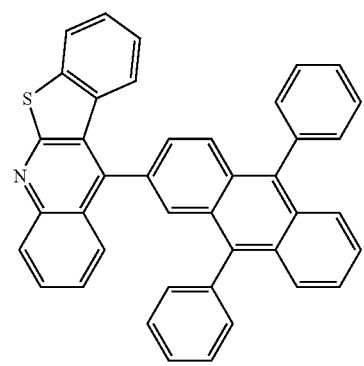
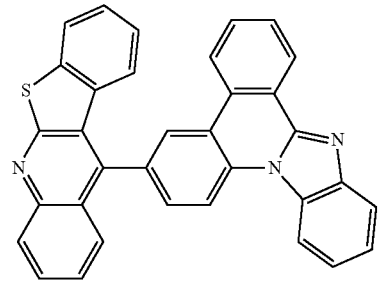
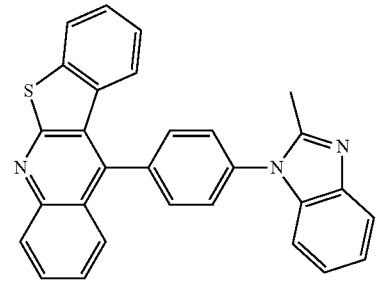
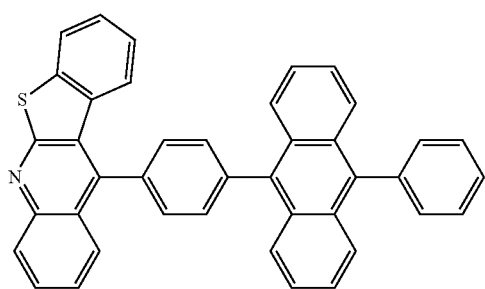
200
-continued
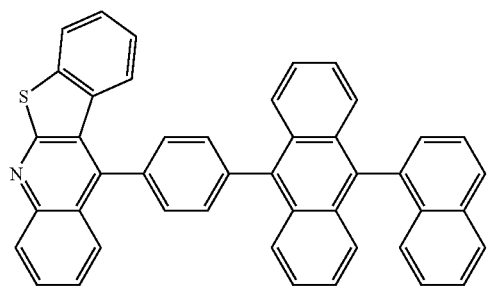
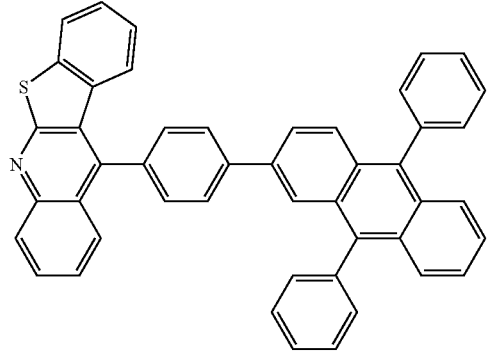
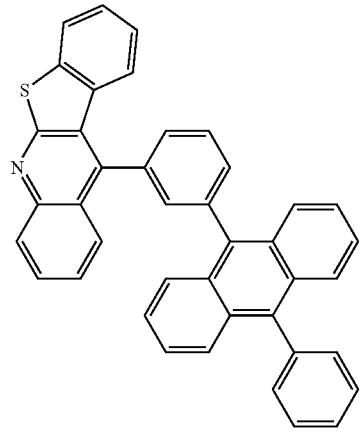
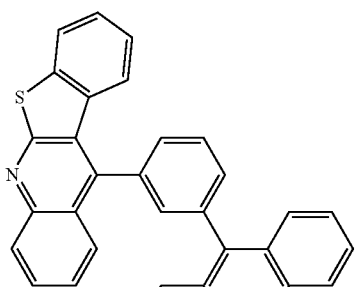
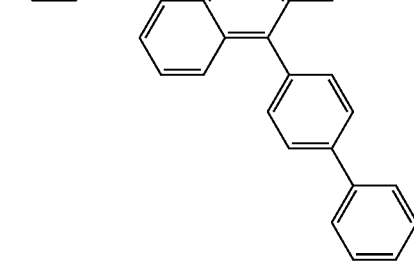

201
-continued
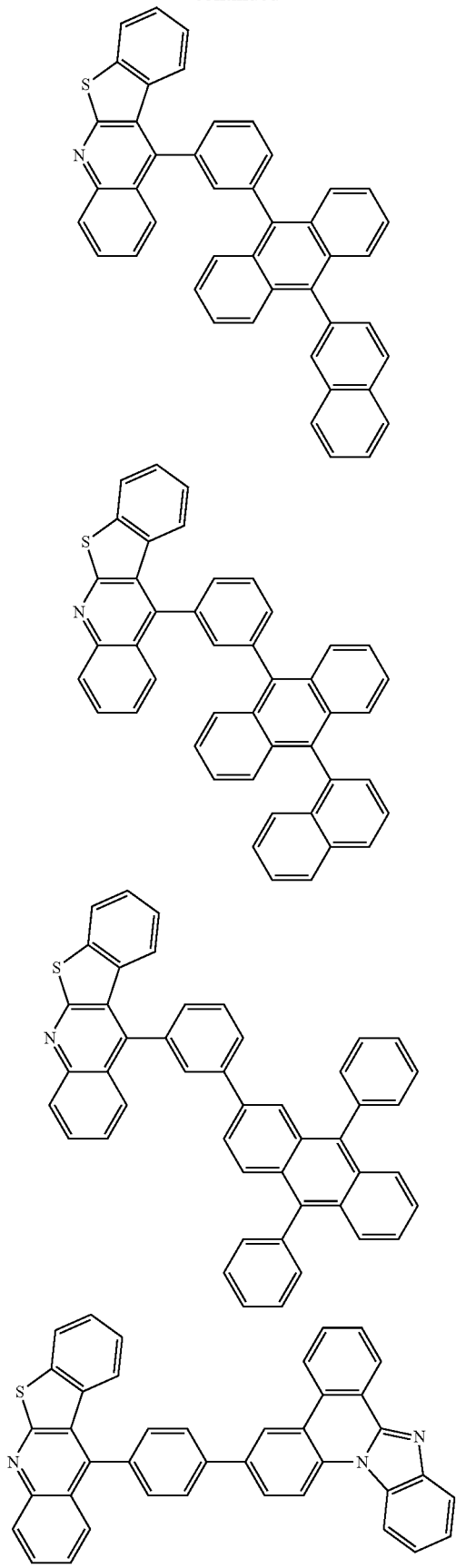
202
-continued
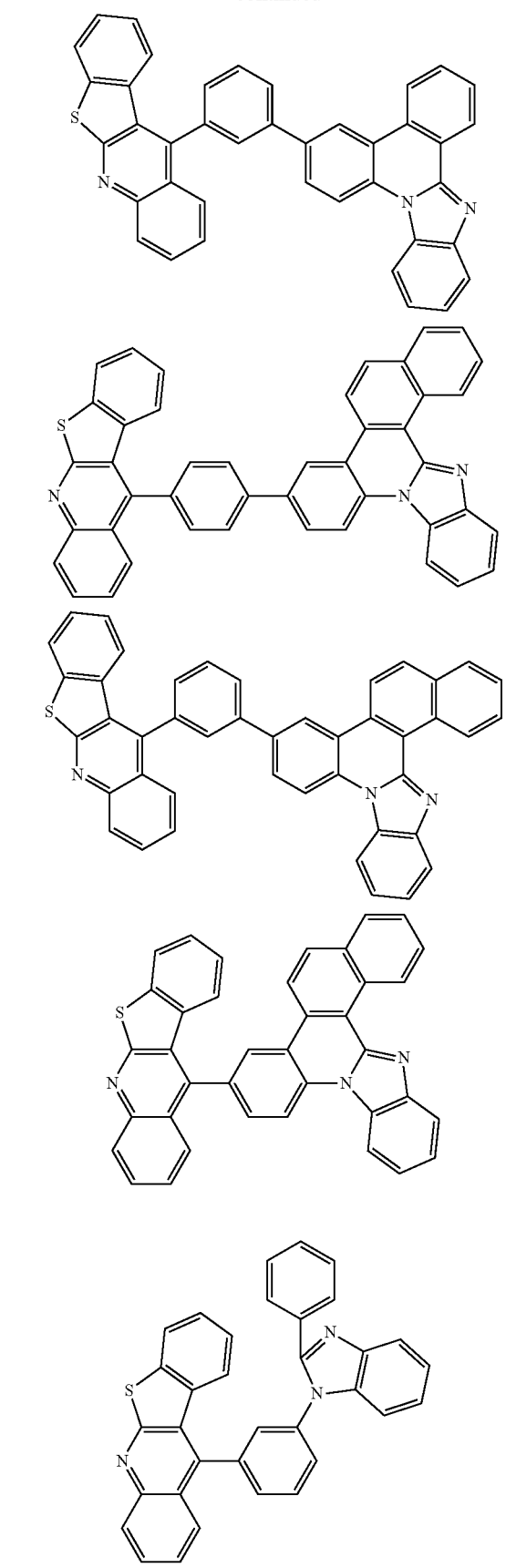

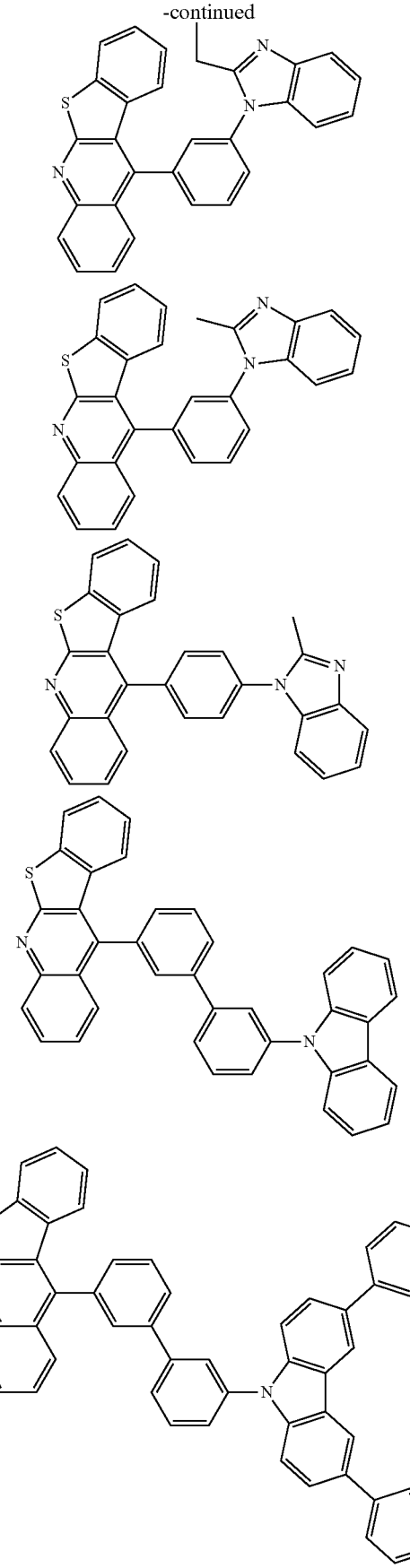

205
-continued
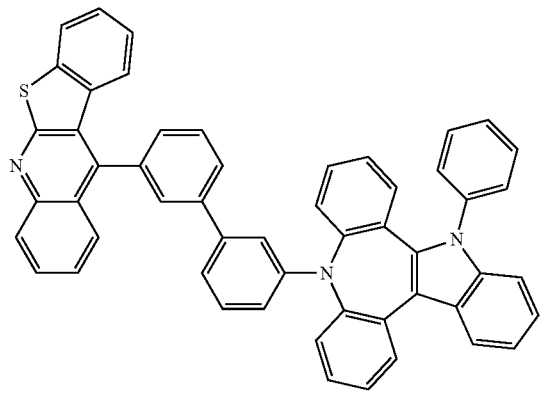
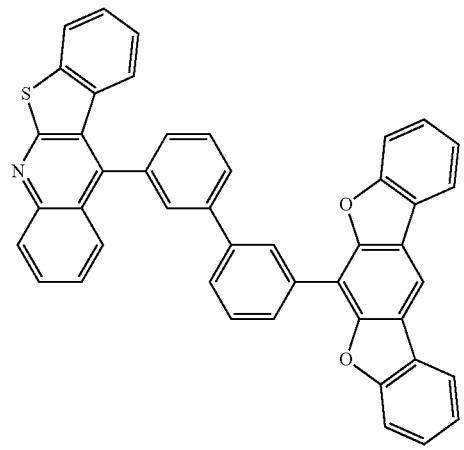
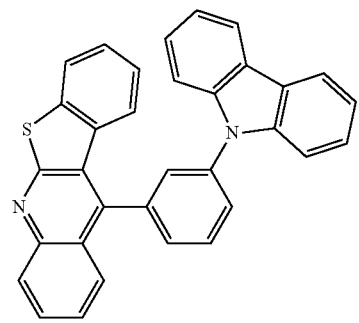
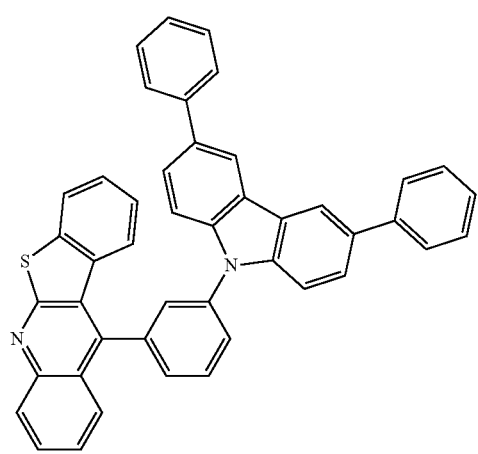
206
-continued
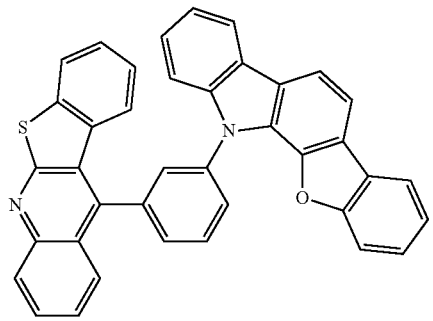
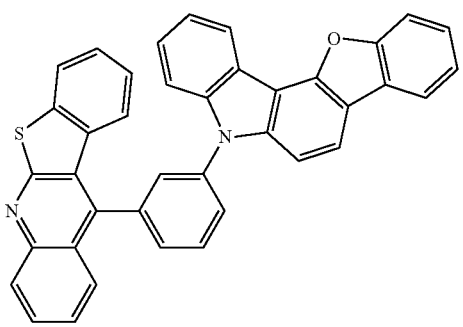
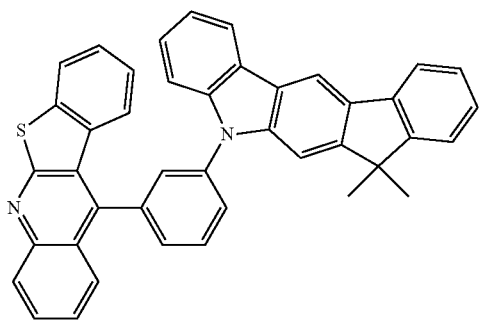
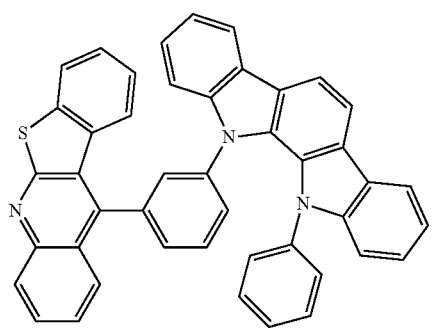
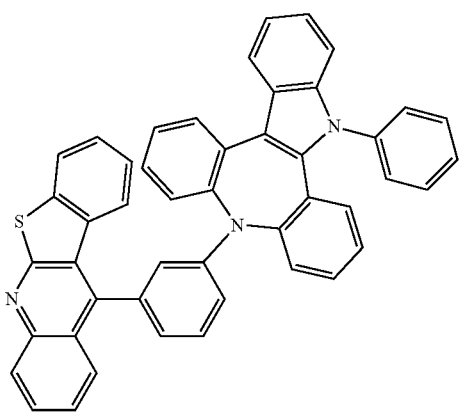

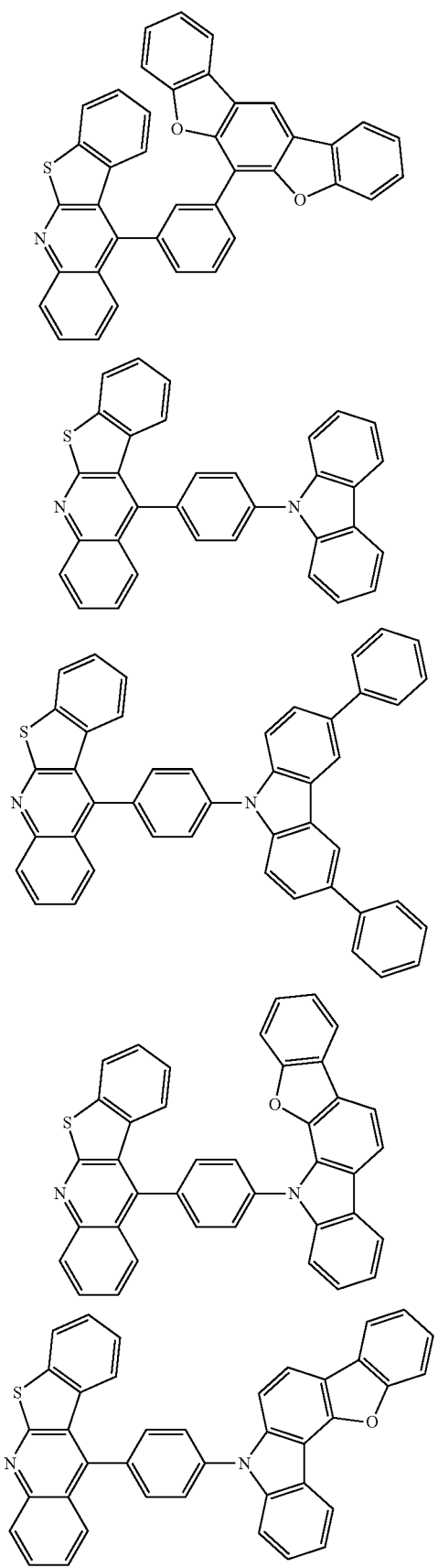
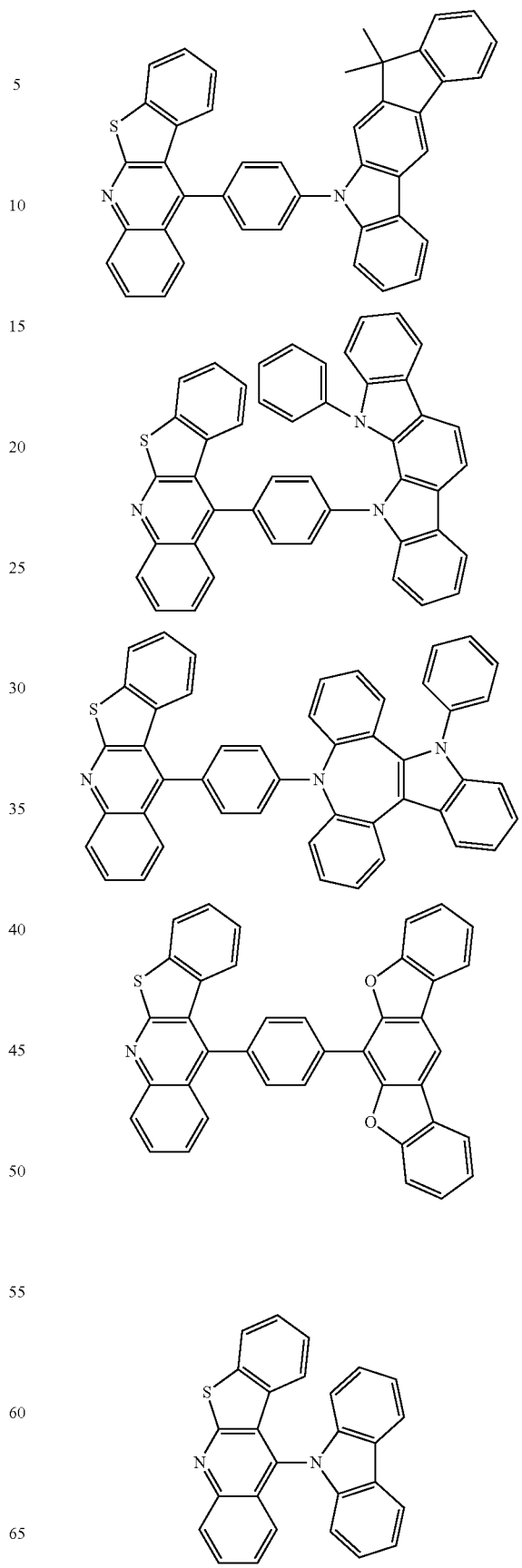

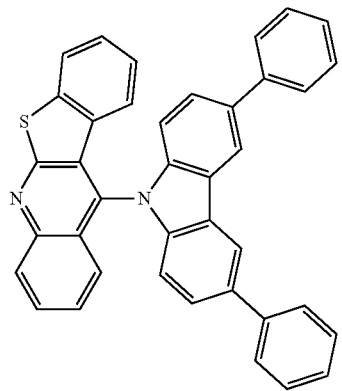
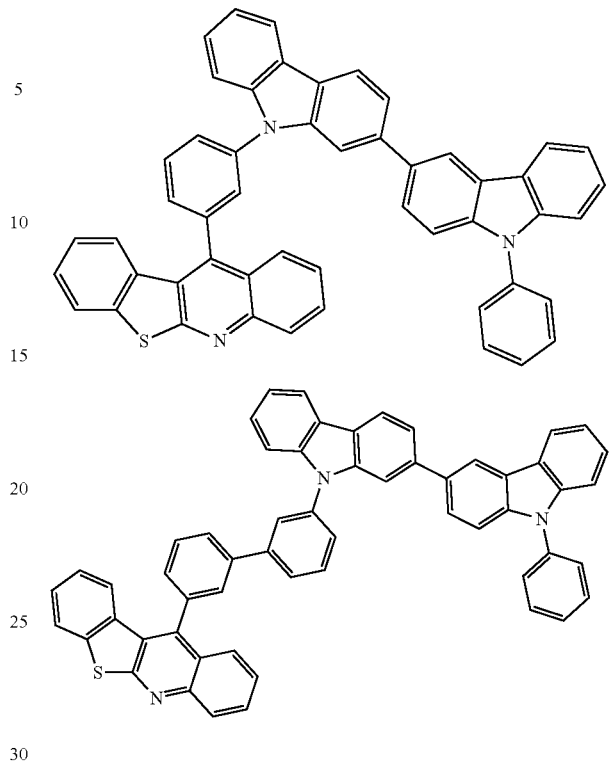
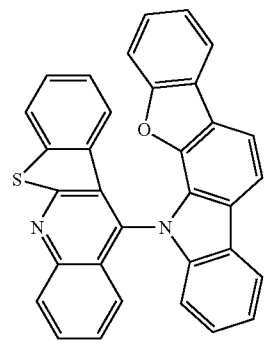
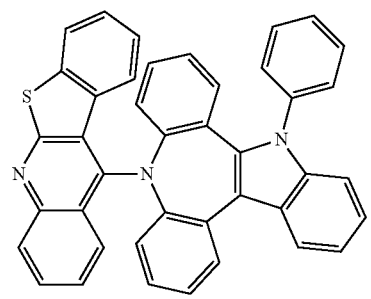
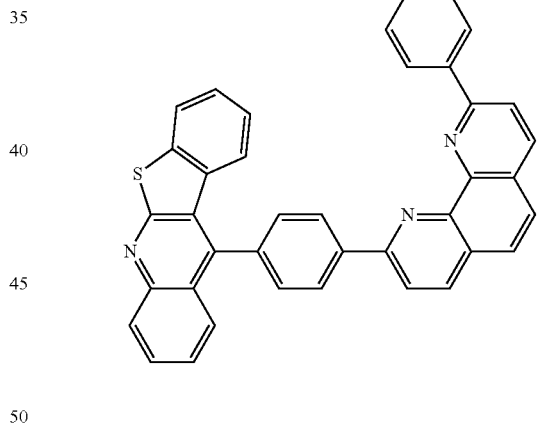
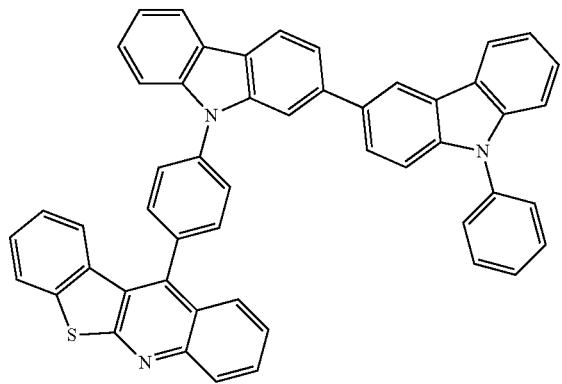
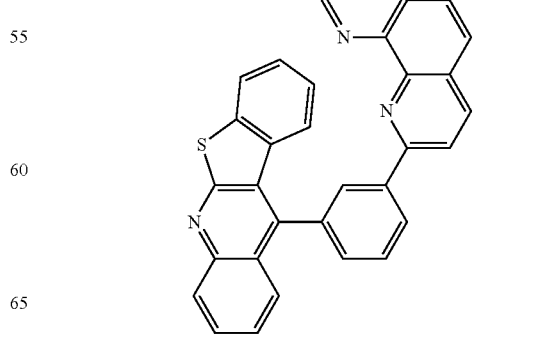

211
-continued
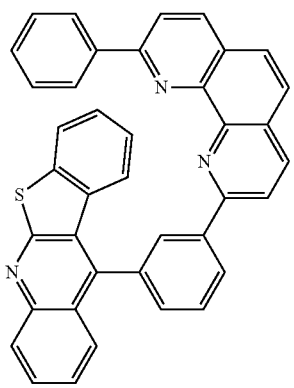
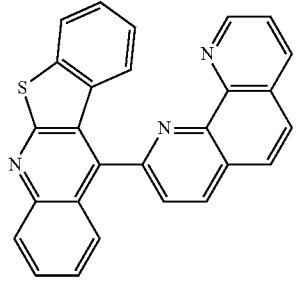
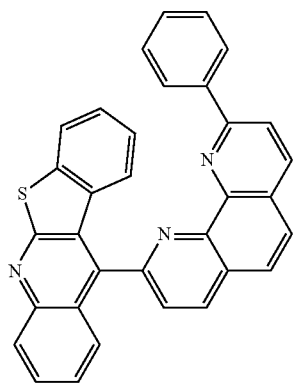
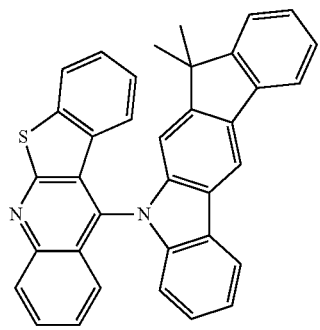
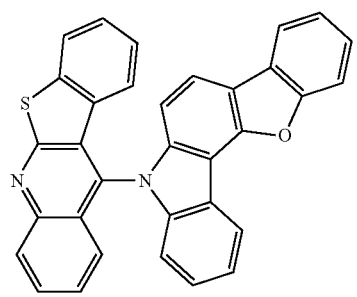
212
-continued
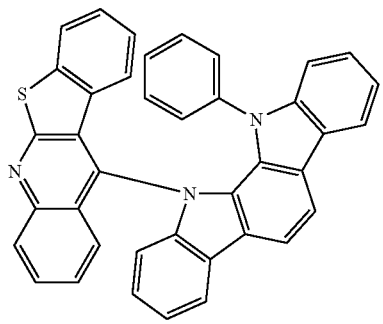
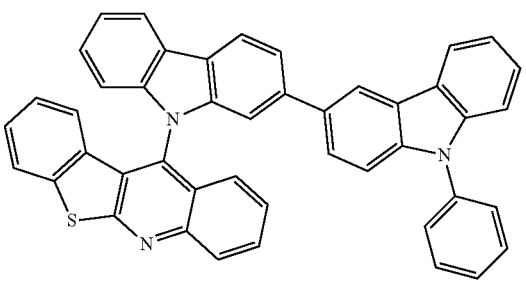
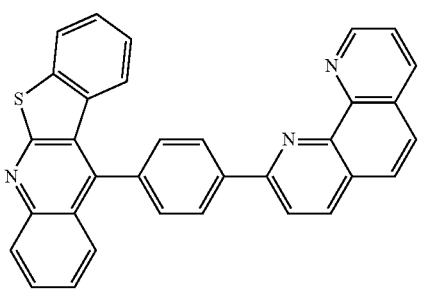
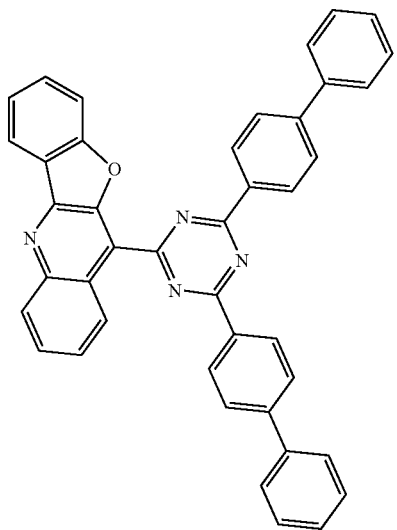

213
-continued
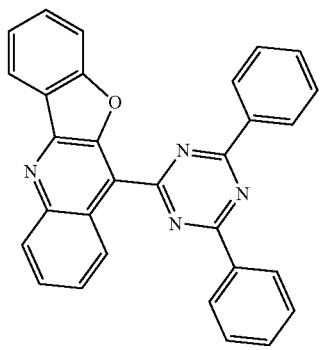
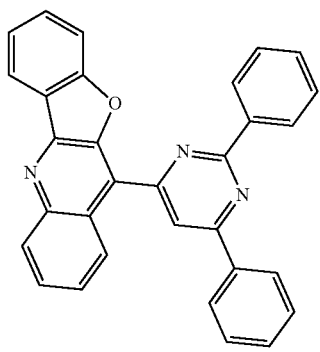
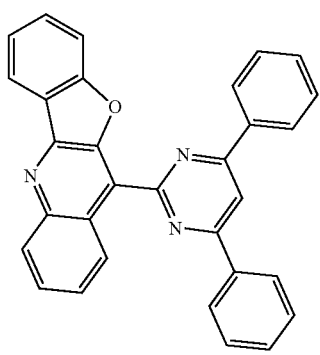
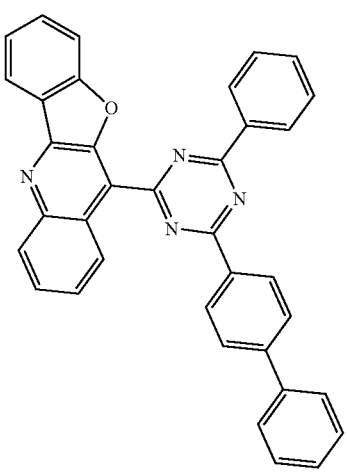
214
-continued
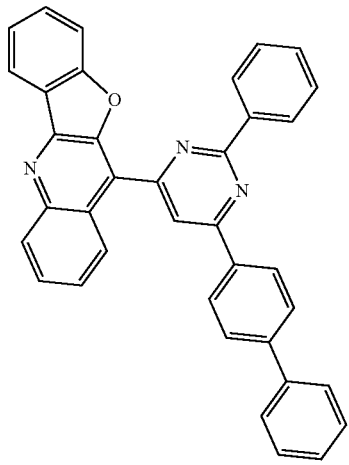
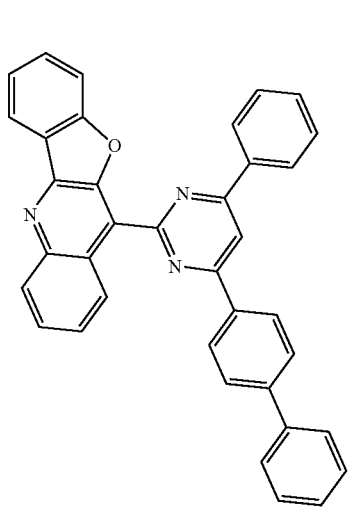
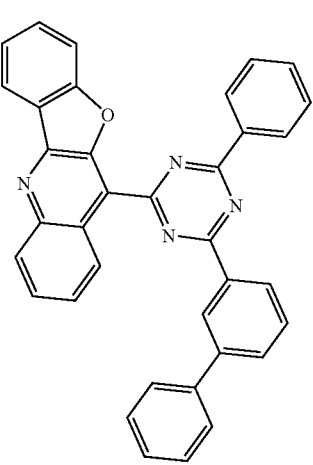

215
-continued
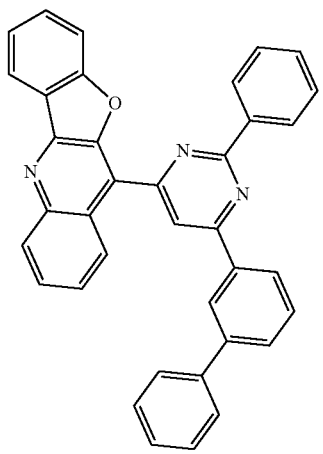
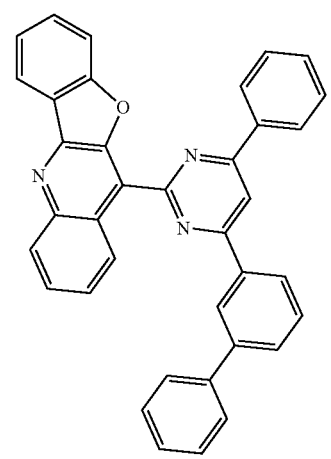
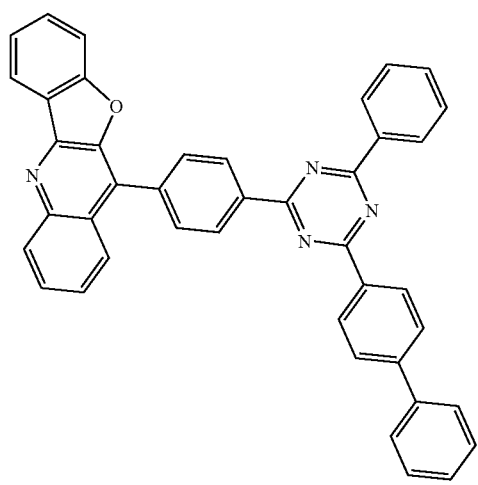
216
-continued
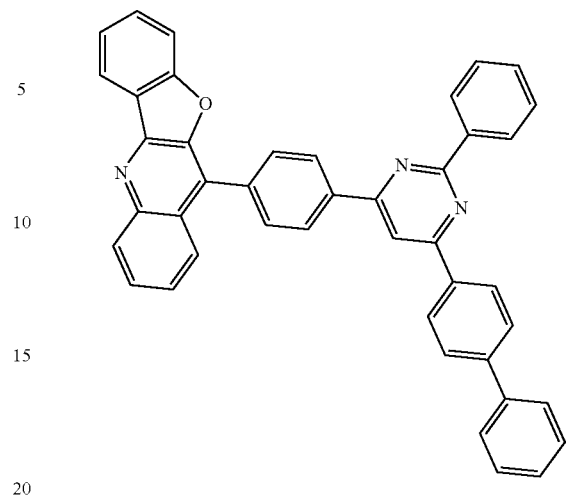
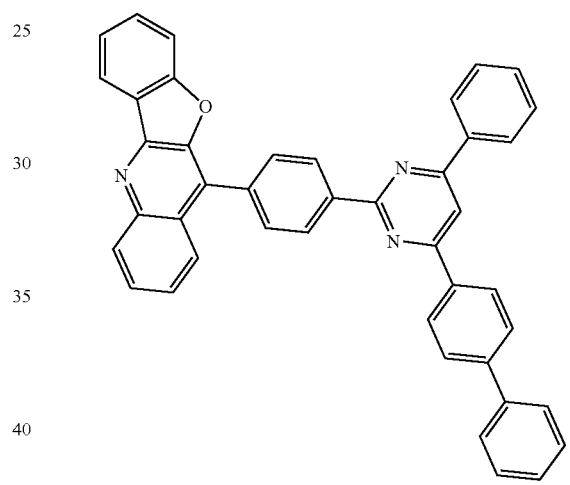
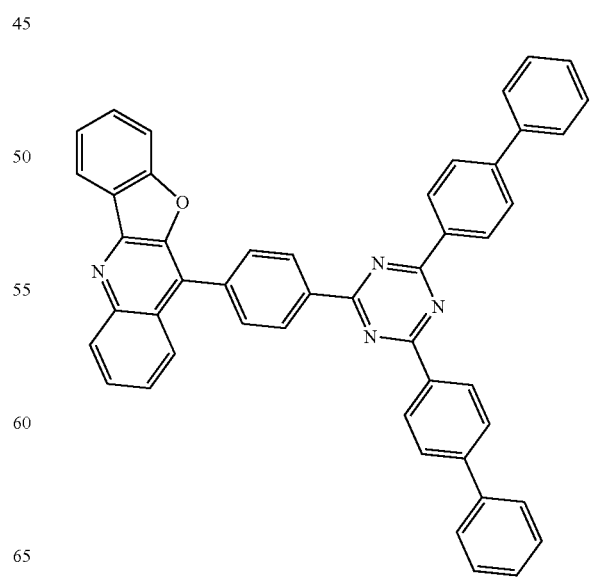

217
-continued
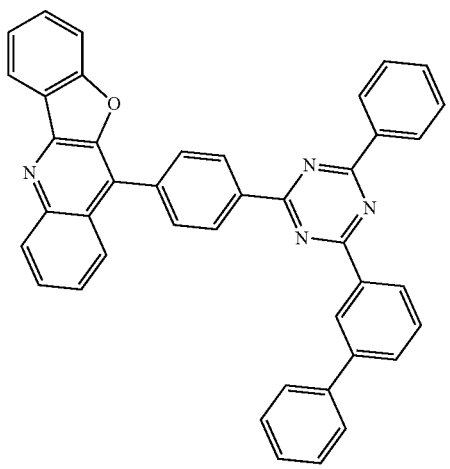
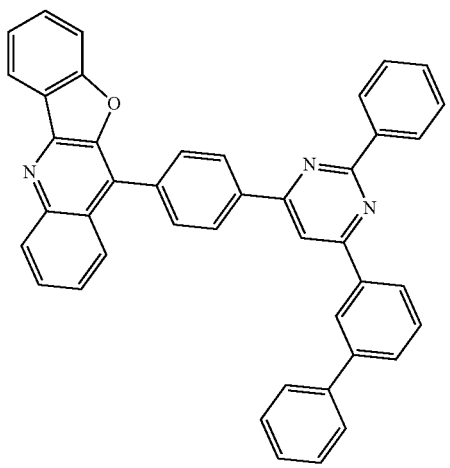
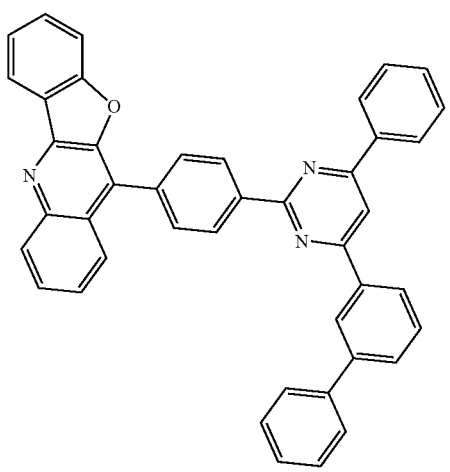
218
-continued
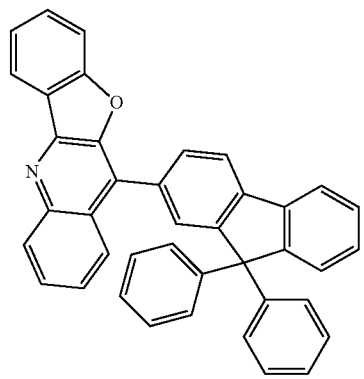
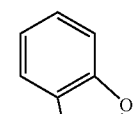
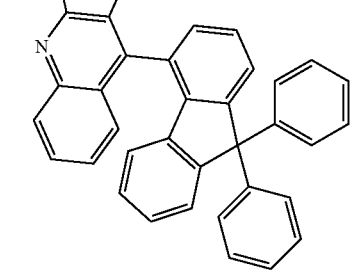
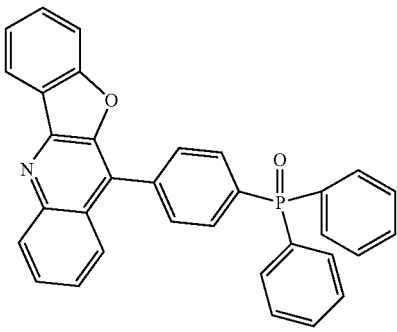
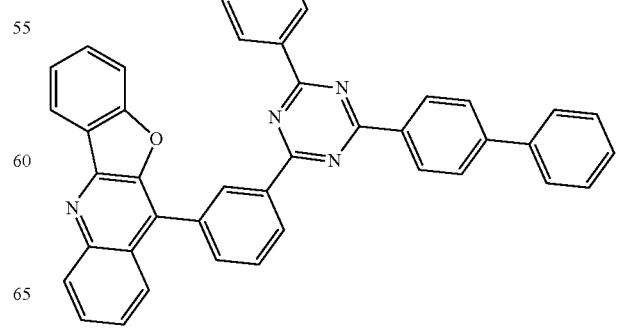

219
-continued
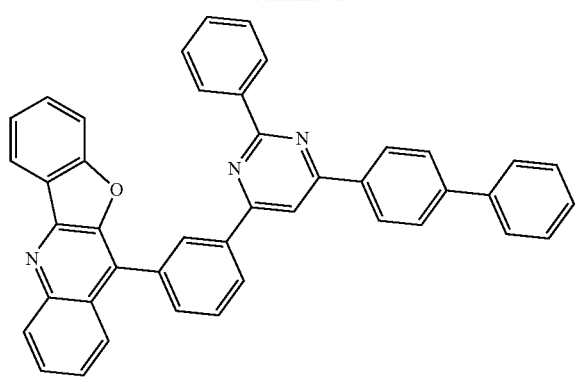
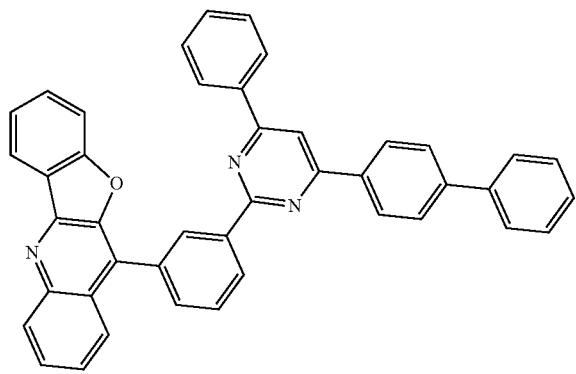
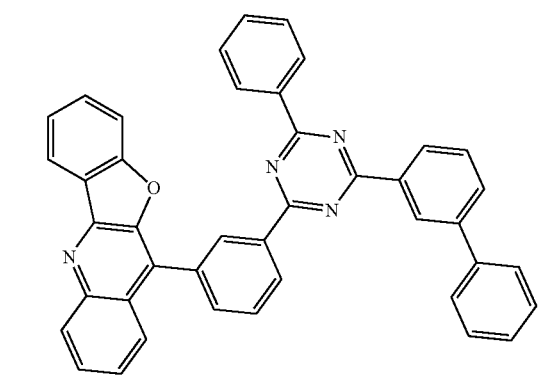
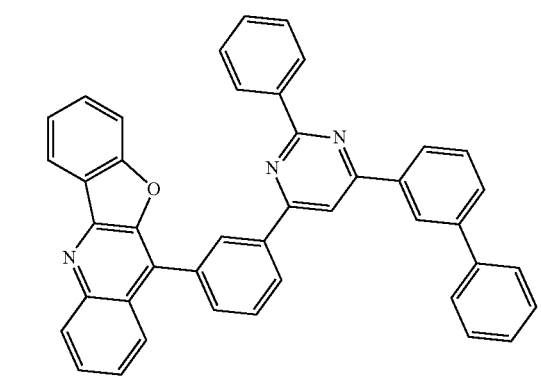
220
-continued
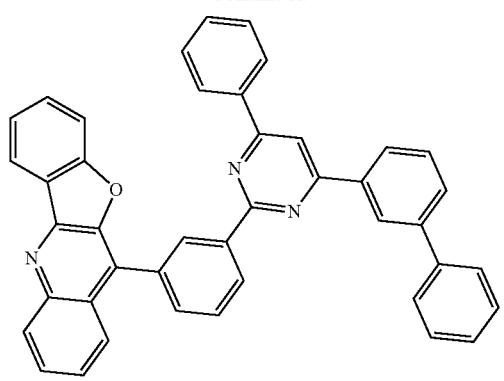
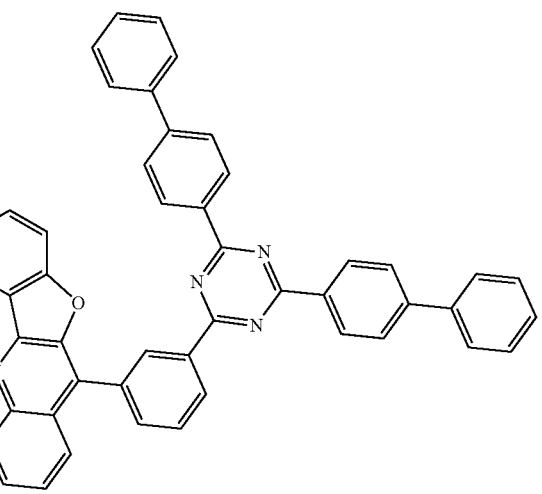
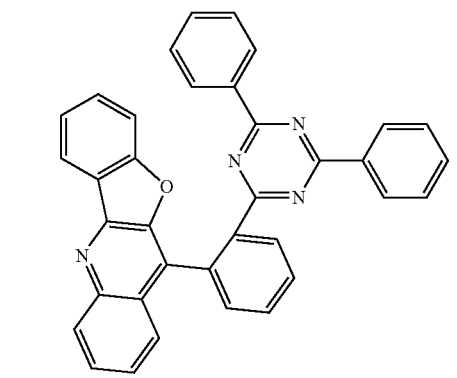
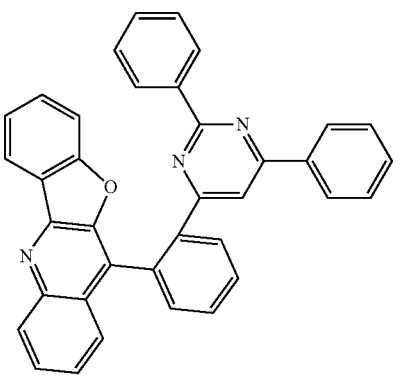

221
-continued
222
-continued
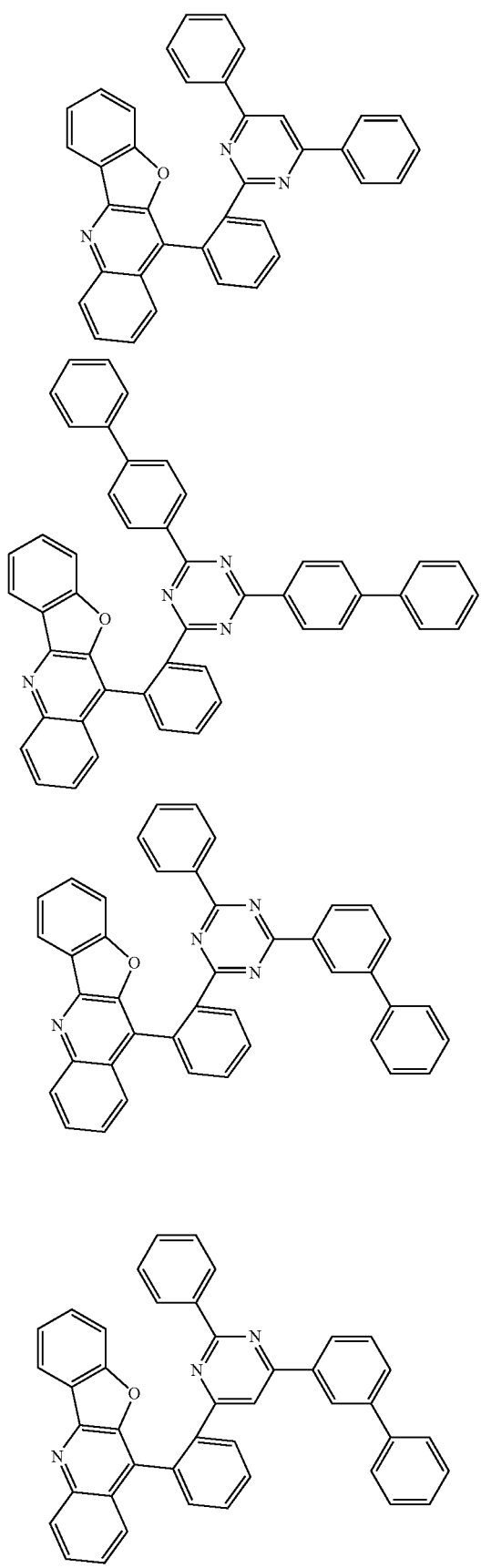
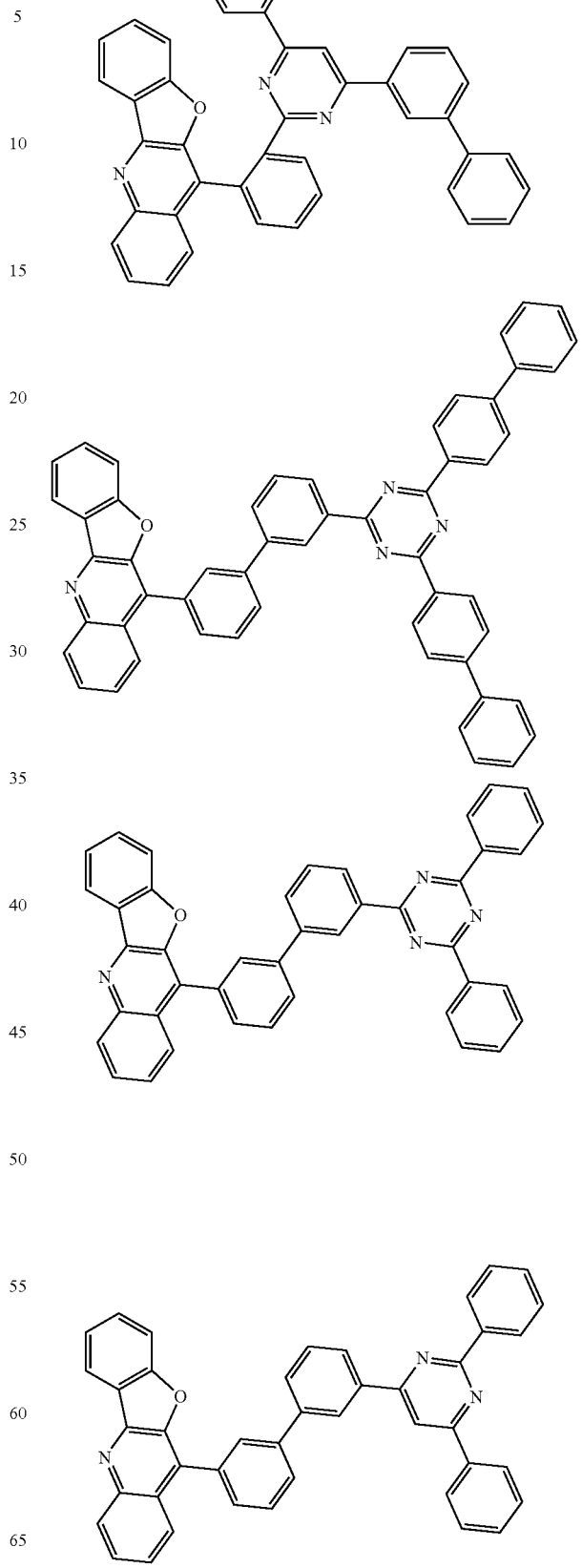

223
-continued
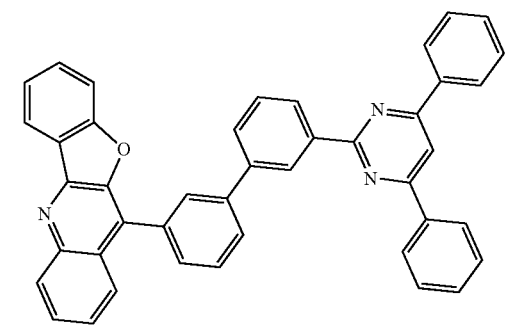
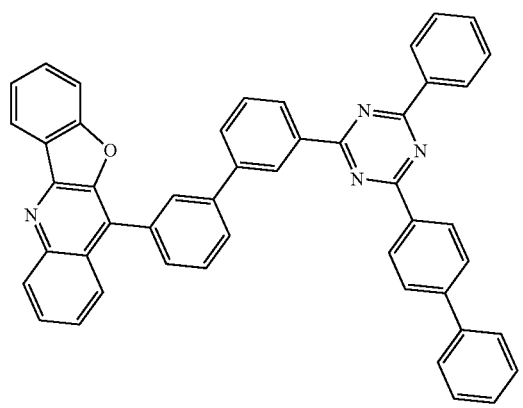
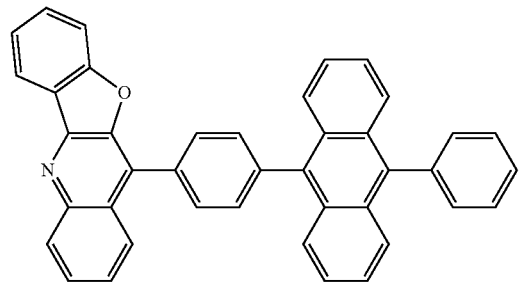
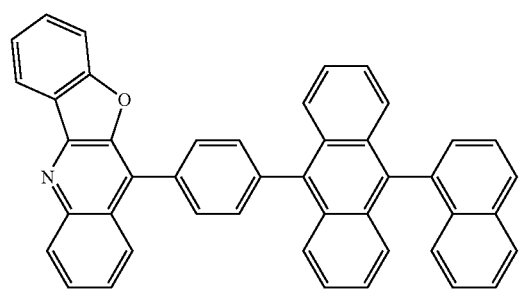
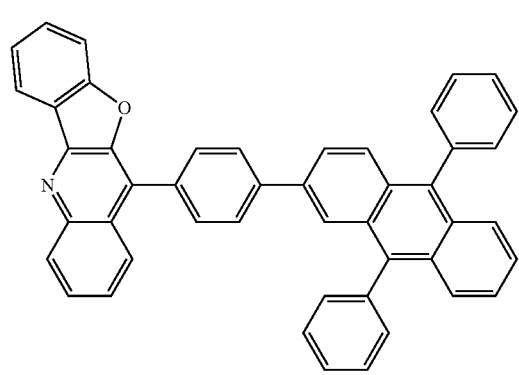
224
-continued
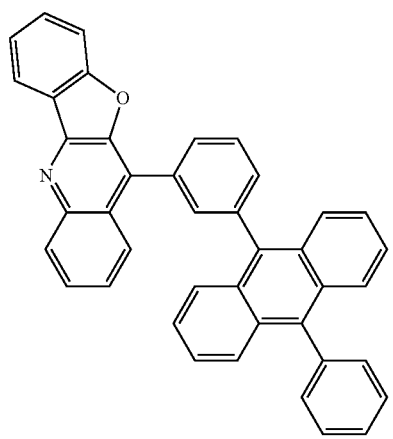
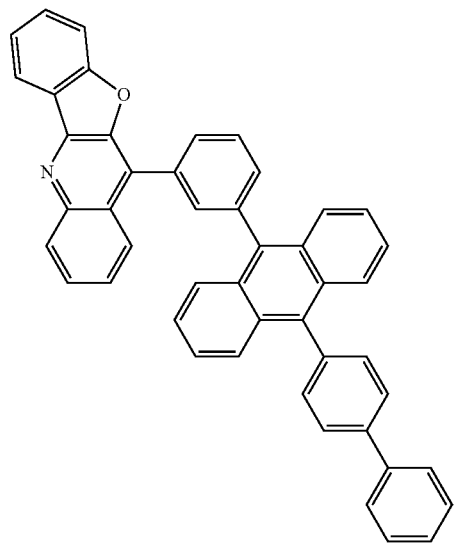
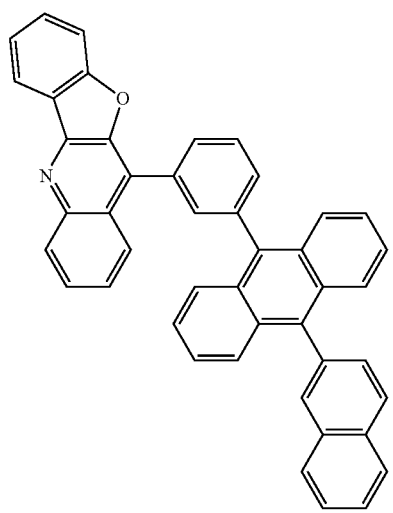

225
-continued
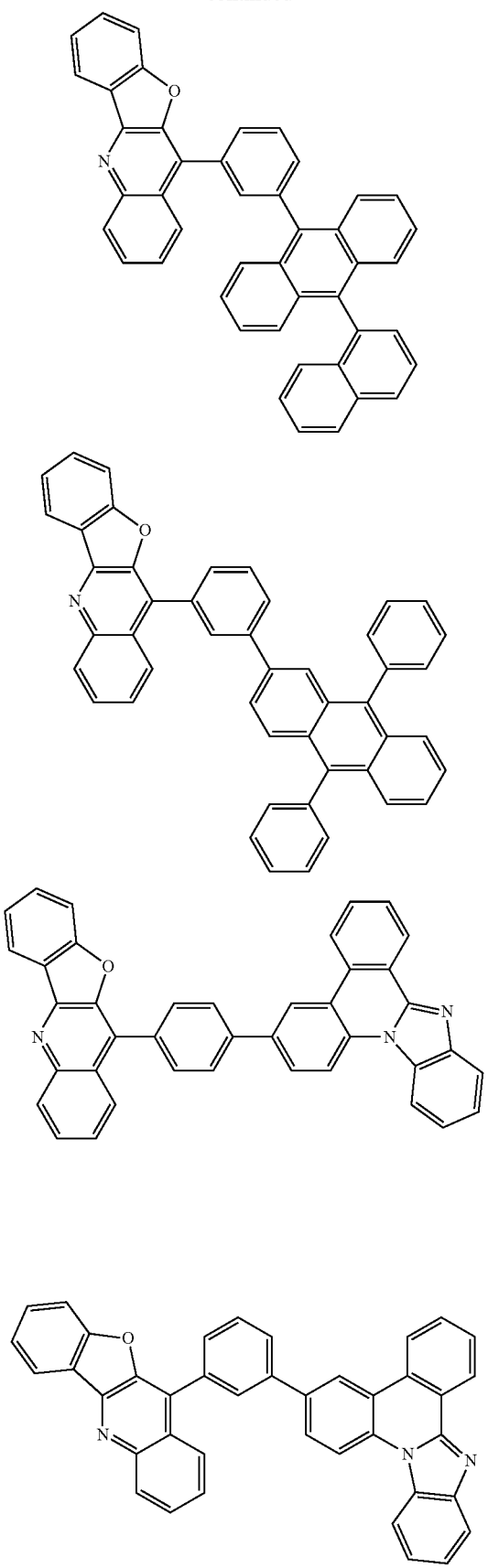
226
-continued
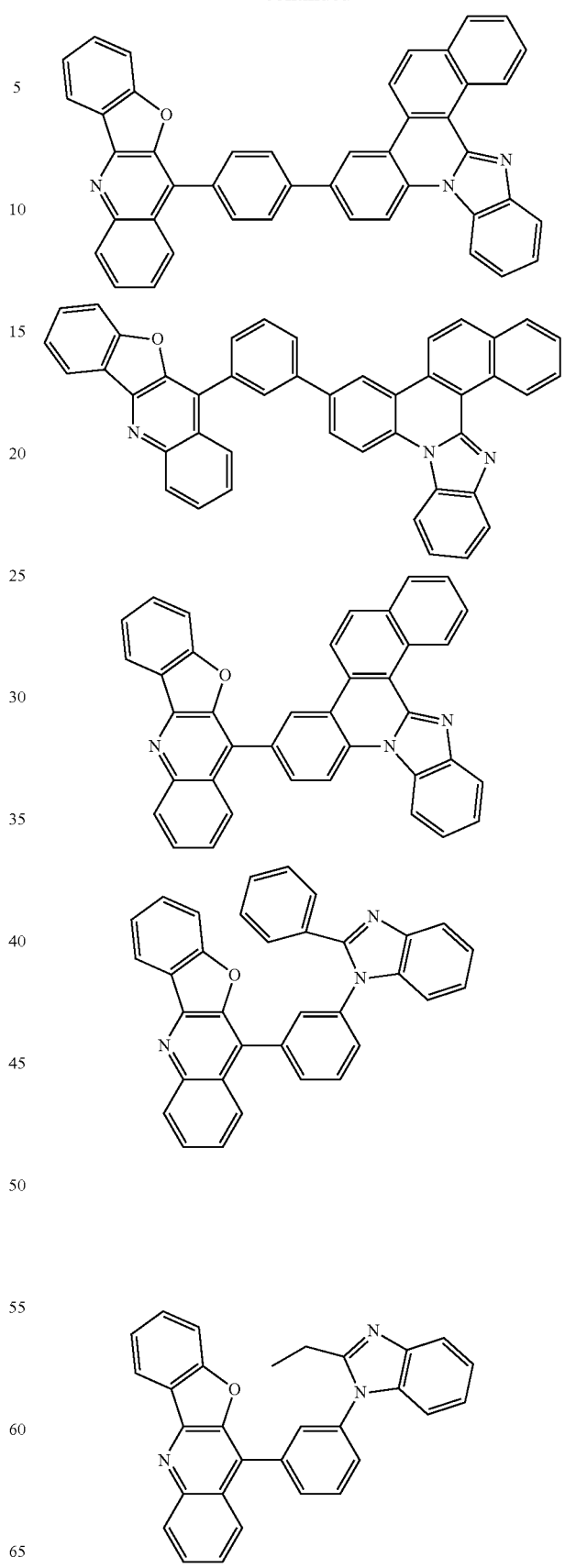

227
-continued
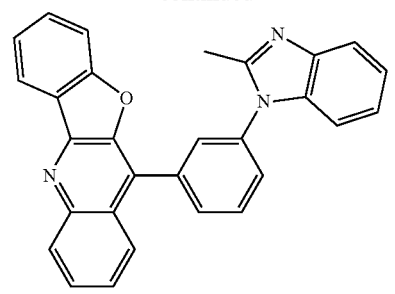
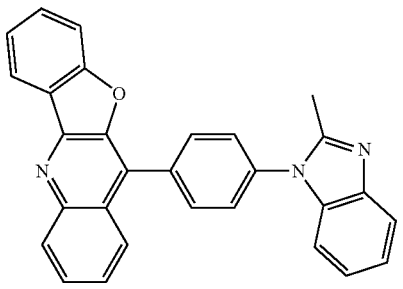
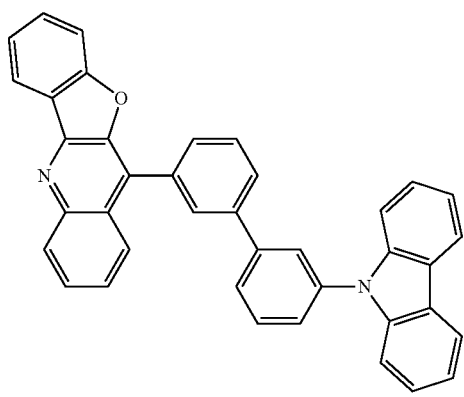
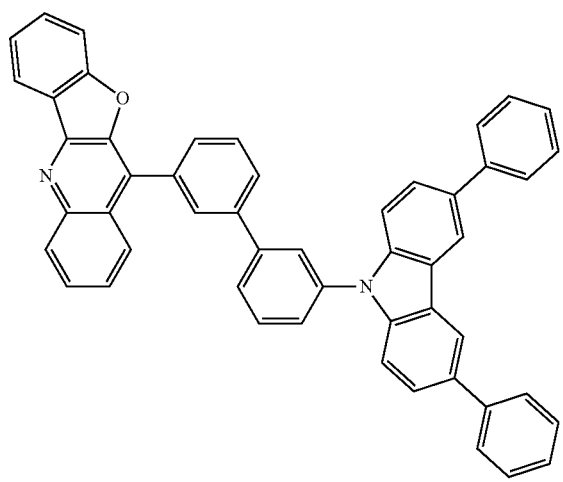
228
-continued
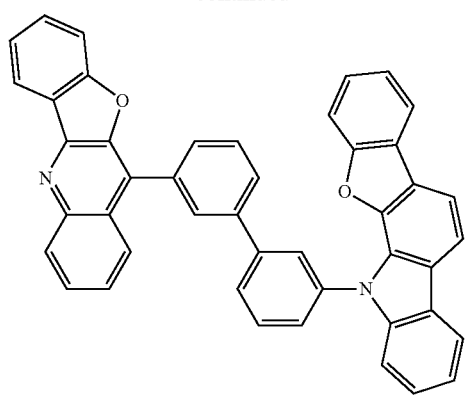
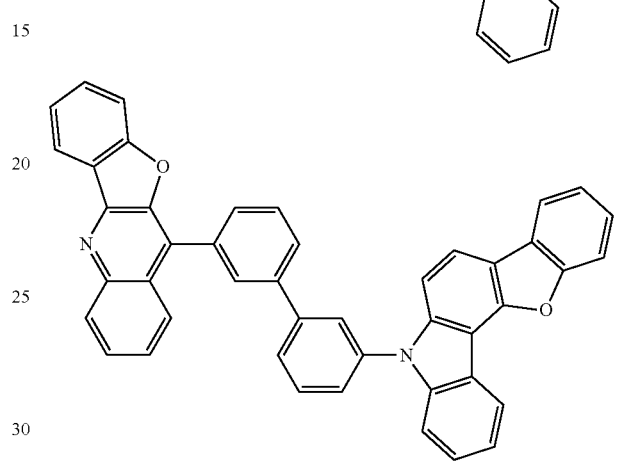
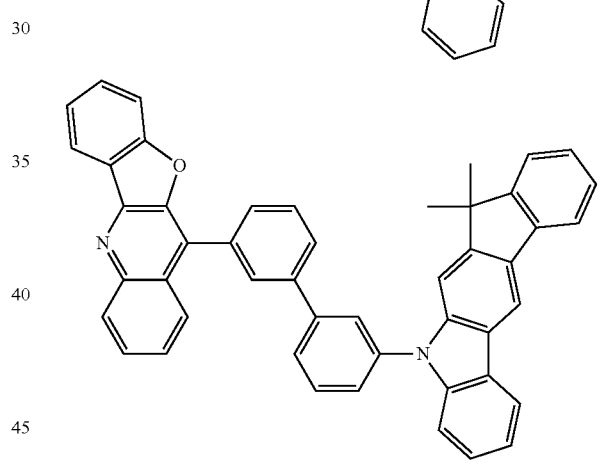
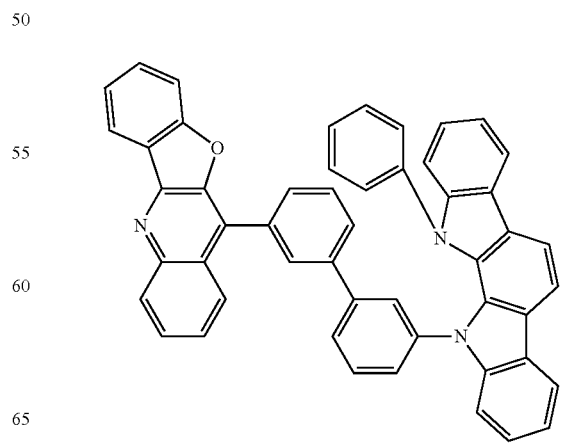

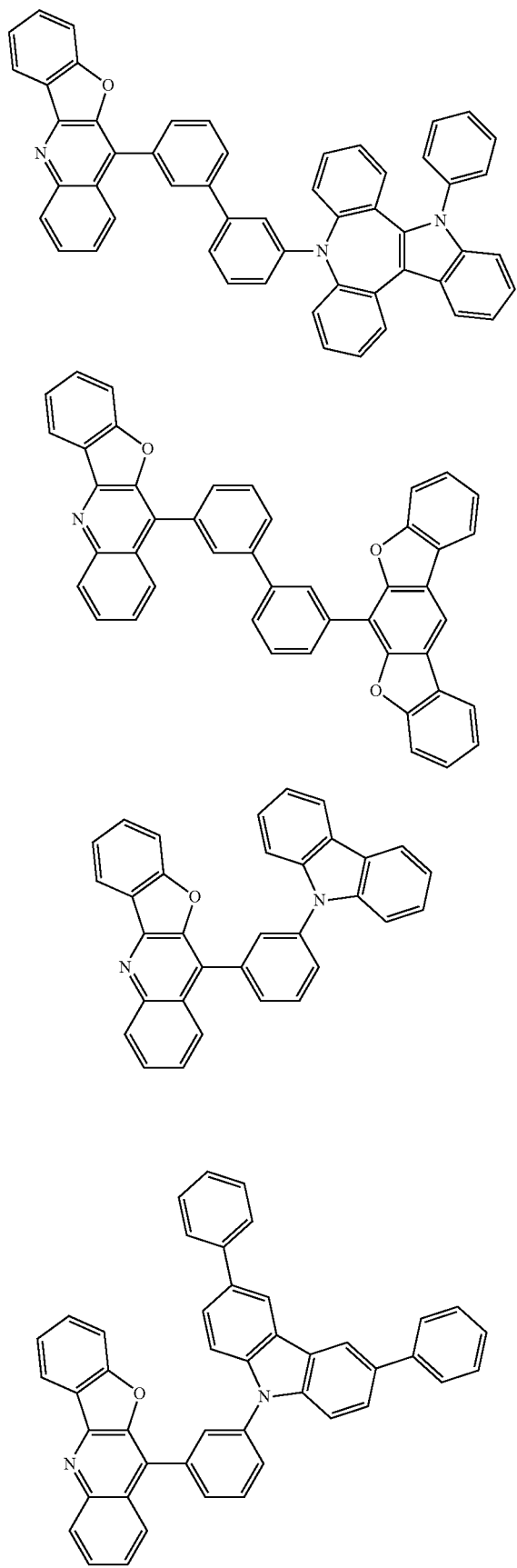
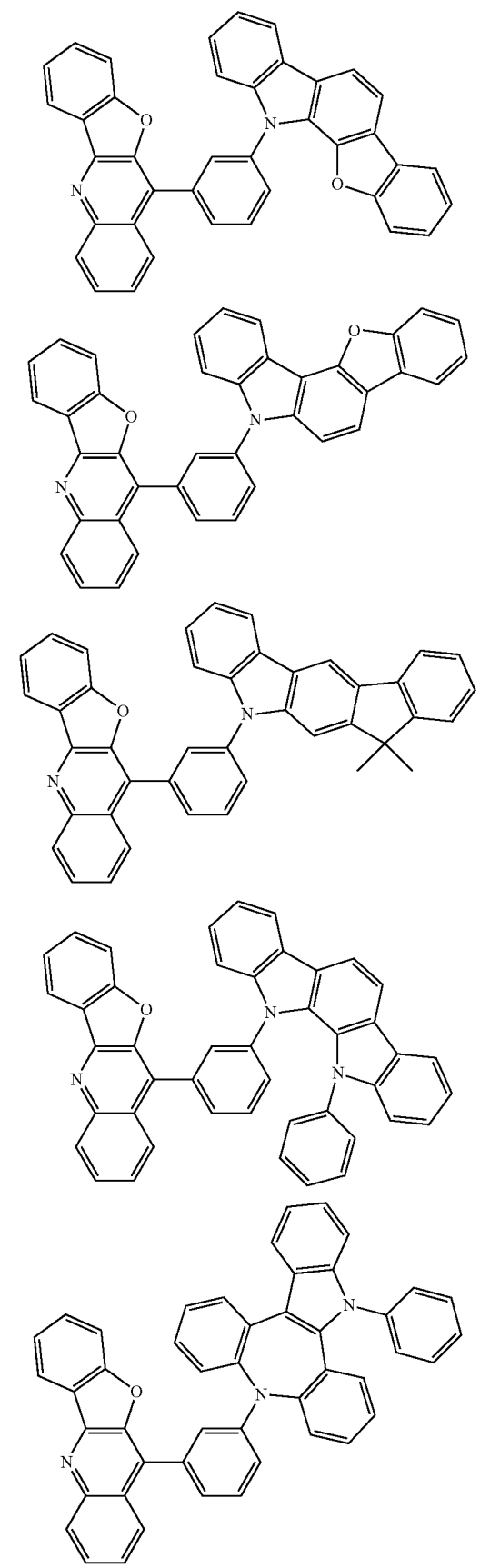

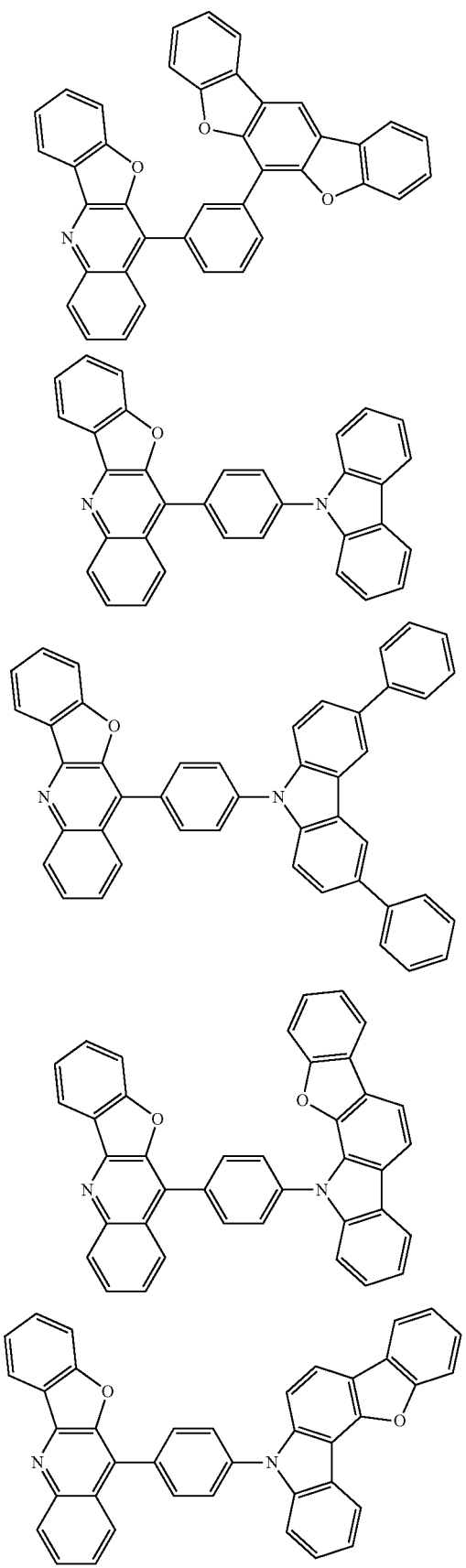
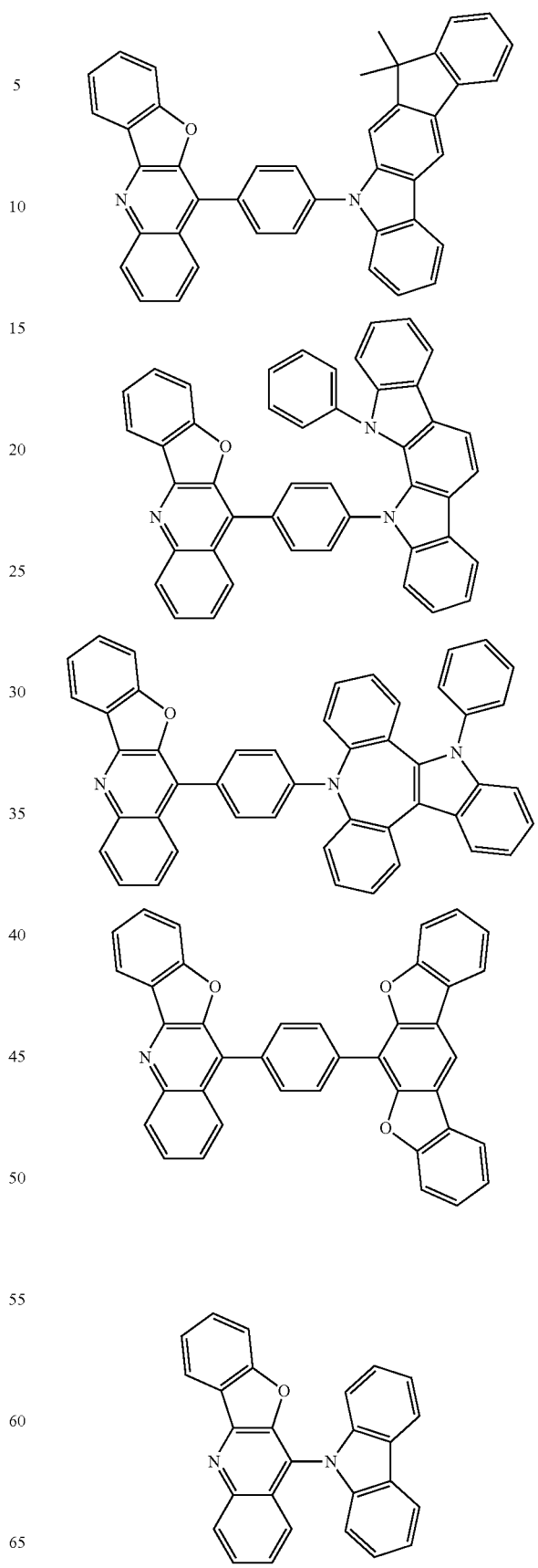

233
-continued
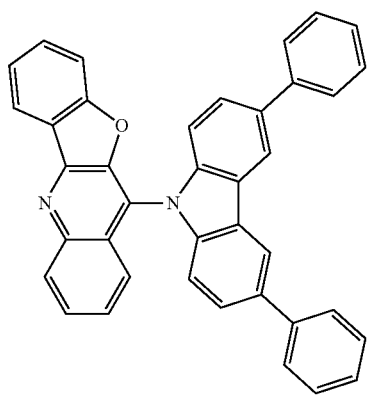
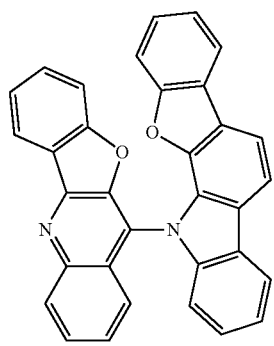
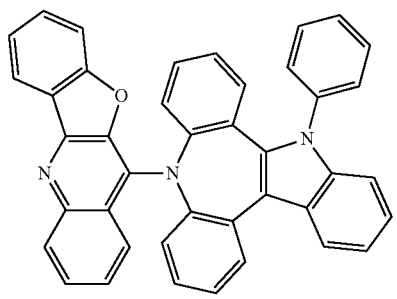
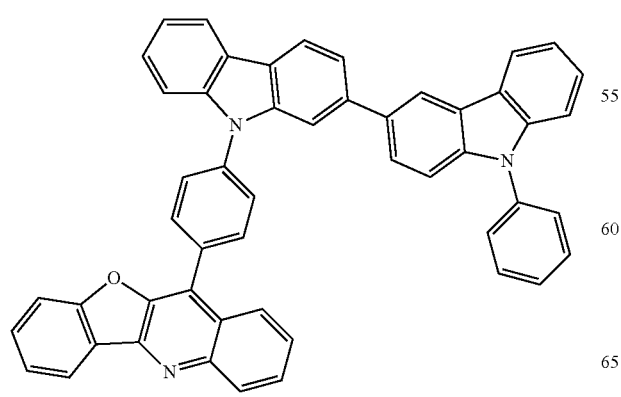
234
-continued
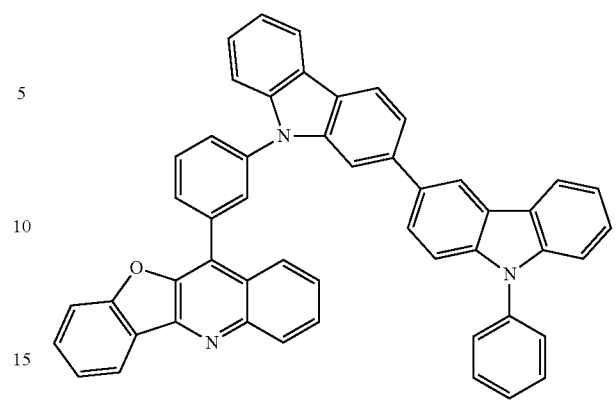
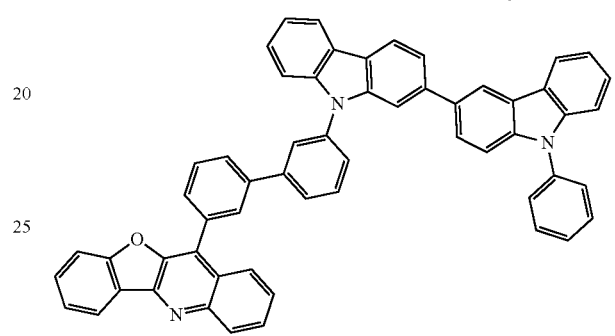
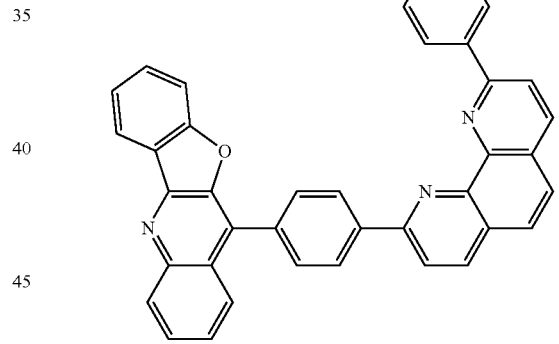
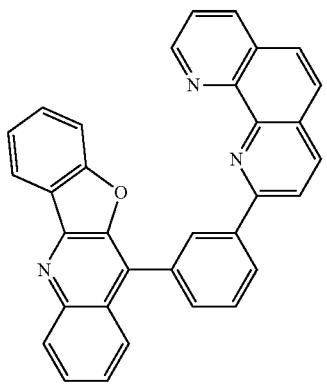

235
-continued
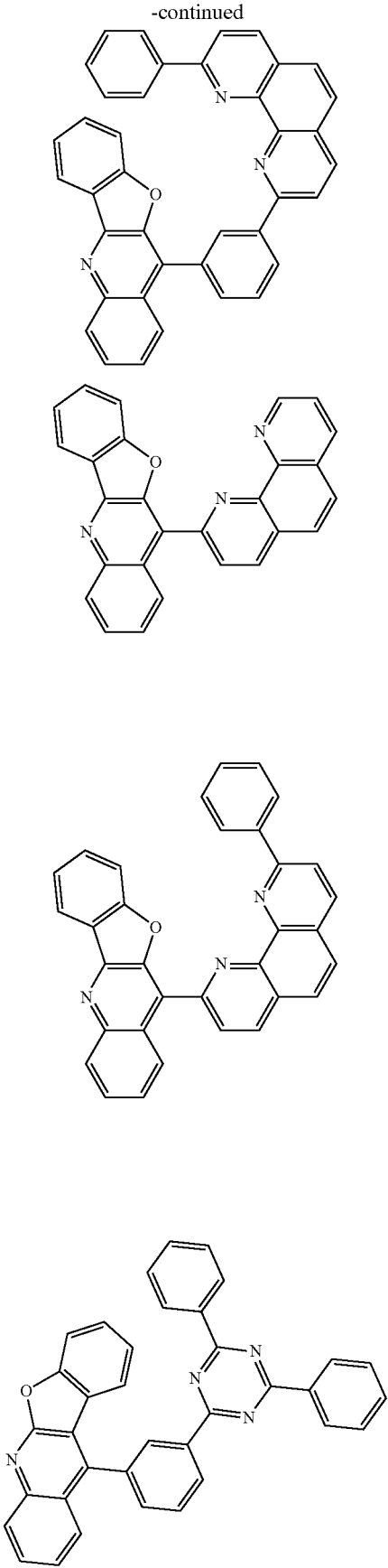
236
-continued
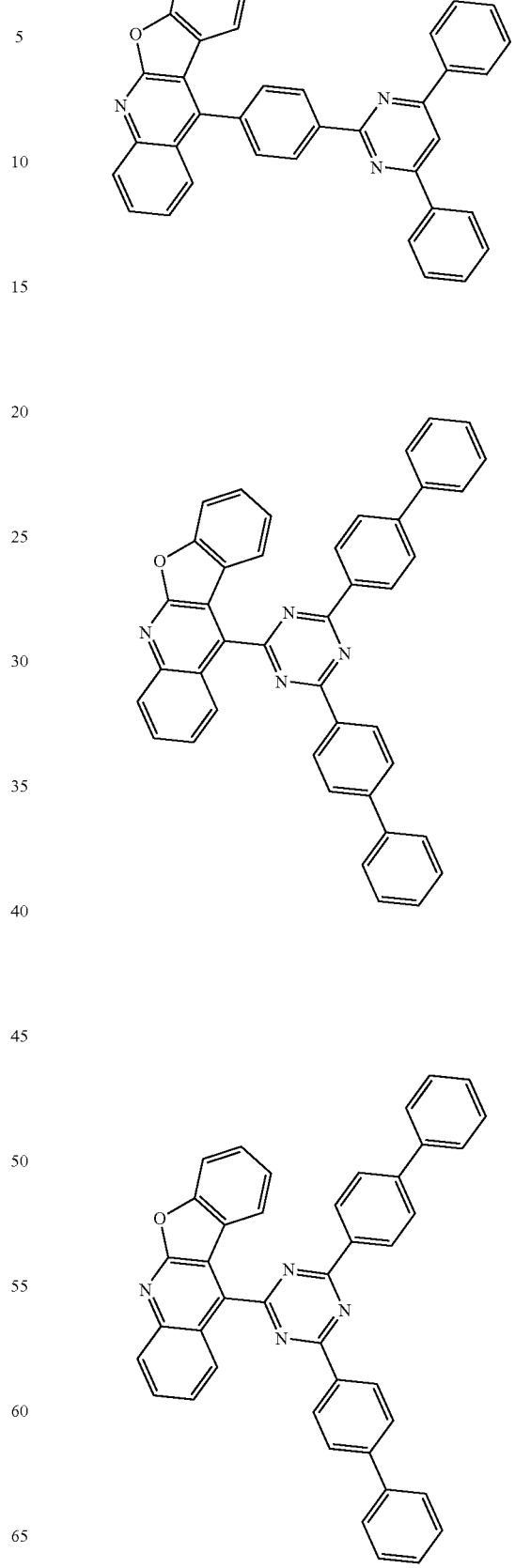

237
-continued
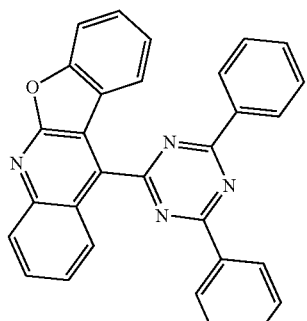
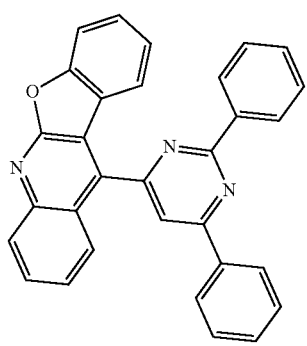
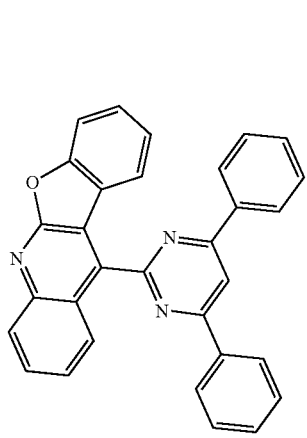
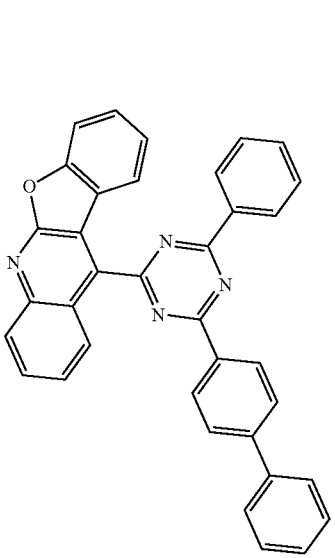
238
-continued
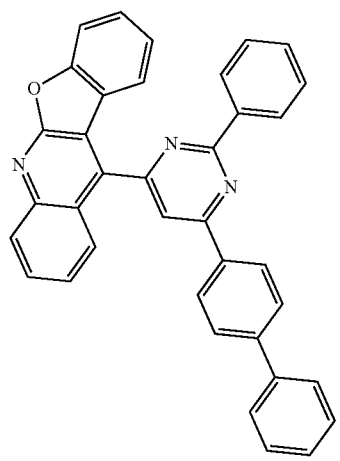
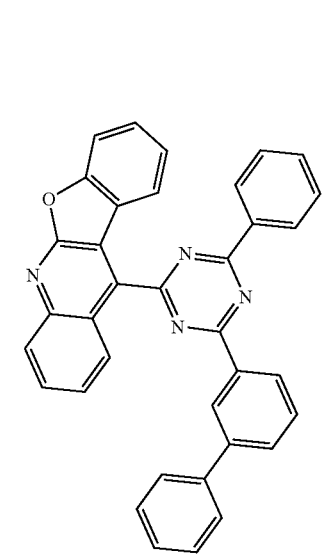
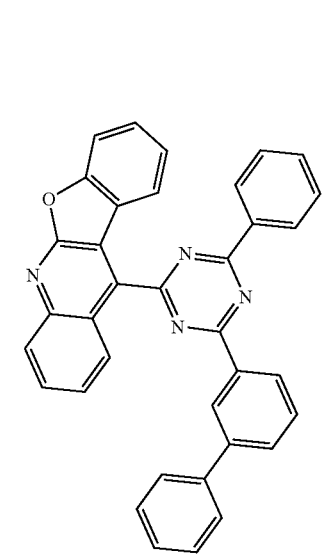

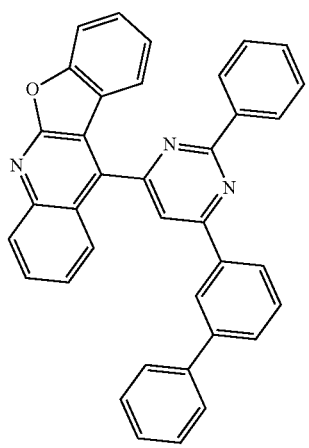
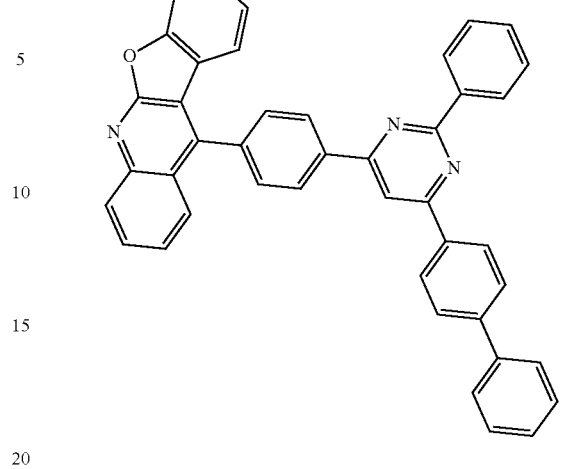
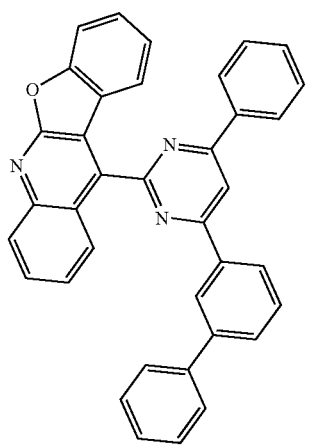
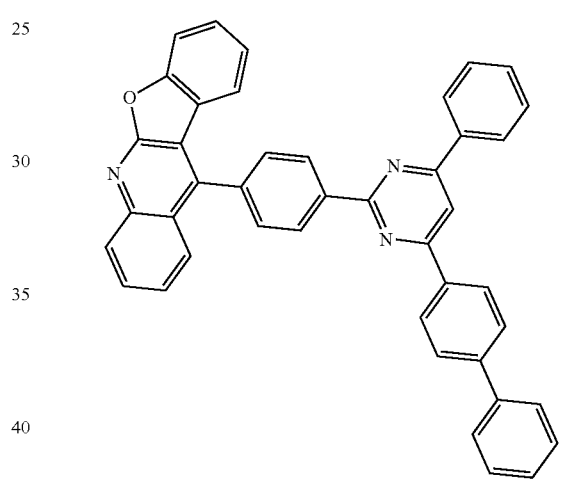
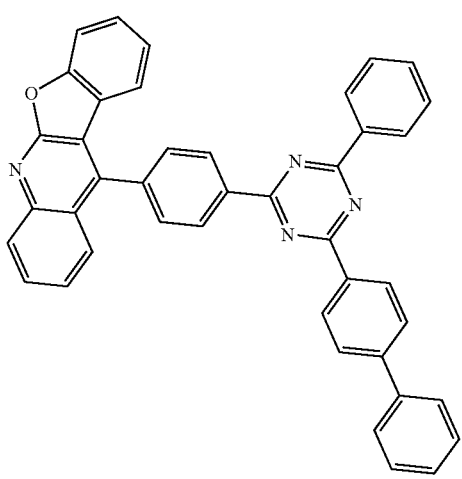
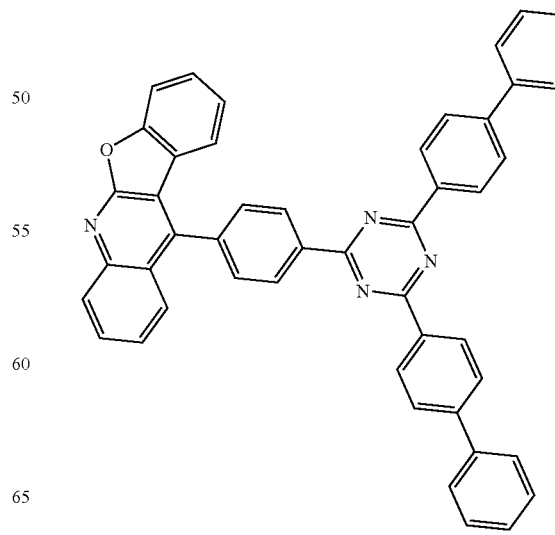

241
-continued
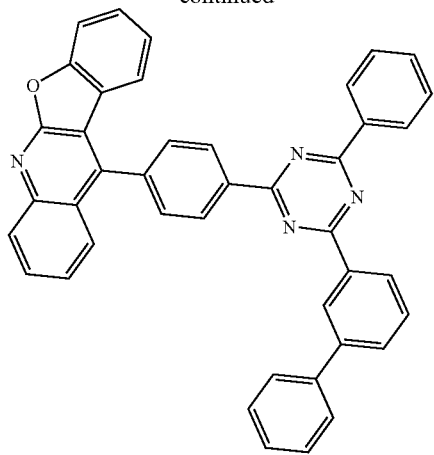
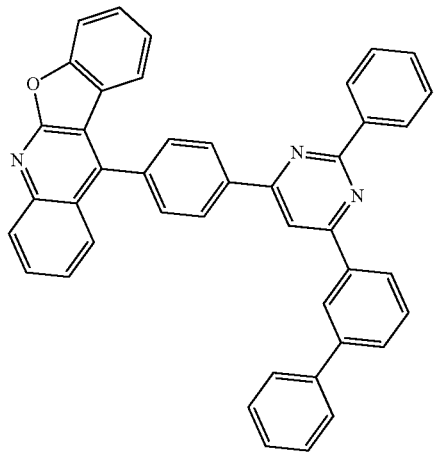
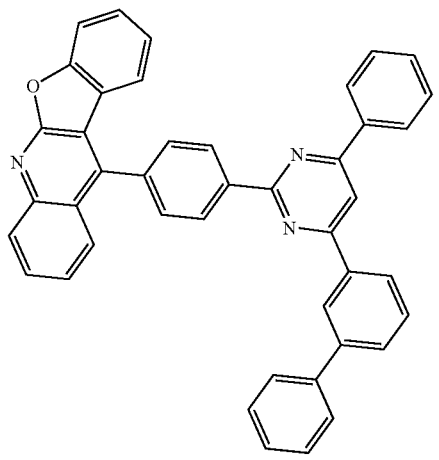
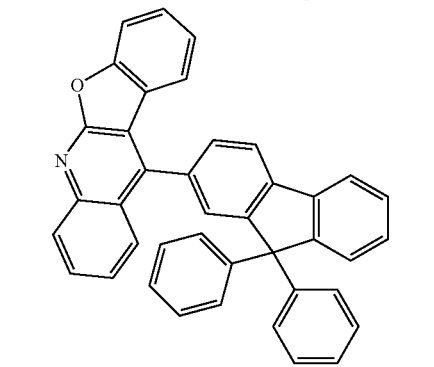
242
-continued
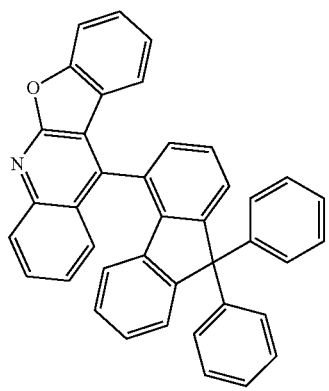
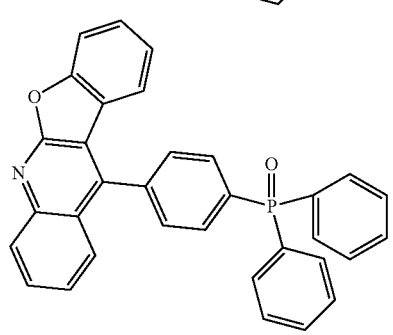
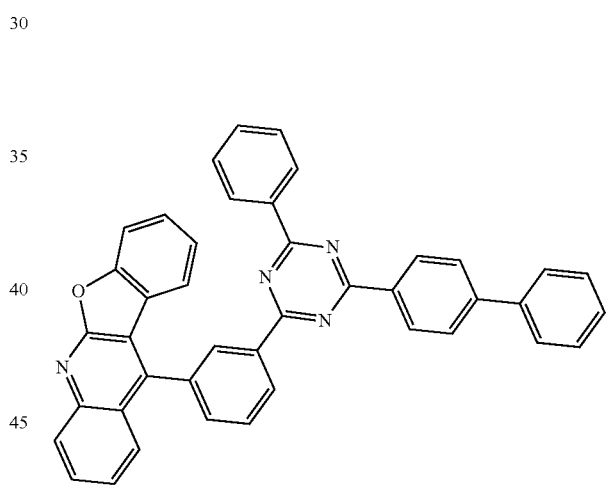
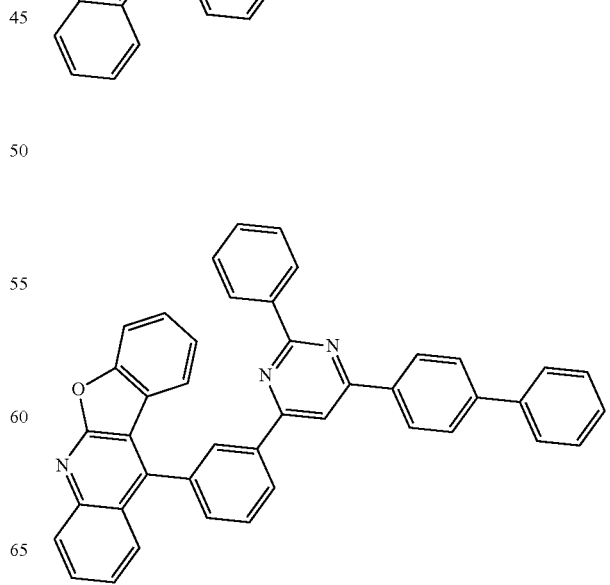

243
-continued
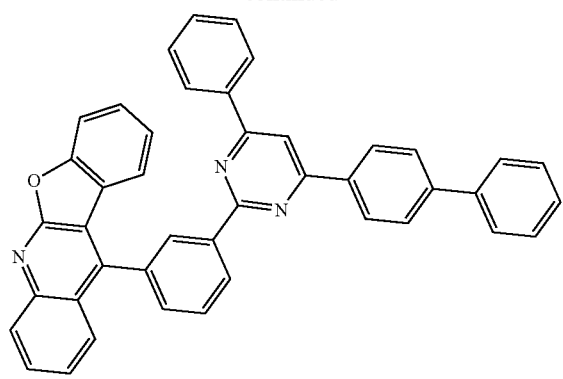
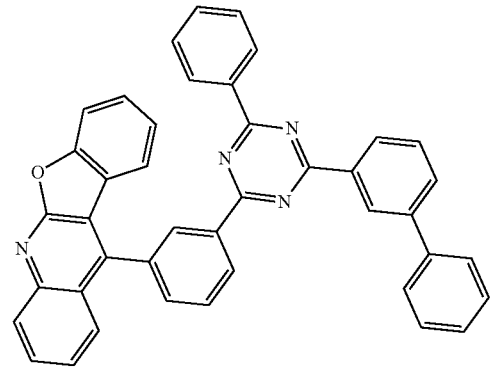
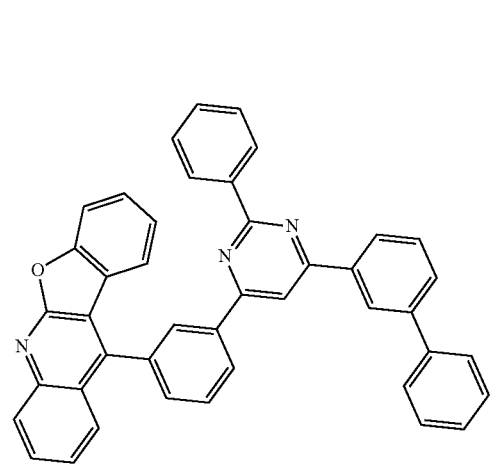
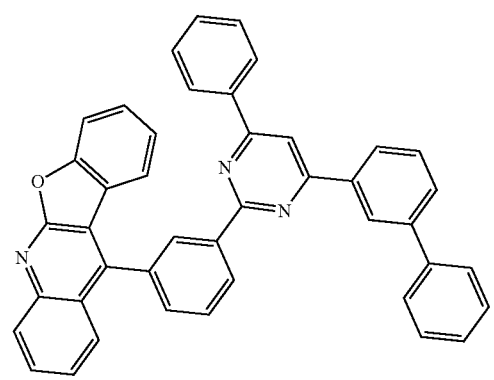
244
-continued
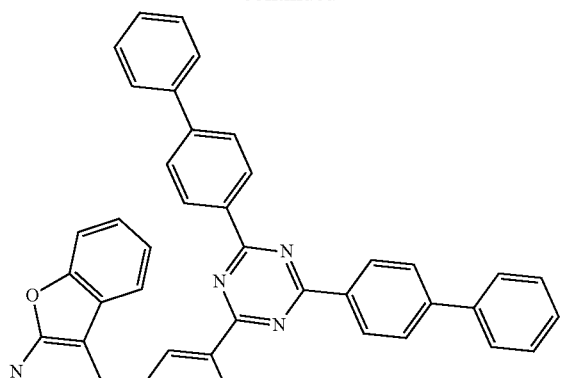
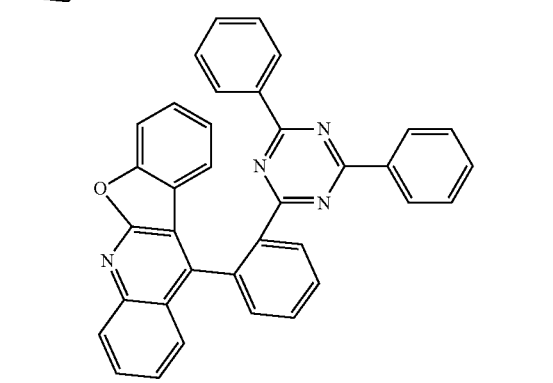
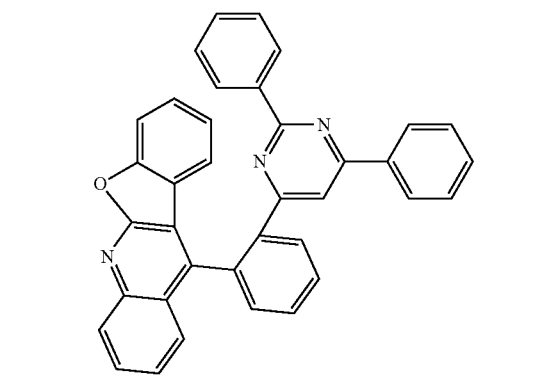
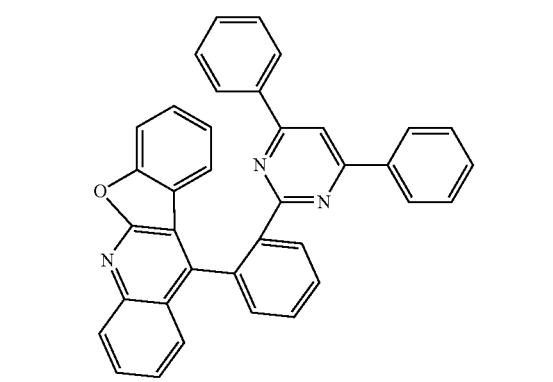

245
-continued
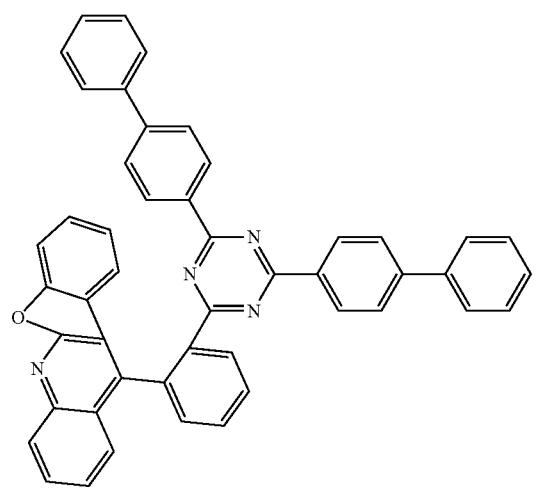
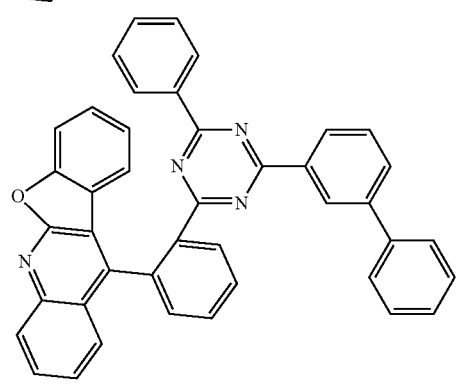
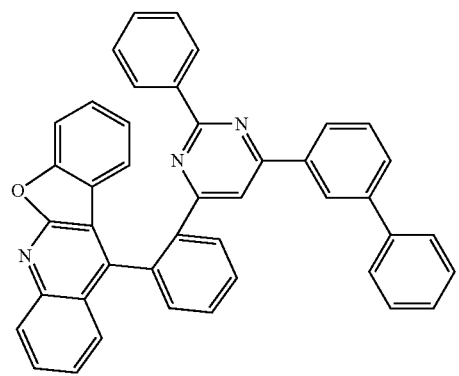
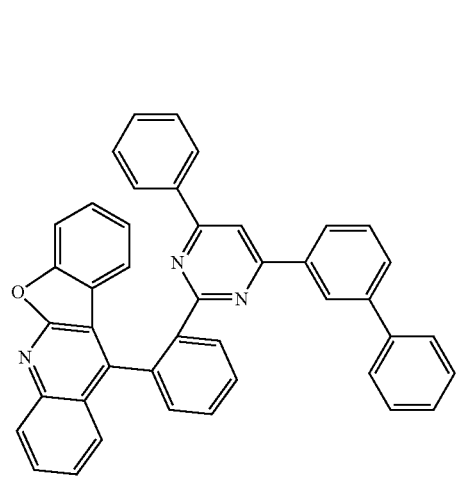
246
-continued
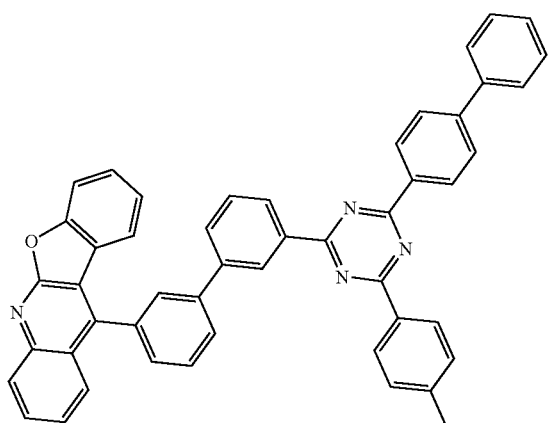
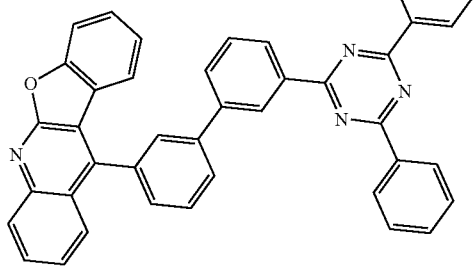
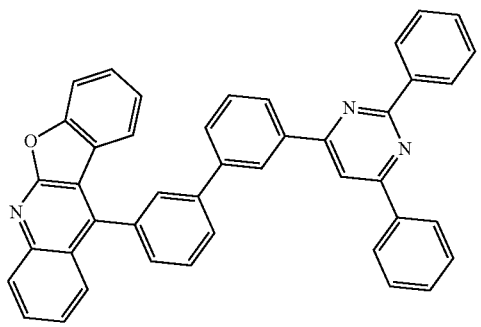
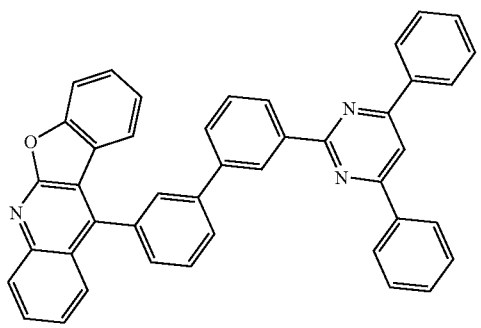

247
-continued
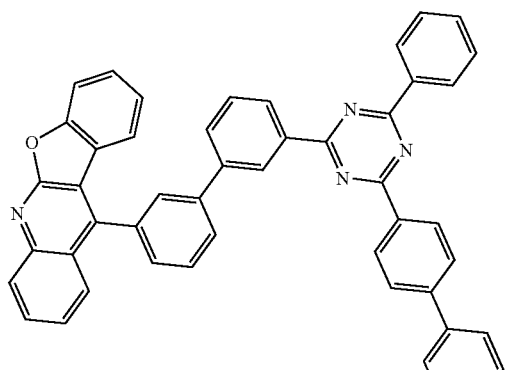
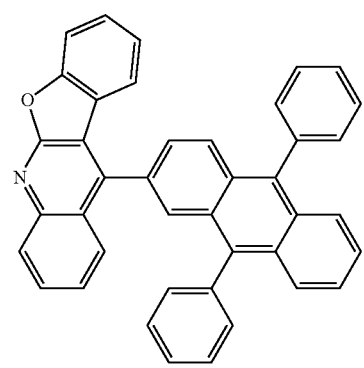
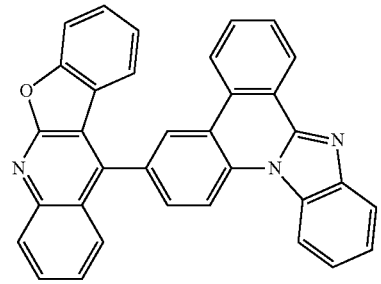
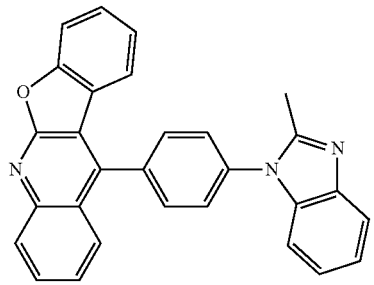
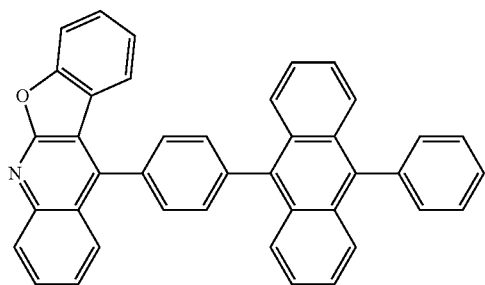
248
-continued
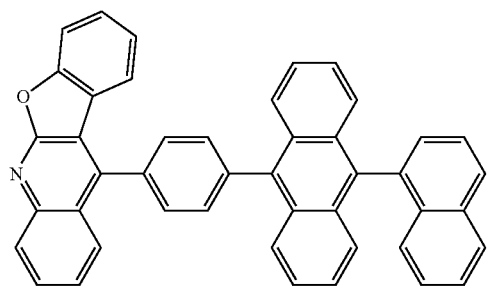
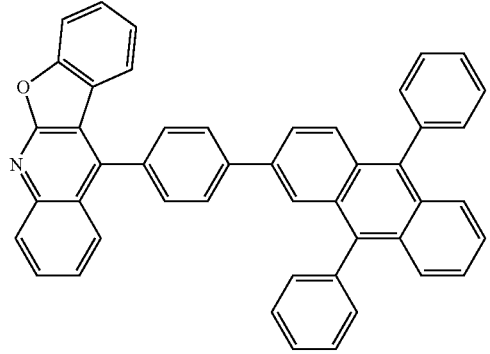
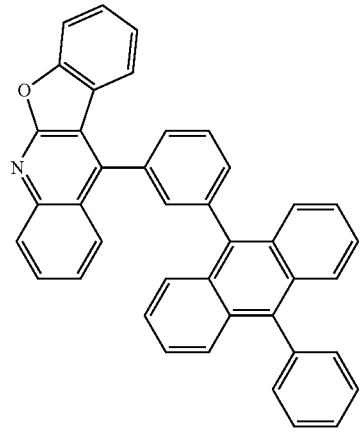
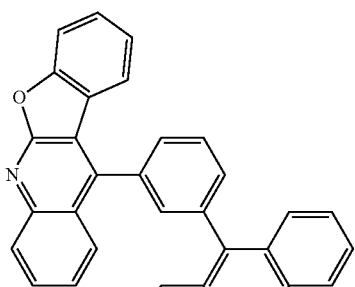
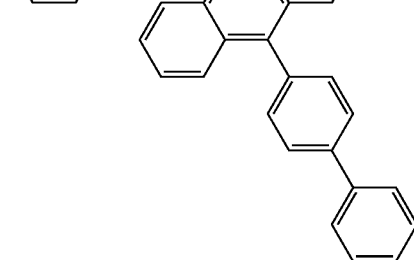

249
-continued
250
-continued
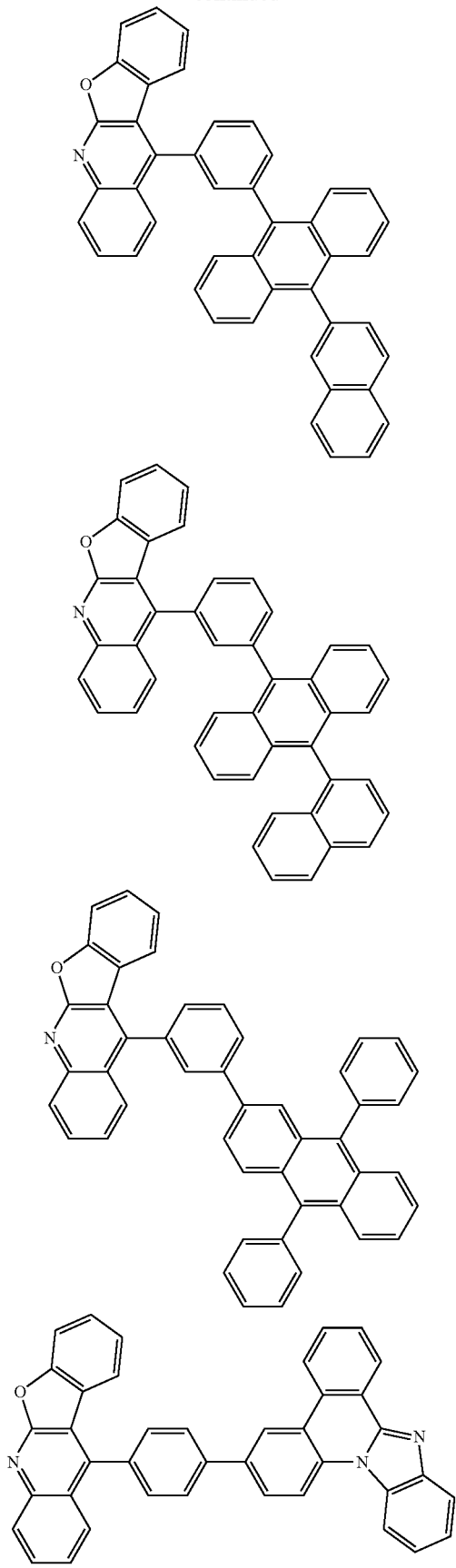
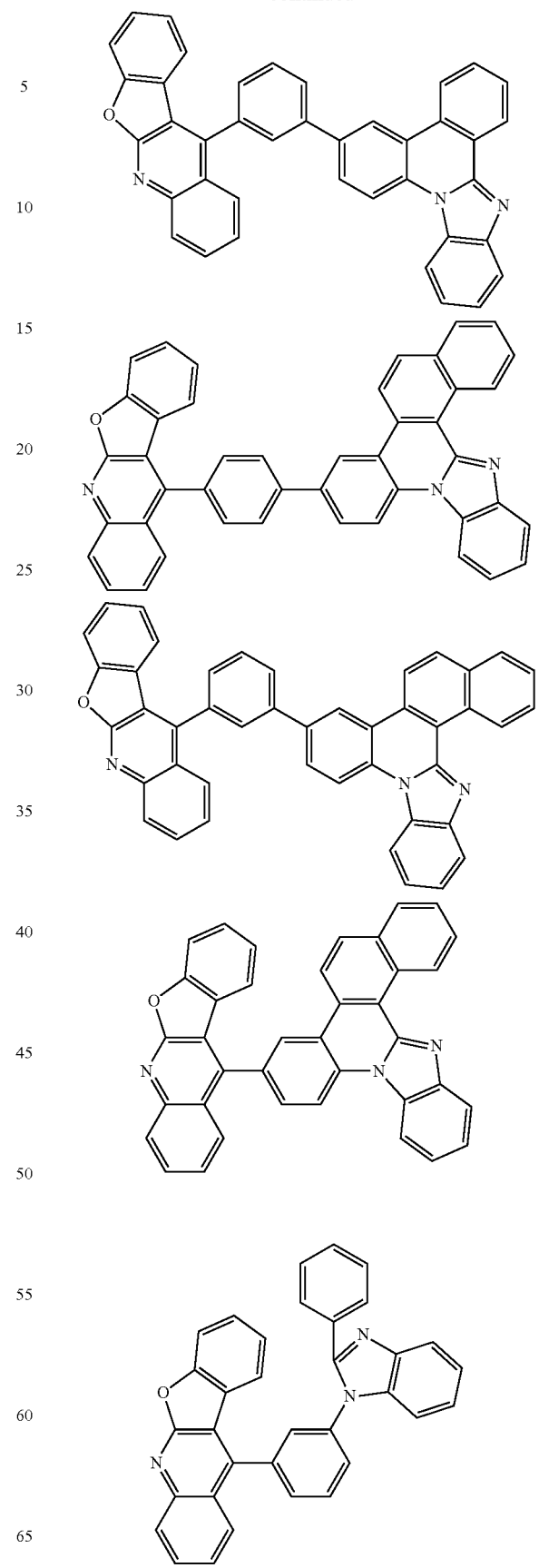

251
-continued
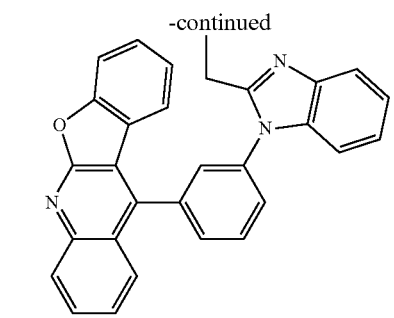
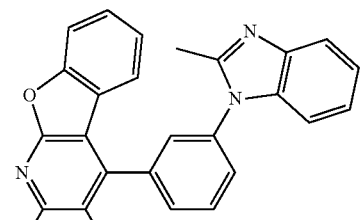
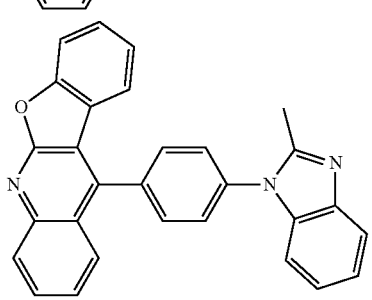
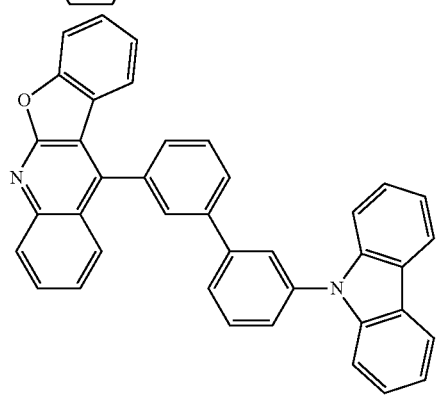
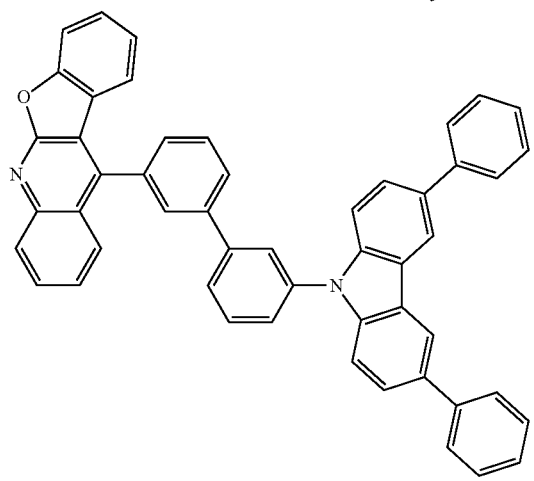
252
-continued
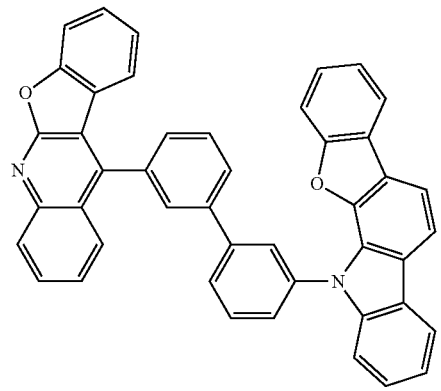
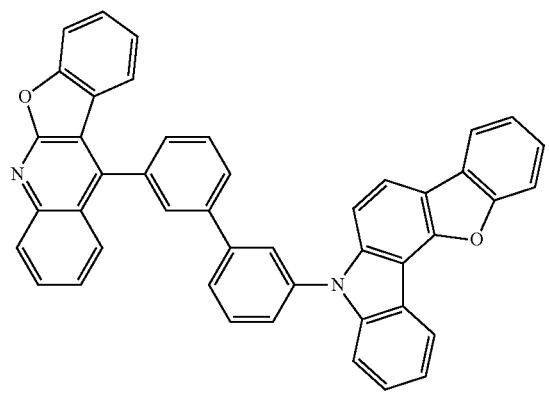
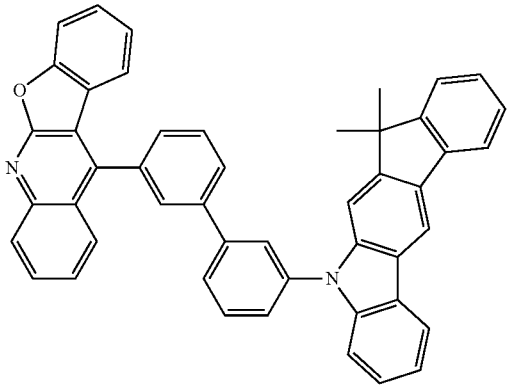
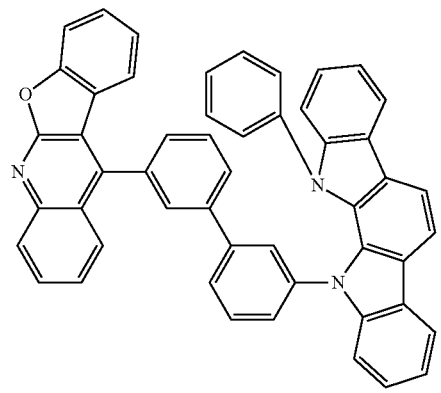

253
-continued
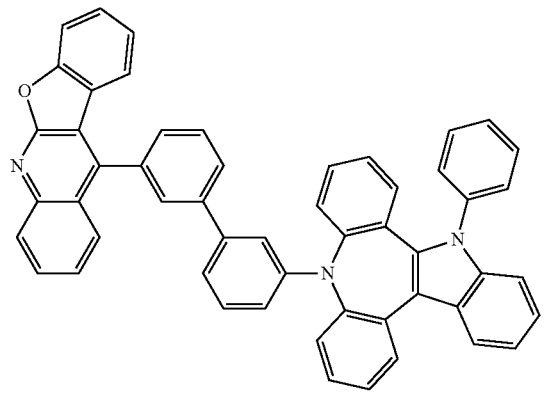
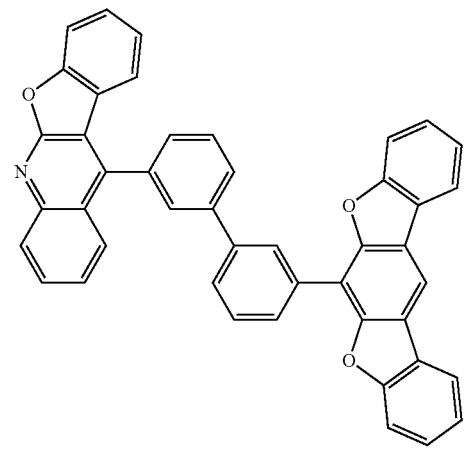
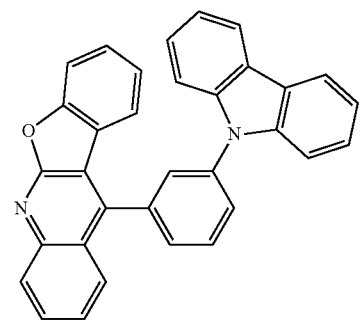
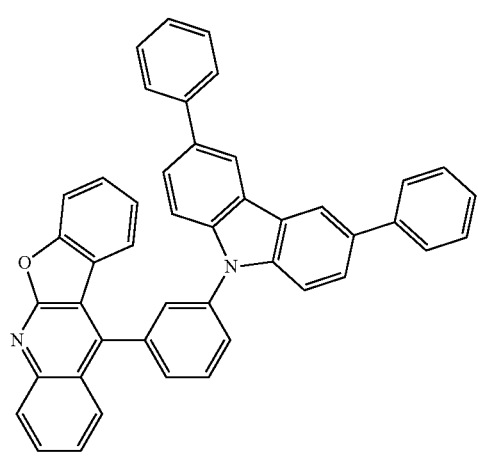
254
-continued
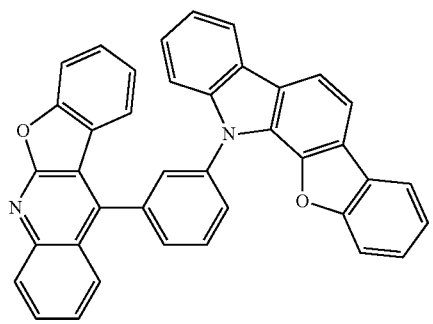
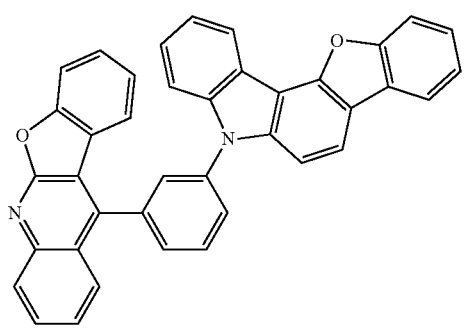
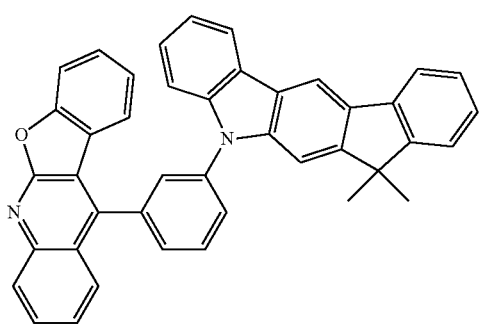
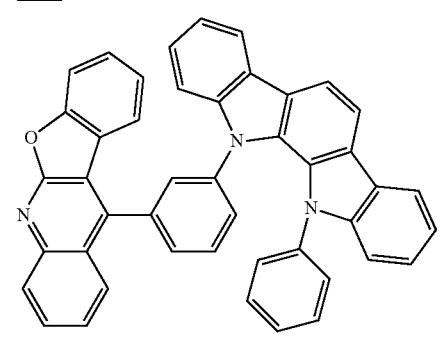
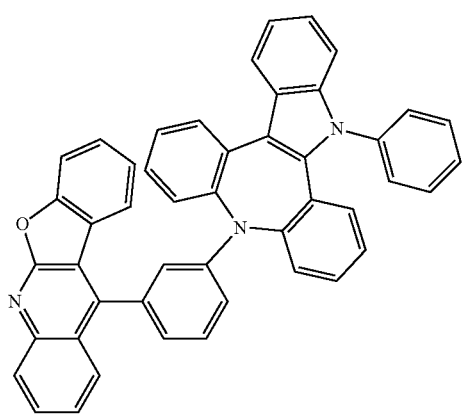

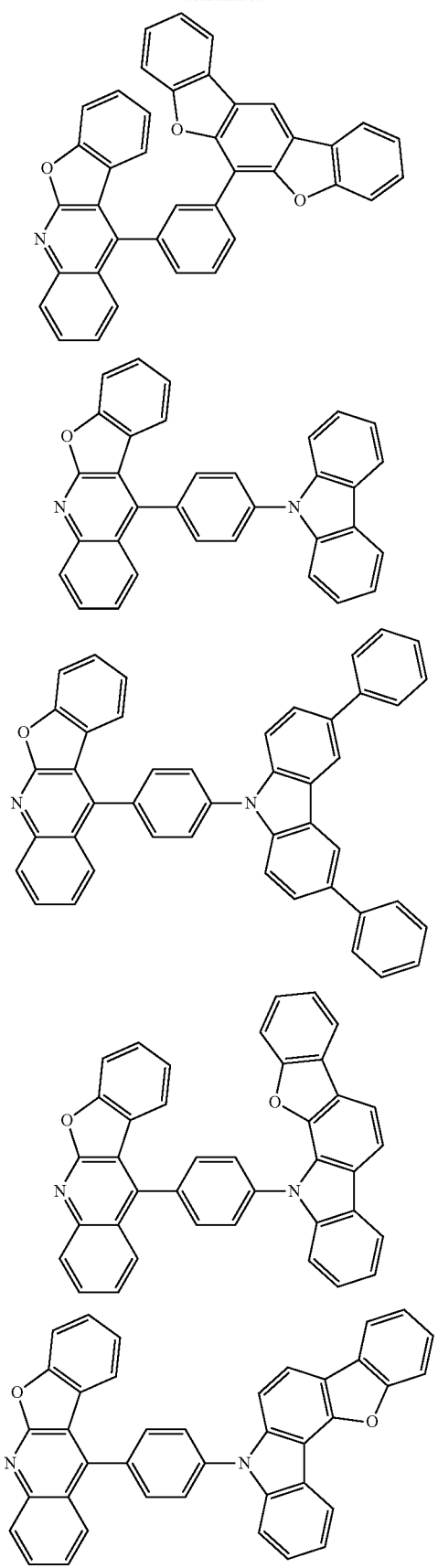
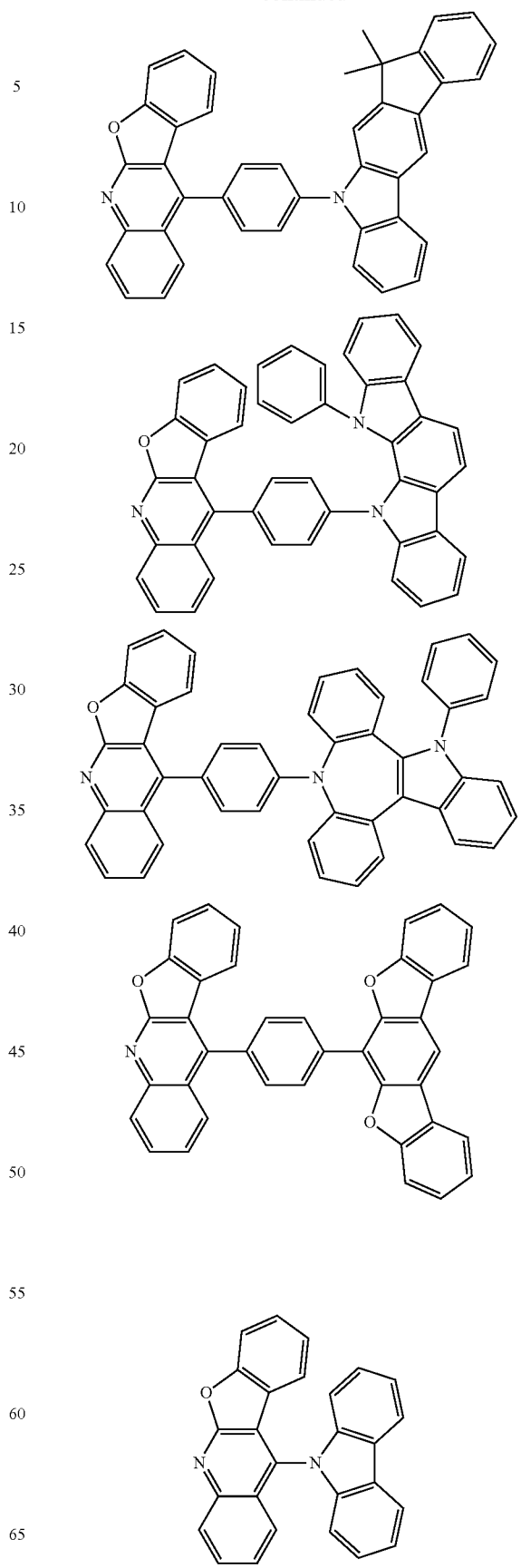

257
-continued
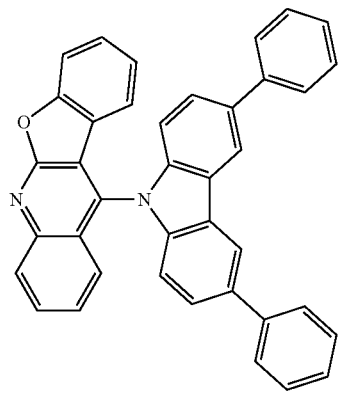
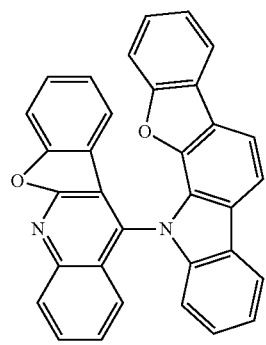
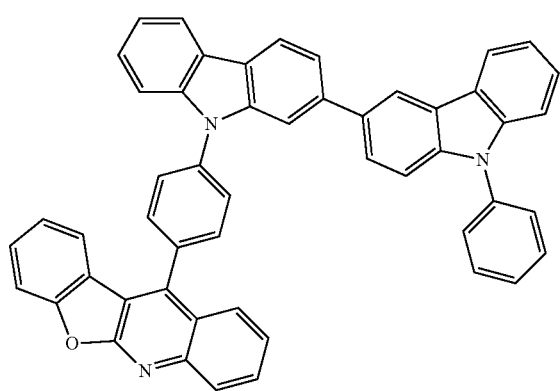
258
-continued
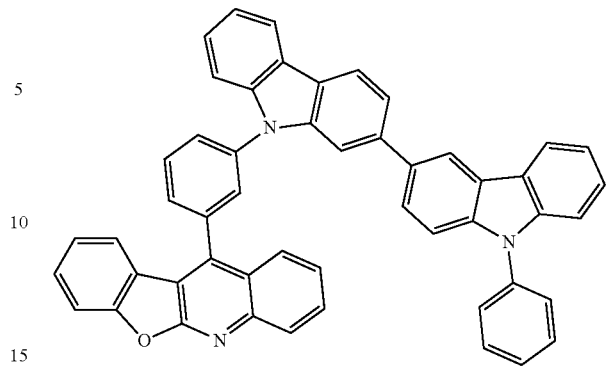
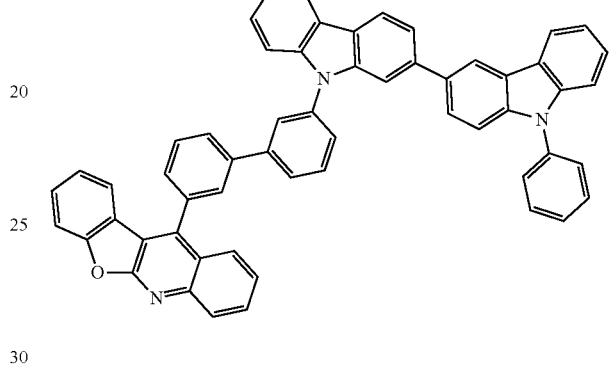
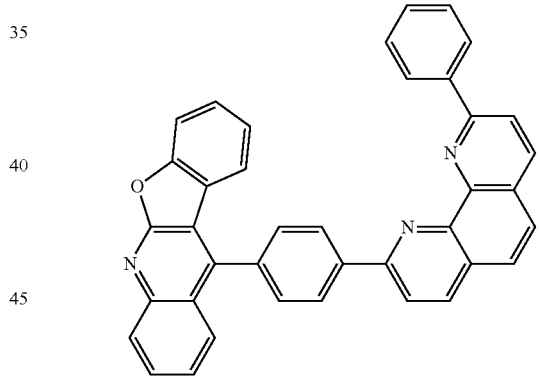
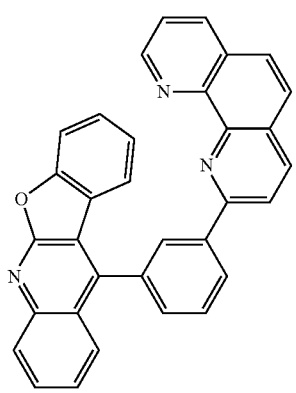

-continued

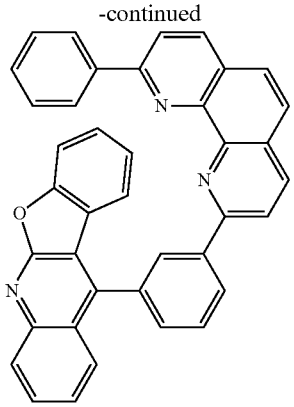

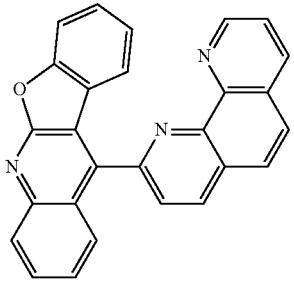

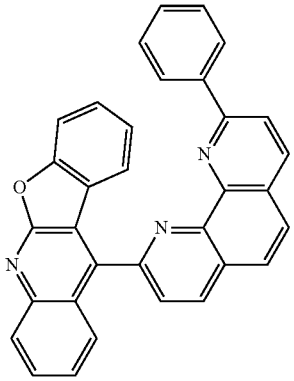

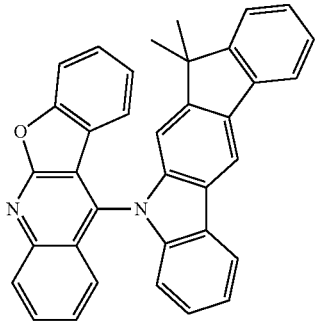

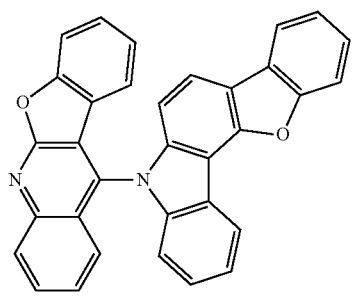

-continued

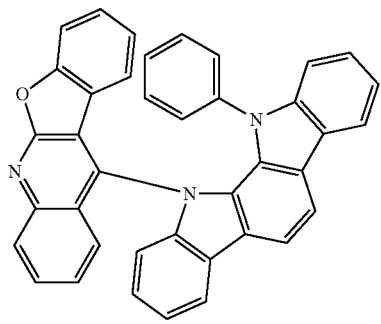

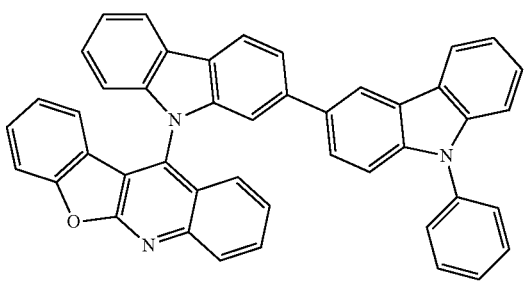

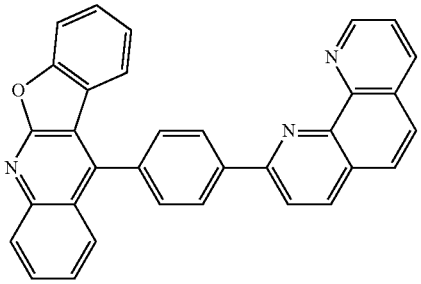

Synthesis of the Compounds of Formula (1)

Generally, the compounds of formula (1) are prepared in analogy to the preparation processes described in the related art, e.g. WO 2014/199637 and J. Med. Chem. 1998, 41, 2754-2764.

Structure (1):

A general process for the preparation of the basic structure (1')

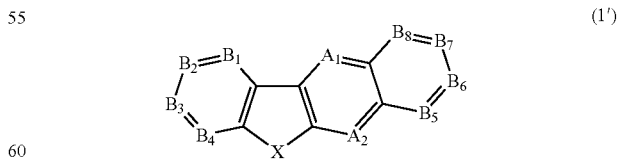

(1')

wherein at least one of $B_1$, $B_3$, $B_4$, $B_5$, $B_6$, $B_7$, $B_8$, $A_1$ and $A_2$ is C-Hal, and all other groups are as defined above, wherein Hal means halogen, preferably F, Cl or Br, more preferably Cl, is described for example in J. Med. Chem. 1998, 41, 2754-2764

Scheme 4 [a,b]

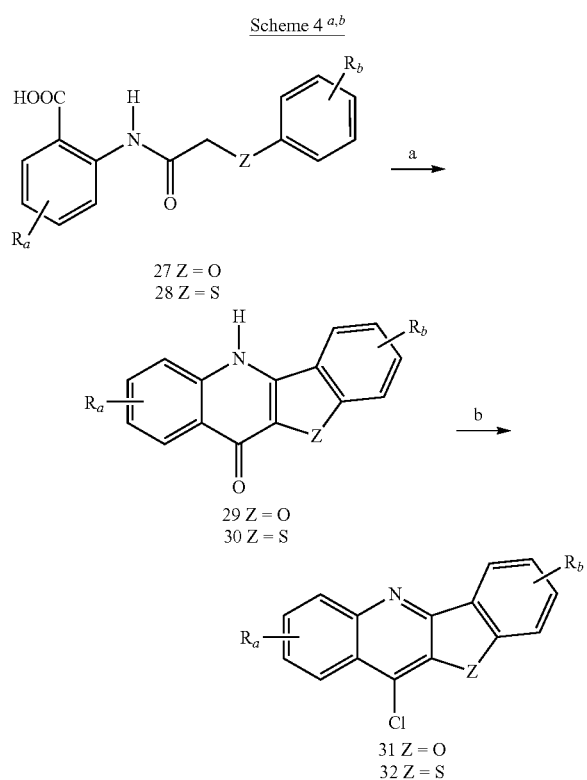

27 Z = O
28 Z = S

29 Z = O
30 Z = S

31 Z = O
32 Z = S (a) PPA; (b) POCl$_3$

It is also possible to introduce Br instead of Cl in step (b) by using POBr$_3$ instead of POCl$_3$.

A functionalization of the basic structure (1') mentioned above with one or more groups R$^{41}$, R$^{42}$, R$^1$, R$^3$, R$^4$, R$^5$, R$^6$, R$^7$, and R$^8$ is preferably carried out by coupling the basic structure at the halogenated position with at least one residue X—R$^{41}$, X—R$^{42}$, X—R$^1$, X—R$^3$, X—R$^4$, X—R$^5$, X—R$^6$, X—R$^7$, or X—R$^8$, (i) wherein X is —B(OR')$_2$ wherein R' is H or C$_1$-C$_3$ alkyl group or phenyl group, provided that two R' may be same or different, and the two R's may form a ring together with the two oxygen atoms and the boron atom;
    in the presence of a catalyst and in the presence of a base, (general procedure 1 shown below)
or
(ii) wherein X is H in the presence of a base (general procedure 2 shown below);
or
(iii) wherein X is H in the presence of a catalyst and in the presence of a base and in the presence of a ligand (general procedure 3 shown below).

The coupling is preferably a Suzuki-Miyaura reaction (coupling). The general conditions for the Suzuki-Miyaura reaction are for example disclosed in US2014/0330013. Especially in paragraphs [136]-[137].

Concerning (i):

Preferably, R' is H, CH$_3$, CH(CH$_3$)$_2$, CH$_2$CH$_2$CH$_3$, and phenyl, when two R's from a ring together with the boron atom bonded to the two R's via the two oxygen atoms, B(OR')$_2$ preferably includes the following groups

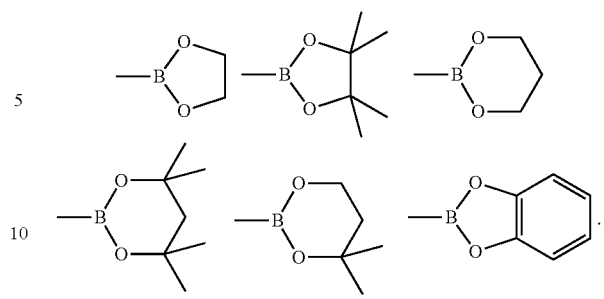

Preferably, the catalyst is a Pd catalyst, e.g. Pd$_2$(dba)$_3$ or Pd(PPh$_3$)$_4$.

Preferably, the base is Na$_2$CO$_3$, K$_2$CO$_3$ or Cs$_2$CO$_3$.

Concerning (ii)

Preferably, the base is K$_3$PO$_4$, Na$_2$CO$_3$, K$_2$CO$_3$, Cs$_2$CO$_3$ or NaH.

Concerning (iii)

Preferably, the catalyst is a Pd catalyst, e.g. Pd$_2$(dba)$_3$.

Preferably, the base is NaO$^t$Bu or KO$^t$Bu.

Preferred ligands are P(tBu)$_3$, Xanthophos, Sphos, and Xphos.

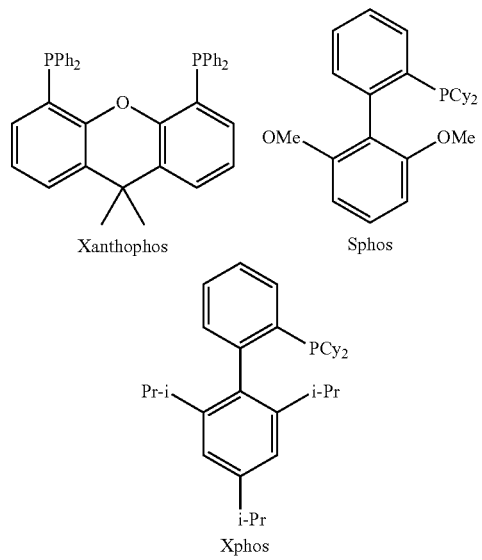

General Procedure 1 (Shown—as a Representative Example—for a Substitution at the A$_2$ Position)

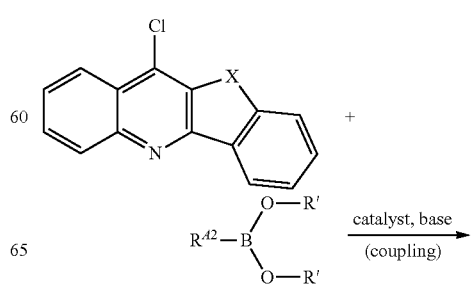

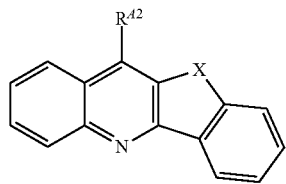

wherein X and $R^{42}$ and R' are defined above.

General Procedure 2 (Shown—as a Representative Example—for a Substitution at the $A_2$ Position)

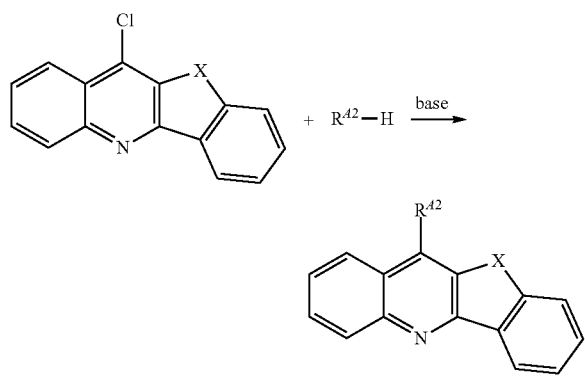

wherein X and $R^{42}$ are defined above.

General Procedure 3 (Shown—as a Representative Example—for a Substitution at the $A_2$ Position)

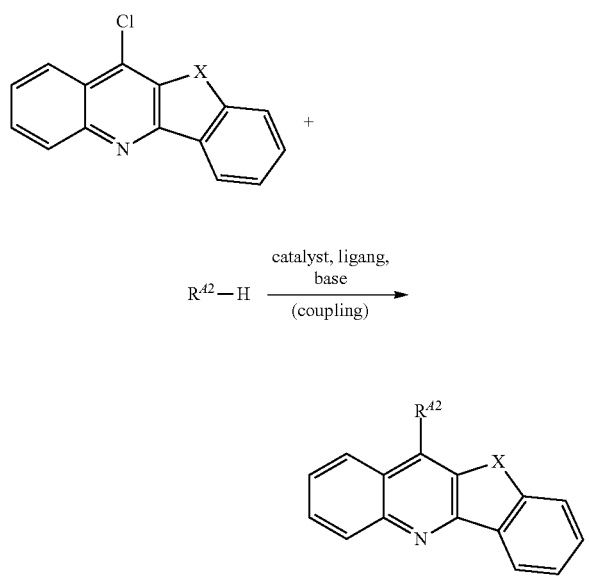

wherein X and $R^{42}$ are defined above.

Examples for a functionalization of the basic structure are shown below:

The present invention therefore further relates to a process for the preparation of the compounds of formula (1) comprising the step:

(a) Coupling a compound of formula (1')

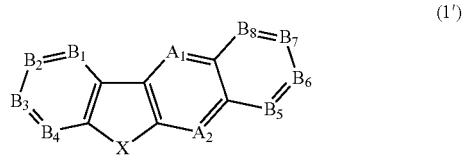

wherein at least one of $B_1$, $B_3$, $B_4$, $A_1$ and $A_2$ is C-Hal, and all other groups are as defined above, wherein Hal means halogen, preferably F, Cl or Br, more preferably Cl, (i) with a compound of formula X—$R^{41}$, X—$R^{42}$, X—$R^1$, X—$R^3$, X—$R^4$, X—$R^5$, X—$R^6$, X—$R^7$, or X—$R^8$, wherein X is —B(OR')$_2$ wherein R' is H or $C_1$-$C_3$ alkyl group or phenyl group, provided that two R' may be same or different, and the two R's may form a ring together with the two oxygen atoms and the boron atom;
in the presence of a catalyst and in the presence of a base; or (ii) wherein X is H in the presence of a base; or (iii) wherein X is H in the presence of a catalyst and in the presence of a base and in the presence of a ligand.

Suitable groups $A_1$, $A_2$, $B_1$, $B_3$, $B_4$, $B_5$, $B_6$, $B_7$, and $B_8$, are mentioned above, wherein at least one of the groups $A_1$, $A_2$, $B_1$, $B_3$, $B_4$, $B_5$, $B_6$, $B_7$, and $B_8$ is C-Hal. Most preferably, the group $A_2$ is C-Hal.

Details of the reaction step and process conditions are mentioned above and in the examples of the present application.

Compounds of Formula (1) in Organic Electronics Applications

It has been found that the compounds of the formula (1) are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs).

The term organic EL device is used interchangeable with the term organic light-emitting diode (OLED) in the following; i.e. both terms have the same meaning in the sense of the present application.

The organic transistor generally includes a semiconductor layer formed from an organic layer with charge transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor. The layers with charge transport capacity may comprise the compounds of formula (1).

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or charge transport capacity. In addition, it is possible for further layers known to those skilled in the art to be present in the organic solar cell. The layers with charge transport capacity may comprise the compounds of formula (1).

The compounds of formula (1) being particularly suitable in OLEDs for use as matrix material in a light-emitting layer and/or as charge and/or exciton blocker material, i.e. as electron/exciton blocker material or as hole/exciton blocker material, and/or charge transport material, i.e. hole transport material or electron transport material, especially in combination with a phosphorescence emitter.

In the case of use of the inventive compounds of formula (1) in OLEDs, OLEDs which have good efficiencies and a long lifetime and which can be operated especially at a low use and operating voltage are obtained. The inventive compounds of formula (1) are suitable especially for use as matrix and/or charge transport, i.e. hole or electron transport, and/or charge blocker material, i.e. hole or electron blocker material, for blue, green, red and yellow, preferably blue, green and red, more preferably blue and red emitters. The blue emitters employed are usually fluorescent emitters. The other emitters employed are usually fluorescent or phosphorescent emitters, preferably phosphorescent emitters. Furthermore, the compounds of the formula (1) can be used as conductor/complementary materials in organic electronics applications selected from switching elements and organic solar cells. (in the sense of the present application, the terms matrix and host are used interchangeable).

Compounds of the formula (1) as matrix material in an emission layer

Most preferably, the compounds of the formula (1) are used as matrix materials (host materials), preferably in an emission layer of an OLED, more preferably in an emission layer of an OLED comprising at least one compound of the formula (1) and at least one emitter material, wherein the emitter material is preferably a fluorescent or phosphorescent emitter material, more preferably a red fluorescent or phosphorescent emitter material.

The present invention therefore relates to an emission layer (light-emitting layer) comprising at least one compound of the formula (1) and at least one emitter material. Suitable emitter materials are mentioned above and below. Suitable structures of the emission layer are mentioned below.

The present invention further relates to an OLED comprising an emission layer (light-emitting layer) comprising at least one compound of the formula (1) and at least one emitter material.

In the emission layer or one of the emission layers of an OLED, it is also possible to combine an emitter material with at least one matrix material of the compound of the formula (1) and one or more, preferably one, further matrix materials (co-host). This may achieve a high quantum efficiency, low driving voltage and/or long lifetime of the OLED devices.

It is likewise possible that the compounds of the formula (1) are present in two or three of the following layers: in the light-emitting layer (preferably as matrix material), in the blocking layer (as charge blocker material) and/or in the charge transport layer (as charge transport material).

When a compound of the formula (1) is used as matrix (host) material in an emission layer and additionally as charge blocking material and/or as charge transport material, owing to the chemical identity or similarity of the materials, an improved interface between the emission layer and the adjacent material, which can lead to a decrease in the voltage with equal luminance and to an extension of the lifetime of the OLED. Moreover, the use of the same material as charge transport material and/or as charge blocker material and as matrix of an emission layer allows the production process of an OLED to be simplified, since the same source can be used for the vapor deposition process of the material of one of the compounds of the formula the compound of the formula (1)

Suitable structures of organic electronic devices, especially organic light-emitting diodes (OLED), are known to those skilled in the art and are specified below.

Compounds of the formula (1) as electron transporting material

In a further most preferred embodiment, the compounds of the formula (1) are used as electron transporting materials (electron transport materials), preferably in an OLED, more preferably in an OLED comprising at least one blue fluorescent emitter material.

The present invention therefore relates to an electron transporting layer (electron transport layer) comprising least one compound of the formula (1).

The present invention further relates to an OLED comprising an electron transporting layer comprising at least one compound of the formula (1) and an emission layer comprising at least one emitter material, preferably a blue fluorescent emitter material. Suitable emitter materials are mentioned above and below. Suitable structures of the electron transporting layer are mentioned below.

In a preferred embodiment, the electron transporting layer comprising at least one compound of the formula (1) of the invention further comprises a reducing dopant.

Examples of the reducing dopant include a donating metal, a donating metal compound, and a donating metal complex. The reducing dopant may be used alone or in combination of two or more.

The reducing dopant referred to herein is an electron-donating material. The electron-donating material is a material which generates radical anions by the interaction with a coexisting organic material in the electron transporting layer or an organic material in a layer adjacent to the electron transporting layer, or a material having an electron-donating radical.

The donating metal is a metal having a work function of 3.8 eV or less, preferably an alkali metal, an alkaline earth metal, or a rare earth metal, and more preferably Cs, Li, Na, Sr, K, Mg, Ca, Ba, Yb, Eu, or Ce.

The donating metal compound is a compound comprising the above donating metal, preferably a compound comprising an alkali metal, an alkaline earth metal, or a rare earth metal, and more preferably a halide, an oxide, a carbonate, or a borate of these metals, for example, a compound represented by MOx (M: donating metal, x: 0.5 to 1.5), MFx (x: 1 to 3), or M(CO$_3$)x (x: 0.5 to 1.5).

The donating metal complex is a complex comprising the above donating metal, preferably an organic metal complex of an alkali metal, an alkaline earth metal or a rare earth metal, and more preferably an organic metal complex represented by formula (I): M–(Q)$_n$, wherein M is a donating metal, Q is a ligand, preferably a carboxylic acid derivative, a diketone derivative, or a quinoline derivative, and n is an integer of 1 to 4.

Examples of the donating metal complex include water-mill-shaped tungsten compounds described in JP 2005-72012A and phthalocyanine compounds having an alkali metal or an alkaline earth metal as the central metal, which are described in JP 11-345687A.

The reducing dopant is preferably at least one selected from the group consisting of an alkali metal, an alkaline earth metal, a rare earth metal, an alkali metal oxide, an alkali metal halide, an alkaline earth metal oxide, an alkaline earth metal halide, a rare earth metal oxide, a rare earth metal halide, an organic complex having an alkali metal, an organic complex having an alkaline earth metal, and an organic complex having a rare earth metal, and more preferably a 8-quinolinol complex of an alkali metal.

Examples of the alkali metal includes: Li (lithium, work function: 2.93 eV), Na (sodium, work function: 2.36 eV), K (potassium, work function: 2.3 eV), Rb (rubidium, work function: 2.16 eV), and Cs (cesium, work function: 1.95 eV).

The values of work functions are based on Handbook of Chemistry (Pure Chemistry II, 1984, p. 493, edited by The Chemical Society of Japan). The same applies hereafter.

Preferred examples of the alkaline earth metals are: Ca (calcium, work function: 2.9 eV), Mg (magnesium, work function: 3.66 eV), Ba (barium, work function: 2.52 eV), and Sr (strontium, work function: 2.0 to 2.5 eV).

The work function of strontium is based of Physics of Semiconductor Device (N.Y., Wiley, 1969, p. 366).

Preferred examples of the rare earth metal are: Yb (ytterbium, work function: 2.6 eV), Eu (europium, work function: 2.5 eV), Gd (gadolinium, work function: 3.1 eV), and Er (erbium, work function: 2.5 eV).

Examples of the alkali metal oxide include $Li_2O$, LiO, and NaO. The alkaline earth metal oxide is preferably CaO, BaO, SrO, BeO, or MgO.

Examples of the alkali metal halide include a fluoride, for example, LiF, NaF, CsF, and KF and a chloride, for example, LiCl, KCl, and NaCl.

The alkaline earth metal halide is preferably a fluoride, such as $CaF_2$, $BaF_2$, $SrF_2$, $MgF_2$, and $BeF_2$ and a halide other than fluoride.

The content of the compound of the formula (1) in the electron transporting layer is preferably 50% by mass or more, i.e. 50 to 100% by weight and more preferably 60% by mass or more, i.e. 60 to 100% by weight, based on the weight of the electron transporting layer.

The present invention further provides an organic light-emitting diode (OLED) comprising an anode and a cathode and a light-emitting layer arranged between the anode and the cathode, and if appropriate at least one further layer selected from the group consisting of at least one blocking layer for holes/excitons, at least one blocking layer for electrons/excitons, at least one hole injection layer, at least one hole transport layer, at least one electron injection layer and at least one electron transport layer, wherein the at least one compound of the formula (1) is present in the light-emitting layer and/or in at least one of the further layers. The at least one compound of the formula (1) is preferably present in the light-emitting layer and/or the charge blocking layer and/or the charge transport layer.

In a preferred embodiment of the present invention, at least one compound of the formula (1) is used as charge transport, i.e. electron transport or hole transport material, especially as electron transport material. Examples of preferred compounds of the formula (1) are shown above.

In a further preferred embodiment of the present invention, at least one compound of the formula (1) is used as charge/exciton blocker, i.e. electron/exciton blocker or hole/exciton blocker material, especially as hole/exciton blocker material. Examples of preferred compounds of the formula (1) are shown above.

The present application further relates to a light-emitting layer comprising at least one compound of the formula (1), preferably as host material or co-host material. Examples of preferred compounds of the formula (1) are shown above.

The material for an organic EL device (OLED) of the invention comprises the compound represented by the above formula (1). The content of the above-mentioned compound in the material for an organic EL device is not particularly restricted. For example, it may be 1 mass % or more, preferably 10 mass % or more, more preferably 50 mass % or more, further preferably 80 mass % or more, and particularly preferably 90 mass % or more. The content may be 100 mass %. As other materials than those represented by the formula (1), materials used in the emitting layer, the electron-transporting layer, the hole-transporting layer or the like (mentioned later) can be given.

The material for an organic EL device of the invention is effective as the material for an organic EL device, and can be used as a host material or a dopant material in the emitting layer of a fluorescent emitting unit or as a host material in the emitting layer of a phosphorescent emitting unit. In any of a fluorescent emitting unit and a phosphorescent emitting unit, the material is effective as a material for an anode-side organic thin film layer provided between an anode and an emitting layer of an organic EL device or as a material for a cathode-side organic thin film layer provided between a cathode and an emitting layer of an organic EL device. That is, it is effective as a material for a hole-transporting layer, a hole-injecting layer, an electron-transporting layer, an electron-injecting layer, a hole-blocking layer, an electron-blocking layer, or the like.

Meanwhile, the "emitting unit" means the minimum unit that comprises one or more organic layers, one of which being an emitting layer, and can emit light by recombination of holes and electrons injected.

Organic EL Device (OLED)

The organic EL device as one embodiment of the invention comprises one or more organic thin film layers including an emitting layer between a cathode and an anode, and at least one layer of the organic thin film layers comprises the above-mentioned material for an organic EL device.

As examples of the organic thin film layers that comprise the above-mentioned material for an organic EL device, an anode-side organic thin film layer (hole-transporting layer, hole-injecting layer, or the like), an emitting layer, a cathode-side organic thin film layer (electron-transporting layer, electron-injecting layer, or the like) provided between a cathode and an emitting layer, a spacing layer, a barrier layer or the like can be given. The examples are not limited thereto. The above-mentioned material for an organic EL device may be contained in any of the above-mentioned layers, and can be used as a host material or a dopant material in the emitting layer of a fluorescent emitting unit, a host material in the emitting layer of a phosphorescent emitting unit, a hole-transporting layer, an electron-transporting layer or the like of an emitting unit.

The organic EL device of the invention may be a fluorescent or phosphorescent monochromatic emitting device or may be a fluorescent/phosphorescent hybrid white emitting device. It may be a simple emitting device having a single emitting unit or a tandem emitting device having plural emitting units. Among them, the organic EL device may preferably be a phosphorescent emitting device.

As the representative device structure of a simple type organic EL device, the following device configuration can be given.

(1) Anode/Emitting Unit/Cathode

The emitting unit mentioned above may be a stacked type emitting unit comprising plural phosphorescent emitting layers or plural fluorescent emitting layers. In this case, in order to prevent diffusion of excitons generated in the phosphorescent emitting layer to the fluorescent emitting layer, a spacing layer may be provided between the emitting layers. The representative layer configuration of the emitting unit is given below.

(a) Hole-transporting layer/Emitting layer (/Electron-transporting layer)
(b) Hole-transporting layer/First phosphorescent emitting layer/Second phosphorescent emitting layer (/Electron-transporting layer)
(c) Hole-transporting layer/Phosphorescent emitting layer/Spacing layer/Fluorescent emitting layer (/Electron-transporting layer)
(d) Hole-transporting layer/First phosphorescent emitting layer/Second phosphorescent emitting layer/Spacing layer/Fluorescent emitting layer (/Electron-transporting layer)
(e) Hole-transporting layer/First phosphorescent emitting layer/Spacing layer/Second phosphorescent emitting layer/Spacing layer/Fluorescent emitting layer (/Electron-transporting layer)
(f) Hole-transporting layer/Phosphorescent emitting layer/Spacing layer/First fluorescent emitting layer/Second fluorescent emitting layer (/Electron-transporting layer)
(g) Hole-transporting layer/Electron barrier layer/Emitting layer (/Electron-transporting layer)
(h) Hole-transporting layer/Emitting layer/Hole barrier layer (/Electron-transporting layer)
(i) Hole-transporting layer/Fluorescent emitting layer/Triplet barrier layer (/Electron-transporting layer)
(j) Hole injecting layer/Hole transporting layer/Phosphorescent emitting layer/Electron transporting layer/Electron injecting layer
(k) Hole injecting layer/First hole transporting layer/Second hole transporting layer/Fluorescent emitting layer/First electron transporting layer/Second electron transporting layer/Electron injecting layer
(l) Hole injecting layer/First hole transporting layer/Second hole transporting layer/Fluorescent emitting layer/Electron transporting layer/Electron injecting layer The phosphorescent or fluorescent emitting layer as mentioned above can emit different colors of light. Specifically, in the stacked emitting layer (d), a layer configuration of the hole-transporting layer/first phosphorescent emitting layer (red emission)/second phosphorescent emitting layer (green emission)/spacing layer/fluorescent emitting layer (blue emission)/electron-transporting layer or the like can be given.

Between each emitting layer and the hole-transporting layer or the spacing layer, an electron-barrier layer may be provided appropriately. Between each emitting layer and the electron-transporting layer, a hole-barrier layer may be provided appropriately. Due to provision of an electron-barrier layer or a hole-barrier layer, electrons or holes can be confined within the emitting layer, whereby possibility of recombination of carriers in the emitting layer can be increased, and the life can be improved.

As the represented device configuration of a tandem organic EL device, the following device configuration can be given.

(2) Anode/First Emitting Unit/Intermediate Layer/Second Emitting Unit/Cathode

Here, as the first emitting unit and the second emitting unit, the same emitting units as those mentioned above can independently be given, for example.

In general, the intermediate layer is called an intermediate electrode, an intermediate conductive layer, a carrier-generating layer, an electron-withdrawing layer, and a known material configuration that supplies electrons to the first emitting unit and supplies holes to the second emitting unit can be used.

FIG. 1 shows a schematic configuration of one example of the organic EL device of the invention. The organic EL device 1 comprises a substrate 2, an anode 3, a cathode 4 and an emitting unit 10 provided between the anode 3 and the cathode 4. The emitting unit 10 comprises an emitting layer 5 preferably comprising a host material and a dopant. A hole-injecting and transporting layer 6 or the like may be provided between the emitting layer 5 and the anode 3 and an electron-injecting layer 8 and an electron transporting layer 7 or the like (electron injecting and transporting unit 11) may be provided between the emitting layer 5 and the cathode 4. An electron-barrier layer may be provided on the anode 3 side of the emitting layer 5 and a hole-barrier layer may be provided on the cathode 4 side of the emitting layer 5. Due to such configuration, electrons or holes can be confined in the emitting layer 5, whereby possibility of generation of excitons in the emitting layer 5 can be improved.

Herein, a host that is combined with a fluorescent dopant is referred to as a fluorescent host and a host that is combined with a phosphorescent dopant is referred to as a phosphorescent host. The fluorescent host and the phosphorescent host are not distinguished only by the molecular structure thereof. That is, the phosphorescent host means a material constituting a phosphorescent emitting layer that contains a phosphorescent dopant and does not mean a material that cannot be used as a material constituting a fluorescent dopant. The same can be applied to a fluorescent host.

Substrate

The organic EL device is usually formed on a transparent substrate. The transparent substrate is a substrate for supporting the organic EL device, and is preferably a flat and smooth substrate having a 400-to-700-nm-visible-light transmittance of 50% or more. Specific examples thereof include glass plates and polymer plates. Examples of the glass plate include those obtained by using as raw materials soda-lime glass, barium/strontium-containing glass, lead glass, aluminosilicate glass, borosilicate glass, barium borosilicate glass, quartz, or the like. Examples of the polymer plate include those obtained by using as raw materials polycarbonate, acrylic polymer, polyethylene terephthalate, polyethersulfide, polysulfone, or the like.

Anode

The anode of the organic EL device plays a role for injecting holes into its hole-transporting layer or emitting layer. It is effective to use one having a work function of 4.5 eV or more. As specific examples of the anode material, indium tin oxide alloy (ITO), tin oxide (NESA), indium zinc oxide, gold, silver, platinum, copper, and the like can be given. The anode can be formed by forming these electrode materials into a thin film by vapor deposition, sputtering or the like. In the case where emission from the emitting layer is taken out through the anode, the transmittance of the anode to the emission is preferably more than 10%. The sheet resistance of the anode is preferably several hundred Ω/□ or less. The film thickness of the anode, which varies depending upon the material thereof, is usually from 10 nm to 1 μm, preferably from 10 to 200 nm.

Cathode

The cathode plays a role for injecting electrons into its electron-injecting layer, electron-transporting layer or emitting layer. The cathode is preferably formed of a material having a small work function. The cathode material is not particularly restricted. As specific examples of the cathode material, indium, aluminum, magnesium, a magnesium-indium alloy, a magnesium-aluminum alloy, an aluminum-lithium alloy, an aluminum-scandium-lithium alloy, a magnesium-silver alloy or the like can be given. As in the case of the anode, the cathode can be formed by forming the materials into a thin film by a deposition method, a sputtering method or the like. If necessary, emission can be outcoupled from the cathode side.

Emitting Layer

The emitting layer is an organic layer having an emitting function, and where a doping system is used, it comprises a host material and a dopant material. The host material has a function of accelerating recombination of electrons and holes and confining excitons within the emitting layer. The dopant material has a function of emitting efficiently excitons obtained by recombination.

In the case of a phosphorescent device, the host material has a function of confining excitons mainly generated by a dopant within the emitting layer.

Here, in the emitting layer, a double host (also referred to as a host/cohost) that adjusts the carrier balance in the emitting layer may be used by combining an electron-transporting host and a hole-transporting host or by other methods. It is preferred that the emitting layer comprise a first host material and a second host material and that the first host material be the material for the organic EL device according to the invention.

Double dopant may be used in which two or more types of dopant materials having a high quantum yield are incorporated, and each dopant emits light. Specifically, by allowing a host, a red dopant and a green dopant to be co-deposited, yellow emission from the common emitting layer, whereby yellow emission is realized.

As for the emitting layer, by allowing plural emitting layers to be a stacked body, electrons and holes are accumulated in the interface of the emitting layers, whereby the recombination region is concentrated in the interface of the emitting layers. As a result, the quantum efficiency is improved.

Easiness in injection of holes to the emitting layer and easiness in injection of electrons to the emitting layer may differ. Further, the hole-transporting performance indicated by the mobility of holes and electrons in the emitting layer may differ from each other.

The emitting layer can be formed by a known method such as a deposition method, a spin coating method, a LB method (Langmuir Blodgett method) or the like, for example. The emitting layer can also be formed by forming a solution obtained by dissolving a binder such as a resin and material compounds in a solvent into a thin film by a spin coating method and the like.

The emitting layer is preferably a molecular deposited film. The "molecular deposited film" means a thin film formed by deposition of a raw material compound in a vapor phase or a film formed by solidification of a raw material compound in a solution state or a liquid phase state. Normally, this molecular deposited film differs from a thin film (molecular accumulated film) formed by a LB method in aggregation structure or high-order structure, or differ in function derived from such difference in structure.

Emitter (Dopant Material)

The dopant material is usually selected from a known fluorescent dopant showing fluorescent emission or a known phosphorescent dopant showing phosphorescent emission.

A phosphorescent dopant (phosphorescent emitting material) that forms the emitting layer is a compound that can emit light from triplet excited state. The phosphorescent dopant is not limited as long as it can emit from triplet excited state. The phosphorescent dopant is preferably an organic metal complex containing at least one metal selected from Ir, Pt, Os, Au, Cu, Re and Ru and a ligand. It is preferred that the ligand have an ortho-metalated bond. In respect of a high phosphorescent quantum yield and capability of improving external quantum yield of an emitting device, the phosphorescent dopant is preferably a compound having a metal atom selected from Ir, Os and Pt. Further preferable are a metal complex such as an iridium complex, an osmium complex and a platinum complex, with an ortho-metalated complex being more preferable. Among them, an iridium complex and a platinum complex are more preferable, and an ortho-metalated iridium complex is particularly preferable.

The content of the emitter materials (dopants), preferably the phosphorescent emitter materials, in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided. The further component in the emitting layer is usually one or more host material, which is preferably present in an amount of 30 to 99.9% by mass, more preferably 70 to 99% by mass, wherein the sum of the emitter material(s) and the host material(s) is 100% by mass.

Suitable metal complexes (dopants, especially phosphorescent dopants) for use in the inventive OLEDs, preferably as emitter material, are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981, WO 2008/000727, WO2010129323, WO2010056669, WO10086089, US2011/0057559, WO2011/106344, US2011/0233528, WO2012/048266 and WO2012/172482.

Further suitable metal complexes are the commercially available metal complexes tris(2-phenylpyridine)iridium (III), iridium(III) tris(2-(4-tolyl)pyridinato-N,$C^{2'}$), bis(2-phenylpyridine)(acetylacetonato)iridium(III), iridium(III) tris(1-phenylisoquinoline), iridium(III) bis(2,2'-benzothienyl)pyridinato-N,$C^{3'}$)(acetylacetonate), tris(2-phenylquinoline)iridium(III), iridium(III) bis(2-(4,6-difluorophenyl)pyridinato-N,$C^2$)picolinate, iridium(III) bis(1-phenylisoquinoline)(acetylacetonate), bis(2-phenylquinoline)(acetylacetonato)iridium(III), iridium(III) bis(di-benzo[f,h]quinoxaline)(acetylacetonate), iridium(III) bis(2-methyldi-benzo[f,h]quinoxaline)(acetylacetonate) and tris(3-methyl-1-phenyl-4-trimethylacetyl-5-pyrazolino)terbium(III), bis[1-(9,9-dimethyl-9H-fluoren-2-yl)isoquinoline](acetyl-acetonato)iridium(III), bis(2-phenylbenzothiazolato)(acetylacetonato)iridium(III), bis(2-(9,9-dihexylfluorenyl)-1-pyridine)(acetylacetonato)iridium(III), bis(2-benzo[b]thiophen-2-yl-pyridine)(acetylacetonato) iridium(III).

In addition, the following commercially available materials are suitable: tris(dibenzoylacetonato)mono(phenanthroline)europium(III), tris(dibenzoylmethane)- mono(phenanthroline)europium(III), tris (dibenzoylmethane)mono(5-aminophenanthroline)-europium(III), tris(di-2-naphthoylmethane)mono(phenanthroline)europium(III), tris(4-bromobenzoylmethane)mono(phenanthroline)europium(III), tris(di(biphenyl)methane)-mono(phenanthroline)europium(III), tris(dibenzoylmethane)mono(4,7-diphenyl-phenanthroline)europium(III), tris(dibenzoylmethane)mono(4,7-di-methyl-phenanthroline)europium(III), tris (dibenzoylmethane)mono(4,7-dimethylphenanthrolinedisulfonic acid)europium(III) disodium salt, tris[di(4-(2-(2-ethoxyethoxy)ethoxy)benzoyl-methane)]mono-(phenanthroline)europium(III) and tris[di [4-(2-(2-ethoxyethoxy)ethoxy)benzoylmethane)]mono(5-aminophenanthroline)europium(III), osmium(II) bis(3-(trifluoromethyl)-5-(4-tert-butylpyridyl)-1,2,4-triazolato) diphenylmethylphosphine, osmium(II) bis(3-(trifluoromethyl)-5-(2-pyridyl)-1,2,4-triazole) dimethylphenylphosphine, osmium(II) bis(3-(trifluoromethyl)-5-(4-tert-butylpyridyl)-1,2,4-triazolato) dimethylphenylphosphine, osmium(II) bis(3-(trifluoromethyl)-5-(2-pyridyl)-pyrazolato) dimethylphenylphosphine, tris[4,4'-di-tert-butyl(2,2')-bipyridine]ruthenium(III), osmium(II) bis(2-(9,9-dibutylfluorenyl)-1-isoquinoline(acetylacetonate).

Particularly suitable metal complexes are described in US2014048784, US2012223295, US2014367667, US2013234119, US2014001446, US2014231794, US2014008633, WO2012108388 and WO2012108389. The emitters mentioned in US2013234119, paragraph [0222], are exemplified. Selected emitters, especially red emitters, of said emitters mentioned in US2013234119, paragraph [0222], are:

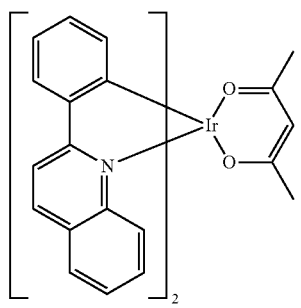
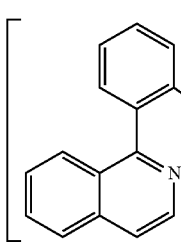
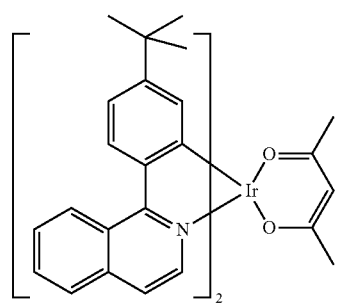

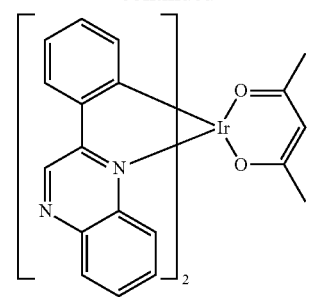
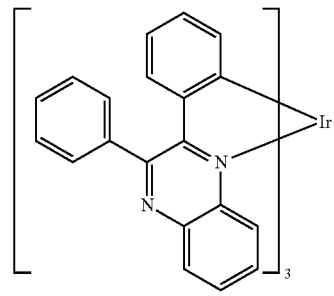
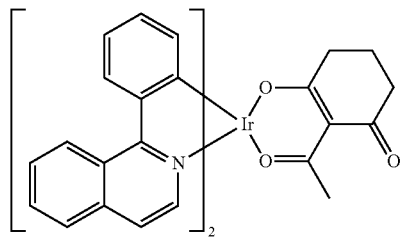
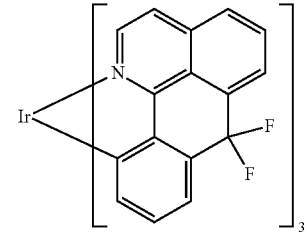
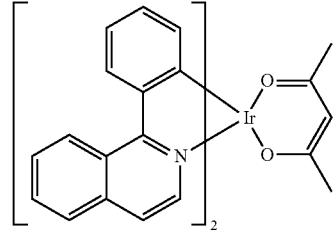
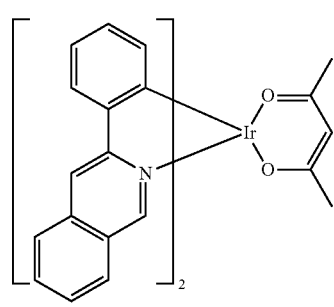

275
-continued
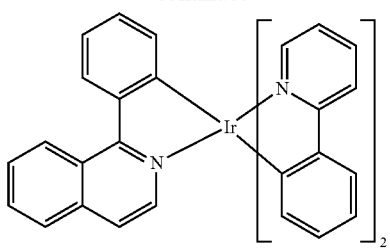
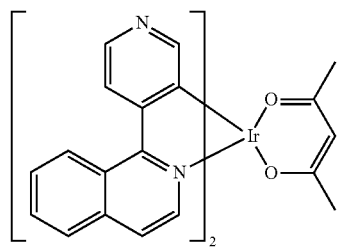
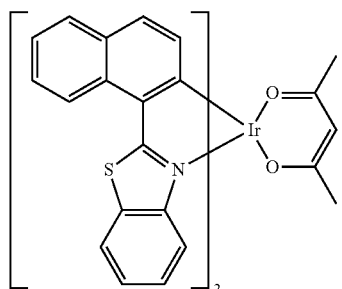
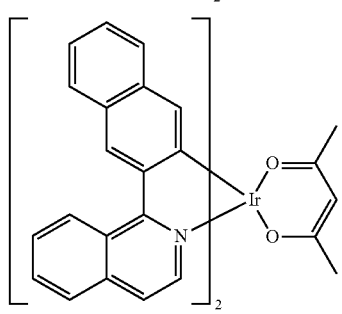
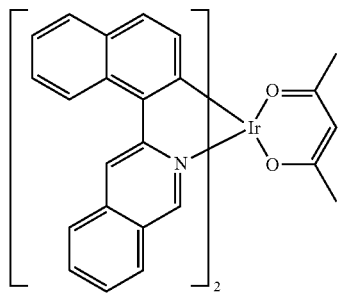
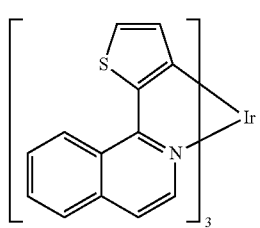
276
-continued
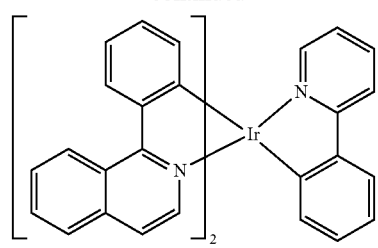
Further suitable Emitters are mentioned in: Mrs Bulletin, 2007, 32, 694:
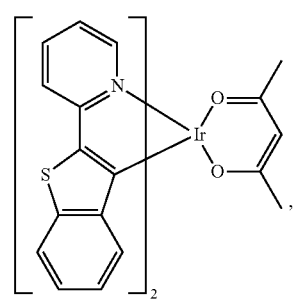
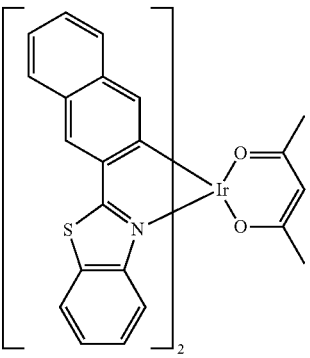
Further suitable Emitters are mentioned in: WO2009100991:
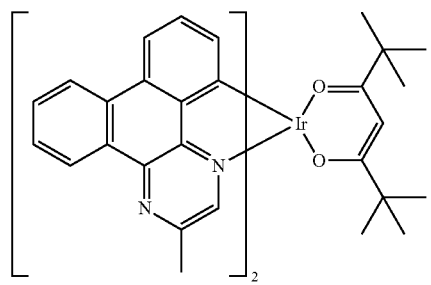

Further suitable Emitters are mentioned in: WO2008101842:
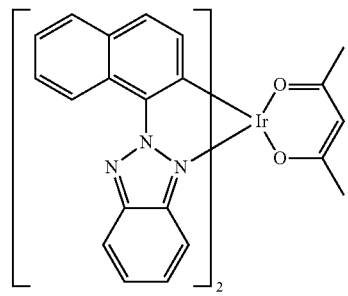
Further suitable Emitters are mentioned in: US 20140048784, especially in paragraph [0159]:
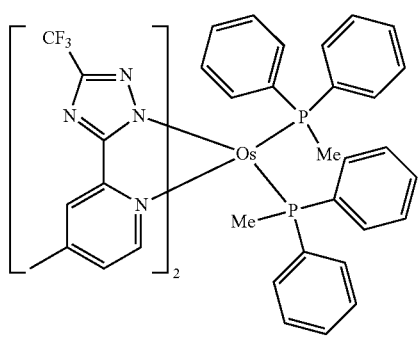
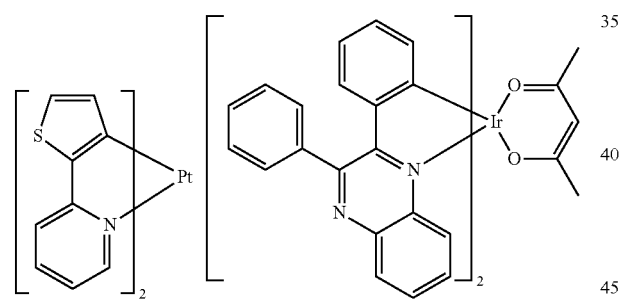
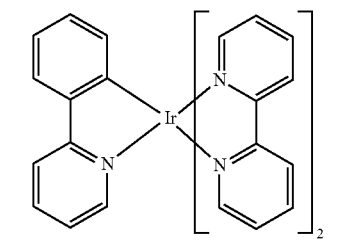
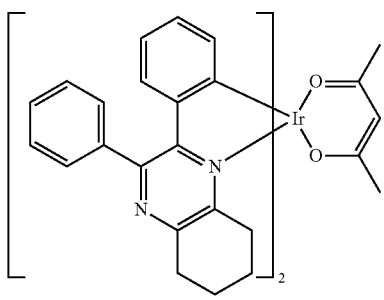
-continued
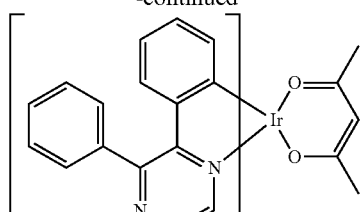
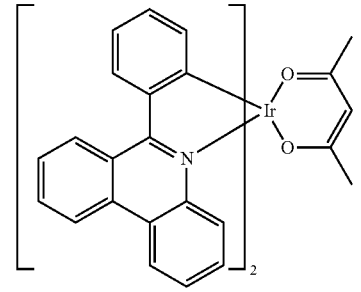
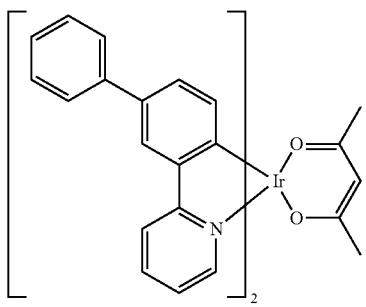
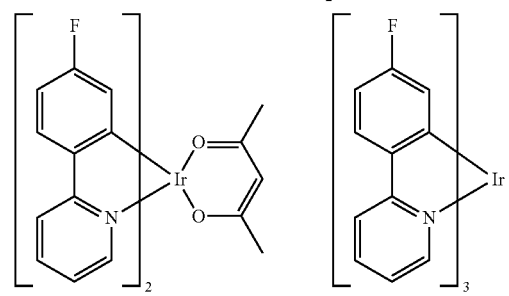
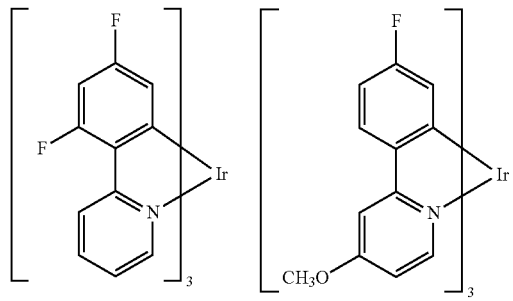
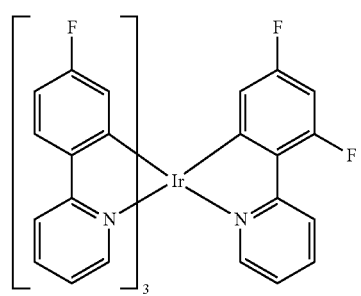

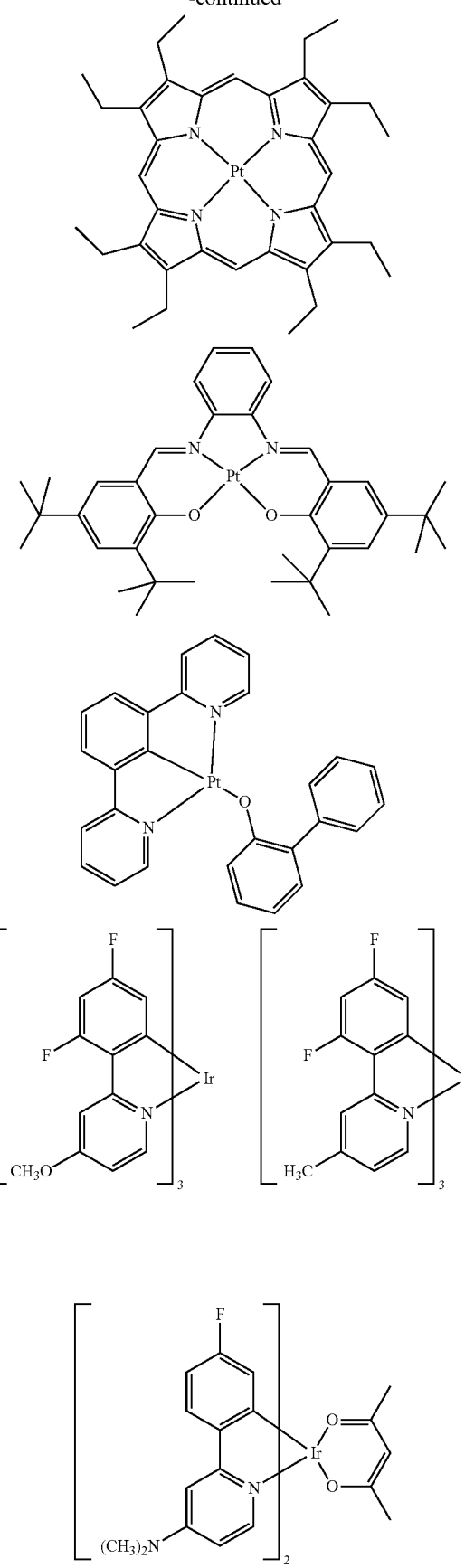
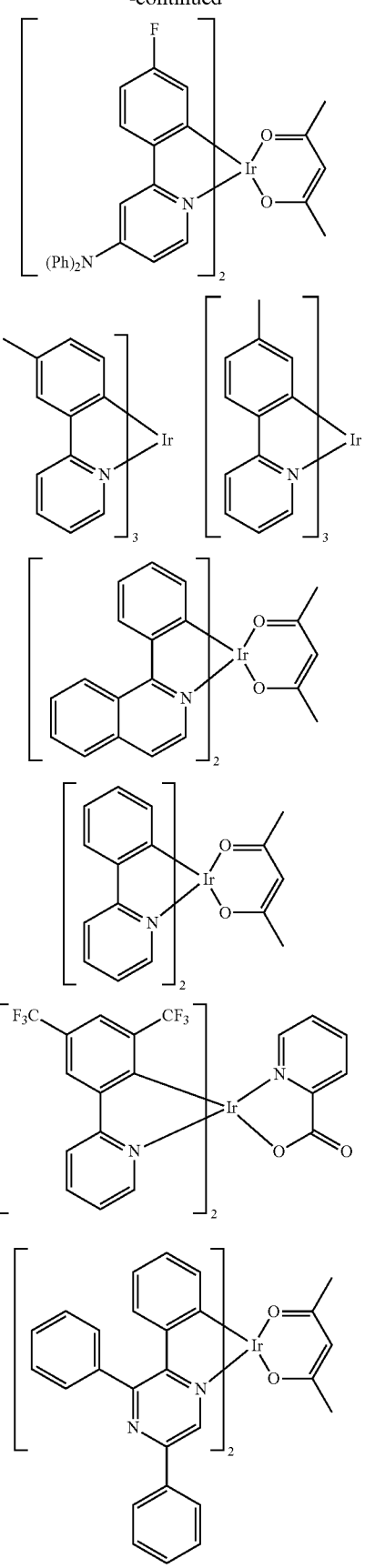

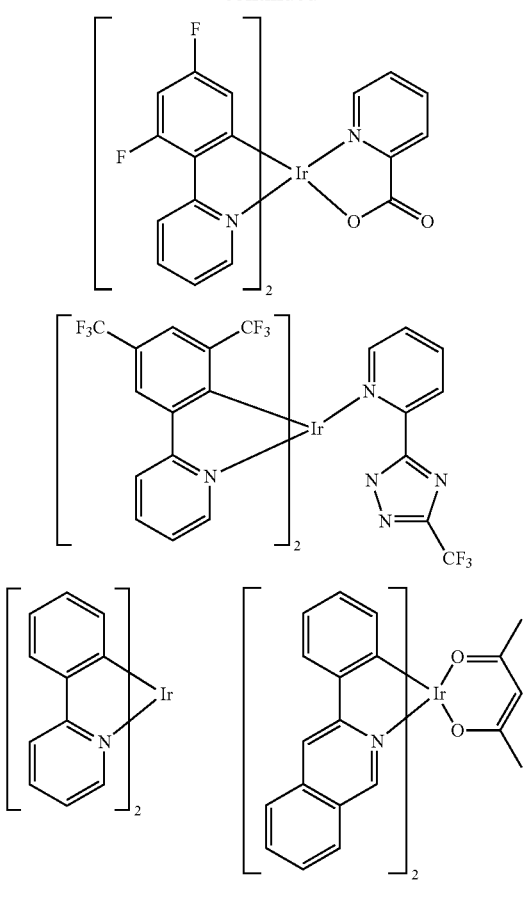
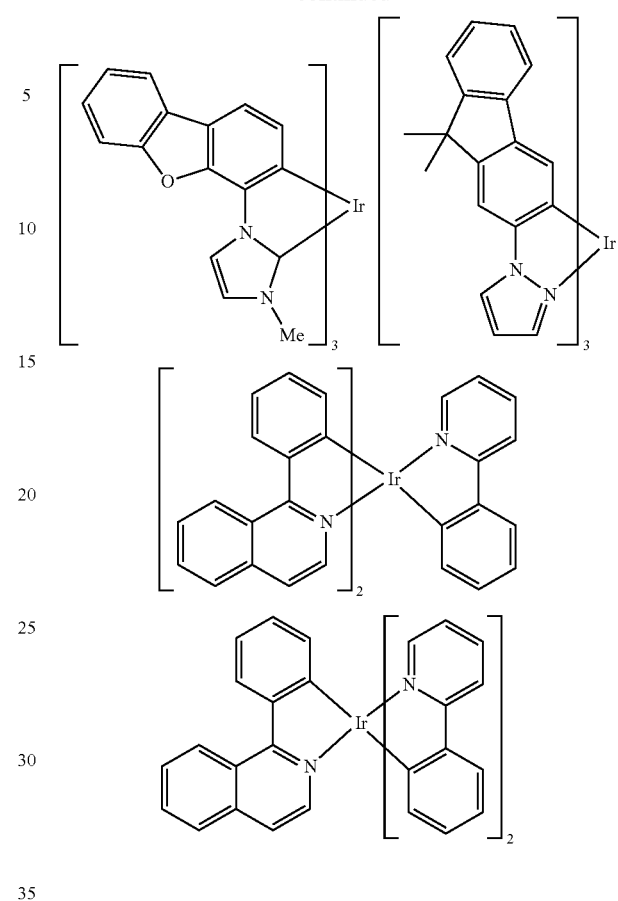
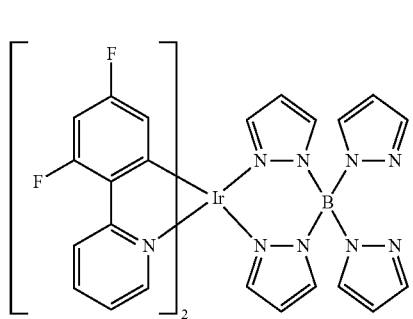
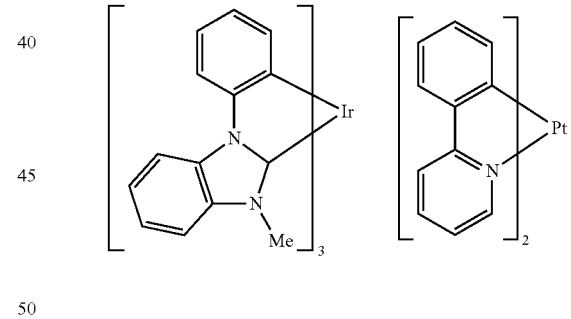
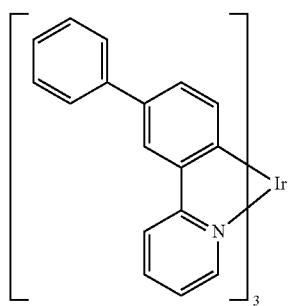
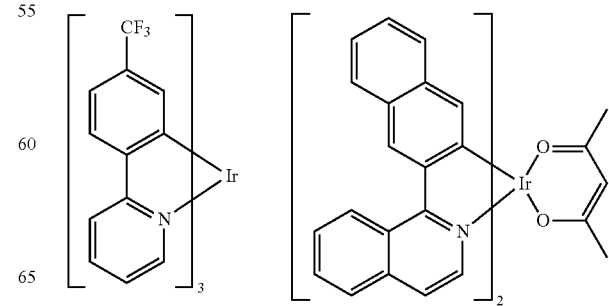

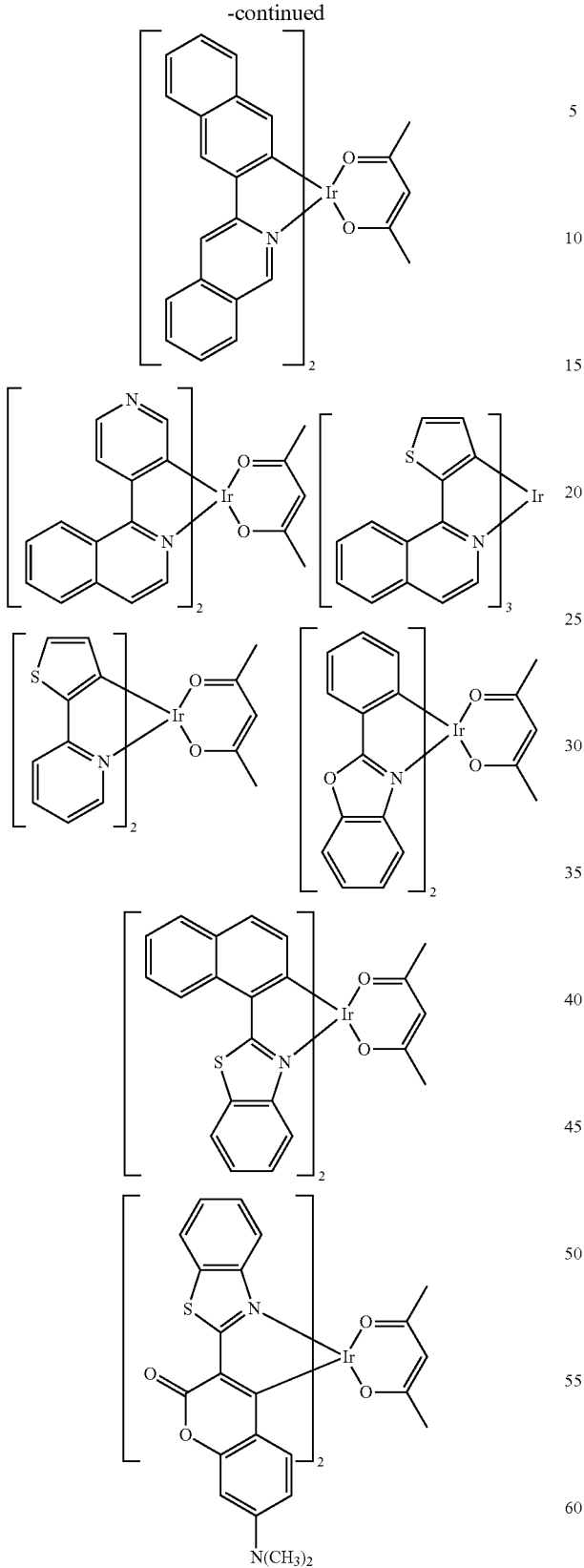
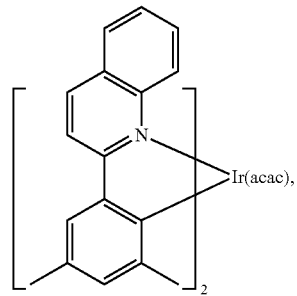
Compound 1
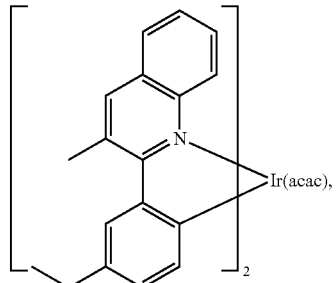
Compound 2
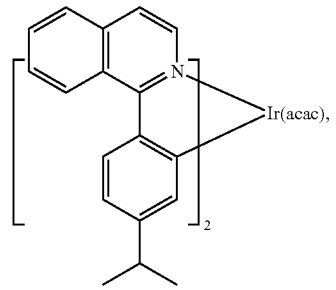
Compound 3
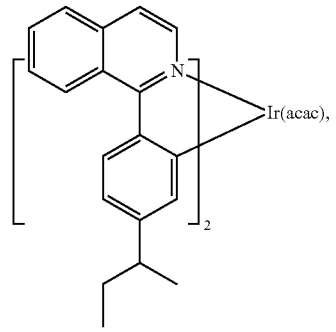
Compound 4
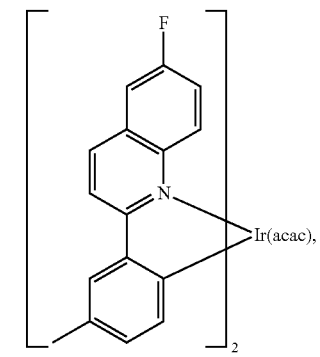
Compound 5
Further suitable red emitters, are shown in WO 2008/109824. Preferred red emitters according to this document are the following compounds:

-continued
Compound 6
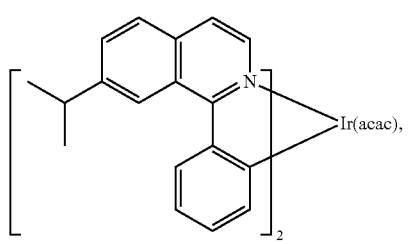
Compound 7
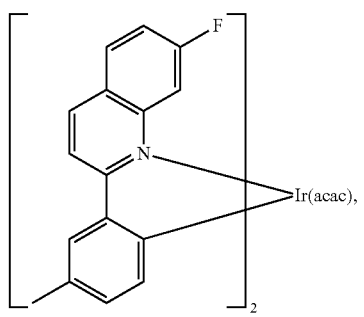
Compound 8
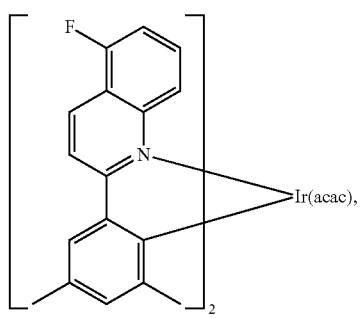
Compound 9
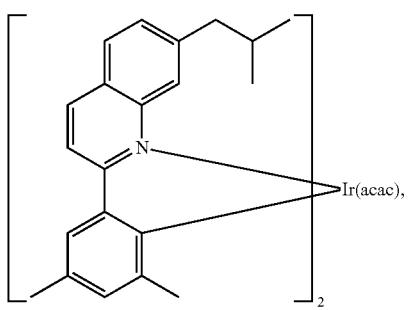
Compound 10
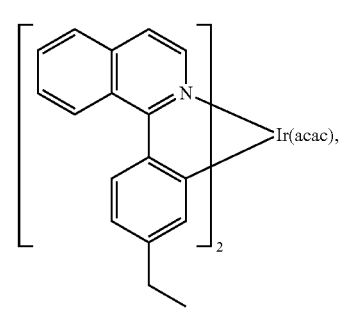
-continued
Compound 11
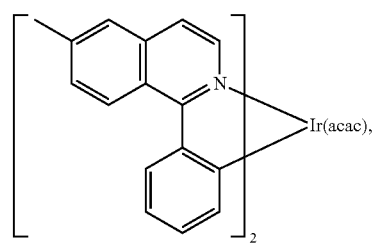
Compound 12
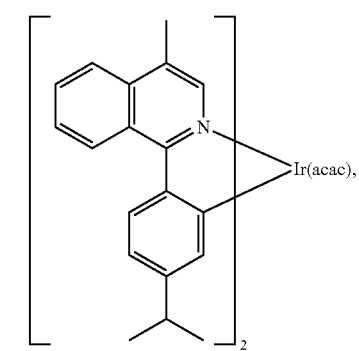
Compound 13
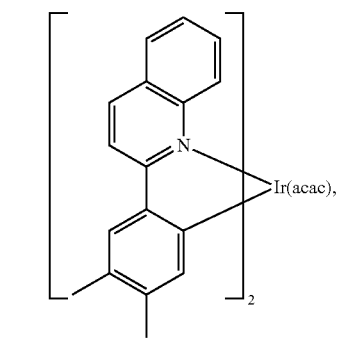
Compound 14
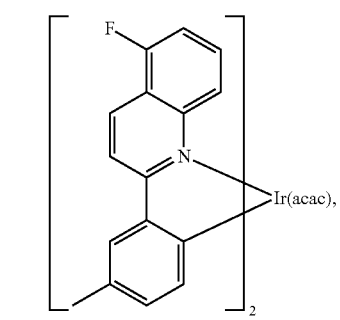
Compound 15
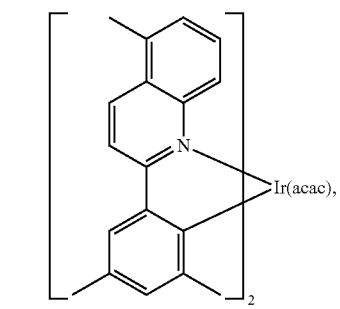

Compound 16

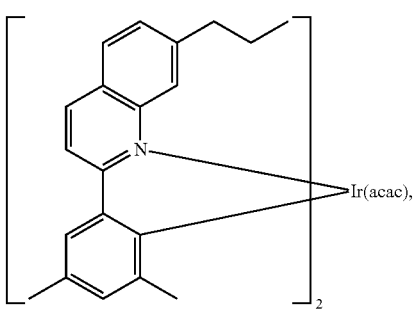

Compound 17

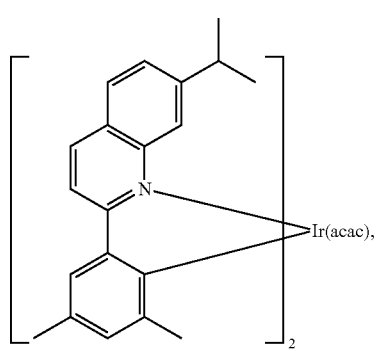

Compound 18

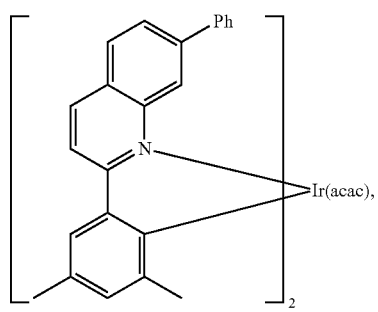

Compound 19

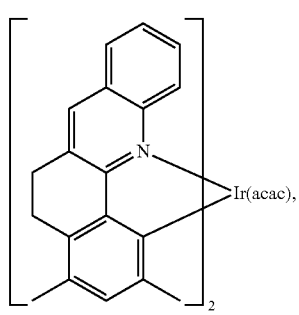

Compound 20

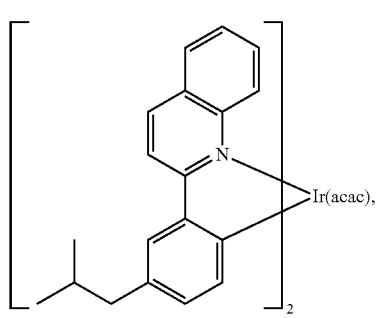

Compound 21

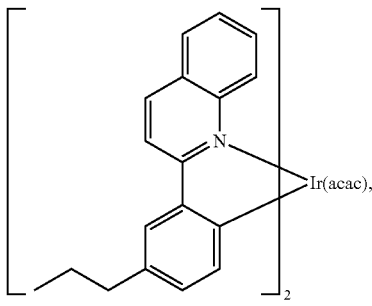

Compound 22

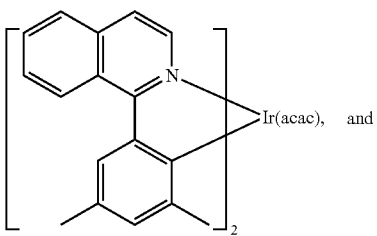

and

Compound 23

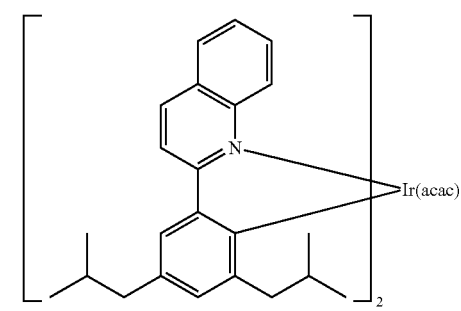

Compound 24

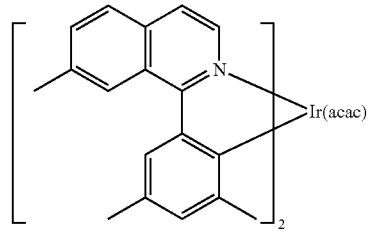

The emitter materials (dopants), preferably the phosphorescent emitter materials, may be used alone or in combination of two or more.

The compounds of formula (1) are also useful in combination with fluorescent dopants, especially as electron transport material, preferably in combination with a blue fluorescent dopant. Preferred blue fluorescent dopants that may be present in the light emitting layer of the OLED according to the present invention are for example polycyclic amine derivatives as mentioned in EP 2924029. Particularly preferred aromatic amine derivatives are selected from compounds according to the following formula (20A):

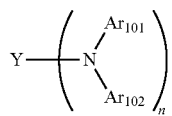

(20A)

In the formula (20A), Y is a substituted or unsubstituted fused aromatic hydrocarbon group including 10 to 50 ring carbon atoms.

$Ar_{101}$, and $Ar_{102}$ are independently a substituted or unsubstituted aryl group including 6 to 50 ring carbon atoms or a substituted or unsubstituted heterocyclic ring group including 5 to 50 ring atoms.

Specific examples of Y include the above-mentioned fused aryl group. Y is preferably a substituted or unsubstituted anthryl group, a substituted or unsubstituted pyrenyl group or a substituted or unsubstituted chrysenyl group.

n is an integer of 1 to 4. It is preferred that n be an integer of 1 to 2.

The above-mentioned formula (20A) is preferably one represented by the following formulas (21A) to (24A).

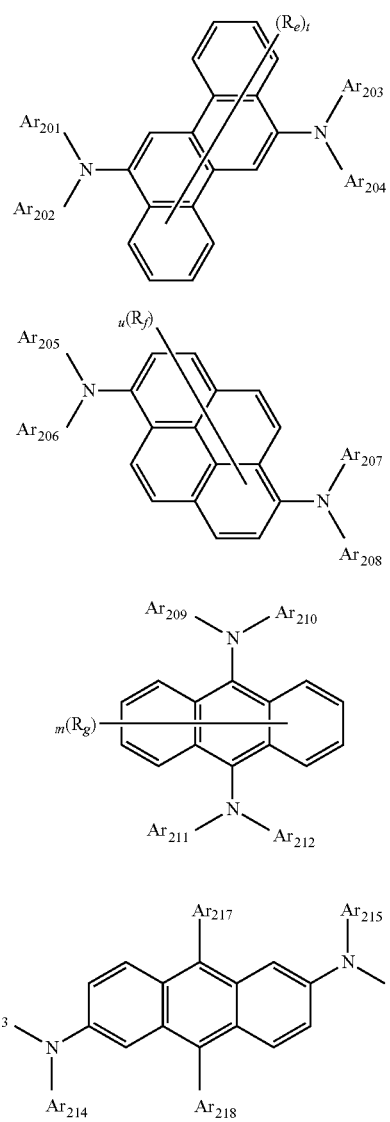

In the formulas (21A) to (24A), $R_e$, $R_f$ and $R_g$ are independently a substituted or unsubstituted alkyl group including 1 to 20 carbon atoms, a substituted or unsubstituted alkenyl group including 2 to 50 carbon atoms, a substituted or unsubstituted alkynyl group including 2 to 50 carbon atoms, a substituted or unsubstituted aralkyl group including 1 to 20 carbon atoms, a substituted or unsubstituted cycloalkyl group including 3 to 20 ring carbon atoms, a substituted or unsubstituted alkoxy group including 1 to 20 carbon atoms, a substituted or unsubstituted aryloxy group including 6 to 20 ring carbon atoms, a substituted or unsubstituted aryl group including 6 to 50 ring carbon atoms, a substituted or unsubstituted silyl group, a substituted or unsubstituted alkyl germanium group including 1 to 50 carbon atoms or a substituted or unsubstituted aryl germanium group including 6 to 50 ring carbon atoms. $R_e$, $R_f$ and $R_g$ may independently be bonded to any of the bonding positions of the benzene rings that constitutes the fused polycyclic skeleton.

As preferable examples of $R_e$, $R_f$ and $R_g$, a substituted or unsubstituted aryl group including 6 to 50 ring carbon atoms can be given. More preferably, $R_e$, $R_f$ and $R_g$ are a substituted or unsubstituted phenyl group, a substituted or unsubstituted naphthyl group, or the like.

t is an integer of 0 to 10. u is an integer of 0 to 8. m is an integer of 0 to 10. $Ar_{201}$ to $Ar_{218}$ are independently an aryl group including 6 to 50 ring carbon atoms or a substituted or unsubstituted heterocyclic group including 5 to 50 ring atoms.

Preferred examples of $Ar_{201}$ to $Ar_{218}$ include a substituted or unsubstituted phenyl group, a substituted or unsubstituted dibenzofuranyl group or the like. As preferable examples of the substituent of $Ar_{201}$ to $Ar_{218}$, an alkyl group, a cyano group and a substituted or unsubstituted silyl group can be given.

In the formulas (21A) to (24A), as examples of the alkyl group, the alkoxy group, the aryl group, the aryloxy group and the heterocyclic group, those exemplified above can be given.

As the alkenyl group including 2 to 50, preferably 2 to 30, more preferably 2 to 20, and particularly preferably 2 to 10, carbon atoms, a vinyl group, an allyl group, a 1-butenyl group, a 2-butenyl group, a 3-butenyl group, a 1,3-butanedienyl group, a 1-methylvinyl group, a styryl group, a 2,2-diphenylvinyl group, a 1,2-diphenylvinyl group, a 1-methylallyl group, a 1,1-dimethylallyl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, a 3-phenyl-1-butenyl group or the like can be given. Preferred are a styryl group, a 2,2-diphenylvinyl group, a 1,2-diphenylvinyl group or the like.

As the alkynyl group including 2 to 50 (preferably 2 to 30, more preferably 2 to 20, particularly preferably 2 to 10) carbon atoms, a propargyl group, a 3-pentynyl group or the like can be given.

As the alkyl germanium group, a methylhydrogermyl group, a trimethylgermyl group, a triethylgermyl group, a tripropylgermyl group, a dimethyl-t-butylgermyl group or the like can be given.

As the aryl germanium group, a phenyldihydrogermyl group, a diphenylhydrogermyl group, a triphenylgermyl group, a tritolylgermyl group, a trinaphthylgermyl group or the like can be given.

As the styrylamine compound and the styryldiamine compound, those represented by the following formulas (17A) and (18A) are preferable.

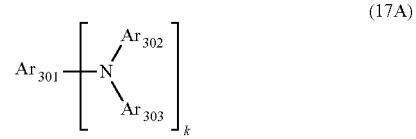

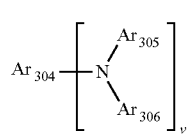

(18A)

In the formula (17A), $Ar_{301}$ is a k-valent group; a k-valent group corresponding to a phenyl group, a naphthyl group, a biphenyl group, a terphenyl group, a stilbene group, a styrylaryl group and a distyrylaryl group. $Ar_{302}$ and $Ar_{303}$ are independently an aryl group including 6 to 20 ring carbon atoms, and $Ar_{301}$, $Ar_{302}$ and $Ar_{303}$ may be substituted.

k is an integer of 1 to 4, with an integer of 1 and 2 being preferable. Any one of $Ar_{301}$ to $Ar_{303}$ is a group including a styryl group. It is further preferred that at least one of $Ar_{302}$ and $Ar_{303}$ be substituted by a styryl group.

As for the aryl group including 6 to 20 ring carbon atoms, the above-mentioned aryl group can be specifically given. Preferable examples include a phenyl group, a naphthyl group, an anthranyl group, a phenanthryl group, a terphenyl group or the like.

In the formula (18A), $Ar_{304}$ to $Ar_{306}$ are a v-valent substituted or unsubstituted aryl group including 6 to 40 ring carbon atoms. v is an integer of 1 to 4, with an integer of 1 and 2 being preferable.

Here, as the aryl group including 6 to 40 ring carbon atoms in the formula (18A), the above-mentioned aryl group can be specifically given. A naphthyl group, an anthranyl group, a chrysenyl group, a pyrenyl group or an aryl group represented by the formula (20A) is preferable.

As preferable substituents that substitute on the aryl group, an alkyl group including 1 to 6 carbon atoms, an alkoxy group including 1 to 6 carbon atoms, an aryl group including 6 to 40 ring carbon atoms, an amino group substituted by an aryl group including 6 to 40 ring carbon atoms, an ester group including an aryl group that includes 5 to 40 ring carbon atoms, an ester group including an alkyl group that includes 1 to 6 carbon atoms, a cyano group, a nitro group, a halogen atom or the like can be given.

Host (Matrix) Materials

The light-emitting layer may comprise further components in addition to the emitter material. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, be a small molecule, for example 4,4'-N,N'-dicarbazolebiphenyl (CDP=CBP) or tertiary aromatic amines, for example tris(4-carbazoyl-9-ylphenyl) amine (TCTA).

In the case that one or more phosphorescent emitter materials are used in the light emitting layer, one or more phosphorescent hosts are employed as host material. The phosphorescent host is a compound which confines the triplet energy of the phosphorescent dopant efficiently in the light emitting layer to cause the phosphorescent dopant to emit light efficiently.

In a preferred embodiment, the light-emitting layer is formed of at least one emitter material and of at least one of the matrix materials mentioned in this application. According to a preferred embodiment, the electronic device according to the present invention, preferably the OLED according to the present invention, comprises at least one compound of the formula (1) as matrix (host) material.

According to one embodiment, the light-emitting layer comprises at least one emitter material and at least two matrix materials, wherein one of the matrix materials is a compound of the formula (1) and the other matrix material(s) is/are used as co-host(s). Suitable other host materials than the compounds of formula (1) (co-hosts) are mentioned below.

According to another embodiment, the light-emitting layer comprises at least one emitter material and a compound of the formula (1) as a single matrix (host) material. Examples of preferred compounds of formula (1) useful as single host material are shown above.

The compounds of the formula (1) are suitable as single host material as well as host material, together with one or more further host materials (co-host). Suitable further host materials are mentioned below. "Further host materials" means in the sense of the present application, host materials different from the compounds of formula (1). However, it is also possible to use two or more different compounds of formula (1) as host material in the light-emitting layer in an OLED of the present application.

In a more preferred embodiment, the light-emitting layer is formed from 0.1 to 70% by weight, preferably 1 to 30% by weight, of at least one of the aforementioned emitter materials and 30 to 99.9% by weight, preferably 70 to 99% by weight, of at least one of the matrix materials mentioned in the specification—in one embodiment at least one compound of the formula (1)—where the sum total of the emitter material and of the matrix material adds up to 100% by weight.

In a further more preferred embodiment, the light-emitting layer comprises a compound of formula (1) as matrix material, at least one further matrix material (co-host) and at least one emitter material. In said embodiment, the light-emitting layer is formed from 0.1 to 70% by weight, preferably 1 to 30% by weight, of the at least one emitter material and 30 to 99.9% by weight, preferably 70 to 99% by weight, of a compound of the formula (1) and the further matrix material, where the sum total of the at least one emitter material, the further matrix material and of the compound of formula (1) adds up to 100% by weight.

The content ratio of the compound of the formula (1) as first host material and the second matrix material as co-host in the light emitting layer is not particularly limited and may be selected accordingly, and the ratio of first host material: second host material is preferably 1:99 to 99:1, more preferably 10:90 to 90:10, each based on mass.

The phosphorescent host is a compound having a function of allowing a phosphorescent dopant to emit light efficiently by efficiently confining the triplet energy of the phosphorescent dopant in the emitting layer. The material for an organic EL device according to the invention is preferable as the phosphorescent host. The emitting layer may comprise one kind of the material for an organic EL device according to the invention or may comprise two or more kinds of the material for an organic EL device according to the invention.

When the material for an organic EL device according to the invention is used as a host material of the emitting layer, the emission wavelength of the phosphorescent dopant contained in the emitting layer is not particularly restricted. It is preferred that at least one kind of the phosphorescent dopant materials contained in the emitting layer have a peak of an emission wavelength of 490 nm or more and 700 nm or less, more preferably 490 nm or more and 650 nm or less. As for the emission color of the emitting layer, red, yellow and green are preferable, for example. By using the compound according to the invention as the host material and by forming an emitting layer by doping the phosphorescent dopant having such an emission wavelength, it is possible to obtain a long-lived organic EL device.

In the organic EL device according to the invention, other compounds than the material for an organic EL device according to the invention can appropriately be selected as the phosphorescent host according to the above-mentioned purpose.

The material for an organic EL device according to the invention and other compounds may be used in combination as the phosphorescent host material in the same emitting layer. When plural emitting layers are present, as the phosphorescent host material for one of these emitting layers, the material for an organic EL device according to the invention is used, and as the phosphorescent host material for one of other emitting layers, other compounds than the material for an organic EL device according to the invention may be used. The material for an organic EL device according to the invention can be used in an organic layer other than the emitting layer. In that case, as the phosphorescent host of the emitting layer, other compounds than the material for an organic EL device according to the invention may be used.

As for the compound other than the material for an organic EL device according to the invention, as specific examples of the compound that is preferable as the phosphorescent host, carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethane derivatives, anthrone derivatives, diphenylquinone derivatives, thiopyrandioxide derivatives, carbodiimide derivatives, fluorenylidene methane derivatives, distyrylpyrazine derivatives and heterocyclic tetracarboxylic anhydrides of naphthaleneperylene or the like, metal complexes of phthalocyanine derivatives and 8-quinolinol derivatives, various metal complex polysilane compounds represented by metal complexes having metal phthalocyanine, benzoxazole or benzothiazole as a ligand, poly(N-vinylcarbazole) derivatives, aniline-based copolymers, conductive polymer oligomers such as thiophene oligomers and polythiophene, and polymer compounds such as polythiophene derivatives, polyphenylene derivatives, polyphenylene vinylene derivatives and polyfluorene derivatives can be given. The phosphorescent host may be used alone or in combination of two or more. As specific examples, the following compounds can be given.

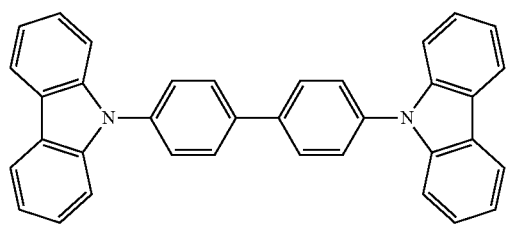

-continued

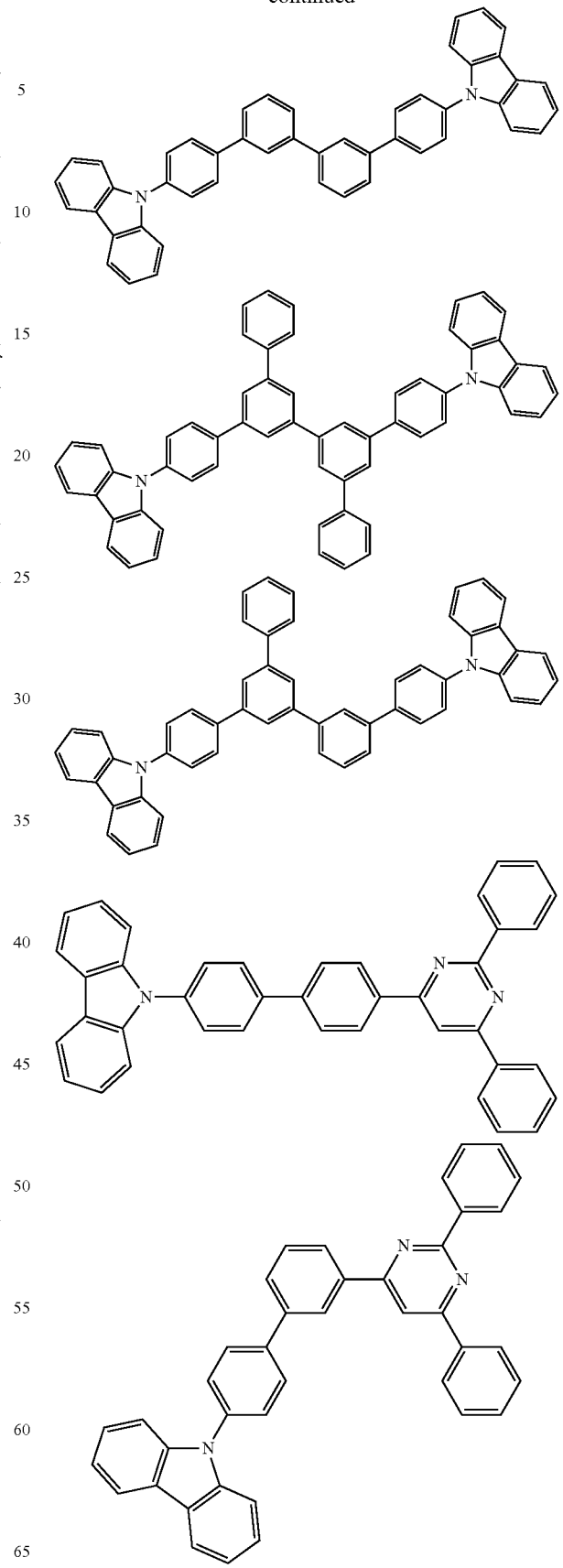

If the emitting layer comprises the first host material and the second host material, the material for an organic EL device according to the invention may be used as the first host material and other compounds than the material for an organic EL device according to the invention may be used as the second host material. The "first host material" and the "second host material" as referred to herein mean that the plural host materials contained in the emitting layer differ from each other in structure, and are not determined by the content of each host material in the emitting layer.

The second host material is not particularly restricted, and compounds other than the material for an organic EL device according to the invention and the same compound mentioned above as being preferable as the phosphorescent host can be given. As the second host, a carbazole derivative, an arylamine derivative, a fluorenone derivative and an aromatic tertiary amine compound are preferable.

The organic EL device of the invention may have an emitting layer that contains a fluorescent emitting material (i.e. fluorescent emitting layer). As the fluorescent emitting layer, a known fluorescent emitting material can be used. As the fluorescent emitting material, at least one selected from an anthracene derivative, a fluororanthene derivative, a styrylamine derivative and an arylamine derivative is preferable. An anthracene derivative and an arylamine derivative are more preferable. In particular, an anthracene derivative is preferable as a host material, and an arylamine derivative is preferable as a dopant. Specifically, preferable materials disclosed in WO2010/134350 or WO2010/134352 can be selected. The material for an organic EL device of the invention may be used as a fluorescent emitting material for the fluorescent emitting layer, or may be used as a host material for the fluorescent emitting layer.

The ring carbon atoms of the anthracene derivative as a fluorescent emitting layer is preferably 26 to 100, more preferably 26 to 80, and further preferably 26 to 60. As the anthracene derivative, more specifically, an anthracene derivative represented by the following formula (10A) is preferable.

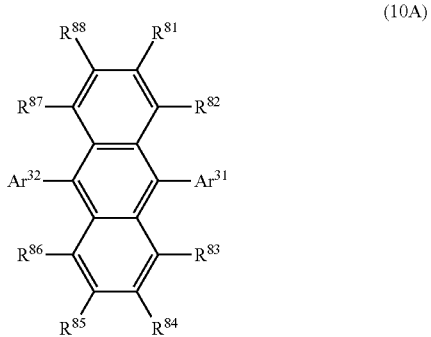

(10A)

In the formula (10A), $Ar^{31}$ and $Ar^{32}$ are independently a substituted or unsubstituted aryl group including 6 to 50 ring carbon atoms or a heterocyclic group including 5 to 50 ring atoms. $R^{81}$ to $R^{88}$ are independently a hydrogen atom, a substituted or unsubstituted aryl group including 6 to 50 ring carbon atoms, a substituted or unsubstituted heterocyclic group including 5 to 50 ring atoms, an alkyl group including 1 to 50 carbon atoms, a substituted or unsubstituted alkoxy group including 1 to 50 carbon atoms, a substituted or unsubstituted aralkyl group including 7 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, a substituted or unsubstituted silyl group, a carboxy group, a halogen atom, a cyano group, a nitro group or a hydroxyl group.

As the above-mentioned any aryl group including 6 to 50 ring carbon atoms, an aryl group including 6 to 40 ring carbon atoms is preferable, with an aryl group including 6 to 30 ring carbon atoms being more preferable.

As the above-mentioned any heterocyclic group including 5 to 50 ring atoms, a heterocyclic group including 5 to 40 ring atoms is preferable, with a heterocyclic group including 5 to 30 ring atoms being more preferable.

As the above-mentioned alkyl group including 1 to 50 carbon atoms, an alkyl group including 1 to 30 carbon atoms is preferable, an alkyl group including 1 to 10 carbon atoms is more preferable, with an alkyl group including 1 to 5 carbon atoms being further preferable.

As the above-mentioned alkoxy group including 1 to 50 carbon atoms, an alkoxy group including 1 to 30 carbon atoms is preferable, an alkoxy group including 1 to 10 carbon atoms is more preferable, with an alkoxy group including 1 to 5 carbon atoms being further preferable.

As the above-mentioned aralkyl group including 7 to 50 carbon atoms, an aralkyl group including 7 to 30 carbon atoms is preferable, with an aralkyl group including 7 to 20 carbon atoms being more preferable.

As the above-mentioned aryloxy group including 6 to 50 ring carbon atoms, an aryloxy group including 6 to 40 ring carbon atoms is preferable, with an aryloxy group including 6 to 30 ring carbon atoms being more preferable.

As the above-mentioned arylthio group including 6 to 50 ring carbon atoms, an arylthio group including 6 to 40 ring carbon atoms is preferable, with an arylthio group including 6 to 30 ring carbon atoms being more preferable.

As the above-mentioned alkoxycarbonyl group including 2 to 50 carbon atoms, an alkoxycarbonyl group including 2 to 30 carbon atoms is preferable, an alkoxycarbonyl group including 2 to 10 carbon atoms is more preferable, with an alkoxycarbonyl group including 2 to 5 carbon atoms being further preferable.

As the above-mentioned halogen atom, a fluorine atoms, a chlorine atom, a bromine atom or the like may be given.

In particular, $Ar^{31}$ and $Ar^{32}$ are preferably a substituted or unsubstituted aryl group including 6 to 50 ring carbon atoms.

In the formula (10A-1), $Ar^{33}$ is a substituted or unsubstituted aryl group including 6 to 50 ring carbon atoms or a heterocyclic group including 5 to 50 ring atoms. $R^{81}$ to $R^{88}$ are as defined above. $R^{89}$ is the same as defined for $R^{81}$ to $R^{88}$. a is an integer of 1 to 7.

Preferable examples of $R^{81}$ to $R^{88}$ are the same as defined above. Preferable examples of $R^{89}$ are the same as those for $R^{81}$ to $R^{88}$. a is preferably an integer of 1 to 3, with 1 or 2 being more preferable.

As the aryl group including 6 to 50 ring carbon atoms represented by $Ar^{33}$, an aryl group including 6 to 40 ring carbon atoms is preferable, an aryl group including 6 to 30 ring carbon atoms is more preferable, an aryl group including 6 to 20 ring carbon atoms is further preferable, with an aryl group including 6 to 12 ring carbon atoms being particularly preferable.

As the arylamine derivative as the fluorescent emitting material, an aryldiamine derivative is preferable, an aryldiamine derivative having a pyrene skeleton is more preferable, and an aryldiamine derivative having a pyrene skeleton and a dibenzofurane skeleton is further preferable.

As the aryldiamine derivative, more specifically, the arylamine derivative represented by the following formula (11A) is preferable.

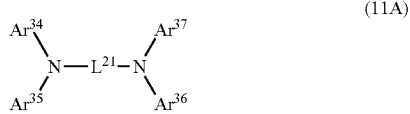

(11A)

In the formula (11A), $Ar^{34}$ to $Ar^{37}$ are independently a substituted or unsubstituted aryl group including 6 to 50 ring carbon atoms or a substituted or unsubstituted heteroaryl group including 5 to 50 ring atoms.

$L^{21}$ is a substituted or unsubstituted arylene group including 6 to 50 ring carbon atoms or a substituted or unsubstituted heteroarylene group including 5 to 50 ring atoms.

As the aryl group including 6 to 50 ring carbon atoms, an aryl group including 6 to 30 ring carbon atoms is preferable, an aryl group including 6 to 20 ring carbon atoms is more preferable, an aryl group including 6 to 12 ring carbon atoms is further preferable, with a phenyl group and a naphthyl group being particularly preferable.

As the heteroaryl group including 5 to 50 ring atoms, a heteroaryl group including 5 to 40 ring atoms is preferable, a heteroaryl group including 5 to 30 ring atoms is more preferable and a heteroaryl group including 5 to 20 ring atoms is further preferable. As the heteroaryl group, a carbazolyl group, a dibenzofuranyl group, a dibenzofuranyl group or the like can be given, and a dibenzofuranyl group is preferable. As the preferable substituent of the heteroaryl group, an aryl group including 6 to 30 (preferably 6 to 20, more preferably 6 to 12) ring carbon atoms can be given, with a phenyl group and a naphthyl group being more preferable.

As the arylene group including 6 to 50 ring carbon atoms, an arylene group including 6 to 40 ring carbon atoms is preferable, an arylene group including 6 to 30 ring carbon atoms is more preferable, an arylene group including 6 to 20 ring carbon atoms is further preferable, with a pyrenyl group being particularly preferable.

The thickness of the emitting layer is preferably 5 to 50 nm, more preferably 7 to 50 nm, and further preferably 10 to 50 nm. If the thickness is 5 nm or more, the formation of the emitting layer is facilitated. If the thickness is 50 nm or less, an increase in driving voltage can be avoided.

Electron-Donating Dopant

In the organic EL device according to the invention, it is preferred that an electron-donating dopant be contained in the interfacial region between the cathode and the emitting unit. Due to such a configuration, the organic EL device can have an increased luminance or a long life. Here, the electron-donating dopant means one having a metal with a work function of 3.8 eV or less. As specific examples thereof, at least one selected from an alkali metal, an alkali metal complex, an alkali metal compound, an alkaline earth metal, an alkaline earth metal complex, an alkaline earth metal compound, a rare earth metal, a rare earth metal complex and a rare earth metal compound or the like can be mentioned.

As the alkali metal, Na (work function: 2.36 eV), K (work function: 2.28 eV), Rb (work function: 2.16 eV), Cs (work function: 1.95 eV) and the like can be given. One having a work function of 2.9 eV or less is particularly preferable.

Among them, K, Rb and Cs are preferable. Rb or Cs is further preferable. Cs is most preferable. As the alkaline earth metal, Ca (work function: 2.9 eV), Sr (work function: 2.0 eV to 2.5 eV), Ba (work function: 2.52 eV) and the like can be given. One having a work function of 2.9 eV or less is particularly preferable. As the rare-earth metal, Sc, Y, Ce, Tb, Yb and the like can be given. One having a work function of 2.9 eV or less is particularly preferable.

Examples of the alkali metal compound include an alkali oxide such as $Li_2O$, $Cs_2O$ or $K_2O$, and an alkali halide such as LiF, NaF, CsF and KF. Among them, LiF, $Li_2O$ and NaF are preferable. Examples of the alkaline earth metal compound include BaO, SrO, CaO, and mixtures thereof such as $Ba_xSr_{1-x}O$ (0<x<1) and $Ba_xCa_{1-x}O$ (0<x<1). Among them, BaO, SrO and CaO are preferable. Examples of the rare earth metal compound include $YbF_3$, $ScF_3$, $ScO_3$, $Y_2O_3$, $Ce_2O_3$, $GdF_3$ and $TbF_3$. Among these, $YbF_3$, $ScF_3$ and $TbF_3$ are preferable.

The alkali metal complexes, the alkaline earth metal complexes and the rare earth metal complexes are not particularly limited as long as they contain, as a metal ion, at least one of alkali metal ions, alkaline earth metal ions, and rare earth metal ions. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, and derivatives thereof.

Regarding the addition form of the electron-donating dopant, it is preferred that the electron-donating dopant be formed in a shape of a layer or an island in the interfacial region. A preferred method for the formation is a method in which an organic compound (a light emitting material or an electron-injecting material) for forming the interfacial region is deposited simultaneously with deposition of the electron-donating dopant by a resistant heating deposition method, thereby dispersing the electron-donating dopant in the organic compound. The dispersion concentration of the organic compound: the electron-donating dopant (molar ratio) is 100:1 to 1:100, preferably 5:1 to 1:5.

In a case where the electron-donating dopant is formed into the shape of a layer, the light-emitting material or electron-injecting material which serves as an organic layer in the interface is formed into the shape of a layer. After that, a reductive dopant is solely deposited by the resistant heating deposition method to form a layer preferably having a thickness of from 0.1 nm to 15 nm. In a case where the electron-donating dopant is formed into the shape of an island, the emitting material or the electron-injecting material which serves as an organic layer in the interface is formed into the shape of an island. After that, the electron-donating dopant is solely deposited by the resistant heating deposition method to form an island preferably having a thickness of from 0.05 nm to 1 nm.

The ratio of the main component and the electron-donating dopant in the organic EL device according to the invention is main component:electron-donating dopant=5:1 to 1:5 in terms of molar ratio, more preferably 2:1 to 1:2.

Electron-Transporting Layer

The electron-transporting layer is an organic layer that is formed between the emitting layer and the cathode and has a function of transporting electrons from the cathode to the emitting layer. As described in the application examples below, the electron-transporting layer may be formed in contact with the emitting layer or an electron transporting zone, such as another electron transporting layer, a hole blocking layer, and an exciton blocking layer, may be disposed between the emitting layer and the electron transporting layer. When the electron-transporting layer is formed of plural layers, an organic layer that is nearer to the cathode is often defined as the electron-injecting layer. The electron-injecting layer has a function of injecting electrons from the cathode efficiently to the organic layer unit. The material for an organic EL device of the invention is also preferable as an electron-transporting layer material that constitutes an electron-transporting layer.

As the electron-transporting material used in the electron-transporting layer other than the material for an organic EL device of the invention, an aromatic heterocyclic compound having one or more hetero atoms in the molecule may preferably be used. In particular, a nitrogen-containing ring derivative is preferable. As the nitrogen-containing ring derivative, an aromatic ring having a nitrogen-containing six-membered or five-membered ring skeleton or a fused aromatic ring compound having a nitrogen-containing six-membered or five-membered ring skeleton is preferable.

As the nitrogen-containing ring derivative, a nitrogen-containing ring metal chelate complex represented by the following formula (A) is preferable, for example.

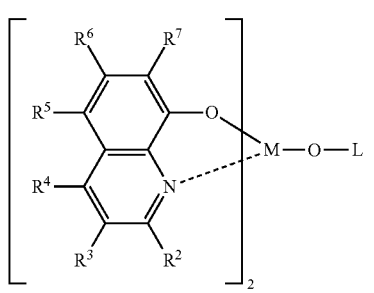

(A)

$R^2$ to $R^7$ in the formula (A), that is a nitrogen-containing ring metal chelate complex, are independently a hydrogen atom, a heavy hydrogen atom, a hydrogen atom, a hydroxy group, an amino group, a hydrocarbon group including 1 to 40 carbon atoms, an alkoxy group including 1 to 40 carbon atoms, an aryloxy group including 6 to 50 carbon atoms, an alkoxycarbonyl group or an aromatic heterocyclic group including 5 to 50 ring carbon atoms. They may be substituted.

As the halogen atom, fluorine, chlorine, bromine, iodine or the like can be given, for example.

As examples of the amino group that may be substituted, an alkylamino group, an arylamino group and an aralkylamino group can be given.

The alkylamino group and the aralkylamino group are represented by $-NQ^1Q^2$. $Q^1$ and $Q^2$ are independently an alkyl group including 1 to 20 carbon atoms or an aralkyl group including 1 to 20 carbon atoms. One of $Q^1$ and $Q^2$ may be a hydrogen atom or a heavy hydrogen atom.

The arylamino group is represented by $-NAr^1Ar^2$, and $Ar^1$ and $Ar^2$ are independently a non-fused aromatic hydrocarbon group or fused aromatic hydrocarbon group including 6 to 50 carbon atoms. One of $Ar^1$ and $Ar^2$ may be either a hydrogen atom or a heavy hydrogen atom.

The hydrocarbon group including 1 to 40 carbon atoms includes an alkyl group, an alkenyl group, a cycloalkyl group, an aryl group and an aralkyl group.

The alkoxycarbonyl group is represented by $-COOY'$ and $Y'$ is an alkyl group including 1 to 20 carbon atoms.

M is aluminum (Al), gallium (Ga) or indium (In), and M is preferably In.

L is a group represented by the following formula (A') or (A").

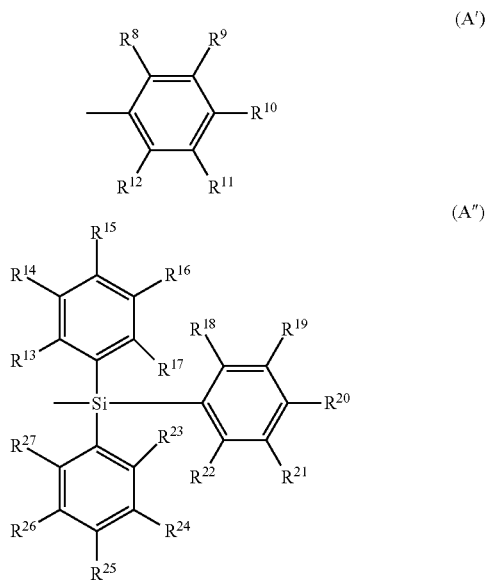

In the formula (A'), $R^8$ to $R^{12}$ are independently a hydrogen atom, a heavy hydrogen atom or a substituted or unsubstituted hydrocarbon group including 1 to 40 carbon atoms, and adjacent groups may form a ring structure. In the formula (A"), $R^{13}$ to $R^{27}$ are independently a hydrogen atom, a heavy hydrogen atom or a substituted or unsubstituted hydrocarbon group including 1 to 40 carbon atoms, and adjacent groups may form a ring structure.

The hydrocarbon group including 1 to 40 carbon atoms represented by $R^8$ to $R^{12}$ and $R^{13}$ to $R^{27}$ in the formulas (A') and (A") is the same as the hydrocarbon group represented by $R^2$ to $R^7$ in the formula (A) that is a nitrogen-containing ring metal chelate complex. As the divalent group formed when the adjacent groups of $R^8$ to $R^{12}$ and $R^{13}$ to $R^{27}$ form a ring structure, a tetramethylene group, a pentamethylene group, a hexamethylene group, a diphenylmethane-2,2'-diyl group, a diphenylethane-3,3'-diyl group, a diphenylpropane-4,4'-diyl group or the like can be mentioned.

As the electron-transmitting material used in the electron-transmitting layer, a metal complex of 8-hydroxyquinoline or a derivative thereof, an oxadiazole derivative and a nitrogen-containing heterocyclic derivative are preferable. Specific examples of the metal complex of the 8-hydroxyquinoline or the derivative thereof include metal chelate oxynoid compounds containing a chelate of oxine (generally, 8-quinolinol or 8-hydroxyquinoline). For example, tris(8-quinolinol)aluminum can be used. As the oxadiazole derivative, the following can be given, for example.

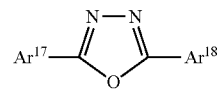

-continued

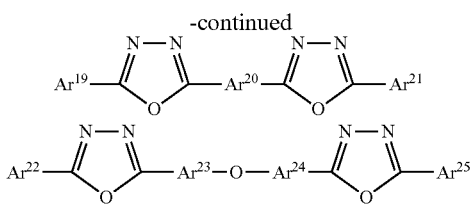

In the formula, $Ar^{17}$, $Ar^{18}$, $Ar^{19}$, $Ar^{21}$, $Ar^{22}$ and $Ar^{25}$ are independently a substituted or unsubstituted aromatic hydrocarbon group or fused aromatic hydrocarbon group including 6 to 50 carbon atoms. $Ar^{17}$ and $Ar^{18}$, $Ar^{19}$ and $Ar^{21}$ and $Ar^{22}$ and $Ar^{25}$ may be the same as or different from each other. As the aromatic hydrocarbon group or the fused aromatic hydrocarbon group, a phenyl group, a naphthyl group, a biphenyl group, an anthranyl group, a perylenyl group, a pyrenyl group or the like can be mentioned. As the substituent of these groups, an alkyl group including 1 to 10 carbon atoms, an alkoxy group including 1 to 10 carbon atoms, a cyano group or the like can be given.

$Ar^{20}$, $Ar^{23}$ and $Ar^{24}$ are independently a substituted or unsubstituted divalent aromatic hydrocarbon group or fused aromatic hydrocarbon group including 6 to 50 carbon atoms, and $Ar^{23}$ and $Ar^{24}$ may be the same as or different from each other. As the divalent aromatic hydrocarbon group or the fused aromatic hydrocarbon group, a phenylene group, a naphthylene group, a biphenylene group, an anthranylene group, a perylenylene group, a pyrenylene group or the like can be given. As the substituent of these, an alkyl group including 1 to 10 carbon atoms, an alkoxy group including 1 to 10 carbon atoms, a cyano group or the like can be given.

As these electron-transmitting compounds, those having excellent thin film-forming capability can be preferably used. As specific examples of these electron-transmitting compounds, the following can be given The nitrogen-containing heterocyclic derivative as the electron-transmitting compound is a nitrogen-containing heterocyclic derivative that comprises an organic compound represented by the following formula and is not a metal complex can be given. For example, a five-membered ring or a six-membered ring having a skeleton represented by the following formula (B) or one having a structure represented by the following formula (C) can be mentioned.

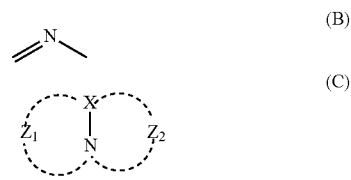

(B)

(C)

In the formula (C), X is a carbon atom or a nitrogen atom. $Z_1$ and $Z_2$ are independently a group of atoms capable of forming a nitrogen-containing heterocyclic ring.

The nitrogen-containing heterocyclic ring derivative is further preferably an organic compound having a nitrogen-containing aromatic polycyclic ring group composed of a five-membered ring or a six-membered ring. Further, in the case of the nitrogen-containing aromatic polycyclic ring group, a nitrogen-containing aromatic polycyclic organic compound having a skeleton obtained by combining the above formulas (B) and (C) or the above formula (B) and the following formula (D) is preferable.

(D)

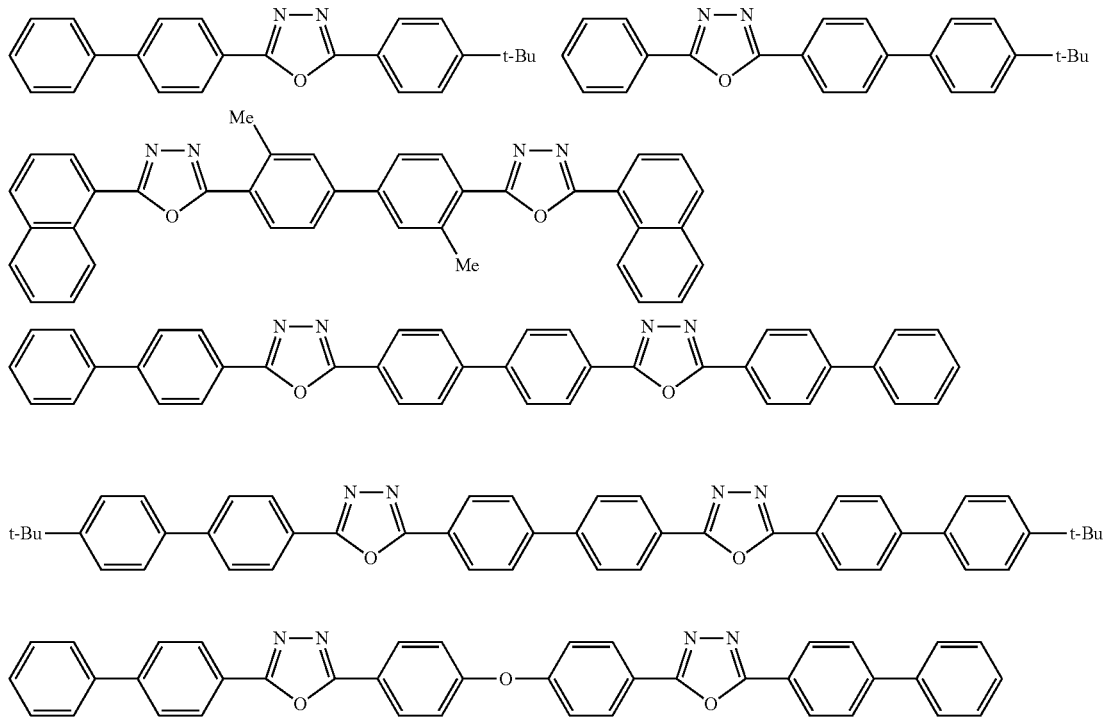

The nitrogen-containing group in the nitrogen-containing aromatic polycyclic organic compound can be selected from the nitrogen-containing heterocyclic groups represented by the following formulas, for example.

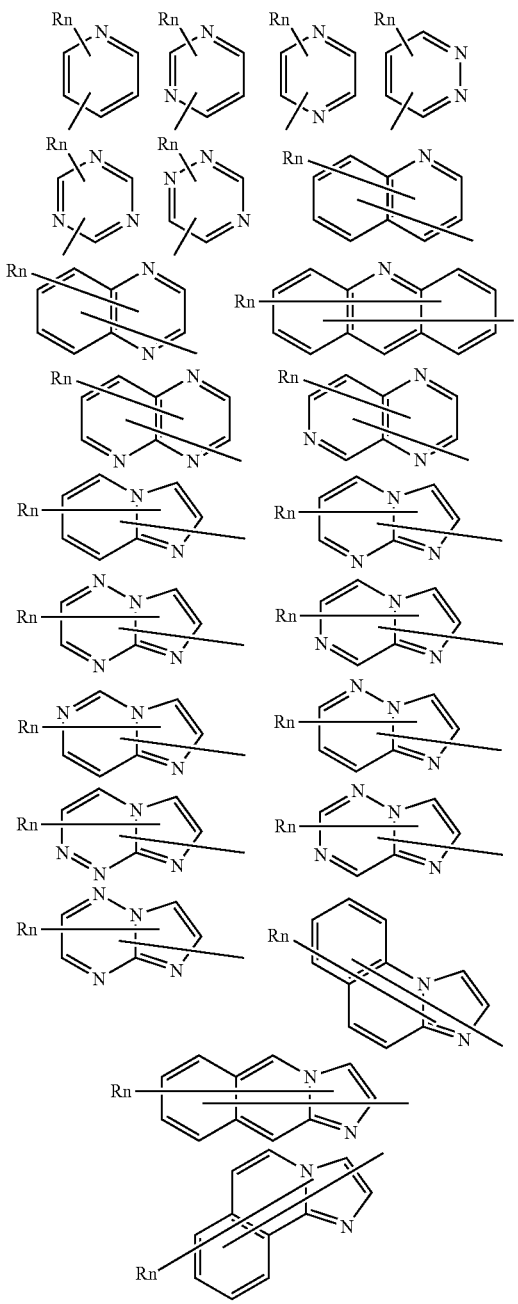

In each of the above formulas, R is an aromatic hydrocarbon group or fused aromatic hydrocarbon group including 6 to 40 carbon atoms, an aromatic heterocyclic group or fused aromatic heterocyclic group including 3 to 40 carbon atoms, an alkyl group including 1 to 20 carbon atoms or an alkoxy group including 1 to 20 carbon atoms. n is an integer of 0 to 5, and when n is an integer of 2 or more, plural Rs may be the same as or different from each other.

As further preferable specific compounds, a nitrogen-containing heterocyclic derivative represented by the following formula (D1) can be mentioned.

$$HAr-L^1-Ar^1-Ar^2 \qquad (D1)$$

In the formula (D1), HAr is a substituted or unsubstituted nitrogen-containing heterocyclic ring group including 3 to 40 carbon atoms, $L^1$ is a single bond, a substituted or unsubstituted aromatic hydrocarbon group or fused aromatic hydrocarbon group including 6 to 40 carbon atoms or a substituted or unsubstituted aromatic heterocyclic group or fused aromatic heterocyclic group including 3 to 40 carbon atoms, $Ar^1$ is a substituted or unsubstituted divalent aromatic hydrocarbon group including 6 to 40 carbon atoms, and $Ar^2$ is a substituted or unsubstituted aromatic hydrocarbon group or fused aromatic hydrocarbon group including 6 to 40 carbon atoms or a substituted or unsubstituted aromatic heterocyclic group or fused aromatic heterocyclic group including 3 to 40 carbon atoms.

HAr is selected from the following group, for example.

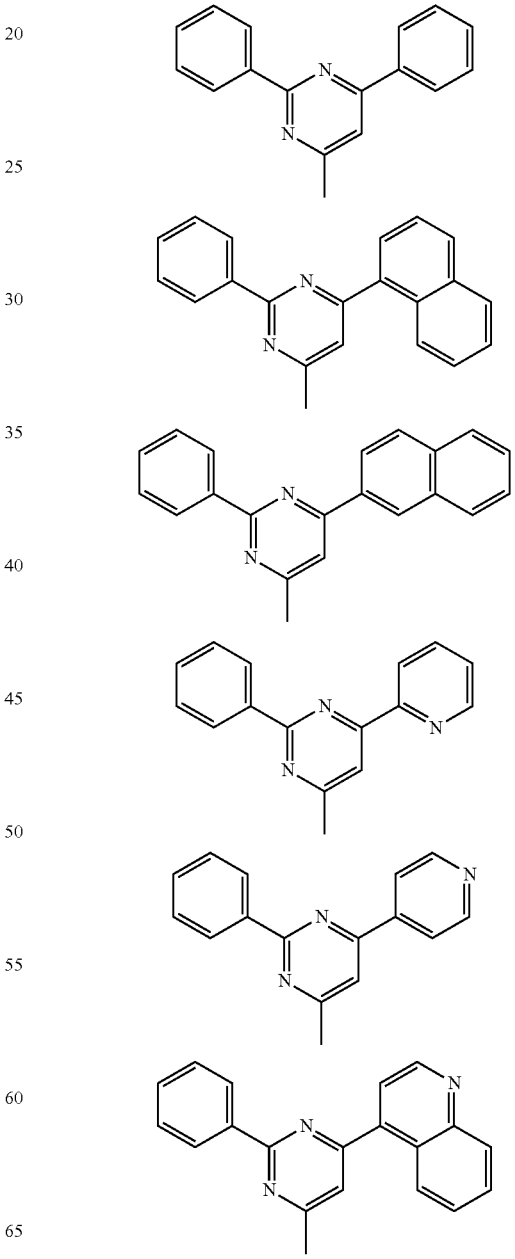

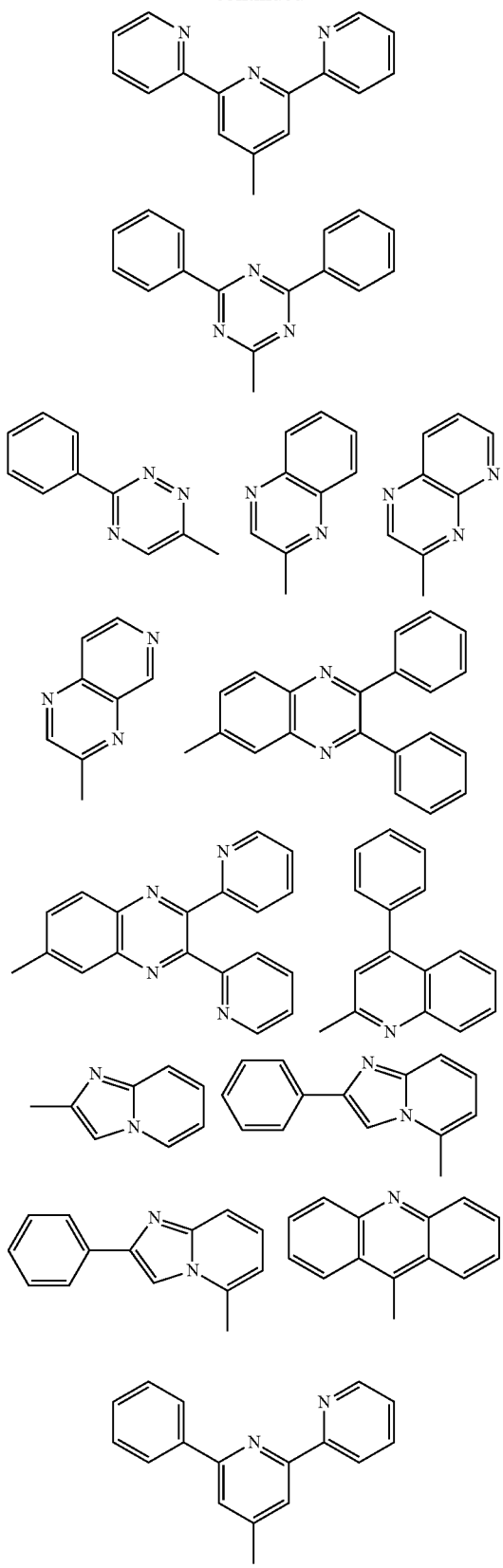

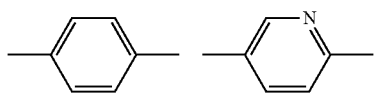

Ar¹ in the formula (D1) is selected from the arylanthranyl group in the following formulas (D2) and (D3).

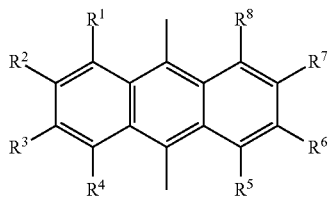

(D2)

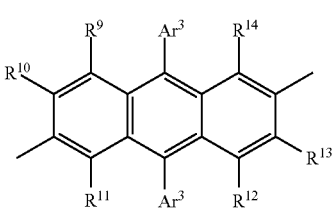

(D3)

In the formulas (D2) and (D3), $R^1$ to $R^{14}$ are independently a hydrogen atom, a heavy hydrogen atom, a halogen atom, an alkyl group including 1 to 20 carbon atoms, an alkoxy group including 1 to 20 carbon atoms, an aryloxy group including 6 to 40 carbon atoms, a substituted or unsubstituted aromatic hydrocarbon group or fused aromatic hydrocarbon group including 6 to 40 carbon atoms or a substituted or unsubstituted aromatic heterocyclic group or fused aromatic heterocyclic group including 3 to 40 carbon atoms; $Ar^3$ is a substituted or unsubstituted aromatic hydrocarbon group or fused aromatic hydrocarbon group including 6 to 40 carbon atoms or a substituted or unsubstituted aromatic heterocyclic group or fused aromatic heterocyclic group including 3 to 40 carbon atoms. The nitrogen-containing heterocyclic derivative may be one in which all of $R^1$ to $R^8$ are a hydrogen atom or a heavy hydrogen atom.

Ar² in the formula (D1) is selected from the following group, for example.

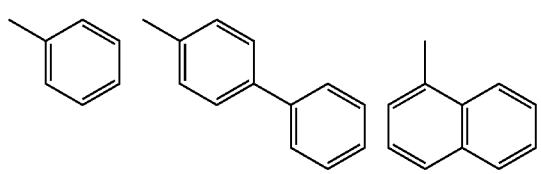

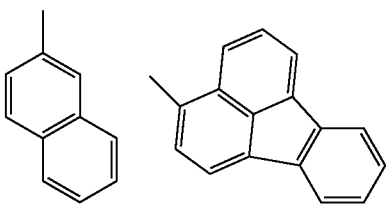

L¹ in the above formula (D1) is selected from the following group, for example.

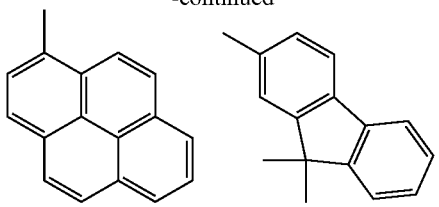

As the nitrogen-containing aromatic polycyclic organic compound as the electron-transmitting compound, in addition to those mentioned above, the following compounds can preferably be used.

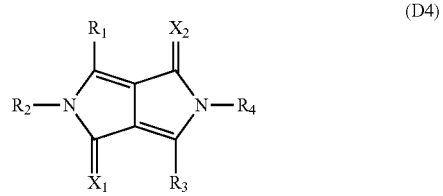

In the formula (D4), $R_1$ to $R_4$ are independently a hydrogen atom, a heavy hydrogen atom, a substituted or unsubstituted aliphatic group including 1 to 20 carbon atoms, a substituted or unsubstituted alicyclic group including 3 to 20 carbon atoms, a substituted or unsubstituted aromatic ring group including 6 to 50 carbon atoms or a substituted or unsubstituted heterocyclic group including 3 to 50 carbon atoms; and $X_1$ and $X_2$ are independently an oxygen atom, a sulfur atom or a dicyanomethylene group.

As the electron-transmitting compound, the following compound is preferably used.

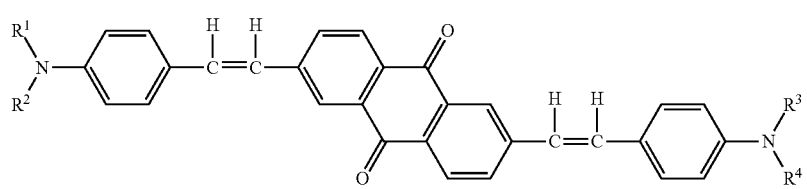

In the formula (D5), $R^1$, $R^2$, $R^3$ and $R^4$ are groups that are the same as or different from each other, and are an aromatic hydrocarbon group or a fused aromatic hydrocarbon group represented by the following formula (D6).

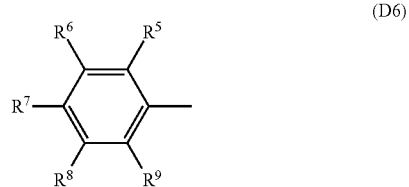

In the formula (D6), $R^5$, $R^6$, $R^7$, $R^8$ and $R^9$ are groups that are the same as or different from each other, and are a hydrogen atom, a heavy hydrogen atom, a saturated or unsaturated alkoxy group including 1 to 20 carbon atoms, a saturated or unsaturated alkyl group including 1 to 20 carbon atoms, an amino group or an alkylamino group including 1 to 20 carbon atoms. At least one of $R^5$, $R^6$, $R^7$, $R^8$ and $R^9$ is a group other than a hydrogen atom or a heavy hydrogen atom.

Further, the electron-transmitting compound may be a high molecular compound that comprises the nitrogen-containing heterocyclic group or the nitrogen-containing heterocyclic derivative.

It is particularly preferred that the electron-transporting layer of the organic EL device according to the invention contains at least one of the nitrogen-containing heterocyclic derivatives represented by the following formulas (E) to (G):

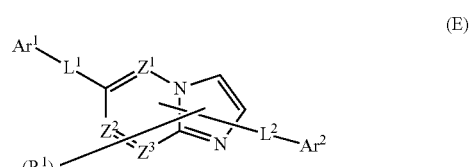

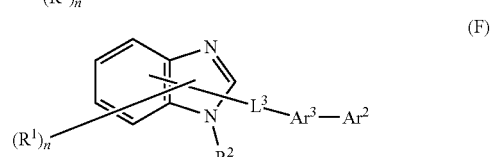

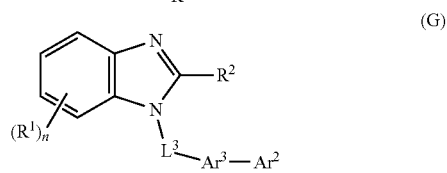

In the formulas (E) to (G), $Z^1$, $Z^2$ and $Z^3$ are independently a nitrogen atom or a carbon atom.

$R^1$ and $R^2$ are independently a substituted or unsubstituted aryl group including 6 to 50 ring carbon atoms, a substituted or unsubstituted heteroaryl group including 5 to 50 ring atoms, a substituted or unsubstituted alkyl group including 1 to 20 carbon atoms, a substituted or unsubstituted haloalkyl group including 1 to 20 carbon atoms or a substituted or unsubstituted alkoxy group including 1 to 20 carbon atoms.

n is an integer of 0 to 5. When n is an integer of 2 or more, plural $R^1$s may be the same or different. The two adjacent $R^1$s may be bonded to each other to form a substituted or unsubstituted hydrocarbon ring.

$Ar^1$ is a substituted or unsubstituted aryl group including 6 to 50 ring carbon atoms or a substituted or unsubstituted heteroaryl group including 5 to 50 ring atoms.

$Ar^2$ is a hydrogen atom, a substituted or unsubstituted alkyl group including 1 to 20 carbon atoms, a substituted or unsubstituted haloalkyl group including 1 to 20 carbon atoms, a substituted or unsubstituted alkoxy group including 1 to 20 carbon atoms, a substituted or unsubstituted aryl group including 6 to 50 ring carbon atoms or a substituted or unsubstituted heteroaryl group including 5 to 50 ring atoms.

Any one of $Ar^1$ and $Ar^2$ is a substituted or unsubstituted fused aromatic hydrocarbon ring group including 10 to 50 ring carbon atoms or a substituted or unsubstituted fused aromatic heterocyclic group including 9 to 50 ring atoms.

$Ar^3$ is a substituted or unsubstituted arylene group including 6 to 50 ring carbon atoms or a substituted or unsubstituted heteroarylene group including 5 to 50 ring atoms.

$L^1$, $L^2$ and $L^3$ are independently a single bond, a substituted or unsubstituted arylene group including 6 to 50 ring carbon atoms or a substituted or unsubstituted divalent fused aromatic heterocyclic group including 9 to 50 ring atoms.

As the aryl group including 6 to 50 ring carbon atoms, a phenyl group, a naphthyl group, an anthryl group, a phenanthryl group, a naphthacenyl group, a chrysenyl group, a pyrenyl group, a biphenyl group, a terphenyl group, a tolyl group, a fluoranthenyl group and a fluorenyl group can be mentioned.

As the heteroaryl group including 5 to 50 ring atoms, a pyrrolyl group, a furyl group, a thienyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, a triazolyl group, a pyrazinyl group, a pyridazinyl group, a triazinyl group, a quinoxalinyl group, an acridinyl group, an imidazo[1,2-a]pyridinyl group, an imidazo[1,2-a]pyrimidinyl group or the like can be given.

As the alkyl group including 1 to 20 carbon atoms, a methyl group, an ethyl group, a propyl group, a butyl group, a pentyl group, a hexyl group or the like can be given.

As the haloalkyl group including 1 to 20 carbon atoms, a group obtained by substituting one or two or more hydrogen atoms in the alkyl group with at least one halogen atom selected from fluorine, chlorine, iodine and bromine can be given.

As the alkoxy group including 1 to 20 carbon atoms, a group having the alkyl group as an alkyl moiety can be given.

As the arylene group including 6 to 50 ring carbon atoms, a group obtained by removing one hydrogen atom from the aryl group can be given.

As the divalent fused aromatic heterocyclic group including 9 to 50 ring atoms, a group obtained by removing one hydrogen atom from the fused aromatic heterocyclic group mentioned above as the heteroaryl group can be given.

The film thickness of the electron-transporting layer is not particularly restricted, but is preferably 1 nm to 100 nm.

As the constituting elements of the electron-injecting layer that can be provided in adjacent to the electron-transporting layer, in addition to the nitrogen-containing ring derivative, as an inorganic compound, it is preferable to use an insulator or a semiconductor. If the electron-injecting layer is formed of an insulator or a semiconductor, current leakage can be effectively prevented, whereby electron-injecting properties can be improved.

As such an insulator, it is preferable to use at least one metal compound selected from the group consisting of an alkali metal chalcogenide, an alkaline earth metal chalcogenide, a halide of an alkali metal and a halide of an alkaline earth metal. It is preferred that the electron-injecting layer be formed of these alkali metal chalcogenides or the like, since the electron-injecting property can be further improved. Specifically, as preferable alkali metal chalcogenides, $Li_2O$, $K_2O$, $Na_2S$, $Na_2Se$ and $Na_2O$ can be given. As preferable alkaline earth metal chalcogenides, CaO, BaO, SrO, BeO, BaS and CaSe can be given, for example. As preferable halides of an alkali metal, LiF, NaF, KF, LiCl, KCl, NaCl and the like can be given, for example. As preferable halides of an alkaline earth metal, a fluoride such as $CaF_2$, $BaF_2$, $SrF_2$, $MgF_2$ and $BeF_2$ and a halide other than a fluoride can be given, for example.

As the semiconductor, an oxide, a nitride or a nitric oxide containing at least one element selected from Ba, Ca, Sr, Yb, Al, Ga, In, Li, Na, Cd, Mg, Si, Ta, Sb and Zn or the like can be given, for example. They can be used singly or in combination of two or more. Further, it is preferred that an inorganic compound constituting the electron-injecting layer be a finely-crystallized or amorphous insulating thin film. If the electron-injecting layer is formed of these insulting thin films, more homogenous thin film is formed, and hence, pixel defects such as dark spots can be decreased. As such an inorganic compound, alkali metal chalcogenide, alkaline earth metal chalcogenide, a halide of an alkali metal and a halide of an alkaline earth metal or the like can be given, for example.

If such an insulator or a semiconductor is used, the preferable thickness of the layer is about 0.1 nm to 15 nm. The electron-injecting layer in the invention may preferably comprise the above-mentioned electron-donating dopant.

Hole-Transporting Layer

The hole-transporting layer is an organic layer that is formed between the emitting layer and the anode, and has a function of transporting holes from the anode to the emitting layer. If the hole-transporting layer is composed of plural layers, an organic layer that is nearer to the anode may often be defined as the hole-injecting layer. The hole-injecting layer has a function of injecting holes efficiently to the organic layer unit from the anode.

As other materials that form the hole-transporting layer, an aromatic amine compound, for example, an aromatic amine derivative represented by the following formula (H) can preferably be used.

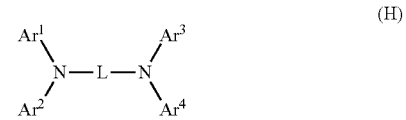
(H)

In the formula (H), $Ar^1$ to $Ar^4$ are a substituted or unsubstituted aromatic hydrocarbon group or fused aromatic hydrocarbon group including 6 to 50 ring carbon atoms, a substituted or unsubstituted aromatic heterocyclic group or fused aromatic heterocyclic group including 5 to 50 ring atoms, or a group formed by bonding of these aromatic hydrocarbon group or the fused aromatic hydrocarbon group with an aromatic heterocyclic group or a fused aromatic heterocyclic group.

In the formula (H), L is a substituted or unsubstituted aromatic hydrocarbon group or fused aromatic hydrocarbon group including 6 to 50 ring carbon atoms or a substituted or unsubstituted aromatic heterocyclic group or fused aromatic heterocyclic group including 5 to 50 ring atoms.

Specific examples of the compound represented by the formula (H) are shown below.

311
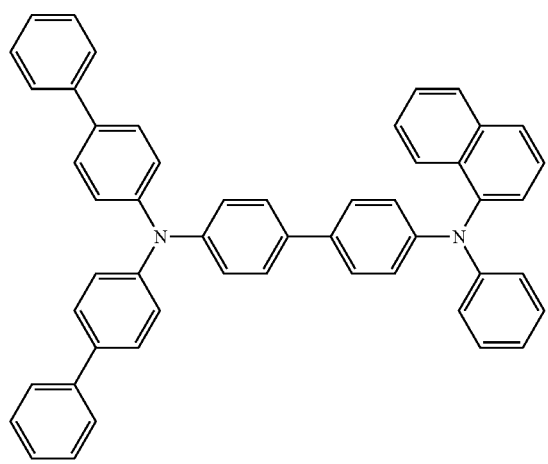
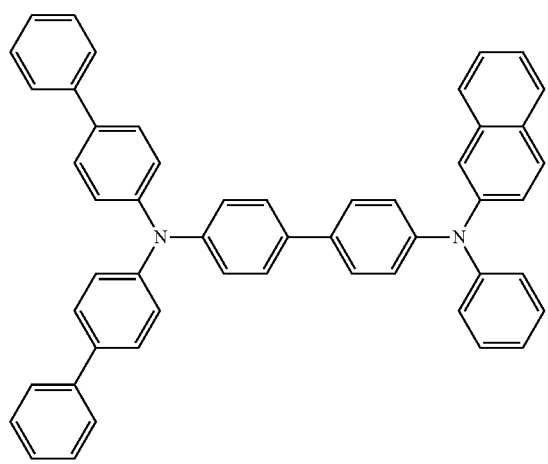
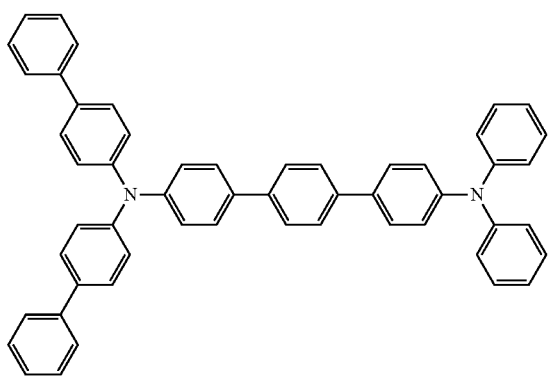
312
-continued
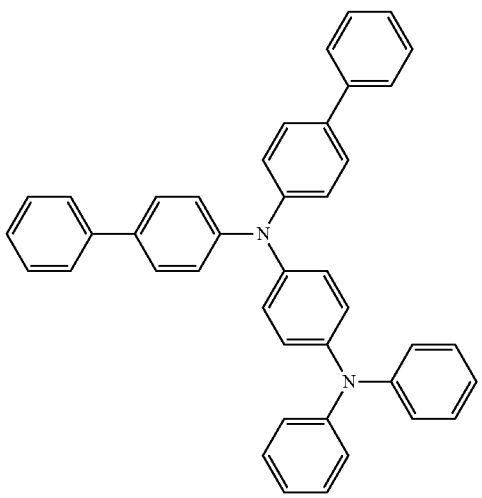
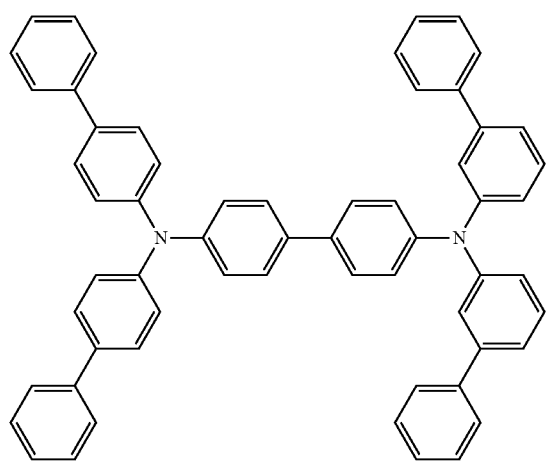
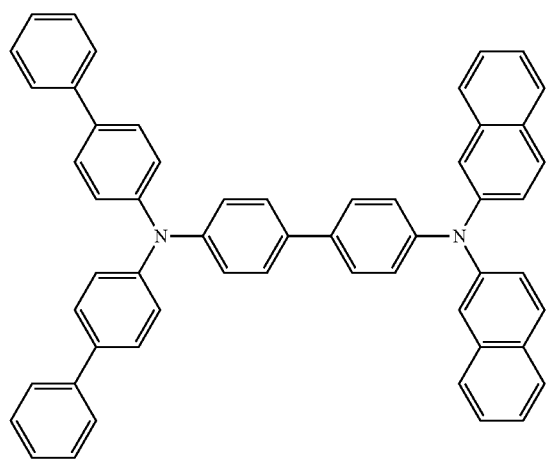

313
-continued
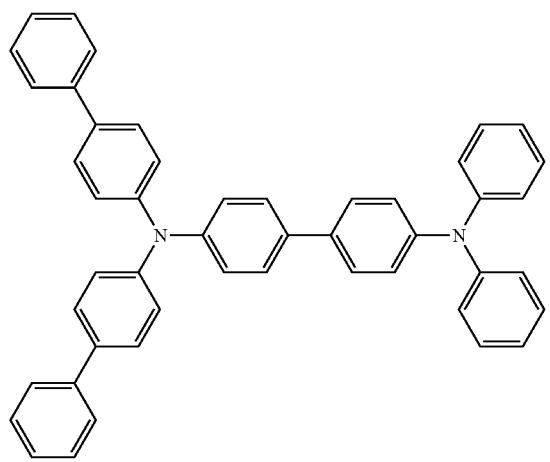
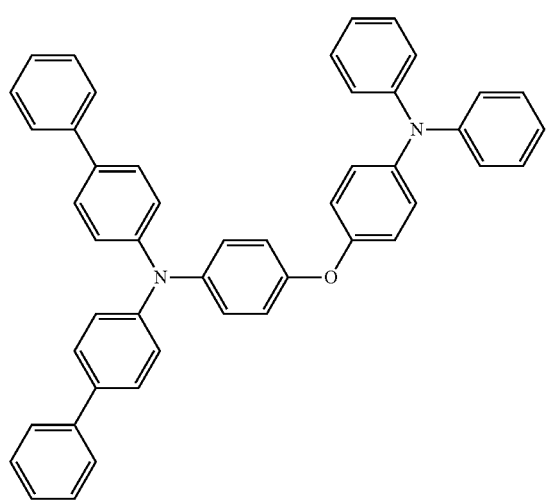
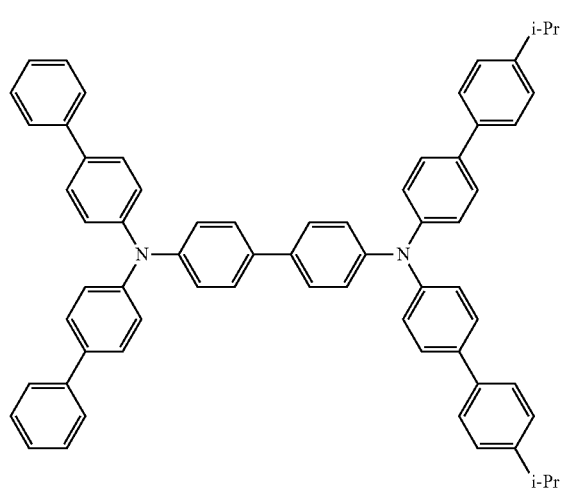
314
-continued
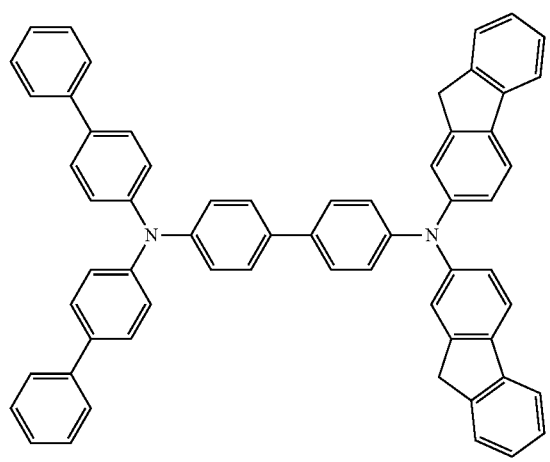
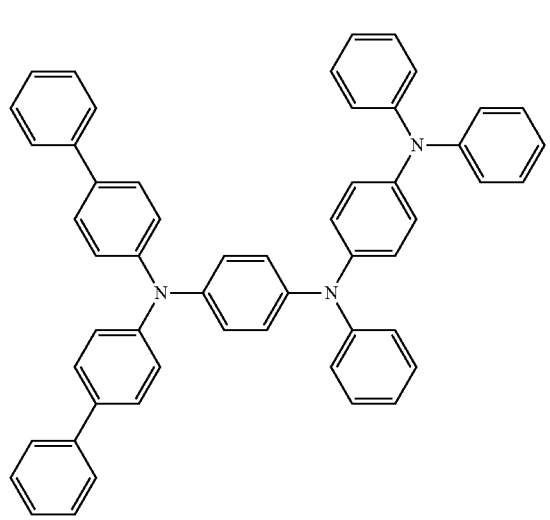
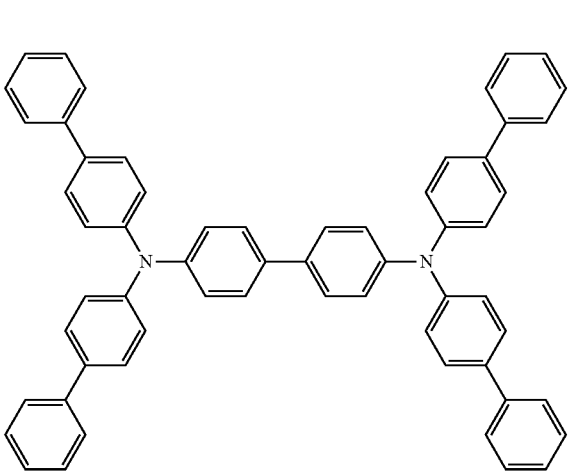

315
-continued
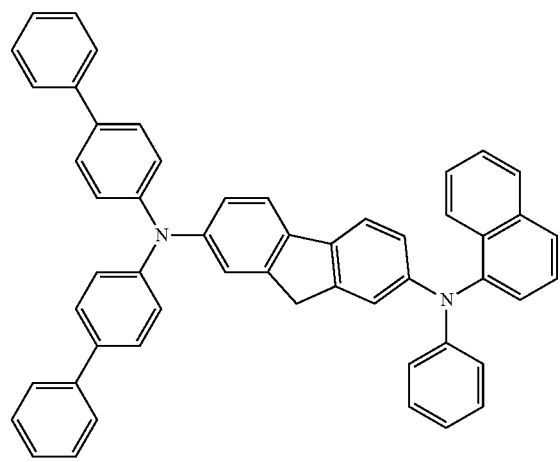 [SMILES: c1ccc(-c2ccc(N(c3ccc(-c4ccccc4)cc3)c3ccc4c(c3)Cc3cc(N(c5ccccc5)c5cccc6ccccc56)ccc3-4)cc2)cc1]
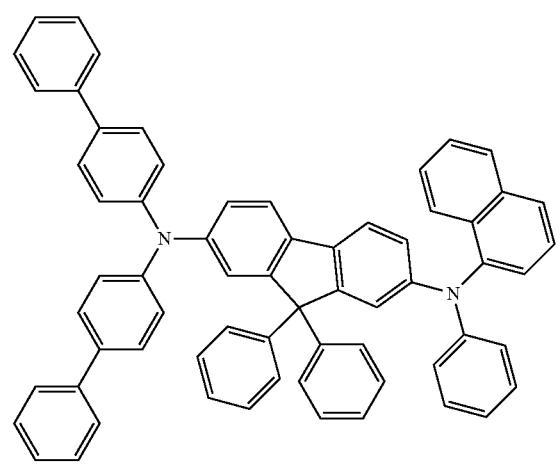
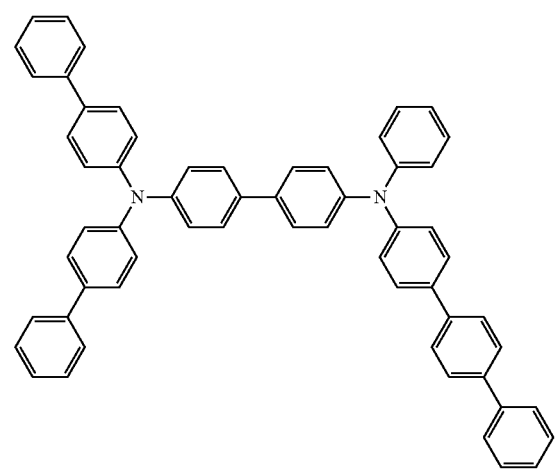
316
-continued
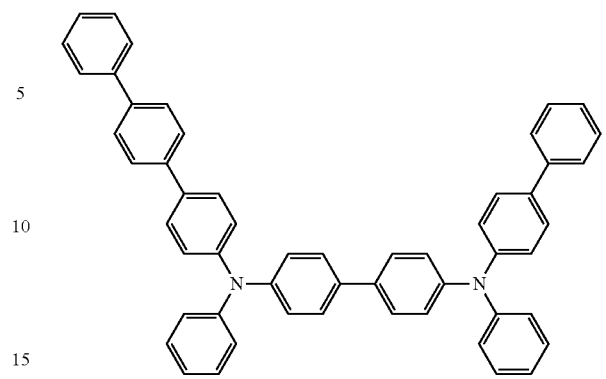
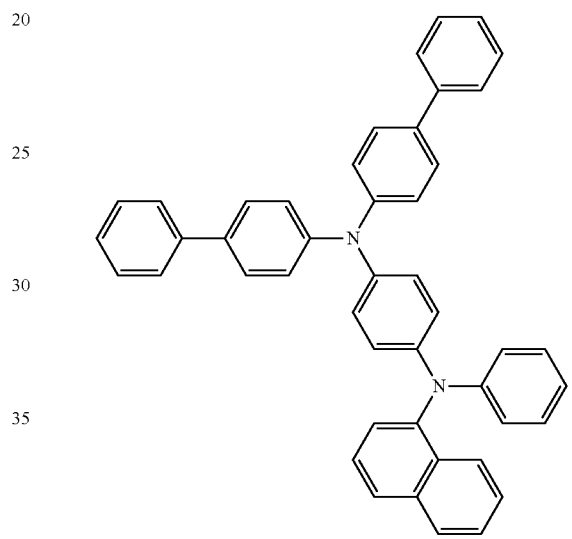
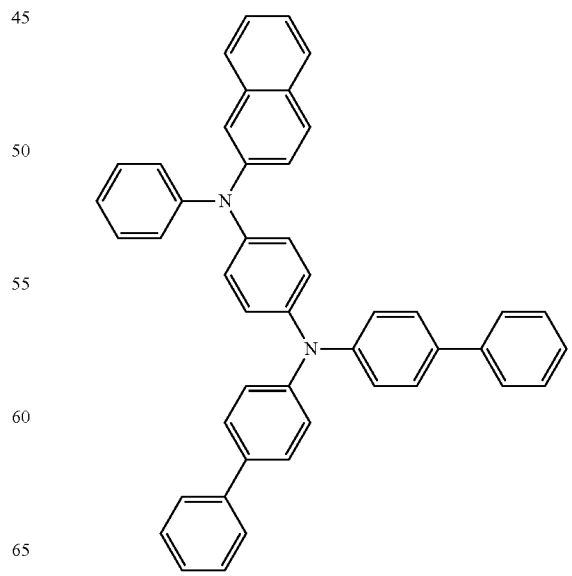

US 11,691,983 B2
317
-continued
318
-continued
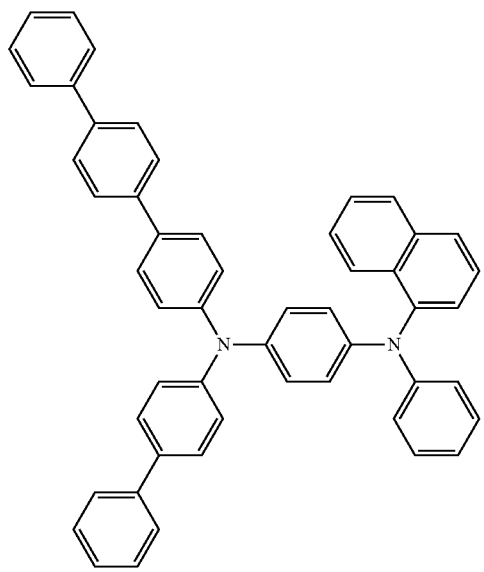
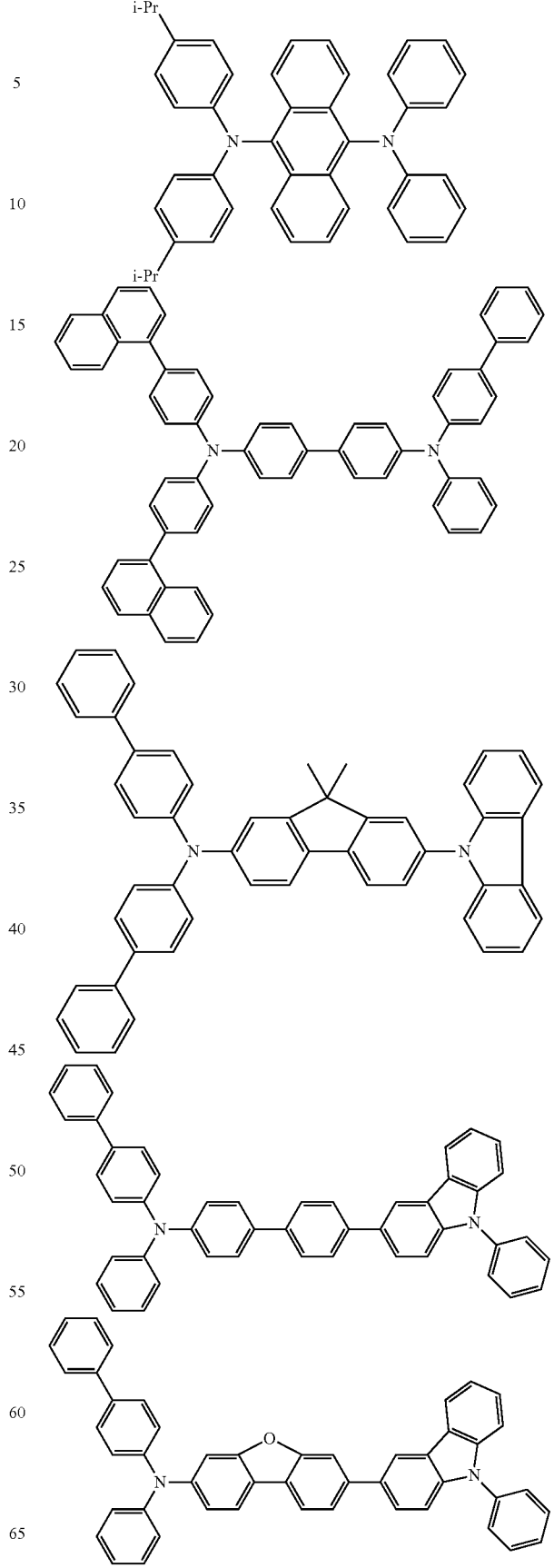

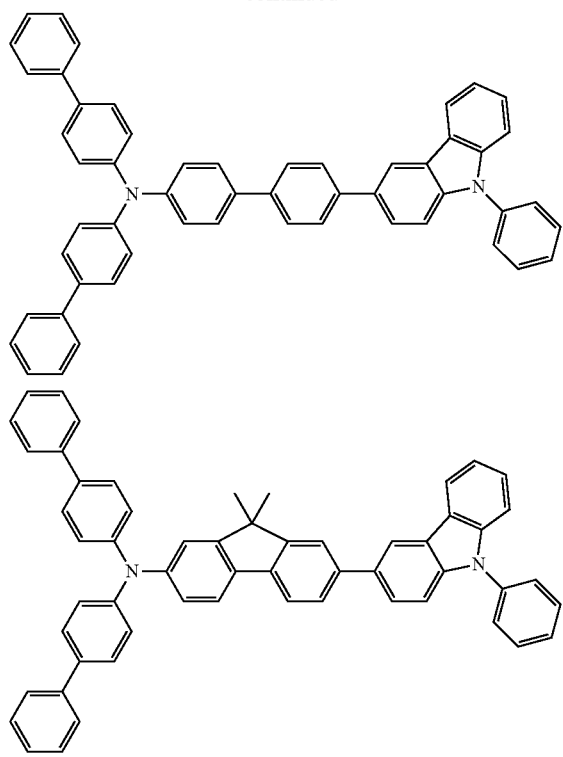
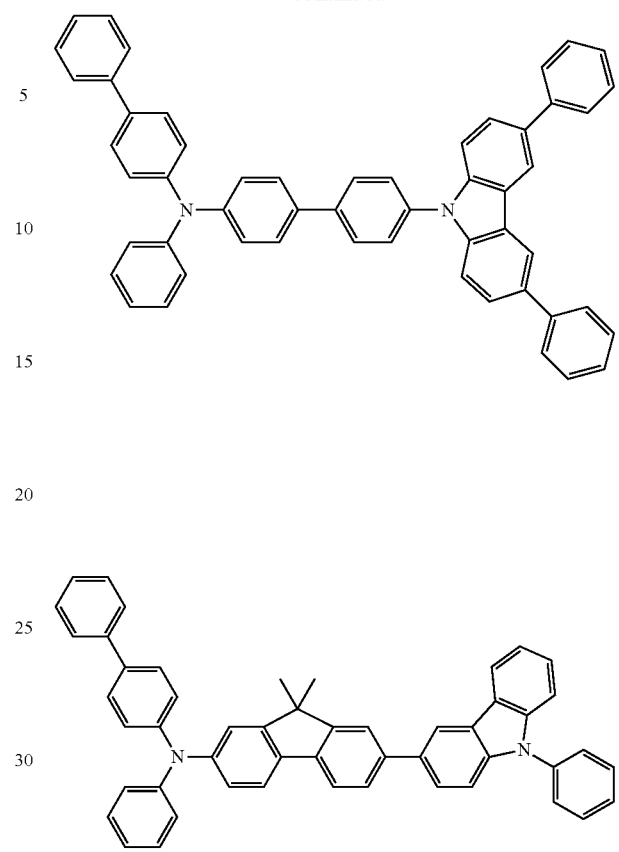
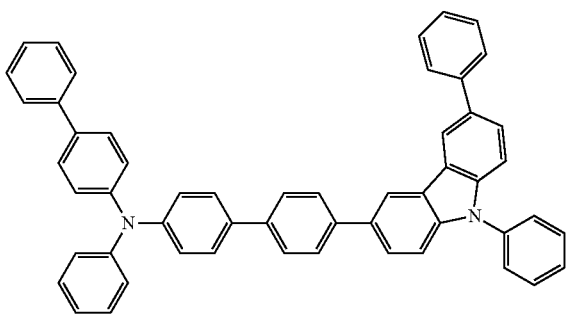
An aromatic amine represented by the following formula (J) is preferably used for forming the hole-transporting layer.
(J)
In the formula (J), $Ar^1$ to $Ar^3$ are as defined for $Ar^1$ to $Ar^4$ in the formula (H). Specific examples of the compound represented by the formula (J) will be shown below. The compound represented by the formula (J) is not limited to these.
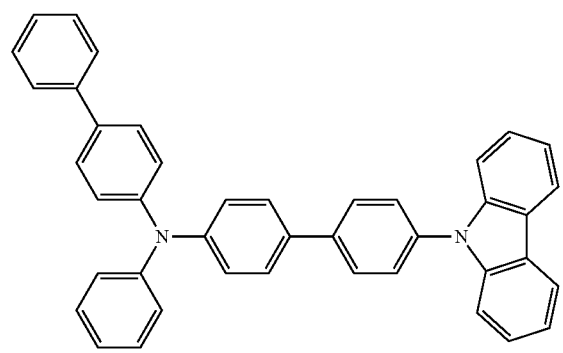
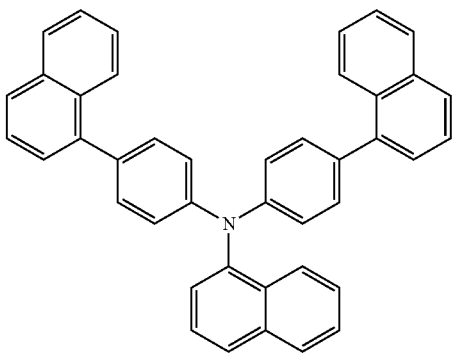

321
-continued
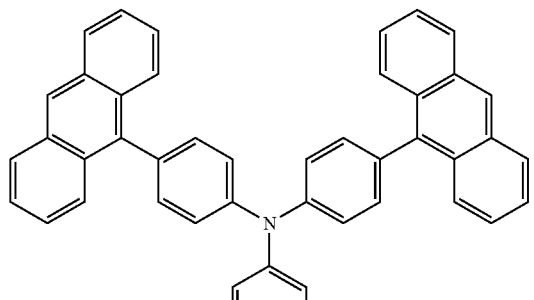
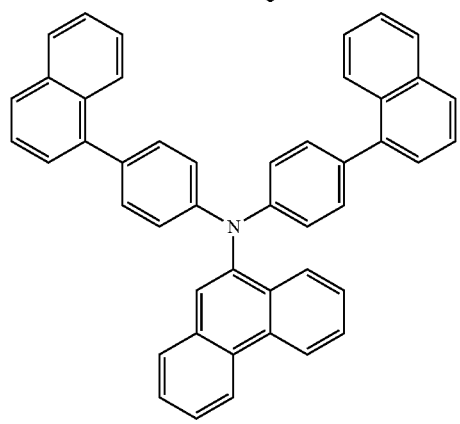
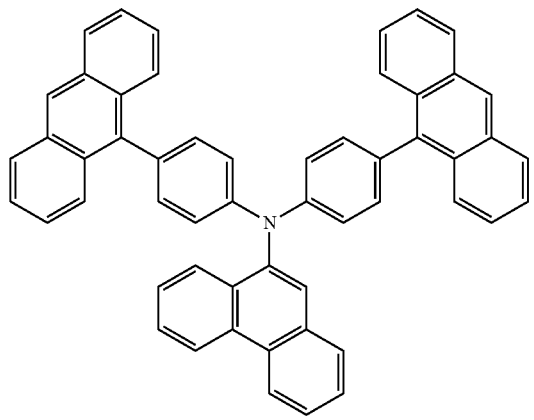
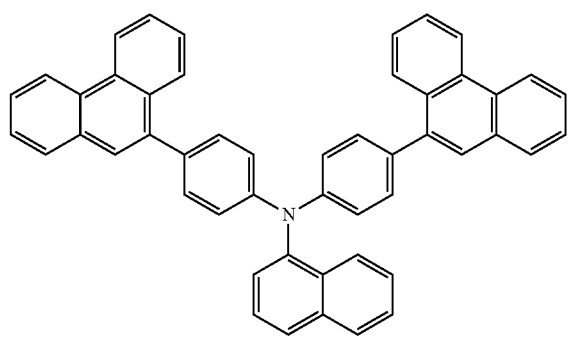
322
-continued
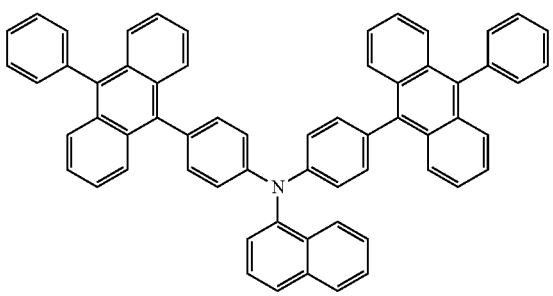
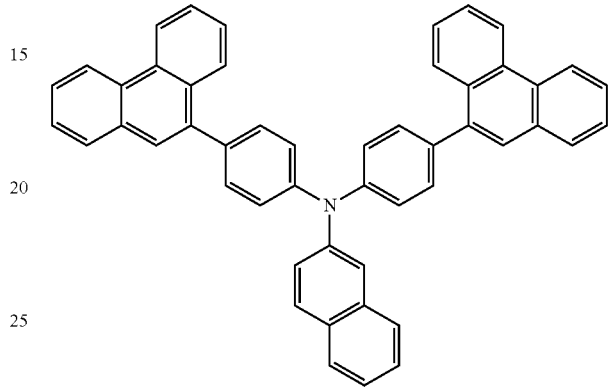
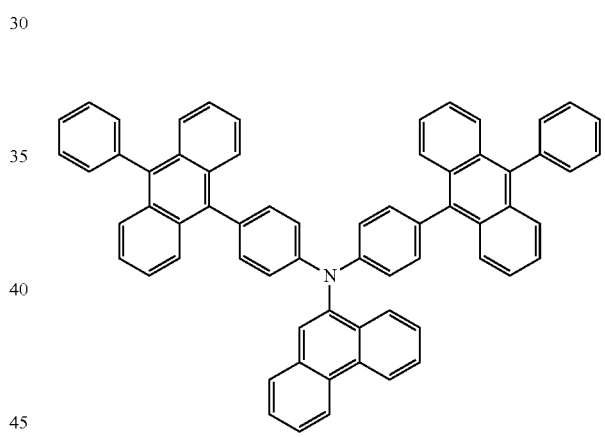
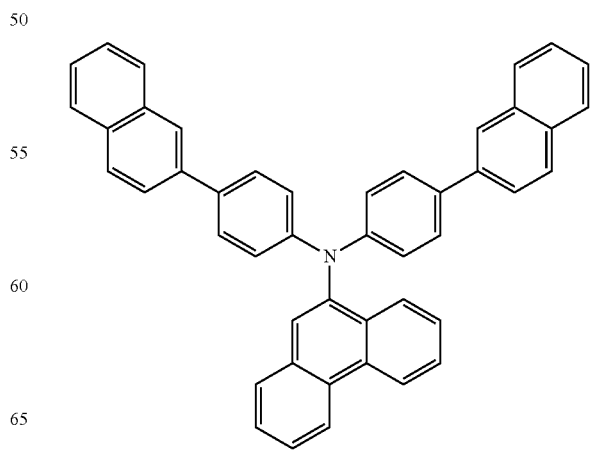

323
-continued
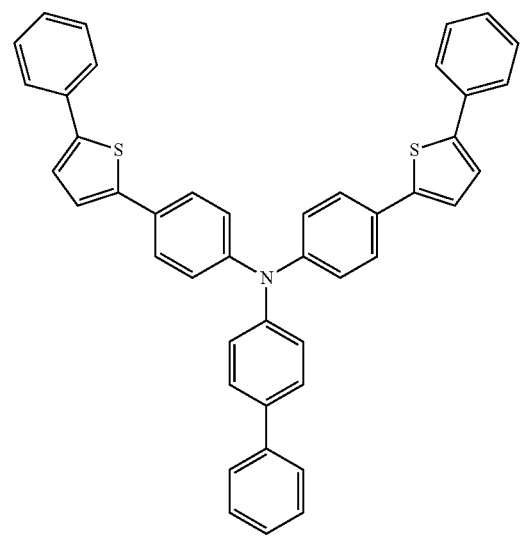
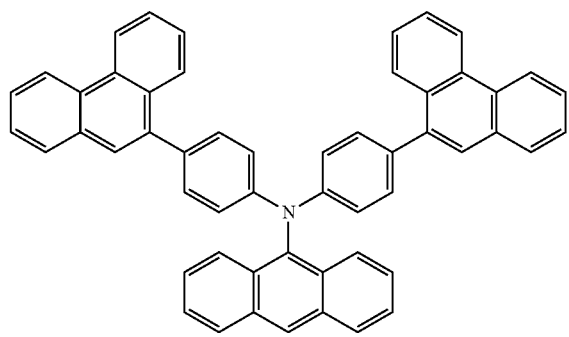
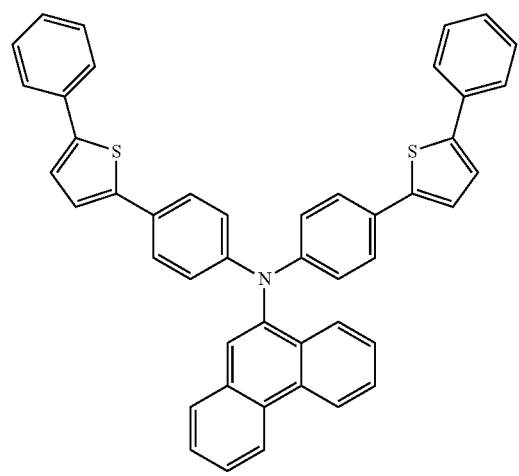
324
-continued
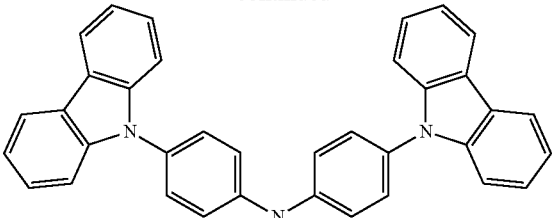
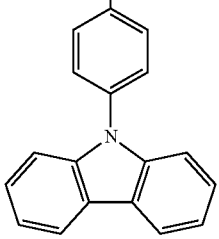
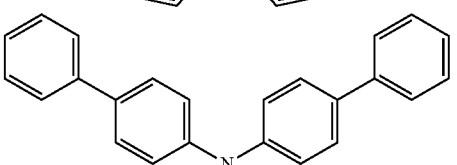
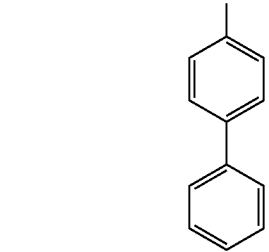
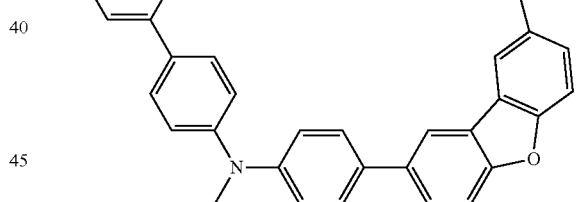
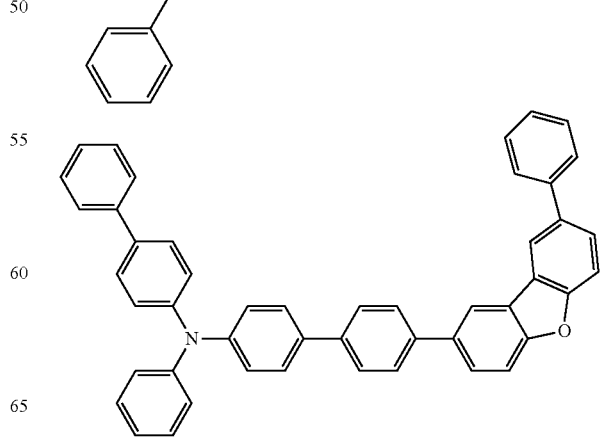

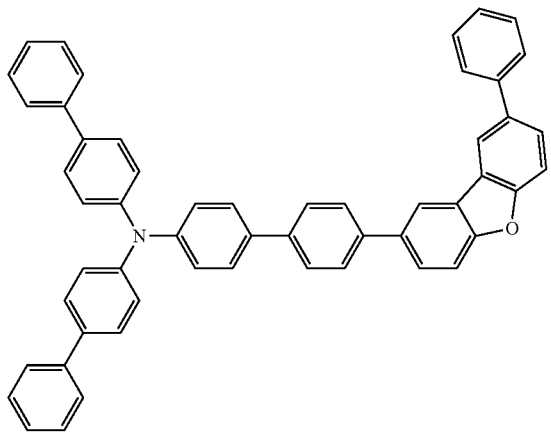 [SMILES: c1ccc(-c2ccc(N(c3ccc(-c4ccccc4)cc3)c3ccc(-c4ccc(-c5ccc6oc7ccc(-c8ccccc8)cc7c6c5)cc4)cc3)cc2)cc1]

The hole-transporting layer of the organic EL device according to the invention may have a two-layer structure of a first hole-transporting layer (anode side) and a second hole-transporting layer (cathode side).

The thickness of the hole-transporting layer is not particularly restricted, but preferably 10 to 200 nm.

In the organic EL device according to the invention, a layer comprising an acceptor material may be stacked to the anode side of the hole-transporting layer or the first hole-transporting layer. As a result, a lowering in driving voltage or a decrease in production cost can be expected.

As the acceptor material, a compound represented by the following formula (K) is preferable.

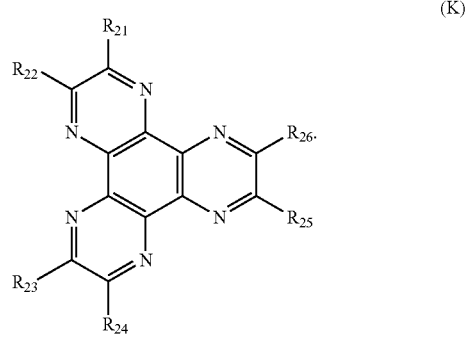

(K)

In the formula (K), $R_{21}$ to $R_{26}$, which may be the same as or different from each other, are independently a cyano group, —$CONH_2$, a carboxyl group or —$COOR_{27}$ ($R_{27}$ is an alkyl group including 1 to 20 carbon atoms or a cycloalkyl group including 3 to 20 carbon atoms); provided that, one or two or more pairs of $R_{21}$ and $R_{22}$; $R_{23}$ and $R_{24}$; and $R_{25}$ and $R_{26}$ may be bonded together to form a group represented by —CO—O—CO—.

As $R_{27}$, a methyl group, an ethyl group, an n-propyl group, an isopropyl group, an n-butyl group, an isobutyl group, a t-butyl group, a cyclopentyl group, a cyclohexyl group or the like can be given.

An example for an acceptor material K is

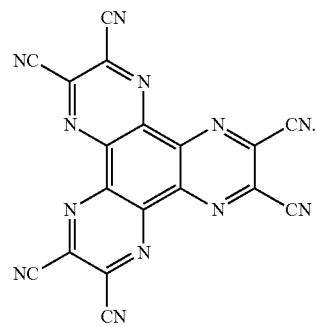 [SMILES: N#Cc1nc2c3nc(C#N)c(C#N)nc3c3nc(C#N)c(C#N)nc3c2nc1C#N]

The thickness of the layer that comprises an acceptor material is not particularly limited, but preferably 5 to 20 nm.

n/p Doping

In the hole-transporting layer or the electron-transporting layer mentioned above, as described in the Japanese Patent No. 3695714, the carrier injecting performance can be adjusted by doping (n) of a donor material or doping (p) of an acceptor material.

As representative examples of the n-doping, a method in which an electron-transporting material is doped with a metal such as Li and Cs can be mentioned. As the represented example of the p-doping, a method in which a hole-transporting material is doped with an acceptor material such as $F_4TCNQ$ (2,3,5,6-tetrafluoro-7,7,8,8-tetracyanoquinodimethane) can be given.

Spacing Layer

The spacing layer is a layer provided between the fluorescent emitting layer and the phosphorescent emitting layer when the fluorescent emitting layer and the phosphorescent emitting layer are stacked in order to prevent diffusion of excitons generated in the phosphorescent emitting layer to the fluorescent emitting layer or in order to adjust the carrier balance. Further, the spacing layer can be provided between the plural phosphorescent emitting layers.

Since the spacing layer is provided between the emitting layers, the material for the spacing layer is preferably a material having both electron-transporting properties and hole-transporting properties. In order to prevent diffusion of the triplet energy in adjacent phosphorescent emitting layers, it is preferred that the spacing layer have a triplet energy of 2.6 eV or more. As the material used for the spacing layer, the same material as those used in the above-mentioned hole-transporting layer can be given.

Barrier Layer

It is preferred that the organic EL device according to the invention have a barrier layer such as an electron-barrier layer, a hole-barrier layer and a triplet barrier layer in a part that is adjacent to the emitting layer. Here, the electron-barrier layer is a layer that serves to prevent leakage of electrons from the emitting layer to the hole-transporting layer, and the hole-barrier layer is a layer that serves to prevent leakage of holes from the emitting layer to the electron-transporting layer.

The triplet barrier layer prevents diffusion of triplet excitons generated in the emitting layer to the surrounding layers, and has a function of preventing energy deactivation of triplet excitons on molecules in the electron-transporting layer other than the emitting dopant by confining the triplet excitons within the emitting layer.

When the triplet barrier layer is provided, in the phosphorescent emitting device, the following is considered. The triplet energy of the phosphorescent emitting dopant is taken as $E^T_d$ and the triplet energy of the compound used as the triplet barrier layer is taken as $E^T_{TB}$. If the energy relationship $E^T_d < E^T_{TB}$ is satisfied, in respect of energy, the triplet excitons of the phosphorescent emitting dopant is confined (i.e. the triplet excitons cannot be moved to other molecules), whereby the energy deactivation route other than emission on the dopant is cut off, leading to efficient emission. However, even when the relationship $E^T_d < E^T_{TB}$ is established, if the energy difference $\Delta E^T = E^T_{TB} - E^T_d$ is small, it is thought that, in an environment at around room temperature where the device is actually driven, due to thermal energy of the surrounding area, the triplet excitons can move to other molecules by endothermically overcoming this energy difference $\Delta E^T$. In particular, in the case of phosphorescent emission that has a longer exciton life as compared with fluorescent emission, effects of the endothermic move of excitons relatively tend to appear. Relative to the thermal energy at room temperature, a larger energy difference $\Delta E^T$ is preferable. The energy difference $\Delta E^T$ is further preferably 0.1 eV or more, and particularly preferably 0.2 eV or more. On the other hand, in a fluorescent device, as the triplet barrier layer of the TTF device configuration disclosed in WO2010/134350A1, the material for an organic EL device according to the invention can be used.

The electron mobility of the material constituting the triplet barrier layer is desirably $10^{-6}$ cm$^2$/Vs or more in a field intensity range of 0.04 to 0.5 MV/cm. As the method for measuring the electron mobility of an organic material, several methods that include the Time of Flight method are known. Here, the electron mobility means an electron mobility that is determined by the impedance spectroscopy.

The electron mobility of the electron-injecting layer is desirably $10^{-6}$ cm$^2$Ns or more in a field intensity range of 0.04 to 0.5 MV/cm. The reason is that, by this electron mobility, injection of electrons from the cathode to the electron-transporting layer is promoted, and as a result, injection of electrons to adjacent barrier layer and emitting layer is promoted, enabling the device to be driven at a lower voltage.

The organic EL device of the invention can be used as an emitting device in a panel module used in various displays.

The organic EL device according to the invention can be used as a display element of a TV, a mobile phone and a PC; or an electronic apparatus such as lightings or the like.

The OLEDs (organic EL devices) can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper. In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES

I Preparation Examples

Intermediate 1-1

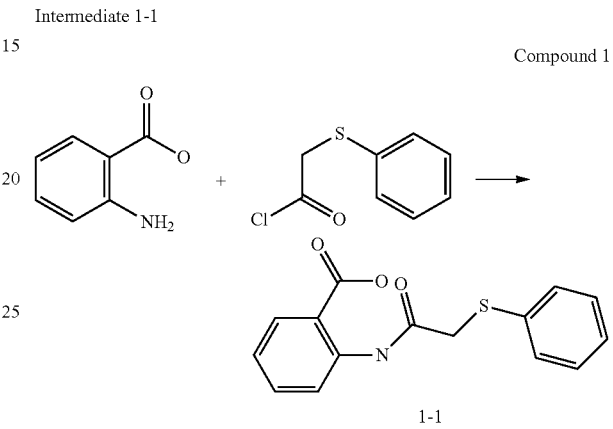

Compound 1

1-1

NaOH (11.7 g, 130 mmol) was dissolved in 117 ml H$_2$O, then 2-Amino-benzoic acid (98%) (18.2 g, 130 mmol) were added and the brown solution was cooled to 0° C. 25.0 g (130 mmol) (Phenylthio)acetyl chloride were added within 15 min, keeping the internal temperature below 5° C. The reaction mixture was stirred at 0° C. for another hour and then warmed to room temperature. To the brown solution 150 ml of a buffer solution pH 7 were added and the mixture is brought to pH 7 by adding 2M HCl. The mixture was extracted three times with EtOAc (250 ml each). The combined organic phases were dried over Na$_2$SO$_4$, filtered and evaporated to yield 37.1 g (115% of theory) of intermediate 1-1 as a beige solid with a purity of 85% according to HPLC.

$^1$H NMR (300 MHz, DMSO-d$_6$) δ 11.79 (s, 1H), 8.49 (d, J=8.2 Hz, 1H), 8.06-7.93 (m, 1H), 7.63-7.52 (m, 1H), 7.44-7.26 (m, 5H), 7.27-7.04 (m, 2H), 3.98 (s, 2H).

Intermediate 1-2

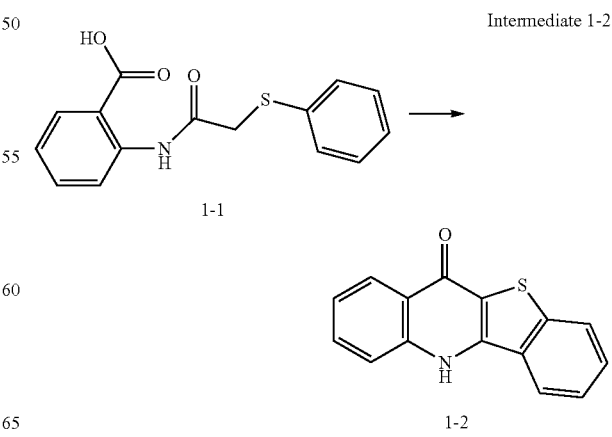

1-1

1-2

Intermediate 1-1 (32.3 g, 112.4 mmol) was added to 210 g Polyphosphoric acid (PPA) and heated to 125° C. internal temperature during 1.5 hours. The reaction mixture was the poured on 1 l of ice/water. 200 ml of buffer pH 7 were added and the mixture was brought to pH 7 with 25% NaOH solution. The suspension was filtered and the residue was washed five times with H₂O (200 ml each) and then dried at 80° C./125 mbar overnight to yield 24.3 g (86.2% of theory) of intermediate 1-2 as a brown solid with a purity of 75% according to HPLC.

¹H NMR (300 MHz, DMSO-d₆) δ 8.60-8.52 (m, 1H), 8.27 (dd, J=8.1, 1.4 Hz, 1H), 8.14 (dd, J=6.8, 1.6 Hz, 1H), 7.88-7.75 (m, 2H), 7.66 (pd, J=7.2, 1.5 Hz, 2H), 7.42 (ddd, J=8.1, 6.5, 1.5 Hz, 1H).

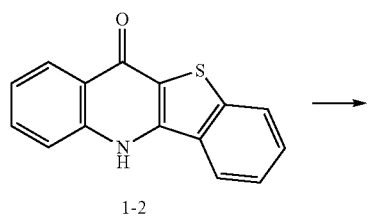

1-2

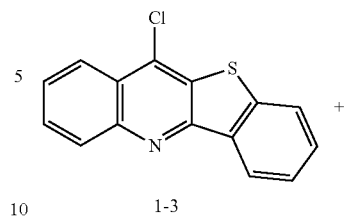

1-3

Intermediate 1-3

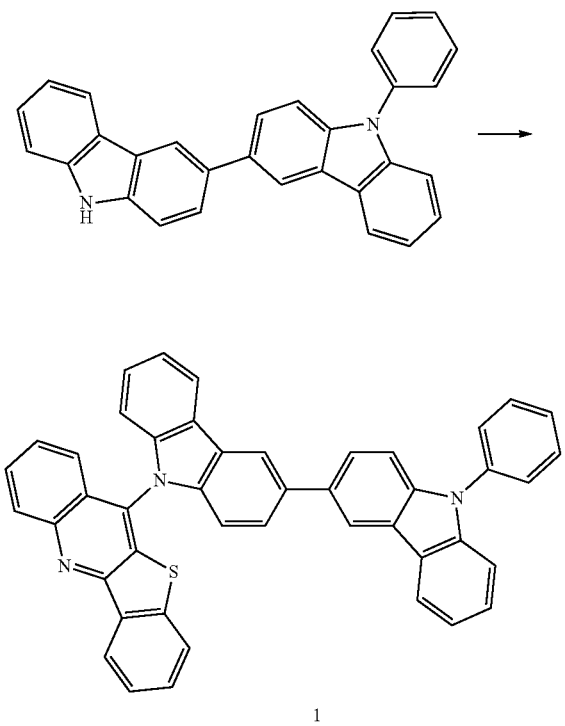

Compound 1

1-3

+

1

Intermediate 1-2 (24.34 g, 71.7 mmol) was added to 125 ml POCl₃. To the brown suspension were added PCl₅ (15.23 g, 71.7 mmol). The reaction mixture was heated to reflux for 2 h, then cooled to room temperature. The POCl₃ was distilled off on the rotavap and 200 ml Toluene were added to the residue and evaporated again. The residue was dissolved in 500 ml CH₂Cl₂ and made basic with the addition of 2M NaOH. The suspension was filtered and the two phases were separated. The organic phase was washed with H₂O twice (200 ml each), dried over Na₂SO₄, filtered and evaporated to yield 23.1 g of a crude product. The crude product was purified by flash chromatography using Chloroform/Heptane=8:2 as an eluent to yield 10.5 g of product with a purity of 97% according to HPLC. The product was further purified by Soxhlet extraction using 100 ml of Heptane. The resulting suspension was cooled to RT, filtered and the residue was dried at 80° C./125 mbar overnight to yield 9.6 g (49.4% of theory) of intermediate 1-3 with a purity of 99.5% according to HPLC.

¹H NMR (400 MHz, DMSO-d₆) δ 8.54 (d, J=7.3 Hz, 1H), 8.32 (d, J=8.6 Hz, 2H), 8.18 (d, J=8.0 Hz, 1H), 7.95 (ddd, J=8.5, 6.8, 1.4 Hz, 1H), 7.85 (ddd, J=8.1, 6.8, 1.1 Hz, 1H), 7.78 (td, J=7.7, 1.3 Hz, 1H), 7.72-7.64 (m, 1H).

Intermediate 1-3 (2.67 g, 9.91 mmol) and 3-(9H-carbazol-3-yl)-9-phenyl-carbazole (4.09 g, 9.91 mmol) were added to 80 ml of Xylene. The reaction mixture was evacuated and purged with Argon three times. In a separate vessel 4,5-bis(diphenylphosphino)-9,9-dimethylxanthene (0.35 g, 0.59 mmol) and Pd₂(dba)₃ (0.27 g, 0.30 mmol) were added to 20 ml Xylene and the solution was evacuated and purged with Argon three times and then added to the reaction mixture with a syringe. Sodium tert-butoxide (1.9 g, 19.8 mmol) were added and the red reaction mixture was heated to 120° C. internal temperature for 20 h. The reaction mixture was diluted with 200 ml Xylene, washed three times with H₂O (100 ml each), dried over Na₂SO₄, filtered and evaporated to yield 8.47 g of a crude product that was purified by flash chromatography using Heptane/EtOAc=8:2 as an eluent to yield 1.64 g (25.8% of theory) of compound 1 (1-[3-(9-phenylcarbazol-3-yl)carbazol-9-yl]benzothiopheno[3,2-b]quinolone) with a purity of 99.8% according to HPLC.

¹H NMR (300 MHz, Chloroform-d) δ 8.82-8.74 (m, 1H), 8.57 (d, J=1.5 Hz, 1H), 8.51 (dt, J=8.7, 0.8 Hz, 1H), 8.48 (d, J=1.5 Hz, 1H), 8.42-8.31 (m, 1H), 8.24 (dt, J=7.7, 1.1 Hz, 1H), 7.91-7.69 (m, 4H), 7.69-7.28 (m, 15H), 7.05 (d, J=8.5 Hz, 1H), 7.02-6.93 (m, 1H).

Compound 2

Intermediate 2-1

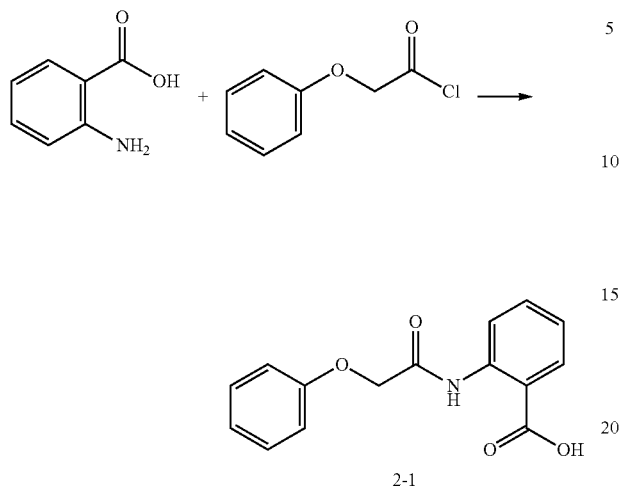

2-1

Anthranilic acid (7.0 g, 51.0 mmol) was added to of 60 mL of 2.5M sodium oxide aqueous solution at 0° C., and phenoxyacetyl chloride (8.71 g, 51.0 mmol) was added dropwise there. The mixture was stirred at 0° C. for 30 min. The reaction mixture was quenched with 1M hydrogen chloride to give a solid. The solid was collected by filtration, and it was dissolved in ethyl acetate. The solution was dried with MgSO$_4$, and concentrated to give a solid. The crude product was recrystallized with ethanol to yield 5.60 g (36%) of intermediate 2-1 as a white solid. The product was used for the next reaction without further purification.

Intermediate 2-2

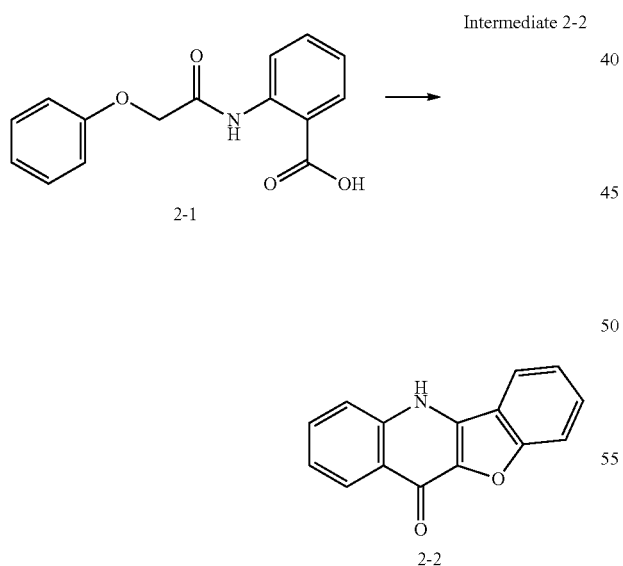

Intermediate 2-1 (4.49 g, 16.55 mmol) was suspended in polyphosphoric acid (PPA) (21.2 g), and the mixture was stirred at 120° C. for 2 h. The reaction mixture was added dropwise into ice-water and sodium carbonate was added there to give a solid. The solid was collected by filtration, and dried to yield 3.44 g (88%) of intermediate 2-2 as a beige powder. The crude product was used for the next reaction without further purification.

LC-MS (m/z) 235

Intermediate 2-3

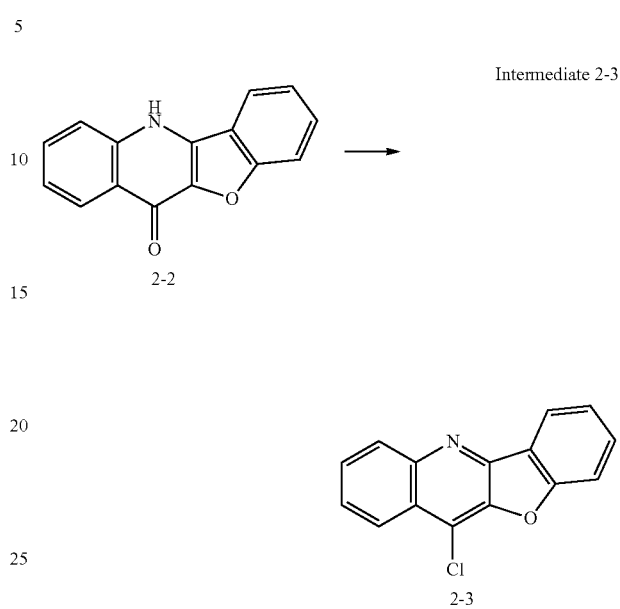

Intermediate 2-2 (3.5 g, 14.88 mmol) was suspended in 30 mL of toluene, and stirred at 50° C. Phosphoryl chloride (17.11 g, 111.6 mmol) was added dropwise, and 1,8-diazabicyclo[5.4.0]undec-7-ene (4.53 g, 29.76 mmol) was added dropwise there. The mixture was stirred at 120° C. for 15 h. After the reaction mixture was cooled at room temperature, the reaction mixture was slowly poured into ice-water. The aqueous layer was extracted with CHCl$_3$. After it was washed with brine and dried with Na$_2$SO$_4$, it was concentrated to give a solid. The crude product was purified by column chromatography on silica gel eluting with toluene to yield 3.41 g (47%) of intermediate 2-3 as a white solid.

LC-MS (m/z) 253

Compound 2

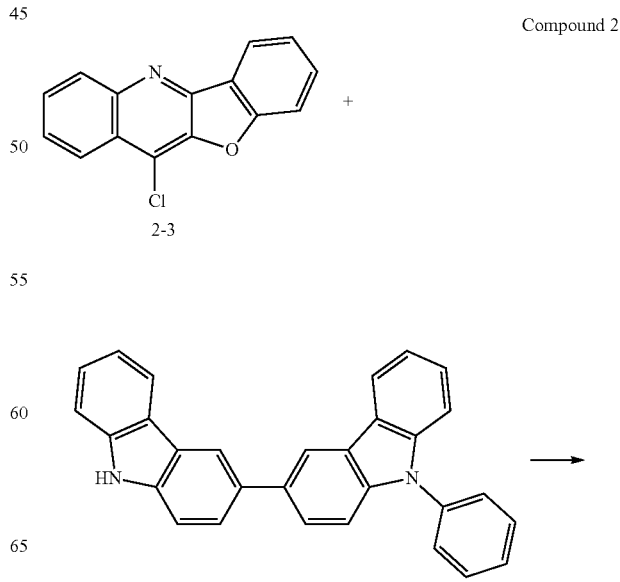

-continued

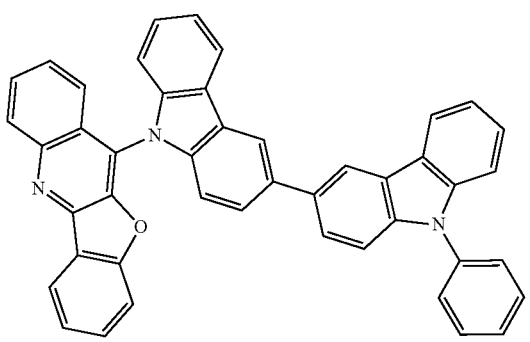

2

Intermediate 2-3 (2.57 g, 10.13 mmol) and 3-(9H-carbazol-3-yl)-9-phenyl-carbazole (4.14 g, 10.13 mmol) were suspended in 51 mL of N-methylpyrrolidone, and the mixture was stirred at 130° C. overnight. After the reaction mixture was cooled at room temperature, it was diluted with 51 mL of ethanol and 102 mL of water, and the mixture was stirred at room temperature for 1 h to give a solid. The solid was collected by filtration and washed with water. The crude product was purified by column chromatography on silica gel eluting with a mixed solvent of heptane-toluene (1:3) to yield 1.15 g (18%) of compound 2 as a yellow powder.

$^1$H NMR (300 MHz, Chloroform-d) δ 8.60 (d, J=1.3 Hz, 1H), 8.54-8.50 (m, 3H), 8.41-8.36 (m, 1H), 8.27 (dt, J=1.1, 7.5 Hz, 1H), 7.90-7.64 (m, 8H), 7.59-7.30 (m, 10H), 7.22-7.18 (m, 1H), 7.12 (d, J=8.6 Hz, 1H), 7.06-7.03 (m, 1H)

LC-MS (m/z) 626

Compound 3

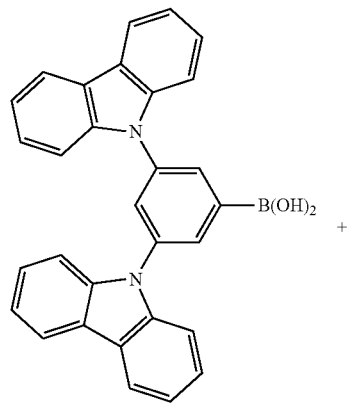

1-3

-continued

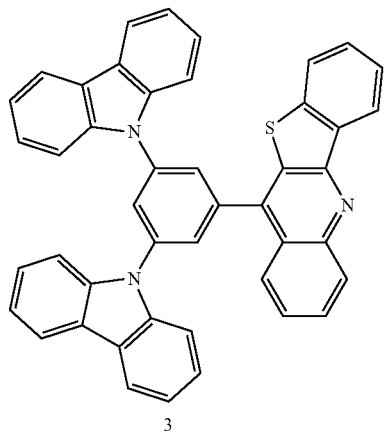

3

[3,5-di(carbazol-9-yl)phenyl]boronic acid (3.1 g, 6.9 mmol)) was combined with intermediate 1-3 (1.7 g, 6.3 mmol) and K$_2$CO$_3$ (1.9 g, 13.9 mmol) in a 3 necked round bottom flask and degassed with N$_2$. Pd(OAc)$_2$ (35 mg, 0.16 mmol) and 2-Dicyclohexylphosphino-2',6'-dimethoxybiphenyl (260 mg, 0.63 mmol) were then added followed by dioxane/H$_2$O (30 mL, 4:1). The resulting reaction mixture was heated under a stream of N$_2$ at an oil bath temperature of 90° C. After 2.5 hours, the reaction was complete. The mixture was cooled to room temperature and concentrated under reduced pressure. The crude residue was taken up in CH$_2$Cl$_2$ and washed with water (×2), dried over anhydrous MgSO$_4$ and solvent evaporated. The crude product was purified by flash chromatography on silica using 60% CH$_2$Cl$_2$ in heptane as eluent. 3.7 g of purified product was obtained which was further purified by washing the product with acetone to yield 3.2 g of compound 3 (80%).

$^1$H NMR (400 MHz, Chloroform-d) δ 8.74 (dd, J=7.4, 1.3 Hz, 1H), 8.43 (d, J=8.5 Hz, 1H), 8.20 (d, J=7.7 Hz, 4H), 8.16-8.09 (m, 2H), 8.00 (d, J=1.9 Hz, 2H), 7.94-7.80 (m, 2H), 7.77 (d, J=8.2 Hz, 4H), 7.72-7.60 (m, 3H), 7.52 (ddd, J=8.3, 7.2, 1.2 Hz, 4H), 7.37 (t, J=7.5 Hz, 4H).

LC-MS (m/z) 642 (M+1)

Compound 4

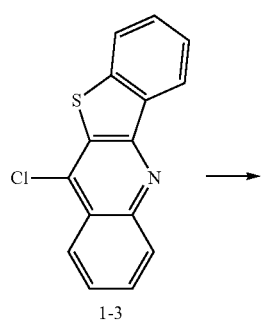

-continued

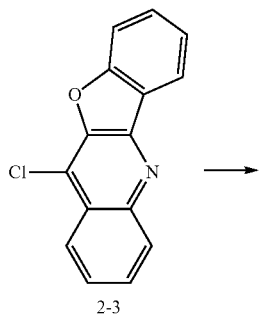
2-3

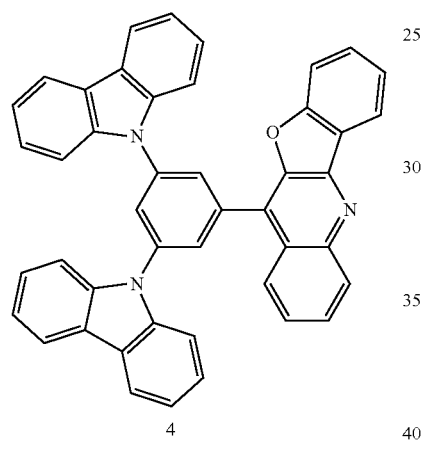
4

[3,5-di(carbazol-9-yl)phenyl]boronic acid (3.6 g, 8 mmol) was combined with intermediate 2-3 (2 g, 8 mmol) and K₂CO₃ (2.2 g, 16 mmol) in a 3 necked round bottom flask and degassed with N₂. Pd(OAc)₂ (44 mg, 0.2 mmol) and 2-Dicyclohexylphosphino-2',6'-dimethoxybiphenyl (330 mg, 0.8 mmol) were then added followed by dioxane/H₂O (50 mL, 4:1). The resulting reaction mixture was heated under a stream of N₂ at an oil bath temperature of 90° C. After 2.5 hours, the reaction was complete. The mixture was cooled to room temperature and was diluted with water and filtered over celite washing well with water. The product was collected by washing the precipitate through with CH₂Cl₂. The crude product was isolated by evaporation of the solvent under reduced pressure. This was then suspended in acetone and stirred in acetone at room temperature for 2 hours. The precipitate was then isolated by filtration washing well with acetone. The product was finally purified by recrystallization from CHCl₃-MeOH to give 4.3 g of compound 4 (86%).

¹H NMR (400 MHz, Chloroform-d) δ 8.49 (d, 1H), 8.43 (dd, J=8.5, 1.2 Hz, 1H), 8.35 (dd, J=8.6, 1.4 Hz, 1H), 8.21 (m, 4H), 8.13 (m, 3H), 7.83 (dd, J=8.3, 1.0 Hz, 5H), 7.72 (dd, J=3.6, 1.8 Hz, 3H), 7.53 (ddd, J=8.4, 7.2, 1.3 Hz, 5H), 7.37 (td, J=7.6, 0.9 Hz, 4H).

LC-MS (m/z) 626 (M+1)

Compound 5

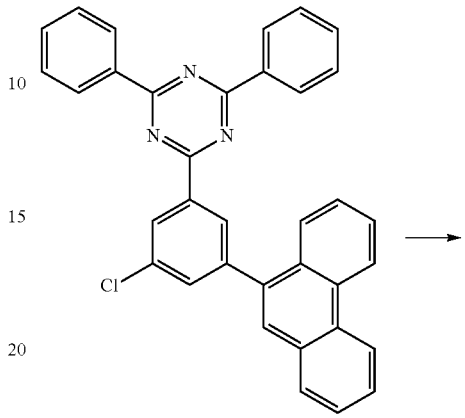

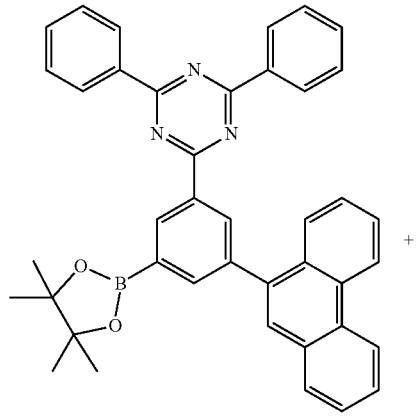
+

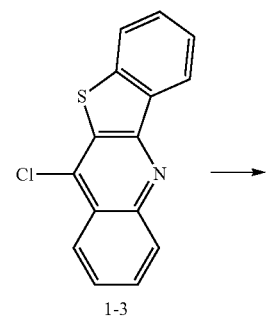
1-3

-continued

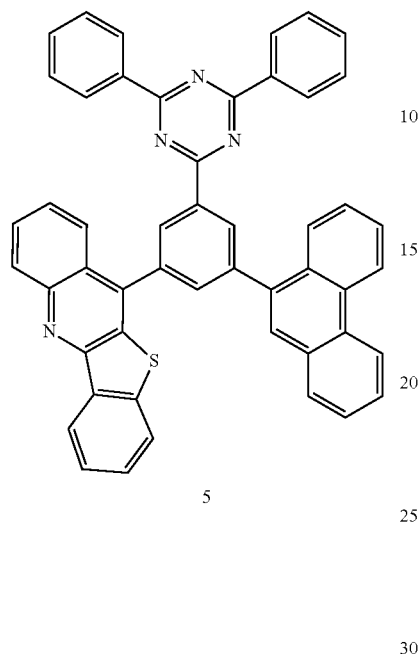

5

2-[3-chloro-5-(9-phenanthryl)phenyl]-4,6-diphenyl-1,3,5-triazine (2 g, 3.8 mmol), Bis(pinacolato)diboron (1.4 g, 5.8 mmol) Pd₂dba₃ (87 mg, 0.095 mmol) 2-Dicyclohexylphosphino-2',6'-dimethoxybiphenyl (80 mg, 0.19 mmol) and KOAc (1.1 g, 1.14 mmol) were added to a 3 necked round bottom flask followed by 1,4-dioxane (50 mL) and the mixture degassed with N₂. The reaction was heated at an oil bath temperature of 90° C. for 18 hours. The reaction was allowed to cool to room temperature and the solvent evaporated under reduced pressure. The crude residue was taken up in CH₂Cl₂ and washed with water, saturated aqueous NaHCO₃ and brine, dried over anhydrous MgSO₄ and solvent evaporated under reduced pressure. The crude product was triturated with methanol and filtered washing well with methanol. The crude boronic ester thus obtained was used without further purification. Into a 3 necked round bottom flask was added the boronic acid (2 g, 3.3 mmol), intermediate 1-3 (0.97 g, 3.6 mmol) Pd(OAc)₂ (18 mg, 0.08 mmol), 2-Dicyclohexylphosphino-2',6'-dimethoxybiphenyl (0.13 g, 0.33 mmol) and K₂CO₃ (1 g, 7.2 mmol) followed by 1,4-dioxane/H₂O (100 mL, 4:1) and the resulting mixture degassed under N₂. The reaction was then heated at an oil bath temperature of 90° C. for 18 hours under N₂. The reaction was then allowed to cool to room temperature and the solvent evaporated under reduced pressure. The crude reside was dissolved in warm CHCl₃ and washed with water and brine, dried over anhydrous MgSO₄ and filtered through a plug of silica gel washing through with CHCl₃. The solvent was evaporated under reduced pressure. The crude material was suspended in acetone and allowed to stir at room temperature for 1 hour in acetone. The product was collected by filtration and further purified by precipitation from CH₂Cl₂ to give 1.44 g of compound 5 (60% yield).

$^1$H NMR (400 MHz, Chloroform-d) δ 9.18 (dt, J=11.1, 1.7 Hz, 2H), 8.90-8.72 (m, 7H), 8.49-8.39 (m, 1H), 8.23-8.06 (m, 3H), 8.06-7.96 (m, 2H), 7.85 (ddd, J=8.5, 6.6, 1.5 Hz, 2H), 7.81-7.48 (m, 13H).

LC-MS (m/z) 720 (M+1)

Compound 6

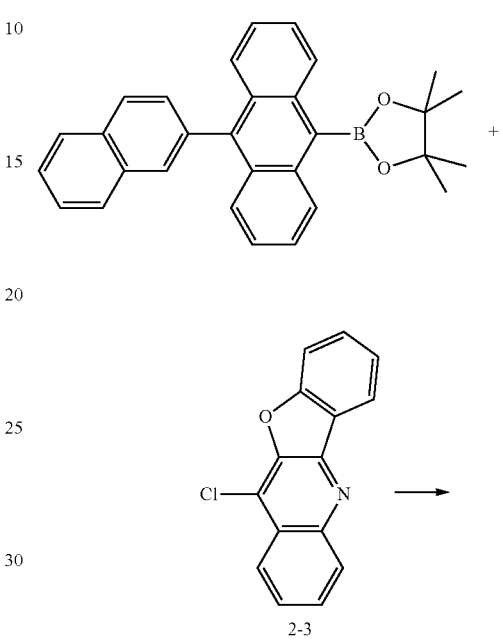

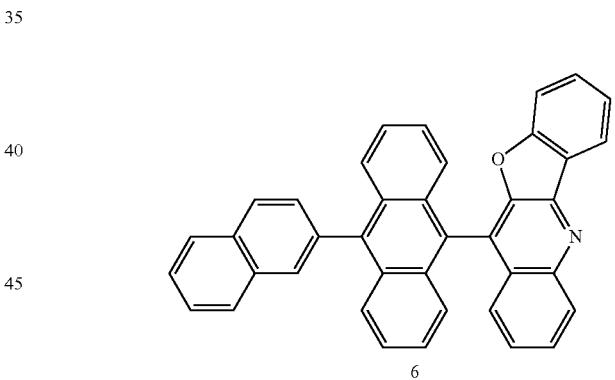

4,4,5,5-tetramethyl-2-[10-(2-naphthyl)-9-anthryl]-1,3,2-dioxaborolane (1.5 g, 4.3 mmol) was combined with intermediate 2-3 (1.3 g, 5.2 mmol) and K₂CO₃ (1.2 g, 8.6 mmol) in a 3 necked round bottom flask and degassed with N₂. Pd(OAc)₂ (19 mg, 0.086 mmol) and 2-Dicyclohexylphosphino-2',6'-dimethoxybiphenyl (140 mg, 0.34 mmol) were then added followed by dioxane/H₂O (30 mL, 4:1). The resulting reaction mixture was heated under a stream of N₂ at an oil bath temperature of 90° C. After 2.5 hours, the reaction was complete. The mixture was cooled to room temperature and the solvent was concentrated under reduced pressure. The crude residue was taken up in CH₂Cl₂ and washed with water twice, dried over anhydrous MgSO₄ and solvent evaporated. The crude product was purified by flash chromatography on silica using CHCl₃ as eluent to give 1.2 g of compound 6 (54% yield).

¹H NMR (400 MHz, DMSO-d₆) δ 8.51-8.47 (m, 2H), 8.27 (dd, J=2.6, 9.0 Hz, 1H), 8.21-8.15 (m, 2H), 8.13-8.08 (m, 1H), 7.88-7.83 (m, 1H), 7.79-7.58 (m, 8H), 7.53-7.43 (m, 3H), 7.36-7.34 (m, 4H), 7.26-7.20 (m, 1H)

LC-MS (m/z) 561 (M+1).

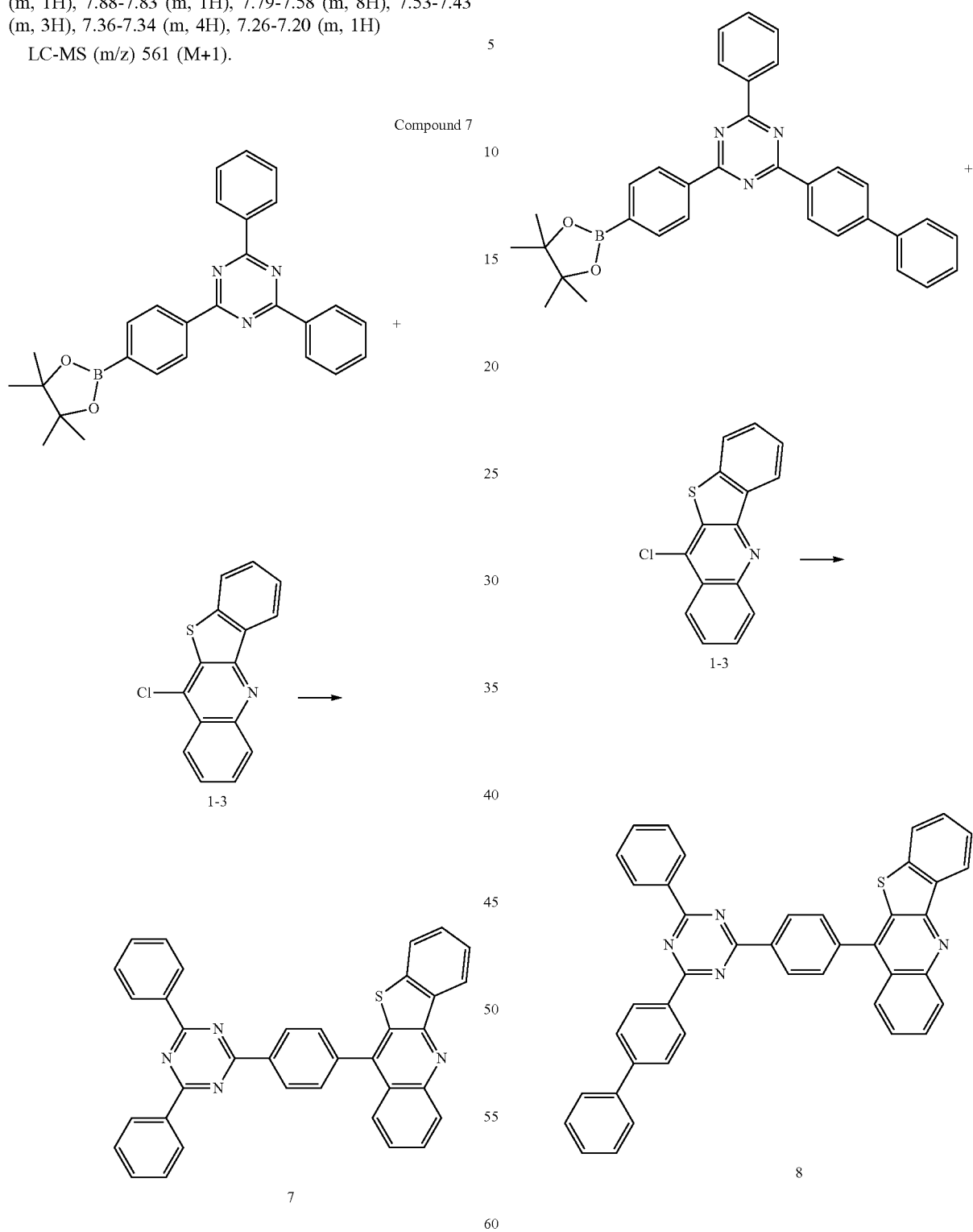

The synthesis of compound 3 was repeated except for replacing [3,5-di(carbazol-9-yl)phenyl]boronic acid with 2,4-diphenyl-6-[4-(4,4,5,5-tetramethyl-1,3,2-dioxaborolan-2-yl)phenyl]-1,3,5-triazine to yield compound 7 (75% yield), which was identified by mass spectroscopy (m/e=542 to Exact mass: 542.16).

The synthesis of compound 3 was repeated except for replacing [3,5-di(carbazol-9-yl)phenyl]boronic acid with 2-phenyl-4-(4-phenylphenyl)-6-[4-(4,4,5,5-tetramethyl-1,3,2-dioxaborolan-2-yl)phenyl]-1,3,5-triazine to yield compound 8 (71% yield), which was identified by mass spectroscopy (m/e=618 to Exact mass: 618.19).

Compound 9

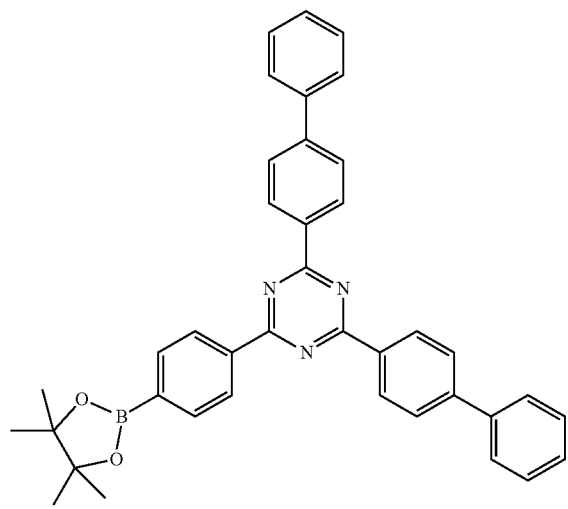

1-3

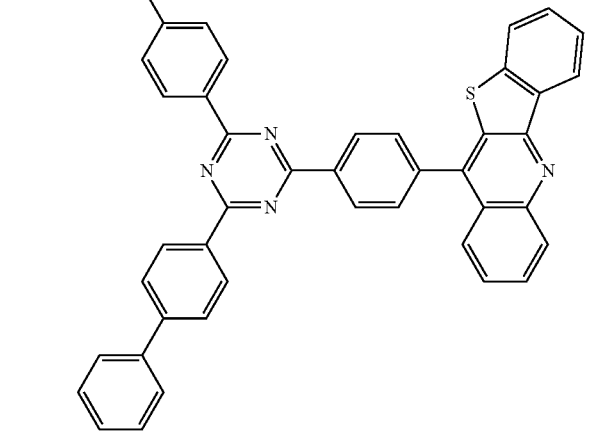

9

The synthesis of compound 3 was repeated except for replacing [3,5-di(carbazol-9-yl)phenyl]boronic acid with 2,4-bis(4-phenylphenyl)-6-[4-(4,4,5,5-tetramethyl-1,3,2-dioxaborolan-2-yl)phenyl]-1,3,5-triazine to yield compound 9 (66% yield), which was identified by mass spectroscopy (m/e=694 to Exact mass: 694.22).

Compound 10

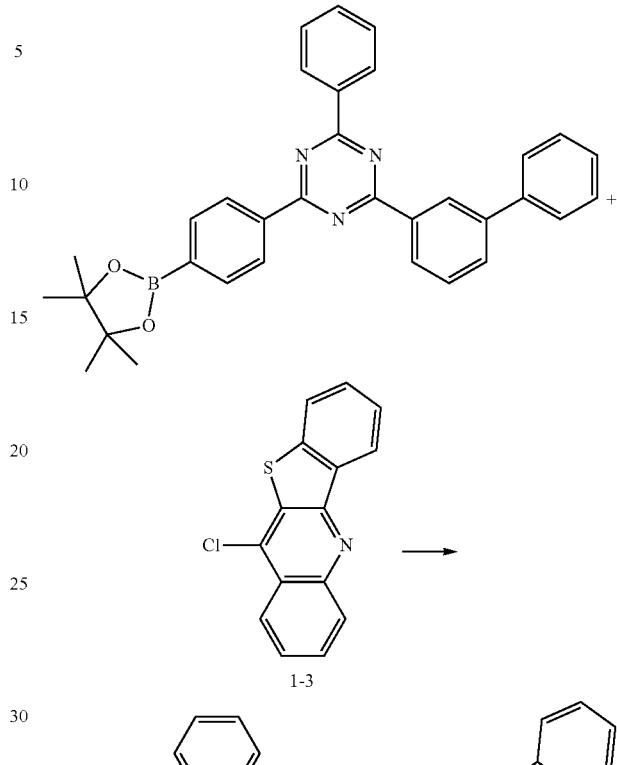

10

The synthesis of compound 3 was repeated except for replacing [3,5-di(carbazol-9-yl)phenyl]boronic acid with 2-phenyl-4-(3-phenylphenyl)-6-[4-(4,4,5,5-tetramethyl-1,3,2-dioxaborolan-2-yl)phenyl]-1,3,5-triazine to yield compound 10 (71% yield), which was identified by mass spectroscopy (m/e=618 to Exact mass: 618.19).

Compound 11

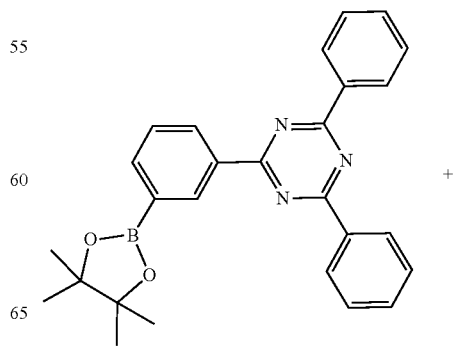

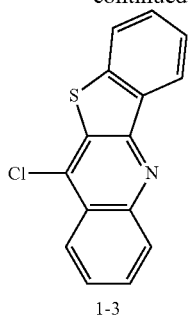

1-3

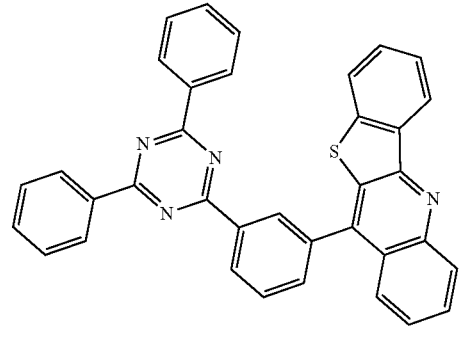

11

The synthesis of compound 3 was repeated except for replacing [3,5-di(carbazol-9-yl)phenyl]boronic acid with 2,4-diphenyl-6-[3-(4,4,5,5-tetramethyl-1,3,2-dioxaborolan-2-yl)phenyl]-1,3,5-triazine to yield compound 11 (72% yield), which was identified by mass spectroscopy (m/e=542 to Exact mass: 542.16).

Compound 12

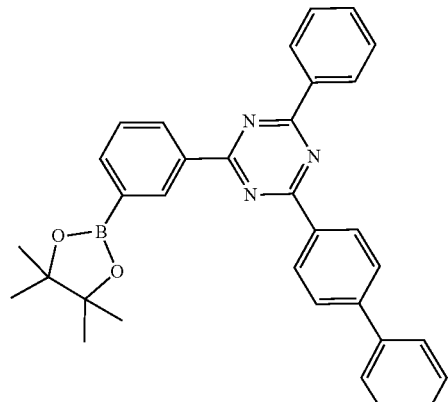

+

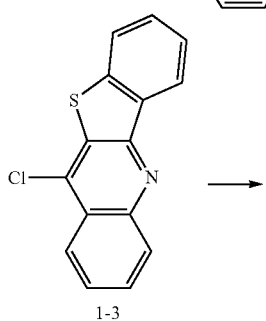

1-3

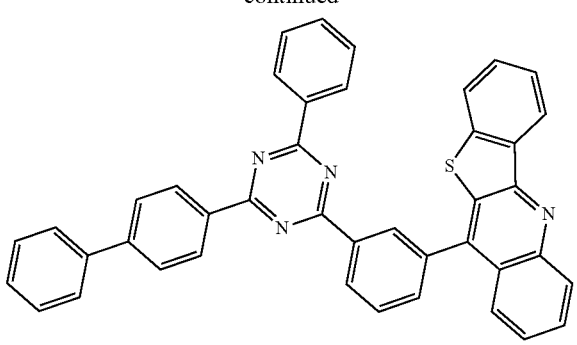

12

The synthesis of compound 3 was repeated except for replacing [3,5-di(carbazol-9-yl)phenyl]boronic acid with 2-phenyl-4-(4-phenylphenyl)-6-[3-(4,4,5,5-tetramethyl-1,3,2-dioxaborolan-2-yl)phenyl]-1,3,5-triazine to yield compound 12 (66% yield), which was identified by mass spectroscopy (m/e=618 to Exact mass: 618.19).

Compound 13

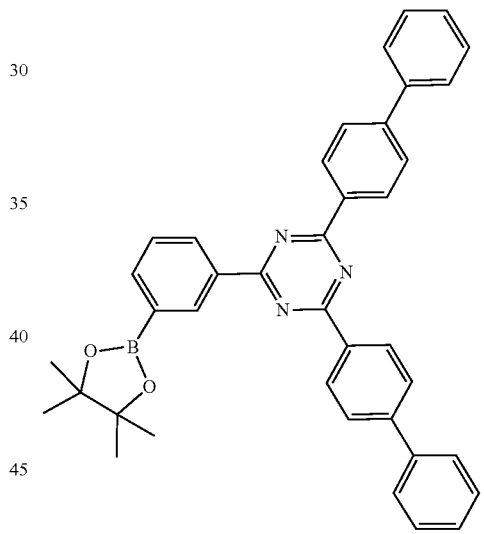

+

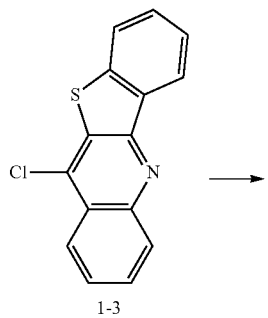

1-3

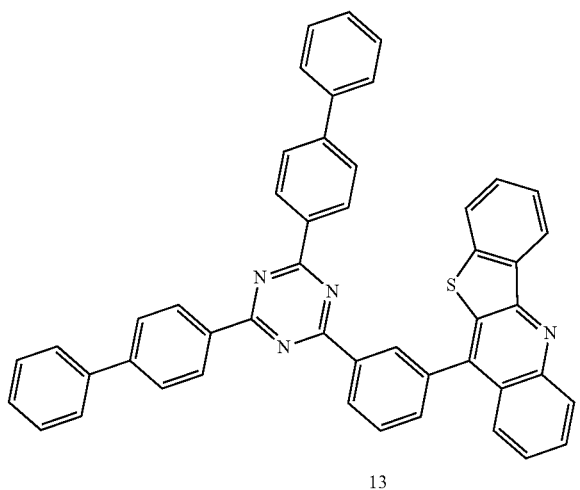

13

The synthesis of compound 3 was repeated except for replacing [3,5-di(carbazol-9-yl)phenyl]boronic acid with 2,4-bis(4-phenylphenyl)-6-[3-(4,4,5,5-tetramethyl-1,3,2-dioxaborolan-2-yl)phenyl]-1,3,5-triazine to yield compound 13 (72% yield), which was identified by mass spectroscopy (m/e=694 to Exact mass: 694.22).

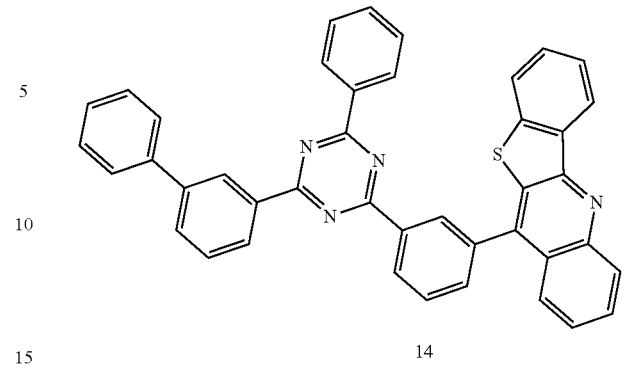

14

The synthesis of compound 3 was repeated except for replacing [3,5-di(carbazol-9-yl)phenyl]boronic acid with 2-phenyl-4-(3-phenylphenyl)-6-[3-(4,4,5,5-tetramethyl-1,3,2-dioxaborolan-2-yl)phenyl]-1,3,5-triazine to yield compound 14 (73% yield), which was identified by mass spectroscopy (m/e=618 to Exact mass: 618.19).

Compound 15

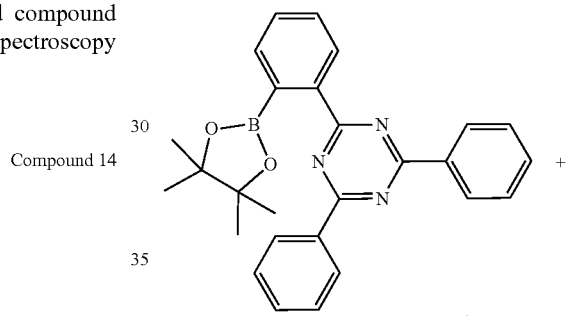

+

Compound 14

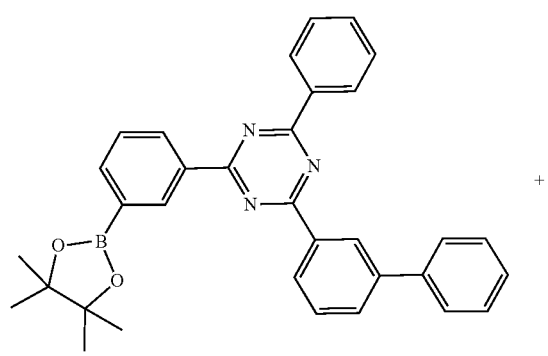

+

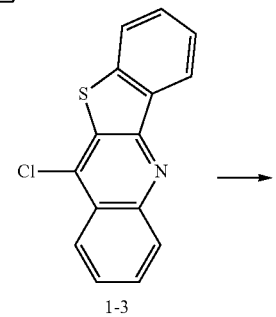

1-3

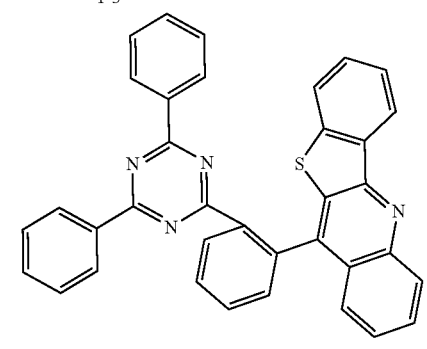

15

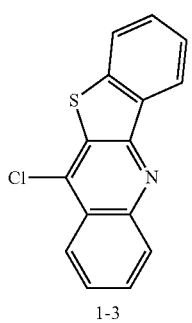

1-3

The synthesis of compound 3 was repeated except for replacing [3,5-di(carbazol-9-yl)phenyl]boronic acid with 2,4-diphenyl-6-[2-(4,4,5,5-tetramethyl-1,3,2-dioxaborolan- 2-yl)phenyl]-1,3,5-triazine to yield compound 15 (62% yield), which was identified by mass spectroscopy (m/e=542 to Exact mass: 542.16).

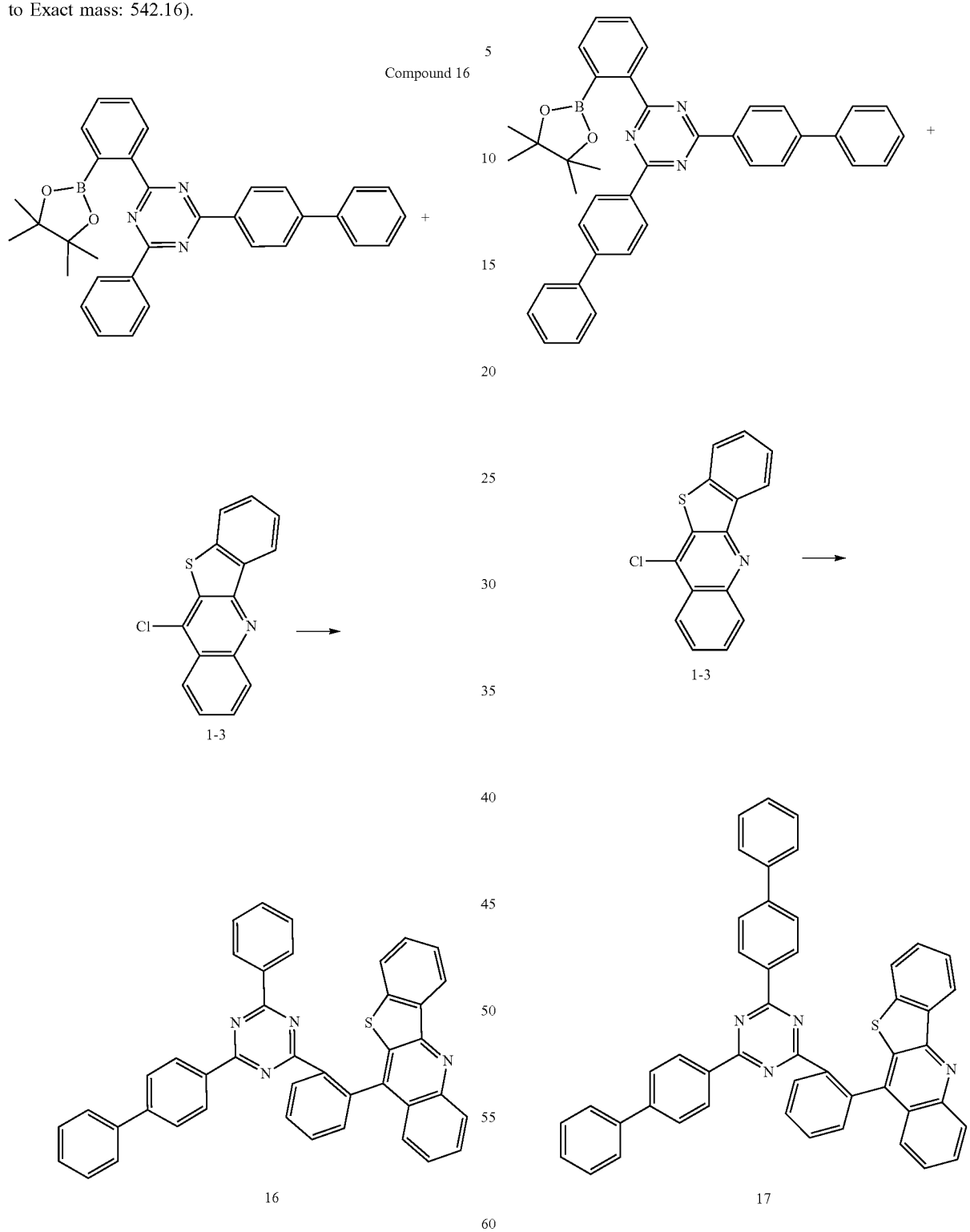

The synthesis of compound 3 was repeated except for replacing [3,5-di(carbazol-9-yl)phenyl]boronic acid with 2-phenyl-4-(4-phenylphenyl)-6-[2-(4,4,5,5-tetramethyl-1,3,2-dioxaborolan-2-yl)phenyl]-1,3,5-triazine to yield compound 16 (60% yield), which was identified by mass spectroscopy (m/e=618 to Exact mass: 618.19).

The synthesis of compound 3 was repeated except for replacing [3,5-di(carbazol-9-yl)phenyl]boronic acid with 2,4-bis(4-phenylphenyl)-6-[2-(4,4,5,5-tetramethyl-1,3,2-dioxaborolan-2-yl)phenyl]-1,3,5-triazine to yield compound 17 (61% yield), which was identified by mass spectroscopy (m/e=694 to Exact mass: 694.22).

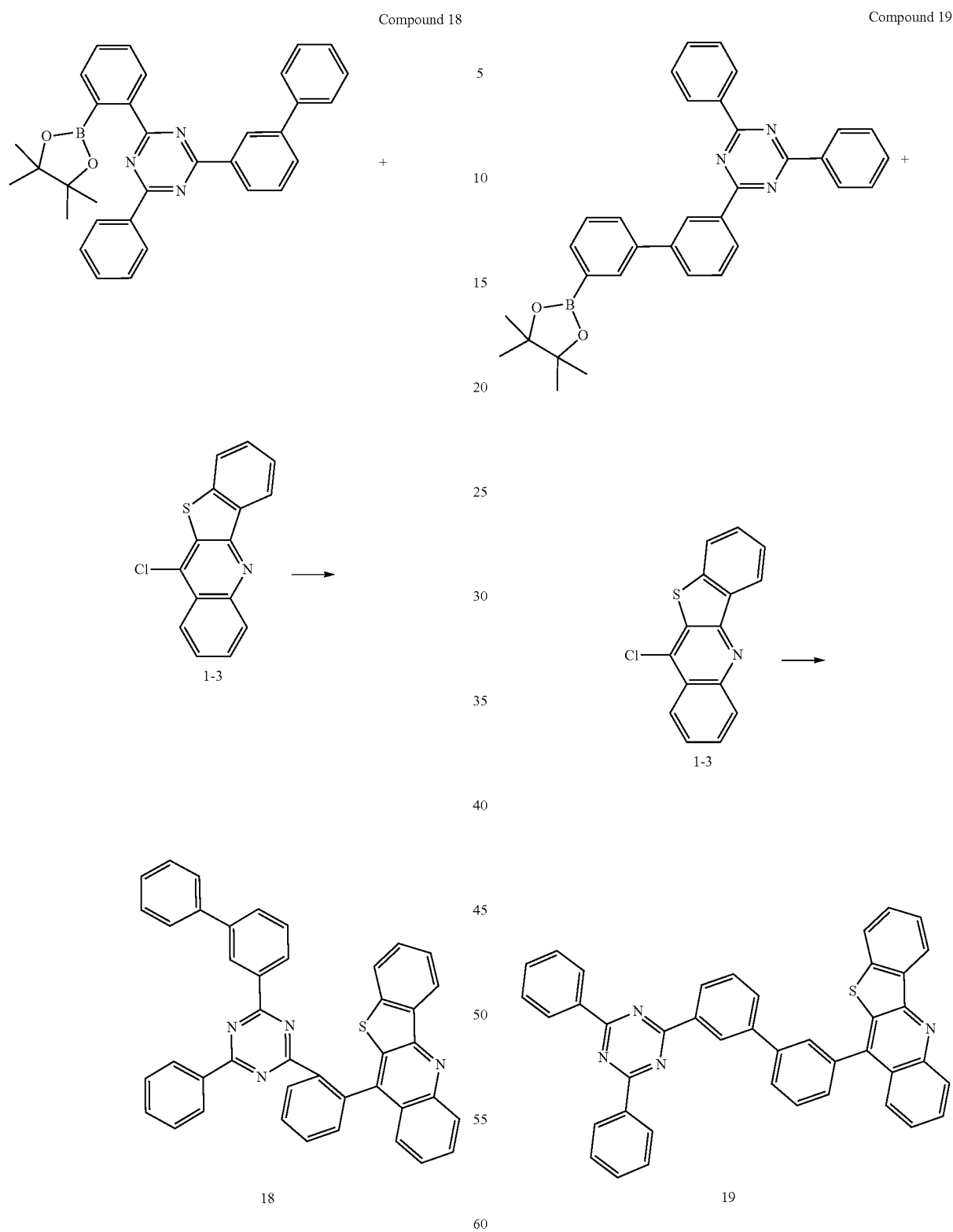

The synthesis of compound 3 was repeated except for replacing [3,5-di(carbazol-9-yl)phenyl]boronic acid with 2-phenyl-4-(3-phenylphenyl)-6-[2-(4,4,5,5-tetramethyl-1,3,2-dioxaborolan-2-yl)phenyl]-1,3,5-triazine to yield compound 18 (60% yield), which was identified by mass spectroscopy (m/e=618 to Exact mass: 618.19).

The synthesis of compound 3 was repeated except for replacing [3,5-di(carbazol-9-yl)phenyl]boronic acid with 2,4-diphenyl-6-[3-[3-(4,4,5,5-tetramethyl-1,3,2-dioxaborolan-2-yl)phenyl]phenyl]-1,3,5-triazine to yield compound 19 (73% yield), which was identified by mass spectroscopy (m/e=618 to Exact mass: 618.19).

Compound 20

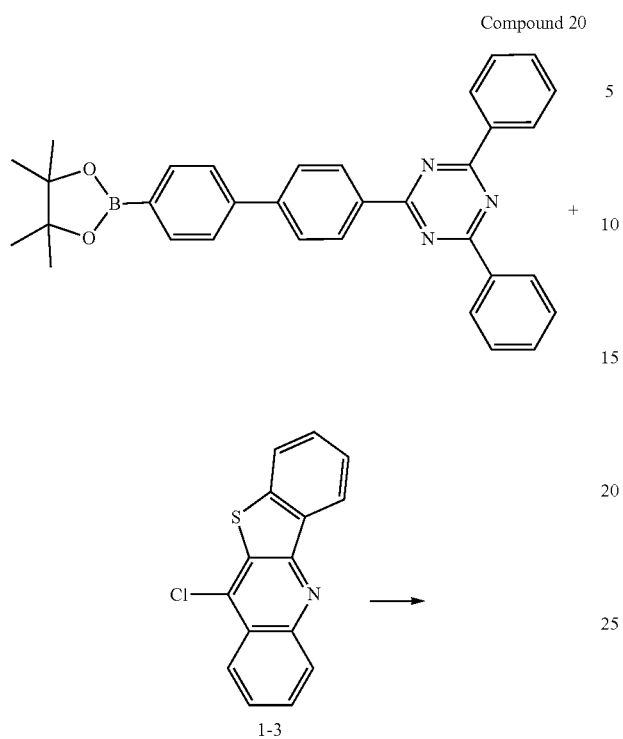

20

The synthesis of compound 3 was repeated except for replacing [3,5-di(carbazol-9-yl)phenyl]boronic acid with 2,4-diphenyl-6-[4-[4-(4,4,5,5-tetramethyl-1,3,2-dioxaborolan-2-yl)phenyl]phenyl]-1,3,5-triazine to yield compound 20 (71% yield), which was identified by mass spectroscopy (m/e=618 to Exact mass: 618.19).

Compound 21

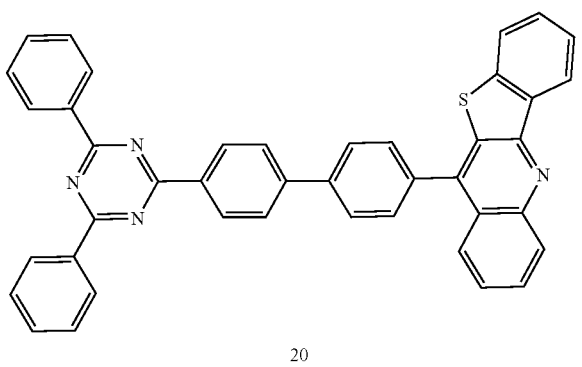

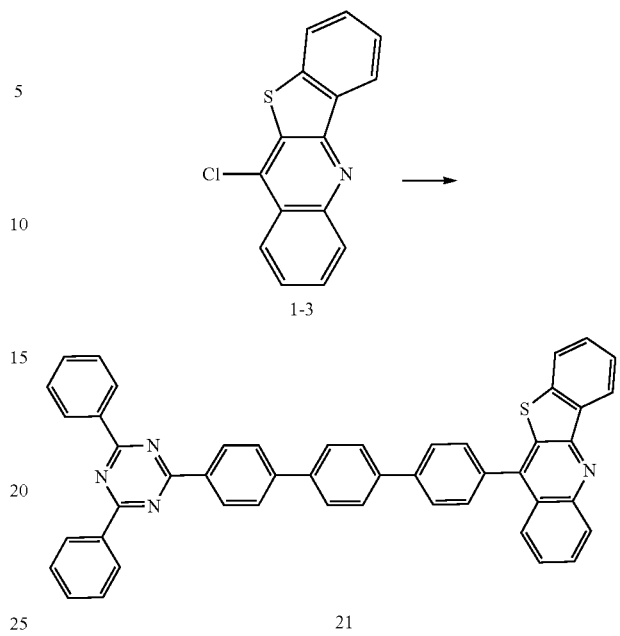

21

The synthesis of compound 3 was repeated except for replacing [3,5-di(carbazol-9-yl)phenyl]boronic acid with 2,4-diphenyl-6-[4-[4-[4-(4,4,5,5-tetramethyl-1,3,2-dioxaborolan-2-yl)phenyl]phenyl]phenyl]-1,3,5-triazine to yield compound 21 (76% yield), which was identified by mass spectroscopy (m/e=694 to Exact mass: 694.22).

intermediate 22-1

Compound 22

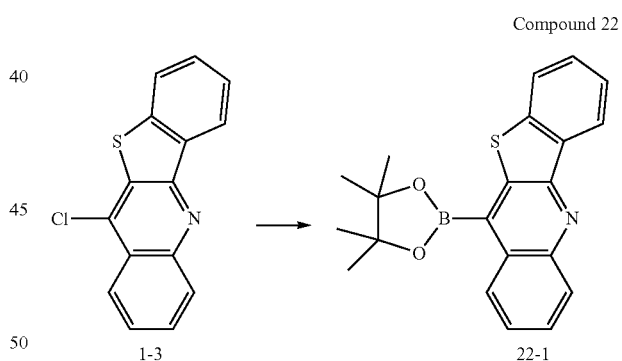

Under an argon atmosphere, intermediate 1-3 (16.2 g, 59.9 mmol), bis(pinacolato)diboron (18.3 g, 71.9 mmol), tris(dibenzylideneacetone)dipalladium(0) (1.10 g, 2.20 mmol), X-phos (2.29 g, 4.79 mmol), and potassium acetate (120 g, 11.8 mmol) were added to 1,4-dioxane (600 mL). The mixture was stirred and refluxed for 8 h under heating. After the reaction, the reaction mixture was cooled to room temperature, then toluene (300 mL) and water (300 mL) were added to the mixture. The phases were separated and the organic phase was concentrated under reduced pressure. The crude product was dissolved in dichloromethane and purified by silica gel column chromatography. The solution was concentrated under reduced pressure to yield 16.4 g (45.5 mmol) of intermediate 22-1 (76% yield).

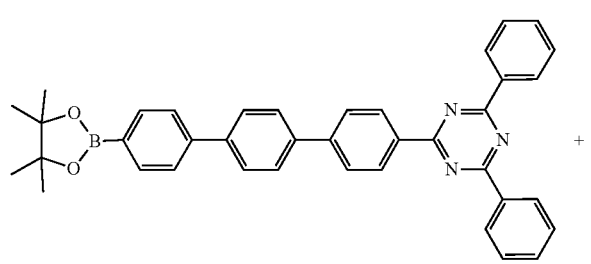

Compound 22

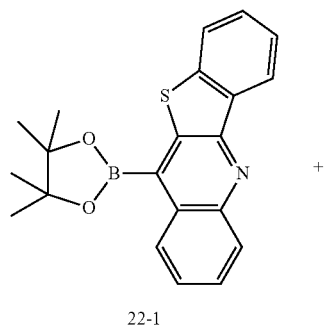

22-1

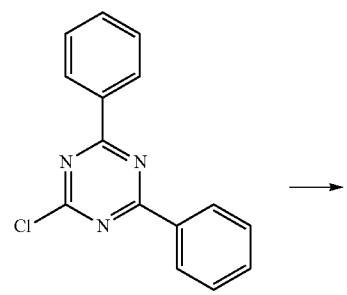

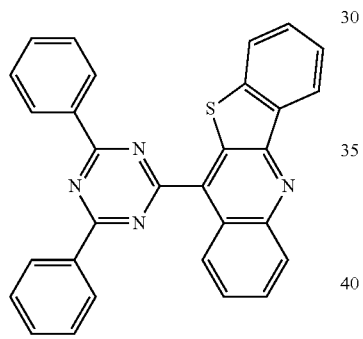

22

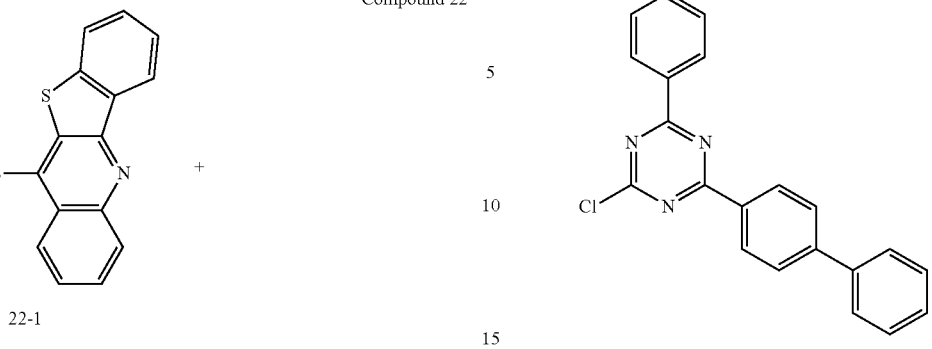

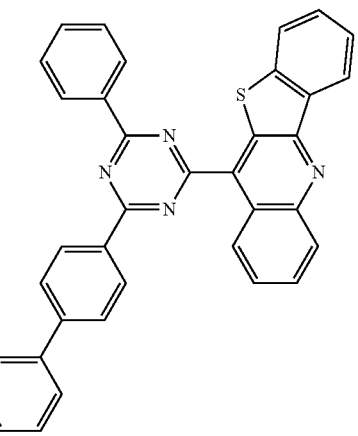

23

The synthesis of compound 3 was repeated except for replacing [3,5-di(carbazol-9-yl)phenyl]boronic acid with intermediate 22-1 and replacing intermediate 1-3 with 2-chloro-4,6-diphenyl-1,3,5-triazine to yield compound 22 (54% yield), which was identified by mass spectroscopy (m/e=466 to Exact mass: 466.13).

The synthesis of compound 3 was repeated except for replacing [3,5-di(carbazol-9-yl)phenyl]boronic acid with intermediate 22-1 and replacing intermediate 1-3 with 2-chloro-4-phenyl-6-(4-phenylphenyl)-1,3,5-triazine to yield compound 23 (58% yield), which was identified by mass spectroscopy (m/e=542 to Exact mass: 542.16).

Compound 23

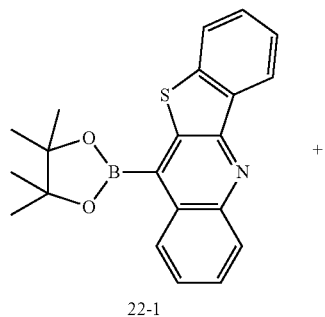

22-1

Compound 24

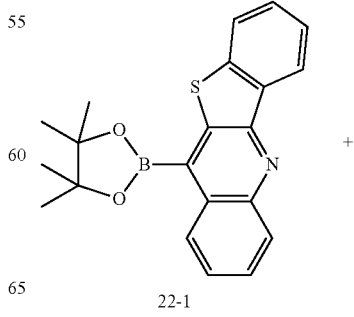

22-1

355

-continued

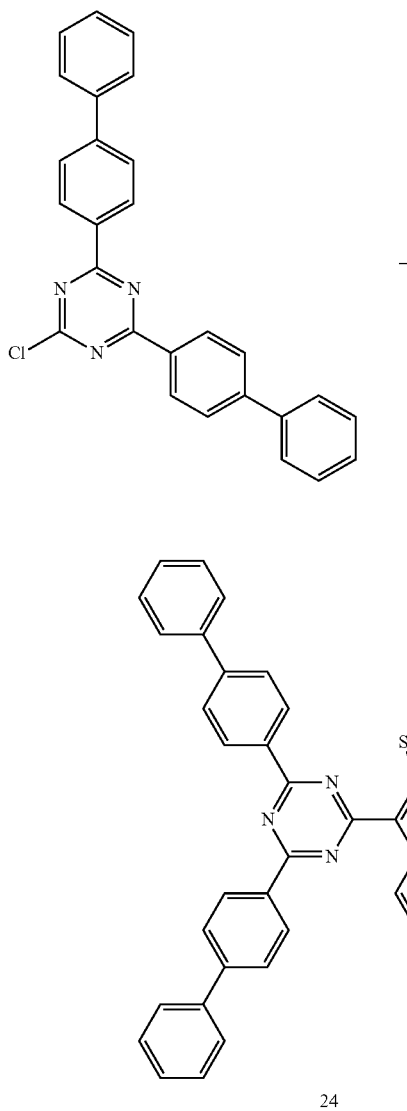

24

The synthesis of compound 3 was repeated except for replacing [3,5-di(carbazol-9-yl)phenyl]boronic acid with intermediate 22-1 and replacing intermediate 1-3 with 2-chloro-4,6-bis(4-phenylphenyl)-1,3,5-triazine to yield compound 24 (61% yield), which was identified by mass spectroscopy (m/e=618 to Exact mass: 618.19).

356

-continued

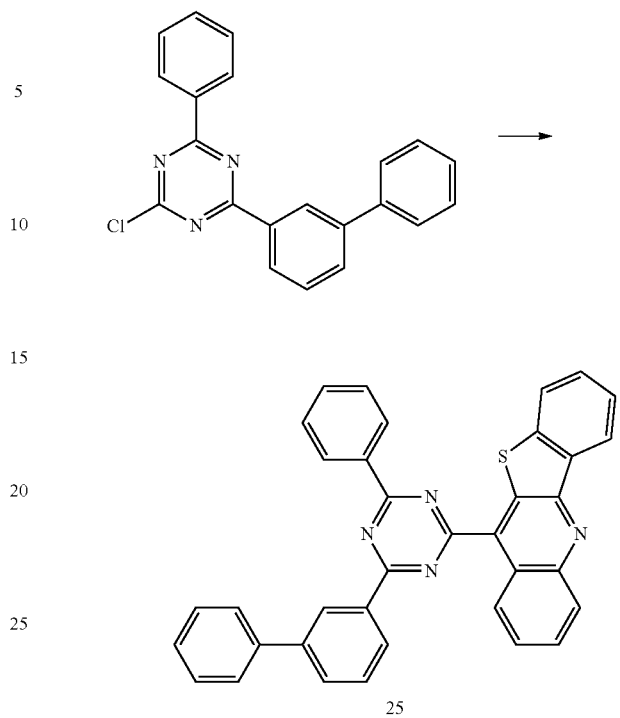

25

The synthesis of compound 3 was repeated except for replacing [3,5-di(carbazol-9-yl)phenyl]boronic acid with intermediate 22-1 and replacing intermediate 1-3 with 2-chloro-4-phenyl-6-(3-phenylphenyl)-1,3,5-triazine to yield compound 25 (60% yield), which was identified by mass spectroscopy (m/e=542 to Exact mass: 542.16).

Compound 26

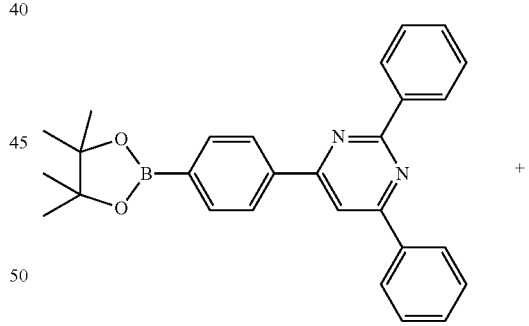

Compound 25

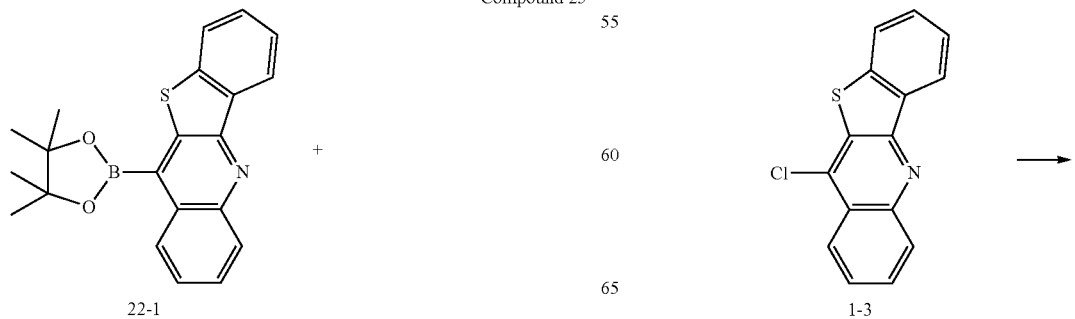

357
-continued

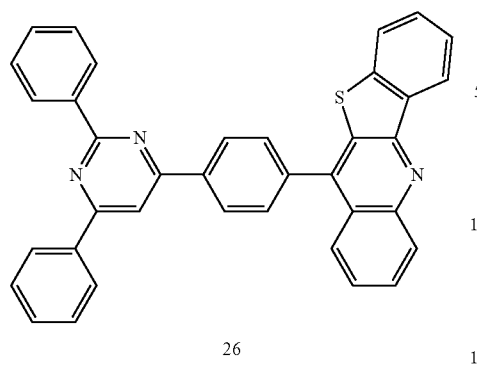

26

The synthesis of compound 3 was repeated except for replacing [3,5-di(carbazol-9-yl)phenyl]boronic acid with 2,4-diphenyl-6-[4-(4,4,5,5-tetramethyl-1,3,2-dioxaborolan-2-yl)phenyl]pyrimidine to yield compound 26 (71% yield), which was identified by mass spectroscopy (m/e=541 to Exact mass: 541.16).

Compound 27

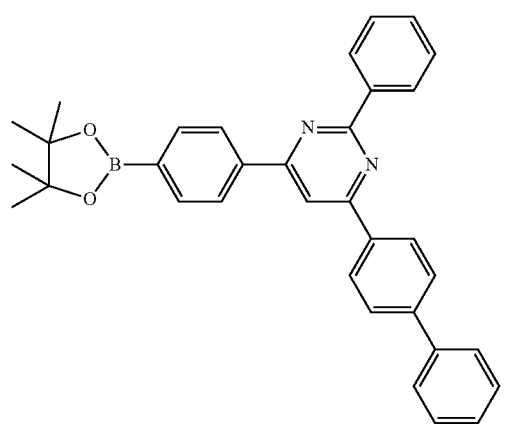

1-3

358
-continued

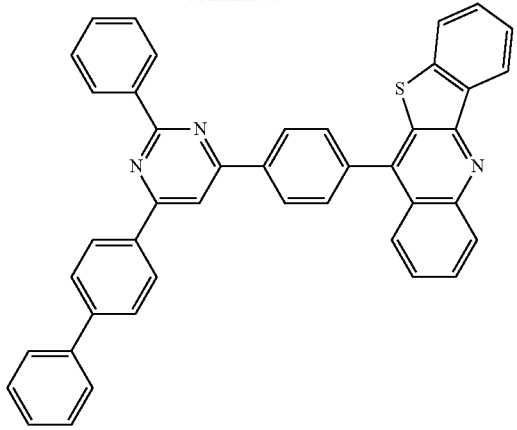

27

The synthesis of compound 3 was repeated except for replacing [3,5-di(carbazol-9-yl)phenyl]boronic acid with 2-phenyl-4-(4-phenylphenyl)-6-[4-(4,4,5,5-tetramethyl-1,3,2-dioxaborolan-2-yl)phenyl]pyrimidine to yield compound 27 (76% yield), which was identified by mass spectroscopy (m/e=617 to Exact mass: 617.19).

Compound 28

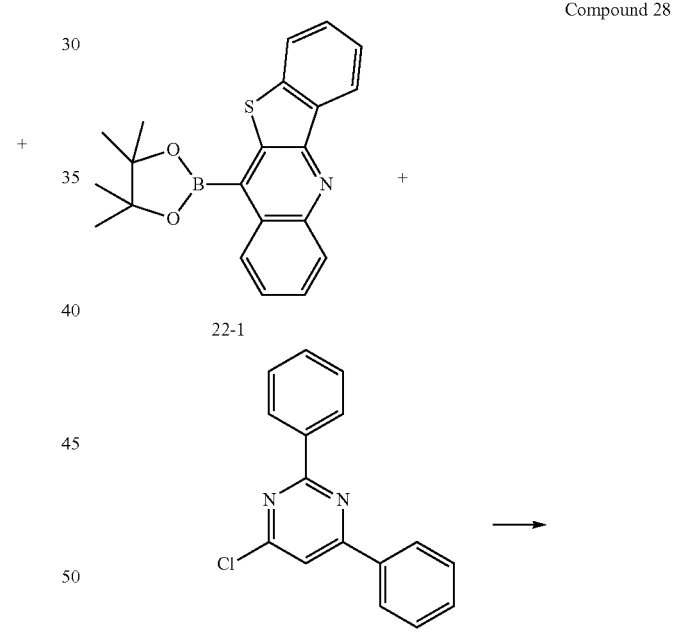

22-1

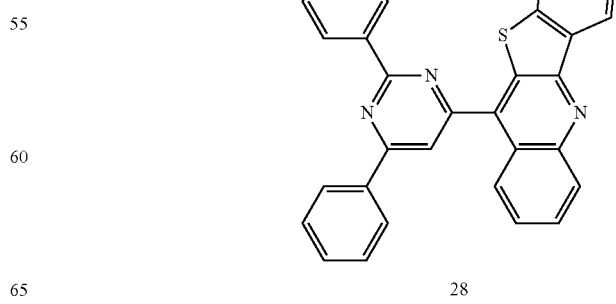

28

The synthesis of compound 3 was repeated except for replacing [3,5-di(carbazol-9-yl)phenyl]boronic acid with intermediate 22-1 and replacing intermediate 1-3 with 4-chloro-2,6-diphenyl-pyrimidine to yield compound 28 (62% yield), which was identified by mass spectroscopy (m/e=465 to Exact mass: 465.13).

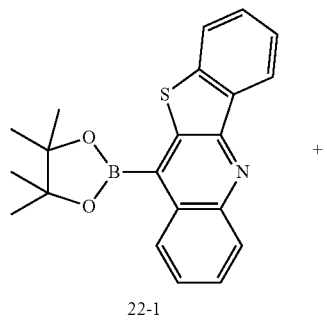

22-1

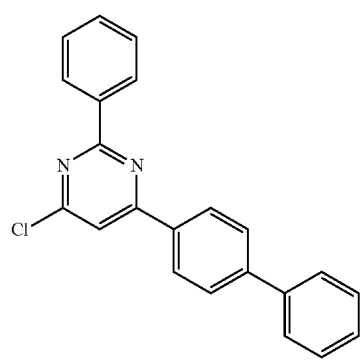

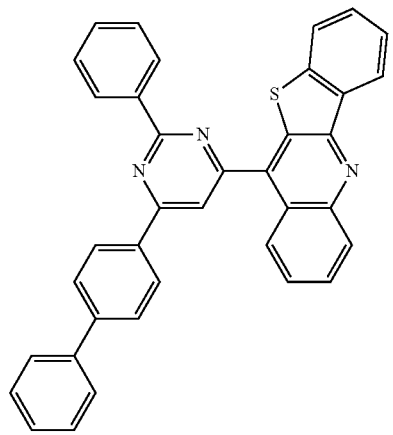

29

The synthesis of compound 3 was repeated except for replacing [3,5-di(carbazol-9-yl)phenyl]boronic acid with intermediate 22-1 and replacing intermediate 1-3 with 4-chloro-2-phenyl-6-(4-phenylphenyl)pyrimidine to yield compound 29 (62% yield), which was identified by mass spectroscopy (m/e=541 to Exact mass: 541.16).

Compound 30

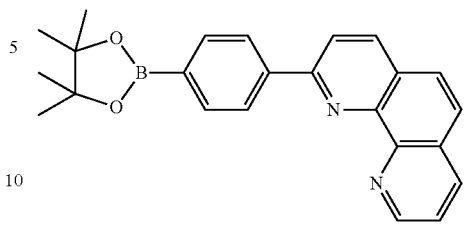

1-3

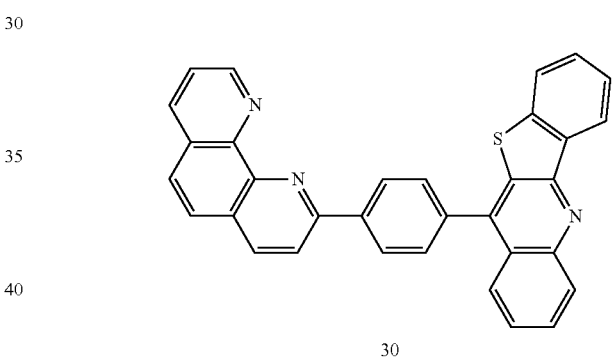

30

The synthesis of compound 3 was repeated except for replacing [3,5-di(carbazol-9-yl)phenyl]boronic acid with 2-[4-(4,4,5,5-tetramethyl-1,3,2-dioxaborolan-2-yl)phenyl]-1,10-phenanthroline to yield compound 30 (51% yield), which was identified by mass spectroscopy (m/e=489 to Exact mass: 489.13).

Compound 31

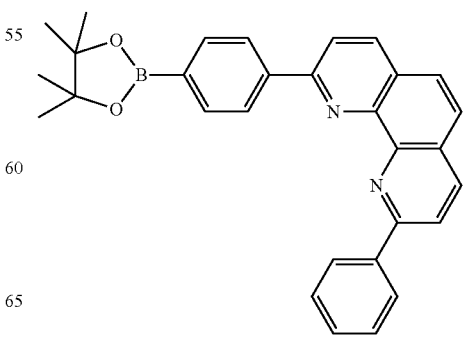

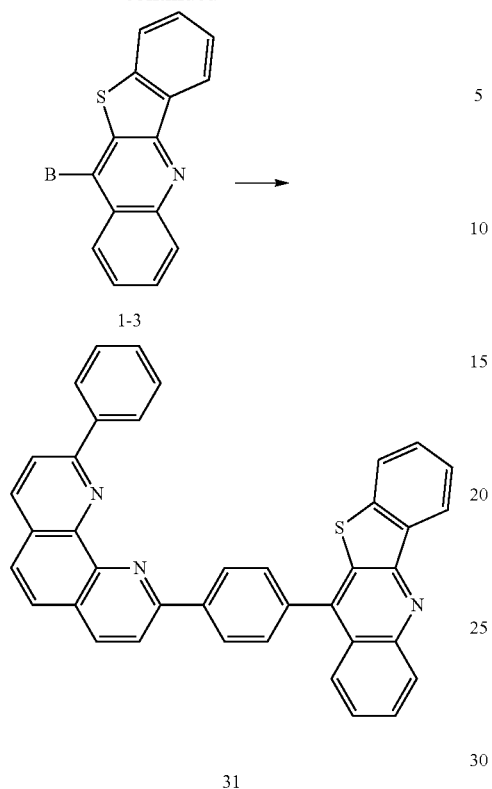

The synthesis of compound 3 was repeated except for replacing [3,5-di(carbazol-9-yl)phenyl]boronic acid with 2-phenyl-9-[4-(4,4,5,5-tetramethyl-1,3,2-dioxaborolan-2-yl)phenyl]-1,10-phenanthroline to yield compound 31 (55% yield), which was identified by mass spectroscopy (m/e=565 to Exact mass: 565.16).

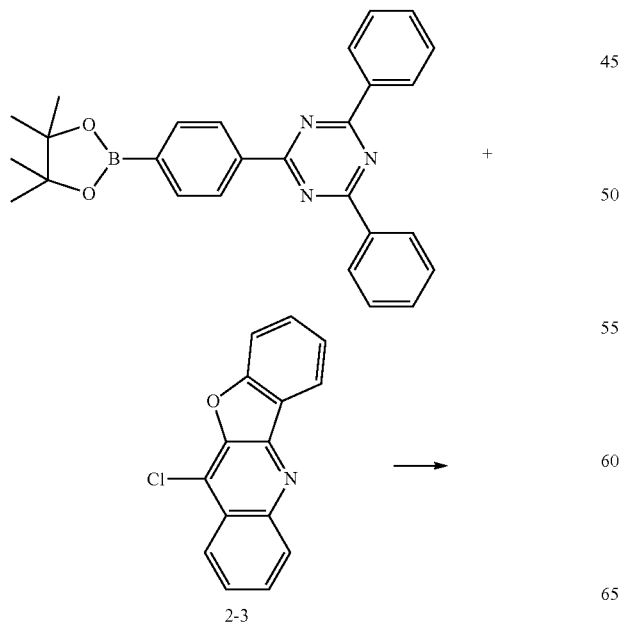

The synthesis of compound 4 was repeated except for replacing [3,5-di(carbazol-9-yl)phenyl]boronic acid with 11-[4-(4,6-diphenyl-1,3,5-triazin-2-yl)phenyl]benzofuro[3,2-b]quinoline to yield compound 32 (70% yield), which was identified by mass spectroscopy (m/e=526 to Exact mass: 526.18).

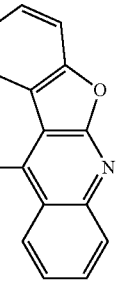

The synthesis of compound 3 was repeated except for replacing [3,5-di(carbazol-9-yl)phenyl]boronic acid with 2,4-diphenyl-6-[4-(4,4,5,5-tetramethyl-1,3,2-dioxaborolan-2-yl)phenyl]-1,3,5-triazine and replacing intermediate 1-3 with intermediate 33-1 to yield compound 33 (60% yield), which was identified by mass spectroscopy (m/e=526 to Exact mass: 526.18). Intermediate 33-1 was synthesized according to Bulletin of the Chemical Society of Japan, 1980, vol. 53, pp. 1057-1060.

Compound 34

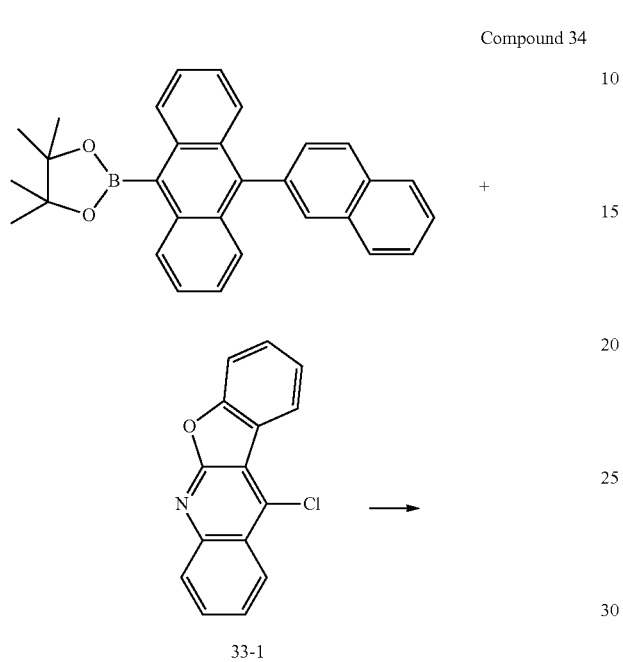

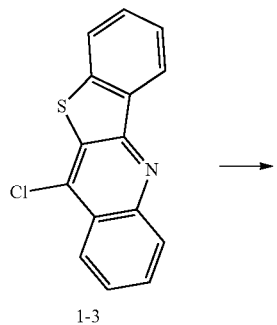

1-3

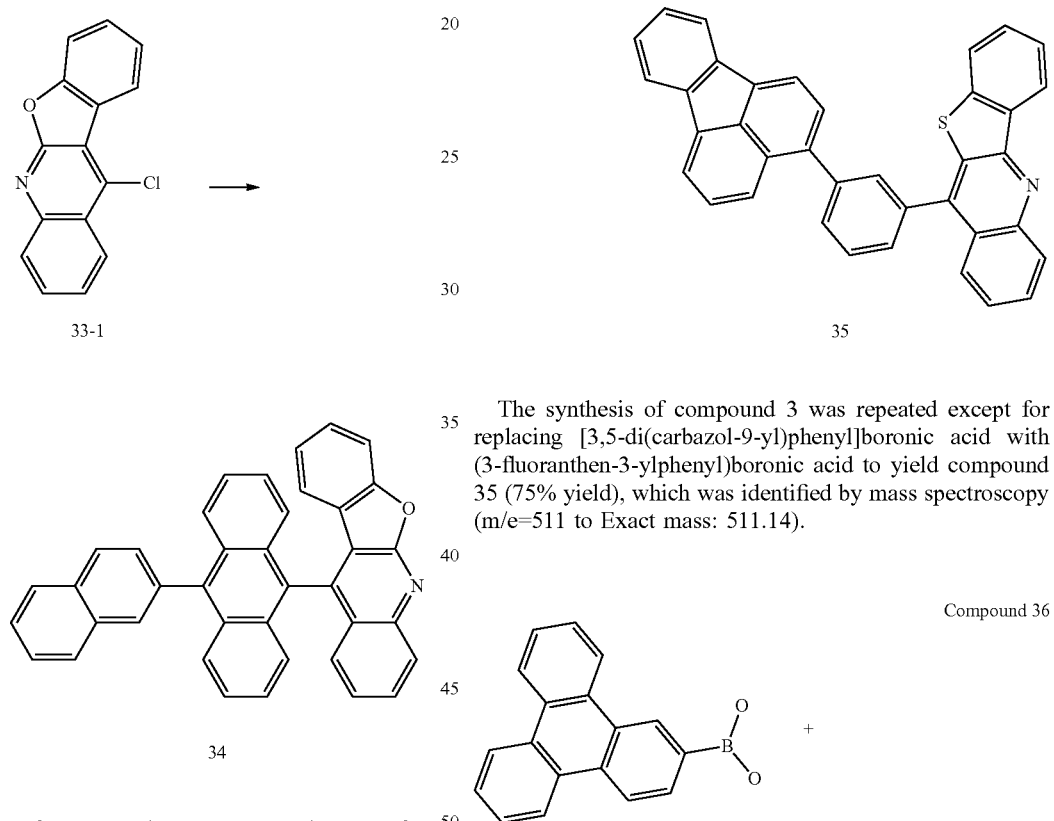

The synthesis of compound 3 was repeated except for replacing [3,5-di(carbazol-9-yl)phenyl]boronic acid with (3-fluoranthen-3-ylphenyl)boronic acid to yield compound 35 (75% yield), which was identified by mass spectroscopy (m/e=511 to Exact mass: 511.14).

The synthesis of compound 6 was repeated except for replacing intermediate 2-3 with intermediate 33-1 to yield compound 34 (56% yield), which was identified by mass spectroscopy (m/e=521 to Exact mass: 521.18).

Compound 35

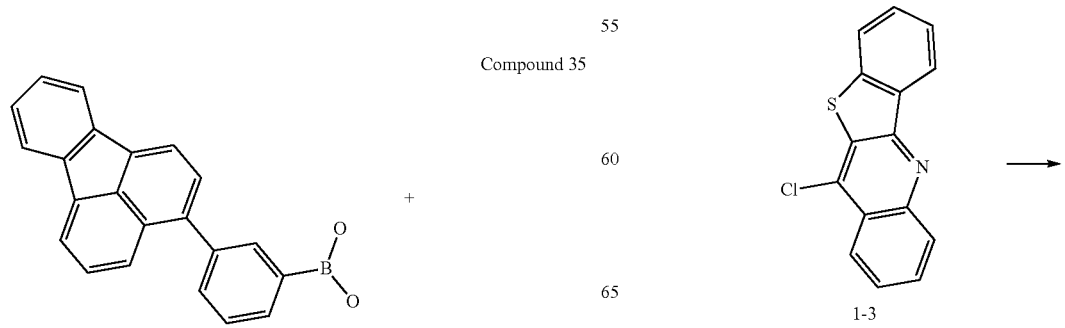

1-3

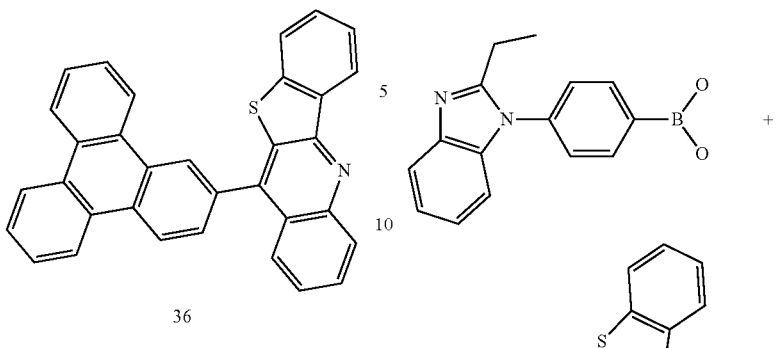

The synthesis of compound 3 was repeated except for replacing [3,5-di(carbazol-9-yl)phenyl]boronic acid with triphenylen-2-ylboronic acid to yield compound 36 (71% yield), which was identified by mass spectroscopy (m/e=461 to Exact mass: 461.12).

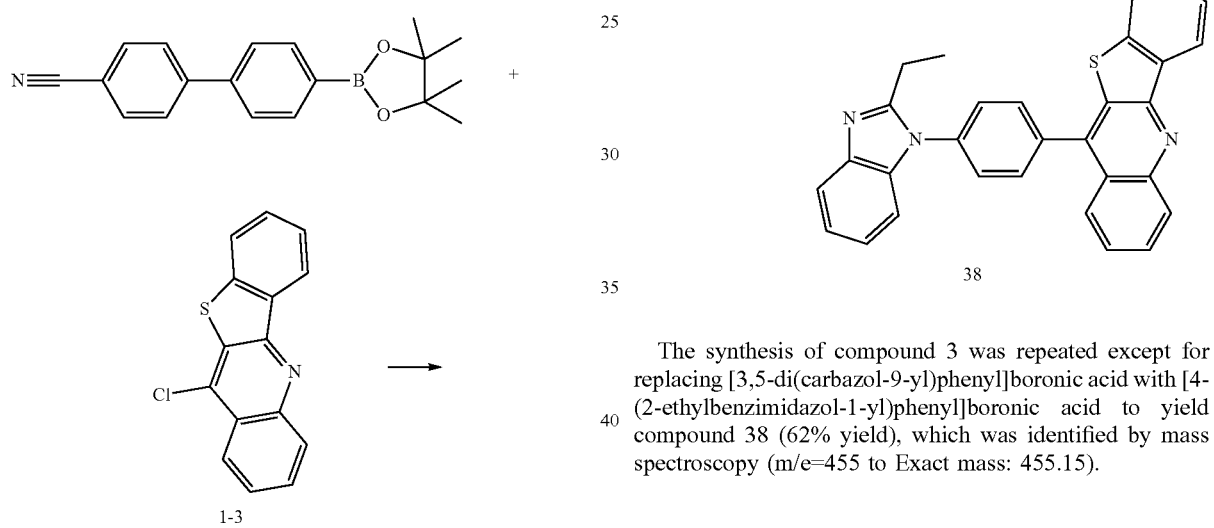

The synthesis of compound 3 was repeated except for replacing [3,5-di(carbazol-9-yl)phenyl]boronic acid with 4-[4-(4,4,5,5-tetramethyl-1,3,2-dioxaborolan-2-yl)phenyl]benzonitrile to yield compound 37 (61% yield), which was identified by mass spectroscopy (m/e=412 to Exact mass: 412.10).

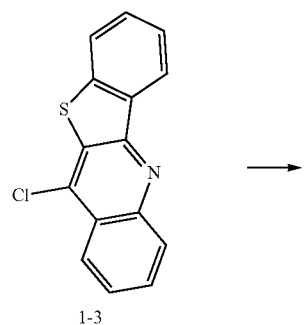

The synthesis of compound 3 was repeated except for replacing [3,5-di(carbazol-9-yl)phenyl]boronic acid with [4-(2-ethylbenzimidazol-1-yl)phenyl]boronic acid to yield compound 38 (62% yield), which was identified by mass spectroscopy (m/e=455 to Exact mass: 455.15).

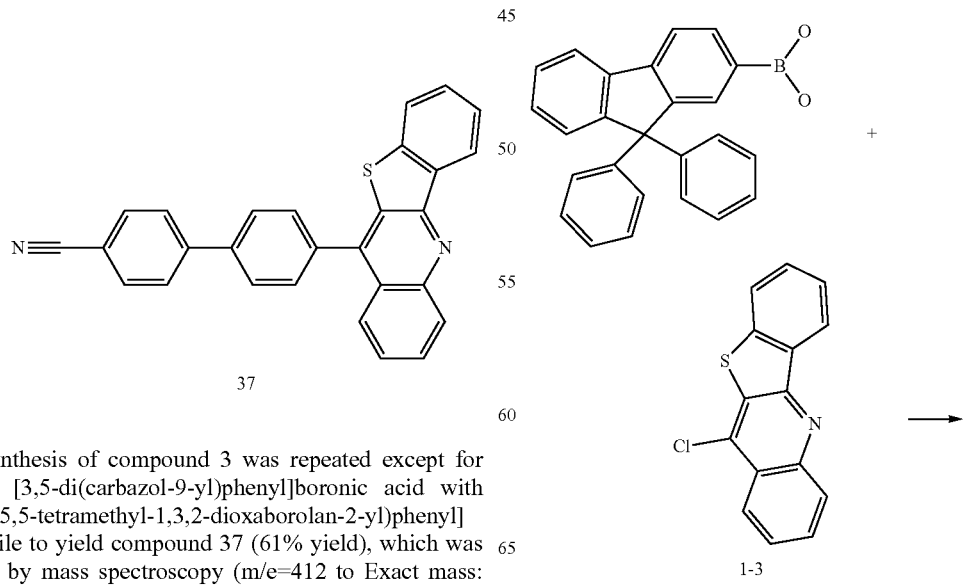

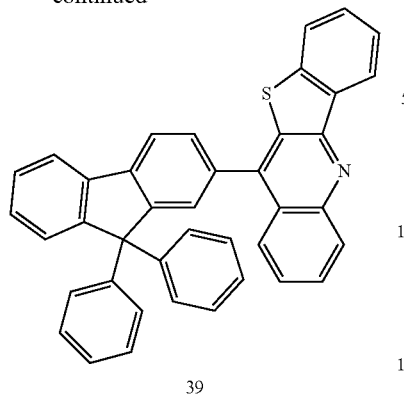

39

The synthesis of compound 3 was repeated except for replacing [3,5-di(carbazol-9-yl)phenyl]boronic acid with (9,9-diphenylfluoren-2-yl)boronic acid to yield compound 39 (71% yield), which was identified by mass spectroscopy (m/e=552 to Exact mass: 551.70).

Intermediate A-1

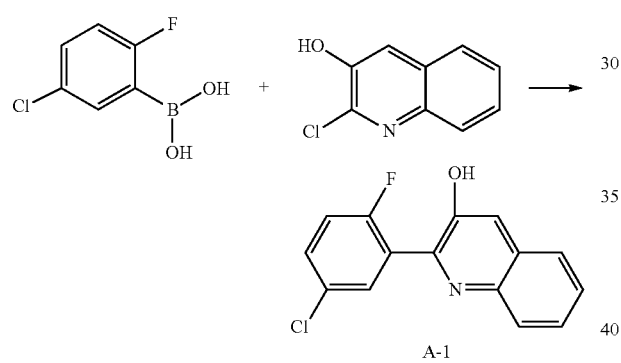

Under an argon atmosphere, a mixture of (5-chloro-2-fluoro-phenyl)boronic acid (9.45 g, 54.2 mmol), 2-chloro-quinolin-3-ol (9.73 g, 54.2 mmol), tetrakis(triphenylphosphine)palladium (1.25 g, 1.08 mmol), toluene (170 mL), and an aqueous solution of sodium carbonate (2M, 80 mL) was stirred for 9 h under refluxing and heating. After cooling to room temperature, the reaction solution was extracted with toluene. After removing the water phase, the organic phase was washed with saturated brine, dried over magnesium sulfate, and then concentrated. The residue was purified by silica gel column chromatography to yield intermediate A-1 (4.90 g, 17.9 mmol, 33% yield).

Intermediate A-2

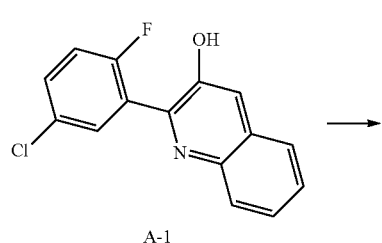

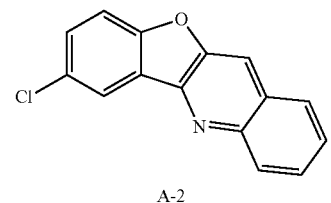

A-2

A mixture of intermediate A-1 (4.90 g, 17.9 mmol), N-methyl-2-pyrrolidinone (60 mL), and $K_2CO_3$ (4.95 g, 35.8 mmol) was stirred at 120° C. for 2 h. After the reaction, the reaction solution was cooled to room temperature, diluted with toluene, washed with water, and then dried over magnesium sulfate. The residue was purified by silica gel column chromatography to yield intermediate A-2 (2.27 g, 8.95 mmol, 50% yield).

Compound ET-5

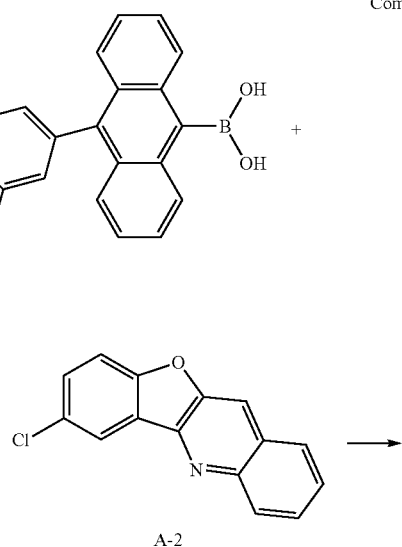

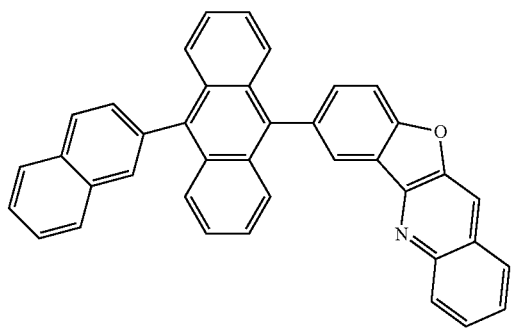

ET-5

The synthesis of compound 3 was repeated except for replacing [3,5-di(carbazol-9-yl)phenyl]boronic acid with [10-(2-naphthyl)-9-anthryl]boronic acid and replacing intermediate 1-3 with intermediate A-2 to yield compound ET-5 (53% yield), which was identified by mass spectroscopy (m/e=521 to Exact mass: 521.18).

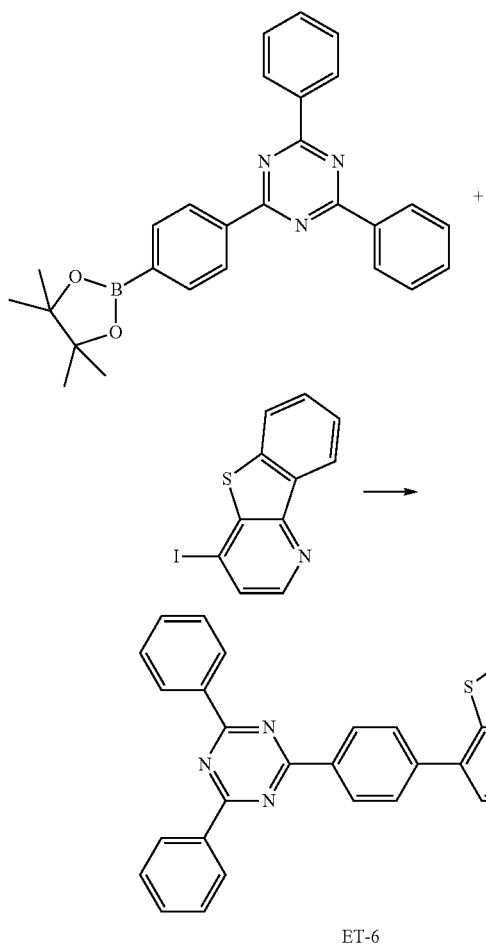

ET-6

The synthesis of compound 3 was repeated except for replacing [3,5-di(carbazol-9-yl)phenyl]boronic acid with 2,4-diphenyl-6-[4-(4,4,5,5-tetramethyl-1,3,2-dioxaborolan-2-yl)phenyl]-1,3,5-triazine and replacing intermediate 1-3 with 4-iodobenzothiopheno[3,2-b]pyridine to yield compound ET-6 (42% yield), which was identified by mass spectroscopy (m/e=492 to Exact mass: 492.14).

II Application Example

Application Example 1

A glass substrate with 120 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improves the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As the first layer, 5 nm-thick of electron accepting compound A was vapor-deposited. Then 220 nm-thick of aromatic amine compound B was applied as hole transporting layer. Then, a mixture of 2% by weight of an emitter compound, (Compound D), 98% by weight of a host (compound 1) was applied to form a 40 nm-thick phosphorescent-emitting layer. On the emitting layer, a mixture of 50% by weight of an electron transporting compound, Compound C, 50% by weight of Liq (8-Hydroxyquinolate lithium) was applied to form a 25 nm-thick electron transport layer. Finally, 1 nm-thick Liq was deposited as an electron injection layer and 80 nm-thick Al was then deposited as a cathode to complete the device. The device was sealed with a glass lid and a getter in an inert nitrogen atmosphere with less than 1 ppm of water and oxygen.

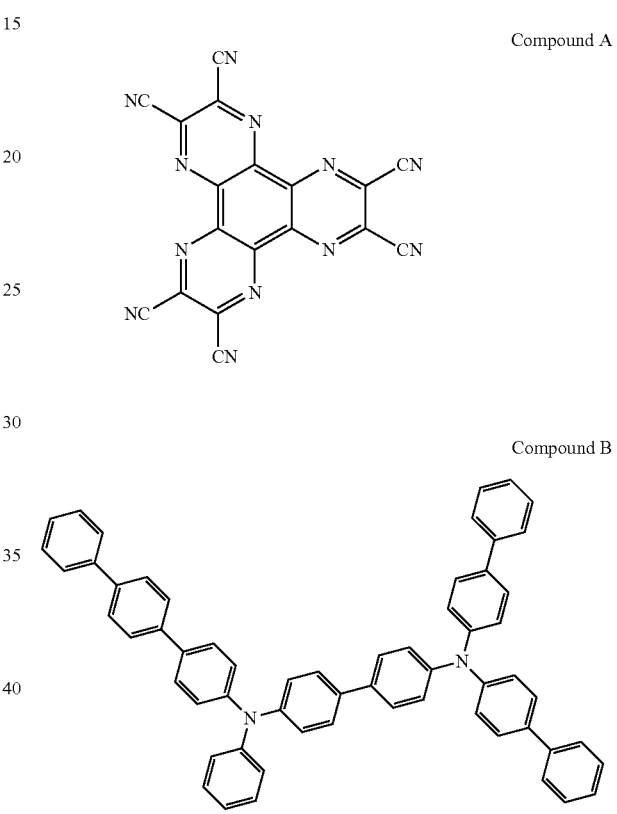

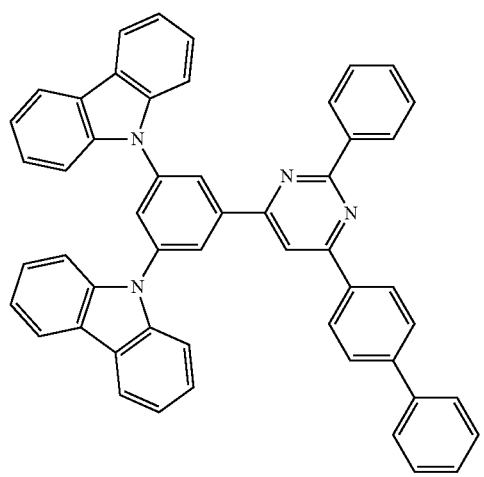

-continued

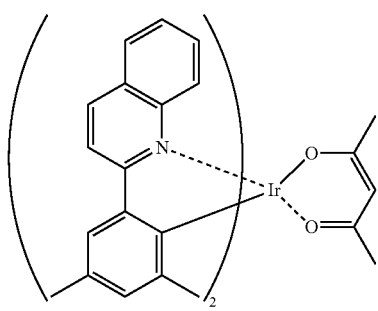
Compound D

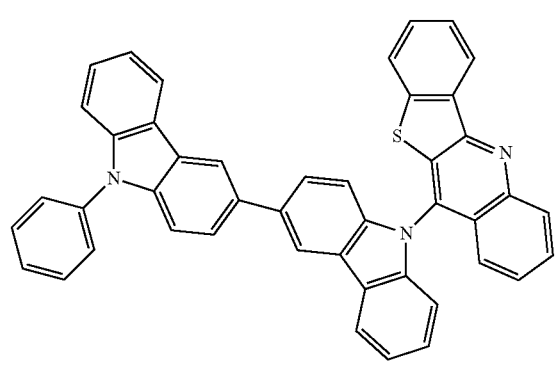
Compound 1

OLED Characterization

To characterize the OLED, electroluminescence spectra were recorded at various currents and voltages. In addition, the current-voltage characteristic was measured in combination with the luminance to determine luminous efficiency and external quantum efficiency (EQE). Driving voltage U, EQE and Commission Internationale de l'Éclairage (CIE) coordinate were given at 10 mA/cm$^2$ except otherwise stated.

Application Example 2

Application Example 1 was repeated except that the host (compound 1) was replaced by compound 2. The device results are shown in Table 1.

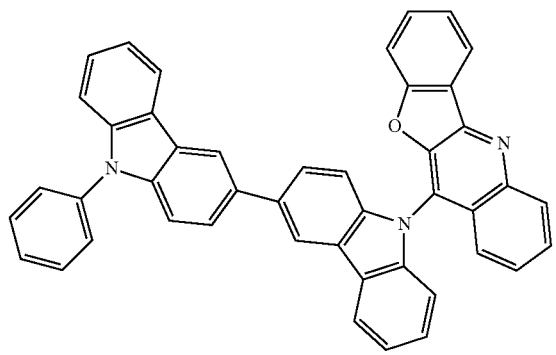
Compound 2

Comparative Examples 1 and 2

Application Example 1 was repeated except that the host (compound 1) was replaced by compound Host-1 (Comparative Example 1) or compound Host-2 (Comparative Example 2). The device results are shown in Table 1

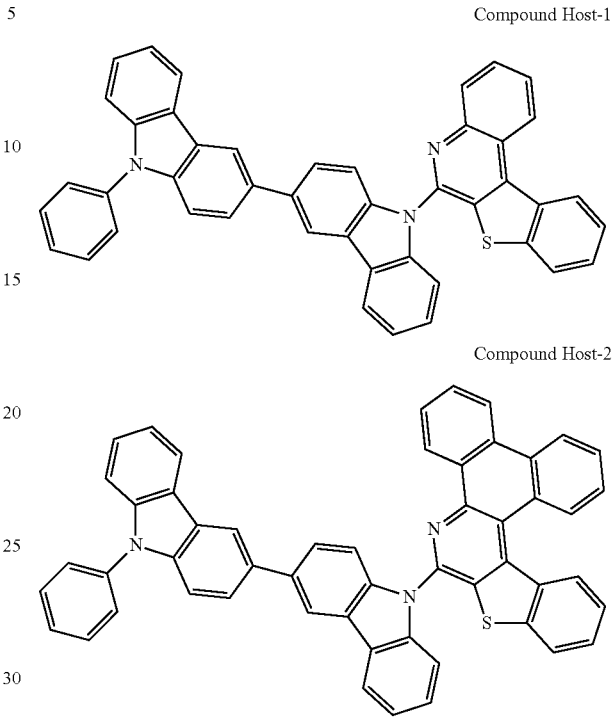
Compound Host-1

Compound Host-2

TABLE 1

| Host | U (V) | EQE (%) | CIE x, y |
|---|---|---|---|
| Appl. Ex. 1 | Compound 1 | 5.1 | 12.6 | 0.65, 0.34 |
| Appl. Ex. 2 | Compound 2 | 5.4 | 15.6 | 0.65, 0.34 |
| Comp. Ex. 1 | Compound Host-1 | 6.12 | 10.2 | 0.65, 0.34 |
| Comp. Ex. 2 | Compound Host-2 | 6.22 | 10.0 | 0.65, 0.34 |

The results are shown in Table 1. The CIE values show that the electroluminescence is originated from the red emitter compound (Ir(piq)$_3$), demonstrating that the compound 1 and 2 can be used as a red phosphorescent hosts. The devices wherein compounds 1 and 2 according to the present invention are used into a phosphorescent-emitting layer as a host exhibit decreased driving voltage and higher EQE as compared to the comparative compounds 1 and 2.

Application Example 3

A glass substrate with 120 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improves the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about 10$^{-6}$-10$^{-8}$ mbar. As a hole injection layer, 5 nm-thick of compound A was applied. Then 90 nm-thick of aromatic amine compound E was applied as a first hole transporting layer, and 10 nm-thick of aromatic amine compound F was applied as a second hole transporting layer. Then, a mixture of 4% by weight of an emitter compound G, 96% by weight of a host compound H were applied to form a 25 nm-thick fluorescent-emitting layer. On the emitting layer, 5 nm-thick compound 1 was applied as a first electron transport layer. Then 20 nm-thick compound I was applied as a second electron transport layer. Finally, 1 nm-thick LiF was deposited as an electron injection layer and 80 nm-thick Al was then deposited as a cathode to complete the device. The device was sealed with a glass lid and a getter in an inert nitrogen atmosphere with less than 1 ppm of water and oxygen.

Compound A

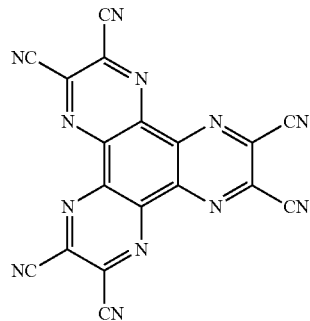

Compound E

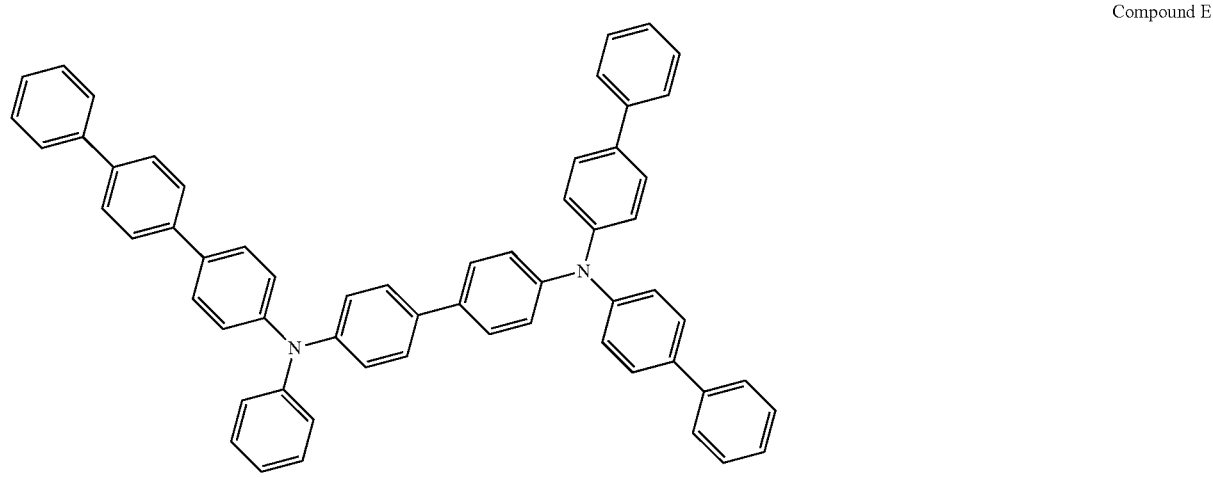

Compound F

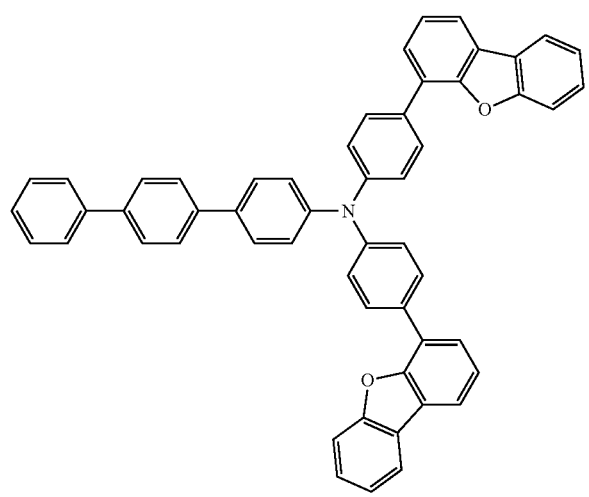

Compound G

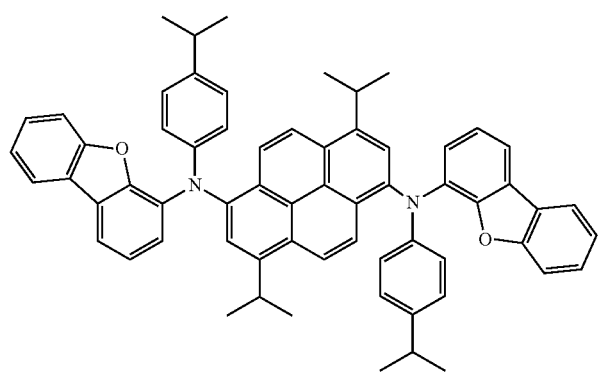

Compound H

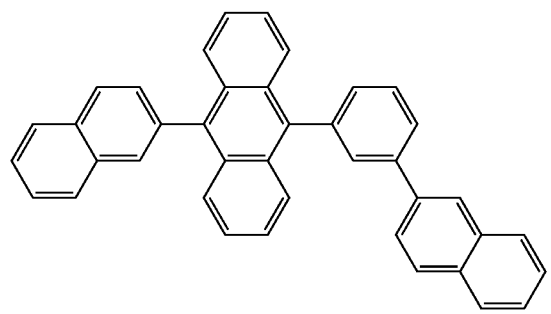

Compound I

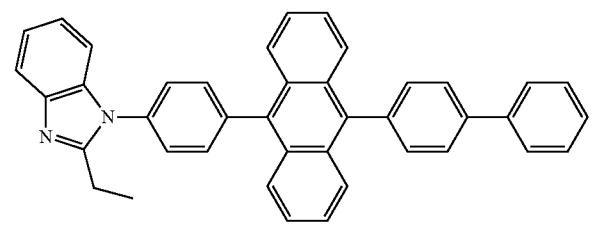

Application Examples 4 to 12

Application Example 3 was repeated except that compound 1 used in the first electron transport layer was replaced by each of compounds 2 to 4 and 35 to 39. The device results are shown in Table 2.

Comparative Examples 3 to 5

Application Example 3 was repeated except that compound 1 used in the first electron transport layer was replaced by compound ET-1, ET-2, or ET-3. The device results are shown in Table 2.

Compound ET-1

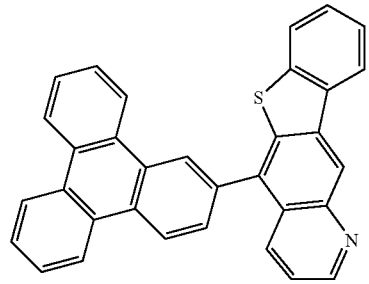

Compound ET-2

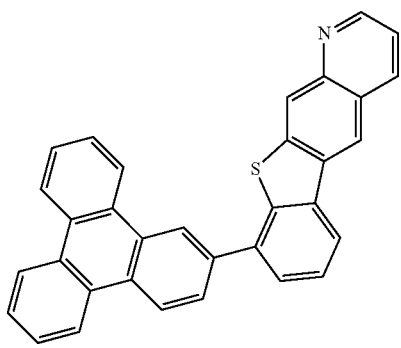

Compound ET-3

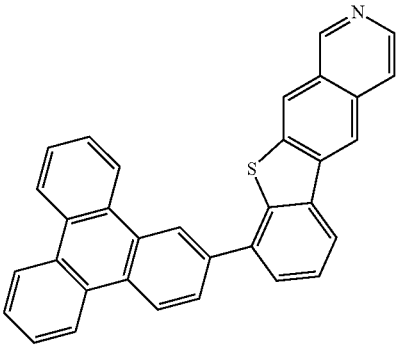

TABLE 2

| | First electron transporting layer | U (V) | EQE (%) | CIE x, y |
|---|---|---|---|---|
| Appl. Ex. 3 | Compound 1 | 3.9 | 8.5 | 0.14, 0.10 |
| Appl. Ex. 4 | Compound 2 | 3.7 | 8.7 | 0.14, 0.10 |
| Appl. Ex. 5 | Compound 3 | 3.9 | 8.7 | 0.14, 0.10 |
| Appl. Ex. 6 | Compound 4 | 3.9 | 9.1 | 0.14, 0.10 |
| Appl. Ex. 7 | Compound 5 | 4.3 | 7.1 | 0.14, 0.10 |
| Appl. Ex. 8 | Compound 35 | 3.60 | 9.31 | 0.14, 0.10 |
| Appl. Ex. 9 | Compound 36 | 4.19 | 8.31 | 0.14, 0.10 |
| Appl. Ex. 10 | Compound 37 | 3.91 | 9.12 | 0.14, 0.10 |
| Appl. Ex. 11 | Compound 38 | 4.02 | 8.95 | 0.14, 0.10 |
| Appl. Ex. 12 | Compound 39 | 4.15 | 8.32 | 0.14, 0.10 |
| Comp. Ex. 3 | Compound ET-1 | 5.21 | 6.42 | 0.14, 0.10 |
| Comp. Ex. 4 | Compound ET-2 | 5.59 | 6.21 | 0.14, 0.10 |
| Comp. Ex. 5 | Compound ET-3 | 5.52 | 6.22 | 0.14, 0.10 |

The results are shown in Table 2. The CIE values show that the electroluminescence is originated from the blue emitter compound G. In addition, application examples 3 to 6 and 8 to 12 show EQEs of more than 8%, which exceeds the theoretical limit of 5%. The results demonstrate that the compounds 1 to 4 and 35 to 39 can overcome the pure theoretical limit of 5% by confining triplet excitons in the emitting layer, which enhances triplet-triplet fusion.

Application Example 13

The process proceeded similar to Example 3. After putting the emitting layer, on the emitting layer, a mixture of 50% by weight of Compound 6, 50% by weight of Liq was applied to form a 25 nm-thick as an electron transporting layer. Finally, 1 nm-thick Liq was deposited as an electron injection layer and 80 nm-thick Al was then deposited as a cathode to complete the device. The device was sealed with a glass lid and a getter in an inert nitrogen atmosphere with less than 1 ppm of water and oxygen.

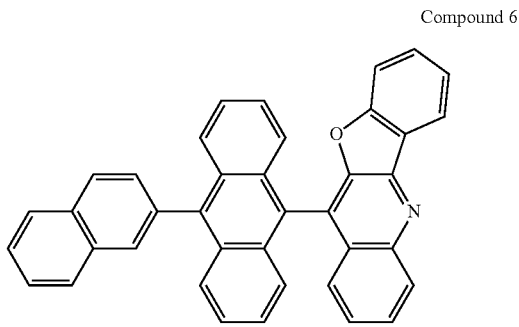 [SMILES: c1ccc2cc(-c3c4ccccc4c(-c4c5ccccc5nc5c4oc4ccccc45)c4ccccc34)ccc2c1]

Compound 6

Application Examples 14 to 16

Application Example 13 was repeated except that the host (compound 6) was replaced by compound 30, 31, or 32. The device results are shown in Table 3.

Comparative Examples 6 and 7

Application Example 13 was repeated except that the host (compound 6) was replaced by Compound ET-4 (Comparative Example 6) or Compound ET-5 (Comparative Example 7). The device results are shown in Table 3.

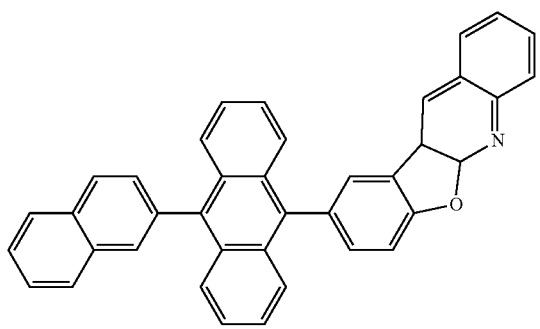

Compound ET-4

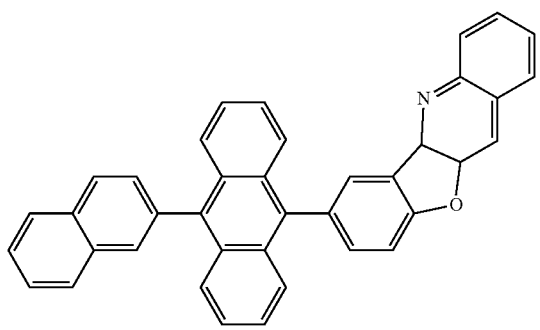

Compound ET-5

TABLE 3

|  | Electron transporting layer | U (V) | EQE (%) | CIE x, y |
|---|---|---|---|---|
| Appl. Ex. 13 | Compound 6 + Liq | 3.90 | 8.37 | 0.14, 0.10 |
| Appl. Ex. 14 | Compound 30 + Liq | 3.84 | 8.28 | 0.14, 0.10 |
| Appl. Ex. 15 | Compound 31 + Liq | 3.85 | 8.26 | 0.14, 0.10 |
| Appl. Ex. 16 | Compound 34 + Liq | 3.91 | 8.32 | 0.14, 0.10 |
| Comp. Ex. 6 | Compound ET-4 + Liq | 4.32 | 7.61 | 0.14, 0.10 |
| Comp. Ex. 7 | Compound ET-5 + Liq | 4.30 | 7.64 | 0.14, 0.10 |

The results are shown in Table 3. The device wherein materials according to the present invention are used into an electron transporting layer exhibit decreased driving voltage and higher EQE as compared to the existing material.

Application Example 17

The process proceeded similar to Example 3. After putting the emitting layer, on the emitting layer, 5 nm-thick compound J was applied as a first electron transport layer. Then a mixture of 50% by weight of Compound 5, 50% by weight of Liq was applied to form a 20 nm-thick as a second electron transporting layer. Finally, 1 nm-thick Liq was deposited as an electron injection layer and 80 nm-thick Al was then deposited as a cathode to complete the device. The device was sealed with a glass lid and a getter in an inert nitrogen atmosphere with less than 1 ppm of water and oxygen.

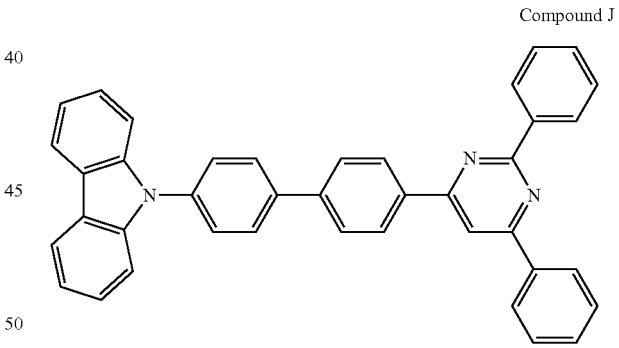

Compound J

Application Examples 18 to 42

Application Example 17 was repeated except that compound 5 was replaced by each of compounds shown in Table 4. The device results are shown in Table 4.

Comparative Examples 8 and 9

Application Example 17 was repeated except that compound 5 was replaced by Compound ET-6 (Comparative Example 8) or Compound ET-7 (Comparative Example 9). The device results are shown in Table 4.

Compound ET-6

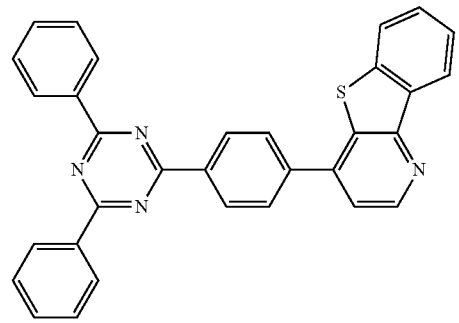

Compound ET-7

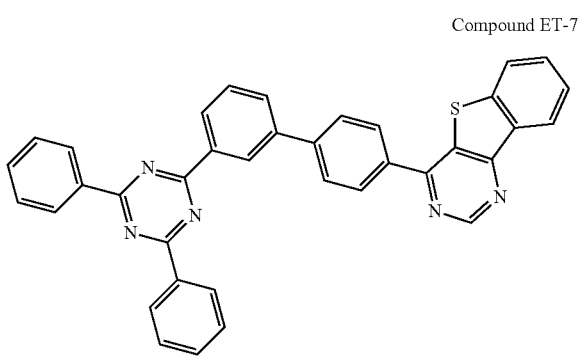

TABLE 4

| | Second electron transporting layer | U (V) | EQE (%) | CIE x, y |
|---|---|---|---|---|
| Appl. Ex. 17 | Compound 5 + Liq | 3.48 | 9.63 | 0.14, 0.10 |
| Appl. Ex. 18 | Compound 7 + Liq | 3.32 | 9.99 | 0.14, 0.10 |
| Appl. Ex. 19 | Compound 8 + Liq | 3.31 | 10.1 | 0.14, 0.10 |

TABLE 4-continued

| | Second electron transporting layer | U (V) | EQE (%) | CIE x, y |
|---|---|---|---|---|
| Appl. Ex. 20 | Compound 9 + Liq | 3.33 | 9.85 | 0.14, 0.10 |
| Appl. Ex. 21 | Compound 10 + Liq | 3.32 | 9.98 | 0.14, 0.10 |
| Appl. Ex. 22 | Compound 11 + Liq | 3.45 | 9.71 | 0.14, 0.10 |
| Appl. Ex. 23 | Compound 12 + Liq | 3.35 | 9.79 | 0.14, 0.10 |
| Appl. Ex. 24 | Compound 13 + Liq | 3.36 | 9.81 | 0.14, 0.10 |
| Appl. Ex. 25 | Compound 14 + Liq | 3.45 | 9.71 | 0.14, 0.10 |
| Appl. Ex. 26 | Compound 15 + Liq | 3.49 | 9.71 | 0.14, 0.10 |
| Appl. Ex. 27 | Compound 16 + Liq | 3.40 | 9.73 | 0.14, 0.10 |
| Appl. Ex. 28 | Compound 17 + Liq | 3.40 | 9.69 | 0.14, 0.10 |
| Appl. Ex. 29 | Compound 18 + Liq | 3.43 | 9.61 | 0.14, 0.10 |
| Appl. Ex. 30 | Compound 19 + Liq | 3.48 | 9.69 | 0.14, 0.10 |
| Appl. Ex. 31 | Compound 20 + Liq | 3.32 | 10.0 | 0.14, 0.10 |
| Appl. Ex. 32 | Compound 21 + Liq | 3.32 | 9.90 | 0.14, 0.10 |
| Appl. Ex. 33 | Compound 22 + Liq | 3.49 | 9.72 | 0.14, 0.10 |
| Appl. Ex. 34 | Compound 23 + Liq | 3.45 | 9.81 | 0.14, 0.10 |
| Appl. Ex. 35 | Compound 24 + Liq | 3.45 | 9.81 | 0.14, 0.10 |
| Appl. Ex. 36 | Compound 25 + Liq | 3.47 | 9.75 | 0.14, 0.10 |
| Appl. Ex. 37 | Compound 26 + Liq | 3.45 | 9.72 | 0.14, 0.10 |
| Appl. Ex. 38 | Compound 27 + Liq | 3.41 | 9.75 | 0.14, 0.10 |
| Appl. Ex. 39 | Compound 28 + Liq | 3.49 | 9.75 | 0.14, 0.10 |
| Appl. Ex. 40 | Compound 29 + Liq | 3.48 | 9.81 | 0.14, 0.10 |
| Appl. Ex. 41 | Compound 32 + Liq | 3.38 | 9.91 | 0.14, 0.10 |
| Appl. Ex. 42 | Compound 33 + Liq | 3.38 | 9.92 | 0.14, 0.10 |
| Comp. Ex. 8 | Compound ET-6 + Liq | 4.05 | 7.96 | 0.14, 0.10 |
| Comp. Ex. 9 | Compound ET-7 + Liq | 3.86 | 8.15 | 0.14, 0.10 |

The results are shown in Table 4. The devices wherein compounds according to the present invention are used into a second electron transporting layer exhibit decreased driving voltage and higher EQE as compared with comparative compounds ET-6 and ET-7.

Reference Example

The following compounds were computed for LUMO by a molecular orbital method using Gaussian98 at the B3LYP/6-31G* level.

TABLE 5

| Compound | LUMO (eV) |
|---|---|
| Invention | 2.0607 |

TABLE 5-continued

| Compound | | LUMO (eV) |
|---|---|---|
| 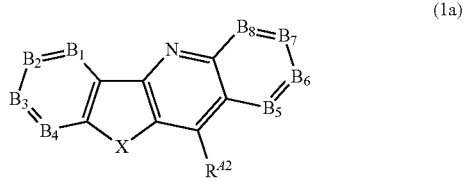 | Invention | 2.0115 |
| 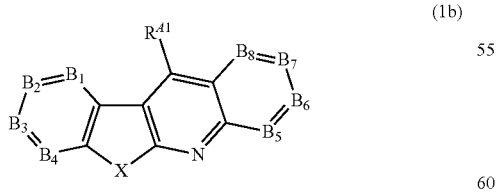 | Comparison | 1.9059 |

The results of Table 5 demonstrate that the compounds according to the present invention have LUMO about 5.5% or 8.1% higher than that of the comparative compound that is isomeric to the inventive compounds. The large LUMO of the inventive compounds may allow an optimum amount of electron to be injected into an adjacent layer, thereby improving the carrier balance in a light emitting layer to give an organic EL device.

The invention claimed is:

1. A heterocyclic derivative of formula (1a) or (1b)

(1a)

(1b)

wherein
X is O or S;
$B_1$ is $CR^1$;
$B_2$ is CH;
$B_3$ is $CR^3$;
$B_4$ is $CR^4$;
$B_5$ is $CR^5$;
$B_6$ is $CR^6$;
$B_7$ is $CR^7$;
$B_8$ is $CR^8$;

$R^1$, $R^3$, $R^4$, $R^5$, $R^6$, $R^7$, and $R^8$ are independently of each other H; E; a group of formula -$(A^1)_o$-$(A^2)_p$-$(A^3)_q$-$(A^4)_r$-$R^{20}$; or a $C_1$-$C_{25}$alkyl group, which is unsubstituted or substituted by at least one group E and/or interrupted by D;

wherein o is 0 or 1, p is 0 or 1, q is 0 or 1, r is 0 or 1 in the formula -$(A^1)_o$-$(A^2)_p$-$(A^3)_q$-$(A^4)_r$-$R^{20}$ for $R^1$, $R^3$, $R^4$, $R^5$, $R^6$, $R^7$, and $R^8$;

$R^{41}$ is a group of formula -$(A^1)_o$-$(A^2)_p$-$(A^3)_q$-$(A^4)_r$-$R^{20}$, wherein o is 1, p is 0 or 1, q is 0 or 1, r is 0 or 1 in the formula -$(A^1)_o$-$(A^2)_p$-$(A^3)_q$-$(A^4)_r$-$R^{20}$ for $R^{41}$;

$R^{42}$ is selected from group consisting of

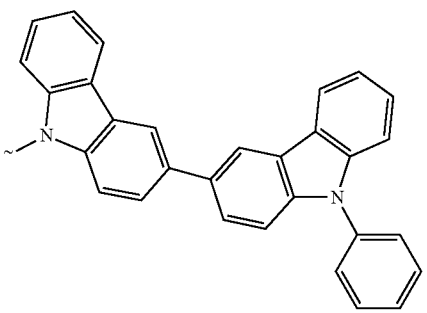

383
-continued
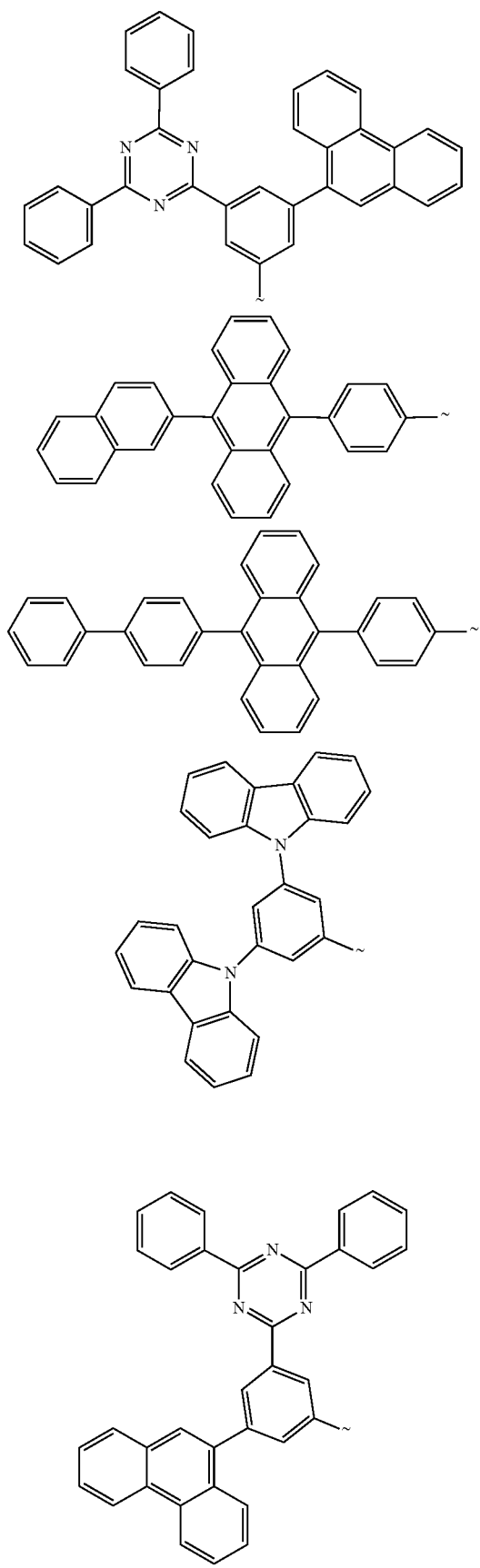
384
-continued
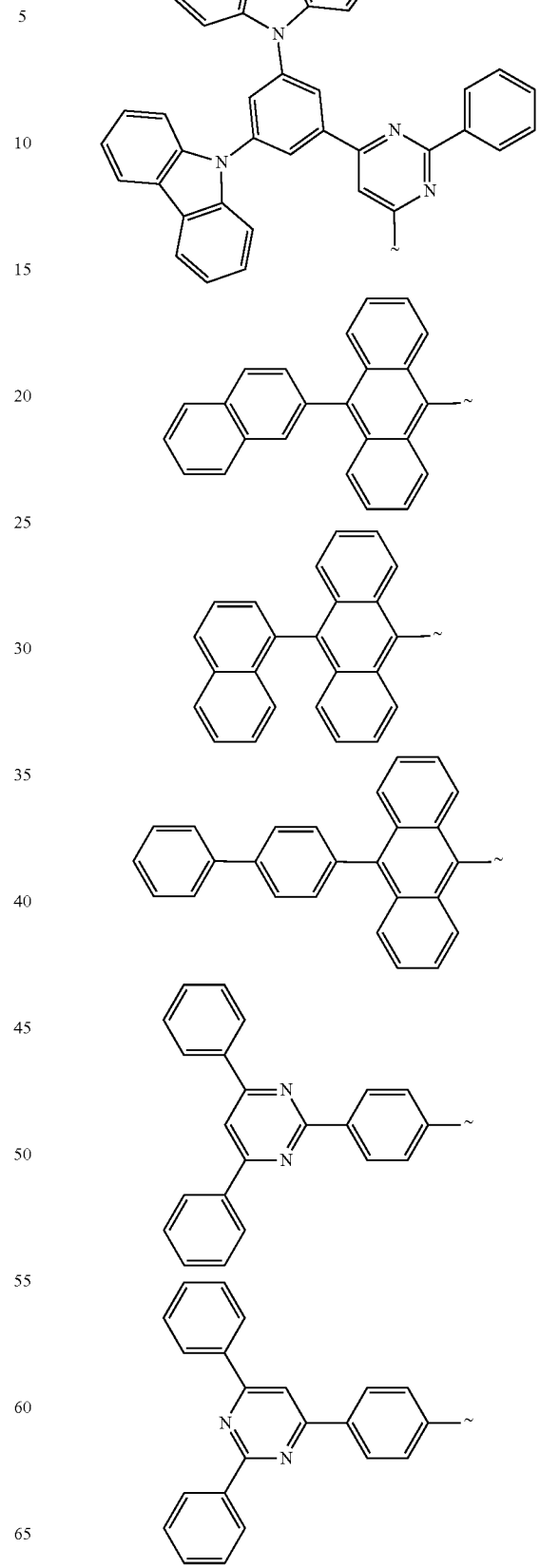

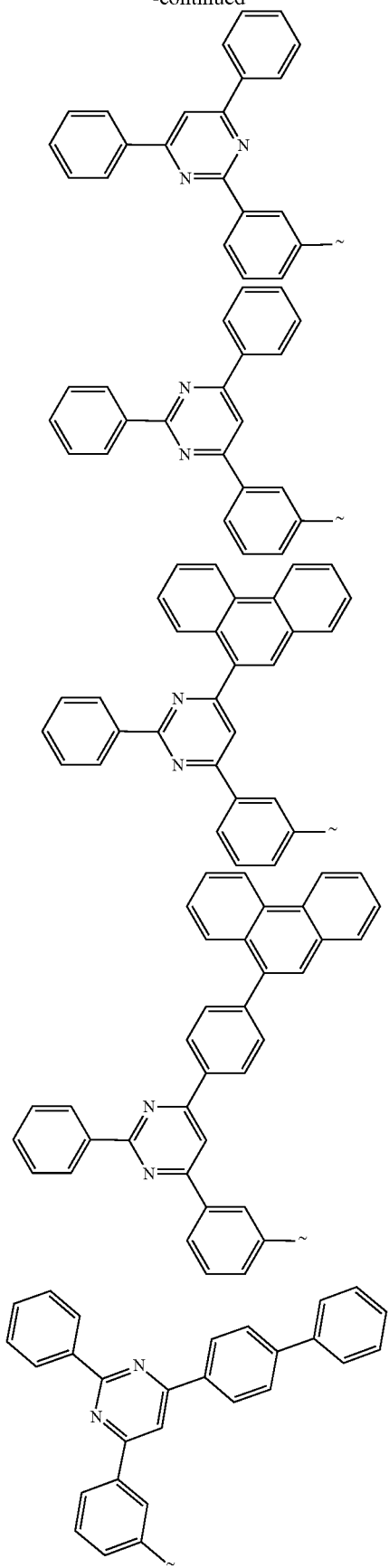
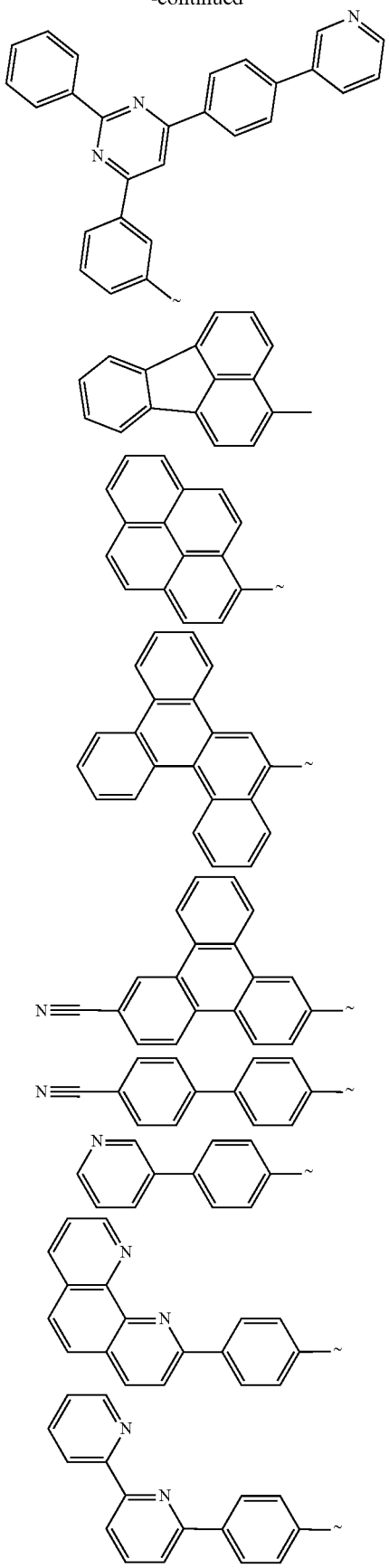

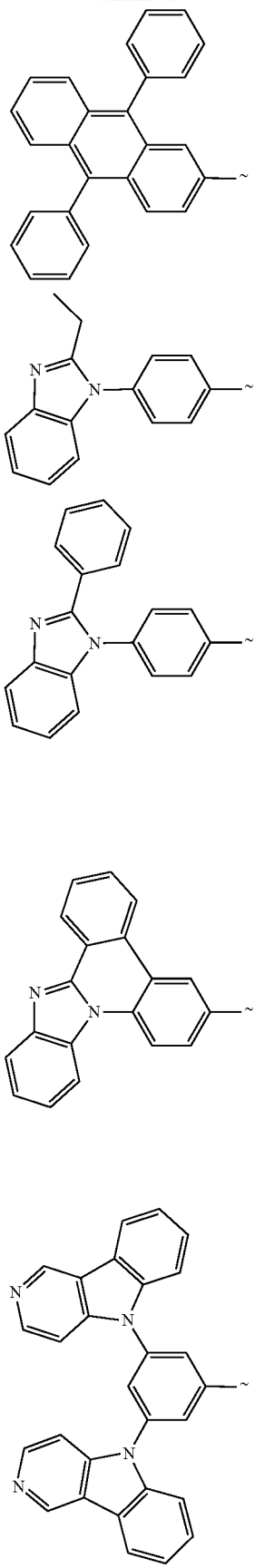
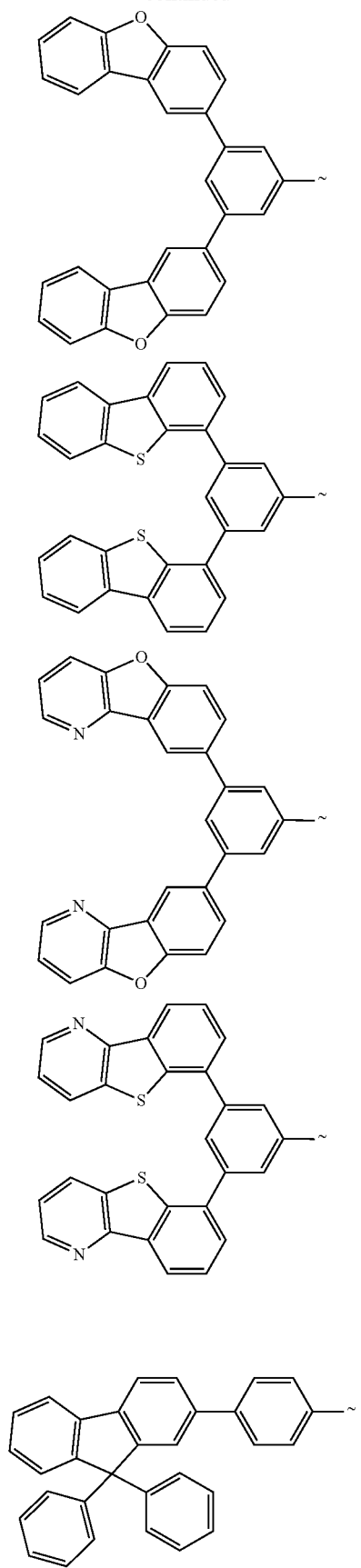

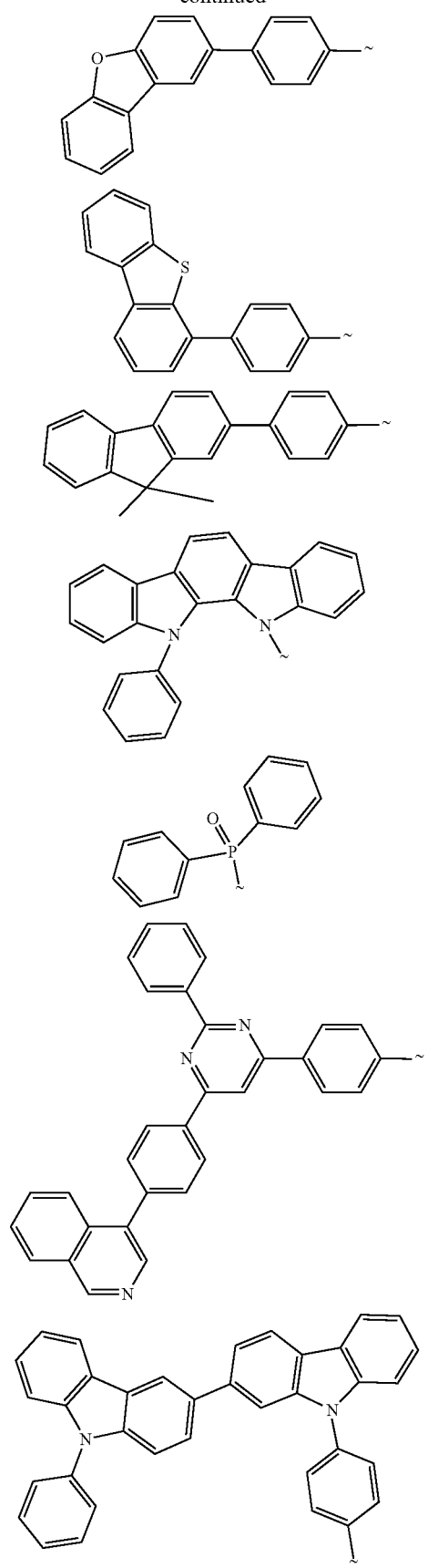
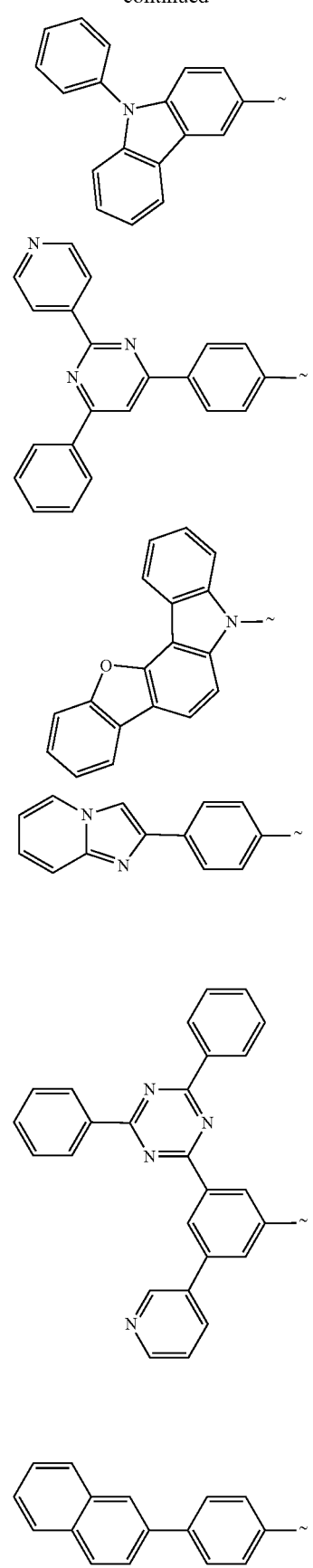

391
-continued
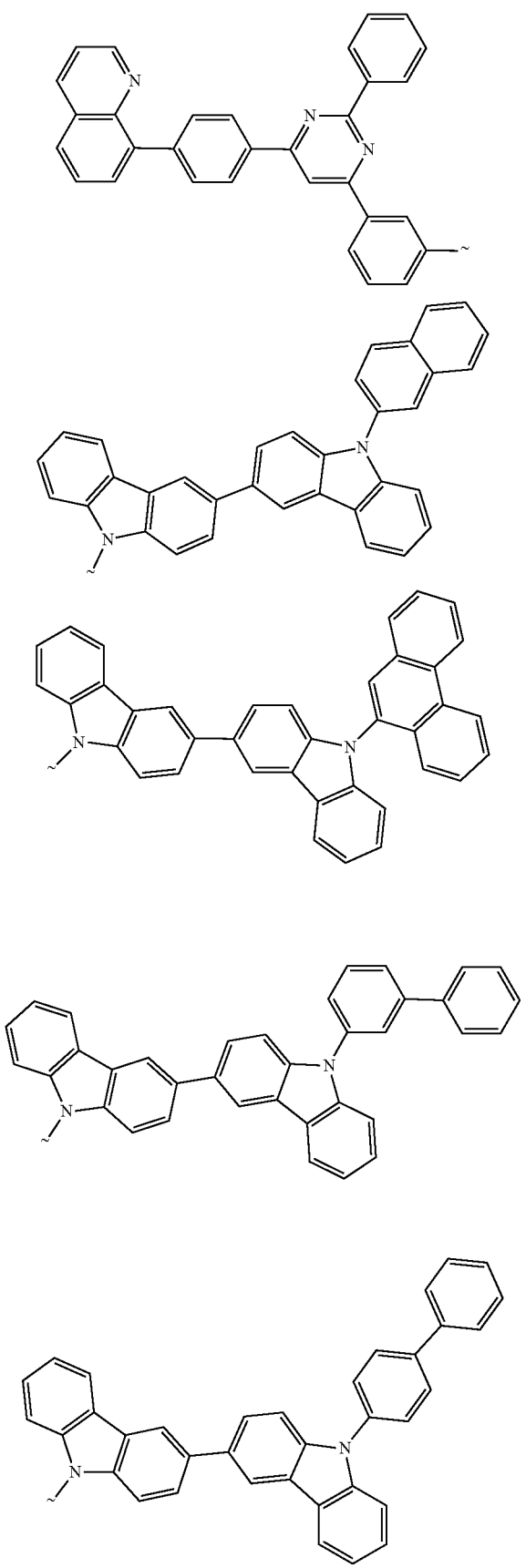
392
-continued
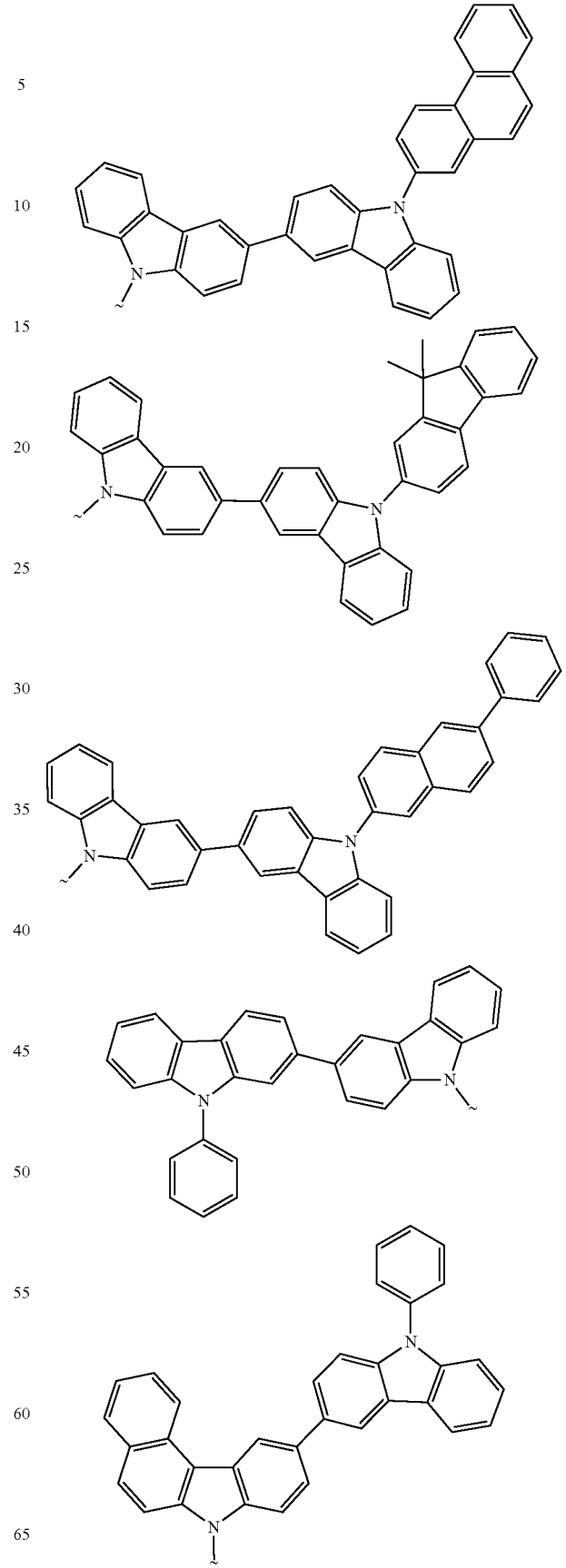

393
-continued
394
-continued
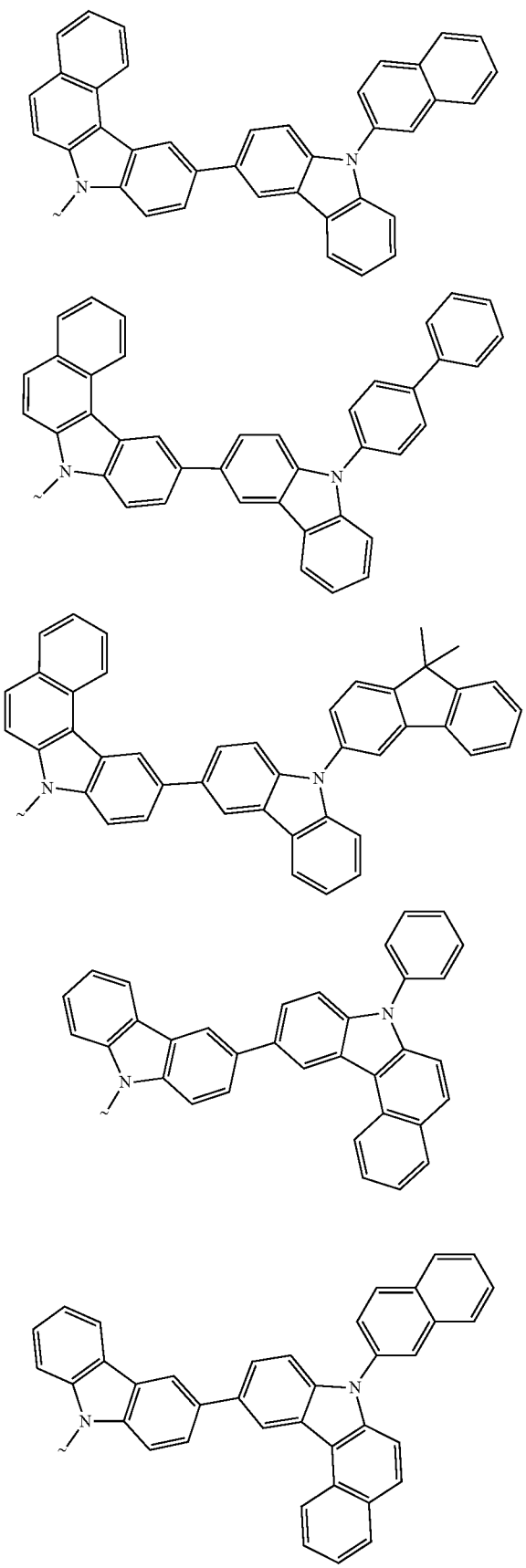
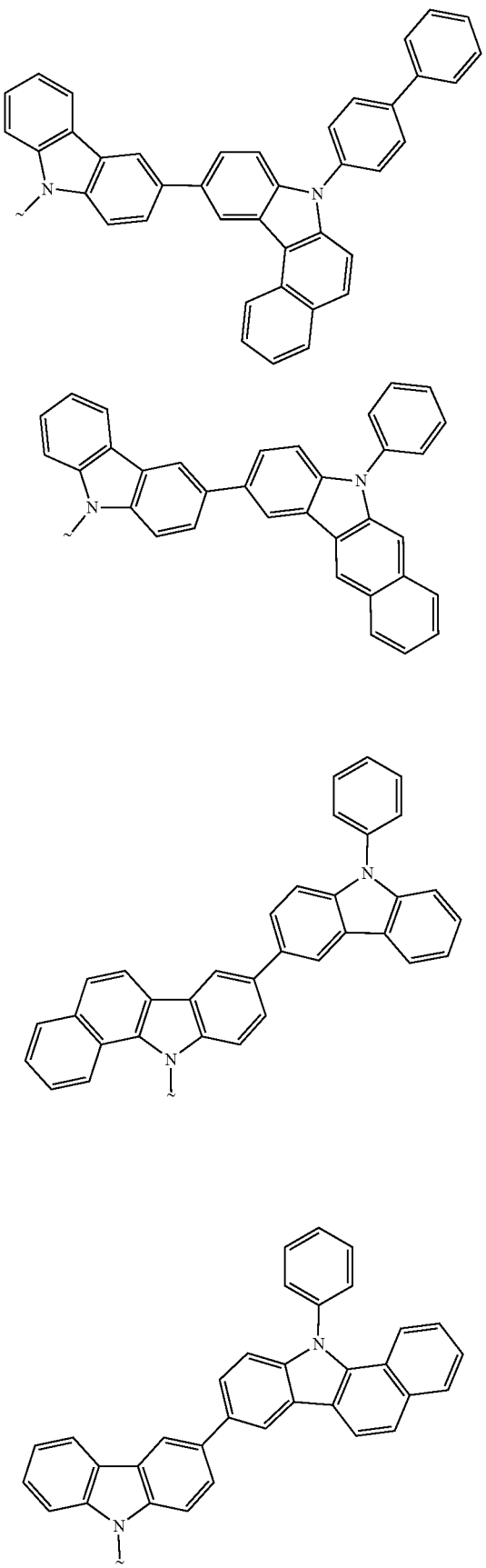

395
-continued
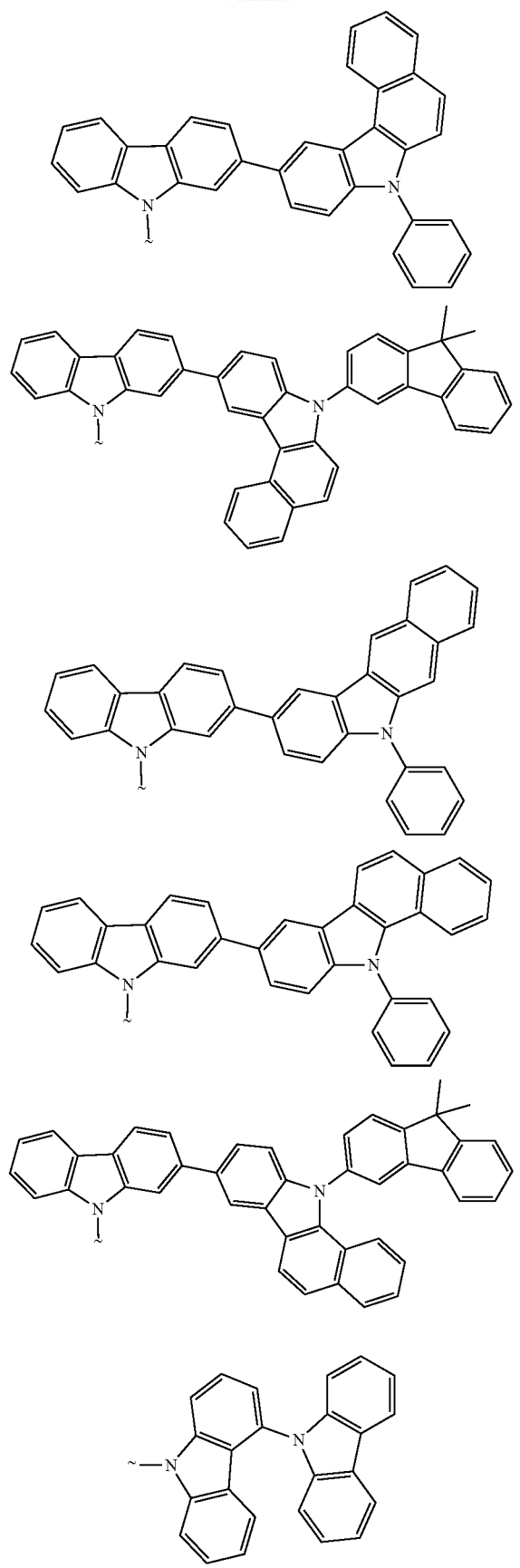
396
-continued
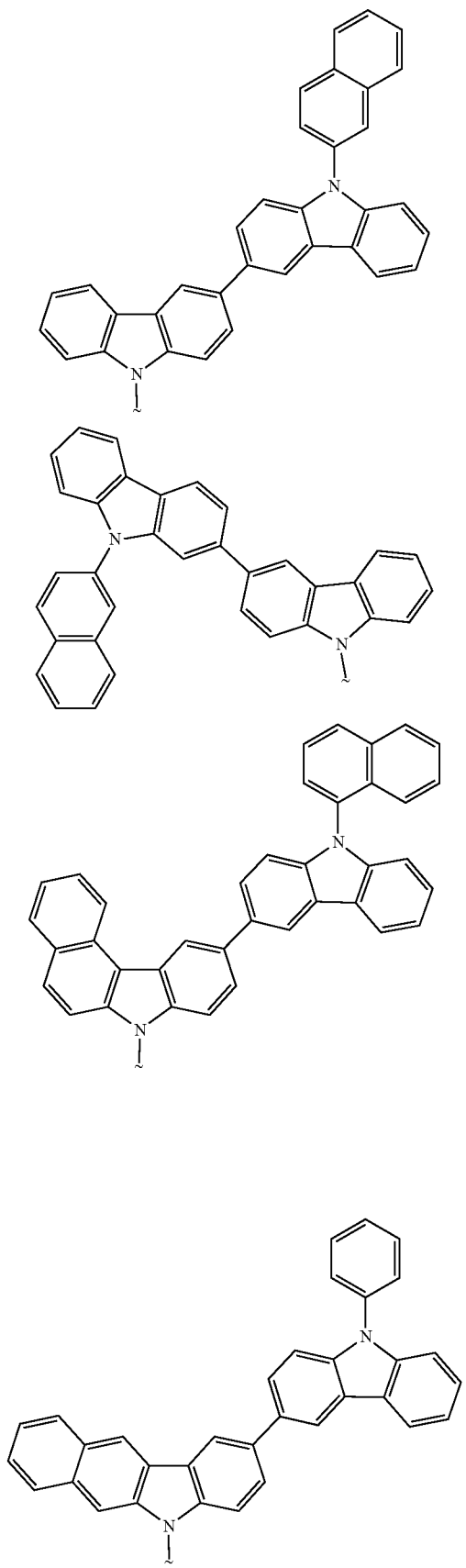

397
-continued
398
-continued
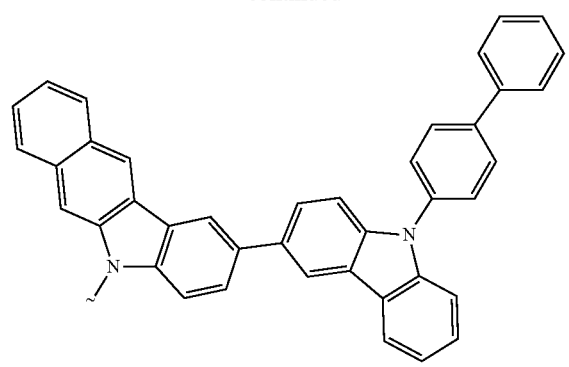
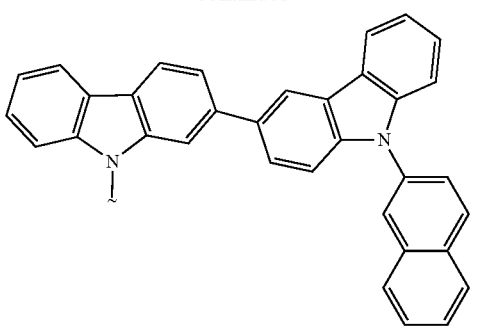
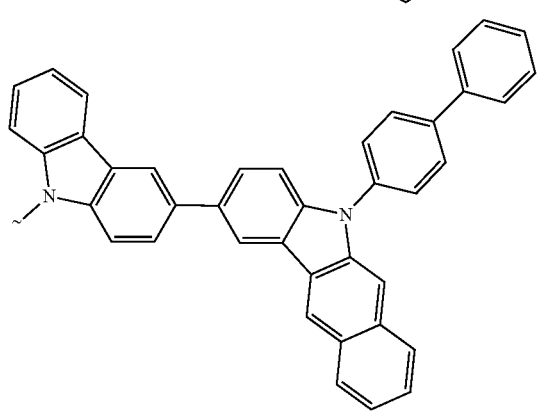
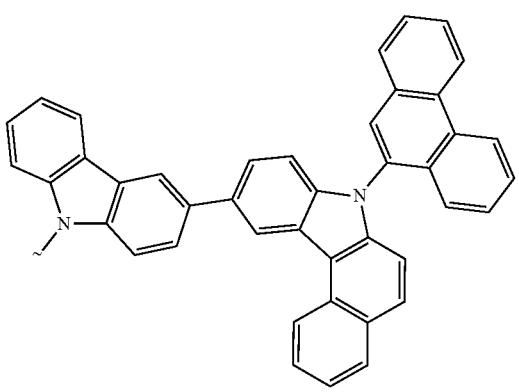
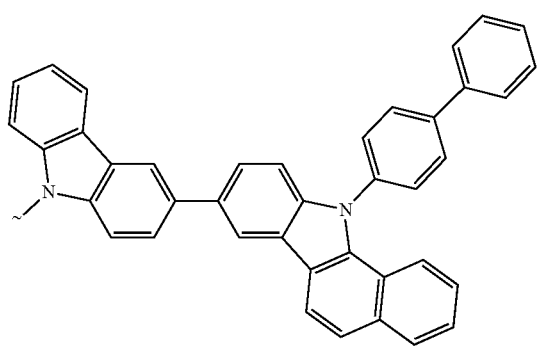
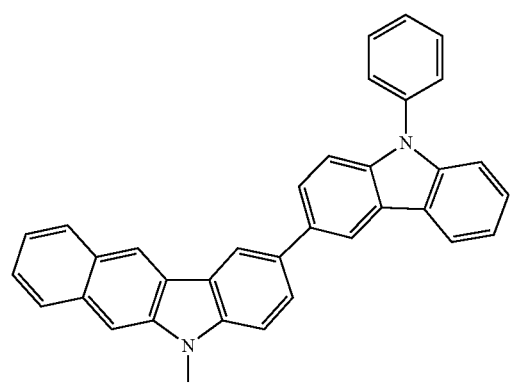
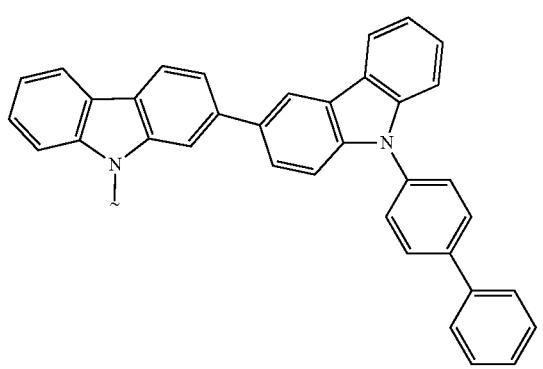
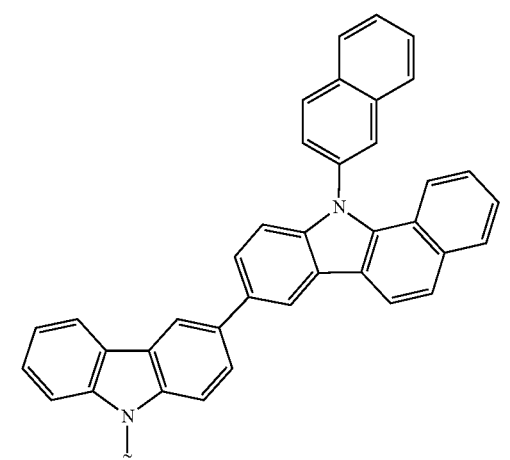

-continued

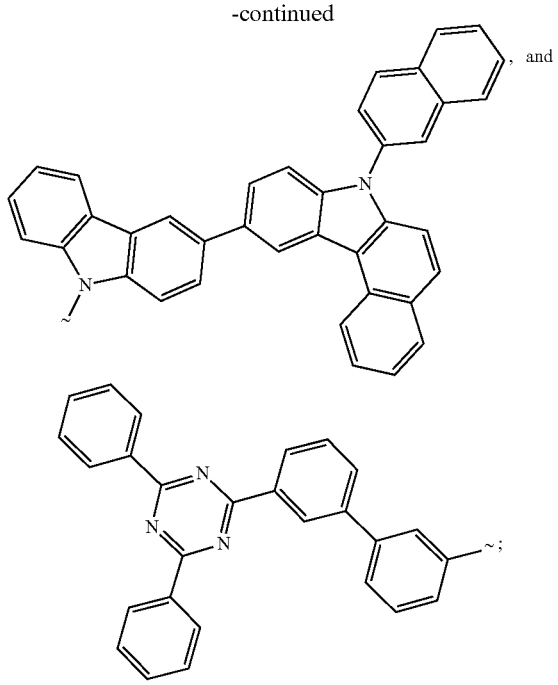

A$^1$, A$^2$, A$^3$, and A$^4$ are independently of each other a C$_6$-C$_{24}$ arylene group which is unsubstituted or substituted by G, a C$_1$-C$_{24}$ heteroarylene group which is unsubstituted or substituted by G;

R$^{20}$ is H; E; a C$_6$-C$_{60}$ aryl group which is unsubstituted or substituted by G, a C$_1$-C$_{60}$ heteroaryl group which is unsubstituted or substituted by G, a C$_1$-C$_{25}$alkyl group, which is unsubstituted or substituted by at least one group G and/or interrupted by D;

D is —CO—, —COO—, —S—, —SO—, —SO$_2$—, —CR$^{63}$=CR$^{64}$—, —NR$^{65}$—, —SiR$^{70}$R$^{71}$—, —POR$^{73}$—, or —C≡C—;

E is —SR$^{69}$, —COR$^{68}$, —COOR$^{67}$, —CONR$^{65}$R$^{66}$, —CN, —SiR$^{70}$R$^{71}$R$^{72}$, or —POR$^{74}$R$^{75}$;

G is E; or a C$_1$-C$_{24}$alkyl group; a C$_1$-C$_{24}$alkyl group, which is interrupted by O; a C$_6$-C$_{60}$aryl group, a C$_6$-C$_{60}$aryl group, which is substituted by F, —CF$_3$, —CF$_2$CF$_3$, —CF$_2$CF$_2$CF$_3$, —CF(CF$_3$)$_2$, —(CF$_2$)$_3$CF$_3$, —C(CF$_3$)$_3$, a C$_1$-C$_{24}$alkyl or a C$_1$-C$_{24}$alkyl which is interrupted by O; a C$_2$-C$_{60}$heteroaryl group; or a C$_2$-C$_{60}$heteroaryl group, which is substituted by F, —CF$_3$, —CF$_2$CF$_3$, —CF$_2$CF$_2$CF$_3$, —CF(CF$_3$)$_2$, —(CF$_2$)$_3$CF$_3$, —C(CF$_3$)$_3$, a C$_1$-C$_{24}$alkyl or a C$_1$-C$_{24}$alkyl which is interrupted by O;

R$^{63}$ and R$^{64}$ are independently of each other a C$_6$-C$_{18}$aryl; a C$_6$-C$_{18}$aryl which is substituted by a C$_1$-C$_{18}$alkyl or a C$_1$-C$_{18}$alkoxy; a C$_1$-C$_{18}$alkyl; or a C$_1$-C$_{18}$alkyl which is interrupted by —O—; H;

R$^{65}$ and R$^{66}$ are independently of each other a C$_6$-C$_{18}$aryl group; a C$_6$-C$_{18}$aryl which is substituted by a C$_1$-C$_{18}$alkyl or a C$_1$-C$_{18}$alkoxy; a C$_1$-C$_{18}$alkyl group; or a C$_1$-C$_{18}$alkyl group, which is interrupted by —O—; or R$^{65}$ and R$^{66}$ together form a five or six membered ring, which can be substituted or benzanullated;

R$^{67}$ is a C$_6$-C$_{18}$aryl group; a C$_6$-C$_{18}$aryl group, which is substituted by a C$_1$-C$_{18}$alkyl, or a C$_1$-C$_{18}$alkoxy; a C$_1$-C$_{18}$alkyl group; or a C$_1$-C$_{18}$alkyl group, which is interrupted by —O—;

R$^{68}$ is H; a C$_6$-C$_{18}$aryl group; a C$_6$-C$_{18}$aryl group, which is substituted by a C$_1$-C$_{18}$alkyl or a C$_1$-C$_{18}$alkoxy; a C$_1$-C$_{18}$alkyl group; or a C$_1$-C$_{18}$alkyl group, which is interrupted by —O—;

R$^{69}$ is a C$_6$-C$_{18}$aryl; a C$_6$-C$_{18}$aryl, which is substituted by a C$_1$-C$_{18}$alkyl or a C$_1$-C$_{18}$alkoxy; a C$_1$-C$_{18}$alkyl group; or a C$_1$-C$_{18}$alkyl group, which is interrupted by —O—;

R$^{70}$, R$^{71}$ and R$^{72}$ are independently of each other a C$_1$-C$_{18}$alkyl group, a C$_6$-C$_{18}$aryl group, or a C$_6$-C$_{18}$aryl group, which is substituted by a C$_1$-C$_{18}$alkyl; and R$^{73}$, R$^{74}$, and R$^{75}$ is a C$_1$-C$_{18}$alkyl group, a C$_6$-C$_{18}$aryl group, or a C$_6$-C$_{18}$aryl group, which is substituted by a C$_1$-C$_{18}$ alkyl;

wherein in the case of formula (1b) B$_3$ is CH and o, p, q and r in the definition of R$^6$ and R$^7$ are 0; and wherein when R$^{41}$ is phenylene and p, q, and r are 0, R$^{20}$ is not hydrogen.

2. The heterocyclic derivative according to claim 1, wherein A$^1$, A$^2$, A$^3$, and A$^4$ are independently of each other a group of the following formula:

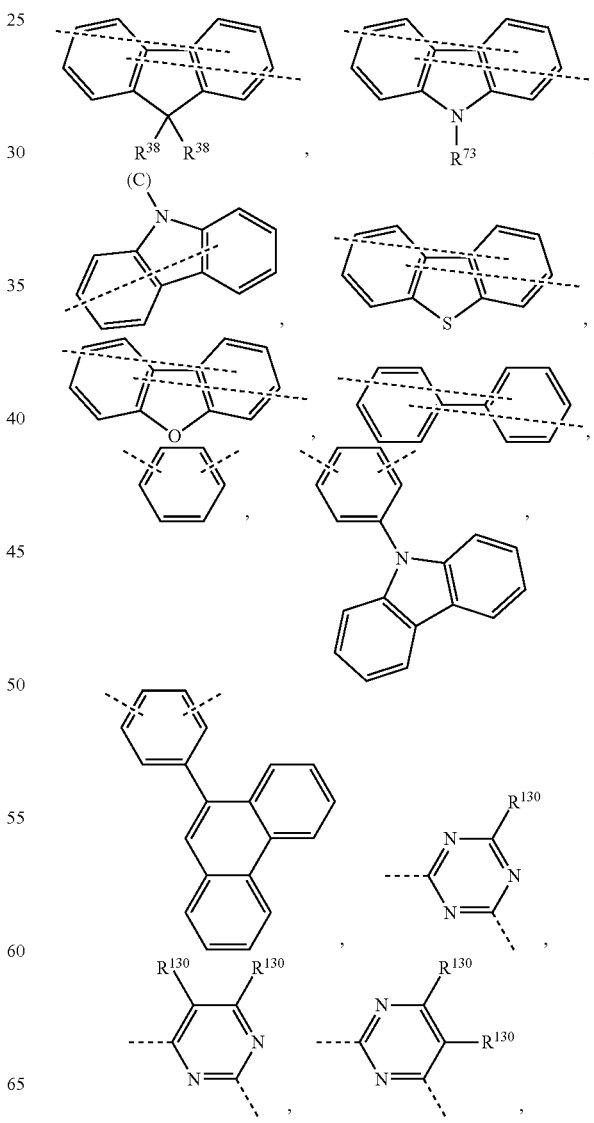

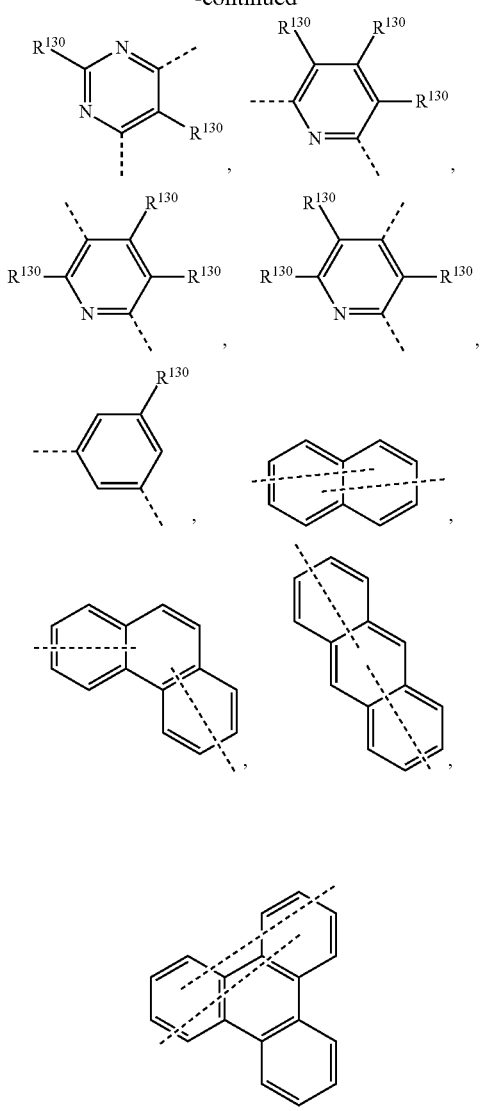

which can be unsubstituted or substituted by G;

R⁷³ is a $C_6$-$C_{18}$aryl group; a $C_6$-$C_{18}$aryl which is substituted by a $C_1$-$C_{18}$alkyl or a $C_1$-$C_{18}$alkoxy; a $C_1$-$C_{18}$alkyl group; or a $C_1$-$C_{18}$alkyl group, which is interrupted by —O—;

R³⁸ is a $C_1$-$C_{25}$alkyl group, which can optionally be substituted by E and or interrupted by D; a $C_6$-$C_{24}$aryl group, which can optionally be substituted by G, or a $C_1$-$C_{24}$heteroaryl group, which can optionally be substituted by G; and/or two adjacent groups of the groups may form together with the atom to which they are bonded a ring structure, which can optionally be substituted by G;

R¹³⁰ is independently in each occurrence H or a $C_6$-$C_{24}$arylene group, which can optionally be substituted by G, or a $C_1$-$C_{30}$heteroarylene group, which can optionally be substituted by G; wherein G is as defined in above; wherein the dotted lines are bonding sites;

wherein (C)— has the meaning that the bonding site of the group A¹, A², A³ and A⁴ is linked to a C-atom.

3. The heterocyclic derivative according to claim 1, wherein R²⁰ is H, CN, —OR⁶⁹, —SiR⁷⁰R⁷¹R⁷² or a group of the following formula

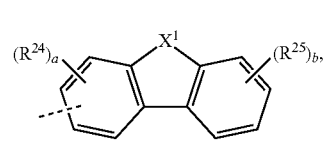
(4)

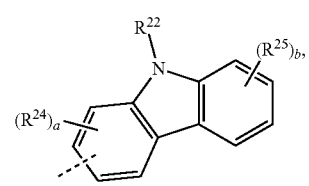
(5)

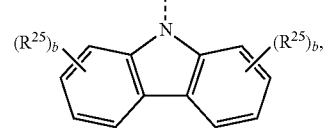
(6)

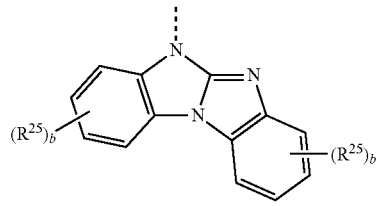
(7)

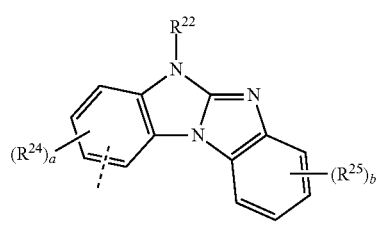
(8)

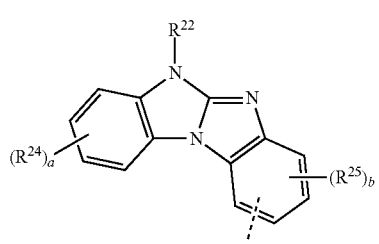
(8a)

wherein
X¹ is S, O, C(R²¹)₂, NR²³;
R²¹ is a $C_1$-$C_{25}$alkyl group, which can optionally be substituted by E and or interrupted by D; a $C_6$-$C_{24}$aryl group, which can optionally be substituted by G, or a $C_1$-$C_{24}$heteroaryl group, which can optionally be substituted by G; and/or two adjacent groups of the groups may form together with the atom to which they are bonded a ring structure, which can optionally be substituted by G;
R²² is a $C_6$-$C_{18}$ aryl group which is unsubstituted or substituted by G, a $C_2$-$C_{18}$ heteroaryl group which is unsubstituted or substituted by G;
R²³ is H, a $C_6$-$C_{18}$ aryl group which is unsubstituted or substituted by G, a $C_2$-$C_{18}$ heteroaryl group which is unsubstituted or substituted by G;

$R^{24}$ and $R^{25}$ are independently of each other H, a $C_6$-$C_{18}$ aryl group which is unsubstituted or substituted by G, a $C_2$-$C_{18}$ heteroaryl group which is unsubstituted or substituted by G, a $C_1$-$C_{25}$alkyl group, which can optionally be substituted by E and or interrupted by D, or —CN;

a is 0, 1, 2 or 3;

b is 0, 1, 2, 3 or 4;

the dotted lines are bonding sites;

or

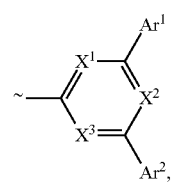
(9)

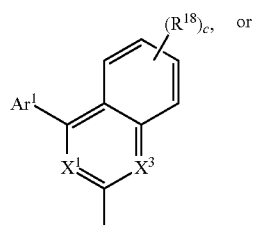
(10)

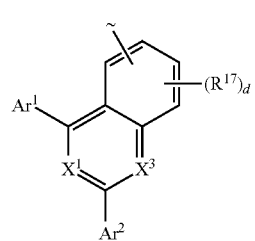
(11)

wherein $X^1$, $X^2$ and $X^3$ are independently of each other $CR^{19}$ or N, wherein in formula (9) at least one of $X^1$ to $X^3$ is N, and wherein in formulae (10) and (11) at least one of $X^1$ and $X^3$ is N;

$Ar_1$ and $Ar_2$ are independently of each other a $C_6$-$C_{24}$ aryl group, which is optionally substituted by G, or a $C_1$-$C_{24}$ heteroaryl group, which is optionally substituted by G;

$R^{17}$, $R^{18}$ and $R^{19}$ are independently of each other H, a $C_6$-$C_{24}$ aryl group which can be substituted by G, a $C_1$-$C_{24}$ heteroaryl group which can be substituted by G or a $C_1$-$C_{25}$alkyl group, which can optionally be substituted by E and/or interrupted by D;

c is 0, 1, 2, 3 or 4; d is 0, 1, 2 or 3; or

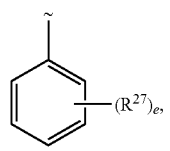
(12)

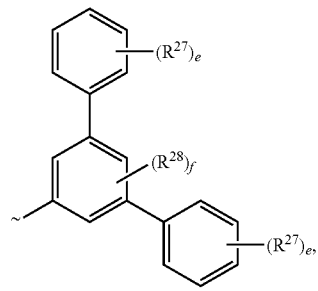
(13)

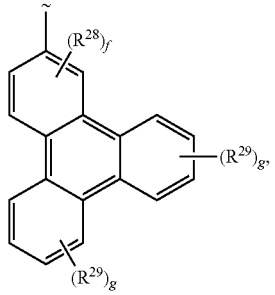
(14)

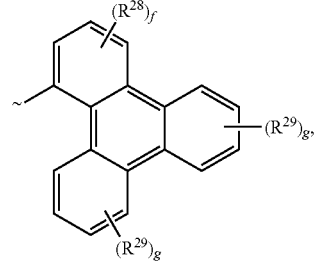
(15)

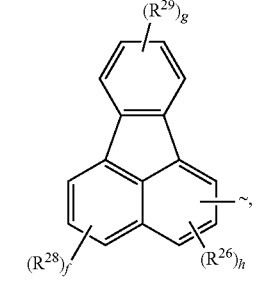
(16)

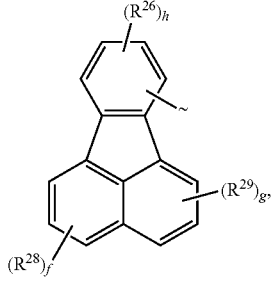
(17)

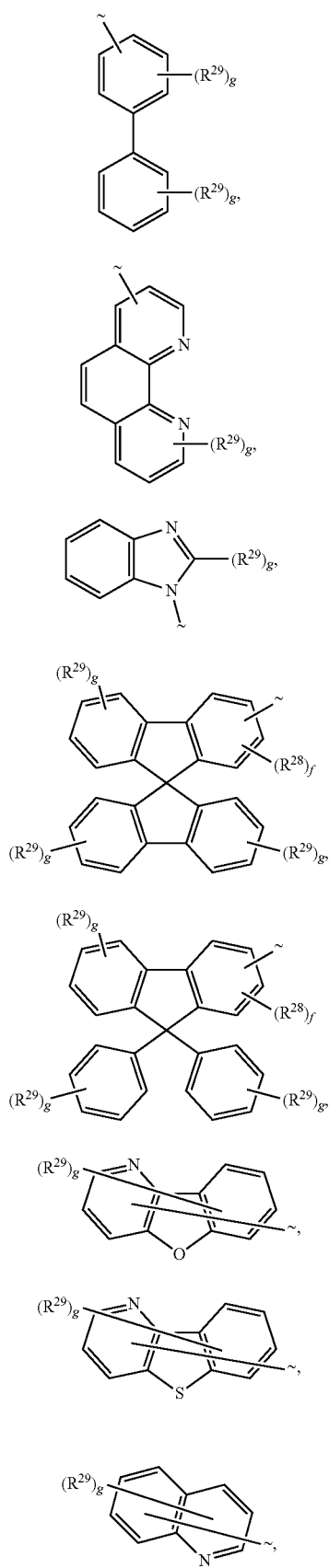
$R^{26}$, $R^{27}$, $R^{28}$ and $R^{29}$ are independently of each other H, a $C_6$-$C_{24}$ aryl group which can be substituted by G, a $C_1$-$C_{24}$ heteroaryl group which can be substituted by G or a $C_1$-$C_{25}$alkyl group, which can optionally be substituted by E and/or interrupted by D; or a substituent E; e is 0, 1, 2, 3, 4 or 5; f is 0, 1, 2 or 3; g is 0, 1, 2, 3 or 4; h is 0, 1 or 2;

or
two adjacent groups $R^{26}$, $R^{27}$ $R^{28}$ or $R^{29}$ may form together with the atoms to which they are bonded a ring structure which may be substituted by G,
wherein ~ is a bonding site.

4. The heterocyclic derivative according to claim 1, wherein $R^1$, $R^3$, $R^4$, $R^5$, $R^6$, $R^7$, and $R^8$ are independently of each other H or a group of formula $-(A^1)_o-(A^2)_p-(A^3)_q-(A^4)_r-R^{20}$.

5. The heterocyclic derivative according to claim 1, wherein one, two, three or four of $R^{A1}$, $R^{A2}$, $R^1$, $R^3$, $R^4$, $R^5$, $R^6$, $R^7$, and $R^8$ is independently of each other E; a group of formula $-(A^1)_o-(A^2)_p-(A^3)_q-(A^4)_r-R^{20}$; or a $C_1$-$C_{25}$alkyl group, which is unsubstituted or substituted by at least one group E and/or interrupted by D; and the other of $R^{A1}$, $R^{A2}$, $R^1$, $R^3$, $R^4$, $R^5$, $R^6$, $R^7$, and $R^8$ are H.

6. The heterocyclic derivative according to claim 1, wherein $A^1$, $A^2$, $A^3$, and $A^4$ are independently phenylene, naphthylene, biphenylene, or terphenylene, each of which is unsubstituted or substituted by G.

7. The heterocyclic derivative according to claim 1, wherein $A^1$, $A^2$, $A^3$, and $A^4$ are independently phenylene, biphenylene, or terphenylene, each of which is unsubstituted or substituted by G.

8. The heterocyclic derivative according to claim 1, wherein $R^{20}$ is anthryl, fluoranthenyl, triphenylenyl, or fluorenyl, each of which is unsubstituted or substituted by G.

9. The heterocyclic derivative according to claim 1, wherein $R^{20}$ is anthryl or fluoranthenyl, each of which is unsubstituted or substituted by G.

10. The heterocyclic derivative according to claim 1, wherein $R^{20}$ is pyridyl which may have a fused ring, pyrimidyl which may have a fused ring, triazinyl, or phenanthrolinyl, each of which is unsubstituted or substituted by G.

11. The heterocyclic derivative according to claim 1, wherein $R^{20}$ is pyridyl, pyrimidyl, triazinyl, or phenanthrolinyl, each of which is unsubstituted or substituted by G.

12. The heterocyclic derivative according to claim 1, wherein $R^{20}$ is pyrimidyl, triazinyl, or phenanthrolinyl, each of which is unsubstituted or substituted by G.

13. A charge transport layer, charge/exciton blocking layer, or an emitting layer comprising a heterocyclic derivative according to claim 1.

14. The emitting layer according to claim 13, comprising the heterocyclic derivative as host material in combination with at least one emitter.

15. The charge transport layer according to claim 13, which is an electron transport layer comprising the heterocyclic derivative as electron transport material.

16. A device, comprising the heterocyclic derivative of claim 1, said device being selected from the group consisting of organic electroluminescent devices, electrophotographic photoreceptors, photoelectric converters, organic solar cells, switching elements, organic light emitting field effect transistors, image sensors and dye lasers.

17. A process for the preparation of a heterocyclic derivative of formula (1a) or (1b) according to claim 1, the process comprising:
(a) Coupling a compound of formula (1')

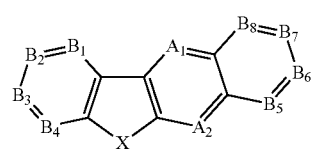

(1')

wherein at least one of $B_1$, $B_3$, $B_4$, $A_1$ and $A_2$ is C-Hal, wherein Hal means halogen;
(i) with a compound of formula Y—$R^{A1}$, Y—$R^{A2}$, Y—$R^1$, Y—$R^3$, Y—$R^4$, Y—$R^5$, Y—$R^6$, Y—$R^7$, or Y—$R^8$, wherein Y is —B(OR')$_2$ in the presence of a catalyst and in the presence of a base;
wherein
X in the formula (1') is O or S;
$A_1$ is N or $CR^{A1}$;
$A_2$ is N or $CR^{A2}$;
wherein one of $A_1$ and $A_2$ is N,
$B_1$ is $CR^1$;
$B_2$ is CH;
$B_3$ is $CR^3$;
$B_4$ is $CR^4$;
$B_5$ is $CR^5$;
$B_6$ is $CR^6$;
$B_7$ is $CR^7$;
$B_8$ is $CR^8$;
$R^1$, $R^3$, $R^4$, $R^5$, $R^6$, $R^7$, and $R^8$,
are independently of each other H; E; a group of formula $-(A^1)_o-(A^2)_p-(A^3)_q-(A^4)_r-R^{20}$; or a $C_1$-$C_{25}$alkyl group, which is unsubstituted or substituted by at least one group E and/or interrupted by D;
wherein o is 0 or 1, p is 0 or 1, q is 0 or 1, r is 0 or 1 in the formula $-(A^1)_o-(A^2)_p-(A^3)_q-(A^4)_r-R^{20}$ for $R^1$, $R^3$, $R^4$, $R^5$, $R^6$, $R^7$, and $R^8$;
$R^{A1}$ is a group of formula $-(A^1)_o-(A^2)_p-(A^3)_q-(A^4)_r-R^{20}$, wherein o is 1, p is 0 or 1, q is 0 or 1, r is 0 or 1 in the formula $-(A^1)_o-(A^2)_p-(A^3)_q-(A^4)_r-R^{20}$ for $R^{A1}$;
$R^{A2}$ is selected from group consisting of

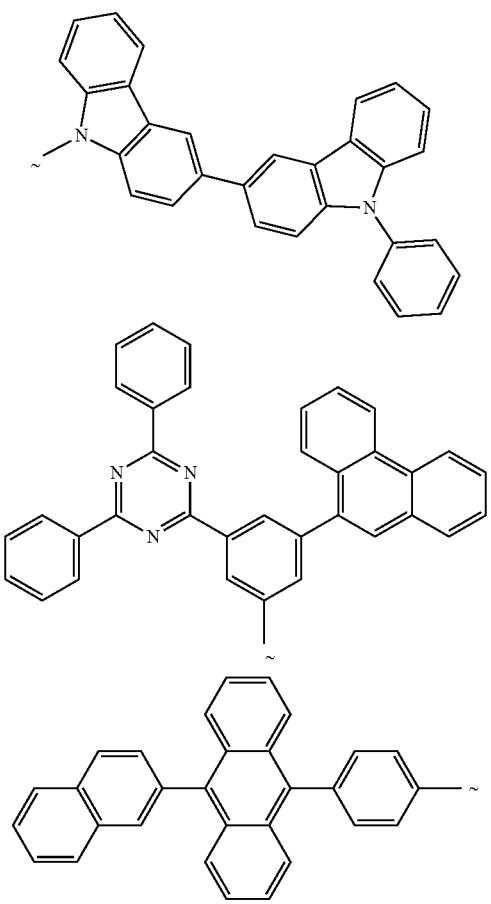

409
-continued
410
-continued
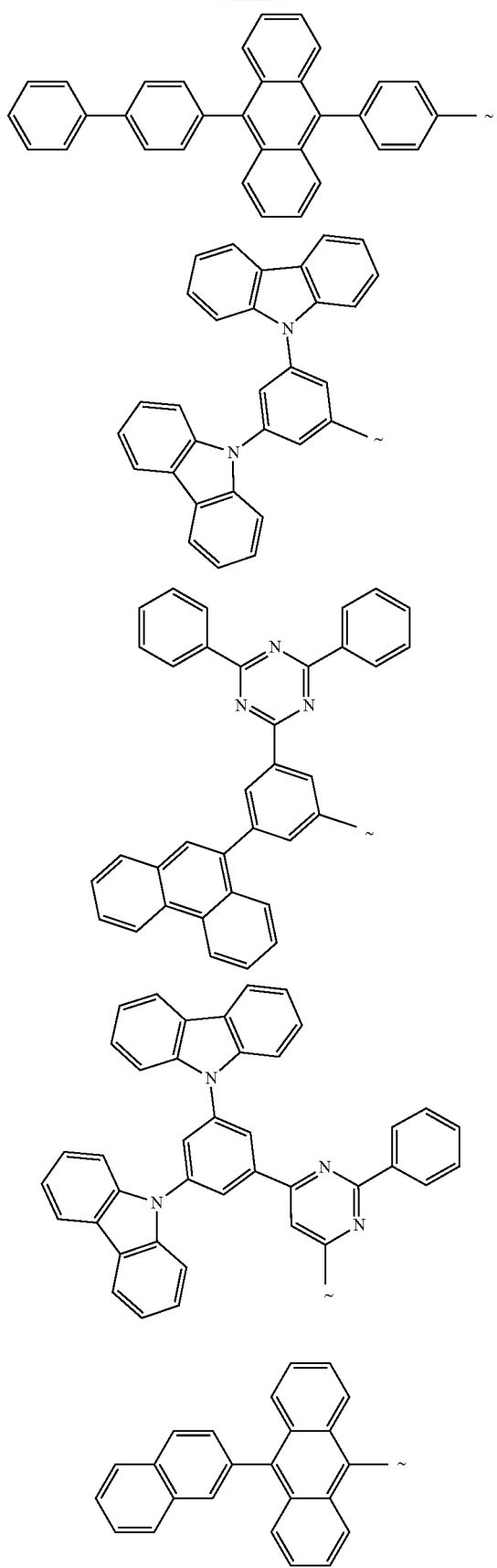
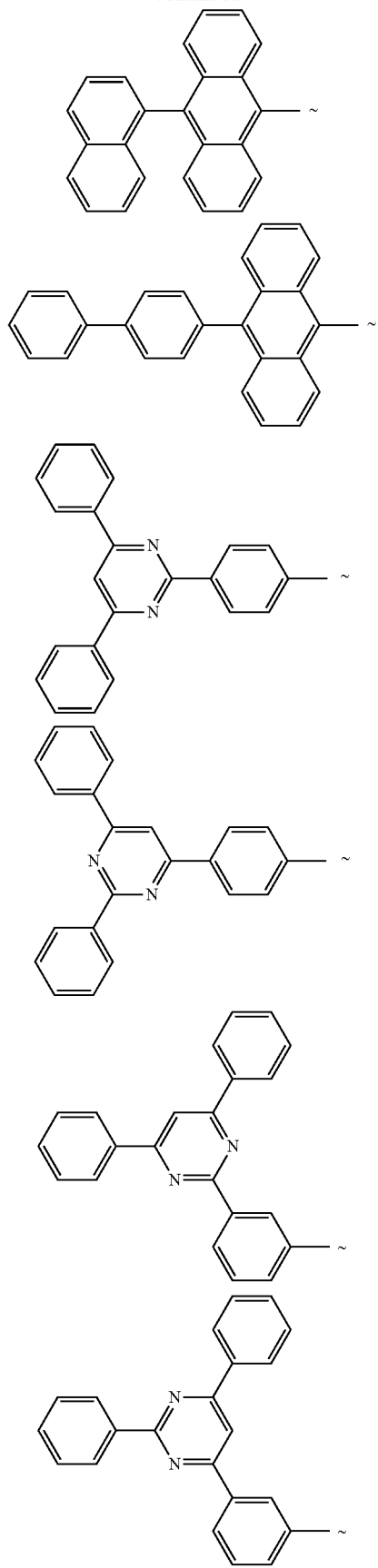

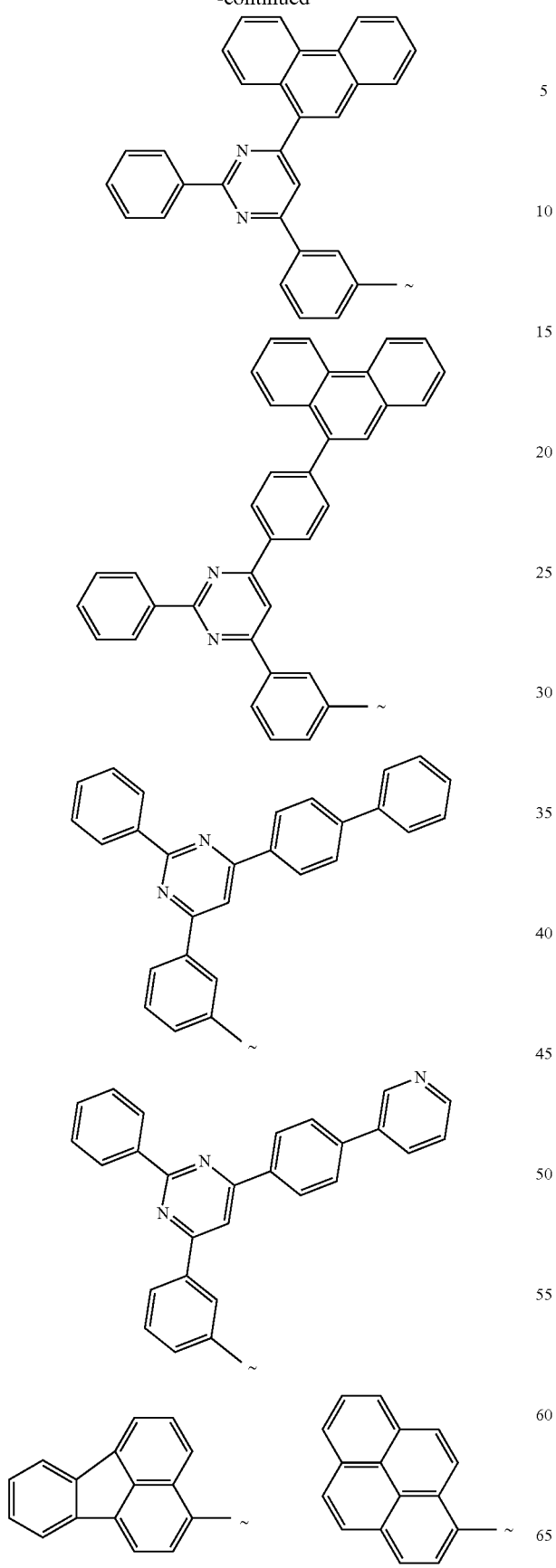
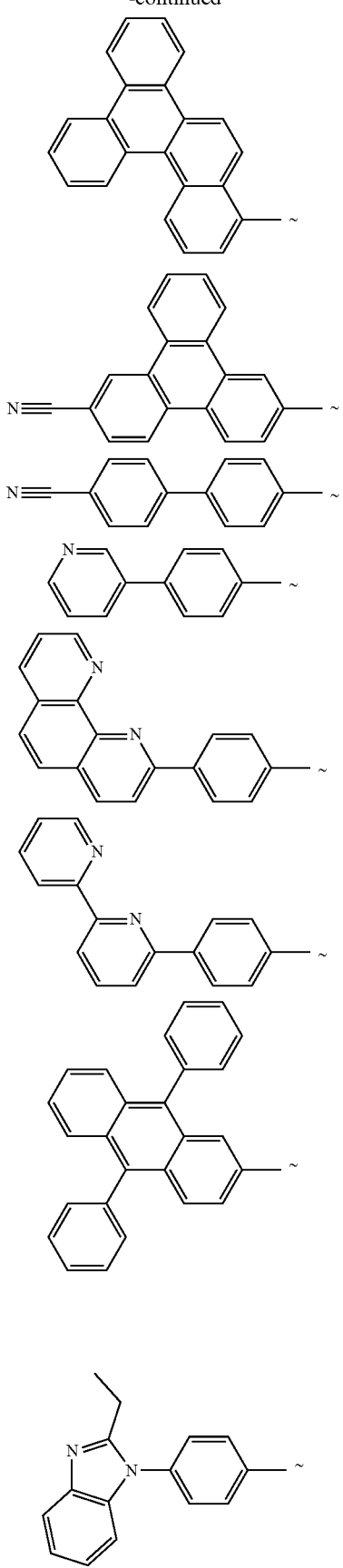

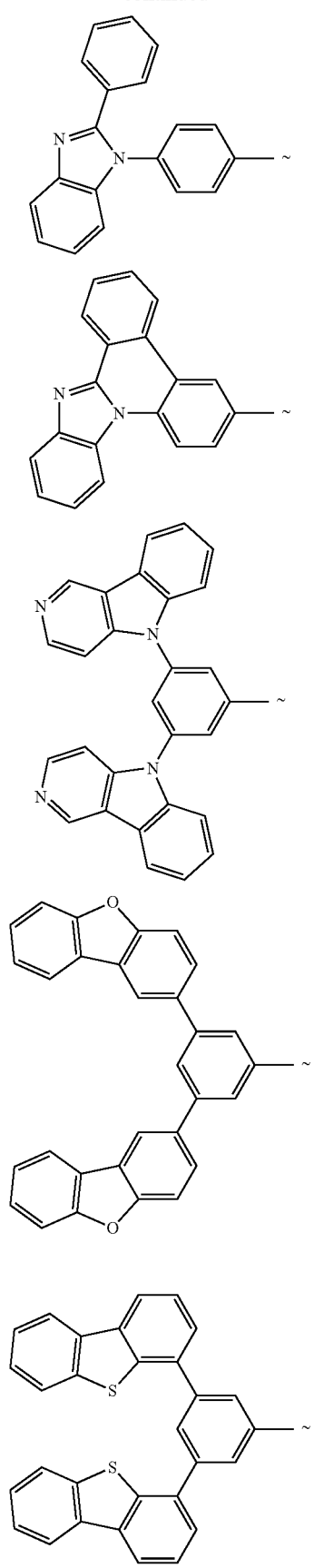
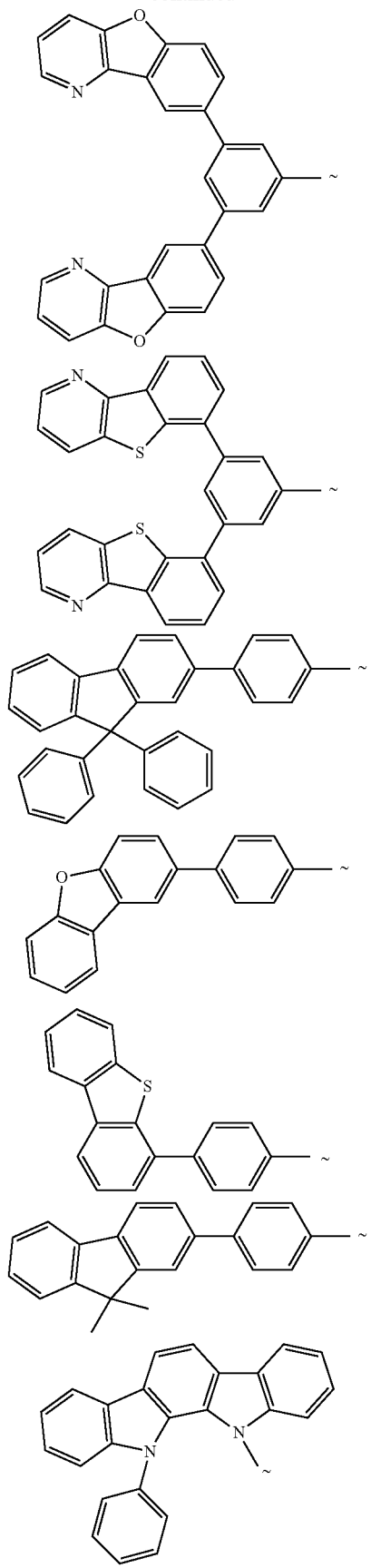

415
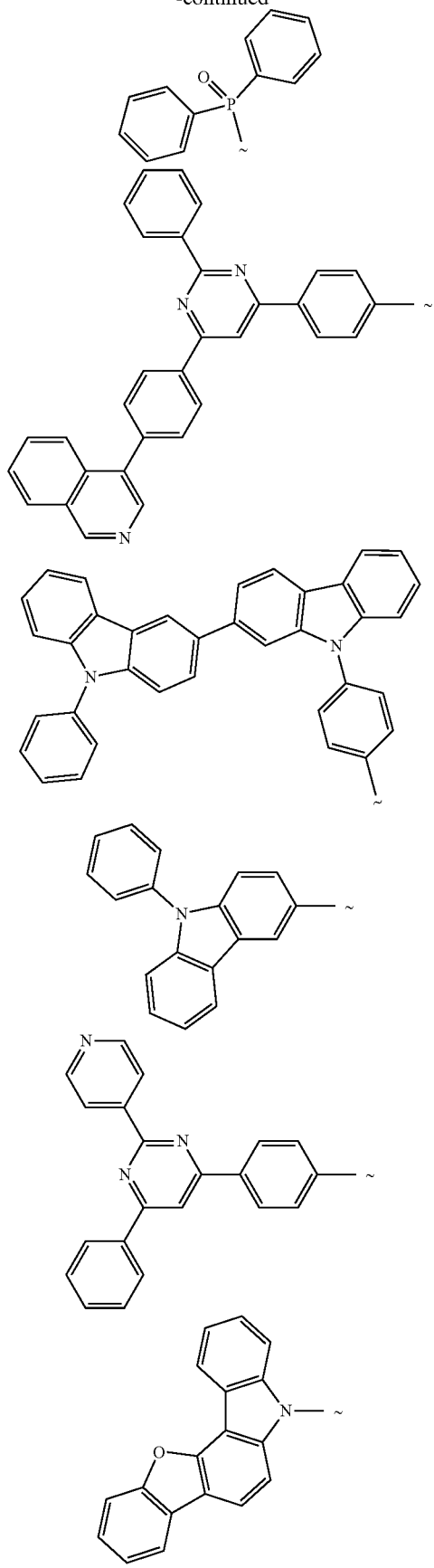
416
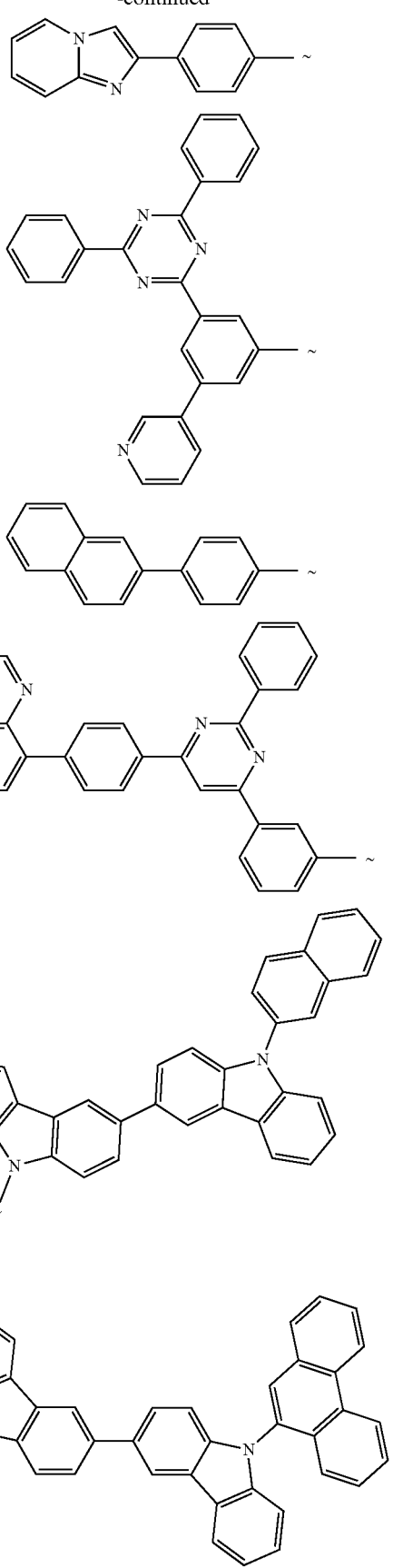

417
-continued
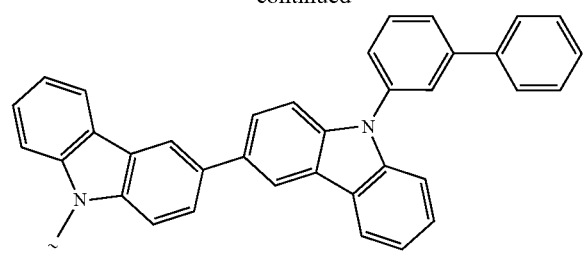
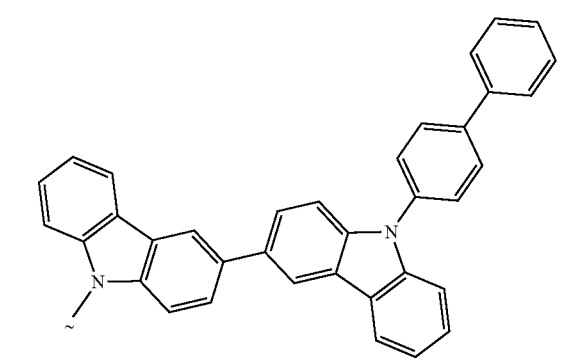
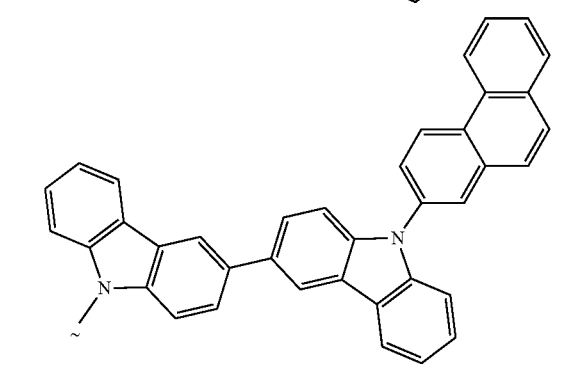
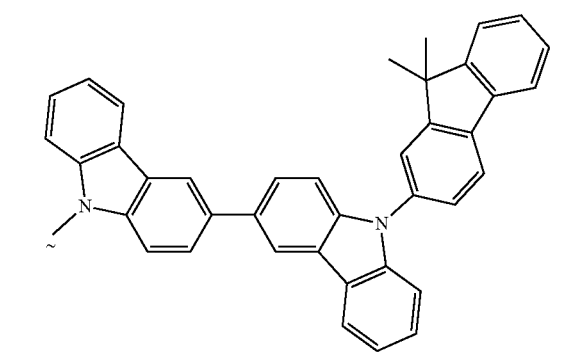
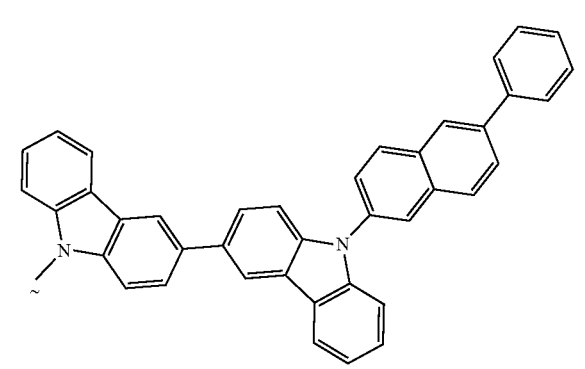
418
-continued
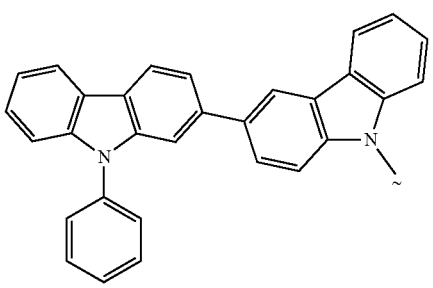
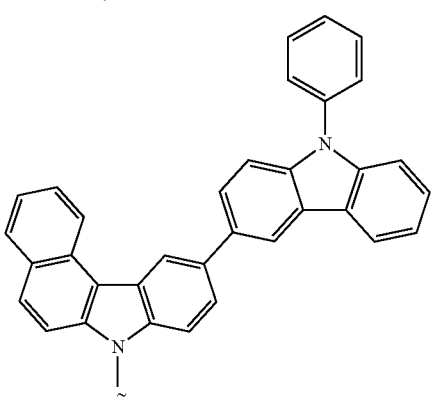
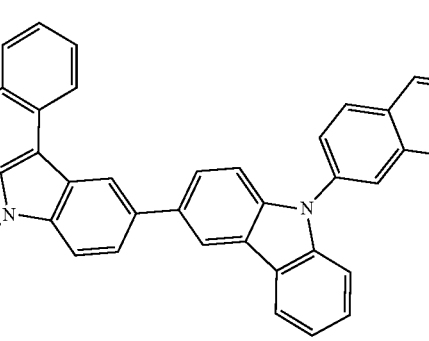
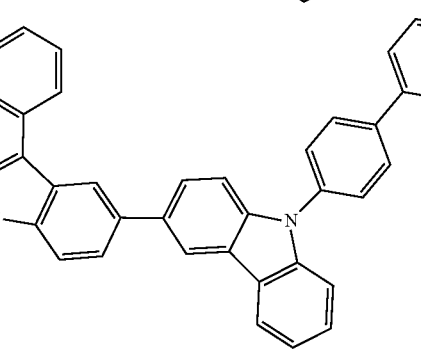
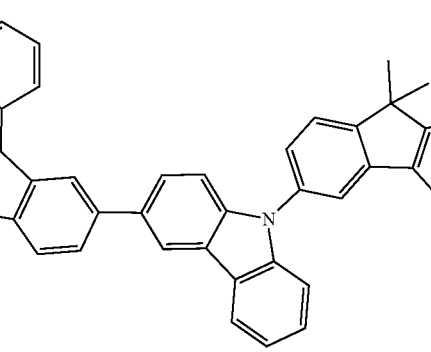

419
-continued
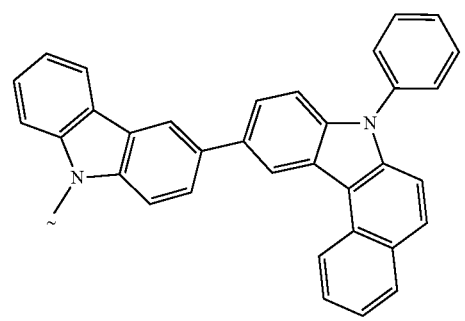
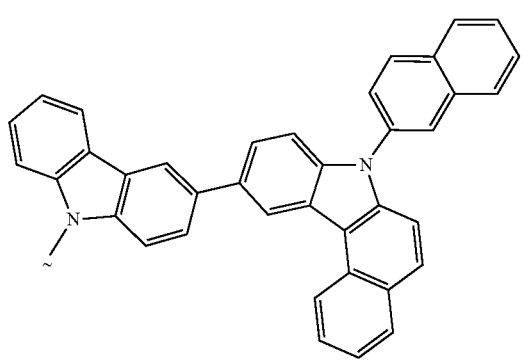
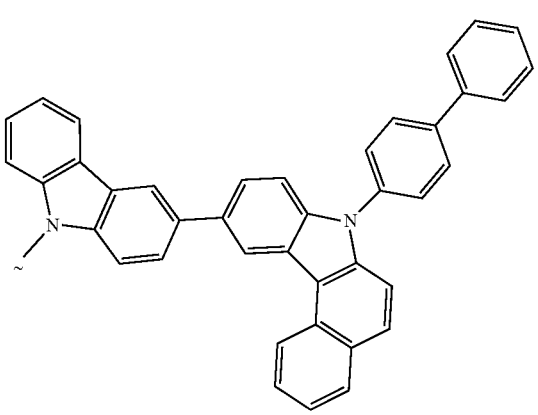
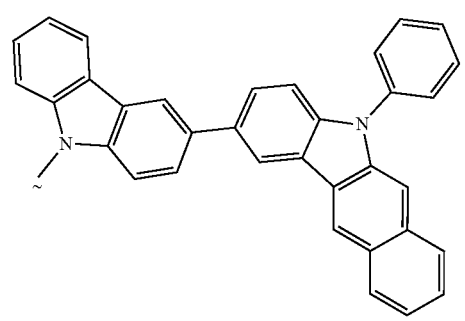
420
-continued
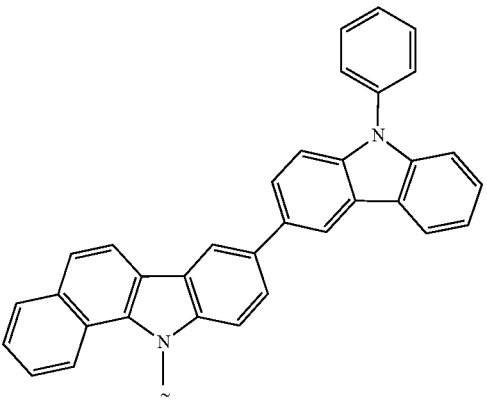
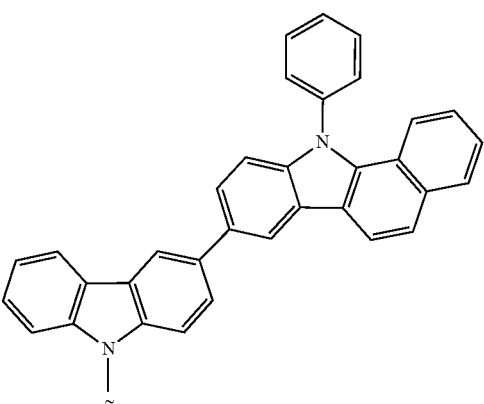
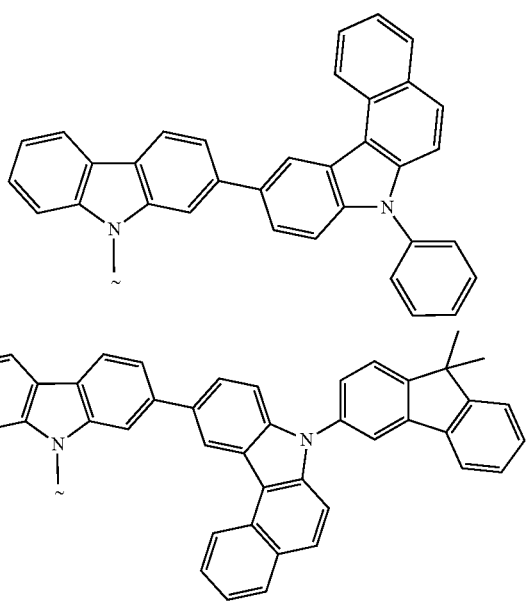
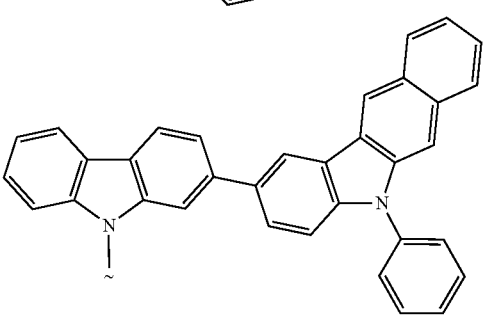

421
-continued
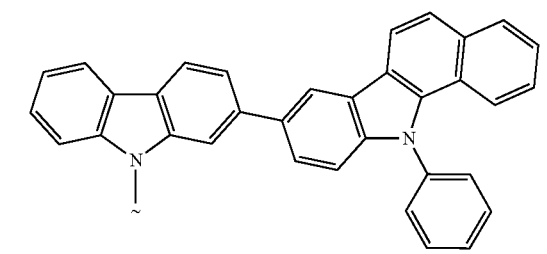
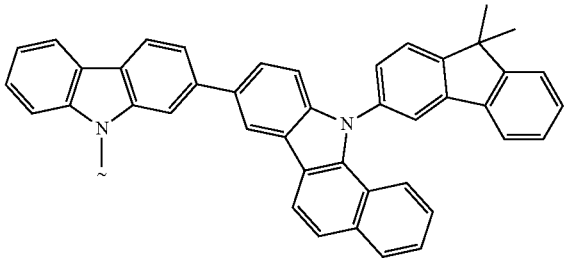
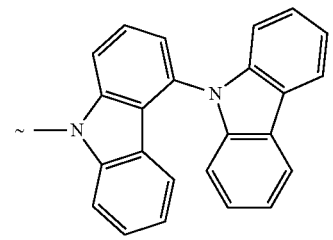
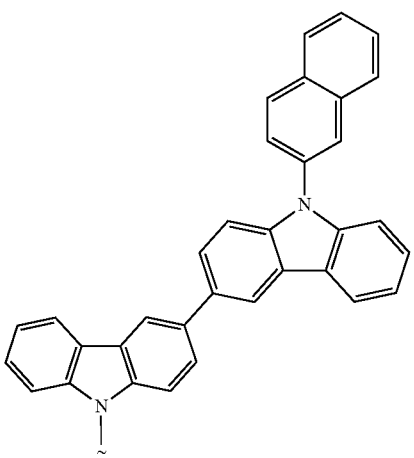
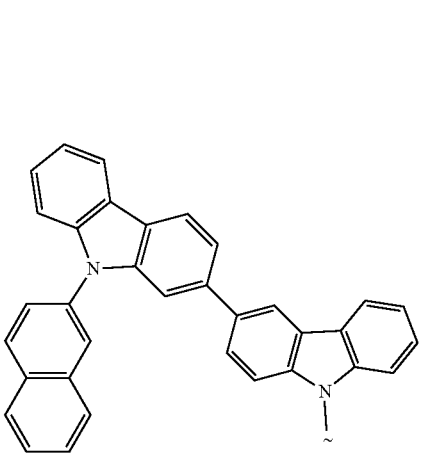
422
-continued
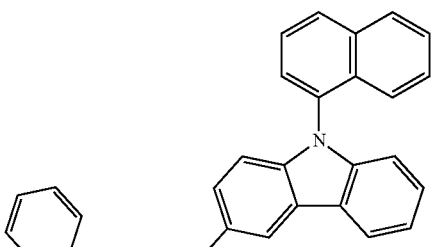
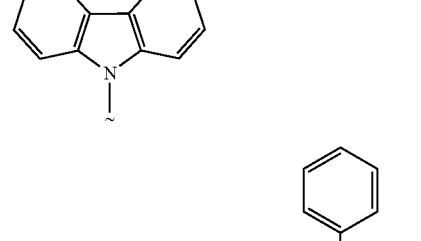
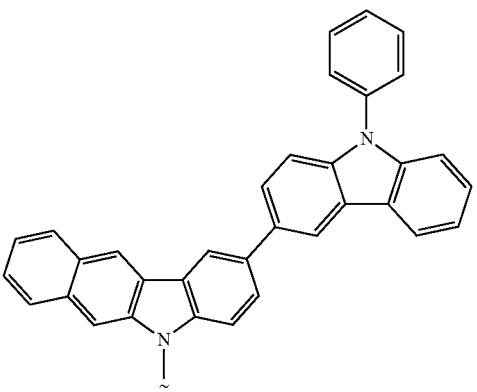
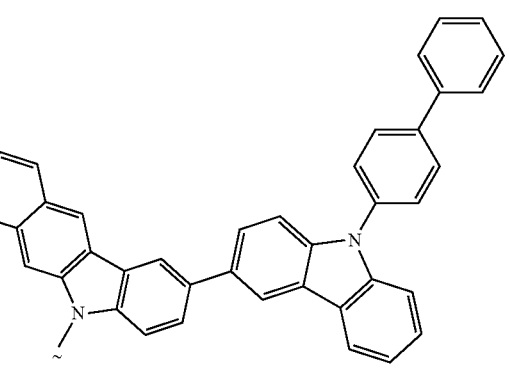
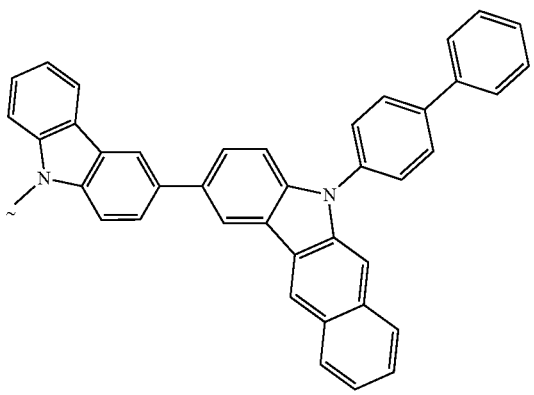

-continued
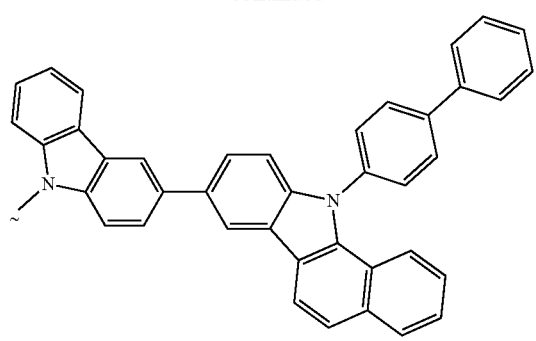
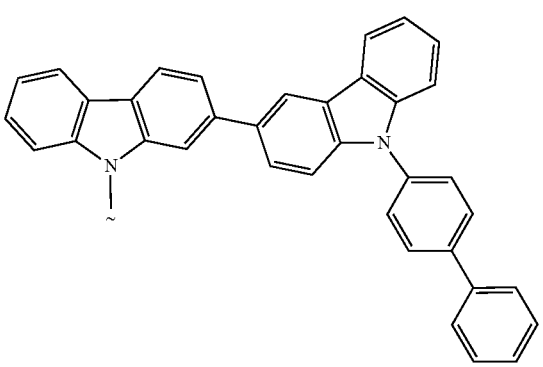
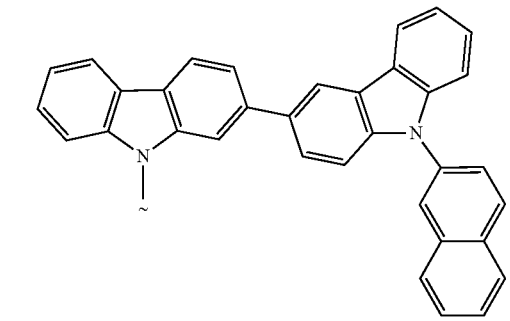
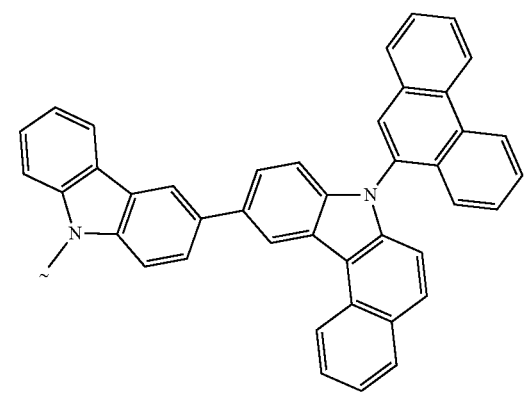
-continued
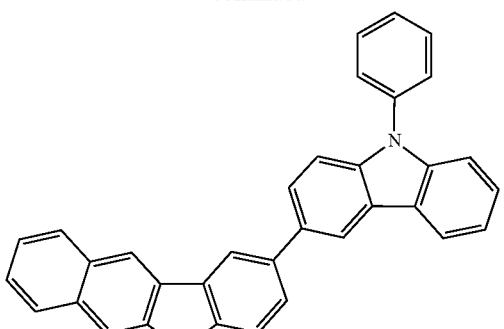
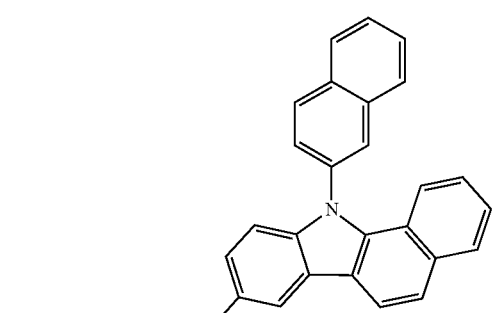
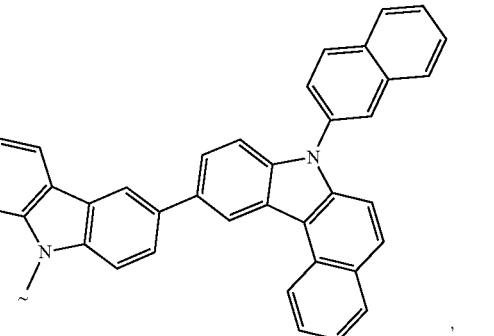
, and
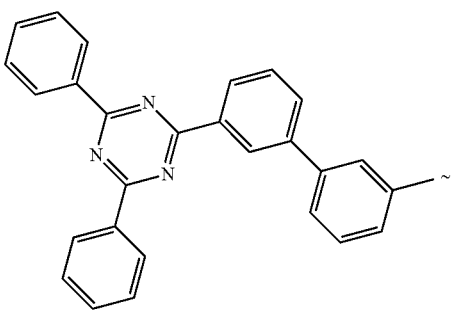
$A^1$, $A^2$, $A^3$, and $A^4$ are independently of each other a $C_6$-$C_{24}$ arylene group which is unsubstituted or substituted by G, a $C_1$-$C_{24}$ heteroarylene group which is unsubstituted or substituted by G;

R²⁰ is H; E; a C₆-C₆₀ aryl group which is unsubstituted or substituted by G, a C₁-C₆₀ heteroaryl group which is unsubstituted or substituted by G, a C₁-C₂₅alkyl group, which is unsubstituted or substituted by at least one group G and/or interrupted by D;

D is —CO—, —COO—, —S—, —SO—, —SO₂—, —O—, —CR⁶³=CR⁶⁴—, —NR⁶⁵—, —SiR⁷⁰R⁷¹—, —POR⁷³—, or —C≡C;

E is —OR⁶⁹, —SR⁶⁹, —NR⁶⁵R⁶⁶, —COR⁶⁸, —COOR⁶⁷, —CONR⁶⁵R⁶⁶, —CN, —SiR⁷⁰R⁷¹R⁷², halogen or —POR⁷⁴R⁷⁵;

G is E; or a C₁-C₂₄alkyl group; a C₁-C₂₄alkyl group, which is interrupted by O; a C₆-C₆₀aryl group, a C₆-C₆₀aryl group, which is substituted by F, —CF₃, —CF₂CF₃, —CF₂CF₂CF₃, —CF(CF₃)₂, —(CF₂)₃CF₃, —C(CF₃)₃, a C₁-C₂₄alkyl or a C₁-C₂₄alkyl which is interrupted by O; a C₂-C₆₀heteroaryl group; or a C₂-C₆₀heteroaryl group, which is substituted by F, —CF₃, —CF₂CF₃, —CF₂CF₂CF₃, —CF(CF₃)₂, —(CF₂)₃CF₃, —C(CF₃)₃, a C₁-C₂₄alkyl or a C₁-C₂₄alkyl which is interrupted by O;

R⁶³ and R⁶⁴ are independently of each other a C₆-C₁₈aryl; a C₆-C₁₈aryl which is substituted by a C₁-C₁₈alkyl or a C₁-C₁₈alkoxy; a C₁-C₁₈alkyl; or a C₁-C₁₈alkyl which is interrupted by —O—; H;

R⁶⁵ and R⁶⁶ are independently of each other a C₆-C₁₈aryl group; a C₆-C₁₈aryl which is substituted by a C₁-C₁₈alkyl or a C₁-C₁₈alkoxy; a C₁-C₁₈alkyl group; or a C₁-C₁₈alkyl group, which is interrupted by —O—; or R⁶⁵ and R⁶⁶ together form a five or six membered ring, which can be substituted or benzanullated;

R⁶⁷ is a C₆-C₁₈aryl group; a C₆-C₁₈aryl group, which is substituted by a C₁-C₁₈alkyl, or a C₁-C₁₈alkoxy; a C₁-C₁₈alkyl group; or a C₁-C₁₈alkyl group, which is interrupted by —O—;

R⁶⁸ is H; a C₆-C₁₈aryl group; a C₆-C₁₈aryl group, which is substituted by a C₁-C₁₈alkyl or a C₁-C₁₈alkoxy; a C₁-C₁₈alkyl group; or a C₁-C₁₈alkyl group, which is interrupted by —O—;

R⁶⁹ is a C₆-C₁₈aryl; a C₆-C₁₈aryl, which is substituted by a C₁-C₁₈alkyl or a C₁-C₁₈alkoxy; a C₁-C₁₈alkyl group; or a C₁-C₁₈alkyl group, which is interrupted by —O—;

R⁷⁰, R⁷¹ and R⁷² are independently of each other a C₁-C₁₈alkyl group, a C₆-C₁₈aryl group, or a C₆-C₁₈aryl group, which is substituted by a C₁-C₁₈alkyl; and R⁷³, R⁷⁴, and R⁷⁵ is a C₁-C₁₈alkyl group, a C₆-C₁₈aryl group, or a C₆-C₁₈aryl group, which is substituted by a C₁-C₁₈alkyl;

wherein in the case that A₁ is CR⁴¹ and A₂ is N, B₃ is CH or N and o, p, q and r in the definition of R⁶ and R⁷ are 0.

18. The heterocyclic derivative according to claim 1, wherein A¹ is selected from the group consisting of naphthalene, biphenylene, triphenylene, terphenylene, pyrenylene, 2-fluorenylene, 9-fluorenylene, and phenylene.

19. The heterocyclic derivative according to claim 1, which is selected from the group consisting of formula 5, formula 19, formula 26, formula 30, formula 33, and formula 38:

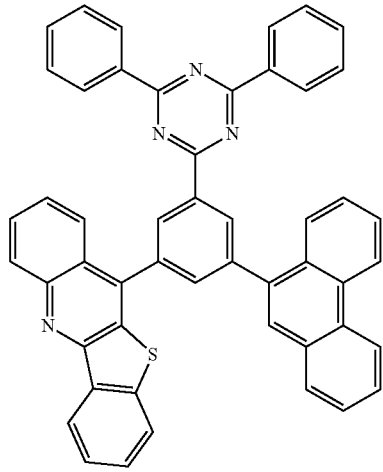

5

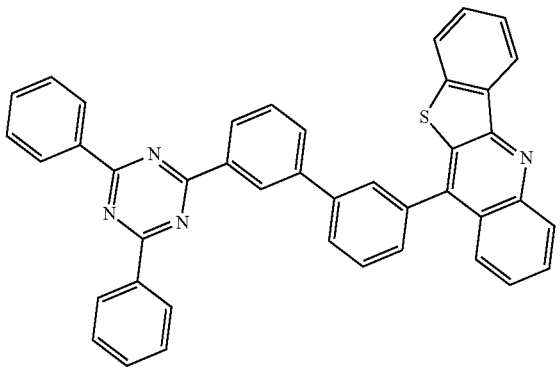

19

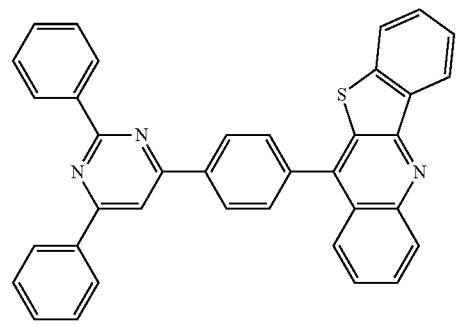

26

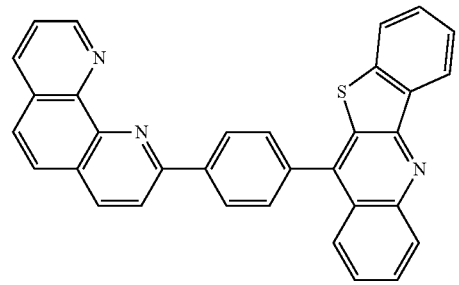

30

-continued

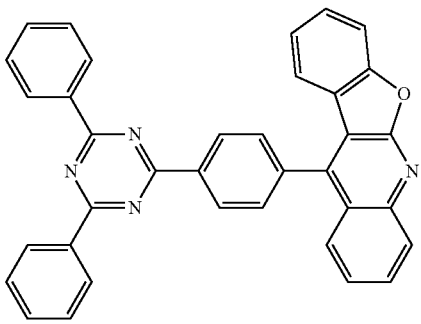

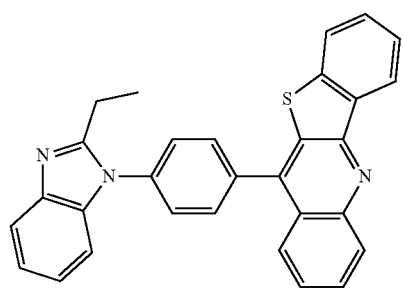

20. The heterocyclic derivative according to claim 1, wherein $R^{42}$ is

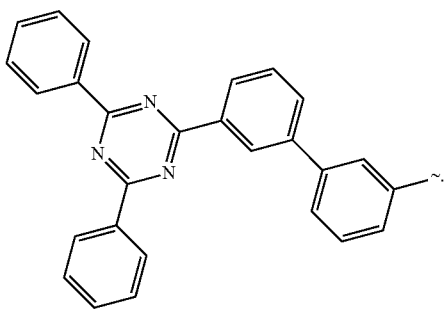

21. An organic electronic device, comprising a heterocyclic derivative of formula (1a) or (1b)

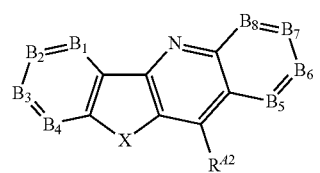
(1a)

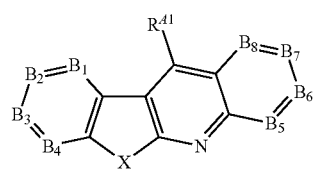
(1b)

wherein
X is O or S;
$B_1$ is $CR^1$;
$B_2$ is CH;
$B_3$ is $CR^3$;
$B_4$ is $CR^4$;
$B_5$ is $CR^5$;
$B_6$ is $CR^6$;
$B_7$ is $CR^7$;
$B_8$ is $CR^8$;
$R^1$, $R^3$, $R^4$, $R^5$, $R^6$, $R^7$, and $R^8$ are independently of each other H; E; a group of formula $-(A^1)_o-(A^2)_p-(A^3)_q-(A^4)_r-R^{20}$; or a $C_1$-$C_{25}$alkyl group, which is unsubstituted or substituted by at least one group E and/or interrupted by D;

wherein o is 0 or 1, p is 0 or 1, q is 0 or 1, r is 0 or 1 in the formula $-(A^1)_o-(A^2)_p-(A^3)_q-(A^4)_r-R^{20}$ for $R^1$, $R^3$, $R^4$, $R^5$, $R^6$, $R^7$, and $R^8$;

$R^{41}$ is a group of formula $-(A^1)_o-(A^2)_p-(A^3)_q-(A^4)_r-R^{20}$, wherein o is 1, p is 0 or 1, q is 0 or 1, r is 0 or 1 in the formula $-(A^1)_o-(A^2)_p-(A^3)_q-(A^4)_r-R^{20}$ for $R^{41}$;

$R^{42}$ is selected from group consisting of

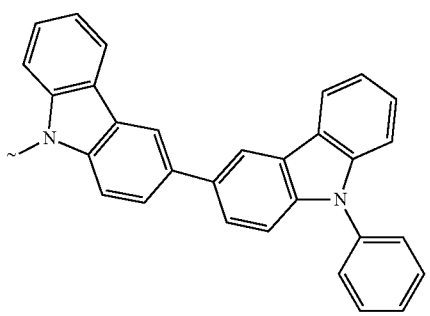

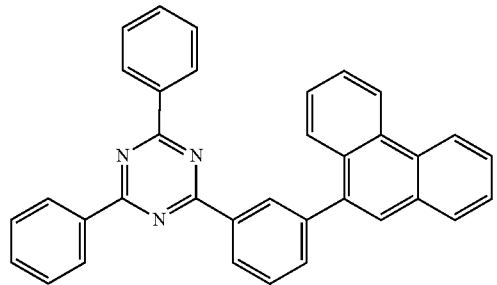

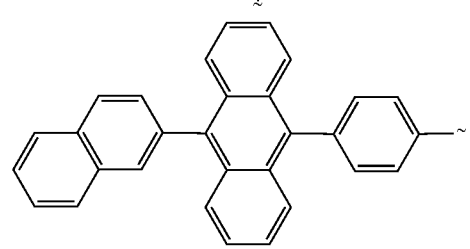

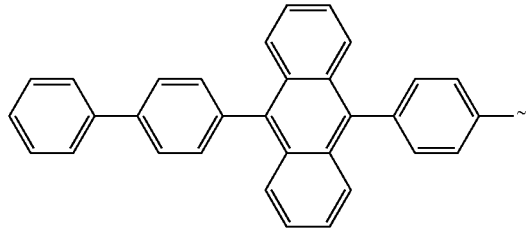

429
-continued
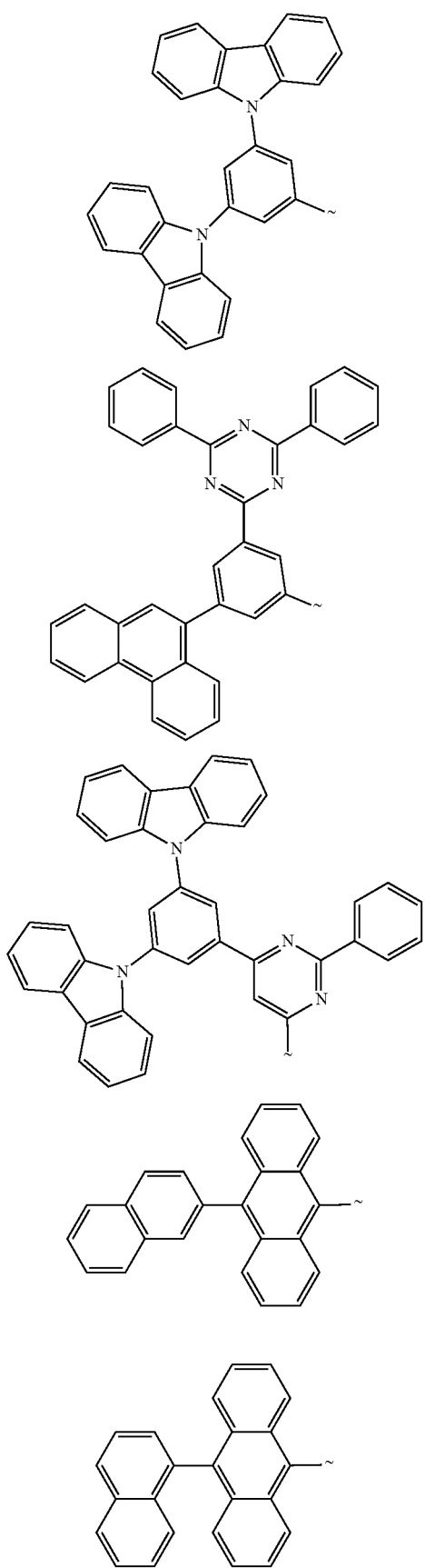
430
-continued
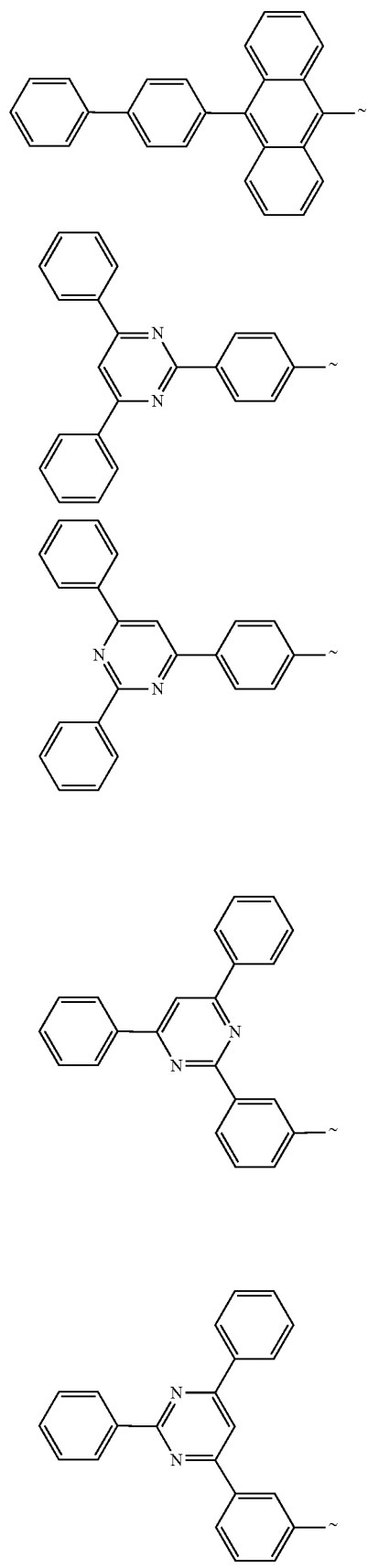

431
-continued
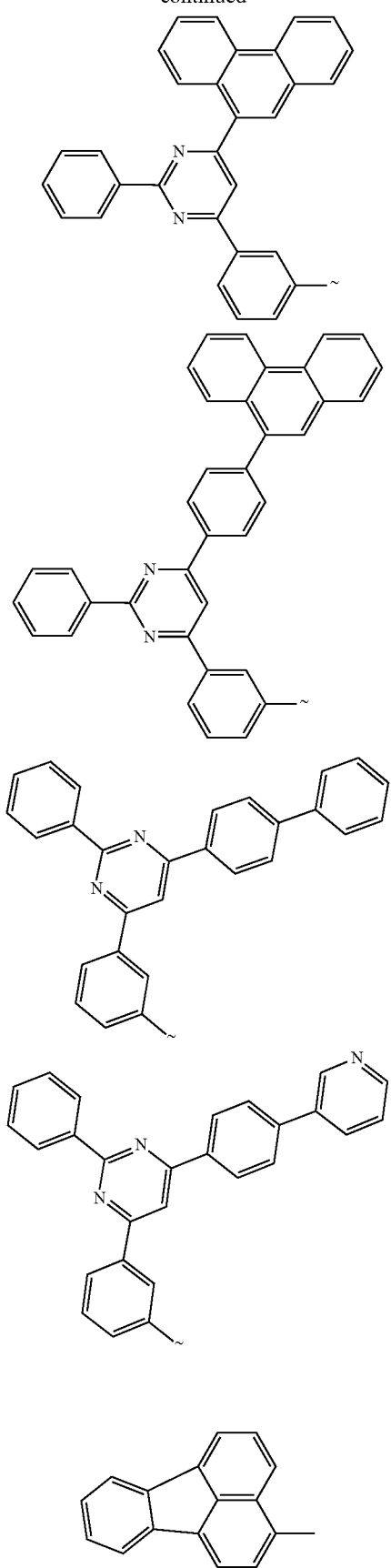
432
-continued
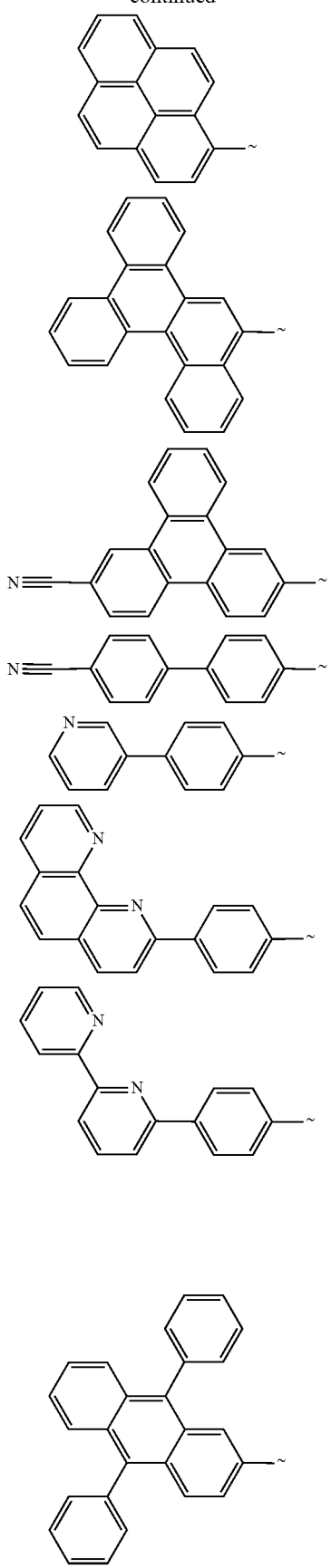

433
-continued
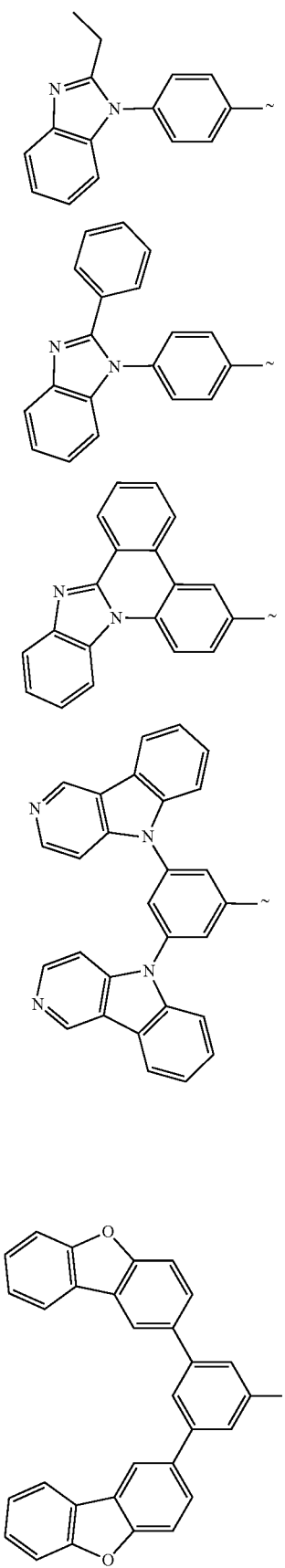
434
-continued
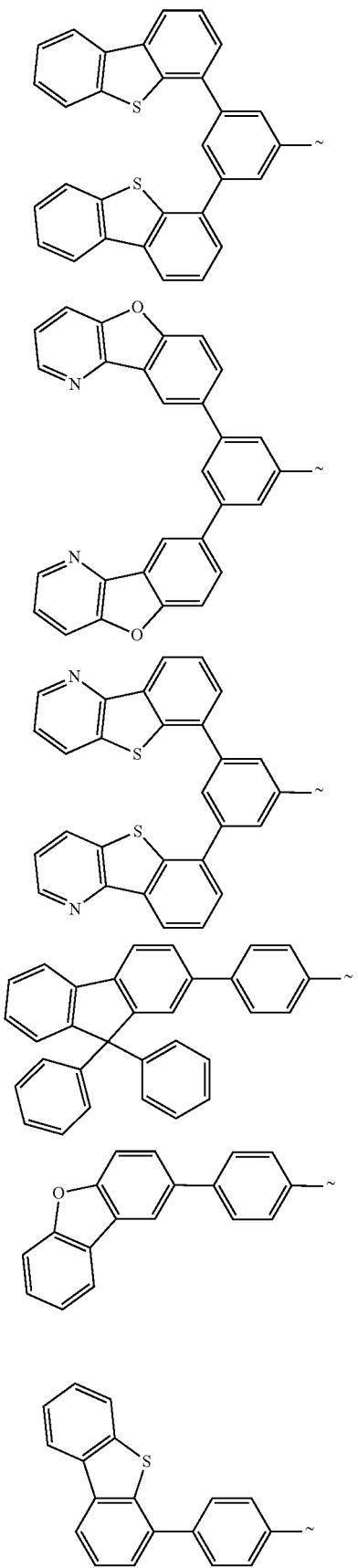

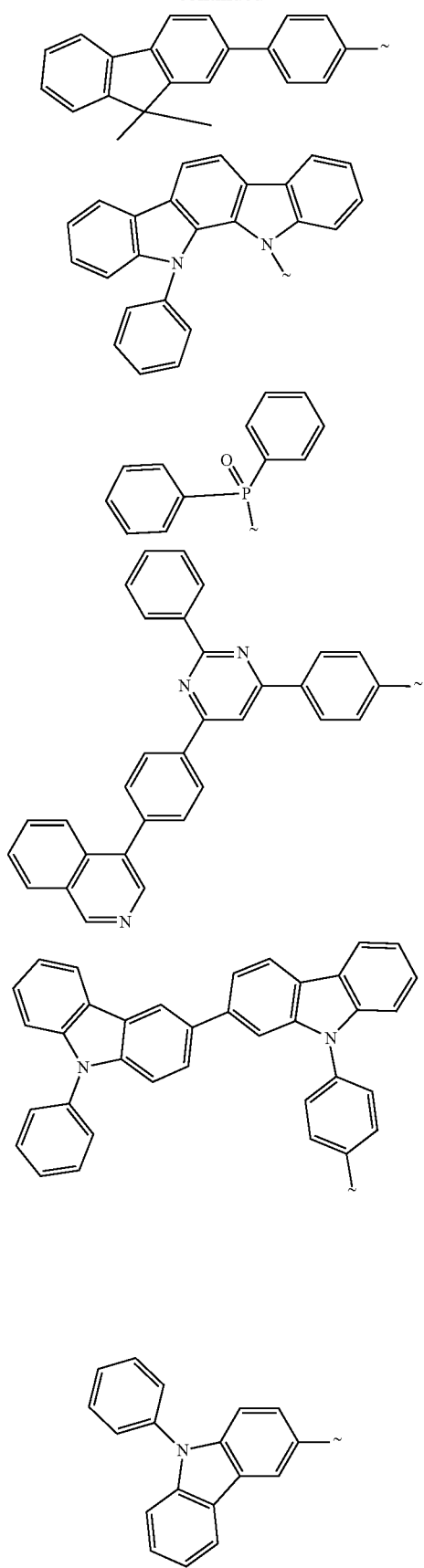
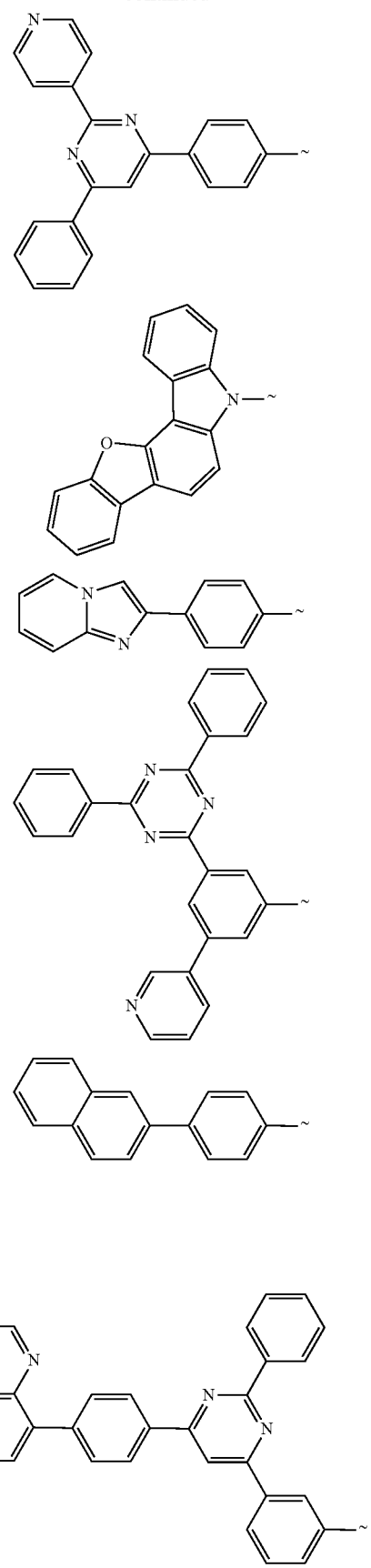

437
-continued
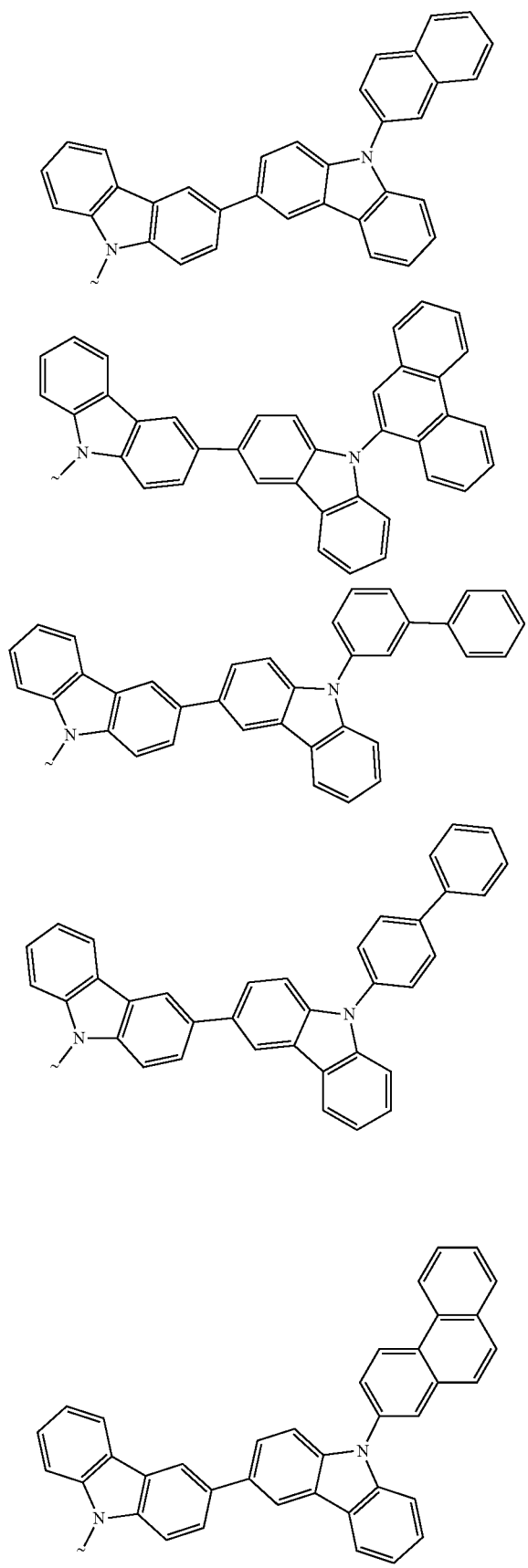
438
-continued
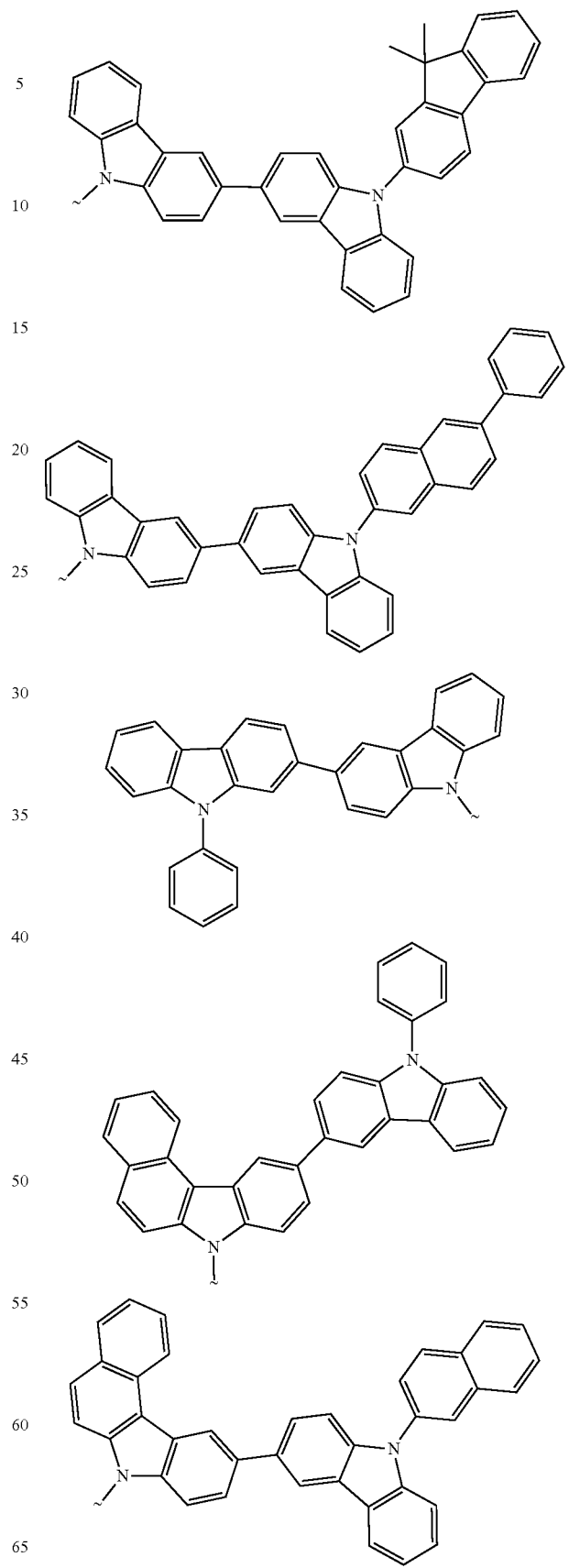

439
-continued
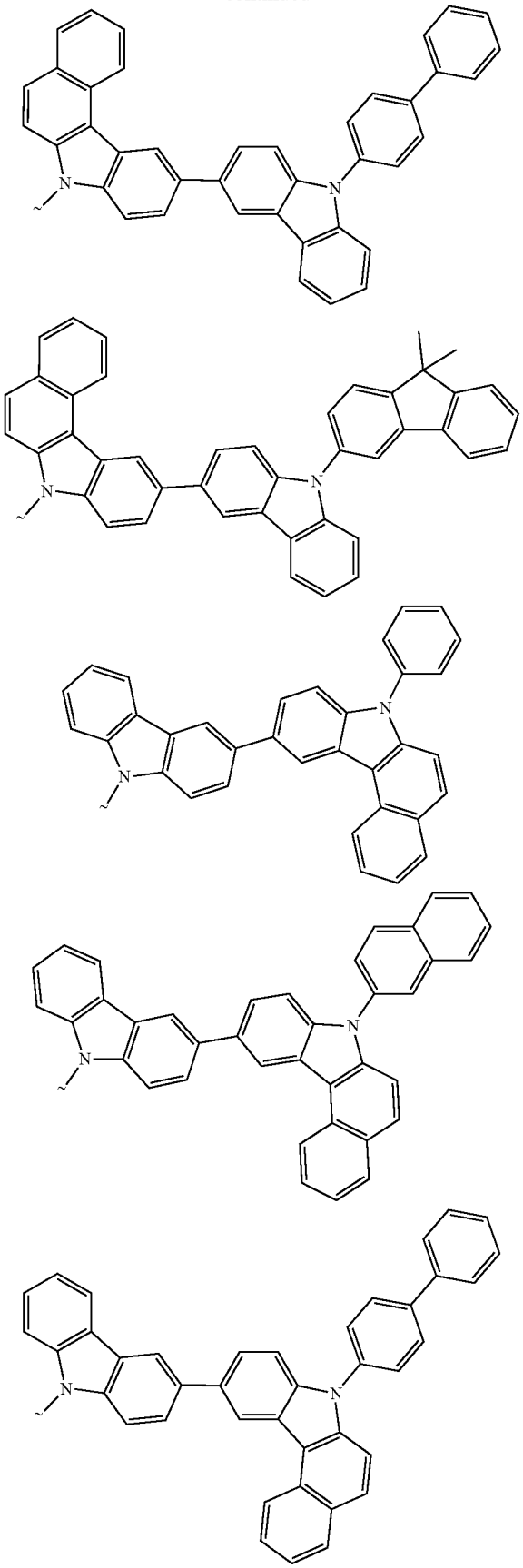
440
-continued
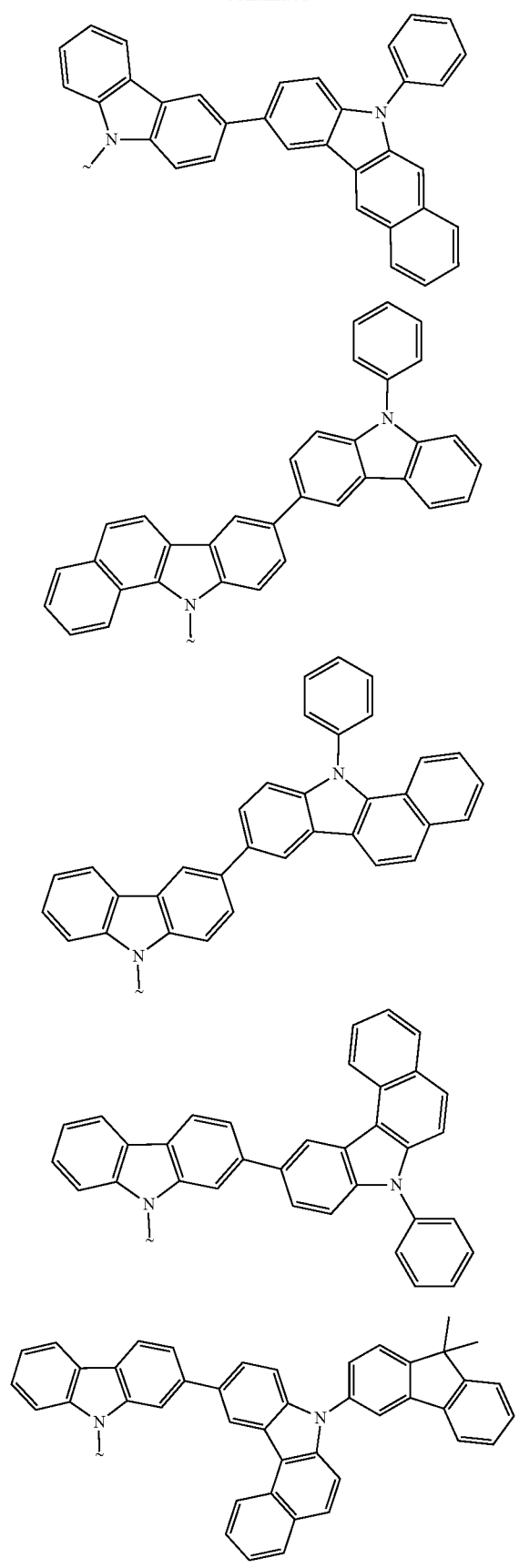

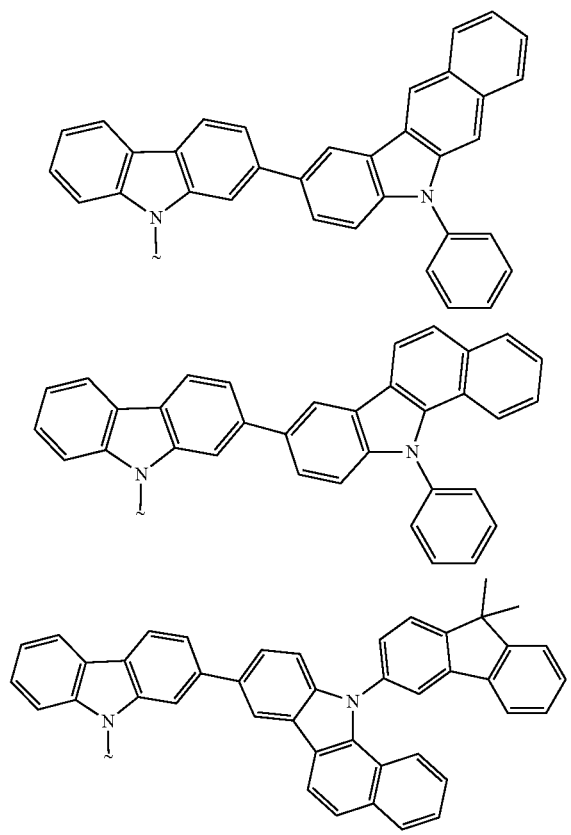
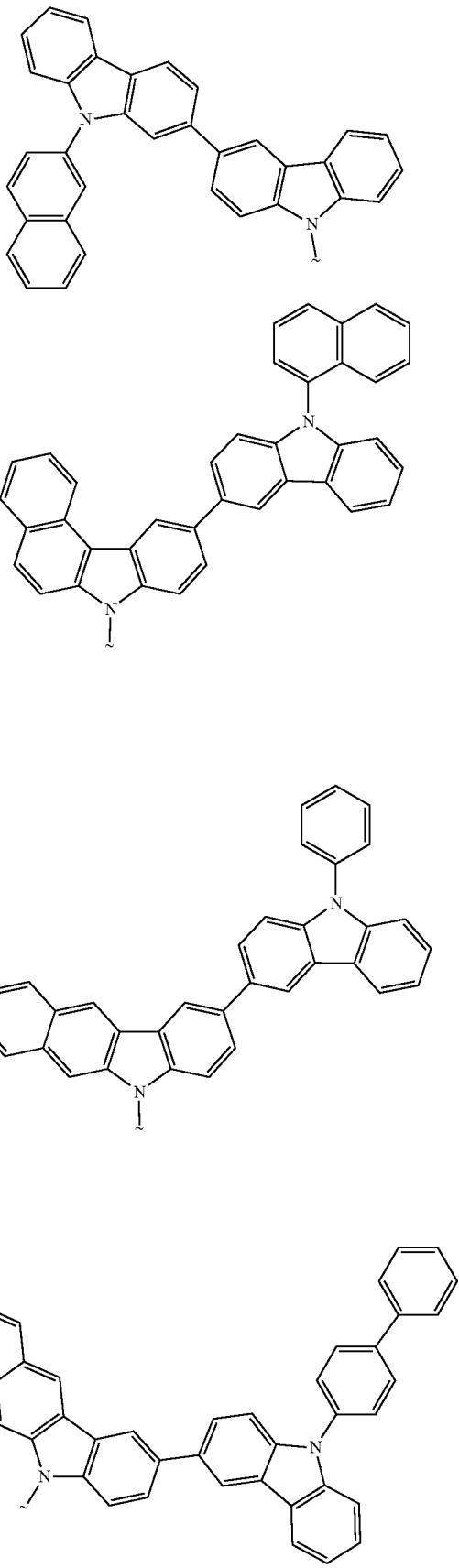

443
-continued
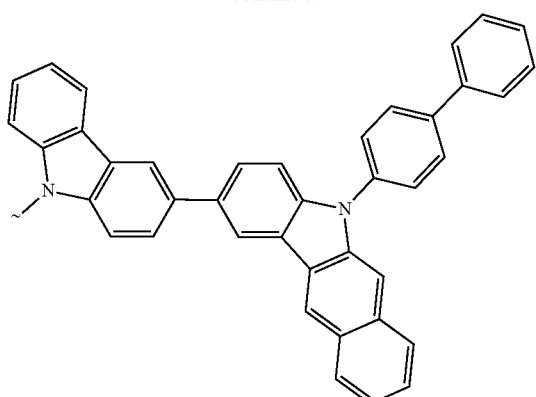
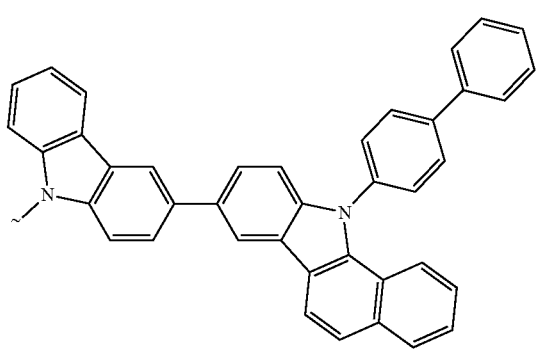
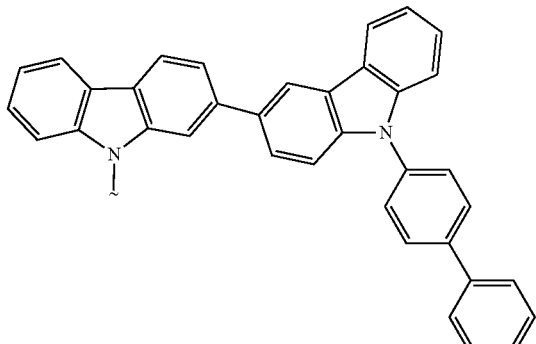
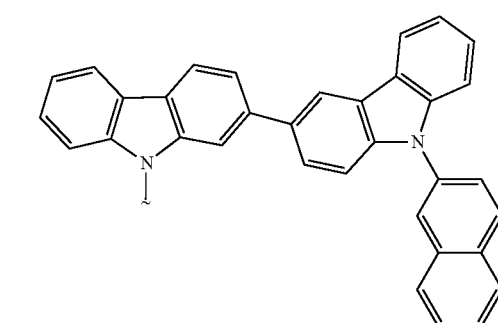
444
-continued
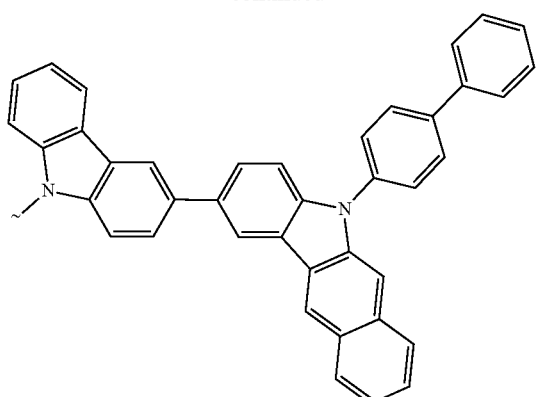
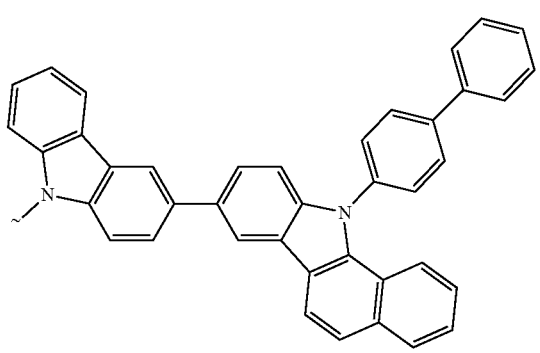
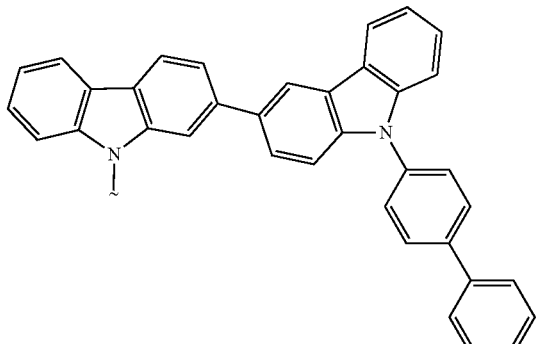
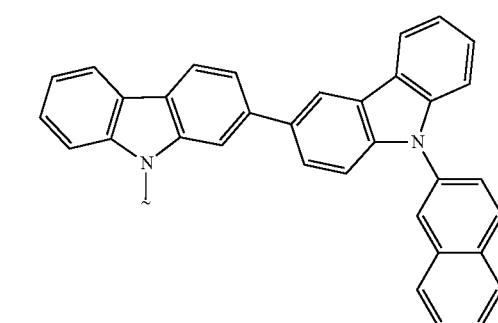, and

445

-continued

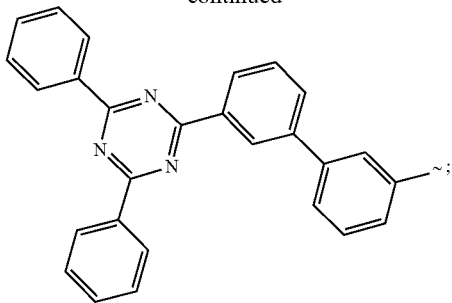

$A^1$, $A^2$, $A^3$, and $A^4$ are independently of each other a $C_6$-$C_{24}$ arylene group which is unsubstituted or substituted by G, a $C_1$-$C_{24}$ heteroarylene group which is unsubstituted or substituted by G;

$R^{20}$ is H; E; a $C_6$-$C_{60}$ aryl group which is unsubstituted or substituted by G, a $C_1$-$C_{60}$ heteroaryl group which is unsubstituted or substituted by G, a $C_1$-$C_{25}$alkyl group, which is unsubstituted or substituted by at least one group G and/or interrupted by D;

D is —CO—, —COO—, —S—, —SO—, —SO$_2$—, —CR$^{63}$=CR$^{64}$—, —NR$^{65}$—, —SiR$^{70}$R$^{71}$—, —POR$^{73}$—, or —C≡C—;

E is —SR$^{69}$, —COR$^{68}$, —COOR$^{67}$, —CONR$^{65}$R$^{66}$, —CN, —SiR$^{70}$R$^{71}$R$^{72}$, or —POR$^{74}$R$^{75}$;

G is E; or a $C_1$-$C_{24}$alkyl group; a $C_1$-$C_{24}$alkyl group, which is interrupted by O; a $C_6$-$C_{60}$aryl group, a $C_6$-$C_{60}$aryl group, which is substituted by F, —CF$_3$, —CF$_2$CF$_3$, —CF$_2$CF$_2$CF$_3$, —CF(CF$_3$)$_2$, —(CF$_2$)$_3$CF$_3$, —C(CF$_3$)$_3$, a $C_1$-$C_{24}$alkyl or a $C_1$-$C_{24}$alkyl which is interrupted by O; a $C_2$-$C_{60}$heteroaryl group; or a $C_2$-$C_{60}$heteroaryl group, which is substituted by F, —CF$_3$, —CF$_2$CF$_3$, —CF$_2$CF$_2$CF$_3$, —CF(CF$_3$)$_2$, —(CF$_2$)$_3$CF$_3$, —C(CF$_3$)$_3$, a $C_1$-$C_{24}$alkyl or a $C_1$-$C_{24}$alkyl which is interrupted by O;

$R^{63}$ and $R^{64}$ are independently of each other a $C_6$-$C_{18}$aryl; a $C_6$-$C_{18}$aryl which is substituted by a $C_1$-$C_{18}$alkyl or a $C_1$-$C_{18}$alkoxy; a $C_1$-$C_{18}$alkyl; or a $C_1$-$C_{18}$alkyl which is interrupted by —O—; H;

$R^{65}$ and $R^{66}$ are independently of each other a $C_6$-$C_{18}$aryl group; a $C_6$-$C_{18}$aryl which is substituted by a $C_1$-$C_{18}$alkyl or a $C_1$-$C_{18}$alkoxy; a $C_1$-$C_{18}$alkyl group; or a $C_1$-$C_{18}$alkyl group, which is interrupted by —O—; or $R^{65}$ and $R^{66}$ together form a five or six membered ring, which can be substituted or benzanullated;

$R^{67}$ is a $C_6$-$C_{18}$aryl group; a $C_6$-$C_{18}$aryl group, which is substituted by a $C_1$-$C_{18}$alkyl, or a $C_1$-$C_{18}$alkoxy; a $C_1$-$C_{18}$alkyl group; or a $C_1$-$C_{18}$alkyl group, which is interrupted by —O—;

$R^{68}$ is H; a $C_6$-$C_{18}$aryl group; a $C_6$-$C_{18}$aryl group, which is substituted by a $C_1$-$C_{18}$alkyl or a $C_1$-$C_{18}$alkoxy; a $C_1$-$C_{18}$alkyl group; or a $C_1$-$C_{18}$alkyl group, which is interrupted by —O—;

$R^{69}$ is a $C_6$-$C_{18}$aryl; a $C_6$-$C_{18}$aryl, which is substituted by a $C_1$-$C_{18}$alkyl or a $C_1$-$C_{18}$alkoxy; a $C_1$-$C_{18}$alkyl group; or a $C_1$-$C_{18}$alkyl group, which is interrupted by —O—;

$R^{70}$, $R^{71}$ and $R^{72}$ are independently of each other a $C_1$-$C_{18}$alkyl group, a $C_6$-$C_{18}$aryl group, or a $C_6$-$C_{18}$aryl group, which is substituted by a $C_1$-$C_{18}$alkyl; and $R^{73}$, $R^{74}$, and $R^{75}$ is a $C_1$-$C_{18}$alkyl group, a $C_6$-$C_{18}$aryl group, or a $C_6$-$C_{18}$aryl group, which is substituted by a $C_1$-$C_{18}$ alkyl;

446 wherein in the case of formula (1b) B$_3$ is CH and o, p, q and r in the definition of R$^6$ and R$^7$ are 0.

22. The electronic device according to claim 21, which is an organic electroluminescent device.

23. The organic electroluminescent device according to claim 22, wherein:
the organic electroluminescent device comprises an anode, a cathode, and a light emitting layer arranged between the anode and the cathode;
the light emitting layer comprises an organic metal complex containing at least one metal selected from Ir, Pt, Os, Au, Cu, Re and Ru and the heterocyclic derivative as a host material.

24. The organic electroluminescent device according to claim 22, wherein the organic electroluminescent device comprises an electron transporting layer comprising the heterocyclic derivative.

25. The organic electroluminescent device according to according to claim 24, wherein the electron transporting layer is in contact with the light emitting layer.

26. The organic electroluminescent device according to according to claim 24, wherein an electron transporting zone is disposed between the light emitting layer and the electron transporting layer.

27. The organic electroluminescent device according to according to claim 24, wherein the electron transporting layer further comprises an alkali metal, an alkaline earth metal, a rare earth metal, a compound comprising an alkali metal, an alkaline earth metal, or a rare earth metal, or a complex comprising an alkali metal, an alkaline earth metal, or a rare earth metal.

28. An apparatus selected from the group consisting of stationary visual display units; mobile visual display units; illumination units; keyboards; items of clothing; furniture; wallpaper, comprising the organic electronic device according to claim 21.

29. An organic electroluminescence device, comprising a first electron transport layer and a second electron transport layer, wherein the second electron transport layer comprises a heterocyclic derivative of formula (1):

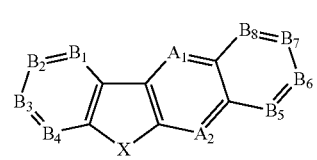

(1)

wherein
X is O or S;
A$_1$ is N or CR$^{A1}$;
A$_2$ is N or CR$^{A2}$;
wherein one of A$_1$ and A$_2$ is N;
B$_1$ is CR$^1$;
B$_2$ is CH;
B$_3$ is CR$^3$;
B$_4$ is CR$^4$;
B$_5$ is CR$^5$;
B$_6$ is CR$^6$;
B$_7$ is CR$^7$;
B$_8$ is CR$^8$;
R$^1$, R$^3$, R$^4$, R$^5$, R$^6$, R$^7$, and R$^8$ are independently of each other H; E; a group of formula -(A$^1$)$_o$-(A$^2$)$_p$-(A$^3$)$_q$-(A$^4$)

$_r$-R$^{20}$; or a C$_1$-C$_{25}$alkyl group, which is unsubstituted or substituted by at least one group E and/or interrupted by D;
wherein o is 0 or 1, p is 0 or 1, q is 0 or 1, r is 0 or 1 in the formula -(A$^1$)$_o$-(A$^2$)$_p$-(A$^3$)$_q$-(A$^4$)$_r$-R$^{20}$ for R$^1$, R$^3$, R$^4$, R$^5$, R$^6$, R$^7$, and R$^8$;
R$^{A1}$ is selected from the group consisting of
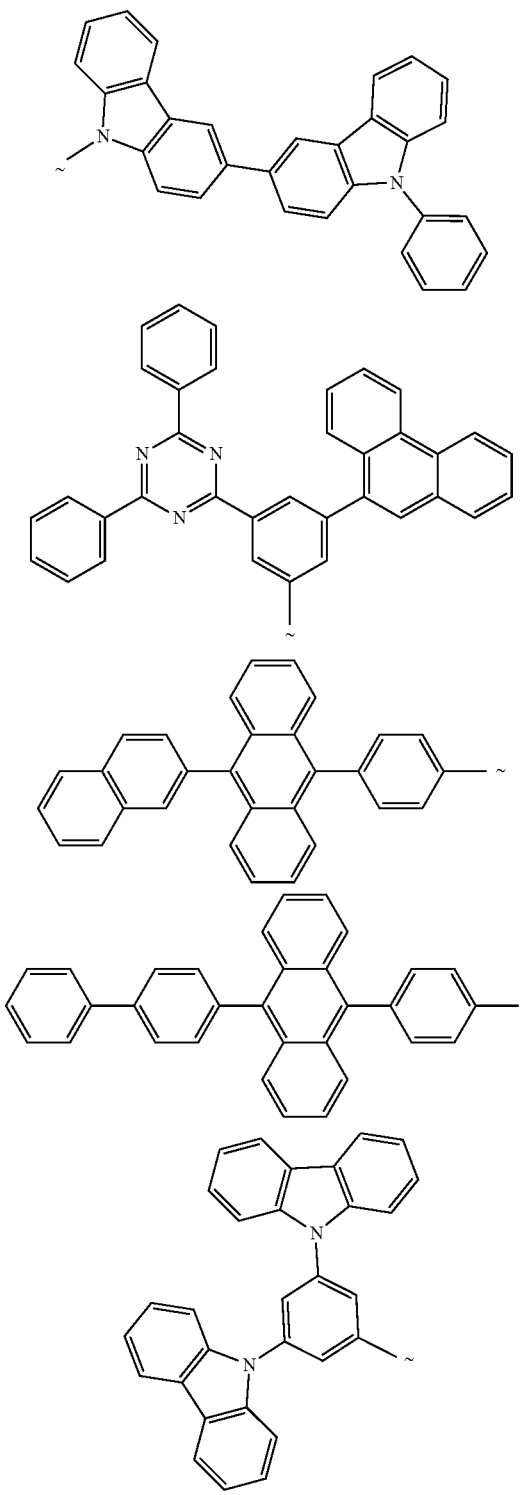
-continued
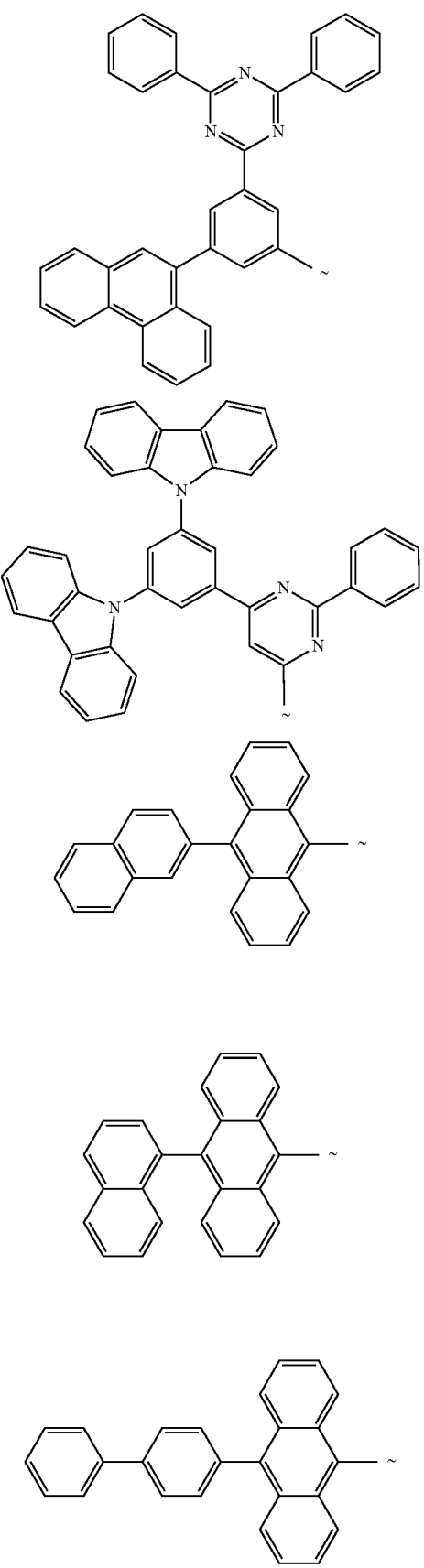

449
-continued
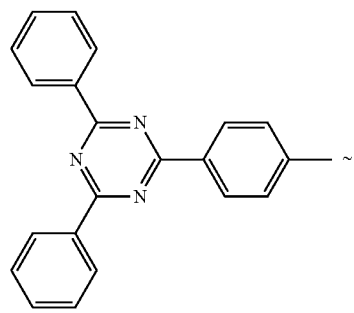
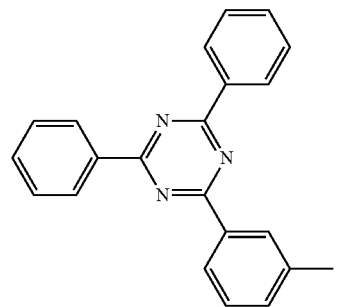
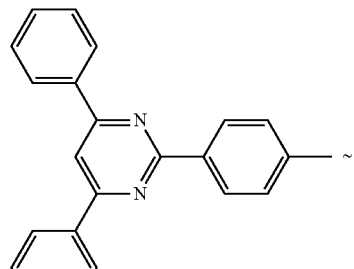
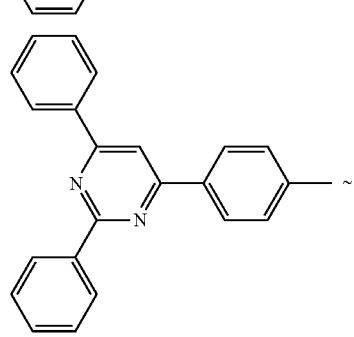
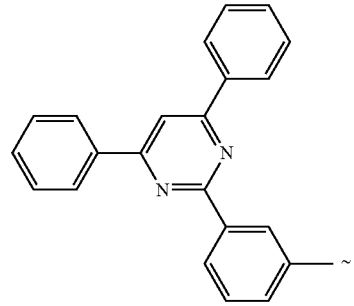
450
-continued
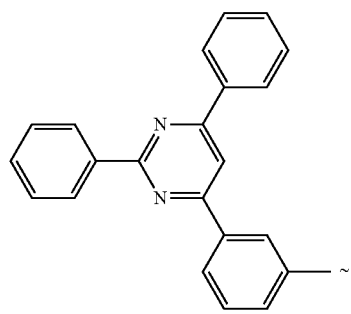
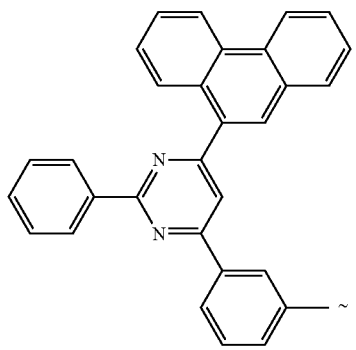
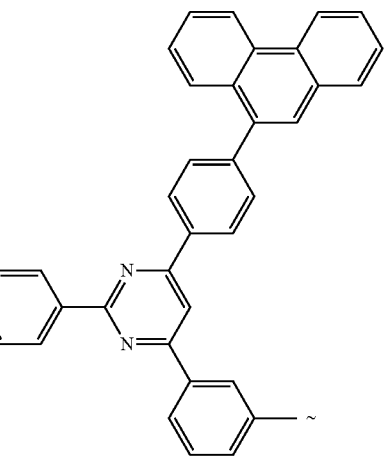
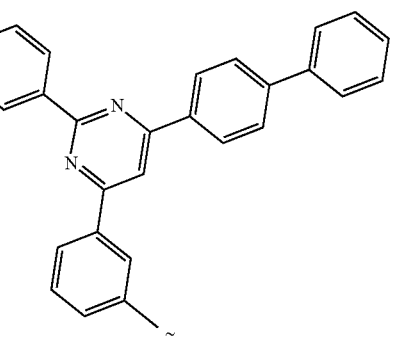

451
-continued
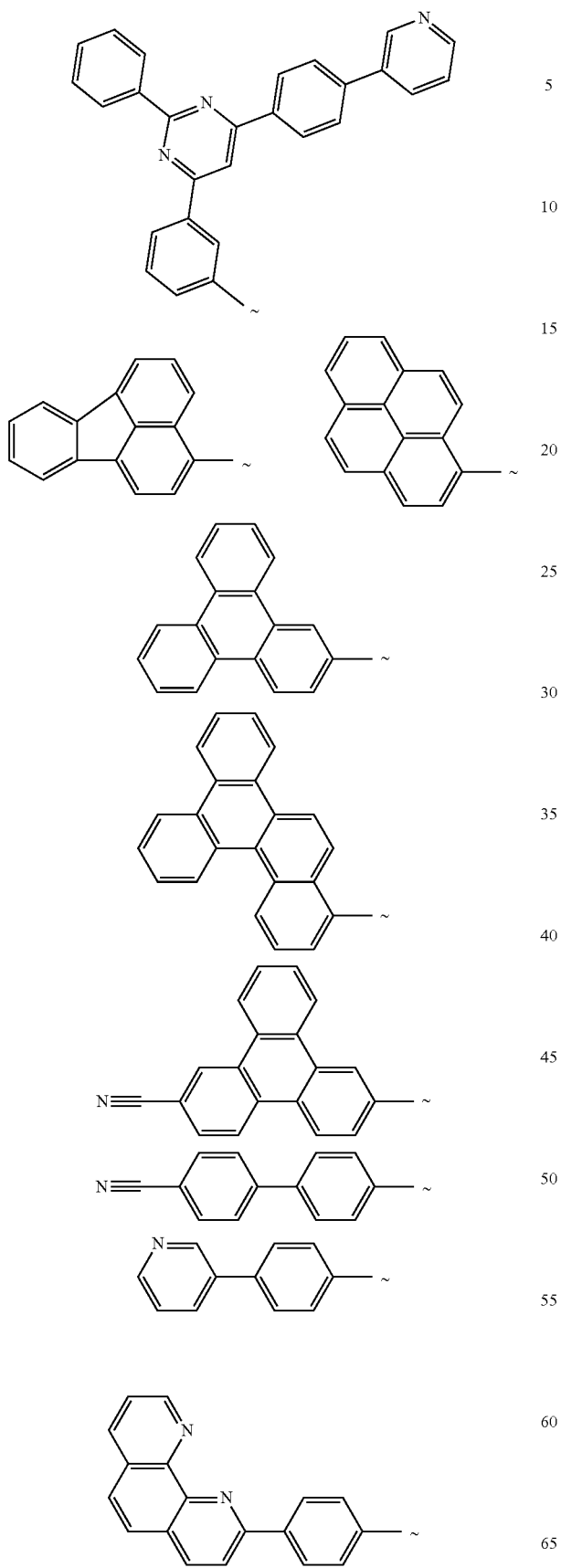
452
-continued
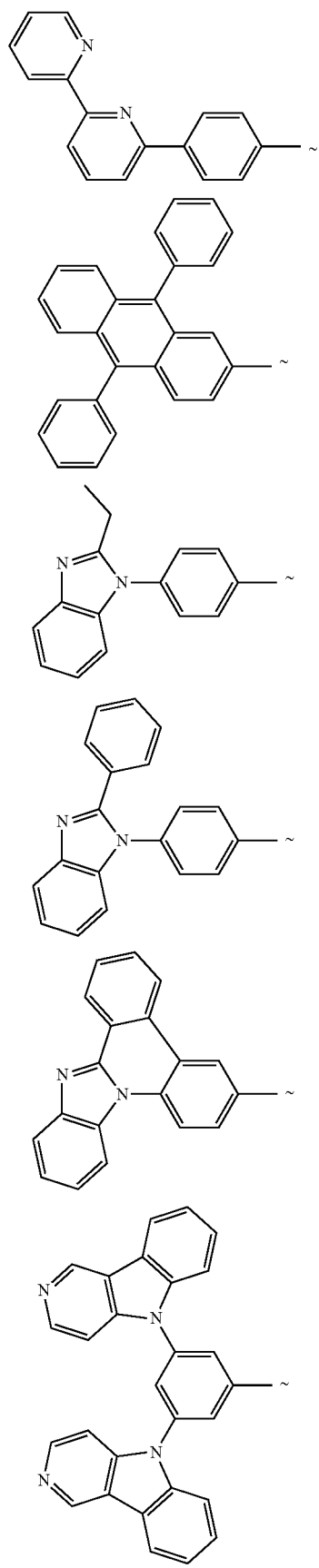

453
-continued
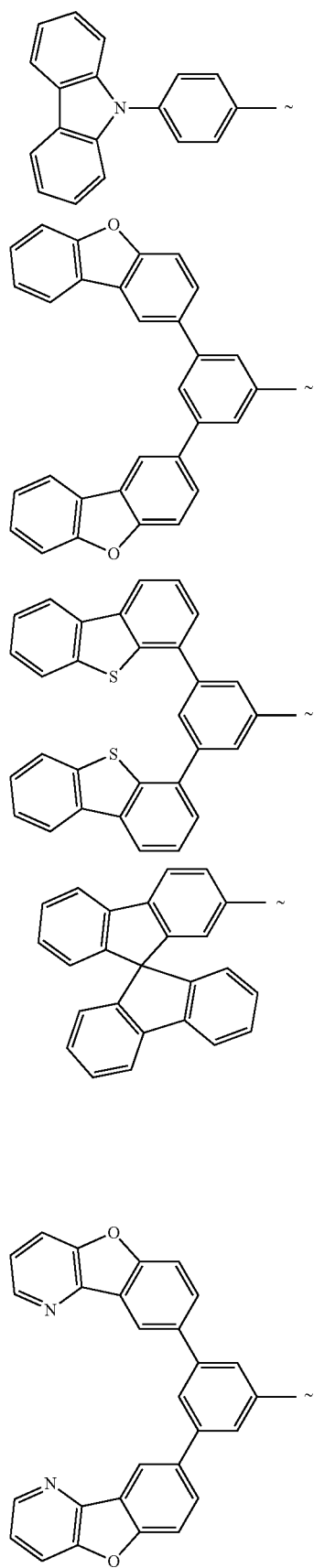
454
-continued
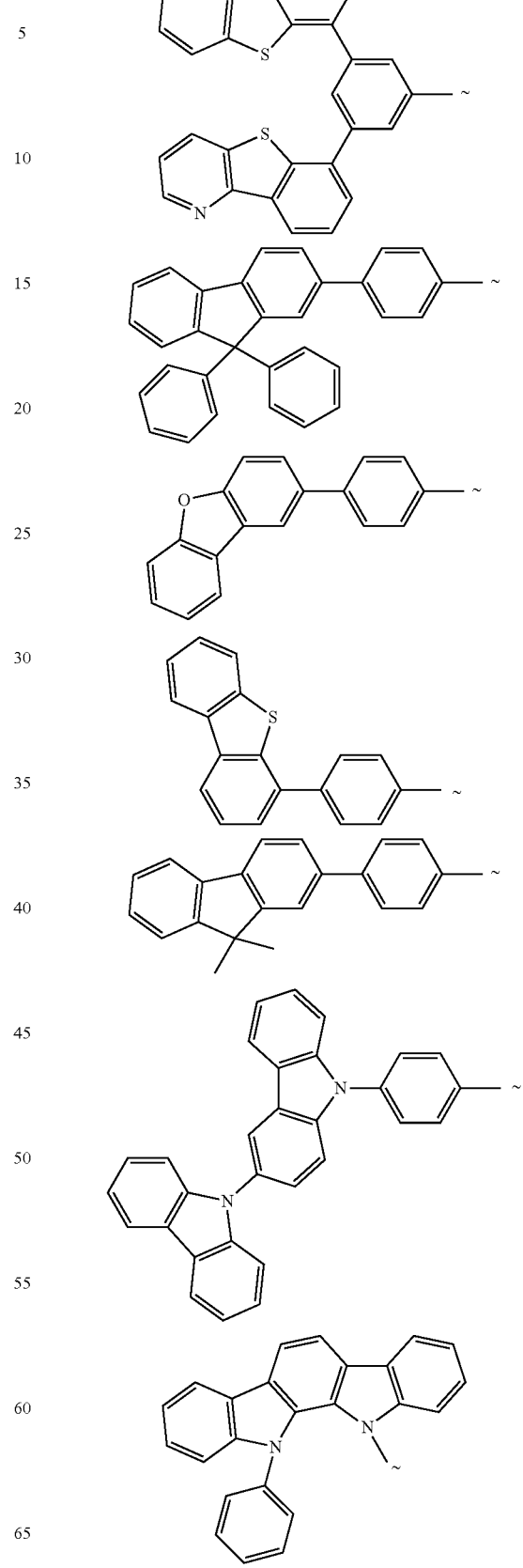

455
-continued
456
-continued
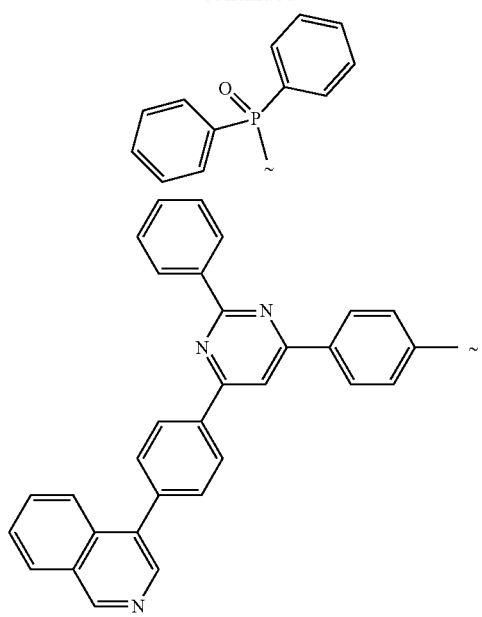
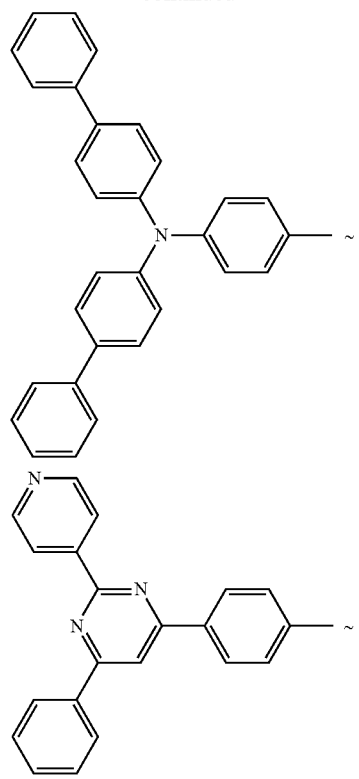
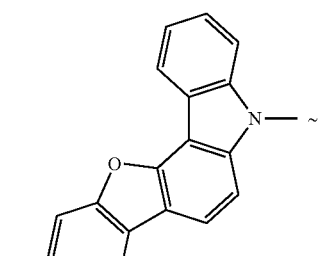
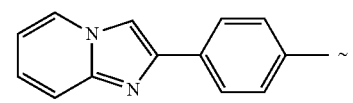
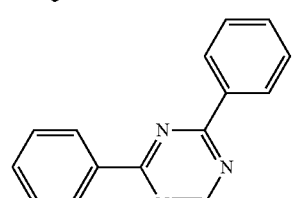
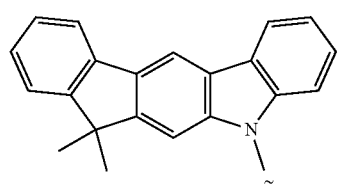
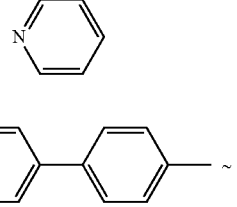

457
-continued
458
-continued
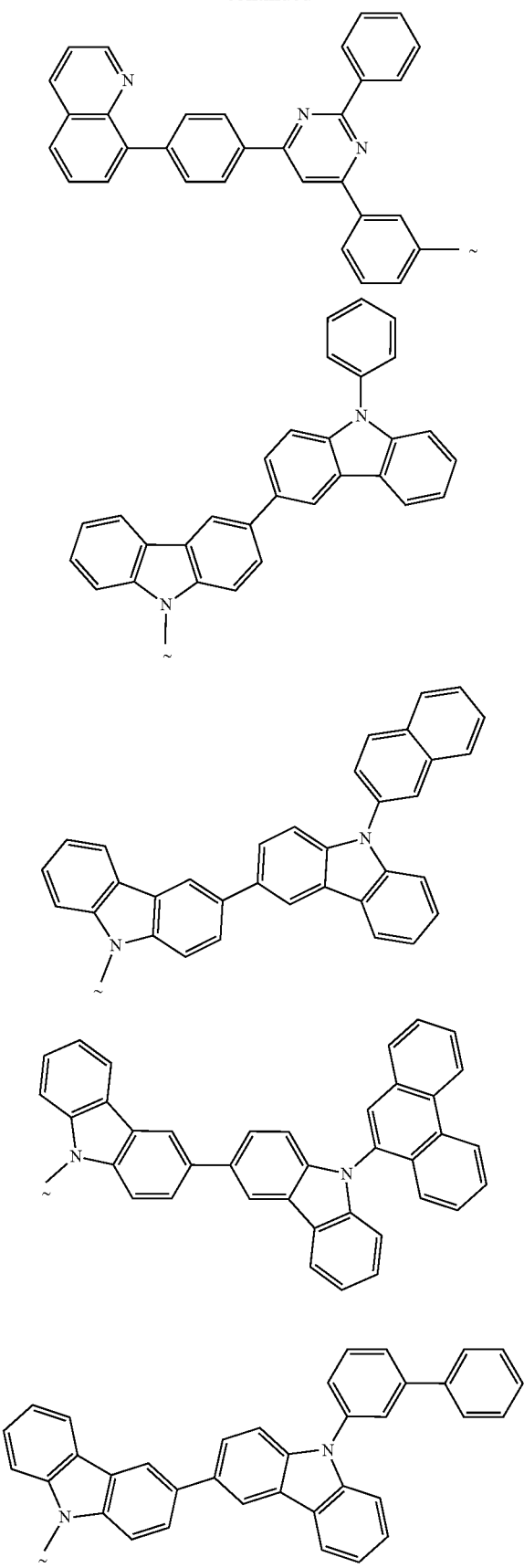
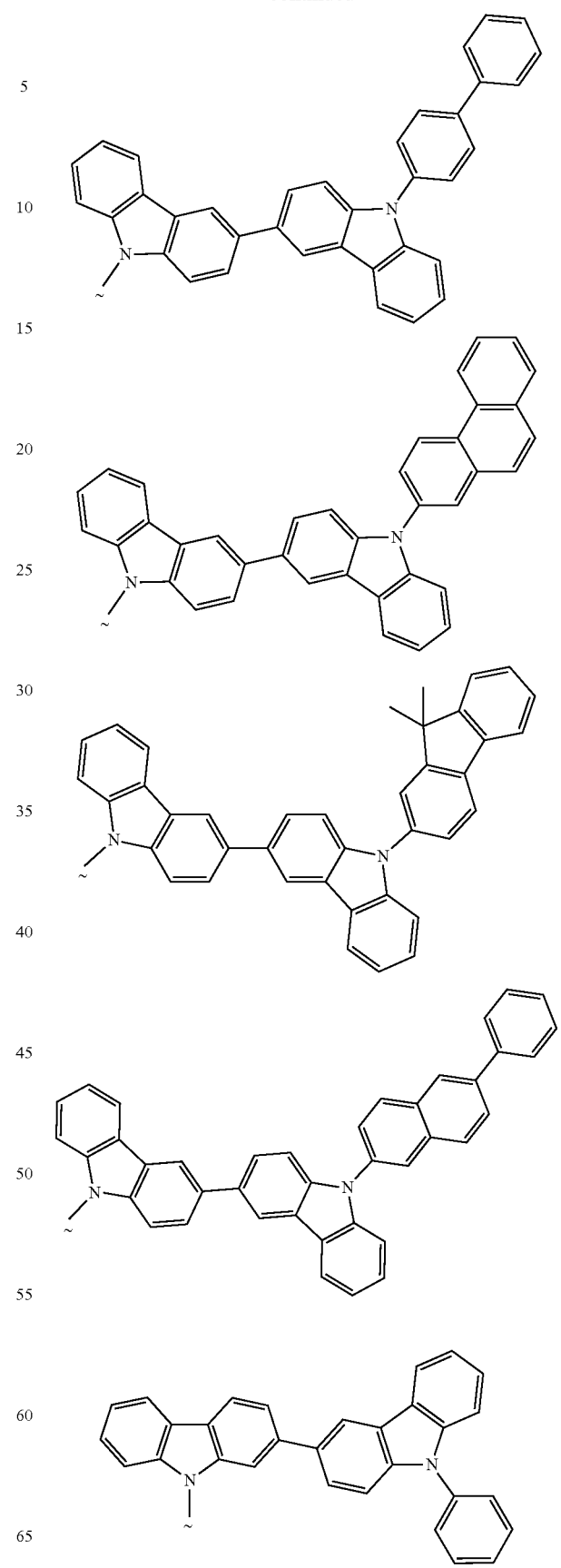

459
-continued
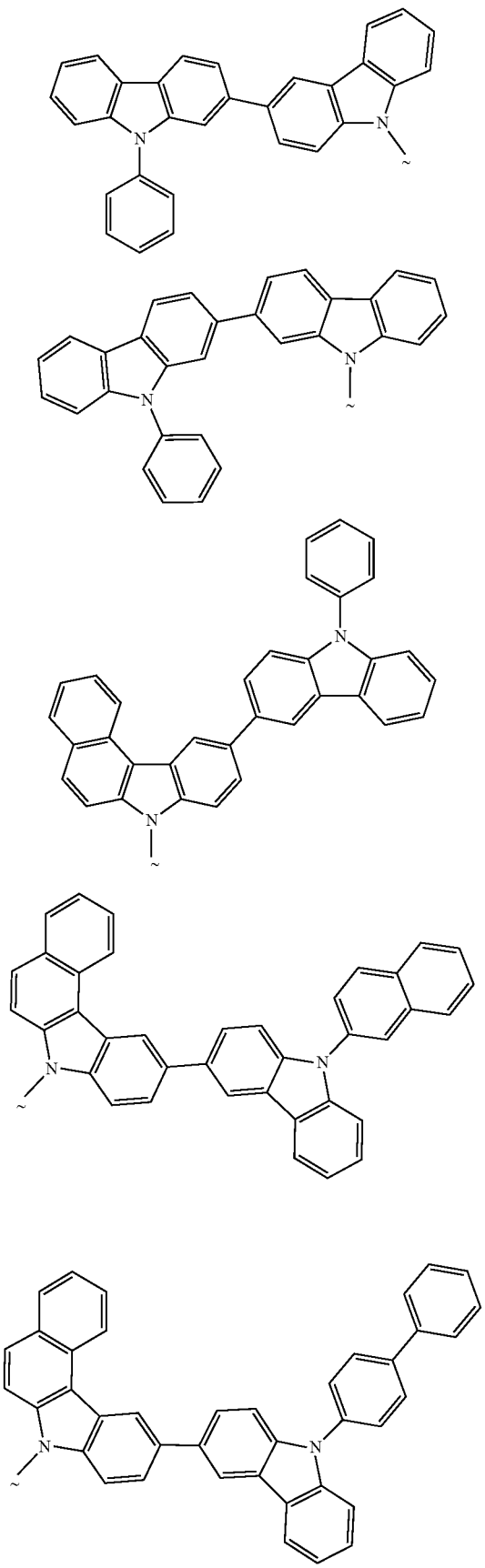
460
-continued
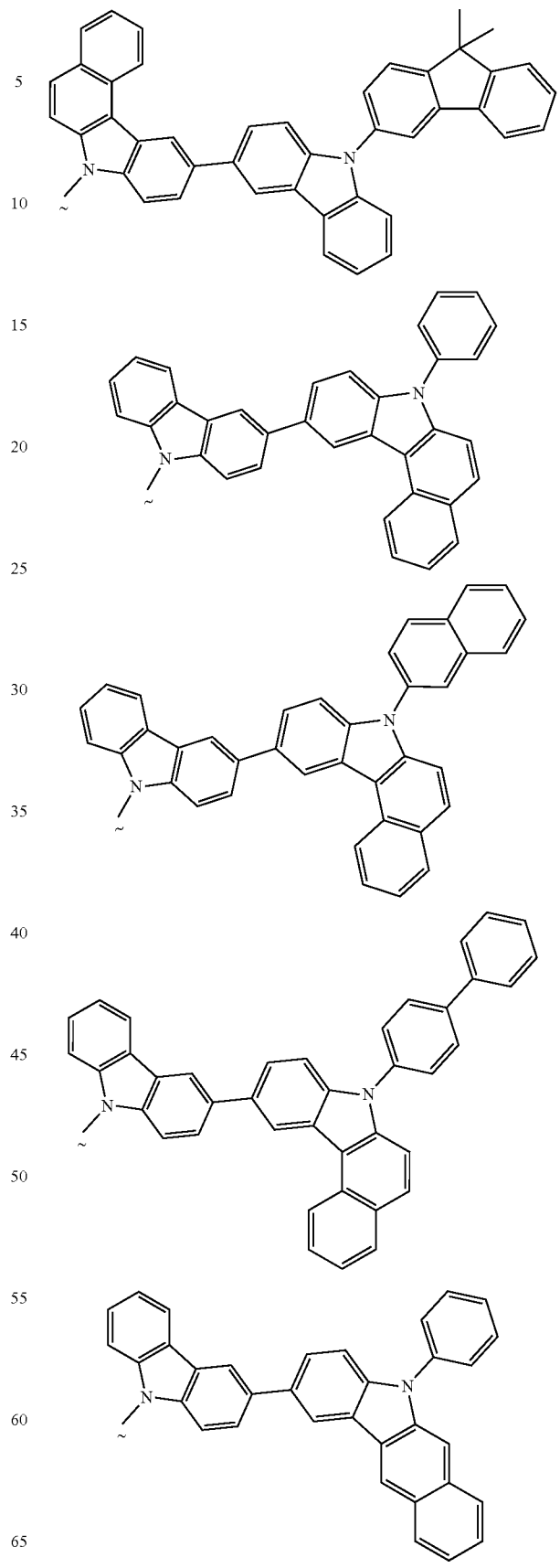

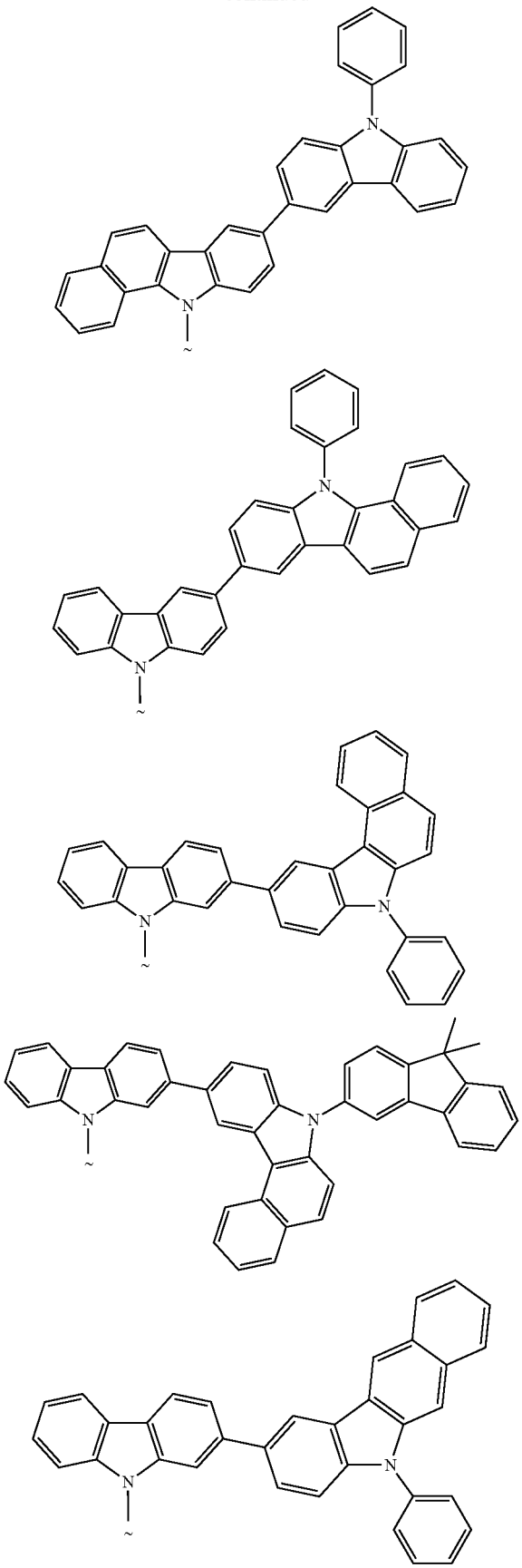
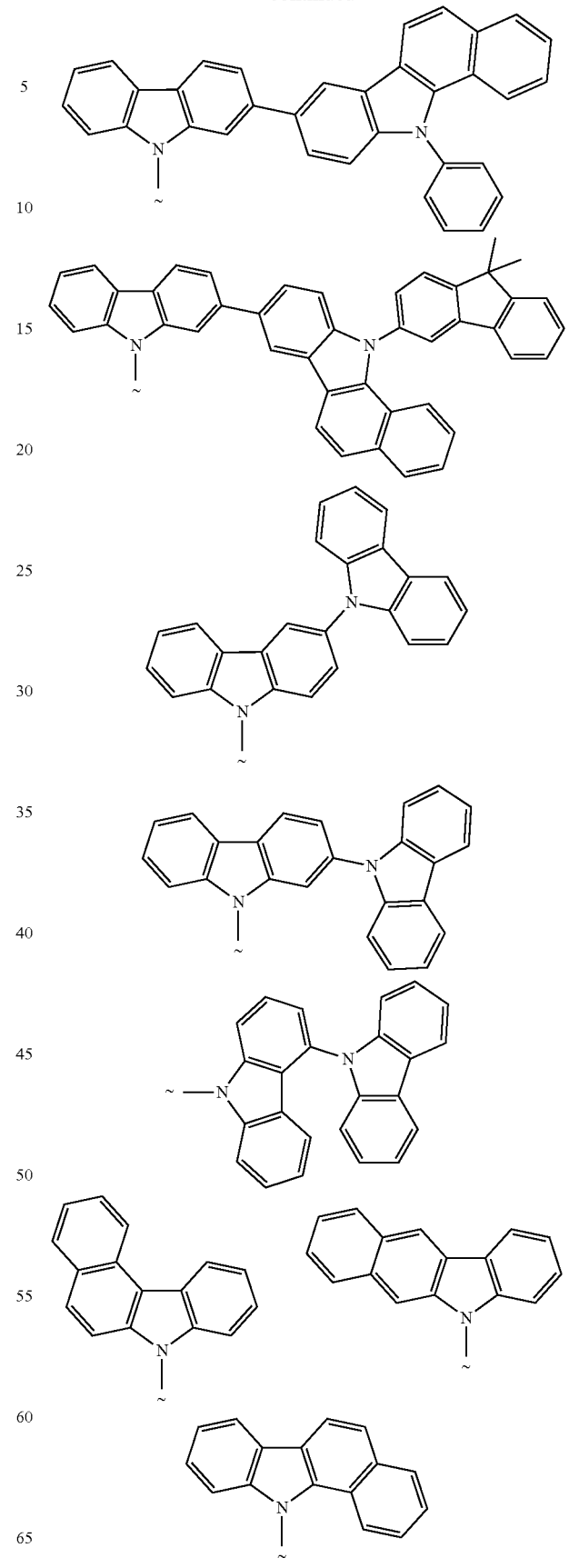

463
-continued
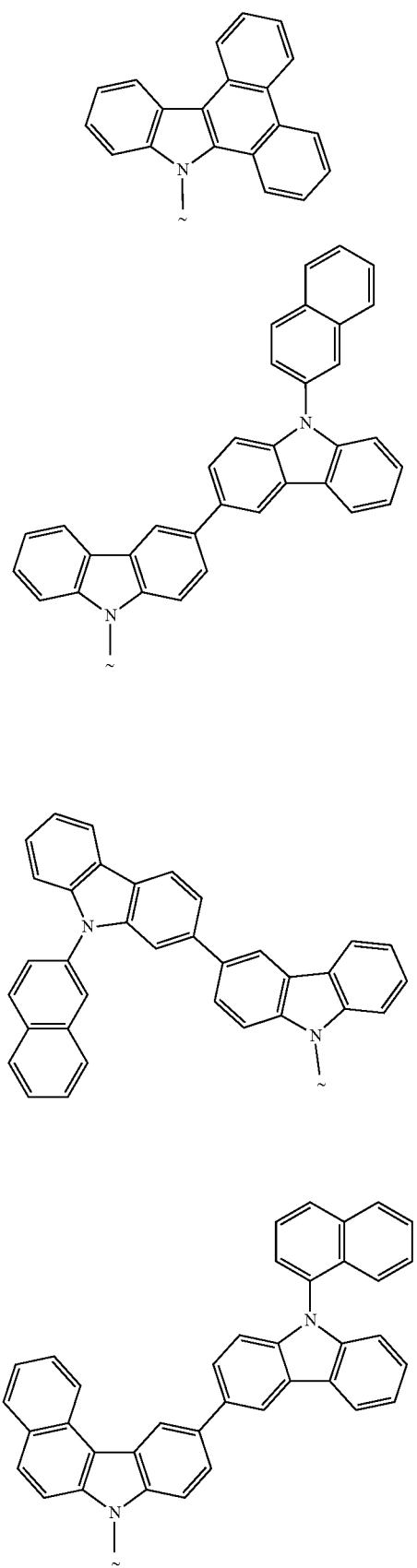
464
-continued
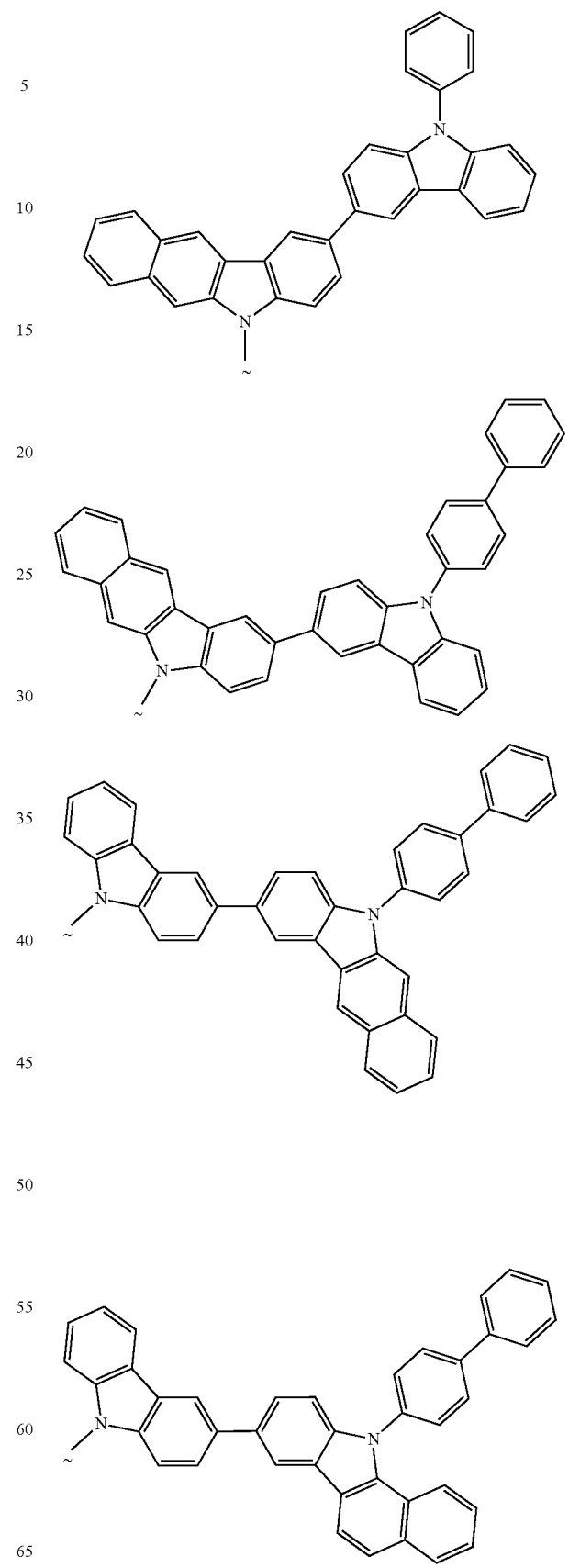

465
-continued
466
-continued
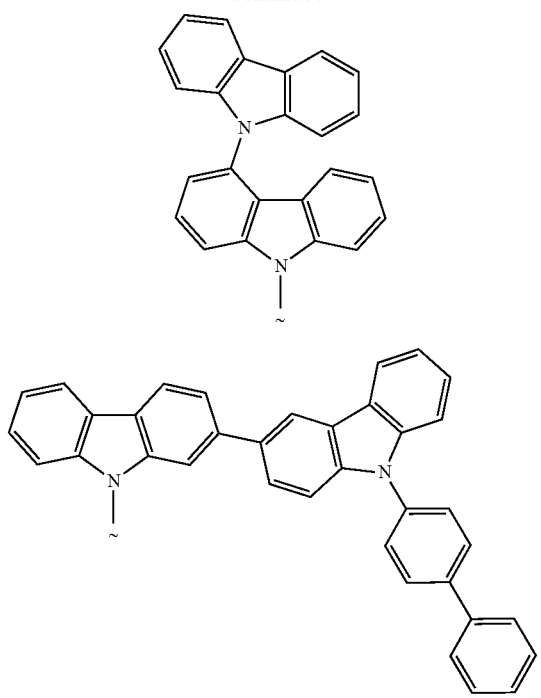
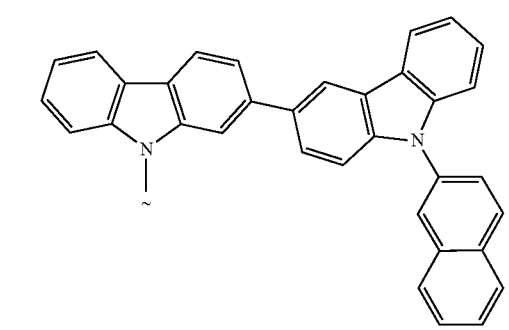
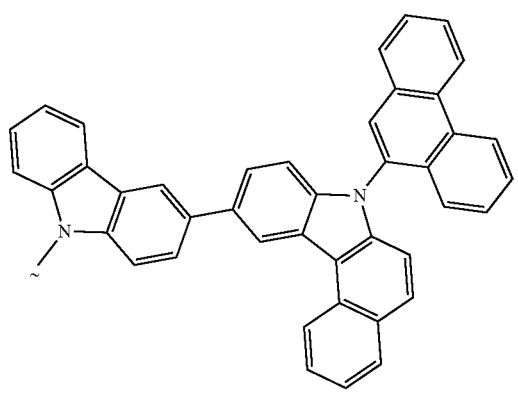
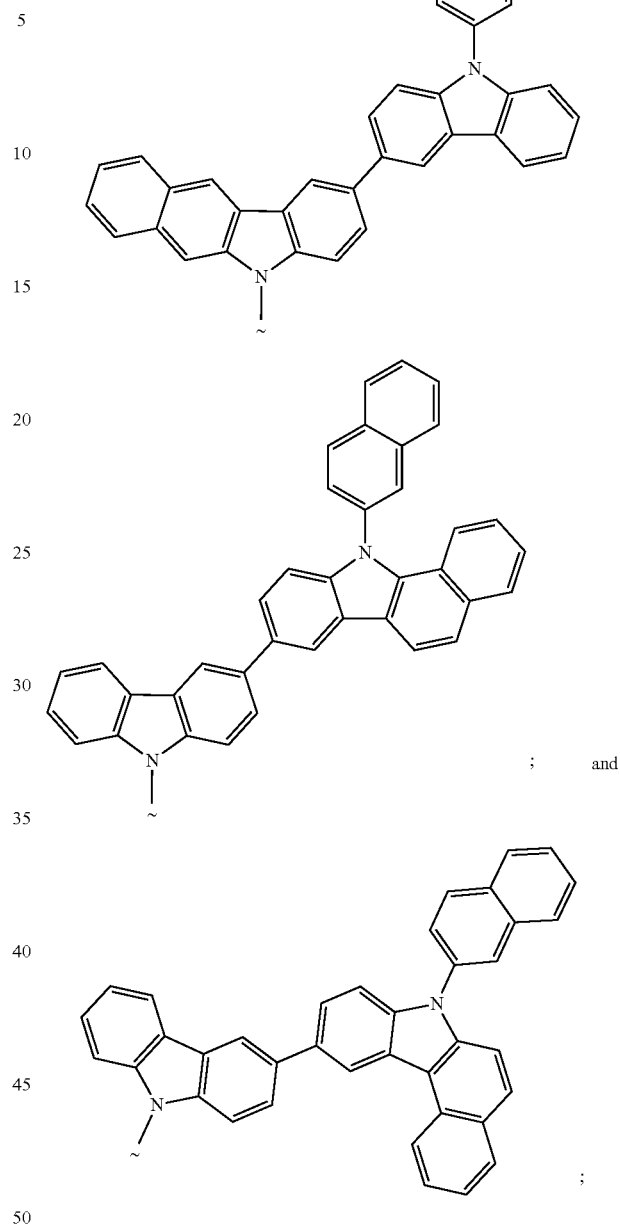
$R^{A2}$ is selected from group consisting of
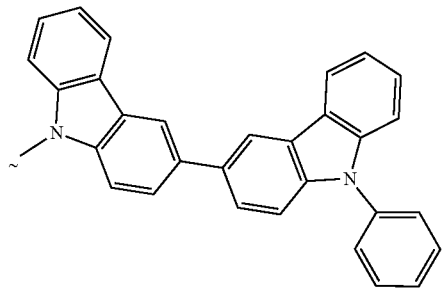

467
-continued
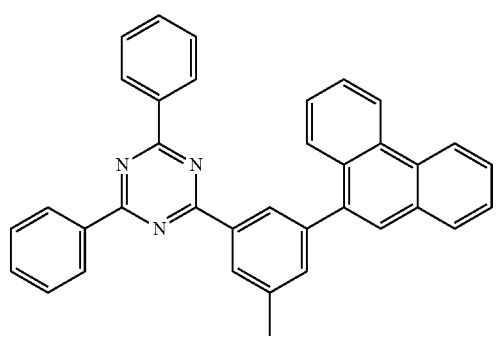
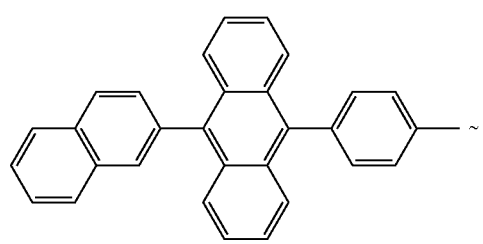
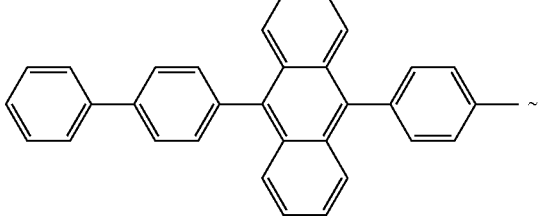
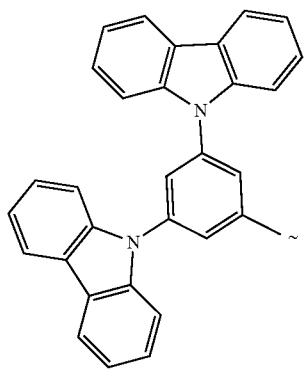
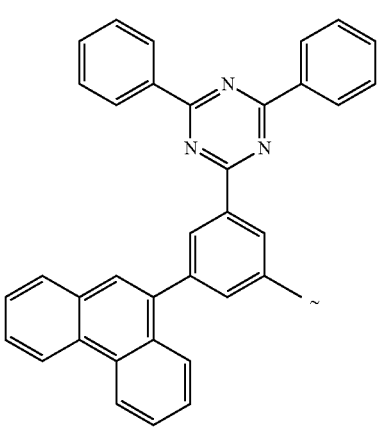
468
-continued
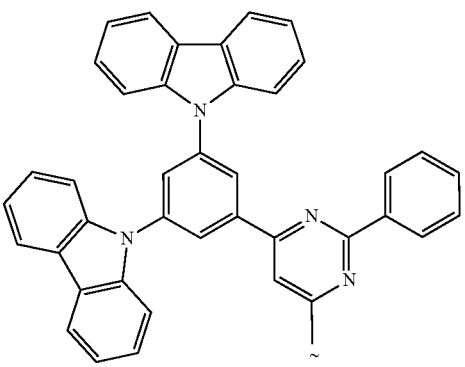
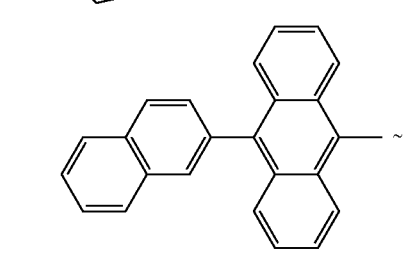
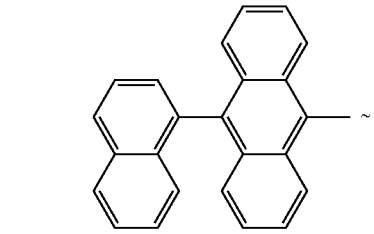
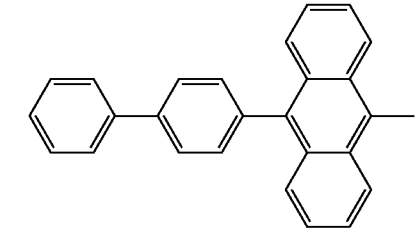
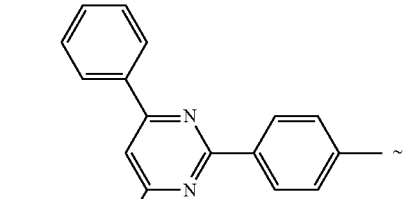
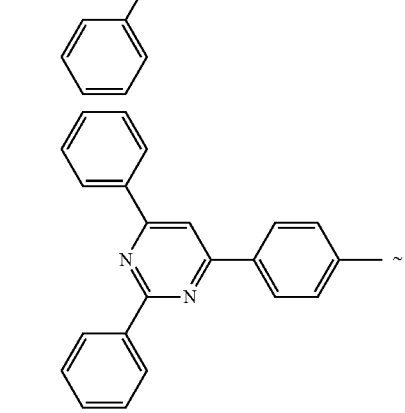

469
-continued
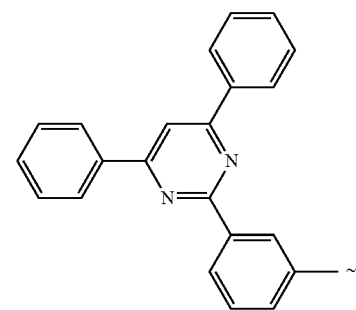
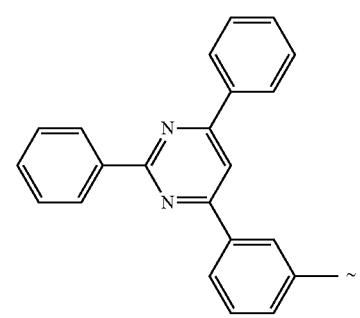
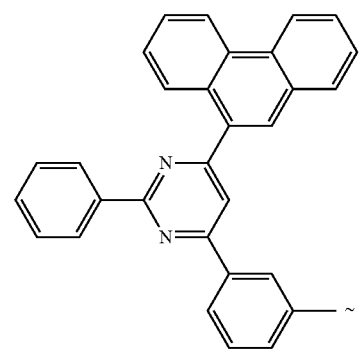
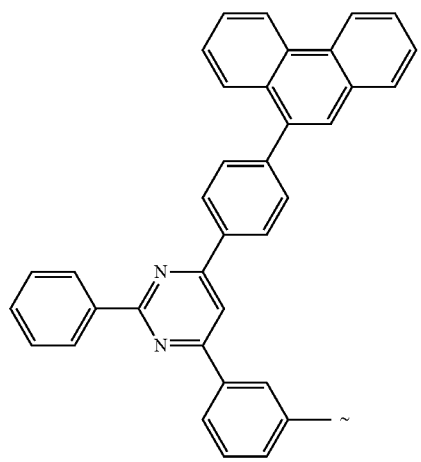
470
-continued
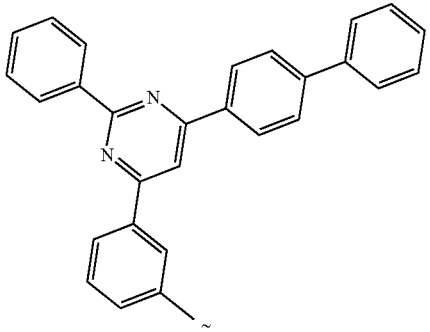
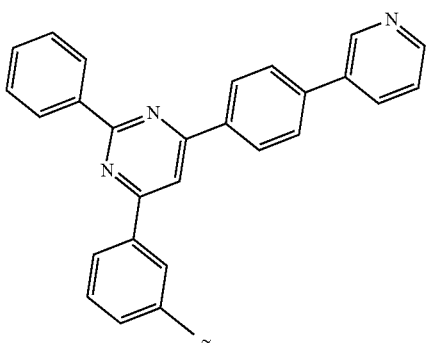
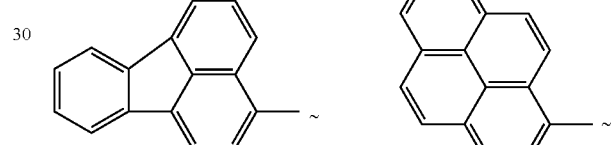
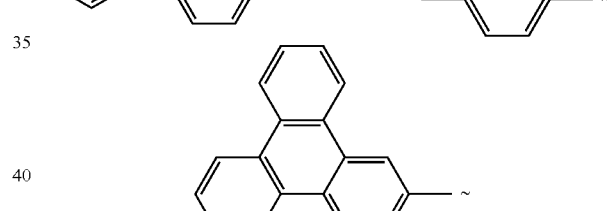
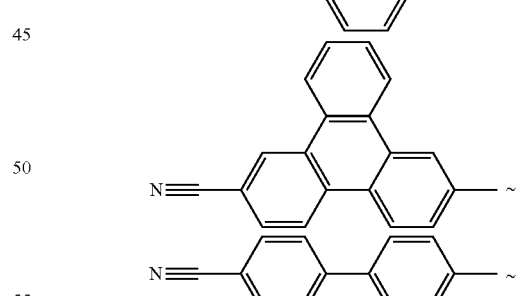
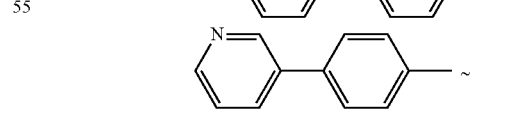
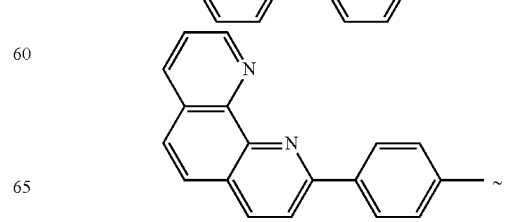

471
-continued
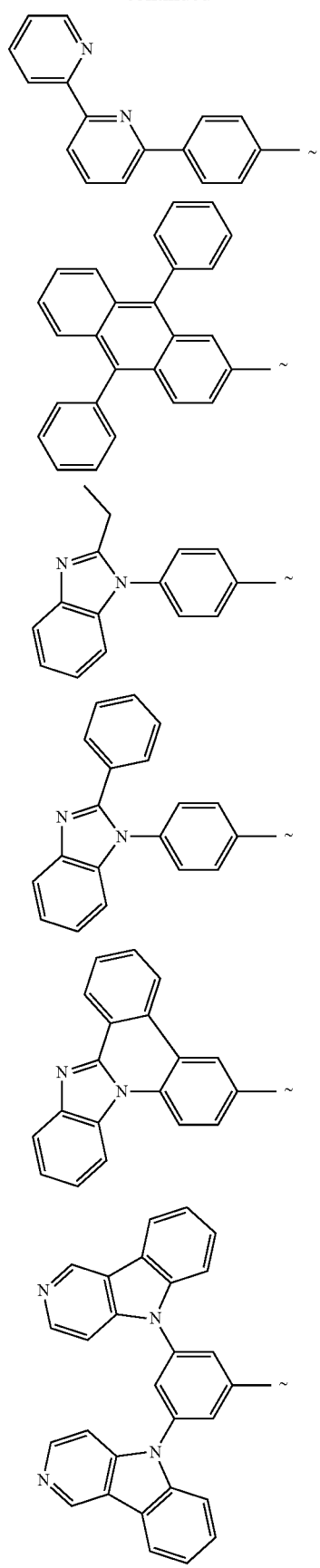
472
-continued
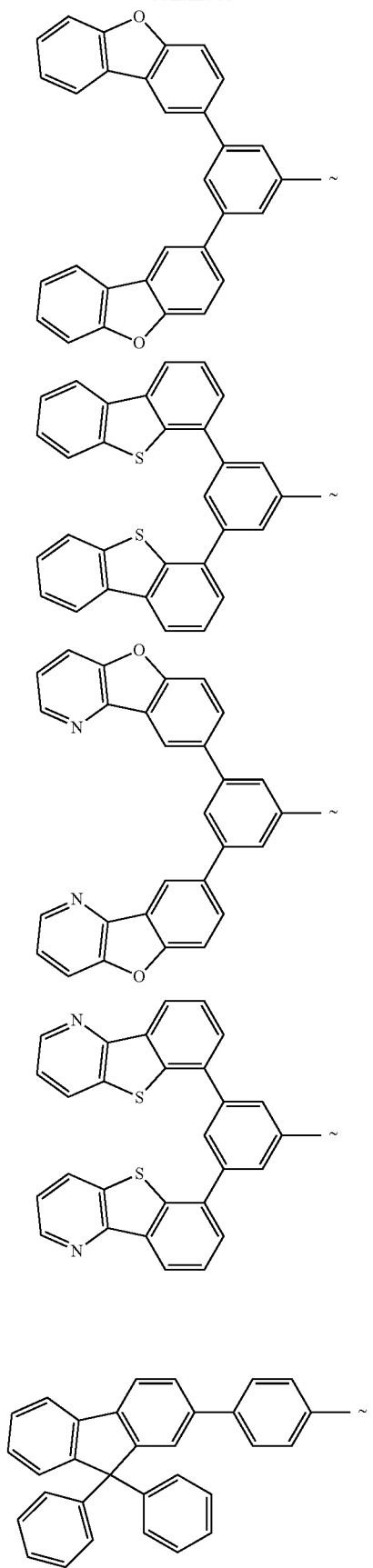

473
-continued
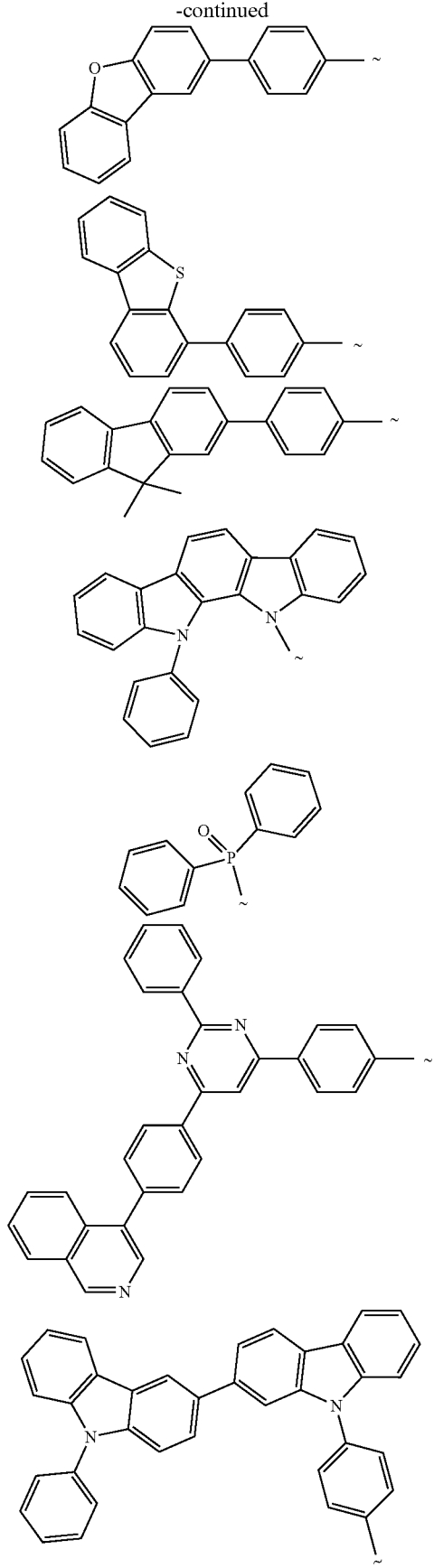
474
-continued
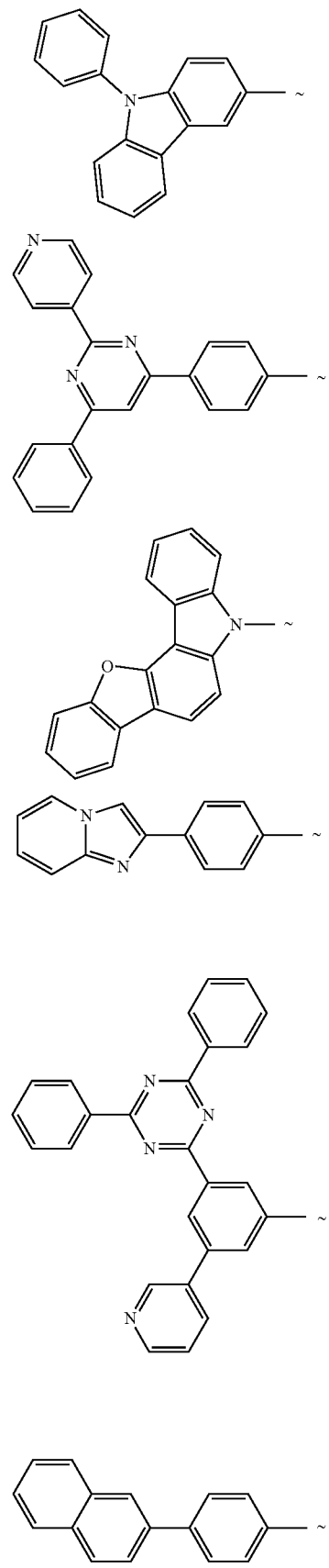

475
-continued
476
-continued
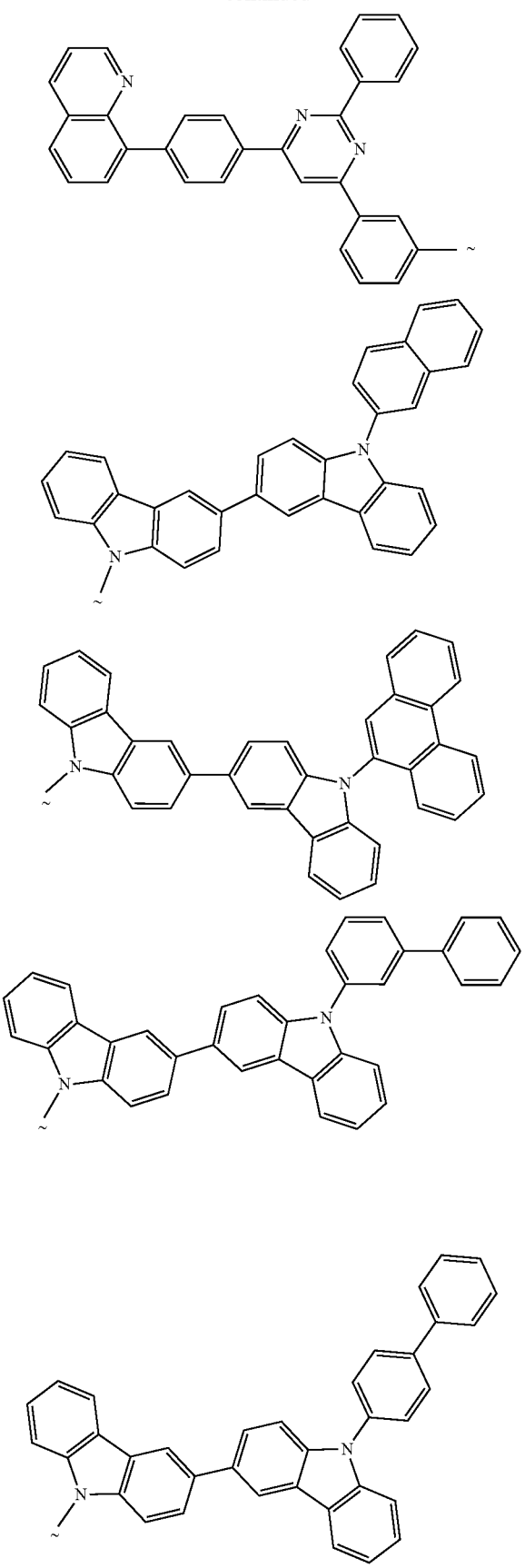
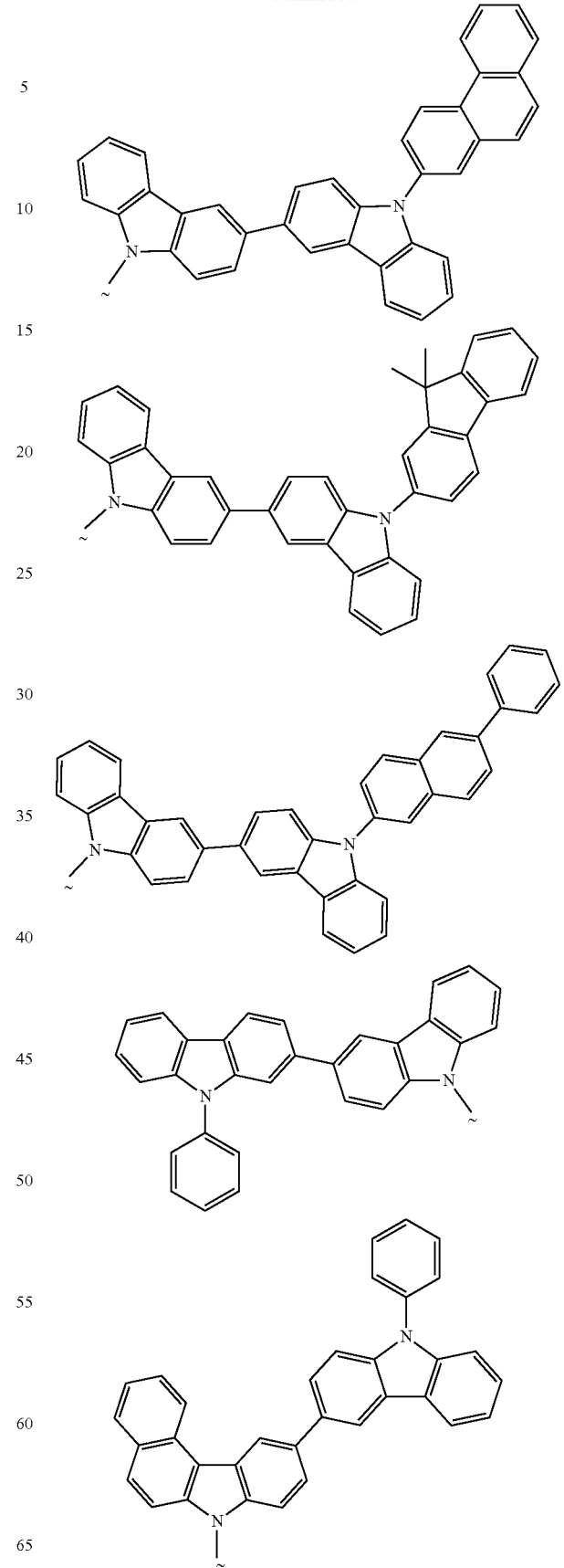

477
-continued
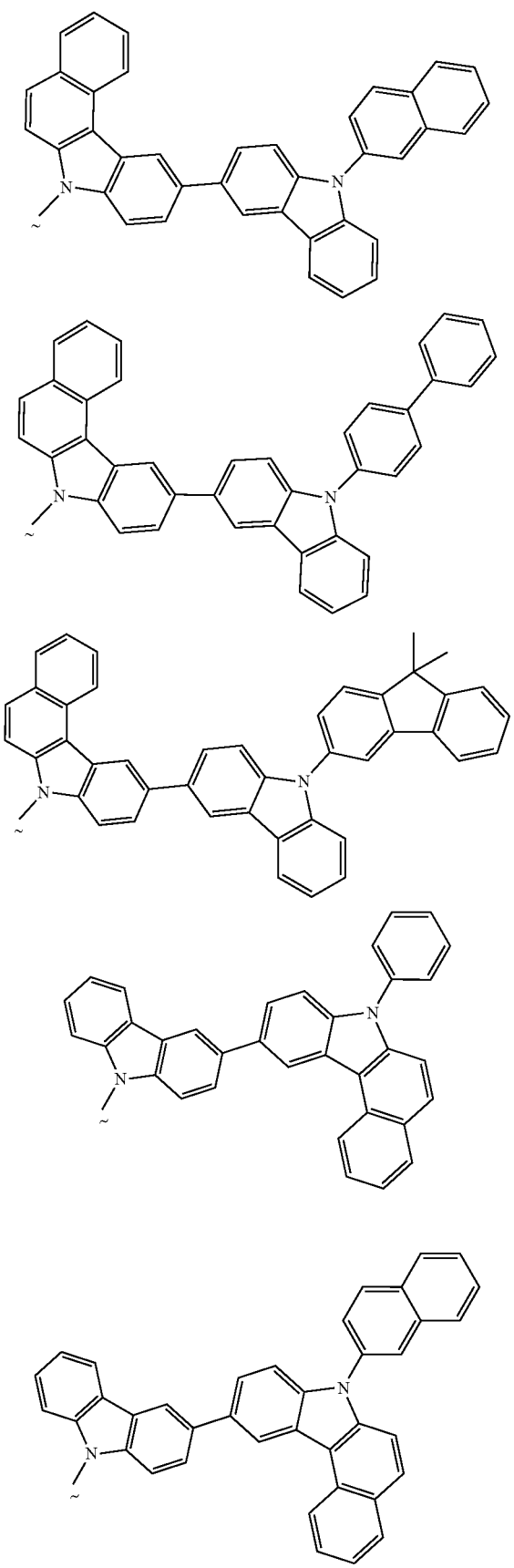
478
-continued
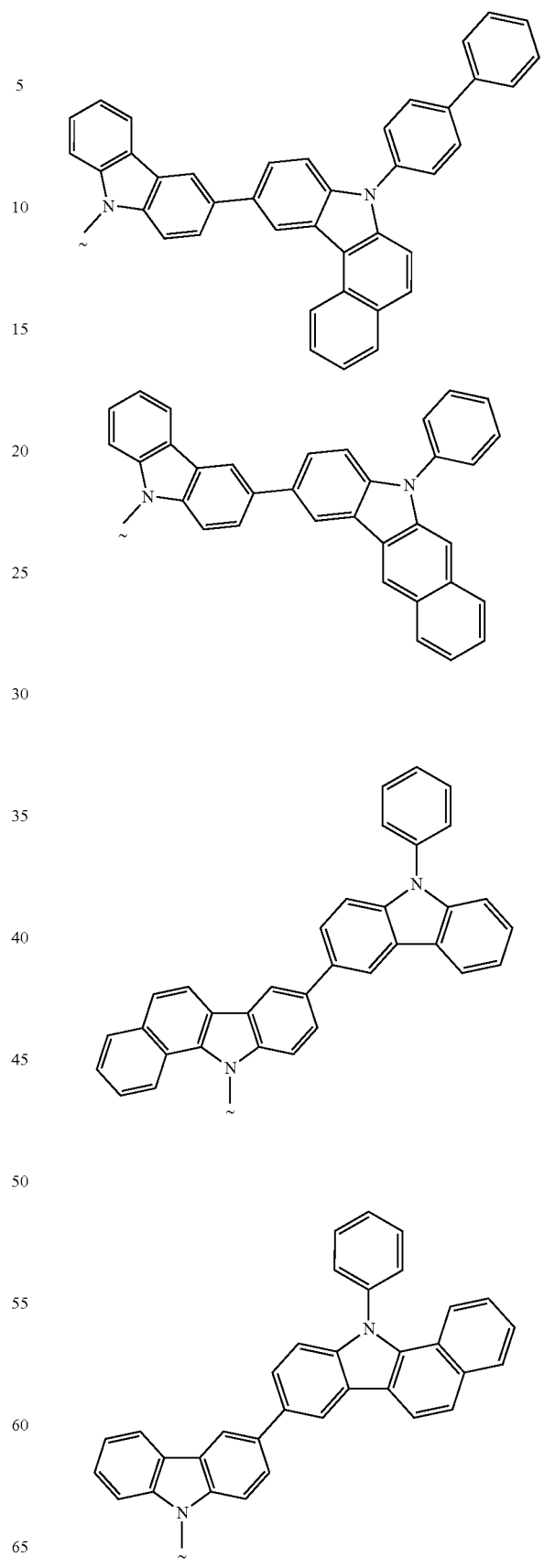

479
-continued
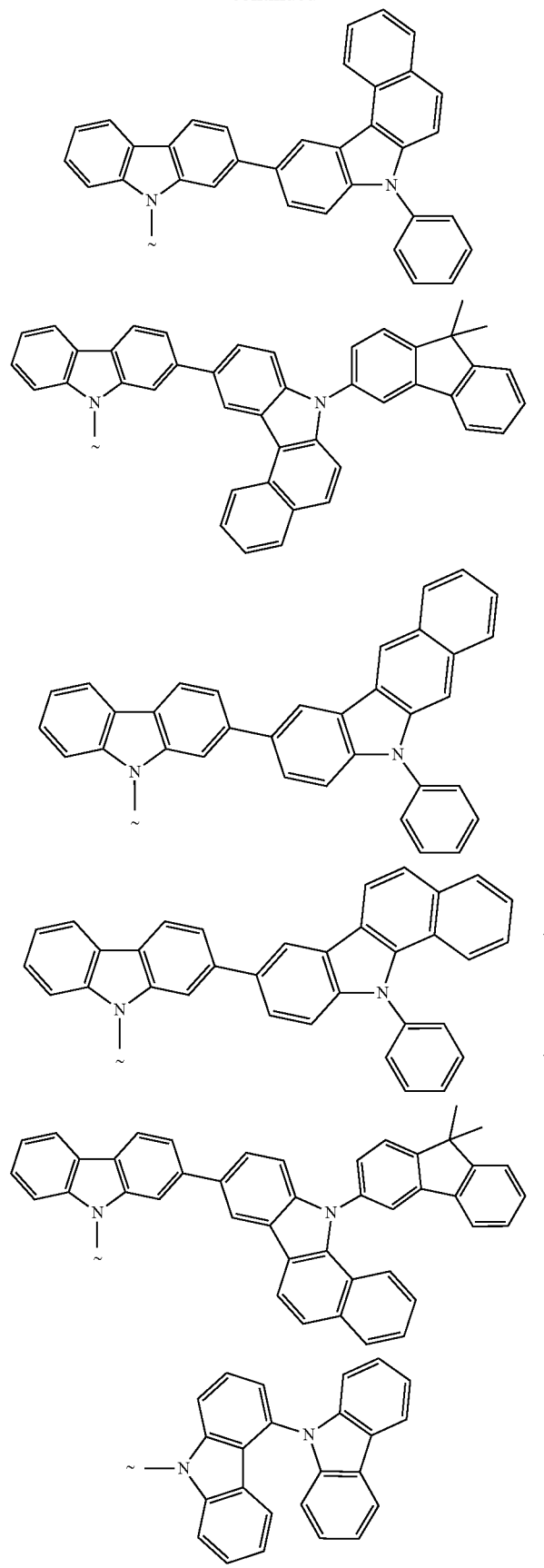
480
-continued
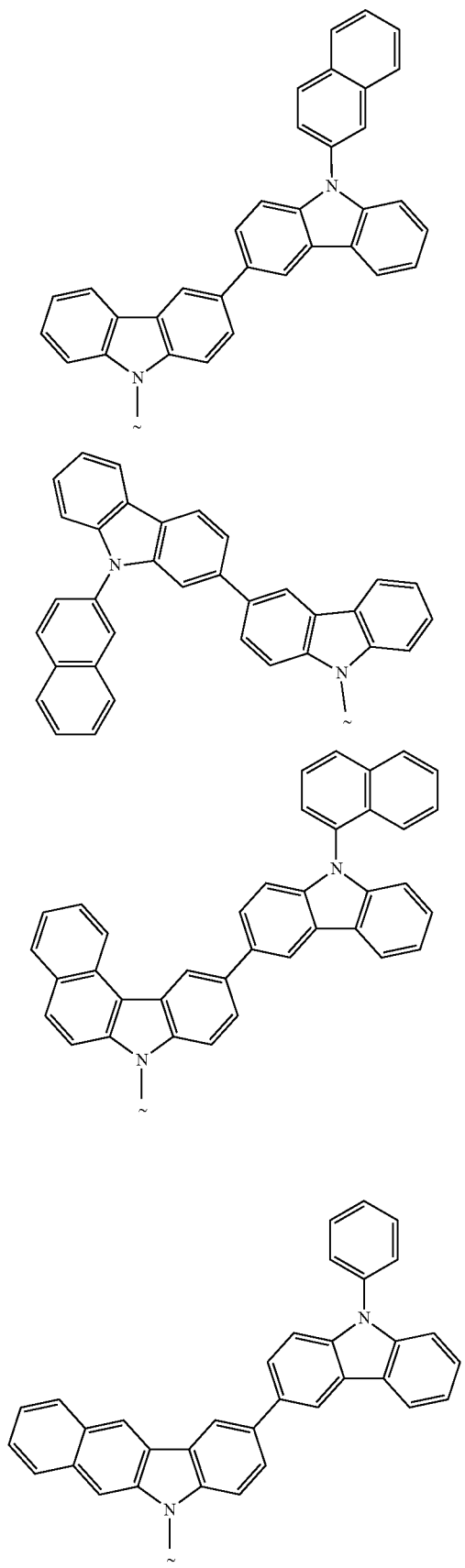

481
-continued
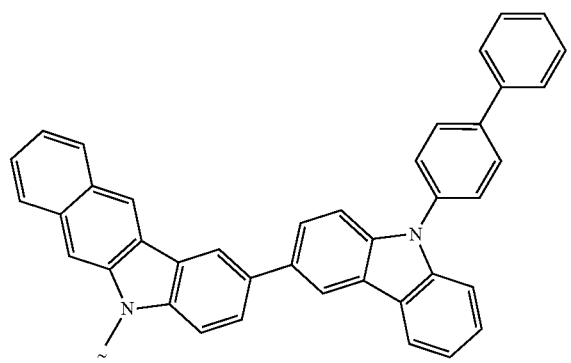
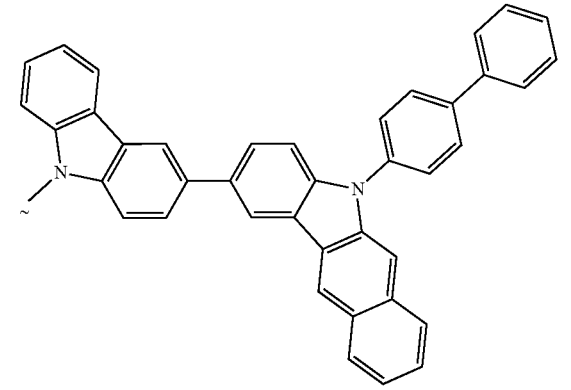
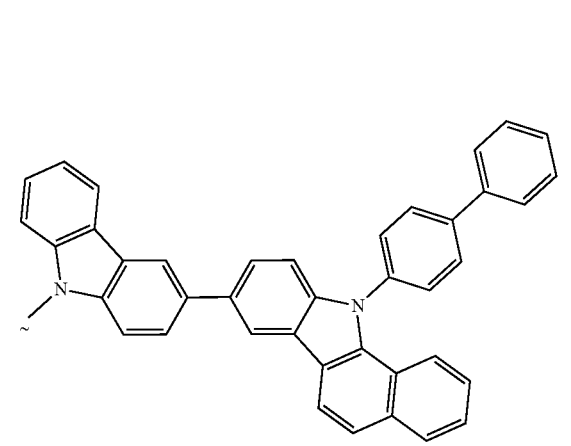
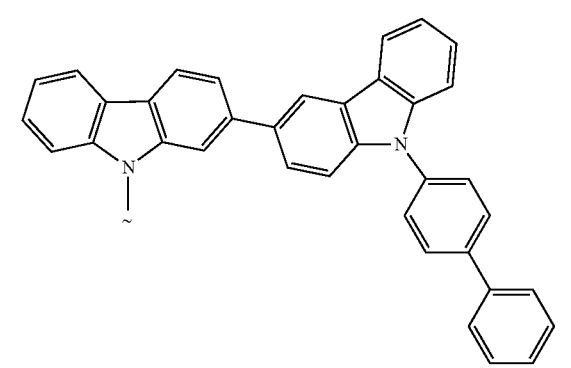
482
-continued
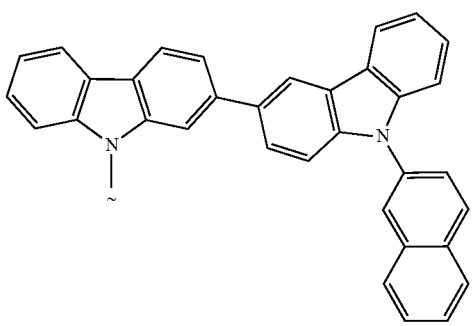
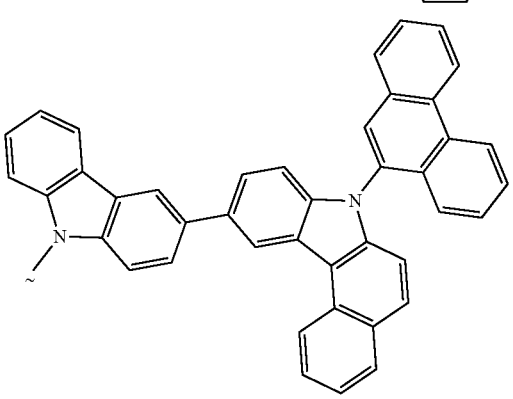
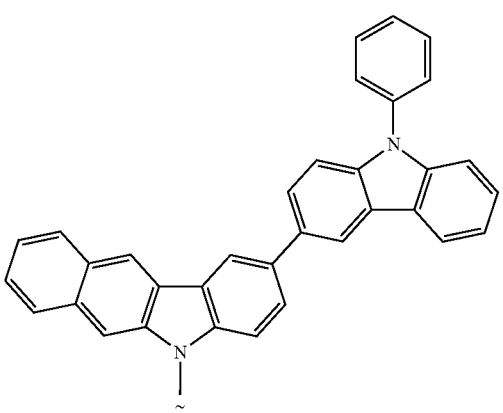
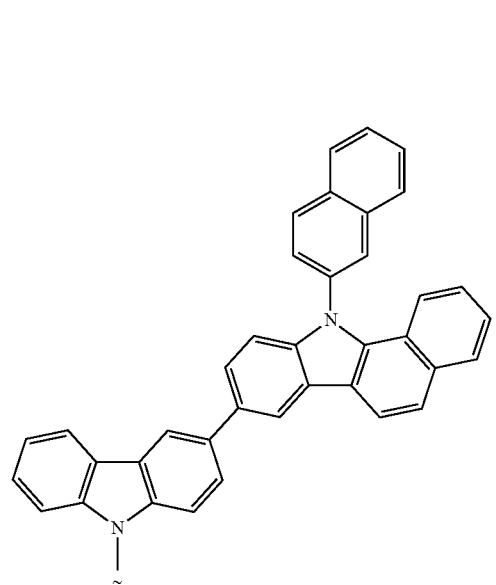

-continued

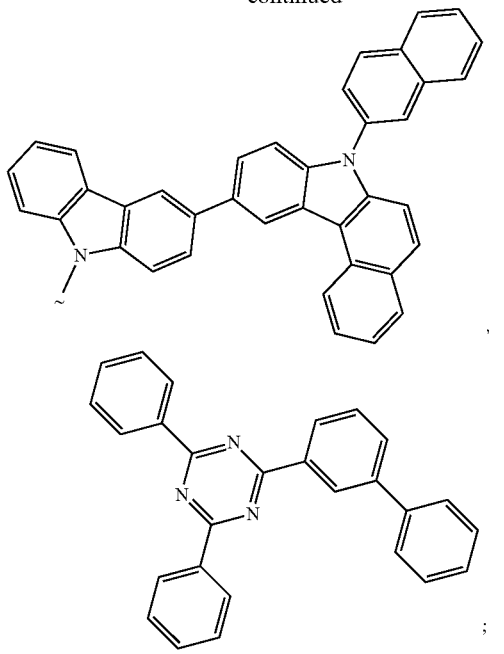
, and

;

A¹, A², A³, and A⁴ are independently of each other a C₆-C₂₄ arylene group which is unsubstituted or substituted by G, a C₁-C₂₄ heteroarylene group which is unsubstituted or substituted by G;

$R^{20}$ is H; E; a $C_6$-$C_{60}$ aryl group which is unsubstituted or substituted by G, a $C_1$-$C_{60}$ heteroaryl group which is unsubstituted or substituted by G, a $C_1$-$C_{25}$alkyl group, which is unsubstituted or substituted by at least one group G and/or interrupted by D;

D is —CO—, —COO—, —S—, —SO—, —SO₂—, —CR⁶³=CR⁶⁴—, —NR⁶⁵—, —SiR⁷⁰R⁷¹—, —POR⁷³—, or —C≡C—;

E is —SR⁶⁹, —COR⁶⁸, —COOR⁶⁷, —CONR⁶⁵R⁶⁶, —CN, —SiR⁷⁰R⁷¹R⁷², or —POR⁷⁴R⁷⁵;

G is E; or a C₁-C₂₄alkyl group; a C₁-C₂₄alkyl group, which is interrupted by O; a C₆-C₆₀aryl group, a C₆-C₆₀aryl group, which is substituted by F, —CF₃, —CF₂CF₃, —CF₂CF₂CF₃, —CF(CF₃)₂, —(CF₂)₃CF₃, —C(CF₃)₃, a C₁-C₂₄alkyl or a C₁-C₂₄alkyl which is interrupted by O; a C₂-C₆₀heteroaryl group; or a C₂-C₆₀heteroaryl group, which is substituted by F, —CF₃, —CF₂CF₃, —CF₂CF₂CF₃, —CF(CF₃)₂, —(CF₂)₃CF₃, —C(CF₃)₃, a C₁-C₂₄alkyl or a C₁-C₂₄alkyl which is interrupted by O;

R⁶³ and R⁶⁴ are independently of each other a C₆-C₁₈aryl; a C₆-C₁₈aryl which is substituted by a C₁-C₁₈alkyl or a C₁-C₁₈alkoxy; a C₁-C₁₈alkyl; or a C₁-C₁₈alkyl which is interrupted by —O—; H;

R⁶⁵ and R⁶⁶ are independently of each other a C₆-C₁₈aryl group; a C₆-C₁₈aryl which is substituted by a C₁-C₁₈alkyl or a C₁-C₁₈alkoxy; a C₁-C₁₈alkyl group; or a C₁-C₁₈alkyl group, which is interrupted by —O—; or R⁶⁵ and R⁶⁶ together form a five or six membered ring, which can be substituted or benzanullated;

R⁶⁷ is a C₆-C₁₈aryl group; a C₆-C₁₈aryl group, which is substituted by a C₁-C₁₈alkyl, or a C₁-C₁₈alkoxy; a C₁-C₁₈alkyl group; or a C₁-C₁₈alkyl group, which is interrupted by —O—;

R⁶⁸ is H; a C₆-C₁₈aryl group; a C₆-C₁₈aryl group, which is substituted by a C₁-C₁₈alkyl or a C₁-C₁₈alkoxy; a C₁-C₁₈alkyl group; or a C₁-C₁₈alkyl group, which is interrupted by —O—;

R⁶⁹ is a C₆-C₁₈aryl; a C₆-C₁₈aryl, which is substituted by a C₁-C₁₈alkyl or a C₁-C₁₈alkoxy; a C₁-C₁₈alkyl group; or a C₁-C₁₈alkyl group, which is interrupted by —O—;

R⁷⁰, R⁷¹ and R⁷² are independently of each other a C₁-C₁₈alkyl group, a C₆-C₁₈aryl group, or a C₆-C₁₈aryl group, which is substituted by a C₁-C₁₈alkyl; and R⁷³, R⁷⁴, and R⁷⁵ is a C₁-C₁₈alkyl group, a C₆-C₁₈aryl group, or a C₆-C₁₈aryl group, which is substituted by a C₁-C₁₈ alkyl;

wherein in the case that $A_1$ is $CR^{41}$ and $A_2$ is N, $B_3$ is CH and o, p, q and r in the definition of $R^6$ and $R^7$ are 0.

* * * * *